US012215327B2

(12) United States Patent
Keasling et al.

(10) Patent No.: US 12,215,327 B2
(45) Date of Patent: *Feb. 4, 2025

(54) MICROORGANISMS AND METHODS FOR PRODUCING CANNABINOIDS AND CANNABINOID DERIVATIVES

(71) Applicant: The Regents of the University of California, Oakland, CA (US)

(72) Inventors: Jay D. Keasling, Berkeley, CA (US); Leo D'Espaux, San Francisco, CA (US); Jeff Wong, Berkeley, CA (US); Xiaozhou Luo, Berkeley, CA (US); Michael Reiter, Berkeley, CA (US); Charles Denby, Berkeley, CA (US); Anna Lechner, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/054,917

(22) Filed: Nov. 14, 2022

(65) Prior Publication Data

US 2023/0340506 A1  Oct. 26, 2023

Related U.S. Application Data

(60) Continuation of application No. 17/206,126, filed on Mar. 19, 2021, now Pat. No. 11,542,512, which is a continuation of application No. 16/791,991, filed on Feb. 14, 2020, now Pat. No. 10,975,379, which is a division of application No. 16/408,492, filed on May 10, 2019, now Pat. No. 10,563,211, which is a continuation of application No. PCT/US2018/029668, filed on Apr. 27, 2018.

(60) Provisional application No. 62/569,532, filed on Oct. 7, 2017, provisional application No. 62/491,114, filed on Apr. 27, 2017.

(51) Int. Cl.
*C12N 15/81* (2006.01)
*C07C 63/04* (2006.01)
*C12N 9/10* (2006.01)
*C12N 15/52* (2006.01)
*C12N 15/70* (2006.01)
*C12N 15/82* (2006.01)
*C12P 7/42* (2006.01)

(52) U.S. Cl.
CPC .............. *C12N 15/81* (2013.01); *C07C 63/04* (2013.01); *C12N 9/1085* (2013.01); *C12N 15/70* (2013.01); *C12N 15/8243* (2013.01); *C12P 7/42* (2013.01); *C12N 15/52* (2013.01); *C12Y 101/01088* (2013.01); *C12Y 203/01086* (2013.01); *C12Y 203/01206* (2015.07); *C12Y 203/0301* (2013.01); *C12Y 205/01102* (2015.07); *C12Y 207/01036* (2013.01); *C12Y 207/04002* (2013.01); *C12Y 401/01033* (2013.01); *C12Y 503/03002* (2013.01); *C12Y 602/01003* (2013.01); *C12Y 604/01002* (2013.01)

(58) Field of Classification Search
None
See application file for complete search history.

(56) References Cited

U.S. PATENT DOCUMENTS 10,563,211 B2 * 2/2020 Keasling .................. C12P 7/42
10,975,379 B2 * 4/2021 Keasling ................ C12N 15/70
11,542,512 B2 * 1/2023 Keasling ............ C12N 15/8243

OTHER PUBLICATIONS

Chica et al. Curr Opin Biotechnol. Aug. 2005;16(4):378-84 (Year: 2005).*
Singh et al. Curr Protein Pept Sci. 2017, 18, 1-11 (Year: 2017).*

* cited by examiner

*Primary Examiner* — Christian L Fronda
(74) *Attorney, Agent, or Firm* — Richard Aron Osman

(57) ABSTRACT

The present disclosure provides genetically modified host cells that produce a cannabinoid, a cannabinoid derivative, a cannabinoid precursor, or a cannabinoid precursor derivative. The present disclosure provides methods of synthesizing a cannabinoid, a cannabinoid derivative, a cannabinoid precursor, or a cannabinoid precursor derivative.

19 Claims, 101 Drawing Sheets

Specification includes a Sequence Listing.

1114a-tCsPT4

511b-GAL1ps-MBP-THCAS-ENO2ts

MICROORGANISMS AND METHODS FOR PRODUCING CANNABINOIDS AND CANNABINOID DERIVATIVES

CROSS-REFERENCE TO RELATED APPLICATIONS

This application is a continuation of Ser. No. 17/206,126, filed Mar. 19, 2021, now U.S. Pat. No. 11,542,512, which is a continuation of Ser. No. 16/791,991, filed Feb. 14, 2020, now U.S. Pat. No. 10,975,379, which is a division of Ser. No. 16/408,492, filed May 10, 2019, now U.S. Pat. No. 10,563,211, which is a continuation of PCT/US2018/029668, filed Apr. 27, 2018, which claims the benefit of Ser. 62/491,114, filed Apr. 27, 2017, and Ser. 62/569,532, filed Oct. 7, 2017, the contents of each of which are incorporated herein by reference in their entirety.

STATEMENT REGARDING FEDERALLY SPONSORED RESEARCH

This invention was made with government support under Grant Numbers 1330914 and 1442724 awarded by the National Science Foundation. The government has certain rights in the invention.

REFERENCE TO A SEQUENCE LISTING

The Sequence Listing associated with this application is provided in XML format in lieu of a paper copy, and is hereby incorporated by reference into the specification. The name of the XML file containing the Sequence Listing is B16-072-8SeqList. The text file is about 422 KB, was created on Apr. 24, 2023, and is being submitted electronically via EFS-Web.

INTRODUCTION

Plants from the genus *Cannabis* have been used by humans for their medicinal properties for thousands of years. In modern times, the bioactive effects of *Cannabis* are attributed to a class of compounds termed "cannabinoids," of which there are hundreds of structural analogs including tetrahydrocannabinol (THC) and cannabidiol (CBD). These molecules and preparations of *Cannabis* material have recently found application as therapeutics for chronic pain, multiple sclerosis, cancer-associated nausea and vomiting, weight loss, appetite loss, spasticity, and other conditions.

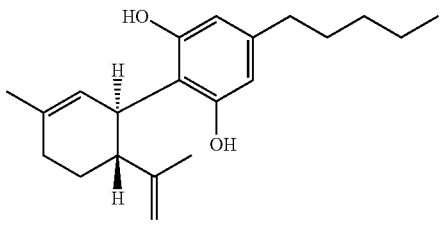

Cannabidiol/CBD

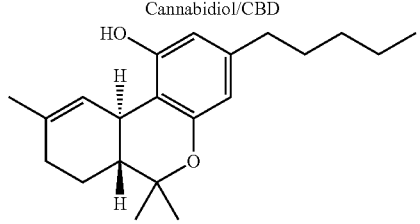

Tetrahydrocannabinol/THC/Dronabinol/Marinol

The physiological effects of certain cannabinoids are thought to be mediated by their interaction with two cellular receptors found in humans and other animals. Cannabinoid receptor type 1 (CB1) is common in the brain, the reproductive system, and the eye. Cannabinoid receptor type 2 (CB2) is common in the immune system and mediates therapeutic effects related to inflammation in animal models. The discovery of cannabinoid receptors and their interactions with plant-derived cannabinoids predated the identification of endogenous ligands.

Besides THC and CBD, hundreds of other cannabinoids have been identified in *Cannabis*. However, many of these compounds exist at low levels and alongside more abundant cannabinoids, making it difficult to obtain pure samples from plants to study their therapeutic potential. Similarly, methods of chemically synthesizing these types of products has been cumbersome and costly, and tends to produce insufficient yield. Accordingly, additional methods of making pure cannabinoids, cannabinoid precursors, cannabinoid derivatives, or cannabinoid precursor derivatives are needed.

SUMMARY

The present disclosure provides methods, polypeptides, nucleic acids encoding said polypeptides, and genetically modified host cells for the production of cannabinoids, cannabinoid derivatives, cannabinoid precursors, or cannabinoid precursor derivatives.

One aspect of the disclosure relates to a genetically modified host cell for producing a cannabinoid or a cannabinoid derivative, the genetically modified host cell comprising one or more heterologous nucleic acids encoding a geranyl pyrophosphate:olivetolic acid geranyltransferase (GOT) polypeptide, wherein said GOT polypeptide catalyzes production of cannabigerolic acid from geranyl pyrophosphate (GPP) and olivetolic acid in an amount at least ten times higher than a polypeptide comprising an amino acid sequence set forth in SEQ ID NO:82.

Another aspect of the disclosure relates to a genetically modified host cell for producing a cannabinoid or a cannabinoid derivative, the genetically modified host cell comprising one or more heterologous nucleic acids encoding a GOT polypeptide comprising an amino acid sequence having at least 65% sequence identity to SEQ ID NO:110.

One aspect of the disclosure relates to a genetically modified host cell for producing a cannabinoid or a cannabinoid derivative, the genetically modified host cell comprising one or more heterologous nucleic acids encoding a GOT polypeptide comprising an amino acid sequence having at least 65% sequence identity to SEQ ID NO:100.

In certain embodiments of any of the foregoing or following, the genetically modified host cell further comprises one or more heterologous nucleic acids encoding a tetraketide synthase (TKS) polypeptide and one or more heterologous nucleic acids encoding an olivetolic acid cyclase (OAC) polypeptide, or one or more heterologous nucleic acids encoding a fusion TKS and OAC polypeptide. In some embodiments, the TKS polypeptide comprises an amino acid sequence having at least 50% sequence identity to SEQ ID NO:11 or SEQ ID NO:76. In some embodiments, the OAC polypeptide comprises an amino acid sequence having at least 50% sequence identity to SEQ ID NO:10 or SEQ ID NO:78.

In certain embodiments of any of the foregoing or following, the genetically modified host cell further comprises one or more of the following: a) one or more heterologous nucleic acids encoding a polypeptide that generates an acyl-CoA compound or an acyl-CoA compound derivative; b) one or more heterologous nucleic acids encoding a polypeptide that generates GPP; or c) one or more heterologous nucleic acids encoding a polypeptide that generates malonyl-CoA. In some embodiments, the genetically modified host cell further comprises one or more heterologous nucleic acids encoding a polypeptide that generates an acyl-CoA compound or an acyl-CoA compound derivative, wherein the polypeptide that generates an acyl-CoA compound or an acyl-CoA compound derivative is an acyl-activating enzyme (AAE) polypeptide. In some embodiments, the AAE polypeptide comprises an amino acid sequence having at least 50% sequence identity to SEQ ID NO:90. In some embodiments, the AAE polypeptide comprises an amino acid sequence having at least 50% sequence identity to SEQ ID NO:92 or SEQ ID NO:149. In some embodiments, the genetically modified host cell further comprises one or more heterologous nucleic acids encoding a polypeptide that generates an acyl-CoA compound or an acyl-CoA compound derivative, wherein the polypeptide that generates an acyl-CoA compound or an acyl-CoA compound derivative is a fatty acyl-CoA ligase polypeptide. In some embodiments, the fatty acyl-CoA ligase polypeptide comprises an amino acid sequence having at least 50% sequence identity to SEQ ID NO:145 or SEQ ID NO:147. In some embodiments, the genetically modified host cell further comprises one or more heterologous nucleic acids encoding a polypeptide that generates an acyl-CoA compound or an acyl-CoA compound derivative, wherein the polypeptide that generates an acyl-CoA compound or an acyl-CoA compound derivative is a fatty acyl-CoA synthetase (FAA) polypeptide. In some embodiments, the FAA polypeptide comprises an amino acid sequence having at least 50% sequence identity to SEQ ID NO:169, SEQ ID NO:192, SEQ ID NO:194, SEQ ID NO:196, SEQ ID NO:198, or SEQ ID NO:200. In some embodiments, the genetically modified host cell further comprises one or more heterologous nucleic acids encoding a polypeptide that generates GPP, wherein the polypeptide that generates GPP is a geranyl pyrophosphate synthetase (GPPS) polypeptide. In some embodiments, the GPPS polypeptide comprises an amino acid sequence having at least 50% sequence identity to SEQ ID NO:7, SEQ ID NO:8, or SEQ ID NO:60. In some embodiments, the genetically modified host cell further comprises one or more heterologous nucleic acids encoding a polypeptide that generates malonyl-CoA, wherein the polypeptide that generates malonyl-CoA is an acetyl-CoA carboxylase-1 (ACC1) polypeptide. In some embodiments, the ACC1 polypeptide comprises an amino acid sequence having at least 50% sequence identity to SEQ ID NO:9, SEQ ID NO:97, or SEQ ID NO:207.

In certain embodiments of any of the foregoing or following, the genetically modified host cell further comprises one or more of the following: a) one or more heterologous nucleic acids encoding a HMG-CoA synthase (HMGS) polypeptide; b) one or more heterologous nucleic acids encoding a 3-hydroxy-3-methyl-glutaryl-CoA reductase (HMGR) polypeptide; c) one or more heterologous nucleic acids encoding a mevalonate kinase (MK) polypeptide; d) one or more heterologous nucleic acids encoding a phosphomevalonate kinase (PMK) polypeptide; e) one or more heterologous nucleic acids encoding a mevalonate pyrophosphate decarboxylase (MVD) polypeptide; or f) one or more heterologous nucleic acids encoding a isopentenyl diphosphate isomerase (IDI) polypeptide. In some embodiments, the genetically modified host cell further comprises one or more heterologous nucleic acids encoding an IDI polypeptide. In some embodiments, the IDI polypeptide comprises an amino acid sequence having at least 50% sequence identity to SEQ ID NO:58. In some embodiments, the genetically modified host cell further comprises one or more heterologous nucleic acids encoding an HMGR polypeptide. In some embodiments, the HMGR polypeptide comprises an amino acid sequence having at least 50% sequence identity to SEQ ID NO:22. In some embodiments, the genetically modified host cell further comprises one or more heterologous nucleic acids encoding an HMGR polypeptide, wherein the HMGR polypeptide is a truncated HMGR (tHMGR) polypeptide. In some embodiments, the tHMGR polypeptide comprises an amino acid sequence having at least 50% sequence identity to SEQ ID NO:17, SEQ ID NO:52, SEQ ID NO:113, or SEQ ID NO:208. In some embodiments, the genetically modified host cell further comprises one or more heterologous nucleic acids encoding an HMGS polypeptide. In some embodiments, the HMGS polypeptide comprises an amino acid sequence having at least 50% sequence identity to SEQ ID NO:23, SEQ ID NO:24, or SEQ ID NO:115. In some embodiments, the genetically modified host cell further comprises one or more heterologous nucleic acids encoding an MK polypeptide. In some embodiments, the MK polypeptide comprises an amino acid sequence having at least 50% sequence identity to SEQ ID NO:64. In some embodiments, the genetically modified host cell further comprises one or more heterologous nucleic acids encoding a PMK polypeptide. In some embodiments, the PMK polypeptide comprises an amino acid sequence having at least 50% sequence identity to SEQ ID NO:62 or SEQ ID NO:205. In some embodiments, the genetically modified host cell further comprises one or more heterologous nucleic acids encoding a MVD polypeptide. In some embodiments, the MVD polypeptide comprises an amino acid sequence having at least 50% sequence identity to SEQ ID NO:66.

In certain embodiments of any of the foregoing or following, the genetically modified host cell further comprises one or more heterologous nucleic acids encoding a polypeptide that condenses two molecules of acetyl-CoA to generate acetoacetyl-CoA. In some embodiments, the polypeptide that condenses two molecules of acetyl-CoA to generate acetoacetyl-CoA is an acetoacetyl-CoA thiolase polypeptide. In some embodiments, the acetoacetyl-CoA thiolase polypeptide comprises an amino acid sequence having at least 50% sequence identity to SEQ ID NO:25.

In certain embodiments of any of the foregoing or following, the genetically modified host cell further comprises one or more heterologous nucleic acids encoding a pyruvate decarboxylase (PDC) polypeptide. In some embodiments, the PDC polypeptide comprises an amino acid sequence having at least 50% sequence identity to SEQ ID NO:117.

In certain embodiments of any of the foregoing or following, the genetically modified host cell is a eukaryotic cell. In some embodiments, the eukaryotic cell is a yeast cell. In some embodiments, the yeast cell is *Saccharomyces cerevisiae*. In some embodiments, the *Saccharomyces cerevisiae* is a protease-deficient strain of *Saccharomyces cerevisiae*. In some embodiments, the genetically modified host cell is a plant cell.

In certain embodiments of any of the foregoing or following, the genetically modified host cell is a prokaryotic cell.

In certain embodiments of any of the foregoing or following, at least one of the one or more heterologous nucleic acids is integrated into the chromosome of the genetically modified host cell.

In certain embodiments of any of the foregoing or following, at least one of the one or more heterologous nucleic acids is maintained extrachromosomally.

In certain embodiments of any of the foregoing or following, two or more of the one or more heterologous nucleic acids are present in a single expression vector.

In certain embodiments of any of the foregoing or following, at least one of the heterologous nucleic acids is operably linked to an inducible promoter.

In certain embodiments of any of the foregoing or following, at least one of the heterologous nucleic acids is operably linked to a constitutive promoter.

In certain embodiments of any of the foregoing or following, culturing of the genetically modified host cell in a suitable medium provides for synthesis of the cannabinoid or the cannabinoid derivative in an increased amount compared to a non-genetically modified host cell cultured under similar conditions.

In certain embodiments of any of the foregoing or following, the genetically modified host cell further comprises one or more heterologous nucleic acids encoding a cannabinoid synthase polypeptide. In some embodiments, the cannabinoid synthase polypeptide is a tetrahydrocannabinolic acid (THCA) synthase polypeptide. In some embodiments, the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155. In some embodiments, the cannabinoid synthase polypeptide is a cannabidiolic acid (CBDA) synthase polypeptide. In some embodiments, the CBDA synthase polypeptide comprises an amino acid sequence having at least 50% sequence identity to SEQ ID NO:88 or SEQ ID NO:151.

In certain embodiments of any of the foregoing or following, the cannabinoid is cannabigerolic acid, cannabigerol, $\Delta^9$-tetrahydrocannabinolic acid, $\Delta^9$-tetrahydrocannabinol, $\Delta^8$-tetrahydrocannabinolic acid, $\Delta^8$-tetrahydrocannabinol, cannabidiolic acid, cannabidiol, cannabichromenic acid, cannabichromene, cannabinolic acid, cannabinol, cannabidivarinic acid, cannabidivarin, tetrahydrocannabivarinic acid, tetrahydrocannabivarin, cannabichromevarinic acid, cannabichromevarin, cannabigerovarinic acid, cannabigerovarin, cannabicyclolic acid, cannabicyclol, cannabielsoinic acid, cannabielsoin, cannabicitranic acid, or cannabicitran.

One aspect of the disclosure relates to a method of producing a cannabinoid or a cannabinoid derivative in a genetically modified host cell, the method comprising: a) culturing the genetically modified host cell in a suitable medium; and b) recovering the produced cannabinoid or cannabinoid derivative.

Another aspect of the disclosure relates to a method of producing a cannabinoid or a cannabinoid derivative in a genetically modified host cell, the method comprising: a) culturing the genetically modified host cell in a suitable medium comprising a carboxylic acid; b) recovering the produced cannabinoid or cannabinoid derivative.

One aspect of the disclosure relates to a method of producing a cannabinoid or a cannabinoid derivative in a genetically modified host cell, the method comprising: a) culturing the genetically modified host cell in a suitable medium comprising olivetolic acid or an olivetolic acid derivative; b) recovering the produced cannabinoid or cannabinoid derivative.

Another aspect of the disclosure relates to a method of producing a cannabinoid or a cannabinoid derivative in a genetically modified host cell, the method comprising: a) culturing a genetically modified host cell comprising one or more heterologous nucleic acids encoding a GOT polypeptide, wherein said GOT polypeptide catalyzes production of cannabigerolic acid from GPP and olivetolic acid in an amount at least ten times higher than a polypeptide comprising an amino acid sequence set forth in SEQ ID NO:82, in a suitable medium; and b) recovering the produced cannabinoid or cannabinoid derivative.

One aspect of the disclosure relates to a method of producing a cannabinoid or a cannabinoid derivative in a genetically modified host cell, the method comprising: a) culturing a genetically modified host cell comprising one or more heterologous nucleic acids encoding a GOT polypeptide comprising an amino acid sequence having at least 65% sequence identity to SEQ ID NO:110 in a suitable medium; and b) recovering the produced cannabinoid or cannabinoid derivative.

Another aspect of the disclosure relates to a method of producing a cannabinoid or a cannabinoid derivative in a genetically modified host cell, the method comprising: a) culturing a genetically modified host cell comprising one or more heterologous nucleic acids encoding a GOT polypeptide comprising an amino acid sequence having at least 65% sequence identity to SEQ ID NO:100 in a suitable medium; and b) recovering the produced cannabinoid or cannabinoid derivative.

In certain embodiments of any of the foregoing or following, the suitable medium comprises a fermentable sugar. In some embodiments, the suitable medium comprises a pretreated cellulosic feedstock.

In certain embodiments of any of the foregoing or following, the suitable medium comprises a non-fermentable carbon source. In some embodiments, the non-fermentable carbon source comprises ethanol.

One aspect of the disclosure relates to an isolated or purified GOT polypeptide, wherein said GOT polypeptide catalyzes production of cannabigerolic acid from GPP and olivetolic acid in an amount at least ten times higher than a polypeptide comprising an amino acid sequence set forth in SEQ ID NO:82.

Another aspect of the disclosure relates to an isolated or purified polypeptide comprising an amino acid sequence having at least 65% sequence identity to SEQ ID NO:110.

One aspect of the disclosure relates to an isolated or purified polypeptide comprising an amino acid sequence having at least 65% sequence identity to SEQ ID NO:100.

Another aspect of the disclosure relates to an isolated or purified nucleic acid encoding a GOT polypeptide, wherein said GOT polypeptide catalyzes production of cannabigerolic acid from GPP and olivetolic acid in an amount at least ten times higher than a polypeptide comprising an amino acid sequence set forth in SEQ ID NO:82.

One aspect of the disclosure relates to an isolated or purified nucleic acid encoding a polypeptide comprising an amino acid sequence having at least 65% sequence identity to SEQ ID NO:110.

Another aspect of the disclosure relates to an isolated or purified nucleic acid encoding a polypeptide comprising an amino acid sequence having at least 65% sequence identity to SEQ ID NO:100.

One aspect of the disclosure relates to a vector comprising a nucleic acid encoding a GOT polypeptide, wherein said GOT polypeptide catalyzes production of cannabigerolic acid from GPP and olivetolic acid in an amount at least ten times higher than a polypeptide comprising an amino acid sequence set forth in SEQ ID NO:82.

Another aspect of the disclosure relates to a vector comprising a nucleic acid encoding a polypeptide comprising an amino acid sequence having at least 65% sequence identity to SEQ ID NO:110.

One aspect of the disclosure relates to a vector comprising a nucleic acid encoding a polypeptide comprising an amino acid sequence having at least 65% sequence identity to SEQ ID NO:100.

Another aspect of the disclosure relates to a method of making a genetically modified host cell for producing a cannabinoid or a cannabinoid derivative, comprising introducing one or more heterologous nucleic acids encoding a GOT polypeptide, wherein said GOT polypeptide catalyzes production of cannabigerolic acid from GPP and olivetolic acid in an amount at least ten times higher than a polypeptide comprising an amino acid sequence set forth in SEQ ID NO:82, into the genetically modified host cell.

One aspect of the disclosure relates to a method of making a genetically modified host cell for producing a cannabinoid or a cannabinoid derivative, comprising introducing one or more heterologous nucleic acids encoding a GOT polypeptide comprising an amino acid sequence having at least 65% sequence identity to SEQ ID NO:110 into the genetically modified host cell.

Another aspect of the disclosure relates to a method of making a genetically modified host cell for producing a cannabinoid or a cannabinoid derivative, comprising introducing one or more heterologous nucleic acids encoding a GOT polypeptide comprising an amino acid sequence having at least 65% sequence identity to SEQ ID NO:100 into the genetically modified host cell.

One aspect of the disclosure relates to a method of making a genetically modified host cell for producing a cannabinoid or a cannabinoid derivative, comprising introducing a vector comprising a nucleic acid encoding a GOT polypeptide, wherein said GOT polypeptide catalyzes production of cannabigerolic acid from GPP and olivetolic acid in an amount at least ten times higher than a polypeptide comprising an amino acid sequence set forth in SEQ ID NO:82; a vector comprising a nucleic acid encoding a polypeptide comprising an amino acid sequence having at least 65% sequence identity to SEQ ID NO:110; or a vector comprising a nucleic acid encoding a polypeptide comprising an amino acid sequence having at least 65% sequence identity to SEQ ID NO:100, into the genetically modified host cell.

BRIEF DESCRIPTION OF THE DRAWINGS

FIG. 12 also depicts production of olivetolic acid or cannabinoid derivatives from these carboxylic acids.

DETAILED DESCRIPTION

Figure 1:
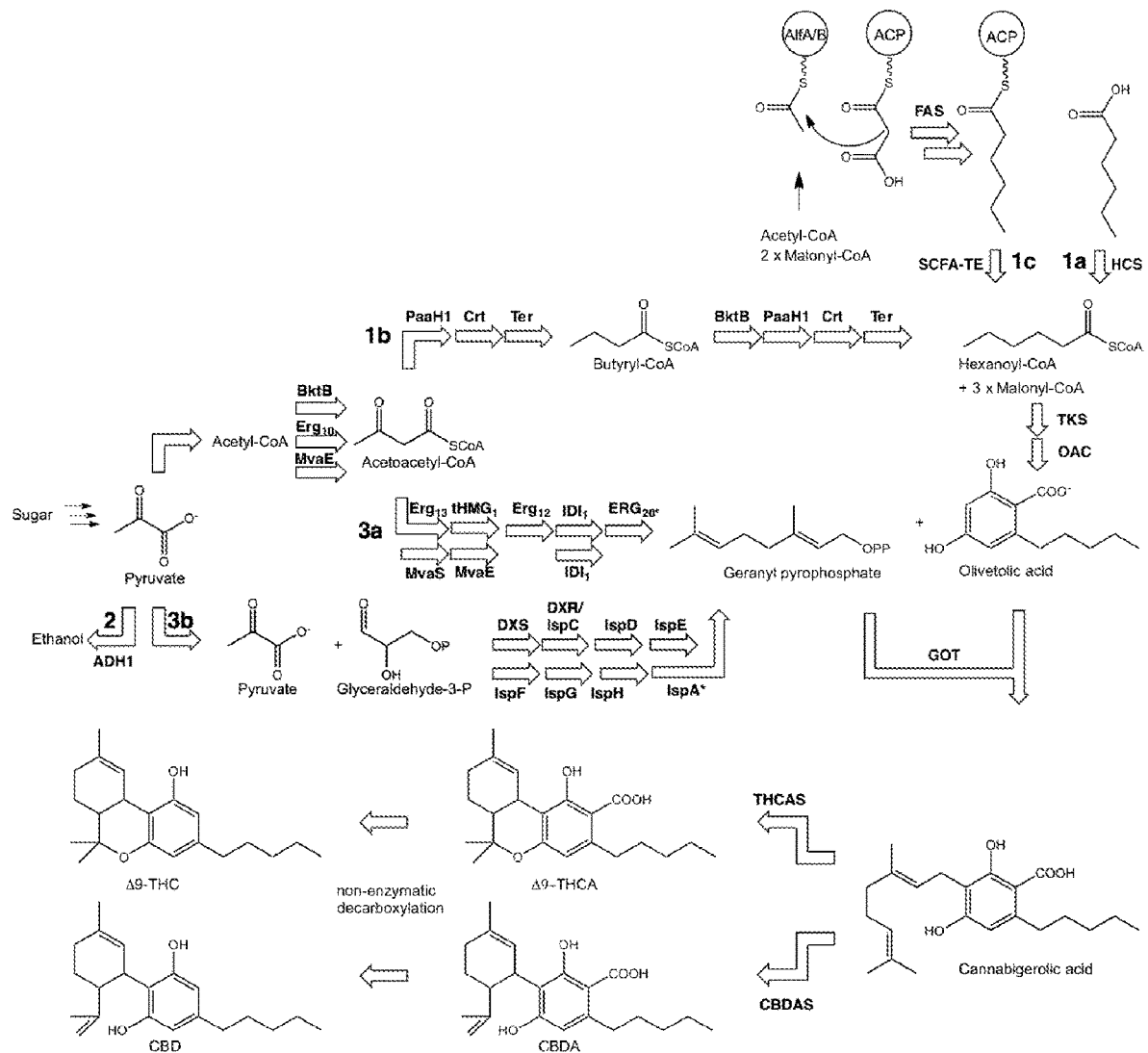
FIG. 1 provides a schematic diagram of biosynthetic pathways for generating cannabinoids, cannabinoid derivatives, cannabinoid precursors, or cannabinoid precursor derivatives.

The present disclosure provides methods, polypeptides, nucleic acids encoding said polypeptides, and genetically modified host cells for producing cannabinoids, cannabinoid precursors, cannabinoid derivatives (e.g., non-naturally occurring cannabinoids), or cannabinoid precursor derivatives (e.g., non-naturally occurring cannabinoid precursors).

Geranyl pyrophosphate:olivetolic acid geranyltransferase (GOT, Enzyme Commission Number 2.5.1.102) polypeptides play an important role in the biosynthesis of cannabinoids, but reconstituting their activity in a genetically modified host cell has proven challenging, hampering progress in the production of cannabinoids or cannabinoid derivatives. Herein, novel genes encoding polypeptides of the disclosure that catalyze production of cannabigerolic acid (CBGA) from GPP and olivetolic acid have been identified, isolated, and characterized. Surprisingly, these polypeptides of the present disclosure can catalyze production of CBGA from GPP and olivetolic acid in an amount at least ten times higher than previously discovered Cannabis polypeptides that catalyze production of CBGA from GPP and olivetolic acid (see, for example, U.S. Patent Application Pub. No. US20120144523 and the GOT polypeptide, CsPT1, disclosed therein; SEQ ID NO:82 herein). The new polypeptides of the present disclosure that catalyze production of CBGA from GPP and olivetolic acid are GOT polypeptides (e.g., the CsPT4 polypeptide) and can generate cannabinoids and cannabinoid derivatives in vivo (e.g., within a genetically modified host cell) and in vitro (e.g., cell-free). These new GOT polypeptides, as well as nucleic acids encoding said GOT polypeptides, are useful in the methods and genetically modified host cells of the disclosure for producing cannabinoids or cannabinoid derivatives.

The methods of the disclosure may include using microorganisms genetically engineered (e.g., genetically modified host cells) to produce naturally-occurring and non-naturally occurring cannabinoids or cannabinoid precursors. Naturally-occurring cannabinoids and cannabinoid precursors and non-naturally occurring cannabinoids and cannabinoid precursors (e.g., cannabinoid derivatives and cannabinoid precursor derivatives) are challenging to synthesize using chemical synthesis due to their complex structures. The methods of the disclosure enable the construction of metabolic pathways inside living cells to produce bespoke cannabinoids, cannabinoid precursors, cannabinoid derivatives, or cannabinoid precursor derivatives from simple precursors such as sugars and carboxylic acids. One or more heterologous nucleic acids disclosed herein encoding one or more polypeptides disclosed herein can be introduced into host microorganisms allowing for the stepwise conversion of inexpensive feedstocks, e.g., sugar, into final products: cannabinoids, cannabinoid precursors, cannabinoid derivatives, or cannabinoid precursor derivatives. These products can be specified by the choice and construction of expression constructs or vectors comprising one or more heterologous nucleic acids disclosed herein, allowing for the efficient bioproduction of chosen cannabinoid precursors; cannabinoids, such as THC or CBD and less common cannabinoid species found at low levels in Cannabis; or cannabinoid derivatives or cannabinoid precursor derivatives. Bioproduction also enables synthesis of cannabinoids, cannabinoid derivatives, cannabinoid precursors, or cannabinoid precursor derivatives with defined stereochemistries, which is challenging to do using chemical synthesis.

Figure 11:
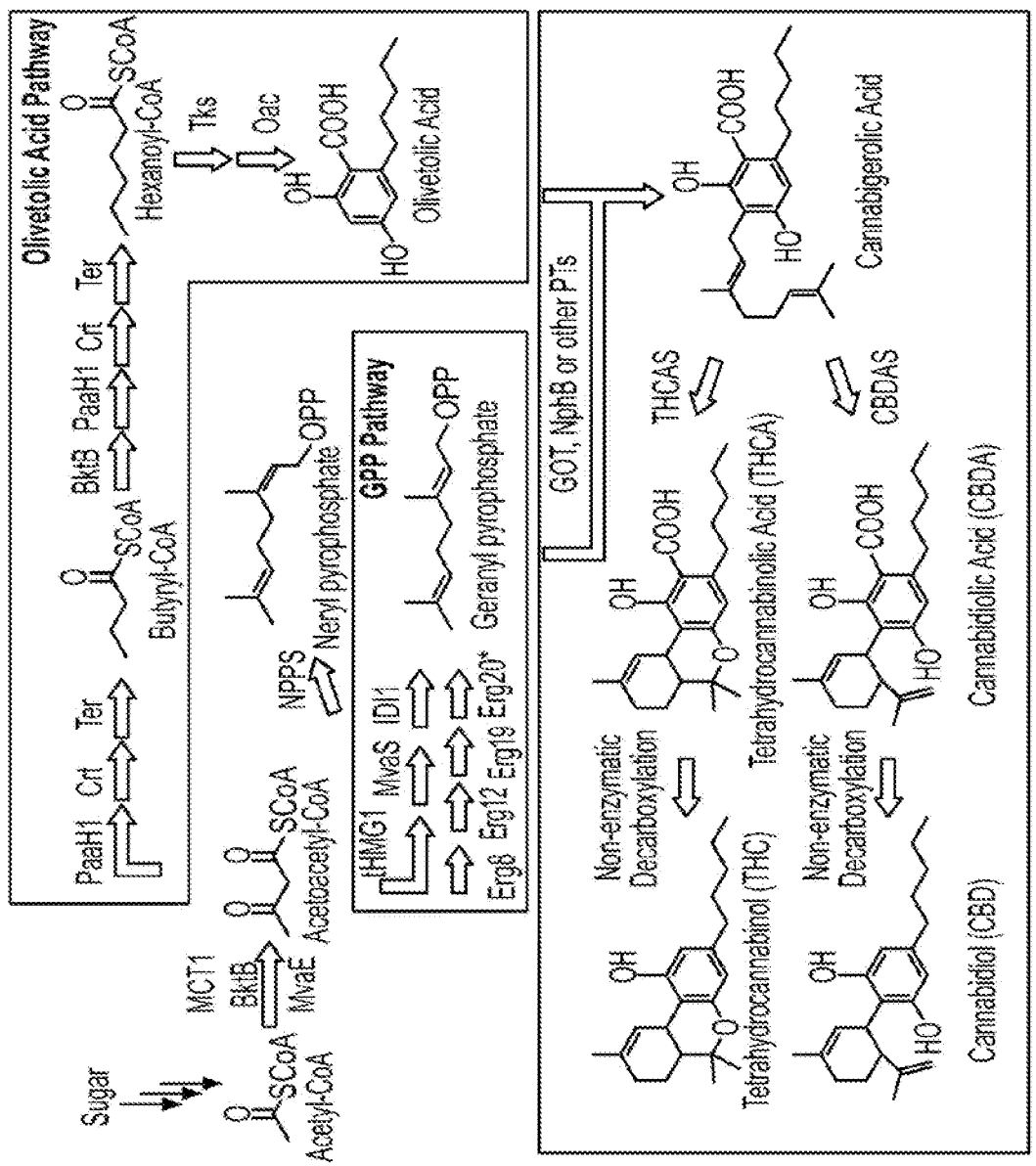
FIG. 11 is a schematic depiction of pathways for production of olivetolic acid derivatives by feeding various representative carboxylic acids, where the carboxylic acids are converted to their CoA forms by a promiscuous acyl-activating enzyme polypeptide (e.g., CsAAE1; CsAAE3), generating olivetolic acid derivatives.
Figure 11:
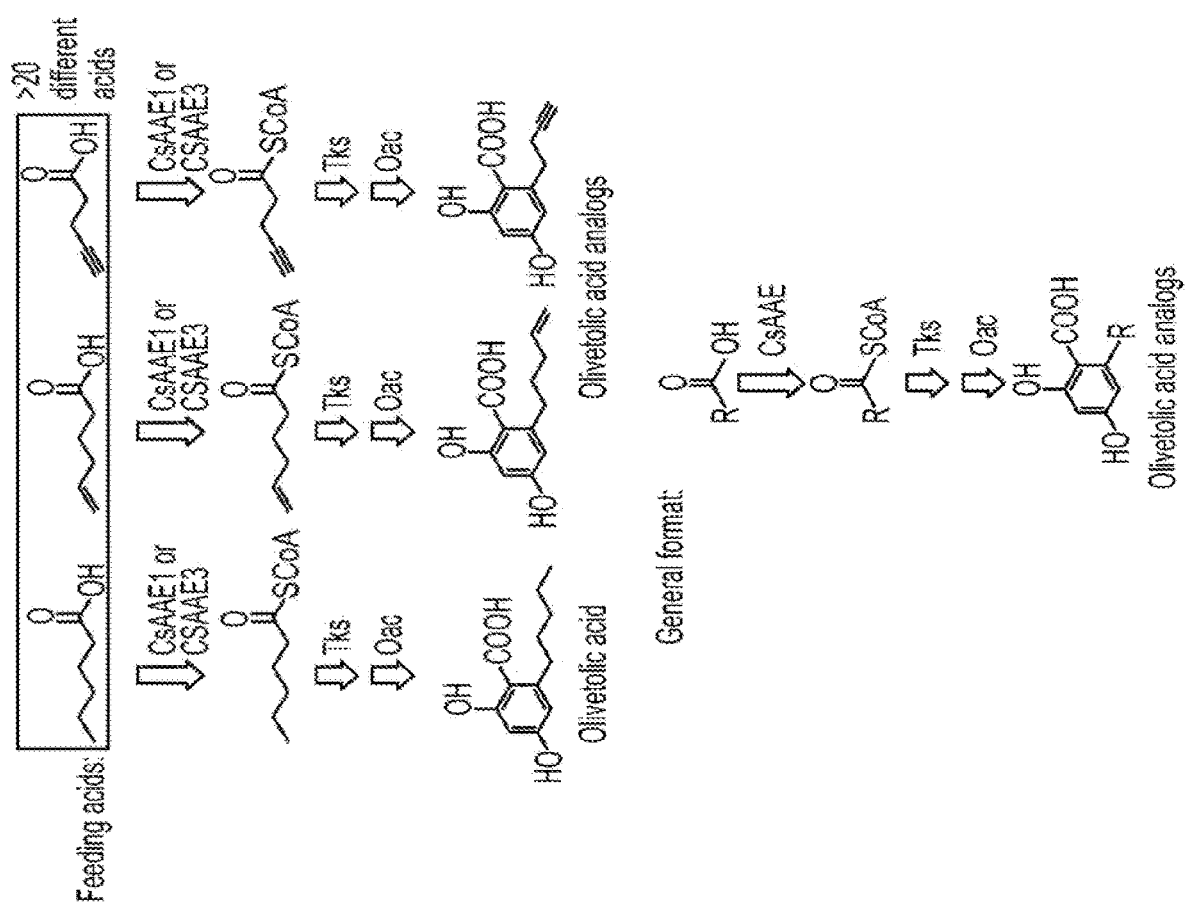

The nucleic acids disclosed herein may include those encoding a polypeptide having at least one activity of a polypeptide present in the cannabinoid biosynthetic pathway, such as a GOT polypeptide (e.g., a CsPT4 polypeptide), responsible for the biosynthesis of the cannabinoid CBGA; a tetraketide synthase (TKS) polypeptide; an olivetolic acid cyclase (OAC) polypeptide; and a CBDA or THCA synthase polypeptide (see FIGS. 1 and 11). Nucleic acids disclosed herein may also include those encoding a polypeptide having at least one activity of a polypeptide involved in the synthesis of cannabinoid precursors. These polypeptides include, but are not limited to, polypeptides having at least one activity of a polypeptide present in the mevalonate pathway; polypeptides that generate acyl-CoA compounds or acyl-CoA compound derivatives (e.g., an acyl-activating enzyme polypeptide, a fatty acyl-CoA synthetase polypeptide, or a fatty acyl-CoA ligase polypeptide); polypeptides that generate GPP; polypeptides that generate malonyl-CoA; polypeptides that condense two molecules of acetyl-CoA to generate acetoacetyl-CoA, or pyruvate decarboxylase polypeptides (see FIGS. 1 and 11).

The disclosure also provides for generation of cannabinoid precursor derivatives or cannabinoid derivatives, as well as cannabinoids or precursors thereof, with polypeptides that generate acyl-CoA compounds or acyl-CoA compound derivatives. In certain such embodiments, genetically modified host cells disclosed herein are modified with one or more heterologous nucleic acids encoding a polypeptide that generates acyl-CoA compounds or acyl-CoA compound derivatives. These polypeptides may permit production of hexanoyl-CoA, acyl-CoA compounds, derivatives of hexanoyl-CoA, or derivatives of acyl-CoA compounds. In some embodiments, hexanoic acid or carboxylic acids other than hexanoic acid are fed to genetically modified host cells expressing a polypeptide that generates acyl-CoA compounds or acyl-CoA compound derivatives (e.g., are present in the culture medium in which the cells are grown) to generate hexanoyl-CoA, acyl-CoA compounds, derivatives of hexanoyl-CoA, or derivatives of acyl-CoA compounds. These compounds are then converted to cannabinoid derivatives or cannabinoid precursor derivatives, as well as cannabinoids or precursors thereof, via one or more polypeptides having at least one activity of a polypeptide present in the cannabinoid biosynthetic pathway or involved in the synthesis of cannabinoid precursors (see FIGS. 1 and 11).

Surprisingly, it was found that polypeptides that generate acyl-CoA compounds or acyl-CoA compound derivatives, as well as many polypeptides having at least one activity of a polypeptide present in the cannabinoid biosynthetic pathway, such as TKS polypeptides, OAC polypeptides, GOT polypeptides (e.g., a CsPT4 polypeptide), and CBDA or THCA synthase polypeptides, have broad substrate specificity. This broad substrate specificity permits generation of not only cannabinoids and cannabinoid precursors, but also cannabinoid derivatives and cannabinoid precursor derivatives that are not naturally occurring, both within a genetically modified host cell or in a cell-free reaction mixture comprising one or more of the polypeptides disclosed herein. Because of this broad substrate specificity, hexanoyl-CoA, acyl-CoA compounds, derivatives of hexanoyl-CoA, or derivatives of acyl-CoA compounds produced in genetically modified host cells by polypeptides that generate acyl-CoA compounds or acyl-CoA compound derivatives can be utilized by TKS and OAC polypeptides to make olivetolic acid or derivatives thereof. The olivetolic acid or derivatives thereof can then be utilized by a GOT polypeptide to afford cannabinoids or cannabinoid derivatives. Alternatively, olivetolic acid or derivatives thereof can be fed to genetically modified host cells comprising a GOT polypeptide to afford cannabinoids or cannabinoid derivatives. These cannabinoids or cannabinoid derivatives can then be converted to THCA or CDBA, or derivatives thereof, via a CBDA or THCA synthase polypeptide.

Besides allowing for the production of desired cannabinoids, cannabinoid derivatives, cannabinoid precursors, or cannabinoid precursor derivatives, the present disclosure provides a more reliable and economical process than agriculture-based production. Microbial fermentations can be completed in days versus the months necessary for an agricultural crop, are not affected by climate variation or soil contamination (e.g., by heavy metals), and can produce pure products at high titer.

The present disclosure also provides a platform for the economical production of cannabinoid precursors, or derivatives thereof, and high-value cannabinoids including THC and CBD, as well as derivatives thereof. It also provides for the production of different cannabinoids, cannabinoid derivatives, cannabinoid precursors, or cannabinoid precursor derivatives for which no viable method of production exists.

Additionally, the disclosure provides methods, genetically modified host cells, polypeptides, and nucleic acids encoding said polypeptides to produce cannabinoids, cannabinoid derivatives, cannabinoid precursors, or cannabinoid precursor derivatives in vivo or in vitro from simple precursors. Nucleic acids disclosed herein encoding one or more polypeptides disclosed herein can be introduced into microorganisms (e.g., genetically modified host cells), resulting in expression or overexpression of the one or more polypeptides, which can then be utilized in vitro or in vivo for the production of cannabinoids, cannabinoid derivatives, cannabinoid precursors, or cannabinoid precursor derivatives. In some embodiments, the in vitro methods are cell-free.

To produce cannabinoids, cannabinoid derivatives, cannabinoid precursors, or cannabinoid precursor derivatives, and create biosynthetic pathways within genetically modified host cells, the genetically modified host cells may express or overexpress combinations of the heterologous nucleic acids disclosed herein encoding polypeptides disclosed herein.

Cannabinoid Biosynthesis

Nucleic acids encoding polypeptides having at least one activity of a polypeptide present in the cannabinoid biosynthesis pathway can be useful in the methods and genetically modified host cells disclosed herein for the synthesis of cannabinoids, cannabinoid precursors, cannabinoid derivatives, or cannabinoid precursor derivatives.

In *Cannabis*, cannabinoids are produced from the common metabolite precursors geranylpyrophosphate (GPP) and hexanoyl-CoA by the action of three polypeptides so far only identified in *Cannabis*. Hexanoyl-CoA and malonyl-CoA are combined to afford a 12-carbon tetraketide intermediate by a TKS polypeptide. This tetraketide intermediate is then cyclized by an OAC polypeptide to produce olivetolic acid. Olivetolic acid is then prenylated with the common isoprenoid precursor GPP by a GOT polypeptide (e.g., a CsPT4 polypeptide) to produce CBGA, the cannabinoid also known as the "mother cannabinoid." Different synthase polypeptides then convert CBGA into other cannabinoids, e.g., a THCA synthase polypeptide produces THCA, a CBDA synthase polypeptide produces CBDA, etc. In the presence of heat or light, the acidic cannabinoids can undergo decarboxylation, e.g., THCA producing THC or CBDA producing CBD.

GPP and hexanoyl-CoA can be generated through several pathways (see FIGS. 1 and 11). One or more nucleic acids encoding one or more polypeptides having at least one activity of a polypeptide present in these pathways can be useful in the methods and genetically modified host cells for the synthesis of cannabinoids, cannabinoid precursors, cannabinoid derivatives, or cannabinoid precursor derivatives.

Polypeptides that generate GPP or are part of a biosynthetic pathway that generates GPP may be one or more polypeptides having at least one activity of a polypeptide present in the mevalonate (MEV) pathway. The term "mevalonate pathway" or "MEV pathway," as used herein, may refer to the biosynthetic pathway that converts acetyl-CoA to isopentenyl pyrophosphate (IPP) and dimethylallyl pyrophosphate (DMAPP). The mevalonate pathway comprises polypeptides that catalyze the following steps: (a) condensing two molecules of acetyl-CoA to generate acetoacetyl-CoA (e.g., by action of an acetoacetyl-CoA thiolase polypeptide); (b) condensing acetoacetyl-CoA with acetyl-CoA to form hydroxymethylglutaryl-CoA (HMG-CoA) (e.g., by action of a HMG-CoA synthase (HMGS) polypeptide); (c) converting HMG-CoA to mevalonate (e.g., by action of a HMG-CoA reductase (HMGR) polypeptide); (d) phosphorylating mevalonate to mevalonate 5-phosphate (e.g., by action of a mevalonate kinase (MK) polypeptide); (e) converting mevalonate 5-phosphate to mevalonate 5-pyrophosphate (e.g., by action of a phosphomevalonate kinase (PMK) polypeptide); (f) converting mevalonate 5-pyrophosphate to isopentenyl pyrophosphate (e.g., by action of a mevalonate pyrophosphate decarboxylase (MVD) polypeptide); and (g) converting isopentenyl pyrophosphate (IPP) to dimethylallyl pyrophosphate (DMAPP) (e.g., by action of an isopentenyl pyrophosphate isomerase (IDI) polypeptide) (FIGS. 1 and 11). A geranyl diphosphate synthase (GPPS) polypeptide then acts on IPP and/or DMAPP to generate GPP. Additionally, polypeptides that generate GPP or are part of a biosynthetic pathway that generates GPP may be one or more polypeptides having at least one activity of a polypeptide present in the deoxyxylulose-5-phosphate (DXP) pathway, instead of those of the MEV pathway (FIG. 1).

Polypeptides that generate hexanoyl-CoA may include polypeptides that generate acyl-CoA compounds or acyl-CoA compound derivatives (e.g., a hexanoyl-CoA synthase (HCS) polypeptide, an acyl-activating enzyme polypeptide, a fatty acyl-CoA synthetase polypeptide, or a fatty acyl-CoA ligase polypeptide). Hexanoyl-CoA may also be generated through pathways comprising one or more polypeptides that generate malonyl-CoA, such as an acetyl-CoA carboxylase (ACC) polypeptide. Additionally, hexanoyl-CoA may be generated with one or more polypeptides that are part of a biosynthetic pathway that produces hexanoyl-CoA, including, but not limited to: a malonyl CoA-acyl carrier protein transacylase (MCT1) polypeptide, a PaaH1 polypeptide, a Crt polypeptide, a Ter polypeptide, and a BktB polypeptide; a MCT1 polypeptide, a PhaB polypeptide, a PhaJ polypeptide, a Ter polypeptide, and a BktB polypeptide; a short chain fatty acyl-CoA thioesterase (SCFA-TE) polypeptide; or a fatty acid synthase (FAS) polypeptide (see FIGS. 1 and 11). Hexanoyl CoA derivatives, acyl-CoA compounds, or acyl-CoA compound derivatives may also be formed via such pathways and polypeptides.

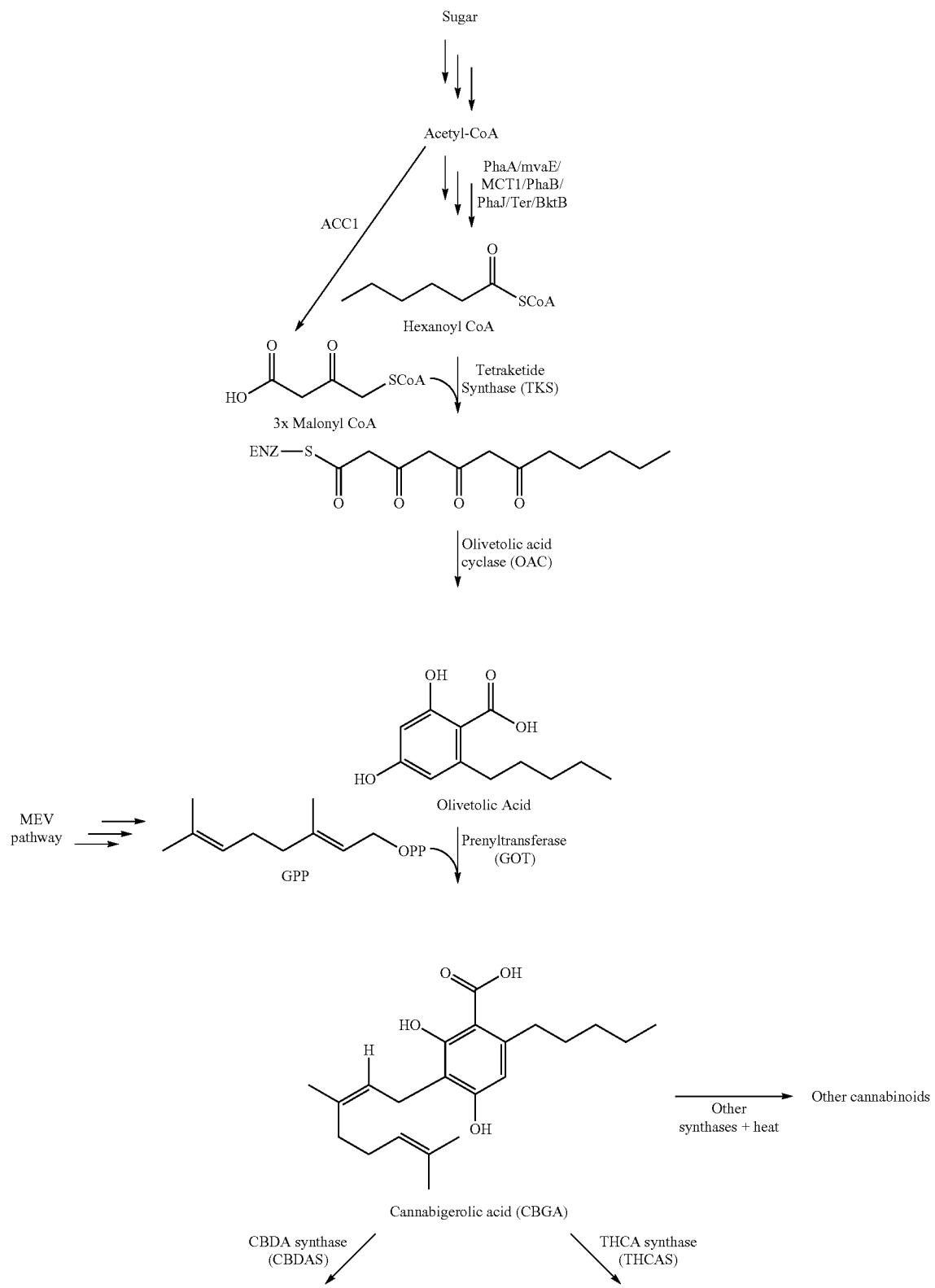

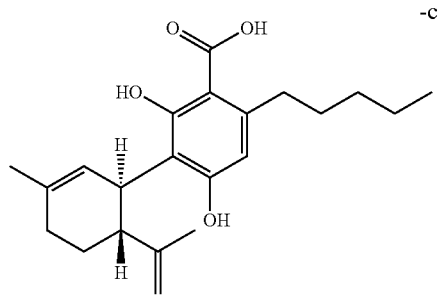

Cannabidiolic acid/CBDA

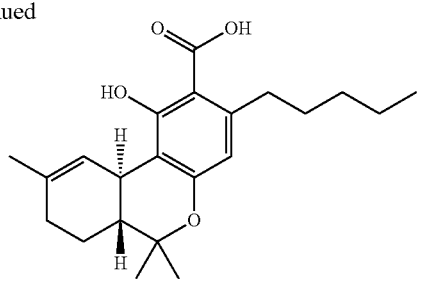

Tetrahydrocannabinolic acid/THCA

↓ Heat

↓ Heat

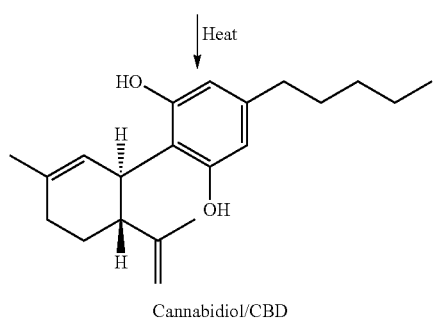

Cannabidiol/CBD

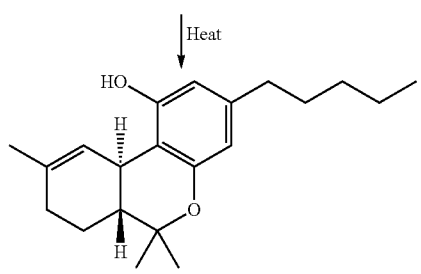

Tetrahydrocannabinol/Dronobinol/Marinol/THC

GPP and hexanoyl-CoA may also be generated through pathways comprising polypeptides that condense two molecules of acetyl-CoA to generate acetoacetyl-CoA and pyruvate decarboxylase polypeptides that generate acetyl-CoA from pyruvate (see FIGS. 1 and 11). Hexanoyl CoA derivatives, acyl-CoA compounds, or acyl-CoA compound derivatives may also be formed via such pathways.

General Information

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature: "*Molecular Cloning: A Laboratory Manual*," second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*," (Mullis et al., eds., 1994). Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

"Cannabinoid" or "cannabinoid compound" as used herein may refer to a member of a class of unique meroterpenoids found until now only in *Cannabis sativa*. Cannabinoids may include, but are not limited to, cannabichromene (CBC) type (e.g. cannabichromenic acid), cannabigerol (CBG) type (e.g. cannabigerolic acid), cannabidiol (CBD) type (e.g. cannabidiolic acid), $\Delta^9$-trans-tetrahydrocannabinol ($\Delta^9$-THC) type (e.g. $\Delta^9$-tetrahydrocannabinolic acid), $\Delta^8$-trans-tetrahydrocannabinol ($\Delta^8$-THC) type, cannabicyclol (CBL) type, cannabielsoin (CBE) type, cannabinol (CBN) type, cannabinodiol (CBND) type, cannabitriol (CBT) type, cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CBD), cannabidiol monomethylether (CBDM), cannabidiol-$C_4$ (CBD-$C_4$), cannabidivarinic acid (CBDVA), cannabidivarin (CBDV), cannabidiorcol (CBD-$C_1$), $\Delta^9$-tetrahydrocannabinolic acid A (THCA-A), $\Delta^9$-tetrahydrocannabinolic acid B (THCA-B), $\Delta^9$-tetrahydrocannabinol (THC), $\Delta^9$-tetrahydrocannabinolic acid-$C_4$ (THCA-$C_4$), $\Delta^9$-tetrahydrocannabinol-$C_4$ (THC-$C_4$), $\Delta^9$-tetrahydrocannabivarinic acid (THCVA), $\Delta^9$-tetrahydrocannabivarin (THCV), $\Delta^9$-tetrahydrocannabiorcolic acid (THCA-$C_1$), $\Delta^9$-tetrahydrocannabiorcol (THC-$C_1$), $\Delta^7$-cis-iso-tetrahydrocannabivarin, $\Delta^8$-tetrahydrocannabinolic acid ($\Delta^8$-THCA), $\Delta^8$-tetrahydrocannabinol ($\Delta^8$-THC), cannabicyclolic acid (CBLA), cannabicyclol (CBL), cannabicyclovarin (CBLV), cannabielsoic acid A (CBEA-A), cannabielsoic acid B (CBEA-B), cannabielsoin (CBE), cannabielsoinic acid, cannabicitranic acid, cannabinolic acid (CBNA), cannabinol (CBN), cannabinol methylether (CBNM), cannabinol-$C_4$, (CBN-$C_4$), cannabivarin (CBV), cannabinol-$C_2$ (CNB-$C_2$), cannabiorcol (CBN-$C_1$), cannabinodiol (CBND), cannabinodivarin (CBVD), cannabitriol (CBT), 10-ethyoxy-9-hydroxy-delta-6a-tetrahydrocannabinol, 8,9-dihydroxyl-delta-6a-tetrahydrocannabinol, cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5, 6-tetrahydro-7-hydroxy-alpha-alpha-2-trimethyl-9-n-propyl-2,6-methano-2H-1-benzoxocin-5-methanol (OH-iso-HHCV), cannabiripsol (CBR), and trihydroxy-delta-9-tetrahydrocannabinol (triOH-THC).

"Cannabinoid precursor" as used herein may refer to any intermediate present in the cannabinoid biosynthetic pathway before the production of the "mother cannabinoid," cannabigerolic acid (CBGA). Cannabinoid precursors may include, but are not limited to, GPP, olivetolic acid, hexanoyl-CoA, pyruvate, acetoacetyl-CoA, butyryl-CoA, acetyl-CoA, HMG-CoA, mevalonate, mevalonate-5-phosphate, mevalonate diphosphate, and malonyl-CoA.

An acyl-CoA compound as detailed herein may include compounds with the following structure:

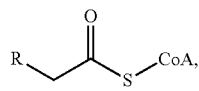

wherein R is a fatty acid side chain optionally comprising one or more functional and/or reactive groups as disclosed herein (i.e., an acyl-CoA compound derivative).

As used herein, a hexanoyl CoA derivative, an acyl-CoA compound derivative, a cannabinoid derivative, or a cannabinoid precursor derivative (e.g., an olivetolic acid derivative) is produced by a genetically modified host cell disclosed herein or in a cell-free reaction mixture comprising one or more of the polypeptides disclosed herein and may refer to hexanoyl CoA, an acyl-CoA compound, a cannabinoid, or a cannabinoid precursor (e.g., olivetolic acid) comprising one or more functional and/or reactive groups. Functional groups may include, but are not limited to, azido, halo (e.g., chloride, bromide, iodide, fluorine), methyl, alkyl (including branched and linear alkyl groups), alkynyl, alkenyl, methoxy, alkoxy, acetyl, amino, carboxyl, carbonyl, oxo, ester, hydroxyl, thio, cyano, aryl, heteroaryl, cycloalkyl, cycloalkenyl, cycloalkylalkenyl, cycloalkylalkynyl, cycloalkenylalkyl, cycloalkenylalkenyl, cycloalkenylalkynyl, heterocyclylalkenyl, heterocyclylalkynyl, heteroarylalkenyl, heteroarylalkynyl, arylalkenyl, arylalkynyl, heterocyclyl, spirocyclyl, heterospirocyclyl, thioalkyl, sulfone, sulfonyl, sulfoxide, amido, alkylamino, dialkylamino, arylamino, alkylarylamino, diarylamino, N-oxide, imide, enamine, imine, oxime, hydrazone, nitrile, aralkyl, cycloalkylalkyl, haloalkyl, heterocyclylalkyl, heteroarylalkyl, nitro, thioxo, and the like. See, e.g., FIGS. 12 and 13. Suitable reactive groups may include, but are not necessarily limited to, azide, carboxyl, carbonyl, amine, (e.g., alkyl amine (e.g., lower alkyl amine), aryl amine), halide, ester (e.g., alkyl ester (e.g., lower alkyl ester, benzyl ester), aryl ester, substituted aryl ester), cyano, thioester, thioether, sulfonyl halide, alcohol, thiol, succinimidyl ester, isothiocyanate, iodoacetamide, maleimide, hydrazine, alkynyl, alkenyl, and the like. A reactive group may facilitate covalent attachment of a molecule of interest. Suitable molecules of interest may include, but are not limited to, a detectable label; imaging agents; a toxin (including cytotoxins); a linker; a peptide; a drug (e.g., small molecule drugs); a member of a specific binding pair; an epitope tag; ligands for binding by a target receptor; tags to aid in purification; molecules that increase solubility; molecules that enhance bioavailability; molecules that increase in vivo half-life; molecules that target to a particular cell type; molecules that target to a particular tissue; molecules that provide for crossing the blood-brain barrier; molecules to facilitate selective attachment to a surface; and the like. Functional and reactive groups may be optionally substituted with one or more additional functional or reactive groups.

A cannabinoid derivative or cannabinoid precursor derivative produced by a genetically modified host cell disclosed herein or in a cell-free reaction mixture comprising one or more of the polypeptides disclosed herein may also refer a naturally-occurring cannabinoid or naturally-occurring cannabinoid precursor lacking one or more chemical moieties. Such chemical moieties may include, but are not limited to, methyl, alkyl, alkenyl, methoxy, alkoxy, acetyl, carboxyl, carbonyl, oxo, ester, hydroxyl, aryl, heteroaryl, cycloalkyl, cycloalkenyl, cycloalkylalkenyl, cycloalkenylalkyl, cycloalkenylalkenyl, heterocyclylalkenyl, heteroarylalkenyl, arylalkenyl, heterocyclyl, aralkyl, cycloalkylalkyl, heterocyclylalkyl, heteroarylalkyl, and the like. In some embodiments, a cannabinoid derivative or cannabinoid precursor derivative lacking one or more chemical moieties found in a naturally-occurring cannabinoid or naturally-occurring cannabinoid precursor, and produced by a genetically modified host cell disclosed herein or in a cell-free reaction mixture comprising one or more of the polypeptides disclosed herein, may also comprise one or more of any of the functional and/or reactive groups described herein. Functional and reactive groups may be optionally substituted with one or more additional functional or reactive groups.

The term "nucleic acid" used herein, may refer to a polymeric form of nucleotides of any length, either ribonucleotides or deoxynucleotides. Thus, this term may include, but is not limited to, single-, double-, or multi-stranded DNA or RNA, genomic DNA, cDNA, genes, synthetic DNA or RNA, DNA-RNA hybrids, or a polymer comprising purine and pyrimidine bases or other naturally-occurring, chemically or biochemically modified, non-naturally-occurring, or derivatized nucleotide bases.

The terms "peptide," "polypeptide," and "protein" may be used interchangeably herein, and may refer to a polymeric form of amino acids of any length, which can include coded and non-coded amino acids, chemically or biochemically modified or derivatized amino acids, full-length polypeptides, fragments of polypeptides, or polypeptides having modified peptide backbones. The polypeptides disclosed herein may be presented as modified or engineered forms, including truncated or fusion forms, retaining the recited activities. The polypeptides disclosed herein may also be variants differing from a specifically recited "reference" polypeptide (e.g., a wild-type polypeptide) by amino acid insertions, deletions, mutations, and/or substitutions, but retains an activity that is substantially similar to the reference polypeptide.

As used herein, the term "heterologous" may refer to what is not normally found in nature. The term "heterologous nucleotide sequence" may refer to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus. The term "heterologous enzyme" or "heterologous polypeptide" may refer to an enzyme or polypeptide that is not normally found in a given cell in nature. The term encompasses an enzyme or polypeptide that is: (a) exogenous to a given cell (i.e., encoded by a nucleic acid that is not naturally present in the host cell or not naturally present in a given context in the host cell); and (b) naturally found in the host cell (e.g., the enzyme or polypeptide is encoded by a nucleic acid that is endogenous to the cell) but that is produced in an unnatural amount (e.g., greater or lesser than that naturally found) in the host cell. As such, a heterologous nucleic acid may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

"Operably linked" may refer to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

"Isolated" may refer to polypeptides or nucleic acids that are substantially or essentially free from components that normally accompany them in their natural state. An isolated polypeptide or nucleic acid may be other than in the form or setting in which it is found in nature. Isolated polypeptides and nucleic acids therefore may be distinguished from the polypeptides and nucleic acids as they exist in natural cells. An isolated nucleic acid or polypeptide may further be purified from one or more other components in a mixture with the isolated nucleic acid or polypeptide, if such components are present.

A "genetically modified host cell" (also referred to as a "recombinant host cell") is a host cell into which has been introduced a heterologous nucleic acid, e.g., an expression vector or construct. For example, a prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

As used herein, a "cell-free system" may refer to a cell lysate, cell extract or other preparation in which substantially all of the cells in the preparation have been disrupted or otherwise processed so that all or selected cellular components, e.g., organelles, proteins, nucleic acids, the cell membrane itself (or fragments or components thereof), or the like, are released from the cell or resuspended into an appropriate medium and/or purified from the cellular milieu. Cell-free systems can include reaction mixtures prepared from purified or isolated polypeptides and suitable reagents and buffers.

In some embodiments, conservative substitutions may be made in the amino acid sequence of a polypeptide without disrupting the three-dimensional structure or function of the polypeptide. Conservative substitutions may be accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins. The term "conservative amino acid substitution" may refer to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/ebi.ac.uk/Tools/msa/muscle/mafft.cbrc.jp/alignment/software/. See, e.g., Altschul et al. (1990), J. Mol. Biol. 215:403-10.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" may include plural referents unless the context clearly dictates otherwise. Thus, for example, reference to "a cannabinoid compound" or "cannabinoid" may include a plurality of such compounds and reference to "the genetically modified host cell" may include reference to one or more genetically modified host cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Geranyl Pyrophosphate:Olivetolic Acid Geranyltransferase Polypeptides and Nucleic Acids Encoding Said Polypeptides As described herein, novel polypeptides for catalyzing production of cannabigerolic acid from GPP and olivetolic acid have been identified and characterized. Surprisingly, these new polypeptides of the present disclosure can catalyze production of cannabigerolic acid from GPP and olivetolic acid in an amount at least ten times higher than previously discovered *Cannabis* polypeptides that catalyze production of cannabigerolic acid from GPP and olivetolic acid (see, for example, U.S. Patent Application Pub. No. US20120144523 and the GOT polypeptide, CsPT1, disclosed therein; SEQ ID NO:82 herein). The new polypeptides of the present disclosure that catalyze production of cannabigerolic acid from GPP and olivetolic acid are new geranyl pyrophosphate:olivetolic acid geranyltransferase (GOT) polypeptides, the CsPT4 polypeptide and truncated versions thereof. These new polypeptides of the present disclosure can generate cannabinoids and cannabinoid derivatives in vivo (e.g., within a genetically modified host cell) and in vitro (e.g., cell-free).

These new GOT polypeptides, as well as nucleic acids encoding said GOT polypeptides, are useful in the methods and genetically modified host cells of the disclosure for producing cannabinoids or cannabinoid derivatives. In some embodiments, the GOT polypeptide of the disclosure cannot catalyze production of 5-geranyl olivetolic acid.

The CsPT4 polypeptide is remarkably different in sequence and activity than the previously identified CsPT1 polypeptide, also a GOT polypeptide. The CsPT1 polypeptide has only 57% homology to the CsPT4 polypeptide. Further, unlike the CsPT1 polypeptide, the activity of the CsPT4 polypeptide, or a truncated version thereof, can be readily reconstituted in a genetically modified host cell of the disclosure, permitting the production of cannabinoids or cannabinoid derivatives by the genetically modified host cells. A truncated version of the CsPT4 polypeptide, the CsPT4t polypeptide, lacking N-terminal amino acids 1-76 of the amino acid sequence set forth in SEQ ID NO:110 (the full-length CsPT4 polypeptide amino acid sequence) was found to readily catalyze the production of cannabigerolic acid from GPP and olivetolic acid, with activity similar to that of the full-length CsPT4 polypeptide. However, other truncated versions of the CsPT4 polypeptide lacking N-terminal amino acids 1-112 (SEQ ID NO:211), 1-131 (SEQ ID NO:213), 1-142 (SEQ ID NO:215), 1-166 (SEQ ID NO:217), or 1-186 (SEQ ID NO:219) were unable to catalyze formation of cannabigerolic acid from GPP and olivetolic acid, suggesting that these truncation polypeptides lacked residues required for catalytic activity.

Surprisingly, it was found that the CsPT4 polypeptide, or a truncated version thereof, has broad substrate specificity, permitting generation of not only cannabinoids, but also cannabinoid derivatives. Because of this broad specificity, olivetolic acid or derivatives thereof produced in genetically modified host cells disclosed herein by TKS and OAC polypeptides can be utilized by a CsPT4 polypeptide, or a truncated version thereof, to afford cannabinoids and cannabinoid derivatives. Alternatively, olivetolic acid or derivatives thereof can be fed to genetically modified host cells disclosed herein comprising a CsPT4 polypeptide, or a truncated version thereof, to afford cannabinoids and cannabinoid derivatives. The cannabinoids and cannabinoid derivatives can then be converted to other cannabinoids or cannabinoid derivatives via a CBDA or THCA synthase polypeptide.

Isolated or Purified Nucleic Acids Encoding GOT Polypeptides

Some embodiments of the disclosure relate to an isolated or purified nucleic acid encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82.

Some embodiments of the disclosure relate to an isolated or purified nucleic acid encoding a GOT polypeptide, a truncated CsPT4 polypeptide (CsPT4t polypeptide, lacking N-terminal amino acids 1-76 of the amino acid sequence set forth in SEQ ID NO:110), comprising the amino acid sequence set forth in SEQ ID NO:100. Some embodiments of the disclosure relate to an isolated or purified nucleic acid encoding a GOT polypeptide, a CsPT4t polypeptide, comprising the amino acid sequence set forth in SEQ ID NO:100, or a conservatively substituted amino acid sequence thereof. Some embodiments of the disclosure relate to an isolated or purified nucleic acid encoding a GOT polypeptide, a CsPT4t polypeptide, comprising an amino acid sequence having at least 65%, at least 70%, or at least 75% amino acid sequence identity to SEQ ID NO:100. Some embodiments of the disclosure relate to an isolated or purified nucleic acid encoding a GOT polypeptide, a CsPT4t polypeptide, comprising an amino acid sequence having at least 80%, at least 81%, at least 82%, at least 83%, or at least 84% amino acid sequence identity to SEQ ID NO:100. Some embodiments of the disclosure relate to an isolated or purified nucleic acid encoding a GOT polypeptide, a CsPT4t polypeptide, comprising an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100. Some embodiments of the disclosure relate to an isolated or purified nucleic acid encoding a GOT polypeptide, a CsPT4t polypeptide, comprising an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100.

Some embodiments of the disclosure relate to an isolated or purified nucleic acid encoding a GOT polypeptide, a CsPT4t polypeptide, comprising an amino acid sequence having at least 65% amino acid sequence identity to SEQ ID NO:100. Some embodiments of the disclosure relate to an isolated or purified nucleic acid encoding a GOT polypeptide, a CsPT4t polypeptide, comprising an amino acid sequence having at least 75% amino acid sequence identity to SEQ ID NO:100. Some embodiments of the disclosure relate to an isolated or purified nucleic acid encoding a GOT polypeptide, a CsPT4t polypeptide, comprising an amino acid sequence having at least 85% amino acid sequence identity to SEQ ID NO:100. Some embodiments of the disclosure relate to an isolated or purified nucleic acid encoding a GOT polypeptide, a CsPT4t polypeptide, comprising an amino acid sequence having at least 95% amino acid sequence identity to SEQ ID NO:100. Some embodiments of the disclosure relate to an isolated or purified nucleic acid encoding a GOT polypeptide, a CsPT4t polypeptide, comprising an amino acid sequence having at least 65% amino acid sequence identity to SEQ ID NO:100, or a conservatively substituted amino acid sequence thereof. Some embodiments of the disclosure relate to an isolated or purified nucleic acid encoding a GOT polypeptide, a CsPT4t polypeptide, comprising an amino acid sequence having at least 75% amino acid sequence identity to SEQ ID NO:100, or a conservatively substituted amino acid sequence thereof. Some embodiments of the disclosure relate to an isolated or purified nucleic acid encoding a GOT polypeptide, a CsPT4t polypeptide, comprising an amino acid sequence having at least 85% amino acid sequence identity to SEQ ID NO:100, or a conservatively substituted amino acid sequence thereof. Some embodiments of the disclosure relate to an isolated or purified nucleic acid encoding a GOT polypeptide, a CsPT4t polypeptide, comprising an amino acid sequence having at least 95% amino acid sequence identity to SEQ ID NO:100, or a conservatively substituted amino acid sequence thereof.

Some embodiments of the disclosure relate to an isolated or purified nucleic acid encoding a full-length GOT polypeptide, a CsPT4 polypeptide, comprising the amino acid sequence set forth in SEQ ID NO:110. Some embodiments of the disclosure relate to an isolated or purified nucleic acid encoding a GOT polypeptide, a CsPT4 polypeptide, comprising the amino acid sequence set forth in SEQ ID NO:110, or a conservatively substituted amino acid sequence thereof. Some embodiments of the disclosure relate to an isolated or purified nucleic acid encoding a GOT polypeptide, a CsPT4 polypeptide, comprising an amino acid sequence having at least 65%, at least 70%, or at least 75% amino acid sequence identity to SEQ ID NO:110. Some embodiments of the disclosure relate to an isolated or purified nucleic acid encoding a GOT polypeptide, a CsPT4 polypeptide, comprising an amino acid sequence having at least 80%, at least 81%, at least 82%, at least 83%, or at least 84% amino acid sequence identity to SEQ ID NO:110. Some embodiments of the disclosure relate to an isolated or purified nucleic acid encoding a GOT polypeptide, a CsPT4 polypeptide, comprising an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110. Some embodiments of the disclosure relate to an isolated or purified nucleic acid encoding a GOT polypeptide, a CsPT4 polypeptide, comprising an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110.

Some embodiments of the disclosure relate to an isolated or purified nucleic acid encoding a GOT polypeptide, a CsPT4 polypeptide, comprising an amino acid sequence having at least 65% amino acid sequence identity to SEQ ID NO:110. Some embodiments of the disclosure relate to an isolated or purified nucleic acid encoding a GOT polypeptide, a CsPT4 polypeptide, comprising an amino acid sequence having at least 75% amino acid sequence identity to SEQ ID NO:110. Some embodiments of the disclosure relate to an isolated or purified nucleic acid encoding a GOT polypeptide, a CsPT4 polypeptide, comprising an amino acid sequence having at least 85% amino acid sequence identity to SEQ ID NO:110. Some embodiments of the disclosure relate to an isolated or purified nucleic acid encoding a GOT polypeptide, a CsPT4 polypeptide, comprising an amino acid sequence having at least 95% amino acid sequence identity to SEQ ID NO:110. Some embodiments of the disclosure relate to an isolated or purified nucleic acid encoding a GOT polypeptide, a CsPT4 polypeptide, comprising an amino acid sequence having at least 65% amino acid sequence identity to SEQ ID NO:110, or a conservatively substituted amino acid sequence thereof. Some embodiments of the disclosure relate to an isolated or purified nucleic acid encoding a GOT polypeptide, a CsPT4 polypeptide, comprising an amino acid sequence having at least 75% amino acid sequence identity to SEQ ID NO:110, or a conservatively substituted amino acid sequence thereof. Some embodiments of the disclosure relate to an isolated or purified nucleic acid encoding a GOT polypeptide, a CsPT4 polypeptide, comprising an amino acid sequence having at least 85% amino acid sequence identity to SEQ ID NO:110, or a conservatively substituted amino acid sequence thereof. Some embodiments of the disclosure relate to an isolated or purified nucleic acid encoding a GOT polypeptide, a CsPT4 polypeptide, comprising an amino acid sequence having at least 95% amino acid sequence identity to SEQ ID NO:110, or a conservatively substituted amino acid sequence thereof.

Some embodiments of the disclosure relate to an isolated or purified CsPT4 nucleic acid comprising the nucleotide sequence set forth in SEQ ID NO:111. Some embodiments of the disclosure relate to an isolated or purified CsPT4 nucleic acid comprising the nucleotide sequence set forth in SEQ ID NO:111, or a codon degenerate nucleotide sequence thereof. Some embodiments of the disclosure relate to an isolated or purified CsPT4 nucleic acid comprising a nucleotide sequence having at least 80%, at least 81%, at least 82%, at least 83%, or at least 84% sequence identity to SEQ ID NO:111. Some embodiments of the disclosure relate to an isolated or purified CsPT4 nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:111. Some embodiments of the disclosure relate to an isolated or purified CsPT4 nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:111.

Some embodiments of the disclosure relate to an isolated or purified CsPT4 nucleic acid comprising a nucleotide sequence having at least 85% sequence identity to SEQ ID NO:111. Some embodiments of the disclosure relate to an isolated or purified CsPT4 nucleic acid comprising a nucleotide sequence having at least 95% sequence identity to SEQ ID NO:111. Some embodiments of the disclosure relate to an isolated or purified CsPT4 nucleic acid comprising a nucleotide sequence having at least 85% sequence identity to SEQ ID NO:111, or a codon degenerate nucleotide sequence thereof. Some embodiments of the disclosure relate to an isolated or purified CsPT4 nucleic acid comprising a nucleotide sequence having at least 95% sequence identity to SEQ ID NO:111, or a codon degenerate nucleotide sequence thereof.

Some embodiments of the disclosure relate to an isolated or purified CsPT4 nucleic acid comprising the nucleotide sequence set forth in SEQ ID NO:225. Some embodiments of the disclosure relate to an isolated or purified CsPT4 nucleic acid comprising the nucleotide sequence set forth in SEQ ID NO:225, or a codon degenerate nucleotide sequence thereof. Some embodiments of the disclosure relate to an isolated or purified CsPT4 nucleic acid comprising a nucleotide sequence having at least 80%, at least 81%, at least 82%, at least 83%, or at least 84% sequence identity to SEQ ID NO:225. Some embodiments of the disclosure relate to an isolated or purified CsPT4 nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:225. Some embodiments of the disclosure relate to an isolated or purified CsPT4 nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:225.

Some embodiments of the disclosure relate to an isolated or purified CsPT4 nucleic acid comprising a nucleotide sequence having at least 85% sequence identity to SEQ ID NO:225. Some embodiments of the disclosure relate to an isolated or purified CsPT4 nucleic acid comprising a nucleotide sequence having at least 95% sequence identity to SEQ ID NO:225. Some embodiments of the disclosure relate to an isolated or purified CsPT4 nucleic acid comprising a nucleotide sequence having at least 85% sequence identity to SEQ ID NO:225, or a codon degenerate nucleotide sequence thereof. Some embodiments of the disclosure relate to an isolated or purified CsPT4 nucleic acid comprising a nucleotide sequence having at least 95% sequence identity to SEQ ID NO:225, or a codon degenerate nucleotide sequence thereof.

Some embodiments of the disclosure relate to an isolated or purified CsPT4t nucleic acid comprising the nucleotide sequence set forth in SEQ ID NO:224. Some embodiments of the disclosure relate to an isolated or purified CsPT4t nucleic acid comprising the nucleotide sequence set forth in SEQ ID NO:224, or a codon degenerate nucleotide sequence thereof. Some embodiments of the disclosure relate to an isolated or purified CsPT4t nucleic acid comprising a nucleotide sequence having at least 80%, at least 81%, at least 82%, at least 83%, or at least 84% sequence identity to SEQ ID NO:224. Some embodiments of the disclosure relate to an isolated or purified CsPT4t nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:224. Some embodiments of the disclosure relate to an isolated or purified CsPT4t nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:224.

Some embodiments of the disclosure relate to an isolated or purified CsPT4t nucleic acid comprising a nucleotide sequence having at least 85% sequence identity to SEQ ID NO:224. Some embodiments of the disclosure relate to an isolated or purified CsPT4t nucleic acid comprising a nucleotide sequence having at least 95% sequence identity to SEQ ID NO:224. Some embodiments of the disclosure relate to an isolated or purified CsPT4t nucleic acid comprising a nucleotide sequence having at least 85% sequence identity to SEQ ID NO:224, or a codon degenerate nucleotide sequence thereof. Some embodiments of the disclosure relate to an isolated or purified CsPT4t nucleic acid comprising a nucleotide sequence having at least 95% sequence identity to SEQ ID NO:224, or a codon degenerate nucleotide sequence thereof.

Some embodiments of the disclosure relate to an isolated or purified CsPT4t nucleic acid comprising the nucleotide sequence set forth in SEQ ID NO:221. Some embodiments of the disclosure relate to an isolated or purified CsPT4t nucleic acid comprising the nucleotide sequence set forth in SEQ ID NO:221, or a codon degenerate nucleotide sequence thereof. Some embodiments of the disclosure relate to an isolated or purified CsPT4t nucleic acid comprising a nucleotide sequence having at least 80%, at least 81%, at least 82%, at least 83%, or at least 84% sequence identity to SEQ ID NO:221. Some embodiments of the disclosure relate to an isolated or purified CsPT4t nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:221. Some embodiments of the disclosure relate to an isolated or purified CsPT4t nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:221.

Some embodiments of the disclosure relate to an isolated or purified CsPT4t nucleic acid comprising a nucleotide sequence having at least 85% sequence identity to SEQ ID NO:221. Some embodiments of the disclosure relate to an isolated or purified CsPT4t nucleic acid comprising a nucleotide sequence having at least 95% sequence identity to SEQ ID NO:221. Some embodiments of the disclosure relate to an isolated or purified CsPT4t nucleic acid comprising a nucleotide sequence having at least 85% sequence identity to SEQ ID NO:221, or a codon degenerate nucleotide sequence thereof. Some embodiments of the disclosure relate to an isolated or purified CsPT4t nucleic acid comprising a nucleotide sequence having at least 95% sequence identity to SEQ ID NO:221, or a codon degenerate nucleotide sequence thereof.

Further included are nucleic acids that hybridize to the nucleic acids disclosed here. Hybridization conditions may be stringent in that hybridization will occur if there is at least a 90%, 95%, or 97% sequence identity with the nucleotide sequence present in the nucleic acid encoding the polypeptides disclosed herein. The stringent conditions may include those used for known Southern hybridizations such as, for example, incubation overnight at 42° C. in a solution having 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, following by washing the hybridization support in 0.1×SSC at about 65° C. Other known hybridization conditions are well known and are described in Sambrook et al., Molecular Cloning: A Laboratory Manual, Third Edition, Cold Spring Harbor, N.Y. (2001).

The length of the nucleic acids disclosed herein may depend on the intended use. For example, if the intended use is as a primer or probe, for example for PCR amplification or for screening a library, the length of the nucleic acid will be less than the full length sequence, for example, 15-50 nucleotides. In certain such embodiments, the primers or probes may be substantially identical to a highly conserved region of the nucleotide sequence or may be substantially identical to either the 5' or 3' end of the nucleotide sequence. In some cases, these primers or probes may use universal bases in some positions so as to be "substantially identical" but still provide flexibility in sequence recognition. It is of note that suitable primer and probe hybridization conditions are well known in the art. Also included are cDNA molecules of the disclosed nucleic acids.

Isolated or Purified GOT Polypeptides

Some embodiments of the disclosure relate to an isolated or purified GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82.

Some embodiments of the disclosure relate to an isolated or purified GOT polypeptide, a CsPT4t polypeptide, comprising the amino acid sequence set forth in SEQ ID NO:100. Some embodiments of the disclosure relate to an isolated or purified GOT polypeptide, a CsPT4t polypeptide, comprising the amino acid sequence set forth in SEQ ID NO:100, or a conservatively substituted amino acid sequence thereof. Some embodiments of the disclosure relate to an isolated or purified GOT polypeptide, a CsPT4t polypeptide, comprising an amino acid sequence having at least 65%, at least 70%, or at least 75% amino acid sequence identity to SEQ ID NO:100. Some embodiments of the disclosure relate to an isolated or purified GOT polypeptide, a CsPT4t polypeptide, comprising an amino acid sequence having at least 80%, at least 81%, at least 82%, at least 83%, or at least 84% amino acid sequence identity to SEQ ID NO:100. Some embodiments of the disclosure relate to an isolated or purified GOT polypeptide, a CsPT4t polypeptide, comprising an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100. Some embodiments of the disclosure relate to an isolated or purified GOT polypeptide, a CsPT4t polypeptide, comprising an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100.

Some embodiments of the disclosure relate to an isolated or purified GOT polypeptide, a CsPT4t polypeptide, comprising an amino acid sequence having at least 65% amino acid sequence identity to SEQ ID NO:100. Some embodiments of the disclosure relate to an isolated or purified GOT polypeptide, a CsPT4t polypeptide, comprising an amino acid sequence having at least 75% amino acid sequence identity to SEQ ID NO:100. Some embodiments of the disclosure relate to an isolated or purified GOT polypeptide, a CsPT4t polypeptide, comprising an amino acid sequence having at least 85% amino acid sequence identity to SEQ ID NO:100. Some embodiments of the disclosure relate to an isolated or purified GOT polypeptide, a CsPT4t polypeptide, comprising an amino acid sequence having at least 95% amino acid sequence identity to SEQ ID NO:100. Some embodiments of the disclosure relate to an isolated or purified GOT polypeptide, a CsPT4t polypeptide, comprising an amino acid sequence having at least 65% amino acid sequence identity to SEQ ID NO:100, or a conservatively substituted amino acid sequence thereof. Some embodiments of the disclosure relate to an isolated or purified GOT polypeptide, a CsPT4t polypeptide, comprising an amino acid sequence having at least 75% amino acid sequence identity to SEQ ID NO:100, or a conservatively substituted amino acid sequence thereof. Some embodiments of the disclosure relate to an isolated or purified GOT polypeptide, a CsPT4t polypeptide, comprising an amino acid sequence having at least 85% amino acid sequence identity to SEQ ID NO:100, or a conservatively substituted amino acid sequence thereof. Some embodiments of the disclosure relate to an isolated or purified GOT polypeptide, a CsPT4t polypeptide, comprising an amino acid sequence having at least 95% amino acid sequence identity to SEQ ID NO:100, or a conservatively substituted amino acid sequence thereof.

Some embodiments of the disclosure relate to an isolated or purified GOT polypeptide, a CsPT4 polypeptide, comprising the amino acid sequence set forth in SEQ ID NO:110. Some embodiments of the disclosure relate to an isolated or purified GOT polypeptide, a CsPT4 polypeptide, comprising the amino acid sequence set forth in SEQ ID NO:110, or a conservatively substituted amino acid sequence thereof. Some embodiments of the disclosure relate to an isolated or purified GOT polypeptide, a CsPT4 polypeptide, comprising an amino acid sequence having at least 65%, at least 70%, or at least 75% amino acid sequence identity to SEQ ID NO:110. Some embodiments of the disclosure relate to an isolated or purified GOT polypeptide, a CsPT4 polypeptide, comprising an amino acid sequence having at least 80%, at least 81%, at least 82%, at least 83%, or at least 84% amino acid sequence identity to SEQ ID NO:110. Some embodiments of the disclosure relate to an isolated or purified GOT polypeptide, a CsPT4 polypeptide, comprising an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110. Some embodiments of the disclosure relate to an isolated or purified GOT polypeptide, a CsPT4 polypeptide, comprising an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110.

Some embodiments of the disclosure relate to an isolated or purified GOT polypeptide, a CsPT4 polypeptide, comprising an amino acid sequence having at least 65% amino acid sequence identity to SEQ ID NO:110. Some embodiments of the disclosure relate to an isolated or purified GOT polypeptide, a CsPT4 polypeptide, comprising an amino acid sequence having at least 75% amino acid sequence identity to SEQ ID NO:110. Some embodiments of the disclosure relate to an isolated or purified GOT polypeptide, a CsPT4 polypeptide, comprising an amino acid sequence having at least 85% amino acid sequence identity to SEQ ID NO:110. Some embodiments of the disclosure relate to an isolated or purified GOT polypeptide, a CsPT4 polypeptide, comprising an amino acid sequence having at least 95% amino acid sequence identity to SEQ ID NO:110. Some embodiments of the disclosure relate to an isolated or purified GOT polypeptide, a CsPT4 polypeptide, comprising an amino acid sequence having at least 65% amino acid sequence identity to SEQ ID NO:110, or a conservatively substituted amino acid sequence thereof. Some embodiments of the disclosure relate to an isolated or purified GOT polypeptide, a CsPT4 polypeptide, comprising an amino acid sequence having at least 75% amino acid sequence identity to SEQ ID NO:110, or a conservatively substituted amino acid sequence thereof. Some embodiments of the disclosure relate to an isolated or purified GOT polypeptide, a CsPT4 polypeptide, comprising an amino acid sequence having at least 85% amino acid sequence identity to SEQ ID NO:110, or a conservatively substituted amino acid sequence thereof. Some embodiments of the disclosure relate to an isolated or purified GOT polypeptide, a CsPT4 polypeptide, comprising an amino acid sequence having at least 95% amino acid sequence identity to SEQ ID NO:110, or a conservatively substituted amino acid sequence thereof.

Vectors Comprising Nucleic Acids Encoding GOT Polypeptides

Some embodiments of the disclosure relate to a vector comprising one or more nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82.

Some embodiments of the disclosure relate to a vector comprising one or more nucleic acids encoding a GOT polypeptide, a CsPT4t polypeptide, comprising the amino acid sequence set forth in SEQ ID NO:100. Some embodiments of the disclosure relate to a vector comprising one or more nucleic acids encoding a GOT polypeptide, a CsPT4t polypeptide, comprising the amino acid sequence set forth in SEQ ID NO:100, or a conservatively substituted amino acid sequence thereof. Some embodiments of the disclosure relate to a vector comprising one or more nucleic acids encoding a GOT polypeptide, a CsPT4t polypeptide, comprising an amino acid sequence having at least 65%, at least 70%, or at least 75% amino acid sequence identity to SEQ ID NO:100. Some embodiments of the disclosure relate to a vector comprising one or more nucleic acids encoding a GOT polypeptide, a CsPT4t polypeptide, comprising an amino acid sequence having at least 80%, at least 81%, at least 82%, at least 83%, or at least 84% amino acid sequence identity to SEQ ID NO:100. Some embodiments of the disclosure relate to a vector comprising one or more nucleic acids encoding a GOT polypeptide, a CsPT4t polypeptide, comprising an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100. Some embodiments of the disclosure relate to a vector comprising one or more nucleic acids encoding a GOT polypeptide, a CsPT4t polypeptide, comprising an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100.

Some embodiments of the disclosure relate to a vector comprising one or more nucleic acids encoding a GOT polypeptide, a CsPT4t polypeptide, comprising an amino acid sequence having at least 65% amino acid sequence identity to SEQ ID NO:100. Some embodiments of the disclosure relate to a vector comprising one or more nucleic acids encoding a GOT polypeptide, a CsPT4t polypeptide, comprising an amino acid sequence having at least 75% amino acid sequence identity to SEQ ID NO:100. Some embodiments of the disclosure relate to a vector comprising one or more nucleic acids encoding a GOT polypeptide, a CsPT4t polypeptide, comprising an amino acid sequence having at least 85% amino acid sequence identity to SEQ ID NO:100. Some embodiments of the disclosure relate to a vector comprising one or more nucleic acids encoding a GOT polypeptide, a CsPT4t polypeptide, comprising an amino acid sequence having at least 95% amino acid sequence identity to SEQ ID NO:100. Some embodiments of the disclosure relate to a vector comprising one or more nucleic acids encoding a GOT polypeptide, a CsPT4t polypeptide, comprising an amino acid sequence having at least 65% amino acid sequence identity to SEQ ID NO:100, or a conservatively substituted amino acid sequence thereof. Some embodiments of the disclosure relate to a vector comprising one or more nucleic acids encoding a GOT polypeptide, a CsPT4t polypeptide, comprising an amino acid sequence having at least 75% amino acid sequence identity to SEQ ID NO:100, or a conservatively substituted amino acid sequence thereof. Some embodiments of the disclosure relate to a vector comprising one or more nucleic acids encoding a GOT polypeptide, a CsPT4t polypeptide, comprising an amino acid sequence having at least 85% amino acid sequence identity to SEQ ID NO:100, or a conservatively substituted amino acid sequence thereof. Some embodiments of the disclosure relate to a vector comprising one or more nucleic acids encoding a GOT polypeptide, a CsPT4t polypeptide, comprising an amino acid sequence having at least 95% amino acid sequence identity to SEQ ID NO:100, or a conservatively substituted amino acid sequence thereof.

Some embodiments of the disclosure relate to a vector comprising one or more nucleic acids encoding a GOT polypeptide, a CsPT4 polypeptide, comprising the amino acid sequence set forth in SEQ ID NO:110. Some embodiments of the disclosure relate to a vector comprising one or more nucleic acids encoding a GOT polypeptide, a CsPT4 polypeptide, comprising the amino acid sequence set forth in SEQ ID NO:110, or a conservatively substituted amino acid sequence thereof. Some embodiments of the disclosure relate to a vector comprising one or more nucleic acids encoding a GOT polypeptide, a CsPT4 polypeptide, comprising an amino acid sequence having at least 65%, at least 70%, or at least 75% amino acid sequence identity to SEQ ID NO:110. Some embodiments of the disclosure relate to a vector comprising one or more nucleic acids encoding a GOT polypeptide, a CsPT4 polypeptide, comprising an amino acid sequence having at least 80%, at least 81%, at least 82%, at least 83%, or at least 84% amino acid sequence identity to SEQ ID NO:110. Some embodiments of the disclosure relate to a vector comprising one or more nucleic acids encoding a GOT polypeptide, a CsPT4 polypeptide, comprising an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110. Some embodiments of the disclosure relate to a vector comprising one or more nucleic acids encoding a GOT polypeptide, a CsPT4 polypeptide, comprising an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110.

Some embodiments of the disclosure relate to a vector comprising one or more nucleic acids encoding a GOT polypeptide, a CsPT4 polypeptide, comprising an amino acid sequence having at least 65% amino acid sequence identity to SEQ ID NO:110. Some embodiments of the disclosure relate to a vector comprising one or more nucleic acids encoding a GOT polypeptide, a CsPT4 polypeptide, comprising an amino acid sequence having at least 75% amino acid sequence identity to SEQ ID NO:110. Some embodiments of the disclosure relate to a vector comprising one or more nucleic acids encoding a GOT polypeptide, a CsPT4 polypeptide, comprising an amino acid sequence having at least 85% amino acid sequence identity to SEQ ID NO:110. Some embodiments of the disclosure relate to a vector comprising one or more nucleic acids encoding a GOT polypeptide, a CsPT4 polypeptide, comprising an amino acid sequence having at least 95% amino acid sequence identity to SEQ ID NO:110. Some embodiments of the disclosure relate to a vector comprising one or more nucleic acids encoding a GOT polypeptide, a CsPT4 polypeptide, comprising an amino acid sequence having at least 65% amino acid sequence identity to SEQ ID NO:110, or a conservatively substituted amino acid sequence thereof. Some embodiments of the disclosure relate to a vector comprising one or more nucleic acids encoding a GOT polypeptide, a CsPT4 polypeptide, comprising an amino acid sequence having at least 75% amino acid sequence identity to SEQ ID NO:110, or a conservatively substituted amino acid sequence thereof. Some embodiments of the disclosure relate to a vector comprising one or more nucleic acids encoding a GOT polypeptide, a CsPT4 polypeptide, comprising an amino acid sequence having at least 85% amino acid sequence identity to SEQ ID NO:110, or a conservatively substituted amino acid sequence thereof. Some embodiments of the disclosure relate to a vector comprising one or more nucleic acids encoding a GOT polypeptide, a CsPT4 polypeptide, comprising an amino acid sequence having at least 95% amino acid sequence identity to SEQ ID NO:110, or a conservatively substituted amino acid sequence thereof.

Some embodiments of the disclosure relate to a vector comprising a CsPT4 nucleic acid comprising the nucleotide sequence set forth in SEQ ID NO:111. Some embodiments of the disclosure relate to a vector comprising a CsPT4 nucleic acid comprising the nucleotide sequence set forth in SEQ ID NO:111, or a codon degenerate nucleotide sequence thereof. Some embodiments of the disclosure relate to a vector comprising a CsPT4 nucleic acid comprising a nucleotide sequence having at least 80%, at least 81%, at least 82%, at least 83%, or at least 84% sequence identity to SEQ ID NO:111. Some embodiments of the disclosure relate to a vector comprising a CsPT4 nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:111. Some embodiments of the disclosure relate to a vector comprising a CsPT4 nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:111.

Some embodiments of the disclosure relate to a vector comprising a CsPT4 nucleic acid comprising a nucleotide sequence having at least 85% sequence identity to SEQ ID NO:111. Some embodiments of the disclosure relate to a vector comprising a CsPT4 nucleic acid comprising a nucleotide sequence having at least 95% sequence identity to SEQ ID NO:111. Some embodiments of the disclosure relate to a vector comprising a CsPT4 nucleic acid comprising a nucleotide sequence having at least 85% sequence identity to SEQ ID NO:111, or a codon degenerate nucleotide sequence thereof. Some embodiments of the disclosure relate to a vector comprising a CsPT4 nucleic acid comprising a nucleotide sequence having at least 95% sequence identity to SEQ ID NO:111, or a codon degenerate nucleotide sequence thereof.

Some embodiments of the disclosure relate to a vector comprising a CsPT4 nucleic acid comprising the nucleotide sequence set forth in SEQ ID NO:225. Some embodiments of the disclosure relate to a vector comprising a CsPT4 nucleic acid comprising the nucleotide sequence set forth in SEQ ID NO:225, or a codon degenerate nucleotide sequence thereof. Some embodiments of the disclosure relate to a vector comprising a CsPT4 nucleic acid comprising a nucleotide sequence having at least 80%, at least 81%, at least 82%, at least 83%, or at least 84% sequence identity to SEQ ID NO:225. Some embodiments of the disclosure relate to a vector comprising a CsPT4 nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:225. Some embodiments of the disclosure relate to a vector comprising a CsPT4 nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:225.

Some embodiments of the disclosure relate to a vector comprising a CsPT4 nucleic acid comprising a nucleotide sequence having at least 85% sequence identity to SEQ ID NO:225. Some embodiments of the disclosure relate to a vector comprising a CsPT4 nucleic acid comprising a nucleotide sequence having at least 95% sequence identity to SEQ ID NO:225. Some embodiments of the disclosure relate to a vector comprising a CsPT4 nucleic acid comprising a nucleotide sequence having at least 85% sequence identity to SEQ ID NO:225, or a codon degenerate nucleotide sequence thereof. Some embodiments of the disclosure relate to a vector comprising a CsPT4 nucleic acid comprising a nucleotide sequence having at least 95% sequence identity to SEQ ID NO:225, or a codon degenerate nucleotide sequence thereof.

Some embodiments of the disclosure relate to a vector comprising a CsPT4t nucleic acid comprising the nucleotide sequence set forth in SEQ ID NO:221. Some embodiments of the disclosure relate to a vector comprising a CsPT4t nucleic acid comprising the nucleotide sequence set forth in SEQ ID NO:221, or a codon degenerate nucleotide sequence thereof. Some embodiments of the disclosure relate to a vector comprising a CsPT4t nucleic acid comprising a nucleotide sequence having at least 80%, at least 81%, at least 82%, at least 83%, or at least 84% sequence identity to SEQ ID NO:221. Some embodiments of the disclosure relate to a vector comprising a CsPT4t nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:221. Some embodiments of the disclosure relate to a vector comprising a CsPT4t nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:221.

Some embodiments of the disclosure relate to a vector comprising a CsPT4t nucleic acid comprising a nucleotide sequence having at least 85% sequence identity to SEQ ID NO:221. Some embodiments of the disclosure relate to a vector comprising a CsPT4t nucleic acid comprising a nucleotide sequence having at least 95% sequence identity to SEQ ID NO:221. Some embodiments of the disclosure relate to a vector comprising a CsPT4t nucleic acid comprising a nucleotide sequence having at least 85% sequence identity to SEQ ID NO:221, or a codon degenerate nucleotide sequence thereof. Some embodiments of the disclosure relate to a vector comprising a CsPT4t nucleic acid comprising a nucleotide sequence having at least 95% sequence identity to SEQ ID NO:221, or a codon degenerate nucleotide sequence thereof.

Some embodiments of the disclosure relate to a vector comprising a CsPT4t nucleic acid comprising the nucleotide sequence set forth in SEQ ID NO:224. Some embodiments of the disclosure relate to a vector comprising a CsPT4t nucleic acid comprising the nucleotide sequence set forth in SEQ ID NO:224, or a codon degenerate nucleotide sequence thereof. Some embodiments of the disclosure relate to a vector comprising a CsPT4t nucleic acid comprising a nucleotide sequence having at least 80%, at least 81%, at least 82%, at least 83%, or at least 84% sequence identity to SEQ ID NO:224. Some embodiments of the disclosure relate to a vector comprising a CsPT4t nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:224. Some embodiments of the disclosure relate to a vector comprising a CsPT4t nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:224.

Some embodiments of the disclosure relate to a vector comprising a CsPT4t nucleic acid comprising a nucleotide sequence having at least 85% sequence identity to SEQ ID NO:224. Some embodiments of the disclosure relate to a vector comprising a CsPT4t nucleic acid comprising a nucleotide sequence having at least 95% sequence identity to SEQ ID NO:224. Some embodiments of the disclosure relate to a vector comprising a CsPT4t nucleic acid comprising a nucleotide sequence having at least 85% sequence identity to SEQ ID NO:224, or a codon degenerate nucleotide sequence thereof. Some embodiments of the disclosure relate to a vector comprising a CsPT4t nucleic acid comprising a nucleotide sequence having at least 95% sequence identity to SEQ ID NO:224, or a codon degenerate nucleotide sequence thereof.

Expression Constructs Comprising Nucleic Acids Encoding GOT Polypeptides

Some embodiments of the disclosure relate to an expression construct comprising one or more nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82.

Some embodiments of the disclosure relate to an expression construct comprising one or more nucleic acids encoding a GOT polypeptide, a CsPT4t polypeptide, comprising the amino acid sequence set forth in SEQ ID NO:100. Some embodiments of the disclosure relate to an expression construct comprising one or more nucleic acids encoding a GOT polypeptide, a CsPT4t polypeptide, comprising the amino acid sequence set forth in SEQ ID NO:100, or a conservatively substituted amino acid sequence thereof. Some embodiments of the disclosure relate to an expression construct comprising one or more nucleic acids encoding a GOT polypeptide, a CsPT4t polypeptide, comprising an amino acid sequence having at least 65%, at least 70%, or at least 75% amino acid sequence identity to SEQ ID NO:100. Some embodiments of the disclosure relate to an expression construct comprising one or more nucleic acids encoding a GOT polypeptide, a CsPT4t polypeptide, comprising an amino acid sequence having at least 80%, at least 81%, at least 82%, at least 83%, or at least 84% amino acid sequence identity to SEQ ID NO:100. Some embodiments of the disclosure relate to an expression construct comprising one or more nucleic acids encoding a GOT polypeptide, a CsPT4t polypeptide, comprising an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100. Some embodiments of the disclosure relate to an expression construct comprising one or more nucleic acids encoding a GOT polypeptide, a CsPT4t polypeptide, comprising an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100.

Some embodiments of the disclosure relate to an expression construct comprising one or more nucleic acids encoding a GOT polypeptide, a CsPT4t polypeptide, comprising an amino acid sequence having at least 65% amino acid sequence identity to SEQ ID NO:100. Some embodiments of the disclosure relate to an expression construct comprising one or more nucleic acids encoding a GOT polypeptide, a CsPT4t polypeptide, comprising an amino acid sequence having at least 75% amino acid sequence identity to SEQ ID NO:100. Some embodiments of the disclosure relate to an expression construct comprising one or more nucleic acids encoding a GOT polypeptide, a CsPT4t polypeptide, comprising an amino acid sequence having at least 85% amino acid sequence identity to SEQ ID NO:100. Some embodiments of the disclosure relate to an expression construct comprising one or more nucleic acids encoding a GOT polypeptide, a CsPT4t polypeptide, comprising an amino acid sequence having at least 95% amino acid sequence identity to SEQ ID NO:100. Some embodiments of the disclosure relate to an expression construct comprising one or more nucleic acids encoding a GOT polypeptide, a CsPT4t polypeptide, comprising an amino acid sequence having at least 65% amino acid sequence identity to SEQ ID NO:100, or a conservatively substituted amino acid sequence thereof. Some embodiments of the disclosure relate to an expression construct comprising one or more nucleic acids encoding a GOT polypeptide, a CsPT4t polypeptide, comprising an amino acid sequence having at least 75% amino acid sequence identity to SEQ ID NO:100, or a conservatively substituted amino acid sequence thereof. Some embodiments of the disclosure relate to an expression construct comprising one or more nucleic acids encoding a GOT polypeptide, a CsPT4t polypeptide, comprising an amino acid sequence having at least 85% amino acid sequence identity to SEQ ID NO:100, or a conservatively substituted amino acid sequence thereof. Some embodiments of the disclosure relate to an expression construct comprising one or more nucleic acids encoding a GOT polypeptide, a CsPT4t polypeptide, comprising an amino acid sequence having at least 95% amino acid sequence identity to SEQ ID NO:100, or a conservatively substituted amino acid sequence thereof.

Some embodiments of the disclosure relate to an expression construct comprising one or more nucleic acids encoding a GOT polypeptide, a CsPT4 polypeptide, comprising the amino acid sequence set forth in SEQ ID NO:110. Some embodiments of the disclosure relate to an expression construct comprising one or more nucleic acids encoding a GOT polypeptide, a CsPT4 polypeptide, comprising the amino acid sequence set forth in SEQ ID NO:110, or a conservatively substituted amino acid sequence thereof. Some embodiments of the disclosure relate to an expression construct comprising one or more nucleic acids encoding a GOT polypeptide, a CsPT4 polypeptide, comprising an amino acid sequence having at least 65%, at least 70%, or at least 75% amino acid sequence identity to SEQ ID NO:110. Some embodiments of the disclosure relate to an expression construct comprising one or more nucleic acids encoding a GOT polypeptide, a CsPT4 polypeptide, comprising an amino acid sequence having at least 80%, at least 81%, at least 82%, at least 83%, or at least 84% amino acid sequence identity to SEQ ID NO:110. Some embodiments of the disclosure relate to an expression construct comprising one or more nucleic acids encoding a GOT polypeptide, a CsPT4 polypeptide, comprising an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110. Some embodiments of the disclosure relate to an expression construct comprising one or more nucleic acids encoding a GOT polypeptide, a CsPT4 polypeptide, comprising an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110.

Some embodiments of the disclosure relate to an expression construct comprising one or more nucleic acids encoding a GOT polypeptide, a CsPT4 polypeptide, comprising an amino acid sequence having at least 65% amino acid sequence identity to SEQ ID NO:110. Some embodiments of the disclosure relate to an expression construct comprising one or more nucleic acids encoding a GOT polypeptide, a CsPT4 polypeptide, comprising an amino acid sequence having at least 75% amino acid sequence identity to SEQ ID NO:110. Some embodiments of the disclosure relate to an expression construct comprising one or more nucleic acids encoding a GOT polypeptide, a CsPT4 polypeptide, comprising an amino acid sequence having at least 85% amino acid sequence identity to SEQ ID NO:110. Some embodiments of the disclosure relate to an expression construct comprising one or more nucleic acids encoding a GOT polypeptide, a CsPT4 polypeptide, comprising an amino acid sequence having at least 95% amino acid sequence identity to SEQ ID NO:110. Some embodiments of the disclosure relate to an expression construct comprising one or more nucleic acids encoding a GOT polypeptide, a CsPT4 polypeptide, comprising an amino acid sequence having at least 65% amino acid sequence identity to SEQ ID NO:110, or a conservatively substituted amino acid sequence thereof. Some embodiments of the disclosure relate to an expression construct comprising one or more nucleic acids encoding a GOT polypeptide, a CsPT4 polypeptide, comprising an amino acid sequence having at least 75% amino acid sequence identity to SEQ ID NO:110, or a conservatively substituted amino acid sequence thereof. Some embodiments of the disclosure relate to an expression construct comprising one or more nucleic acids encoding a GOT polypeptide, a CsPT4 polypeptide, comprising an amino acid sequence having at least 85% amino acid sequence identity to SEQ ID NO:110, or a conservatively substituted amino acid sequence thereof. Some embodiments of the disclosure relate to an expression construct comprising one or more nucleic acids encoding a GOT polypeptide, a CsPT4 polypeptide, comprising an amino acid sequence having at least 95% amino acid sequence identity to SEQ ID NO:110, or a conservatively substituted amino acid sequence thereof.

Some embodiments of the disclosure relate to an expression construct comprising a CsPT4 nucleic acid comprising the nucleotide sequence set forth in SEQ ID NO:111. Some embodiments of the disclosure relate to an expression construct comprising a CsPT4 nucleic acid comprising the nucleotide sequence set forth in SEQ ID NO:111, or a codon degenerate nucleotide sequence thereof. Some embodiments of the disclosure relate to an expression construct comprising a CsPT4 nucleic acid comprising a nucleotide sequence having at least 80%, at least 81%, at least 82%, at least 83%, or at least 84% sequence identity to SEQ ID NO:111. Some embodiments of the disclosure relate to an expression construct comprising a CsPT4 nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:111. Some embodiments of the disclosure relate to an expression construct comprising a CsPT4 nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:111.

Some embodiments of the disclosure relate to an expression construct comprising a CsPT4 nucleic acid comprising a nucleotide sequence having at least 85% sequence identity to SEQ ID NO:111. Some embodiments of the disclosure relate to an expression construct comprising a CsPT4 nucleic acid comprising a nucleotide sequence having at least 95% sequence identity to SEQ ID NO:111. Some embodiments of the disclosure relate to an expression construct comprising a CsPT4 nucleic acid comprising a nucleotide sequence having at least 85% sequence identity to SEQ ID NO:111, or a codon degenerate nucleotide sequence thereof. Some embodiments of the disclosure relate to an expression construct comprising a CsPT4 nucleic acid comprising a nucleotide sequence having at least 95% sequence identity to SEQ ID NO:111, or a codon degenerate nucleotide sequence thereof.

Some embodiments of the disclosure relate to an expression construct comprising a CsPT4 nucleic acid comprising the nucleotide sequence set forth in SEQ ID NO:225. Some embodiments of the disclosure relate to an expression construct comprising a CsPT4 nucleic acid comprising the nucleotide sequence set forth in SEQ ID NO:225, or a codon degenerate nucleotide sequence thereof. Some embodiments of the disclosure relate to an expression construct comprising a CsPT4 nucleic acid comprising a nucleotide sequence having at least 80%, at least 81%, at least 82%, at least 83%, or at least 84% sequence identity to SEQ ID NO:225. Some embodiments of the disclosure relate to an expression construct comprising a CsPT4 nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:225. Some embodiments of the disclosure relate to an expression construct comprising a CsPT4 nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:225.

Some embodiments of the disclosure relate to an expression construct comprising a CsPT4 nucleic acid comprising a nucleotide sequence having at least 85% sequence identity to SEQ ID NO:225. Some embodiments of the disclosure relate to an expression construct comprising a CsPT4 nucleic acid comprising a nucleotide sequence having at least 95% sequence identity to SEQ ID NO:225. Some embodiments of the disclosure relate to an expression construct comprising a CsPT4 nucleic acid comprising a nucleotide sequence having at least 85% sequence identity to SEQ ID NO:225, or a codon degenerate nucleotide sequence thereof. Some embodiments of the disclosure relate to an expression construct comprising a CsPT4 nucleic acid comprising a nucleotide sequence having at least 95% sequence identity to SEQ ID NO:225, or a codon degenerate nucleotide sequence thereof.

Some embodiments of the disclosure relate to an expression construct comprising a CsPT4t nucleic acid comprising the nucleotide sequence set forth in SEQ ID NO:221. Some embodiments of the disclosure relate to an expression construct comprising a CsPT4t nucleic acid comprising the nucleotide sequence set forth in SEQ ID NO:221, or a codon degenerate nucleotide sequence thereof. Some embodiments of the disclosure relate to an expression construct comprising a CsPT4t nucleic acid comprising a nucleotide sequence having at least 80%, at least 81%, at least 82%, at least 83%, or at least 84% sequence identity to SEQ ID NO:221. Some embodiments of the disclosure relate to an expression construct comprising a CsPT4t nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:221. Some embodiments of the disclosure relate to an expression construct comprising a CsPT4t nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:221.

Some embodiments of the disclosure relate to an expression construct comprising a CsPT4t nucleic acid comprising a nucleotide sequence having at least 85% sequence identity to SEQ ID NO:221. Some embodiments of the disclosure relate to an expression construct comprising a CsPT4t nucleic acid comprising a nucleotide sequence having at least 95% sequence identity to SEQ ID NO:221. Some embodiments of the disclosure relate to an expression construct comprising a CsPT4t nucleic acid comprising a nucleotide sequence having at least 85% sequence identity to SEQ ID NO:221, or a codon degenerate nucleotide sequence thereof. Some embodiments of the disclosure relate to an expression construct comprising a CsPT4t nucleic acid comprising a nucleotide sequence having at least 95% sequence identity to SEQ ID NO:221, or a codon degenerate nucleotide sequence thereof.

Some embodiments of the disclosure relate to an expression construct comprising a CsPT4t nucleic acid comprising the nucleotide sequence set forth in SEQ ID NO: 224. Some embodiments of the disclosure relate to an expression construct comprising a CsPT4t nucleic acid comprising the nucleotide sequence set forth in SEQ ID NO:224, or a codon degenerate nucleotide sequence thereof. Some embodiments of the disclosure relate to an expression construct comprising a CsPT4t nucleic acid comprising a nucleotide sequence having at least 80%, at least 81%, at least 82%, at least 83%, or at least 84% sequence identity to SEQ ID NO:224. Some embodiments of the disclosure relate to an expression construct comprising a CsPT4t nucleic acid comprising a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:224. Some embodiments of the disclosure relate to an expression construct comprising a CsPT4t nucleic acid comprising a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:224.

Some embodiments of the disclosure relate to an expression construct comprising a CsPT4t nucleic acid comprising a nucleotide sequence having at least 85% sequence identity to SEQ ID NO:224. Some embodiments of the disclosure relate to an expression construct comprising a CsPT4t nucleic acid comprising a nucleotide sequence having at least 95% sequence identity to SEQ ID NO:224. Some embodiments of the disclosure relate to an expression construct comprising a CsPT4t nucleic acid comprising a nucleotide sequence having at least 85% sequence identity to SEQ ID NO:224, or a codon degenerate nucleotide sequence thereof. Some embodiments of the disclosure relate to an expression construct comprising a CsPT4t nucleic acid comprising a nucleotide sequence having at least 95% sequence identity to SEQ ID NO:224, or a codon degenerate nucleotide sequence thereof.

Polypeptides, Nucleic Acids, and Genetically Modified Host Cells for the Production of Cannabinoids, Cannabinoid Derivatives, Cannabinoid Precursors, or Cannabinoid Precursor Derivatives The present disclosure provides genetically modified host cells for producing a cannabinoid, a cannabinoid derivative, a cannabinoid precursor, or a cannabinoid precursor derivative. A genetically modified host cell of the present disclosure may be genetically modified with one or more heterologous nucleic acids disclosed herein encoding one or more polypeptides disclosed herein. Culturing of the genetically modified host cell in a suitable medium provides for synthesis of the cannabinoid, the cannabinoid derivative, the cannabinoid precursor, or the cannabinoid precursor derivative in a recoverable amount. In some embodiments, the genetically modified host cell of the disclosure produces a cannabinoid or a cannabinoid derivative.

The disclosure also provides nucleic acids, which can be introduced into microorganisms (e.g., genetically modified host cells), resulting in expression or overexpression of the one or more polypeptides, which can then be utilized in vitro (e.g., cell-free) or in vivo for the production of cannabinoids, cannabinoid derivatives, cannabinoid precursors, or cannabinoid precursor derivatives. In certain such embodiments, cannabinoids or cannabinoid derivatives are produced.

One or more polypeptides which can be utilized for the production of a cannabinoid, a cannabinoid derivative, a cannabinoid precursor, or a cannabinoid precursor derivative are disclosed herein, and may include, but are not limited to: one or more polypeptides having at least one activity of a polypeptide present in the cannabinoid biosynthetic pathway, such as, a GOT polypeptide, a CBDA or THCA synthase polypeptide, a TKS polypeptide, and an OAC polypeptide; one or more polypeptides having at least one activity of a polypeptide present in the mevalonate (MEV) pathway; a polypeptide that generates acyl-CoA compounds or acyl-CoA compound derivatives (e.g., an acyl-activating enzyme polypeptide, a fatty acyl-CoA synthetase polypeptide, or a fatty acyl-CoA ligase polypeptide); a polypeptide that generates GPP; a polypeptide that generates malonyl-CoA; a polypeptide that condenses two molecules of acetyl-CoA to generate acetoacetyl-CoA, and a pyruvate decarboxylase polypeptide. Additionally, polypeptides which can be utilized for the production of a cannabinoid, a cannabinoid derivative, a cannabinoid precursor, or a cannabinoid precursor derivative may be one or more polypeptides having at least one activity of a polypeptide present in the DXP pathway, instead of those of the MEV pathway.

Polypeptides which can be utilized for the production of a cannabinoid, a cannabinoid derivative, a cannabinoid precursor, or a cannabinoid precursor derivative may also include a hexanoyl-CoA synthase (HCS) polypeptide or one or more polypeptides that are part of a biosynthetic pathway that produces hexanoyl-CoA, including, but not limited to: a MCT1 polypeptide, a PaaH1 polypeptide, a Crt polypeptide, a Ter polypeptide, and a BktB polypeptide; a MCT1 polypeptide, a PhaB polypeptide, a PhaJ polypeptide, a Ter polypeptide, and a BktB polypeptide; a short chain fatty acyl-CoA thioesterase (SCFA-TE) polypeptide; or a fatty acid synthase (FAS) polypeptide. Hexanoyl CoA derivatives, acyl-CoA compounds, or acyl-CoA compound derivatives may also be formed via such pathways and polypeptides.

Polypeptides which can be utilized for the production of a cannabinoid, a cannabinoid derivative, a cannabinoid precursor, or a cannabinoid precursor derivative may also include polypeptides that modulate NADH or NADPH redox balance, polypeptides that generate neryl pyrophosphate, and NphB polypeptides.

The disclosure also provides nucleic acids encoding said polypeptides which can be utilized for the production of a cannabinoid, a cannabinoid derivative, a cannabinoid precursor, or a cannabinoid precursor derivative. The disclosure also provides genetically modified host cells comprising one or more of said nucleic acids and polypeptides which can be utilized for the production of a cannabinoid, a cannabinoid derivative, a cannabinoid precursor, or a cannabinoid precursor derivative.

Geranyl Pyrophosphate:Olivetolic Acid Geranyltransferase (GOT) Polypeptides, Nucleic Acids, and Genetically Modified Host Cells Expressing Said Polypeptides In some embodiments, a genetically modified host cell of the present disclosure is genetically modified with one or more heterologous nucleic acids encoding a geranyl pyrophosphate:olivetolic acid geranyltransferase (GOT) polypeptide.

Exemplary GOT polypeptides disclosed herein may include a full-length GOT polypeptide, a fragment of a GOT polypeptide, a variant of a GOT polypeptide, a truncated GOT polypeptide, or a fusion polypeptide that has at least one activity of a GOT polypeptide. In some embodiments, the GOT polypeptide has aromatic prenyltransferase (PT) activity. In some embodiments, the GOT polypeptide modifies a cannabinoid precursor or a cannabinoid precursor derivative. In certain such embodiments, the GOT polypeptide modifies olivetolic acid or an olivetolic acid derivative. In some embodiments, the GOT polypeptide cannot catalyze the production of 5-geranyl olivetolic acid.

In some embodiments, a genetically modified host cell of the present disclosure is genetically modified with one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82. In some embodiments, a genetically modified host cell of the present disclosure is genetically modified with one or more heterologous nucleic acids encoding a GOT polypeptide, wherein said GOT polypeptide can catalyze production of cannabigerolic acid from GPP and olivetolic acid in an amount at least 200-500 times higher than a polypeptide comprising an amino acid sequence set forth in SEQ ID NO:82. In some embodiments, a genetically modified host cell of the present disclosure is genetically modified with one or more heterologous nucleic acids encoding a GOT polypeptide, wherein said GOT polypeptide can catalyze production of cannabigerolic acid from GPP and olivetolic acid in an amount at least 10, at least 20, at least 30, at least 40, at least 50, at least 60, at least 70, at least 80, at least 90, at least 100, at least 200, at least 300, at least 400, or at least 500 times higher than a polypeptide comprising an amino acid sequence set forth in SEQ ID NO:82. In some embodiments, a genetically modified host cell of the present disclosure is genetically modified with one or more heterologous nucleic acids encoding a GOT polypeptide, wherein said GOT polypeptide can catalyze production of cannabigerolic acid from GPP and olivetolic acid in an amount at least 10-50, at least 50-100, at least 100-200, at least 100-300, at least 100-400, at least 200-400, at least 100-500, at least 200-500, or at least 300-500 times higher than a polypeptide comprising an amino acid sequence set forth in SEQ ID NO:82.

In some embodiments, the GOT polypeptide encoded by the one or more heterologous nucleic acids comprises the amino acid sequence set forth in SEQ ID NO:100 or SEQ ID NO:110. In some embodiments, the GOT polypeptide encoded by the one or more heterologous nucleic acids comprises the amino acid sequence set forth in SEQ ID NO:100 or SEQ ID NO:110, or a conservatively substituted amino acid sequence thereof. In some embodiments, the GOT polypeptide encoded by the one or more heterologous nucleic acids comprises an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100 or SEQ ID NO:110.

In some embodiments, the GOT polypeptide encoded by the one or more heterologous nucleic acids comprises the amino acid sequence set forth in SEQ ID NO:12, SEQ ID NO:82, SEQ ID NO:98, SEQ ID NO:99, or SEQ ID NO:223. In some embodiments, the GOT polypeptide encoded by the one or more heterologous nucleic acids comprises the amino acid sequence set forth in SEQ ID NO:12, SEQ ID NO:82, SEQ ID NO:98, SEQ ID NO:99, or SEQ ID NO:223, or a conservatively substituted amino acid sequence thereof. In some embodiments, the GOT polypeptide encoded by the one or more heterologous nucleic acids comprises an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:12, SEQ ID NO:82, SEQ ID NO:98, SEQ ID NO:99, or SEQ ID NO:223.

In some embodiments, the GOT polypeptide encoded by the one or more heterologous nucleic acids comprises the amino acid sequence set forth in SEQ ID NO:13, SEQ ID NO:101, SEQ ID NO:102, or SEQ ID NO:103. In some embodiments, the GOT polypeptide encoded by the one or more heterologous nucleic acids comprises the amino acid sequence set forth in SEQ ID NO:13, SEQ ID NO:101, SEQ ID NO:102, or SEQ ID NO:103, or a conservatively substituted amino acid sequence thereof. In some embodiments, the GOT polypeptide encoded by the one or more heterologous nucleic acids comprises an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:13, SEQ ID NO:101, SEQ ID NO:102, or SEQ ID NO:103.

In some embodiments, the GOT polypeptide encoded by the one or more heterologous nucleic acids comprises the amino acid sequence set forth in SEQ ID NO:211, SEQ ID NO:213, SEQ ID NO:215, SEQ ID NO:217, or SEQ ID NO:219. In some embodiments, the GOT polypeptide encoded by the one or more heterologous nucleic acids comprises the amino acid sequence set forth in SEQ ID NO:211, SEQ ID NO:213, SEQ ID NO:215, SEQ ID NO:217, or SEQ ID NO:219, or a conservatively substituted amino acid sequence thereof. In some embodiments, the GOT polypeptide encoded by the one or more heterologous nucleic acids comprises an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:211, SEQ ID NO:213, SEQ ID NO:215, SEQ ID NO:217, or SEQ ID NO:219.

In some embodiments, the GOT polypeptide encoded by the one or more heterologous nucleic acids comprises the amino acid sequence set forth in SEQ ID NO:12. In some embodiments, the GOT polypeptide encoded by the one or more heterologous nucleic acids comprises the amino acid sequence set forth in SEQ ID NO:12, or a conservatively substituted amino acid sequence thereof. In some embodiments, the GOT polypeptide encoded by the one or more heterologous nucleic acids comprises an amino acid sequence having at least 65%, at least 70%, or at least 75% amino acid sequence identity to SEQ ID NO:12. In some embodiments, the GOT polypeptide encoded by the one or more heterologous nucleic acids comprises an amino acid sequence having at least 80%, at least 81%, at least 82%, at least 83%, or at least 84% amino acid sequence identity to SEQ ID NO:12. In some embodiments, the GOT polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:12.

In some embodiments, the GOT polypeptide encoded by the one or more heterologous nucleic acids comprises the amino acid sequence set forth in SEQ ID NO:13. In some embodiments, the GOT polypeptide encoded by the one or more heterologous nucleic acids comprises the amino acid sequence set forth in SEQ ID NO:13, or a conservatively substituted amino acid sequence thereof. In some embodiments, the GOT polypeptide encoded by the one or more heterologous nucleic acids comprises an amino acid sequence having at least 65%, at least 70%, or at least 75% amino acid sequence identity to SEQ ID NO:13. In some embodiments, the GOT polypeptide encoded by the one or more heterologous nucleic acids comprises an amino acid sequence having at least 80%, at least 81%, at least 82%, at least 83%, or at least 84% amino acid sequence identity to SEQ ID NO:13. In some embodiments, the GOT polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:13.

In some embodiments, the GOT polypeptide encoded by the one or more heterologous nucleic acids is a CsPT1 polypeptide and comprises the amino acid sequence set forth in SEQ ID NO:82. In some embodiments, the GOT polypeptide encoded by the one or more heterologous nucleic acids is a CsPT1 polypeptide and comprises the amino acid sequence set forth in SEQ ID NO:82, or a conservatively substituted amino acid sequence thereof. In some embodiments, the GOT polypeptide encoded by the one or more heterologous nucleic acids is a CsPT1 polypeptide and comprises an amino acid sequence having at least 65%, at least 70%, or at least 75% amino acid sequence identity to SEQ ID NO:82. In some embodiments, the GOT polypeptide encoded by the one or more heterologous nucleic acids is a CsPT1 polypeptide and comprises an amino acid sequence having at least 80%, at least 81%, at least 82%, at least 83%, or at least 84% amino acid sequence identity to SEQ ID NO:82. In some embodiments, the GOT polypeptide encoded by the one or more heterologous nucleic acids is a CsPT1 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:82.

In some embodiments, the GOT polypeptide encoded by the one or more heterologous nucleic acids is a truncated CsPT1 (CsPT1_t75) polypeptide and comprises the amino acid sequence set forth in SEQ ID NO:223. In some embodiments, the GOT polypeptide encoded by the one or more heterologous nucleic acids is a CsPT1_t75 polypeptide and comprises the amino acid sequence set forth in SEQ ID NO:223, or a conservatively substituted amino acid sequence thereof. In some embodiments, the GOT polypeptide encoded by the one or more heterologous nucleic acids is a CsPT1_t75 polypeptide and comprises an amino acid sequence having at least 65%, at least 70%, or at least 75% amino acid sequence identity to SEQ ID NO:223. In some embodiments, the GOT polypeptide encoded by the one or more heterologous nucleic acids is a CsPT1_t75 polypeptide and comprises an amino acid sequence having at least 80%, at least 81%, at least 82%, at least 83%, or at least 84% amino acid sequence identity to SEQ ID NO:223. In some embodiments, the GOT polypeptide encoded by the one or more heterologous nucleic acids is a CsPT1_t75 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:223.

In some embodiments, the GOT polypeptide encoded by the one or more heterologous nucleic acids is a CsGOTt75 polypeptide and comprises the amino acid sequence set forth in SEQ ID NO:98. In some embodiments, the GOT polypeptide encoded by the one or more heterologous nucleic acids is a CsGOTt75 polypeptide and comprises the amino acid sequence set forth in SEQ ID NO:98, or a conservatively substituted amino acid sequence thereof. In some embodiments, the GOT polypeptide encoded by the one or more heterologous nucleic acids is a CsGOTt75 polypeptide and comprises an amino acid sequence having at least 65%, at least 70%, or at least 75% amino acid sequence identity to SEQ ID NO:98. In some embodiments, the GOT polypeptide encoded by the one or more heterologous nucleic acids is a CsGOTt75 polypeptide and comprises an amino acid sequence having at least 80%, at least 81%, at least 82%, at least 83%, or at least 84% amino acid sequence identity to SEQ ID NO:98. In some embodiments, the GOT polypeptide encoded by the one or more heterologous nucleic acids is a CsGOTt75 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:98.

In some embodiments, the GOT polypeptide encoded by the one or more heterologous nucleic acids is a CsGOTt33 polypeptide and comprises the amino acid sequence set forth in SEQ ID NO:99. In some embodiments, the GOT polypeptide encoded by the one or more heterologous nucleic acids is a CsGOTt33 polypeptide and comprises the amino acid sequence set forth in SEQ ID NO:99, or a conservatively substituted amino acid sequence thereof. In some embodiments, the GOT polypeptide encoded by the one or more heterologous nucleic acids is a CsGOTt33 polypeptide and comprises an amino acid sequence having at least 65%, at least 70%, or at least 75% amino acid sequence identity to SEQ ID NO:99. In some embodiments, the GOT polypeptide encoded by the one or more heterologous nucleic acids is a CsGOTt33 polypeptide and comprises an amino acid sequence having at least 80%, at least 81%, at least 82%, at least 83%, or at least 84% amino acid sequence identity to SEQ ID NO:99. In some embodiments, the GOT polypeptide encoded by the one or more heterologous nucleic acids is a CsGOTt33 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:99.

In some embodiments, the GOT polypeptide encoded by the one or more heterologous nucleic acids is a CsPT4t polypeptide and comprises the amino acid sequence set forth in SEQ ID NO:100. In some embodiments, the GOT polypeptide encoded by the one or more heterologous nucleic acids is a CsPT4t polypeptide and comprises the amino acid sequence set forth in SEQ ID NO:100, or a conservatively substituted amino acid sequence thereof. In some embodiments, the GOT polypeptide encoded by the one or more heterologous nucleic acids is a CsPT4t polypeptide and comprises an amino acid sequence having at least 65%, at least 70%, or at least 75% amino acid sequence identity to SEQ ID NO:100. In some embodiments, the GOT polypeptide encoded by the one or more heterologous nucleic acids is a CsPT4t polypeptide and comprises an amino acid sequence having at least 80%, at least 81%, at least 82%, at least 83%, or at least 84% amino acid sequence identity to SEQ ID NO:100. In some embodiments, the GOT polypeptide encoded by the one or more heterologous nucleic acids is a CsPT4t polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100. In some embodiments, the GOT polypeptide encoded by the one or more heterologous nucleic acids is a CsPT4t polypeptide and comprises an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100.

In some embodiments, the GOT polypeptide encoded by the one or more heterologous nucleic acids is a CsPT4t polypeptide and comprises an amino acid sequence having at least 65% amino acid sequence identity to SEQ ID NO:100. In some embodiments, the GOT polypeptide encoded by the one or more heterologous nucleic acids is a CsPT4t polypeptide and comprises an amino acid sequence having at least 75% amino acid sequence identity to SEQ ID NO:100. In some embodiments, the GOT polypeptide encoded by the one or more heterologous nucleic acids is a CsPT4t polypeptide and comprises an amino acid sequence having at least 85% amino acid sequence identity to SEQ ID NO:100. In some embodiments, the GOT polypeptide encoded by the one or more heterologous nucleic acids is a CsPT4t polypeptide and comprises an amino acid sequence having at least 95% amino acid sequence identity to SEQ ID NO:100. In some embodiments, the GOT polypeptide encoded by the one or more heterologous nucleic acids is a CsPT4t polypeptide and comprises an amino acid sequence having at least 65% amino acid sequence identity to SEQ ID NO:100, or a conservatively substituted amino acid sequence thereof. In some embodiments, the GOT polypeptide encoded by the one or more heterologous nucleic acids is a CsPT4t polypeptide and comprises an amino acid sequence having at least 75% amino acid sequence identity to SEQ ID NO:100, or a conservatively substituted amino acid sequence thereof. In some embodiments, the GOT polypeptide encoded by the one or more heterologous nucleic acids is a CsPT4t polypeptide and comprises an amino acid sequence having at least 85% amino acid sequence identity to SEQ ID NO:100, or a conservatively substituted amino acid sequence thereof. In some embodiments, the GOT polypeptide encoded by the one or more heterologous nucleic acids is a CsPT4t polypeptide and comprises an amino acid sequence having at least 95% amino acid sequence identity to SEQ ID NO:100, or a conservatively substituted amino acid sequence thereof.

In some embodiments, the GOT polypeptide encoded by the one or more heterologous nucleic acids is a CsPT7t polypeptide and comprises the amino acid sequence set forth in SEQ ID NO:101. In some embodiments, the GOT polypeptide encoded by the one or more heterologous nucleic acids is a CsPT7t polypeptide and comprises the amino acid sequence set forth in SEQ ID NO:101, or a conservatively substituted amino acid sequence thereof. In some embodiments, the GOT polypeptide encoded by the one or more heterologous nucleic acids is a CsPT7t polypeptide and comprises an amino acid sequence having at least 65%, at least 70%, or at least 75% amino acid sequence identity to SEQ ID NO:101. In some embodiments, the GOT polypeptide encoded by the one or more heterologous nucleic acids is a CsPT7t polypeptide and comprises an amino acid sequence having at least 80%, at least 81%, at least 82%, at least 83%, or at least 84% amino acid sequence identity to SEQ ID NO:101. In some embodiments, the GOT polypeptide encoded by the one or more heterologous nucleic acids is a CsPT7t polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:101.

In some embodiments, the GOT polypeptide encoded by the one or more heterologous nucleic acids is a H1PT1Lt polypeptide and comprises the amino acid sequence set forth in SEQ ID NO:102. In some embodiments, the GOT polypeptide encoded by the one or more heterologous nucleic acids is a H1PT1Lt polypeptide and comprises the amino acid sequence set forth in SEQ ID NO:102, or a conservatively substituted amino acid sequence thereof. In some embodiments, the GOT polypeptide encoded by the one or more heterologous nucleic acids is a H1PT1Lt polypeptide and comprises an amino acid sequence having at least 65%, at least 70%, or at least 75% amino acid sequence identity to SEQ ID NO:102. In some embodiments, the GOT polypeptide encoded by the one or more heterologous nucleic acids is a H1PT1Lt polypeptide and comprises an amino acid sequence having at least 80%, at least 81%, at least 82%, at least 83%, or at least 84% amino acid sequence identity to SEQ ID NO:102. In some embodiments, the GOT polypeptide encoded by the one or more heterologous nucleic acids is a H1PT1Lt polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:102.

In some embodiments, the GOT polypeptide encoded by the one or more heterologous nucleic acids is a H1PT2Lt polypeptide and comprises the amino acid sequence set forth in SEQ ID NO:103. In some embodiments, the GOT polypeptide encoded by the one or more heterologous nucleic acids is a H1PT2Lt polypeptide and comprises the amino acid sequence set forth in SEQ ID NO:103, or a conservatively substituted amino acid sequence thereof. In some embodiments, the GOT polypeptide encoded by the one or more heterologous nucleic acids is a H1PT2Lt polypeptide and comprises an amino acid sequence having at least 65%, at least 70%, or at least 75% amino acid sequence identity to SEQ ID NO:103. In some embodiments, the GOT polypeptide encoded by the one or more heterologous nucleic acids is a H1PT2Lt polypeptide and comprises an amino acid sequence having at least 80%, at least 81%, at least 82%, at least 83%, or at least 84% amino acid sequence identity to SEQ ID NO:103. In some embodiments, the GOT polypeptide encoded by the one or more heterologous nucleic acids is a H1PT2Lt polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:103.

In some embodiments, the GOT polypeptide encoded by the one or more heterologous nucleic acids is a CsPT4 polypeptide and comprises the amino acid sequence set forth in SEQ ID NO:110. In some embodiments, the GOT polypeptide encoded by the one or more heterologous nucleic acids is a CsPT4 polypeptide and comprises the amino acid sequence set forth in SEQ ID NO:110, or a conservatively substituted amino acid sequence thereof. In some embodiments, the GOT polypeptide encoded by the one or more heterologous nucleic acids is a CsPT4 polypeptide and comprises an amino acid sequence having at least 65%, at least 70%, or at least 75% amino acid sequence identity to SEQ ID NO:110. In some embodiments, the GOT polypeptide encoded by the one or more heterologous nucleic acids is a CsPT4 polypeptide and comprises an amino acid sequence having at least 80%, at least 81%, at least 82%, at least 83%, or at least 84% amino acid sequence identity to SEQ ID NO:110. In some embodiments, the GOT polypeptide encoded by the one or more heterologous nucleic acids is a CsPT4 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110. In some embodiments, the GOT polypeptide encoded by the one or more heterologous nucleic acids is a CsPT4 polypeptide and comprises an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110.

In some embodiments, the GOT polypeptide encoded by the one or more heterologous nucleic acids is a CsPT4 polypeptide and comprises an amino acid sequence having at least 65% amino acid sequence identity to SEQ ID NO:110. In some embodiments, the GOT polypeptide encoded by the one or more heterologous nucleic acids is a CsPT4 polypeptide and comprises an amino acid sequence having at least 75% amino acid sequence identity to SEQ ID NO:110. In some embodiments, the GOT polypeptide encoded by the one or more heterologous nucleic acids is a CsPT4 polypeptide and comprises an amino acid sequence having at least 85% amino acid sequence identity to SEQ ID NO:110. In some embodiments, the GOT polypeptide encoded by the one or more heterologous nucleic acids is a CsPT4 polypeptide and comprises an amino acid sequence having at least 95% amino acid sequence identity to SEQ ID NO:110. In some embodiments, the GOT polypeptide encoded by the one or more heterologous nucleic acids is a CsPT4 polypeptide and comprises an amino acid sequence having at least 65% amino acid sequence identity to SEQ ID NO:110, or a conservatively substituted amino acid sequence thereof. In some embodiments, the GOT polypeptide encoded by the one or more heterologous nucleic acids is a CsPT4 polypeptide and comprises an amino acid sequence having at least 75% amino acid sequence identity to SEQ ID NO:110, or a conservatively substituted amino acid sequence thereof. In some embodiments, the GOT polypeptide encoded by the one or more heterologous nucleic acids is a CsPT4 polypeptide and comprises an amino acid sequence having at least 85% amino acid sequence identity to SEQ ID NO:110, or a conservatively substituted amino acid sequence thereof. In some embodiments, the GOT polypeptide encoded by the one or more heterologous nucleic acids is a CsPT4 polypeptide and comprises an amino acid sequence having at least 95% amino acid sequence identity to SEQ ID NO:110, or a conservatively substituted amino acid sequence thereof.

In some embodiments, the GOT polypeptide encoded by the one or more heterologous nucleic acids is a truncated CsPT4 (CsPT4_t112) polypeptide and comprises the amino acid sequence set forth in SEQ ID NO:211. In some embodiments, the GOT polypeptide encoded by the one or more heterologous nucleic acids is a CsPT4_t112 polypeptide and comprises the amino acid sequence set forth in SEQ ID NO:211, or a conservatively substituted amino acid sequence thereof. In some embodiments, the GOT polypeptide encoded by the one or more heterologous nucleic acids is a CsPT4_t112 polypeptide and comprises an amino acid sequence having at least 65%, at least 70%, or at least 75% amino acid sequence identity to SEQ ID NO:211. In some embodiments, the GOT polypeptide encoded by the one or more heterologous nucleic acids is a CsPT4_t112 polypeptide and comprises an amino acid sequence having at least 80%, at least 81%, at least 82%, at least 83%, or at least 84% amino acid sequence identity to SEQ ID NO:211. In some embodiments, the GOT polypeptide encoded by the one or more heterologous nucleic acids is a CsPT4_t112 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:211.

In some embodiments, the GOT polypeptide encoded by the one or more heterologous nucleic acids is a truncated CsPT4 (CsPT4_t131) polypeptide and comprises the amino acid sequence set forth in SEQ ID NO:213. In some embodiments, the GOT polypeptide encoded by the one or more heterologous nucleic acids is a CsPT4_t131 polypeptide and comprises the amino acid sequence set forth in SEQ ID NO:213, or a conservatively substituted amino acid sequence thereof. In some embodiments, the GOT polypeptide encoded by the one or more heterologous nucleic acids is a CsPT4_t131 polypeptide and comprises an amino acid sequence having at least 65%, at least 70%, or at least 75% amino acid sequence identity to SEQ ID NO:213. In some embodiments, the GOT polypeptide encoded by the one or more heterologous nucleic acids is a CsPT4_t131 polypeptide and comprises an amino acid sequence having at least 80%, at least 81%, at least 82%, at least 83%, or at least 84% amino acid sequence identity to SEQ ID NO:213. In some embodiments, the GOT polypeptide encoded by the one or more heterologous nucleic acids is a CsPT4_t131 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:213.

In some embodiments, the GOT polypeptide encoded by the one or more heterologous nucleic acids is a truncated CsPT4 (CsPT4_t142) polypeptide and comprises the amino acid sequence set forth in SEQ ID NO:215. In some embodiments, the GOT polypeptide encoded by the one or more heterologous nucleic acids is a CsPT4_t142 polypeptide and comprises the amino acid sequence set forth in SEQ ID NO:215, or a conservatively substituted amino acid sequence thereof. In some embodiments, the GOT polypeptide encoded by the one or more heterologous nucleic acids is a CsPT4_t142 polypeptide and comprises an amino acid sequence having at least 65%, at least 70%, or at least 75% amino acid sequence identity to SEQ ID NO:215. In some embodiments, the GOT polypeptide encoded by the one or more heterologous nucleic acids is a CsPT4_t142 polypeptide and comprises an amino acid sequence having at least 80%, at least 81%, at least 82%, at least 83%, or at least 84% amino acid sequence identity to SEQ ID NO:215. In some embodiments, the GOT polypeptide encoded by the one or more heterologous nucleic acids is a CsPT4_t142 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:215.

In some embodiments, the GOT polypeptide encoded by the one or more heterologous nucleic acids is a truncated CsPT4 (CsPT4_t166) polypeptide and comprises the amino acid sequence set forth in SEQ ID NO:217. In some embodiments, the GOT polypeptide encoded by the one or more heterologous nucleic acids is a CsPT4_t166 polypeptide and comprises the amino acid sequence set forth in SEQ ID NO:217, or a conservatively substituted amino acid sequence thereof. In some embodiments, the GOT polypeptide encoded by the one or more heterologous nucleic acids is a CsPT4_t166 polypeptide and comprises an amino acid sequence having at least 65%, at least 70%, or at least 75% amino acid sequence identity to SEQ ID NO:217. In some embodiments, the GOT polypeptide encoded by the one or more heterologous nucleic acids is a CsPT4_t166 polypeptide and comprises an amino acid sequence having at least 80%, at least 81%, at least 82%, at least 83%, or at least 84% amino acid sequence identity to SEQ ID NO:217. In some embodiments, the GOT polypeptide encoded by the one or more heterologous nucleic acids is a CsPT4_t166 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:217.

In some embodiments, the GOT polypeptide encoded by the one or more heterologous nucleic acids is a truncated CsPT4 (CsPT4_t186) polypeptide and comprises the amino acid sequence set forth in SEQ ID NO:219. In some embodiments, the GOT polypeptide encoded by the one or more heterologous nucleic acids is a CsPT4_t186 polypeptide and comprises the amino acid sequence set forth in SEQ ID NO:219, or a conservatively substituted amino acid sequence thereof. In some embodiments, the GOT polypeptide encoded by the one or more heterologous nucleic acids is a CsPT4_t186 polypeptide and comprises an amino acid sequence having at least 65%, at least 70%, or at least 75% amino acid sequence identity to SEQ ID NO:219. In some embodiments, the GOT polypeptide encoded by the one or more heterologous nucleic acids is a CsPT4_t186 polypeptide and comprises an amino acid sequence having at least 80%, at least 81%, at least 82%, at least 83%, or at least 84% amino acid sequence identity to SEQ ID NO:219. In some embodiments, the GOT polypeptide encoded by the one or more heterologous nucleic acids is a CsPT4_t186 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:219.

Exemplary GOT heterologous nucleic acids disclosed herein may include nucleic acids that encode a GOT polypeptide, such as, a full-length GOT polypeptide, a fragment of a GOT polypeptide, a variant of a GOT polypeptide, a truncated GOT polypeptide, or a fusion polypeptide that has at least one activity of a GOT polypeptide.

In some embodiments, the GOT polypeptide is overexpressed in the genetically modified host cell. Overexpression may be achieved by increasing the copy number of the GOT polypeptide-encoding heterologous nucleic acid, e.g., through use of a high copy number expression vector (e.g., a plasmid that exists at 10-40 copies per cell) and/or by operably linking the GOT polypeptide-encoding heterologous nucleic acid to a strong promoter. In some embodiments, the genetically modified host cell has one copy of a GOT polypeptide-encoding heterologous nucleic acid. In some embodiments, the genetically modified host cell has two copies of a GOT polypeptide-encoding heterologous nucleic acid. In some embodiments, the genetically modified host cell has three copies of a GOT polypeptide-encoding heterologous nucleic acid. In some embodiments, the genetically modified host cell has four copies of a GOT polypeptide-encoding heterologous nucleic acid. In some embodiments, the genetically modified host cell has five copies of a GOT polypeptide-encoding heterologous nucleic acid. In some embodiments, the genetically modified host cell has four copies of a GOT polypeptide-encoding heterologous nucleic acid. In some embodiments, the genetically modified host cell has six copies of a GOT polypeptide-encoding heterologous nucleic acid. In some embodiments, the genetically modified host cell has four copies of a GOT polypeptide-encoding heterologous nucleic acid. In some embodiments, the genetically modified host cell has seven copies of a GOT polypeptide-encoding heterologous nucleic acid. In some embodiments, the genetically modified host cell has four copies of a GOT polypeptide-encoding heterologous nucleic acid. In some embodiments, the genetically modified host cell has eight copies of a GOT polypeptide-encoding heterologous nucleic acid.

In some embodiments, the one or more heterologous nucleic acids encoding a GOT polypeptide comprise a nucleotide sequence encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82.

In some embodiments, the one or more heterologous nucleic acids encoding a GOT polypeptide comprise the nucleotide sequence set forth in SEQ ID NO:111, SEQ ID NO:221, SEQ ID NO:224, or SEQ ID NO:225. In some embodiments, the one or more heterologous nucleic acids encoding a GOT polypeptide comprise the nucleotide sequence set forth in SEQ ID NO:111, SEQ ID NO:221, SEQ ID NO:224, or SEQ ID NO:225, or a codon degenerate nucleotide sequence thereof. In some embodiments, the one or more heterologous nucleic acids encoding a GOT polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:111, SEQ ID NO:221, SEQ ID NO:224, or SEQ ID NO:225.

In some embodiments, the one or more heterologous nucleic acids encoding a GOT polypeptide comprise the nucleotide sequence set forth in SEQ ID NO:220 or SEQ ID NO:222. In some embodiments, the one or more heterologous nucleic acids encoding a GOT polypeptide comprise the nucleotide sequence set forth in SEQ ID NO:220 or SEQ ID NO:222, or a codon degenerate nucleotide sequence thereof. In some embodiments, the one or more heterologous nucleic acids encoding a GOT polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:220 or SEQ ID NO:222.

In some embodiments, the one or more heterologous nucleic acids encoding a GOT polypeptide comprise the nucleotide sequence set forth in SEQ ID NO:210, SEQ ID NO:212, SEQ ID NO:214, SEQ ID NO:216, or SEQ ID NO:218. In some embodiments, the one or more heterologous nucleic acids encoding a GOT polypeptide comprise the nucleotide sequence set forth in SEQ ID NO:210, SEQ ID NO:212, SEQ ID NO:214, SEQ ID NO:216, or SEQ ID NO:218, or a codon degenerate nucleotide sequence thereof. In some embodiments, the one or more heterologous nucleic acids encoding a GOT polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:210, SEQ ID NO:212, SEQ ID NO:214, SEQ ID NO:216, or SEQ ID NO:218.

In some embodiments, the one or more heterologous nucleic acids encoding a CsPT4 polypeptide comprise the nucleotide sequence set forth in SEQ ID NO:111. In some embodiments, the one or more heterologous nucleic acids encoding a CsPT4 polypeptide comprise the nucleotide sequence set forth in SEQ ID NO:111, or a codon degenerate nucleotide sequence thereof. In some embodiments, the one or more heterologous nucleic acids encoding a CsPT4 polypeptide comprise a nucleotide sequence having at least 80%, at least 81%, at least 82%, at least 83%, or at least 84% sequence identity to SEQ ID NO:111. In some embodiments, the one or more heterologous nucleic acids encoding a CsPT4 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:111. In some embodiments, the one or more heterologous nucleic acids encoding a CsPT4 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:111.

In some embodiments, the one or more heterologous nucleic acids encoding a CsPT4 polypeptide comprise a nucleotide sequence having at least 85% sequence identity to SEQ ID NO:111. In some embodiments, the one or more heterologous nucleic acids encoding a CsPT4 polypeptide comprise a nucleotide sequence having at least 95% sequence identity to SEQ ID NO:111. In some embodiments, the one or more heterologous nucleic acids encoding a CsPT4 polypeptide comprise a nucleotide sequence having at least 85% sequence identity to SEQ ID NO:111, or a codon degenerate nucleotide sequence thereof. In some embodiments, the one or more heterologous nucleic acids encoding a CsPT4 polypeptide comprise a nucleotide sequence having at least 95% sequence identity to SEQ ID NO:111, or a codon degenerate nucleotide sequence thereof.

In some embodiments, the one or more heterologous nucleic acids encoding a CsPT4 polypeptide comprise the nucleotide sequence set forth in SEQ ID NO:225. In some embodiments, the one or more heterologous nucleic acids encoding a CsPT4 polypeptide comprise the nucleotide sequence set forth in SEQ ID NO:225, or a codon degenerate nucleotide sequence thereof. In some embodiments, the one or more heterologous nucleic acids encoding a CsPT4 polypeptide comprise a nucleotide sequence having at least 80%, at least 81%, at least 82%, at least 83%, or at least 84% sequence identity to SEQ ID NO:225. In some embodiments, the one or more heterologous nucleic acids encoding a CsPT4 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:225. In some embodiments, the one or more heterologous nucleic acids encoding a CsPT4 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:225.

In some embodiments, the one or more heterologous nucleic acids encoding a CsPT4 polypeptide comprise a nucleotide sequence having at least 85% sequence identity to SEQ ID NO:225. In some embodiments, the one or more heterologous nucleic acids encoding a CsPT4 polypeptide comprise a nucleotide sequence having at least 95% sequence identity to SEQ ID NO:225. In some embodiments, the one or more heterologous nucleic acids encoding a CsPT4 polypeptide comprise a nucleotide sequence having at least 85% sequence identity to SEQ ID NO:225, or a codon degenerate nucleotide sequence thereof. In some embodiments, the one or more heterologous nucleic acids encoding a CsPT4 polypeptide comprise a nucleotide sequence having at least 95% sequence identity to SEQ ID NO:225, or a codon degenerate nucleotide sequence thereof.

In some embodiments, the one or more heterologous nucleic acids encoding a CsPT4t polypeptide comprise the nucleotide sequence set forth in SEQ ID NO:221. In some embodiments, the one or more heterologous nucleic acids encoding a CsPT4t polypeptide comprise the nucleotide sequence set forth in SEQ ID NO:221, or a codon degenerate nucleotide sequence thereof. In some embodiments, the one or more heterologous nucleic acids encoding a CsPT4t polypeptide comprise a nucleotide sequence having at least 80%, at least 81%, at least 82%, at least 83%, or at least 84% sequence identity to SEQ ID NO:221. In some embodiments, the one or more heterologous nucleic acids encoding a CsPT4t polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:221. In some embodiments, the one or more heterologous nucleic acids encoding a CsPT4t polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:221.

In some embodiments, the one or more heterologous nucleic acids encoding a CsPT4t polypeptide comprise a nucleotide sequence having at least 85% sequence identity to SEQ ID NO:221. In some embodiments, the one or more heterologous nucleic acids encoding a CsPT4t polypeptide comprise a nucleotide sequence having at least 95% sequence identity to SEQ ID NO:221. In some embodiments, the one or more heterologous nucleic acids encoding a CsPT4t polypeptide comprise a nucleotide sequence having at least 85% sequence identity to SEQ ID NO:221, or a codon degenerate nucleotide sequence thereof. In some embodiments, the one or more heterologous nucleic acids encoding a CsPT4t polypeptide comprise a nucleotide sequence having at least 95% sequence identity to SEQ ID NO:221, or a codon degenerate nucleotide sequence thereof.

In some embodiments, the one or more heterologous nucleic acids encoding a CsPT4t polypeptide comprise the nucleotide sequence set forth in SEQ ID NO:224. In some embodiments, the one or more heterologous nucleic acids encoding a CsPT4t polypeptide comprise the nucleotide sequence set forth in SEQ ID NO:224, or a codon degenerate nucleotide sequence thereof. In some embodiments, the one or more heterologous nucleic acids encoding a CsPT4t polypeptide comprise a nucleotide sequence having at least 80%, at least 81%, at least 82%, at least 83%, or at least 84% sequence identity to SEQ ID NO:224. In some embodiments, the one or more heterologous nucleic acids encoding a CsPT4t polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:224. In some embodiments, the one or more heterologous nucleic acids encoding a CsPT4t polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:224.

In some embodiments, the one or more heterologous nucleic acids encoding a CsPT4t polypeptide comprise a nucleotide sequence having at least 85% sequence identity to SEQ ID NO:224. In some embodiments, the one or more heterologous nucleic acids encoding a CsPT4t polypeptide comprise a nucleotide sequence having at least 95% sequence identity to SEQ ID NO:224. In some embodiments, the one or more heterologous nucleic acids encoding a CsPT4t polypeptide comprise a nucleotide sequence having at least 85% sequence identity to SEQ ID NO:224, or a codon degenerate nucleotide sequence thereof. In some embodiments, the one or more heterologous nucleic acids encoding a CsPT4t polypeptide comprise a nucleotide sequence having at least 95% sequence identity to SEQ ID NO:224, or a codon degenerate nucleotide sequence thereof.

In some embodiments, the one or more heterologous nucleic acids encoding a CsPT4_t112 polypeptide comprise the nucleotide sequence set forth in SEQ ID NO:210. In some embodiments, the one or more heterologous nucleic acids encoding a CsPT4_t112 polypeptide comprise the nucleotide sequence set forth in SEQ ID NO:210, or a codon degenerate nucleotide sequence thereof. In some embodiments, the one or more heterologous nucleic acids encoding a CsPT4_t112 polypeptide comprise a nucleotide sequence having at least 80%, at least 81%, at least 82%, at least 83%, or at least 84% sequence identity to SEQ ID NO:210. In some embodiments, the one or more heterologous nucleic acids encoding a CsPT4_t112 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:210. In some embodiments, the one or more heterologous nucleic acids encoding a CsPT4_t112 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:210.

In some embodiments, the one or more heterologous nucleic acids encoding a CsPT4_t131 polypeptide comprise the nucleotide sequence set forth in SEQ ID NO:212. In some embodiments, the one or more heterologous nucleic acids encoding a CsPT4_t131 polypeptide comprise the nucleotide sequence set forth in SEQ ID NO:212, or a codon degenerate nucleotide sequence thereof. In some embodiments, the one or more heterologous nucleic acids encoding a CsPT4_t131 polypeptide comprise a nucleotide sequence having at least 80%, at least 81%, at least 82%, at least 83%, or at least 84% sequence identity to SEQ ID NO:212. In some embodiments, the one or more heterologous nucleic acids encoding a CsPT4_t131 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:212. In some embodiments, the one or more heterologous nucleic acids encoding a CsPT4_t131 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:212.

In some embodiments, the one or more heterologous nucleic acids encoding a CsPT4_t142 polypeptide comprise the nucleotide sequence set forth in SEQ ID NO:214. In some embodiments, the one or more heterologous nucleic acids encoding a CsPT4_t142 polypeptide comprise the nucleotide sequence set forth in SEQ ID NO:214, or a codon degenerate nucleotide sequence thereof. In some embodiments, the one or more heterologous nucleic acids encoding a CsPT4_t142 polypeptide comprise a nucleotide sequence having at least 80%, at least 81%, at least 82%, at least 83%, or at least 84% sequence identity to SEQ ID NO:214. In some embodiments, the one or more heterologous nucleic acids encoding a CsPT4_t142 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:214. In some embodiments, the one or more heterologous nucleic acids encoding a CsPT4_t142 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:214.

In some embodiments, the one or more heterologous nucleic acids encoding a CsPT4_t166 polypeptide comprise the nucleotide sequence set forth in SEQ ID NO:216. In some embodiments, the one or more heterologous nucleic acids encoding a CsPT4_t166 polypeptide comprise the nucleotide sequence set forth in SEQ ID NO:216, or a codon degenerate nucleotide sequence thereof. In some embodiments, the one or more heterologous nucleic acids encoding a CsPT4_t166 polypeptide comprise a nucleotide sequence having at least 80%, at least 81%, at least 82%, at least 83%, or at least 84% sequence identity to SEQ ID NO:216. In some embodiments, the one or more heterologous nucleic acids encoding a CsPT4_t166 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:216. In some embodiments, the one or more heterologous nucleic acids encoding a CsPT4_t166 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:216.

In some embodiments, the one or more heterologous nucleic acids encoding a CsPT4_t186 polypeptide comprise the nucleotide sequence set forth in SEQ ID NO:218. In some embodiments, the one or more heterologous nucleic acids encoding a CsPT4_t186 polypeptide comprise the nucleotide sequence set forth in SEQ ID NO:218, or a codon degenerate nucleotide sequence thereof. In some embodiments, the one or more heterologous nucleic acids encoding a CsPT4_t186 polypeptide comprise a nucleotide sequence having at least 80%, at least 81%, at least 82%, at least 83%, or at least 84% sequence identity to SEQ ID NO:218. In some embodiments, the one or more heterologous nucleic acids encoding a CsPT4_t186 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:218. In some embodiments, the one or more heterologous nucleic acids encoding a CsPT4_t186 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:218.

In some embodiments, the one or more heterologous nucleic acids encoding a CsPT1 polypeptide comprise the nucleotide sequence set forth in SEQ ID NO:220. In some embodiments, the one or more heterologous nucleic acids encoding a CsPT1 polypeptide comprise the nucleotide sequence set forth in SEQ ID NO:220, or a codon degenerate nucleotide sequence thereof. In some embodiments, the one or more heterologous nucleic acids encoding a CsPT1 polypeptide comprise a nucleotide sequence having at least 80%, at least 81%, at least 82%, at least 83%, or at least 84% sequence identity to SEQ ID NO:220. In some embodiments, the one or more heterologous nucleic acids encoding a CsPT1 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:220. In some embodiments, the one or more heterologous nucleic acids encoding a CsPT1 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:220.

In some embodiments, the one or more heterologous nucleic acids encoding a CsPT1_t75 polypeptide comprise the nucleotide sequence set forth in SEQ ID NO:222. In some embodiments, the one or more heterologous nucleic acids encoding a CsPT1_t75 polypeptide comprise the nucleotide sequence set forth in SEQ ID NO:222, or a codon degenerate nucleotide sequence thereof. In some embodiments, the one or more heterologous nucleic acids encoding a CsPT1_t75 polypeptide comprise a nucleotide sequence having at least 80%, at least 81%, at least 82%, at least 83%, or at least 84% sequence identity to SEQ ID NO:222. In some embodiments, the one or more heterologous nucleic acids encoding a CsPT1_t75 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:222. In some embodiments, the one or more heterologous nucleic acids encoding a CsPT1_t75 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:222.

Cannabinoid Synthase Polypeptides, Nucleic Acids Comprising Said Polypeptides, and Genetically Modified Host Cells Expressing Said Polypeptides In some embodiments, a genetically modified host cell of the present disclosure is genetically modified with one or more heterologous nucleic acids encoding a cannabinoid synthase polypeptide.

In some embodiments, a genetically modified host cell of the present disclosure is genetically modified with one or more heterologous nucleic acids encoding more than one cannabinoid synthase polypeptide. In some embodiments, a genetically modified host cell of the present disclosure is genetically modified with one or more heterologous nucleic acids encoding more than two cannabinoid synthase polypeptides. In some embodiments, a genetically modified host cell of the present disclosure is genetically modified with one or more heterologous nucleic acids encoding more than three cannabinoid synthase polypeptides. In some embodiments, a genetically modified host cell of the present disclosure is genetically modified with one or more heterologous nucleic acids encoding two cannabinoid synthase polypeptides. In some embodiments, a genetically modified host cell of the present disclosure is genetically modified with one or more heterologous nucleic acids encoding three cannabinoid synthase polypeptides. In some embodiments, a genetically modified host cell of the present disclosure is genetically modified with one or more heterologous nucleic acids encoding 1, 2, 3, or more cannabinoid synthase polypeptides. In some embodiments, a genetically modified host cell of the present disclosure is genetically modified with one or more heterologous nucleic acids encoding 1, 2, or 3 cannabinoid synthase polypeptides.

In some embodiments, a cannabinoid synthase polypeptide is a tetrahydrocannabinolic acid synthase (THCAS) polypeptide. THCAS polypeptides can catalyze the conversion of cannabigerolic acid to THCA. Exemplary THCAS polypeptides disclosed herein may include a fragment of a THCAS polypeptide, a full-length THCAS polypeptide, a variant of a THCAS polypeptide, a truncated THCAS polypeptide, or a fusion polypeptide that has at least one activity of a THCAS polypeptide.

In some embodiments, a genetically modified host cell of the present disclosure is genetically modified with one or more heterologous nucleic acids encoding a THCAS polypeptide. In some embodiments, a genetically modified host cell of the present disclosure is genetically modified with one or more heterologous nucleic acids encoding more than one THCAS polypeptide. In some embodiments, a genetically modified host cell of the present disclosure is genetically modified with one or more heterologous nucleic acids encoding more than two THCAS polypeptides. In some embodiments, a genetically modified host cell of the present disclosure is genetically modified with one or more heterologous nucleic acids encoding more than three THCAS polypeptides. In some embodiments, a genetically modified host cell of the present disclosure is genetically modified with one or more heterologous nucleic acids encoding two THCAS polypeptides. In some embodiments, a genetically modified host cell of the present disclosure is genetically modified with one or more heterologous nucleic acids encoding three THCAS polypeptides. In some embodiments, a genetically modified host cell of the present disclosure is genetically modified with one or more heterologous nucleic acids encoding 1, 2, 3, or more THCAS polypeptides. In some embodiments, a genetically modified host cell of the present disclosure is genetically modified with one or more heterologous nucleic acids encoding 1, 2, or 3 THCAS polypeptides.

In some embodiments, the THCAS polypeptide encoded by the one or more heterologous nucleic acids comprises the amino acid sequence set forth in SEQ ID NO:14, SEQ ID NO:86, SEQ ID NO:104, SEQ ID NO:153, or SEQ ID NO:155. In some embodiments, the THCAS polypeptide encoded by the one or more heterologous nucleic acids comprises the amino acid sequence set forth in SEQ ID NO:14, SEQ ID NO:86, SEQ ID NO:104, SEQ ID NO:153, or SEQ ID NO:155, or a conservatively substituted amino acid sequence thereof. In some embodiments, the THCAS polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:14, SEQ ID NO:86, SEQ ID NO:104, SEQ ID NO:153, or SEQ ID NO:155.

In some embodiments, the THCAS polypeptide encoded by the one or more heterologous nucleic acids comprises the amino acid sequence set forth in SEQ ID NO:14. In some embodiments, the THCAS polypeptide encoded by the one or more heterologous nucleic acids comprises the amino acid sequence set forth in SEQ ID NO:14, or a conservatively substituted amino acid sequence thereof. In some embodiments, the THCAS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:14. In some embodiments, the THCAS polypeptide encoded by the one or more heterologous nucleic acids comprises an amino acid sequence having at least 80%, at least 81%, at least 82%, at least 83%, or at least 84% amino acid sequence identity to SEQ ID NO:14. In some embodiments, the THCAS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:14.

In some embodiments, the THCAS polypeptide encoded by the one or more heterologous nucleic acids comprises the amino acid sequence set forth in SEQ ID NO:86. In some embodiments, the THCAS polypeptide encoded by the one or more heterologous nucleic acids comprises the amino acid sequence set forth in SEQ ID NO:86, or a conservatively substituted amino acid sequence thereof. In some embodiments, the THCAS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:86. In some embodiments, the THCAS polypeptide encoded by the one or more heterologous nucleic acids comprises an amino acid sequence having at least 80%, at least 81%, at least 82%, at least 83%, or at least 84% amino acid sequence identity to SEQ ID NO:86. In some embodiments, the THCAS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:86.

In some embodiments, the THCAS polypeptide encoded by the one or more heterologous nucleic acids comprises the amino acid sequence set forth in SEQ ID NO:155. In some embodiments, the THCAS polypeptide encoded by the one or more heterologous nucleic acids comprises the amino acid sequence set forth in SEQ ID NO:155, or a conservatively substituted amino acid sequence thereof. In some embodiments, the THCAS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:155. In some embodiments, the THCAS polypeptide encoded by the one or more heterologous nucleic acids comprises an amino acid sequence having at least 80%, at least 81%, at least 82%, at least 83%, or at least 84% amino acid sequence identity to SEQ ID NO:155. In some embodiments, the THCAS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:155.

In some embodiments, the THCAS polypeptide may include a modified THCAS polypeptide with an N-terminal truncation to remove the secretion peptide and localize to cytoplasm. For example, in some embodiments, the THCAS polypeptide lacks N-terminal amino acids 1-28 of the amino acid sequence set forth in SEQ ID NO:14, or a corresponding signal peptide of another THCAS polypeptide.

In some embodiments, the THCAS polypeptide encoded by the one or more heterologous nucleic acids comprises the amino acid sequence set forth in SEQ ID NO:15. In some embodiments, the THCAS polypeptide encoded by the one or more heterologous nucleic acids comprises the amino acid sequence set forth in SEQ ID NO:15, or a conservatively substituted amino acid sequence thereof. In some embodiments, the THCAS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:15. In some embodiments, the THCAS polypeptide encoded by the one or more heterologous nucleic acids comprises an amino acid sequence having at least 80%, at least 81%, at least 82%, at least 83%, or at least 84% amino acid sequence identity to SEQ ID NO:15.

In some embodiments, the THCAS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:15.

In some embodiments, the THCAS polypeptide encoded by the one or more heterologous nucleic acids comprises the amino acid sequence set forth in SEQ ID NO: 104. In some embodiments, the THCAS polypeptide encoded by the one or more heterologous nucleic acids comprises the amino acid sequence set forth in SEQ ID NO: 104, or a conservatively substituted amino acid sequence thereof. In some embodiments, the THCAS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:104. In some embodiments, the THCAS polypeptide encoded by the one or more heterologous nucleic acids comprises an amino acid sequence having at least 80%, at least 81%, at least 82%, at least 83%, or at least 84% amino acid sequence identity to SEQ ID NO:104. In some embodiments, the THCAS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:104.

In some embodiments, the THCAS polypeptide encoded by the one or more heterologous nucleic acids comprises the amino acid sequence set forth in SEQ ID NO: 153. In some embodiments, the THCAS polypeptide encoded by the one or more heterologous nucleic acids comprises the amino acid sequence set forth in SEQ ID NO: 153, or a conservatively substituted amino acid sequence thereof. In some embodiments, the THCAS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:153. In some embodiments, the THCAS polypeptide encoded by the one or more heterologous nucleic acids comprises an amino acid sequence having at least 80%, at least 81%, at least 82%, at least 83%, or at least 84% amino acid sequence identity to SEQ ID NO:153. In some embodiments, the THCAS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:153.

Exemplary THCAS heterologous nucleic acids disclosed herein may include nucleic acids that encode a THCAS polypeptide, such as, a fragment of a THCAS polypeptide, a variant of a THCAS polypeptide, a full-length THCAS polypeptide, a truncated THCAS polypeptide, or a fusion polypeptide that has at least one activity of a THCAS polypeptide.

In some embodiments, the THCAS polypeptide is overexpressed in the genetically modified host cell. Overexpression may be achieved by increasing the copy number of the THCAS polypeptide-encoding heterologous nucleic acid, e.g., through use of a high copy number expression vector (e.g., a plasmid that exists at 10-40 copies per cell) and/or by operably linking the THCAS polypeptide-encoding heterologous nucleic acid to a strong promoter. In some embodiments, the genetically modified host cell has one copy of a THCAS polypeptide-encoding heterologous nucleic acid. In some embodiments, the genetically modified host cell has two copies of a THCAS polypeptide-encoding heterologous nucleic acid. In some embodiments, the genetically modified host cell has three copies of a THCAS polypeptide-encoding heterologous nucleic acid. In some embodiments, the genetically modified host cell has four copies of a THCAS polypeptide-encoding heterologous nucleic acid. In some embodiments, the genetically modified host cell has five copies of a THCAS polypeptide-encoding heterologous nucleic acid. In some embodiments, the genetically modified host cell has six copies of a THCAS polypeptide-encoding heterologous nucleic acid. In some embodiments, the genetically modified host cell has seven copies of a THCAS polypeptide-encoding heterologous nucleic acid. In some embodiments, the genetically modified host cell has eight copies of a THCAS polypeptide-encoding heterologous nucleic acid.

In some embodiments, the one or more heterologous nucleic acids encoding a THCAS polypeptide comprise the nucleotide sequence set forth in SEQ ID NO:85, SEQ ID NO:154, or SEQ ID NO:156. In some embodiments, the one or more heterologous nucleic acids encoding a THCAS polypeptide comprise the nucleotide sequence set forth in SEQ ID NO:85, SEQ ID NO:154, or SEQ ID NO:156, or a codon degenerate nucleotide sequence thereof. In some embodiments, the one or more heterologous nucleic acids encoding a THCAS polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:85, SEQ ID NO:154, or SEQ ID NO:156.

In some embodiments, the one or more heterologous nucleic acids encoding a THCAS polypeptide comprise the nucleotide sequence set forth in SEQ ID NO:85. In some embodiments, the one or more heterologous nucleic acids encoding a THCAS polypeptide comprise the nucleotide sequence set forth in SEQ ID NO:85, or a codon degenerate nucleotide sequence thereof. In some embodiments, the one or more heterologous nucleic acids encoding a THCAS polypeptide comprise a nucleotide sequence having at least 80%, at least 81%, at least 82%, at least 83%, or at least 84% sequence identity to SEQ ID NO:85. In some embodiments, the one or more heterologous nucleic acids encoding a THCAS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:85.

In some embodiments, the one or more heterologous nucleic acids encoding a THCAS polypeptide comprise the nucleotide sequence set forth in SEQ ID NO:154. In some embodiments, the one or more heterologous nucleic acids encoding a THCAS polypeptide comprise the nucleotide sequence set forth in SEQ ID NO:154, or a codon degenerate nucleotide sequence thereof. In some embodiments, the one or more heterologous nucleic acids encoding a THCAS polypeptide comprise a nucleotide sequence having at least 80%, at least 81%, at least 82%, at least 83%, or at least 84% sequence identity to SEQ ID NO:154. In some embodiments, the one or more heterologous nucleic acids encoding a THCAS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:154.

In some embodiments, the one or more heterologous nucleic acids encoding a THCAS polypeptide comprise the nucleotide sequence set forth in SEQ ID NO:156. In some embodiments, the one or more heterologous nucleic acids encoding a THCAS polypeptide comprise the nucleotide sequence set forth in SEQ ID NO:156, or a codon degenerate nucleotide sequence thereof. In some embodiments, the one or more heterologous nucleic acids encoding a THCAS polypeptide comprise a nucleotide sequence having at least 80%, at least 81%, at least 82%, at least 83%, or at least 84% sequence identity to SEQ ID NO:156. In some embodiments, the one or more heterologous nucleic acids encoding a THCAS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:156.

In some embodiments, a cannabinoid synthase polypeptide is cannabidiolic acid synthase (CBDAS) polypeptide. CBDAS polypeptides can catalyze the conversion of cannabigerolic acid to cannabidiolic acid (CBDA). Exemplary CBDAS polypeptides disclosed herein may include a full-length CBDAS polypeptide, a fragment of a CBDAS polypeptide, a variant of a CBDAS polypeptide, a truncated CBDAS polypeptide, or a fusion polypeptide that has at least one activity of a CBDAS polypeptide.

In some embodiments, a genetically modified host cell of the present disclosure is genetically modified with one or more heterologous nucleic acids encoding a CBDAS polypeptide. In some embodiments, a genetically modified host cell of the present disclosure is genetically modified with one or more heterologous nucleic acids encoding more than one CBDAS polypeptide. In some embodiments, a genetically modified host cell of the present disclosure is genetically modified with one or more heterologous nucleic acids encoding more than two CBDAS polypeptides. In some embodiments, a genetically modified host cell of the present disclosure is genetically modified with one or more heterologous nucleic acids encoding more than three CBDAS polypeptides. In some embodiments, a genetically modified host cell of the present disclosure is genetically modified with one or more heterologous nucleic acids encoding two CBDAS polypeptides. In some embodiments, a genetically modified host cell of the present disclosure is genetically modified with one or more heterologous nucleic acids encoding three CBDAS polypeptides. In some embodiments, a genetically modified host cell of the present disclosure is genetically modified with one or more heterologous nucleic acids encoding 1, 2, 3, or more CBDAS polypeptides. In some embodiments, a genetically modified host cell of the present disclosure is genetically modified with one or more heterologous nucleic acids encoding 1, 2, or 3 CBDAS polypeptides.

In some embodiments, the CBDAS polypeptide encoded by the one or more heterologous nucleic acids comprises the amino acid sequence set forth in SEQ ID NO:88 or SEQ ID NO:151. In some embodiments, the CBDAS polypeptide encoded by the one or more heterologous nucleic acids comprises the amino acid sequence set forth in SEQ ID NO:88 or SEQ ID NO:151, or a conservatively substituted amino acid sequence thereof. In some embodiments, the CBDAS polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:88 or SEQ ID NO:151.

In some embodiments, the CBDAS polypeptide encoded by the one or more heterologous nucleic acids comprises the amino acid sequence set forth in SEQ ID NO:88. In some embodiments, the CBDAS polypeptide encoded by the one or more heterologous nucleic acids comprises the amino acid sequence set forth in SEQ ID NO:88, or a conservatively substituted amino acid sequence thereof. In some embodiments, the CBDAS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:88. In some embodiments, the CBDAS polypeptide encoded by the one or more heterologous nucleic acids comprises an amino acid sequence having at least 80%, at least 81%, at least 82%, at least 83%, or at least 84% amino acid sequence identity to SEQ ID NO:88. In some embodiments, the CBDAS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:88.

In some embodiments, the CBDAS polypeptide may include a modified CBDAS polypeptide with an N-terminal truncation to remove the secretion peptide and localize to cytoplasm. For example, in some embodiments, the CBDAS polypeptide lacks N-terminal amino acids 1-28 of the amino acid sequence set forth in SEQ ID NO:88, or a corresponding signal peptide of another CBDAS polypeptide.

In some embodiments, the CBDAS polypeptide encoded by the one or more heterologous nucleic acids comprises the amino acid sequence set forth in SEQ ID NO:16. In some embodiments, the CBDAS polypeptide encoded by the one or more heterologous nucleic acids comprises the amino acid sequence set forth in SEQ ID NO:16, or a conservatively substituted amino acid sequence thereof. In some embodiments, the CBDAS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:16. In some embodiments, the CBDAS polypeptide encoded by the one or more heterologous nucleic acids comprises an amino acid sequence having at least 80%, at least 81%, at least 82%, at least 83%, or at least 84% amino acid sequence identity to SEQ ID NO:16. In some embodiments, the CBDAS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:16.

In some embodiments, the CBDAS polypeptide encoded by the one or more heterologous nucleic acids comprises the amino acid sequence set forth in SEQ ID NO:105. In some embodiments, the CBDAS polypeptide encoded by the one or more heterologous nucleic acids comprises the amino acid sequence set forth in SEQ ID NO:105, or a conservatively substituted amino acid sequence thereof. In some embodiments, the CBDAS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:105. In some embodiments, the CBDAS polypeptide encoded by the one or more heterologous nucleic acids comprises an amino acid sequence having at least 80%, at least 81%, at least 82%, at least 83%, or at least 84% amino acid sequence identity to SEQ ID NO:105. In some embodiments, the CBDAS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:105.

In some embodiments, the CBDAS polypeptide encoded by the one or more heterologous nucleic acids comprises the amino acid sequence set forth in SEQ ID NO:151. In some embodiments, the CBDAS polypeptide encoded by the one or more heterologous nucleic acids comprises the amino acid sequence set forth in SEQ ID NO:151, or a conservatively substituted amino acid sequence thereof. In some embodiments, the CBDAS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:151. In some embodiments, the CBDAS polypeptide encoded by the one or more heterologous nucleic acids comprises an amino acid sequence having at least 80%, at least 81%, at least 82%, at least 83%, or at least 84% amino acid sequence identity to SEQ ID NO:151. In some embodiments, the CBDAS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:151.

Exemplary CBDAS heterologous nucleic acids disclosed herein may include nucleic acids that encode a CBDAS polypeptide, such as, a full-length CBDAS polypeptide, a fragment of a CBDAS polypeptide, a variant of a CBDAS polypeptide, a truncated CBDAS polypeptide, or a fusion polypeptide that has at least one activity of a CBDAS polypeptide.

In some embodiments, the CBDAS polypeptide is overexpressed in the genetically modified host cell. Overexpression may be achieved by increasing the copy number of the CBDAS polypeptide-encoding heterologous nucleic acid, e.g., through use of a high copy number expression vector (e.g., a plasmid that exists at 10-40 copies per cell) and/or by operably linking the CBDAS polypeptide-encoding heterologous nucleic acid to a strong promoter. In some embodiments, the genetically modified host cell has one copy of a CBDAS polypeptide-encoding heterologous nucleic acid. In some embodiments, the genetically modified host cell has two copies of a CBDAS polypeptide-encoding heterologous nucleic acid. In some embodiments, the genetically modified host cell has three copies of a CBDAS polypeptide-encoding heterologous nucleic acid. In some embodiments, the genetically modified host cell has four copies of a CBDAS polypeptide-encoding heterologous nucleic acid. In some embodiments, the genetically modified host cell has five copies of a CBDAS polypeptide-encoding heterologous nucleic acid. In some embodiments, the genetically modified host cell has six copies of a CBDAS polypeptide-encoding heterologous nucleic acid. In some embodiments, the genetically modified host cell has seven copies of a CBDAS polypeptide-encoding heterologous nucleic acid. In some embodiments, the genetically modified host cell has eight copies of a CBDAS polypeptide-encoding heterologous nucleic acid.

In some embodiments, the one or more heterologous nucleic acids encoding a CBDAS polypeptide comprise the nucleotide sequence set forth in SEQ ID NO:152 or SEQ ID NO:167. In some embodiments, the one or more heterologous nucleic acids encoding a CBDAS polypeptide comprise the nucleotide sequence set forth in SEQ ID NO:152 or SEQ ID NO:167, or a codon degenerate nucleotide sequence thereof. In some embodiments, the one or more heterologous nucleic acids encoding a CBDAS polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:152 or SEQ ID NO:167.

In some embodiments, the one or more heterologous nucleic acids encoding a CBDAS polypeptide comprise the nucleotide sequence set forth in SEQ ID NO:87. In some embodiments, the one or more heterologous nucleic acids encoding a CBDAS polypeptide comprise the nucleotide sequence set forth in SEQ ID NO:87, or a codon degenerate nucleotide sequence thereof. In some embodiments, the one or more heterologous nucleic acids encoding a CBDAS polypeptide comprise a nucleotide sequence having at least 80%, at least 81%, at least 82%, at least 83%, or at least 84% sequence identity to SEQ ID NO:87. In some embodiments, the one or more heterologous nucleic acids encoding a CBDAS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:87.

In some embodiments, the one or more heterologous nucleic acids encoding a CBDAS polypeptide comprise the nucleotide sequence set forth in SEQ ID NO:152. In some embodiments, the one or more heterologous nucleic acids encoding a CBDAS polypeptide comprise the nucleotide sequence set forth in SEQ ID NO:152, or a codon degenerate nucleotide sequence thereof. In some embodiments, the one or more heterologous nucleic acids encoding a CBDAS polypeptide comprise a nucleotide sequence having at least 80%, at least 81%, at least 82%, at least 83%, or at least 84% sequence identity to SEQ ID NO:152. In some embodiments, the one or more heterologous nucleic acids encoding a CBDAS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:152.

In some embodiments, the one or more heterologous nucleic acids encoding a CBDAS polypeptide comprise the nucleotide sequence set forth in SEQ ID NO:167. In some embodiments, the one or more heterologous nucleic acids encoding a CBDAS polypeptide comprise the nucleotide sequence set forth in SEQ ID NO:167, or a codon degenerate nucleotide sequence thereof. In some embodiments, the one or more heterologous nucleic acids encoding a CBDAS polypeptide comprise a nucleotide sequence having at least 80%, at least 81%, at least 82%, at least 83%, or at least 84% sequence identity to SEQ ID NO:167. In some embodiments, the one or more heterologous nucleic acids encoding a CBDAS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:167.

In some embodiments, at least one of the heterologous nucleic acids encoding a cannabinoid synthase polypeptide is operably linked to an inducible promoter. In some embodiments, at least one of the heterologous nucleic acids encoding a cannabinoid synthase polypeptide is operably linked to a constitutive promoter. In some embodiments, a signal peptide is linked to the N-terminus of a THCAS or CBDAS polypeptide or other cannabinoid synthase polypeptide.

Polypeptides that Generate Acyl-CoA Compounds or Acyl-CoA Compound Derivatives, Nucleic Acids Comprising Said Polypeptides, and Genetically Modified Host Cells Expressing Said Polypeptides In some embodiments, a genetically modified host cell of the present disclosure is genetically modified with one or more heterologous nucleic acids encoding a polypeptide that generates acyl-CoA compounds or acyl-CoA compound derivatives. Such polypeptides may include, but are not limited to, acyl-activating enzyme (AAE) polypeptides, fatty acyl-CoA synthetases (FAA) polypeptides, or fatty acyl-CoA ligase polypeptides.

In some embodiments, a genetically modified host cell of the present disclosure is genetically modified with one or more heterologous nucleic acids encoding an AAE, FAA, or fatty acyl-CoA ligase polypeptide. In some embodiments, a genetically modified host cell of the present disclosure is genetically modified with one or more heterologous nucleic acids encoding more than one AAE, FAA, or fatty acyl-CoA ligase polypeptide. In some embodiments, a genetically modified host cell of the present disclosure is genetically modified with one or more heterologous nucleic acids encoding more than two AAE, FAA, or fatty acyl-CoA ligase polypeptides. In some embodiments, a genetically modified host cell of the present disclosure is genetically modified with one or more heterologous nucleic acids encoding more than three AAE, FAA, or fatty acyl-CoA ligase polypeptides. In some embodiments, a genetically modified host cell of the present disclosure is genetically modified with one or more heterologous nucleic acids encoding two AAE, FAA, or fatty acyl-CoA ligase polypeptides. In some embodiments, a genetically modified host cell of the present disclosure is genetically modified with one or more heterologous nucleic acids encoding three AAE, FAA, or fatty acyl-CoA ligase polypeptides. In some embodiments, a genetically modified host cell of the present disclosure is genetically modified with one or more heterologous nucleic acids encoding 1, 2, 3, or more AAE, FAA, or fatty acyl-CoA ligase polypeptides. In some embodiments, a genetically modified host cell of the present disclosure is genetically modified with one or more heterologous nucleic acids encoding 1, 2, or 3 AAE, FAA, or fatty acyl-CoA ligase polypeptides.

AAE polypeptides, FAA polypeptides, and fatty acyl-CoA ligase polypeptides can convert carboxylic acids to their CoA forms and generate acyl-CoA compounds or acyl-CoA compound derivatives. Promiscuous acyl-activating enzyme polypeptides, such as CsAAE1 and CsAAE3, FAA polypeptides, or fatty acyl-CoA ligase polypeptides, may permit generation of cannabinoid derivatives (e.g., cannabigerolic acid derivatives) or cannabinoid precursor derivatives (e.g., olivetolic acid derivatives), as well as cannabinoids (e.g., cannabigerolic acid) or precursors thereof (e.g., olivetolic acid). In some embodiments, hexanoic acid or carboxylic acids other than hexanoic acid are fed to genetically modified host cells expressing an AAE polypeptide, FAA polypeptide, or fatty acyl-CoA ligase polypeptide (e.g., are present in the culture medium in which the cells are grown) to generate hexanoyl-CoA, acyl-CoA compounds, derivatives of hexanoyl-CoA, or derivatives of acyl-CoA compounds. In certain such embodiments, the cell culture medium comprising the genetically modified host cells comprises hexanoate. In some embodiments, the cell culture medium comprising the genetically modified host cells comprises a carboxylic acid other than hexanoate.

Exemplary AAE, FAA, or fatty acyl-CoA ligase polypeptides disclosed herein may include a full-length AAE, FAA, or fatty acyl-CoA ligase polypeptide; a fragment of a AAE, FAA, or fatty acyl-CoA ligase polypeptide; a variant of a AAE, FAA, or fatty acyl-CoA ligase polypeptide; a truncated AAE, FAA, or fatty acyl-CoA ligase polypeptide; or a fusion polypeptide that has at least one activity of an AAE, FAA, or fatty acyl-CoA ligase polypeptide.

In some embodiments, the AAE polypeptide encoded by the one or more heterologous nucleic acids is a CsAAE1 polypeptide and comprises the amino acid sequence set forth in SEQ ID NO:90. In some embodiments, the AAE polypeptide encoded by the one or more heterologous nucleic acids is a CsAAE1 polypeptide and comprises the amino acid sequence set forth in SEQ ID NO:90, or a conservatively substituted amino acid sequence thereof. In some embodiments, the AAE polypeptide encoded by the one or more heterologous nucleic acids is a CsAAE1 polypeptide and comprises an amino acid sequence having at least 50%, at least 55%, at least 60%, at least 65%, at least 70%, or at least 75% amino acid sequence identity to SEQ ID NO:90. In some embodiments, the AAE polypeptide encoded by the one or more heterologous nucleic acids is a CsAAE1 polypeptide and comprises an amino acid sequence having at least 80%, at least 81%, at least 82%, at least 83%, or at least 84% amino acid sequence identity to SEQ ID NO:90. In some embodiments, the AAE polypeptide encoded by the one or more heterologous nucleic acids is a CsAAE1 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:90. In some embodiments, the AAE polypeptide encoded by the one or more heterologous nucleic acids is a CsAAE1 polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:90.

In some embodiments, the AAE polypeptide encoded by the one or more heterologous nucleic acids is a CsAAE3 polypeptide and comprises the amino acid sequence set forth in SEQ ID NO:92 or SEQ ID NO:149. In some embodiments, the AAE polypeptide encoded by the one or more heterologous nucleic acids is a CsAAE3 polypeptide and comprises the amino acid sequence set forth in SEQ ID NO:92 or SEQ ID NO:149, or a conservatively substituted amino acid sequence thereof. In some embodiments, the AAE polypeptide encoded by the one or more heterologous nucleic acids is a CsAAE3 polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:92 or SEQ ID NO:149.

In some embodiments, the AAE polypeptide encoded by the one or more heterologous nucleic acids is a CsAAE3 polypeptide and comprises the amino acid sequence set forth in SEQ ID NO:92. In some embodiments, the AAE polypeptide encoded by the one or more heterologous nucleic acids is a CsAAE3 polypeptide and comprises the amino acid sequence set forth in SEQ ID NO:92, or a conservatively substituted amino acid sequence thereof. In some embodiments, the AAE polypeptide encoded by the one or more heterologous nucleic acids is a CsAAE3 polypeptide and comprises an amino acid sequence having at least 50%, at least 55%, at least 60%, at least 65%, at least 70%, or at least 75% amino acid sequence identity to SEQ ID NO:92. In some embodiments, the AAE polypeptide encoded by the one or more heterologous nucleic acids is a CsAAE3 polypeptide and comprises an amino acid sequence having at least 80%, at least 81%, at least 82%, at least 83%, or at least 84% amino acid sequence identity to SEQ ID NO:92. In some embodiments, the AAE polypeptide encoded by the one or more heterologous nucleic acids is a CsAAE3 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:92.

In some embodiments, the AAE polypeptide encoded by the one or more heterologous nucleic acids is a CsAAE3 polypeptide and comprises the amino acid sequence set forth in SEQ ID NO:112. In some embodiments, the AAE polypeptide encoded by the one or more heterologous nucleic acids is a CsAAE3 polypeptide and comprises the amino acid sequence set forth in SEQ ID NO:112, or a conservatively substituted amino acid sequence thereof. In some embodiments, the AAE polypeptide encoded by the one or more heterologous nucleic acids is a CsAAE3 polypeptide and comprises an amino acid sequence having at least 50%, at least 55%, at least 60%, at least 65%, at least 70%, or at least 75% amino acid sequence identity to SEQ ID NO:112. In some embodiments, the AAE polypeptide encoded by the one or more heterologous nucleic acids is a CsAAE3 polypeptide and comprises an amino acid sequence having at least 80%, at least 81%, at least 82%, at least 83%, or at least 84% amino acid sequence identity to SEQ ID NO:112. In some embodiments, the AAE polypeptide encoded by the one or more heterologous nucleic acids is a CsAAE3 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:112. In these proceeding embodiments, the CsAAE3 polypeptide lacks the RELIQKVRSNM C-terminal amino acids.

In some embodiments, the AAE polypeptide encoded by the one or more heterologous nucleic acids is a CsAAE3 polypeptide and comprises the amino acid sequence set forth in SEQ ID NO:149. In some embodiments, the AAE polypeptide encoded by the one or more heterologous nucleic acids is a CsAAE3 polypeptide and comprises the amino acid sequence set forth in SEQ ID NO:149, or a conservatively substituted amino acid sequence thereof. In some embodiments, the AAE polypeptide encoded by the one or more heterologous nucleic acids is a CsAAE3 polypeptide and comprises an amino acid sequence having at least 50%, at least 55%, at least 60%, at least 65%, at least 70%, or at least 75% amino acid sequence identity to SEQ ID NO:149. In some embodiments, the AAE polypeptide encoded by the one or more heterologous nucleic acids is a CsAAE3 polypeptide and comprises an amino acid sequence having at least 80%, at least 81%, at least 82%, at least 83%, or at least 84% amino acid sequence identity to SEQ ID NO:149. In some embodiments, the AAE polypeptide encoded by the one or more heterologous nucleic acids is a CsAAE3 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:149. In these proceeding embodiments, the CsAAE3 polypeptide lacks the RRELIQKVRSNM C-terminal amino acids.

In some embodiments, the fatty acyl-CoA ligase polypeptide encoded by the one or more heterologous nucleic acids is a FADK polypeptide and comprises the amino acid sequence set forth in SEQ ID NO:145 or SEQ ID NO:147. In some embodiments, the fatty acyl-CoA ligase polypeptide encoded by the one or more heterologous nucleic acids is a FADK polypeptide and comprises the amino acid sequence set forth in SEQ ID NO:145 or SEQ ID NO:147, or a conservatively substituted amino acid sequence thereof. In some embodiments, the fatty acyl-CoA ligase polypeptide encoded by the one or more heterologous nucleic acids is a FADK polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:145 or SEQ ID NO:147.

In some embodiments, the fatty acyl-CoA ligase polypeptide encoded by the one or more heterologous nucleic acids is a FADK polypeptide and comprises the amino acid sequence set forth in SEQ ID NO:145. In some embodiments, the fatty acyl-CoA ligase polypeptide encoded by the one or more heterologous nucleic acids is a FADK polypeptide and comprises the amino acid sequence set forth in SEQ ID NO:145, or a conservatively substituted amino acid sequence thereof. In some embodiments, the fatty acyl-CoA ligase polypeptide encoded by the one or more heterologous nucleic acids is a FADK polypeptide and comprises an amino acid sequence having at least 50%, at least 55%, at least 60%, at least 65%, at least 70%, or at least 75% amino acid sequence identity to SEQ ID NO:145. In some embodiments, the fatty acyl-CoA ligase polypeptide encoded by the one or more heterologous nucleic acids is a FADK polypeptide and comprises an amino acid sequence having at least 80%, at least 81%, at least 82%, at least 83%, or at least 84% amino acid sequence identity to SEQ ID NO:145. In some embodiments, the fatty acyl-CoA ligase polypeptide encoded by the one or more heterologous nucleic acids is a FADK polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:145.

In some embodiments, the fatty acyl-CoA ligase polypeptide encoded by the one or more heterologous nucleic acids is a FADK polypeptide and comprises the amino acid sequence set forth in SEQ ID NO:147. In some embodiments, the fatty acyl-CoA ligase polypeptide encoded by the one or more heterologous nucleic acids is a FADK polypeptide and comprises the amino acid sequence set forth in SEQ ID NO:147, or a conservatively substituted amino acid sequence thereof. In some embodiments, the fatty acyl-CoA ligase polypeptide encoded by the one or more heterologous nucleic acids is a FADK polypeptide and comprises an amino acid sequence having at least 50%, at least 55%, at least 60%, at least 65%, at least 70%, or at least 75% amino acid sequence identity to SEQ ID NO:147. In some embodiments, the fatty acyl-CoA ligase polypeptide encoded by the one or more heterologous nucleic acids is a FADK polypeptide and comprises an amino acid sequence having at least 80%, at least 81%, at least 82%, at least 83%, or at least 84% amino acid sequence identity to SEQ ID NO:147. In some embodiments, the fatty acyl-CoA ligase polypeptide encoded by the one or more heterologous nucleic acids is a FADK polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:147.

In some embodiments, the FAA polypeptide encoded by the one or more heterologous nucleic acids comprises the amino acid sequence set forth in SEQ ID NO:169, SEQ ID NO:192, SEQ ID NO:194, SEQ ID NO:196, SEQ ID NO:198, or SEQ ID NO:200. In some embodiments, the FAA polypeptide encoded by the one or more heterologous nucleic acids comprises the amino acid sequence set forth in SEQ ID NO:169, SEQ ID NO:192, SEQ ID NO:194, SEQ ID NO:196, SEQ ID NO:198, or SEQ ID NO:200, or a conservatively substituted amino acid sequence thereof. In some embodiments, the FAA polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:169, SEQ ID NO:192, SEQ ID NO:194, SEQ ID NO:196, SEQ ID NO:198, or SEQ ID NO:200.

In some embodiments, the FAA polypeptide encoded by the one or more heterologous nucleic acids is a FAA2 polypeptide and comprises the amino acid sequence set forth in SEQ ID NO:169. In some embodiments, the FAA polypeptide encoded by the one or more heterologous nucleic acids is a FAA2 polypeptide and comprises the amino acid sequence set forth in SEQ ID NO:169, or a conservatively substituted amino acid sequence thereof. In some embodiments, the FAA polypeptide encoded by the one or more heterologous nucleic acids is a FAA2 polypeptide and comprises an amino acid sequence having at least 50%, at least 55%, at least 60%, at least 65%, at least 70%, or at least 75% amino acid sequence identity to SEQ ID NO:169. In some embodiments, the FAA polypeptide encoded by the one or more heterologous nucleic acids is a FAA2 polypeptide and comprises an amino acid sequence having at least 80%, at least 81%, at least 82%, at least 83%, or at least 84% amino acid sequence identity to SEQ ID NO:169. In some embodiments, the FAA polypeptide encoded by the one or more heterologous nucleic acids is a FAA2 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:169. In some embodiments, the FAA polypeptide encoded by the one or more heterologous nucleic acids is a FAA2 polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:169.

In some embodiments, the FAA polypeptide encoded by the one or more heterologous nucleic acids is a truncated FAA2 (tFAA2) polypeptide. In some embodiments, the FAA polypeptide encoded by the one or more heterologous nucleic acids is a tFAA2 polypeptide and comprises the amino acid sequence set forth in SEQ ID NO:194. In some embodiments, the FAA polypeptide encoded by the one or more heterologous nucleic acids is a tFAA2 polypeptide and comprises the amino acid sequence set forth in SEQ ID NO:194, or a conservatively substituted amino acid sequence thereof. In some embodiments, the FAA polypeptide encoded by the one or more heterologous nucleic acids is a tFAA2 polypeptide and comprises an amino acid sequence having at least 50%, at least 55%, at least 60%, at least 65%, at least 70%, or at least 75% amino acid sequence identity to SEQ ID NO:194. In some embodiments, the FAA polypeptide encoded by the one or more heterologous nucleic acids is a tFAA2 polypeptide and comprises an amino acid sequence having at least 80%, at least 81%, at least 82%, at least 83%, or at least 84% amino acid sequence identity to SEQ ID NO:194. In some embodiments, the FAA polypeptide encoded by the one or more heterologous nucleic acids is a tFAA2 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:194. In some embodiments, the FAA polypeptide encoded by the one or more heterologous nucleic acids is a tFAA2 polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:194.

In some embodiments, the FAA polypeptide encoded by the one or more heterologous nucleic acids is a mutated FAA2 (FAA2mut) polypeptide. In some embodiments, the FAA polypeptide encoded by the one or more heterologous nucleic acids is a FAA2mut polypeptide and comprises the amino acid sequence set forth in SEQ ID NO:196. In some embodiments, the FAA polypeptide encoded by the one or more heterologous nucleic acids is a FAA2mut polypeptide and comprises the amino acid sequence set forth in SEQ ID NO:196, or a conservatively substituted amino acid sequence thereof. In some embodiments, the FAA polypeptide encoded by the one or more heterologous nucleic acids is a FAA2mut polypeptide and comprises an amino acid sequence having at least 50%, at least 55%, at least 60%, at least 65%, at least 70%, or at least 75% amino acid sequence identity to SEQ ID NO:196. In some embodiments, the FAA polypeptide encoded by the one or more heterologous nucleic acids is a FAA2mut polypeptide and comprises an amino acid sequence having at least 80%, at least 81%, at least 82%, at least 83%, or at least 84% amino acid sequence identity to SEQ ID NO:196. In some embodiments, the FAA polypeptide encoded by the one or more heterologous nucleic acids is a FAA2mut polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:196. In some embodiments, the FAA polypeptide encoded by the one or more heterologous nucleic acids is a FAA2mut polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:196.

In some embodiments, the FAA polypeptide encoded by the one or more heterologous nucleic acids is a FAA1 polypeptide and comprises the amino acid sequence set forth in SEQ ID NO:192. In some embodiments, the FAA polypeptide encoded by the one or more heterologous nucleic acids is a FAA1 polypeptide and comprises the amino acid sequence set forth in SEQ ID NO:192, or a conservatively substituted amino acid sequence thereof. In some embodiments, the FAA polypeptide encoded by the one or more heterologous nucleic acids is a FAA1 polypeptide and comprises an amino acid sequence having at least 50%, at least 55%, at least 60%, at least 65%, at least 70%, or at least 75% amino acid sequence identity to SEQ ID NO:192. In some embodiments, the FAA polypeptide encoded by the one or more heterologous nucleic acids is a FAA1 polypeptide and comprises an amino acid sequence having at least 80%, at least 81%, at least 82%, at least 83%, or at least 84% amino acid sequence identity to SEQ ID NO:192. In some embodiments, the FAA polypeptide encoded by the one or more heterologous nucleic acids is a FAA1 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:192. In some embodiments, the FAA polypeptide encoded by the one or more heterologous nucleic acids is a FAA1 polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:192.

In some embodiments, the FAA polypeptide encoded by the one or more heterologous nucleic acids is a FAA3 polypeptide and comprises the amino acid sequence set forth in SEQ ID NO:198. In some embodiments, the FAA polypeptide encoded by the one or more heterologous nucleic acids is a FAA3 polypeptide and comprises the amino acid sequence set forth in SEQ ID NO:198, or a conservatively substituted amino acid sequence thereof. In some embodiments, the FAA polypeptide encoded by the one or more heterologous nucleic acids is a FAA3 polypeptide and comprises an amino acid sequence having at least 50%, at least 55%, at least 60%, at least 65%, at least 70%, or at least 75% amino acid sequence identity to SEQ ID NO:198. In some embodiments, the FAA polypeptide encoded by the one or more heterologous nucleic acids is a FAA3 polypeptide and comprises an amino acid sequence having at least 80%, at least 81%, at least 82%, at least 83%, or at least 84% amino acid sequence identity to SEQ ID NO:198. In some embodiments, the FAA polypeptide encoded by the one or more heterologous nucleic acids is a FAA3 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:198. In some embodiments, the FAA polypeptide encoded by the one or more heterologous nucleic acids is a FAA3 polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:198.

In some embodiments, the FAA polypeptide encoded by the one or more heterologous nucleic acids is a FAA4 polypeptide and comprises the amino acid sequence set forth in SEQ ID NO:200. In some embodiments, the FAA polypeptide encoded by the one or more heterologous nucleic acids is a FAA4 polypeptide and comprises the amino acid sequence set forth in SEQ ID NO:200, or a conservatively substituted amino acid sequence thereof. In some embodiments, the FAA polypeptide encoded by the one or more heterologous nucleic acids is a FAA4 polypeptide and comprises an amino acid sequence having at least 50%, at least 55%, at least 60%, at least 65%, at least 70%, or at least 75% amino acid sequence identity to SEQ ID NO:200. In some embodiments, the FAA polypeptide encoded by the one or more heterologous nucleic acids is a FAA4 polypeptide and comprises an amino acid sequence having at least 80%, at least 81%, at least 82%, at least 83%, or at least 84% amino acid sequence identity to SEQ ID NO:200. In some embodiments, the FAA polypeptide encoded by the one or more heterologous nucleic acids is a FAA4 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:200. In some embodiments, the FAA polypeptide encoded by the one or more heterologous nucleic acids is a FAA4 polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:200.

Exemplary AAE, FAA, or fatty acyl-CoA ligase heterologous nucleic acids disclosed herein may include nucleic acids that encode an AAE, FAA, or fatty acyl-CoA ligase polypeptide, such as, a full-length AAE, FAA, or fatty acyl-CoA ligase polypeptide; a fragment of a AAE, FAA, or fatty acyl-CoA ligase polypeptide; a variant of a AAE, FAA, or fatty acyl-CoA ligase polypeptide; a truncated AAE, FAA, or fatty acyl-CoA ligase polypeptide; or a fusion polypeptide that has at least one activity of an AAE, FAA, or fatty acyl-CoA ligase polypeptide.

In some embodiments, the AAE, FAA, or fatty acyl-CoA ligase polypeptide is overexpressed in the genetically modified host cell. Overexpression may be achieved by increasing the copy number of the AAE, FAA, or fatty acyl-CoA ligase polypeptide-encoding heterologous nucleic acid, e.g., through use of a high copy number expression vector (e.g., a plasmid that exists at 10-40 copies per cell) and/or by operably linking the AAE, FAA, or fatty acyl-CoA ligase polypeptide-encoding heterologous nucleic acid to a strong promoter. In some embodiments, the genetically modified host cell has one copy of an AAE, FAA, or fatty acyl-CoA ligase polypeptide-encoding heterologous nucleic acid. In some embodiments, the genetically modified host cell has two copies of an AAE, FAA, or fatty acyl-CoA ligase polypeptide-encoding heterologous nucleic acid. In some embodiments, the genetically modified host cell has three copies of an AAE, FAA, or fatty acyl-CoA ligase polypeptide-encoding heterologous nucleic acid. In some embodiments, the genetically modified host cell has four copies of an AAE, FAA, or fatty acyl-CoA ligase polypeptide-encoding heterologous nucleic acid. In some embodiments, the genetically modified host cell has five copies of an AAE, FAA, or fatty acyl-CoA ligase polypeptide-encoding heterologous nucleic acid. In some embodiments, the genetically modified host cell has six copies of an AAE, FAA, or fatty acyl-CoA ligase polypeptide-encoding heterologous nucleic acid. In some embodiments, the genetically modified host cell has seven copies of an AAE, FAA, or fatty acyl-CoA ligase polypeptide-encoding heterologous nucleic acid. In some embodiments, the genetically modified host cell has eight copies of an AAE, FAA, or fatty acyl-CoA ligase polypeptide-encoding heterologous nucleic acid.

In some embodiments, the one or more heterologous nucleic acids encoding a CsAAE1 polypeptide comprise the nucleotide sequence set forth in SEQ ID NO:164 or SEQ ID NO:165. In some embodiments, the one or more heterologous nucleic acids encoding a CsAAE1 polypeptide comprise the nucleotide sequence set forth in SEQ ID NO:164 or SEQ ID NO:165, or a codon degenerate nucleotide sequence thereof. In some embodiments, the one or more heterologous nucleic acids encoding a CsAAE1 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:164 or SEQ ID NO:165.

In some embodiments, the one or more heterologous nucleic acids encoding a CsAAE1 polypeptide comprise the nucleotide sequence set forth in SEQ ID NO:89. In some embodiments, the one or more heterologous nucleic acids encoding a CsAAE1 polypeptide comprise the nucleotide sequence set forth in SEQ ID NO:89, or a codon degenerate nucleotide sequence thereof. In some embodiments, the one or more heterologous nucleic acids encoding a CsAAE1 polypeptide comprise a nucleotide sequence having at least 80%, at least 81%, at least 82%, at least 83%, or at least 84% sequence identity to SEQ ID NO:89. In some embodiments, the one or more heterologous nucleic acids encoding a CsAAE1 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:89.

In some embodiments, the one or more heterologous nucleic acids encoding a CsAAE1 polypeptide comprise the nucleotide sequence set forth in SEQ ID NO:164. In some embodiments, the one or more heterologous nucleic acids encoding a CsAAE1 polypeptide comprise the nucleotide sequence set forth in SEQ ID NO:164, or a codon degenerate nucleotide sequence thereof. In some embodiments, the one or more heterologous nucleic acids encoding a CsAAE1 polypeptide comprise a nucleotide sequence having at least 80%, at least 81%, at least 82%, at least 83%, or at least 84% sequence identity to SEQ ID NO:164. In some embodiments, the one or more heterologous nucleic acids encoding a CsAAE1 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:164.

In some embodiments, the one or more heterologous nucleic acids encoding a CsAAE1 polypeptide comprise the nucleotide sequence set forth in SEQ ID NO:165. In some embodiments, the one or more heterologous nucleic acids encoding a CsAAE1 polypeptide comprise the nucleotide sequence set forth in SEQ ID NO:165, or a codon degenerate nucleotide sequence thereof. In some embodiments, the one or more heterologous nucleic acids encoding a CsAAE1 polypeptide comprise a nucleotide sequence having at least 80%, at least 81%, at least 82%, at least 83%, or at least 84% sequence identity to SEQ ID NO:165. In some embodiments, the one or more heterologous nucleic acids encoding a CsAAE1 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:165.

In some embodiments, the one or more heterologous nucleic acids encoding a CsAAE3 polypeptide comprise the nucleotide sequence set forth in SEQ ID NO:150 or SEQ ID NO:166. In some embodiments, the one or more heterologous nucleic acids encoding a CsAAE3 polypeptide comprise the nucleotide sequence set forth in SEQ ID NO:150 or SEQ ID NO:166, or a codon degenerate nucleotide sequence thereof. In some embodiments, the one or more heterologous nucleic acids encoding a CsAAE3 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:150 or SEQ ID NO:166.

In some embodiments, the one or more heterologous nucleic acids encoding a CsAAE3 polypeptide comprise the nucleotide sequence set forth in SEQ ID NO: 91. In some embodiments, the one or more heterologous nucleic acids encoding a CsAAE3 polypeptide comprise the nucleotide sequence set forth in SEQ ID NO: 91, or a codon degenerate nucleotide sequence thereof. In some embodiments, the one or more heterologous nucleic acids encoding a CsAAE3 polypeptide comprise a nucleotide sequence having at least 80%, at least 81%, at least 82%, at least 83%, or at least 84% sequence identity to SEQ ID NO:91. In some embodiments, the one or more heterologous nucleic acids encoding a CsAAE3 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:91.

In some embodiments, the one or more heterologous nucleic acids encoding a CsAAE3 polypeptide comprise the nucleotide sequence set forth in SEQ ID NO:150. In some embodiments, the one or more heterologous nucleic acids encoding a CsAAE3 polypeptide comprise the nucleotide sequence set forth in SEQ ID NO:150, or a codon degenerate nucleotide sequence thereof. In some embodiments, the one or more heterologous nucleic acids encoding a CsAAE3 polypeptide comprise a nucleotide sequence having at least 80%, at least 81%, at least 82%, at least 83%, or at least 84% sequence identity to SEQ ID NO:150. In some embodiments, the one or more heterologous nucleic acids encoding a CsAAE3 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:150.

In some embodiments, the one or more heterologous nucleic acids encoding a CsAAE3 polypeptide comprise the nucleotide sequence set forth in SEQ ID NO:166. In some embodiments, the one or more heterologous nucleic acids encoding a CsAAE3 polypeptide comprise the nucleotide sequence set forth in SEQ ID NO:166, or a codon degenerate nucleotide sequence thereof. In some embodiments, the one or more heterologous nucleic acids encoding a CsAAE3 polypeptide comprise a nucleotide sequence having at least 80%, at least 81%, at least 82%, at least 83%, or at least 84% sequence identity to SEQ ID NO:166. In some embodiments, the one or more heterologous nucleic acids encoding a CsAAE3 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:166.

In some embodiments, the one or more heterologous nucleic acids encoding a FADK polypeptide comprise the nucleotide sequence set forth in SEQ ID NO:146 or SEQ ID NO:148. In some embodiments, the one or more heterologous nucleic acids encoding a FADK polypeptide comprise the nucleotide sequence set forth in SEQ ID NO:146 or SEQ ID NO:148, or a codon degenerate nucleotide sequence thereof. In some embodiments, the one or more heterologous nucleic acids encoding a FADK polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:146 or SEQ ID NO:148.

In some embodiments, the one or more heterologous nucleic acids encoding a FADK polypeptide comprise the nucleotide sequence set forth in SEQ ID NO:146. In some embodiments, the one or more heterologous nucleic acids encoding a FADK polypeptide comprise the nucleotide sequence set forth in SEQ ID NO:146, or a codon degenerate nucleotide sequence thereof. In some embodiments, the one or more heterologous nucleic acids encoding a FADK polypeptide comprise a nucleotide sequence having at least 80%, at least 81%, at least 82%, at least 83%, or at least 84% sequence identity to SEQ ID NO:146. In some embodiments, the one or more heterologous nucleic acids encoding a FADK polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:146.

In some embodiments, the one or more heterologous nucleic acids encoding a FADK polypeptide comprise the nucleotide sequence set forth in SEQ ID NO:148. In some embodiments, the one or more heterologous nucleic acids encoding a FADK polypeptide comprise the nucleotide sequence set forth in SEQ ID NO:148, or a codon degenerate nucleotide sequence thereof. In some embodiments, the one or more heterologous nucleic acids encoding a FADK polypeptide comprise a nucleotide sequence having at least 80%, at least 81%, at least 82%, at least 83%, or at least 84% sequence identity to SEQ ID NO:148. In some embodiments, the one or more heterologous nucleic acids encoding a FADK polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:148.

In some embodiments, the one or more heterologous nucleic acids encoding a FAA polypeptide comprise the nucleotide sequence set forth in SEQ ID NO:168, SEQ ID NO:191, SEQ ID NO:193, SEQ ID NO:195, SEQ ID NO:197, or SEQ ID NO:199. In some embodiments, the one or more heterologous nucleic acids encoding a FAA polypeptide comprise the nucleotide sequence set forth in SEQ ID NO:168, SEQ ID NO:191, SEQ ID NO:193, SEQ ID NO:195, SEQ ID NO:197, or SEQ ID NO:199, or a codon degenerate nucleotide sequence thereof. In some embodiments, the one or more heterologous nucleic acids encoding a FAA polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:168, SEQ ID NO:191, SEQ ID NO:193, SEQ ID NO:195, SEQ ID NO:197, or SEQ ID NO:199.

In some embodiments, the one or more heterologous nucleic acids encoding a FAA2 polypeptide comprise the nucleotide sequence set forth in SEQ ID NO:168. In some embodiments, the one or more heterologous nucleic acids encoding a FAA2 polypeptide comprise the nucleotide sequence set forth in SEQ ID NO:168, or a codon degenerate nucleotide sequence thereof. In some embodiments, the one or more heterologous nucleic acids encoding a FAA2 polypeptide comprise a nucleotide sequence having at least 80%, at least 81%, at least 82%, at least 83%, or at least 84% sequence identity to SEQ ID NO:168. In some embodiments, the one or more heterologous nucleic acids encoding a FAA2 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:168. In some embodiments, the one or more heterologous nucleic acids encoding a FAA2 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:168.

In some embodiments, the one or more heterologous nucleic acids encoding a tFAA2 polypeptide comprise the nucleotide sequence set forth in SEQ ID NO:193. In some embodiments, the one or more heterologous nucleic acids encoding a tFAA2 polypeptide comprise the nucleotide sequence set forth in SEQ ID NO:193, or a codon degenerate nucleotide sequence thereof. In some embodiments, the one or more heterologous nucleic acids encoding a tFAA2 polypeptide comprise a nucleotide sequence having at least 80%, at least 81%, at least 82%, at least 83%, or at least 84% sequence identity to SEQ ID NO:193. In some embodiments, the one or more heterologous nucleic acids encoding a tFAA2 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:193. In some embodiments, the one or more heterologous nucleic acids encoding a tFAA2 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:193.

In some embodiments, the one or more heterologous nucleic acids encoding a FAA2mut polypeptide comprise the nucleotide sequence set forth in SEQ ID NO:195. In some embodiments, the one or more heterologous nucleic acids encoding a FAA2mut polypeptide comprise the nucleotide sequence set forth in SEQ ID NO:195, or a codon degenerate nucleotide sequence thereof. In some embodiments, the one or more heterologous nucleic acids encoding a FAA2mut polypeptide comprise a nucleotide sequence having at least 80%, at least 81%, at least 82%, at least 83%, or at least 84% sequence identity to SEQ ID NO:195. In some embodiments, the one or more heterologous nucleic acids encoding a FAA2mut polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:195. In some embodiments, the one or more heterologous nucleic acids encoding a FAA2mut polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:195.

In some embodiments, the one or more heterologous nucleic acids encoding a FAA1 polypeptide comprise the nucleotide sequence set forth in SEQ ID NO:191. In some embodiments, the one or more heterologous nucleic acids encoding a FAA1 polypeptide comprise the nucleotide sequence set forth in SEQ ID NO:191, or a codon degenerate nucleotide sequence thereof. In some embodiments, the one or more heterologous nucleic acids encoding a FAA1 polypeptide comprise a nucleotide sequence having at least 80%, at least 81%, at least 82%, at least 83%, or at least 84% sequence identity to SEQ ID NO:191. In some embodiments, the one or more heterologous nucleic acids encoding a FAA1 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:191. In some embodiments, the one or more heterologous nucleic acids encoding a FAA1 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:191.

In some embodiments, the one or more heterologous nucleic acids encoding a FAA3 polypeptide comprise the nucleotide sequence set forth in SEQ ID NO:197. In some embodiments, the one or more heterologous nucleic acids encoding a FAA3 polypeptide comprise the nucleotide sequence set forth in SEQ ID NO:197, or a codon degenerate nucleotide sequence thereof. In some embodiments, the one or more heterologous nucleic acids encoding a FAA3 polypeptide comprise a nucleotide sequence having at least 80%, at least 81%, at least 82%, at least 83%, or at least 84% sequence identity to SEQ ID NO:197. In some embodiments, the one or more heterologous nucleic acids encoding a FAA3 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:197. In some embodiments, the one or more heterologous nucleic acids encoding a FAA3 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:197.

In some embodiments, the one or more heterologous nucleic acids encoding a FAA4 polypeptide comprise the nucleotide sequence set forth in SEQ ID NO:199. In some embodiments, the one or more heterologous nucleic acids encoding a FAA4 polypeptide comprise the nucleotide sequence set forth in SEQ ID NO:199, or a codon degenerate nucleotide sequence thereof. In some embodiments, the one or more heterologous nucleic acids encoding a FAA4 polypeptide comprise a nucleotide sequence having at least 80%, at least 81%, at least 82%, at least 83%, or at least 84% sequence identity to SEQ ID NO:199. In some embodiments, the one or more heterologous nucleic acids encoding a FAA4 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:199. In some embodiments, the one or more heterologous nucleic acids encoding a FAA4 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:199.

Polypeptides that Generate or are Part of a Pathway that Generates Hexanoyl-CoA, Hexanoyl-CoA Derivatives, Acyl-CoA Compounds, or Acyl-CoA Compound Derivatives, Nucleic Acids Comprising Said Polypeptides, and Genetically Modified Host Cells Expressing Said Polypeptides In some embodiments, a genetically modified host cell of the present disclosure is genetically modified with one or more heterologous nucleic acids encoding one or more polypeptides that generate or are part of a biosynthetic pathway that generates hexanoyl-CoA, derivatives of hexanoyl-CoA, acyl-CoA compounds, or acyl-CoA compound derivatives.

In some embodiments, a genetically modified host cell of the present disclosure is genetically modified with one or more heterologous nucleic acids encoding more than one polypeptide that generates or are part of a biosynthetic pathway that generates hexanoyl-CoA, derivatives of hexanoyl-CoA, acyl-CoA compounds, or acyl-CoA compound derivatives. In some embodiments, a genetically modified host cell of the present disclosure is genetically modified with one or more heterologous nucleic acids encoding more than two polypeptides that generate or are part of a biosynthetic pathway that generates hexanoyl-CoA, derivatives of hexanoyl-CoA, acyl-CoA compounds, or acyl-CoA compound derivatives. In some embodiments, a genetically modified host cell of the present disclosure is genetically modified with one or more heterologous nucleic acids encoding more than three polypeptides that generate or are part of a biosynthetic pathway that generates hexanoyl-CoA, derivatives of hexanoyl-CoA, acyl-CoA compounds, or acyl-CoA compound derivatives. In some embodiments, a genetically modified host cell of the present disclosure is genetically modified with one or more heterologous nucleic acids encoding more than four polypeptides that generate or are part of a biosynthetic pathway that generates hexanoyl-CoA, derivatives of hexanoyl-CoA, acyl-CoA compounds, or acyl-CoA compound derivatives. In some embodiments, a genetically modified host cell of the present disclosure is genetically modified with one or more heterologous nucleic acids encoding more than five polypeptides that generate or are part of a biosynthetic pathway that generates hexanoyl-CoA, derivatives of hexanoyl-CoA, acyl-CoA compounds, or acyl-CoA compound derivatives. In some embodiments, a genetically modified host cell of the present disclosure is genetically modified with one or more heterologous nucleic acids encoding two polypeptides that generate or are part of a biosynthetic pathway that generates hexanoyl-CoA, derivatives of hexanoyl-CoA, acyl-CoA compounds, or acyl-CoA compound derivatives. In some embodiments, a genetically modified host cell of the present disclosure is genetically modified with one or more heterologous nucleic acids encoding three polypeptides that generate or are part of a biosynthetic pathway that generates hexanoyl-CoA, derivatives of hexanoyl-CoA, acyl-CoA compounds, or acyl-CoA compound derivatives. In some embodiments, a genetically modified host cell of the present disclosure is genetically modified with one or more heterologous nucleic acids encoding four polypeptides that generate or are part of a biosynthetic pathway that generates hexanoyl-CoA, derivatives of hexanoyl-CoA, acyl-CoA compounds, or acyl-CoA compound derivatives. In some embodiments, a genetically modified host cell of the present disclosure is genetically modified with one or more heterologous nucleic acids encoding five polypeptides that generate or are part of a biosynthetic pathway that generates hexanoyl-CoA, derivatives of hexanoyl-CoA, acyl-CoA compounds, or acyl-CoA compound derivatives. In some embodiments, a genetically modified host cell of the present disclosure is genetically modified with one or more heterologous nucleic acids encoding 1, 2, 3, 4, 5 or more polypeptides that generate or are part of a biosynthetic pathway that generates hexanoyl-CoA, derivatives of hexanoyl-CoA, acyl-CoA compounds, or acyl-CoA compound derivatives. In some embodiments, a genetically modified host cell of the present disclosure is genetically modified with one or more heterologous nucleic acids encoding 1, 2, 3, 4, or 5 polypeptides that generate or are part of a biosynthetic pathway that generates hexanoyl-CoA, derivatives of hexanoyl-CoA, acyl-CoA compounds, or acyl-CoA compound derivatives.

Exemplary polypeptides disclosed herein that generate or are part of a biosynthetic pathway that generates hexanoyl-CoA, derivatives of hexanoyl-CoA, acyl-CoA compounds, or acyl-CoA compound derivatives may include a full-length polypeptide that generates or is part of a biosynthetic pathway that generates hexanoyl-CoA, derivatives of hexanoyl-CoA, acyl-CoA compounds, or acyl-CoA compound derivatives; a fragment of a polypeptide that generates or is part of a biosynthetic pathway that generates hexanoyl-CoA, derivatives of hexanoyl-CoA, acyl-CoA compounds, or acyl-CoA compound derivatives; a variant of a polypeptide that generates or is part of a biosynthetic pathway that generates hexanoyl-CoA, derivatives of hexanoyl-CoA, acyl-CoA compounds, or acyl-CoA compound derivatives; a truncated polypeptide that generates or is part of a biosynthetic pathway that generates hexanoyl-CoA, derivatives of hexanoyl-CoA, acyl-CoA compounds, or acyl-CoA compound derivatives; or a fusion polypeptide that has at least one activity of a polypeptide that generates or is part of a biosynthetic pathway that generates hexanoyl-CoA, derivatives of hexanoyl-CoA, acyl-CoA compounds, or acyl-CoA compound derivatives.

In some embodiments, the one or more polypeptides that generate hexanoyl-CoA, derivatives of hexanoyl-CoA, acyl-CoA compounds, or acyl-CoA compound derivatives may include a hexanoyl-CoA synthase (HCS) polypeptide (e.g., as depicted in Box 1a of FIG. 1). In some embodiments, the one or more polypeptides that generate hexanoyl-CoA, derivatives of hexanoyl-CoA, acyl-CoA compounds, or acyl-CoA compound derivatives is an HCS polypeptide and the cell culture medium comprising the genetically modified host cell comprises hexanoate. In some embodiments, the one or more polypeptides that generate hexanoyl-CoA, derivatives of hexanoyl-CoA, acyl-CoA compounds, or acyl-CoA compound derivatives is an HCS polypeptide and the cell culture medium comprising the genetically modified host cell comprises a carboxylic acid other than hexanoate. In some embodiments, hexanoic acid or carboxylic acids other than hexanoic acid are fed to a genetically modified host cell expressing the HCS polypeptide (e.g., are present in the culture medium in which the cells are grown) to generate hexanoyl-CoA, acyl-CoA compounds, derivatives of hexanoyl-CoA, or derivatives of acyl-CoA compounds.

In some embodiments, the HCS polypeptide encoded by the one or more heterologous nucleic acids comprises the amino acid sequence set forth in SEQ ID NO:1. In some embodiments, the HCS polypeptide encoded by the one or more heterologous nucleic acids comprises the amino acid sequence set forth in SEQ ID NO:1, or a conservatively substituted amino acid sequence thereof. In some embodiments, the HCS polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1.

In some embodiments, the HCS polypeptide encoded by the one or more heterologous nucleic acids is a RevS polypeptide and comprises the amino acid sequence set forth in SEQ ID NO:2. In some embodiments, the HCS polypeptide encoded by the one or more heterologous nucleic acids is a RevS polypeptide and comprises the amino acid sequence set forth in SEQ ID NO:2, or a conservatively substituted amino acid sequence thereof. In some embodiments, the HCS polypeptide encoded by the one or more heterologous nucleic acids is a RevS polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:2.

In some embodiments, the HCS polypeptide encoded by the one or more heterologous nucleic acids is an AflA polypeptide and comprises the amino acid sequence set forth in SEQ ID NO:3. In some embodiments, the HCS polypeptide encoded by the one or more heterologous nucleic acids is an AflA polypeptide and comprises the amino acid sequence set forth in SEQ ID NO:3, or a conservatively substituted amino acid sequence thereof. In some embodiments, the HCS polypeptide encoded by the one or more heterologous nucleic acids is an AflA polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:3.

In some embodiments, the HCS polypeptide encoded by the one or more heterologous nucleic acids is an AflB polypeptide and comprises the amino acid sequence set forth in SEQ ID NO:4. In some embodiments, the HCS polypeptide encoded by the one or more heterologous nucleic acids is an AflB polypeptide and comprises the amino acid sequence set forth in SEQ ID NO:4, or a conservatively substituted amino acid sequence thereof. In some embodiments, the HCS polypeptide encoded by the one or more heterologous nucleic acids is an AflB polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:4.

In some embodiments, a genetically modified host cell of the present disclosure is genetically modified with: i) one or more heterologous nucleic acids that encode an AflA polypeptide and ii) one or more heterologous nucleic acids that encode an AflB polypeptide.

In some embodiments, one or more polypeptides that generate hexanoyl-CoA, derivatives of hexanoyl-CoA, acyl-CoA compounds, or acyl-CoA compound derivatives or are part of a biosynthetic pathway that generates hexanoyl-CoA, derivatives of hexanoyl-CoA, acyl-CoA compounds, or acyl-CoA compound derivatives comprise a MCT1 polypeptide, a PaaH1 polypeptide, a Crt polypeptide, a Ter polypeptide, and a BktB polypeptide. See, e.g., Machado et al. (2012) *Metabolic Engineering* 14:504. In some embodiments, the PaaH1 (3-hydroxyacyl-CoA dehydrogenase) polypeptide encoded by the one or more heterologous nucleic acids comprises the amino acid sequence set forth in SEQ ID NO:18 or SEQ ID NO:46. In some embodiments, the PaaH1 polypeptide encoded by the one or more heterologous nucleic acids comprises the amino acid sequence set forth in SEQ ID NO:18 or SEQ ID NO:46, or a conservatively substituted amino acid sequence thereof. In some embodiments, the PaaH1 polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:18 or SEQ ID NO:46. In some embodiments, the Crt (crotonase) polypeptide encoded by the one or more heterologous nucleic acids comprises the amino acid sequence set forth in SEQ ID NO:19 or SEQ ID NO:48. In some embodiments, the Crt polypeptide encoded by the one or more heterologous nucleic acids comprises the amino acid sequence set forth in SEQ ID NO:19 or SEQ ID NO:48, or a conservatively substituted amino acid sequence thereof. In some embodiments, the Crt polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:19 or SEQ ID NO:48. In some embodiments, the Ter (trans-2-enoyl-CoA reductase) polypeptide encoded by the one or more heterologous nucleic acids comprises the amino acid sequence set forth in SEQ ID NO:20 or SEQ ID NO:50. In some embodiments, the Ter polypeptide encoded by the one or more heterologous nucleic acids comprises the amino acid sequence set forth in SEQ ID NO:20 or SEQ ID NO:50, or a conservatively substituted amino acid sequence thereof. In some embodiments, the Ter polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:20 or SEQ ID NO:50. In some embodiments, the BktB (0-ketothiolase) polypeptide encoded by the one or more heterologous nucleic acids comprises the amino acid sequence set forth in SEQ ID NO:21 or SEQ ID NO:44. In some embodiments, the BktB polypeptide encoded by the one or more heterologous nucleic acids comprises the amino acid sequence set forth in SEQ ID NO:21 or SEQ ID NO:44, or a conservatively substituted amino acid sequence thereof. In some embodiments, the BktB polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:21 or SEQ ID NO:44.

In some embodiments, the one or more polypeptides that generate hexanoyl-CoA, derivatives of hexanoyl-CoA, acyl-CoA compounds, or acyl-CoA compound derivatives or are part of a biosynthetic pathway that generates hexanoyl-CoA, derivatives of hexanoyl-CoA, acyl-CoA compounds, or acyl-CoA compound derivatives comprise a MCT1 polypeptide, a PhaB polypeptide, a PhaJ polypeptide, a Ter polypeptide, and a BktB polypeptide. In some embodiments, the PhaB (acetoacetyl-CoA reductase) polypeptide encoded by the one or more heterologous nucleic acids comprises the amino acid sequence set forth in SEQ ID NO:94. In some embodiments, the PhaB polypeptide encoded by the one or more heterologous nucleic acids comprises the amino acid sequence set forth in SEQ ID NO:94, or a conservatively substituted amino acid sequence thereof. In some embodiments, the PhaB polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:94. In some embodiments, the PhaJ ((R)-specific enoyl-CoA hydratase) polypeptide encoded by the one or more heterologous nucleic acids comprises the amino acid sequence set forth in SEQ ID NO:96. In some embodiments, the PhaJ polypeptide encoded by the one or more heterologous nucleic acids comprises the amino acid sequence set forth in SEQ ID NO:96, or a conservatively substituted amino acid sequence thereof. In some embodiments, the PhaJ polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:96. In some embodiments, the Ter (trans-2-enoyl-CoA reductase) and the BktB (0-ketothiolase) polypeptides used are selected from the Ter and BktB polypeptides disclosed herein.

In some embodiments, the one or more polypeptides that generate hexanoyl-CoA, derivatives of hexanoyl-CoA, acyl-CoA compounds, or acyl-CoA compound derivatives or are part of a biosynthetic pathway that generates hexanoyl-CoA, derivatives of hexanoyl-CoA, acyl-CoA compounds, or acyl-CoA compound derivatives comprise a polypeptide that condenses an acetyl-CoA and a malonyl-CoA to generate acetoacetyl-CoA. Polypeptides that condense an acetyl-CoA and a malonyl-CoA to generate acetoacetyl-CoA may include a malonyl CoA-acyl carrier protein transacylase (MCT1) polypeptide. In some embodiments, the MCT1 polypeptide encoded by the one or more heterologous nucleic acids comprises the amino acid sequence set forth in SEQ ID NO:42. In some embodiments, the MCT1 polypeptide encoded by the one or more heterologous nucleic acids comprises the amino acid sequence set forth in SEQ ID NO:42, or a conservatively substituted amino acid sequence thereof. In some embodiments, the MCT1 polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:42. In some embodiments, the host cell is genetically modified with one or more heterologous nucleic acids encoding a polypeptide that condense an acetyl-CoA and a malonyl-CoA to generate acetoacetyl-CoA. In certain such embodiments, the polypeptide that condenses an acetyl-CoA and a malonyl-CoA to generate acetoacetyl-CoA is an MCT1 polypeptide.

The one or more polypeptides that generate hexanoyl-CoA, derivatives of hexanoyl-CoA, acyl-CoA compounds, or acyl-CoA compound derivatives may also include a short chain fatty acyl-CoA thioesterase (SCFA-TE) polypeptide (e.g., as depicted in Box 1c of FIG. 1). In some embodiments, the SCFA-TE polypeptide encoded by the one or more heterologous nucleic acids comprises the amino acid sequence set forth in SEQ ID NO:26, SEQ ID NO:27, SEQ ID NO:28, SEQ ID NO:29, SEQ ID NO:30, or SEQ ID NO:31. In some embodiments, the SCFA-TE polypeptide encoded by the one or more heterologous nucleic acids comprises the amino acid sequence set forth in SEQ ID NO:26, SEQ ID NO:27, SEQ ID NO:28, SEQ ID NO:29, SEQ ID NO:30, or SEQ ID NO:31, or a conservatively substituted amino acid sequence thereof. In some embodiments, the SCFA-TE polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:26, SEQ ID NO:27, SEQ ID NO:28, SEQ ID NO:29, SEQ ID NO:30, or SEQ ID NO:31.

In some embodiments, the one or more polypeptides that are part of a biosynthetic pathway that generates hexanoyl-CoA, derivatives of hexanoyl-CoA, acyl-CoA compounds, or acyl-CoA compound derivatives comprise a fatty acid synthase polypeptide, such as a FAS1 or FAS2 polypeptide. In some embodiments, the FAS1 polypeptide encoded by the one or more heterologous nucleic acids is a FAS1 (I306A, R1834K) polypeptide and comprises the amino acid sequence set forth in SEQ ID NO:106. In some embodiments, the FAS1 polypeptide encoded by the one or more heterologous nucleic acids is a FAS1 (I306A, R1834K) polypeptide and comprises the amino acid sequence set forth in SEQ ID NO:106, or a conservatively substituted amino acid sequence thereof. In some embodiments, the FAS1 polypeptide encoded by the one or more heterologous nucleic acids is a FAS1 (I306A, R1834K) polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:106. In some embodiments, the FAS2 polypeptide encoded by the one or more heterologous nucleic acids is a FAS2 (G1250S) polypeptide and comprises the amino acid sequence set forth in SEQ ID NO:107. In some embodiments, the FAS2 polypeptide encoded by the one or more heterologous nucleic acids is a FAS2 (G1250S) polypeptide and comprises the amino acid sequence set forth in SEQ ID NO:107, or a conservatively substituted amino acid sequence thereof. In some embodiments, the FAS2 polypeptide encoded by the one or more heterologous nucleic acids is a FAS2 (G1250S) polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:107.

Exemplary heterologous nucleic acids disclosed herein may include nucleic acids that encode a polypeptide that generates or is part of a biosynthetic pathway that generates hexanoyl-CoA, derivatives of hexanoyl-CoA, acyl-CoA compounds, or acyl-CoA compound derivatives, such as, a full-length polypeptide that generates or is part of a biosynthetic pathway that generates hexanoyl-CoA, derivatives of hexanoyl-CoA, acyl-CoA compounds, or acyl-CoA compound derivatives; a fragment of a polypeptide that generates or is part of a biosynthetic pathway that generates hexanoyl-CoA, derivatives of hexanoyl-CoA, acyl-CoA compounds, or acyl-CoA compound derivatives; a variant of a polypeptide that generates or is part of a biosynthetic pathway that generates hexanoyl-CoA, derivatives of hexanoyl-CoA, acyl-CoA compounds, or acyl-CoA compound derivatives; a truncated polypeptide that generates or is part of a biosynthetic pathway that generates hexanoyl-CoA, derivatives of hexanoyl-CoA, acyl-CoA compounds, or acyl-CoA compound derivatives; or a fusion polypeptide that has at least one activity of a polypeptide that generates or is part of a biosynthetic pathway that generates hexanoyl-CoA, derivatives of hexanoyl-CoA, acyl-CoA compounds, or acyl-CoA compound derivatives.

In some embodiments, the polypeptide that generates or is part of a biosynthetic pathway that generates hexanoyl-CoA, derivatives of hexanoyl-CoA, acyl-CoA compounds, or acyl-CoA compound derivatives is overexpressed in the genetically modified host cell. Overexpression may be achieved by increasing the copy number of the heterologous nucleic acid encoding a polypeptide that generates or is part of a biosynthetic pathway that generates hexanoyl-CoA, derivatives of hexanoyl-CoA, acyl-CoA compounds, or acyl-CoA compound derivatives, e.g., through use of a high copy number expression vector (e.g., a plasmid that exists at 10-40 copies per cell) and/or by operably linking the polypeptide that generates or is part of a biosynthetic pathway that generates hexanoyl-CoA, derivatives of hexanoyl-CoA, acyl-CoA compounds, or acyl-CoA compound derivatives encoding heterologous nucleic acid to a strong promoter. In some embodiments, the genetically modified host cell has one copy of a heterologous nucleic acid encoding a polypeptide that generates or is part of a biosynthetic pathway that generates hexanoyl-CoA, derivatives of hexanoyl-CoA, acyl-CoA compounds, or acyl-CoA compound derivatives. In some embodiments, the genetically modified host cell has two copies of a heterologous nucleic acid encoding a polypeptide that generates or is part of a biosynthetic pathway that generates hexanoyl-CoA, derivatives of hexanoyl-CoA, acyl-CoA compounds, or acyl-CoA compound derivatives. In some embodiments, the genetically modified host cell has three copies of a heterologous nucleic acid encoding a polypeptide that generates or is part of a biosynthetic pathway that generates hexanoyl-CoA, derivatives of hexanoyl-CoA, acyl-CoA compounds, or acyl-CoA compound derivatives. In some embodiments, the genetically modified host cell has four copies of a heterologous nucleic acid encoding a polypeptide that generates or is part of a biosynthetic pathway that generates hexanoyl-CoA, derivatives of hexanoyl-CoA, acyl-CoA compounds, or acyl-CoA compound derivatives. In some embodiments, the genetically modified host cell has five copies of a heterologous nucleic acid encoding a polypeptide that generates or is part of a biosynthetic pathway that generates hexanoyl-CoA, derivatives of hexanoyl-CoA, acyl-CoA compounds, or acyl-CoA compound derivatives.

In some embodiments, the one or more heterologous nucleic acids encoding an MCT1 polypeptide comprise the nucleotide sequence set forth in SEQ ID NO:41. In some embodiments, the one or more heterologous nucleic acids encoding an MCT1 polypeptide comprise the nucleotide sequence set forth in SEQ ID NO:41, or a codon degenerate nucleotide sequence thereof. In some embodiments, the one or more heterologous nucleic acids encoding an MCT1 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:41. In some embodiments, the one or more heterologous nucleic acids encoding a BktB polypeptide comprise the nucleotide sequence set forth in SEQ ID NO:43. In some embodiments, the one or more heterologous nucleic acids encoding a BktB polypeptide comprise the nucleotide sequence set forth in SEQ ID NO:43, or a codon degenerate nucleotide sequence thereof. In some embodiments, the one or more heterologous nucleic acids encoding a BktB polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:43. In some embodiments, the one or more heterologous nucleic acids encoding a PaaH1 polypeptide comprise the nucleotide sequence set forth in SEQ ID NO:45. In some embodiments, the one or more heterologous nucleic acids encoding a PaaH1 polypeptide comprise the nucleotide sequence set forth in SEQ ID NO:45, or a codon degenerate nucleotide sequence thereof. In some embodiments, the one or more heterologous nucleic acids encoding a PaaH1 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:45. In some embodiments, the one or more heterologous nucleic acids encoding a Crt polypeptide comprise the nucleotide sequence set forth in SEQ ID NO:47. In some embodiments, the one or more heterologous nucleic acids encoding a Crt polypeptide comprise the nucleotide sequence set forth in SEQ ID NO:47, or a codon degenerate nucleotide sequence thereof. In some embodiments, the one or more heterologous nucleic acids encoding a Crt polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:47. In some embodiments, the one or more heterologous nucleic acids encoding a Ter polypeptide comprise the nucleotide sequence set forth in SEQ ID NO:49. In some embodiments, the one or more heterologous nucleic acids encoding a Ter polypeptide comprise the nucleotide sequence set forth in SEQ ID NO:49, or a codon degenerate nucleotide sequence thereof. In some embodiments, the one or more heterologous nucleic acids encoding a Ter polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:49. In some embodiments, the one or more heterologous nucleic acids encoding a PhaB polypeptide comprise the nucleotide sequence set forth in SEQ ID NO:93. In some embodiments, the one or more heterologous nucleic acids encoding a PhaB polypeptide comprise the nucleotide sequence set forth in SEQ ID NO:93, or a codon degenerate nucleotide sequence thereof. In some embodiments, the one or more heterologous nucleic acids encoding a PhaB polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:93. In some embodiments, the one or more heterologous nucleic acids encoding a PhaJ polypeptide comprise the nucleotide sequence set forth in SEQ ID NO:95. In some embodiments, the one or more heterologous nucleic acids encoding a PhaJ polypeptide comprise the nucleotide sequence set forth in SEQ ID NO:95, or a codon degenerate nucleotide sequence thereof. In some embodiments, the one or more heterologous nucleic acids encoding a PhaJ polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:95.

Polypeptides that Generate Malonyl-CoA, Nucleic Acids Comprising Said Polypeptides, and Genetically Modified Host Cells Expressing Said Polypeptides In some embodiments, the host cell is genetically modified with one or more heterologous nucleic acids encoding a polypeptide that generates malonyl-CoA. In some embodiments, the polypeptide that generates malonyl-CoA is an acetyl-CoA carboxylate (ACC) polypeptide. In some embodiments, a genetically modified host cell of the present disclosure is genetically modified with one or more heterologous nucleic acids encoding an ACC polypeptide.

Exemplary ACC polypeptides disclosed herein may include a full-length ACC polypeptide, a fragment of an ACC polypeptide, a variant of an ACC polypeptide, a truncated ACC polypeptide, or a fusion polypeptide that has at least one activity of an ACC polypeptide.

In some embodiments, the ACC polypeptide encoded by the one or more heterologous nucleic acids comprises the amino acid sequence set forth in SEQ ID NO:9, SEQ ID NO:97, or SEQ ID NO:207. In some embodiments, the ACC polypeptide encoded by the one or more heterologous nucleic acids comprises the amino acid sequence set forth in SEQ ID NO:9, SEQ ID NO:97, or SEQ ID NO:207, or a conservatively substituted amino acid sequence thereof. In some embodiments, the ACC polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:9, SEQ ID NO:97, or SEQ ID NO:207.

In some embodiments, the ACC polypeptide encoded by the one or more heterologous nucleic acids is an ACC1 polypeptide and comprises the amino acid sequence set forth in SEQ ID NO:9. In some embodiments, the ACC polypeptide encoded by the one or more heterologous nucleic acids is an ACC1 polypeptide and comprises the amino acid sequence set forth in SEQ ID NO:9, or a conservatively substituted amino acid sequence thereof. In some embodiments, the ACC polypeptide encoded by the one or more heterologous nucleic acids is an ACC1 polypeptide and comprises an amino acid sequence having at least 50%, at least 55%, at least 60%, at least 65%, at least 70%, or at least 75% amino acid sequence identity to SEQ ID NO:9. In some embodiments, the ACC polypeptide encoded by the one or more heterologous nucleic acids is an ACC1 polypeptide and comprises an amino acid sequence having at least 80%, at least 81%, at least 82%, at least 83%, or at least 84% amino acid sequence identity to SEQ ID NO:9. In some embodiments, the ACC polypeptide encoded by the one or more heterologous nucleic acids is an ACC1 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:9.

In some embodiments, the ACC polypeptide encoded by the one or more heterologous nucleic acids is an ACC1 (S659A, S1157A) polypeptide and comprises the amino acid sequence set forth in SEQ ID NO:97. In some embodiments, the ACC polypeptide encoded by the one or more heterologous nucleic acids is an ACC1 (S659A, S1157A) polypeptide and comprises the amino acid sequence set forth in SEQ ID NO:97, or a conservatively substituted amino acid sequence thereof. In some embodiments, the ACC polypeptide encoded by the one or more heterologous nucleic acids is an ACC1 (S659A, S1157A) polypeptide and comprises an amino acid sequence having at least 50%, at least 55%, at least 60%, at least 65%, at least 70%, or at least 75% amino acid sequence identity to SEQ ID NO:97. In some embodiments, the ACC polypeptide encoded by the one or more heterologous nucleic acids is an ACC1 (S659A, S1157A) polypeptide and comprises an amino acid sequence having at least 80%, at least 81%, at least 82%, at least 83%, or at least 84% amino acid sequence identity to SEQ ID NO:97. In some embodiments, the ACC polypeptide encoded by the one or more heterologous nucleic acids is an ACC1 (S659A, S1157A) polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:97.

In some embodiments, the ACC polypeptide encoded by the one or more heterologous nucleic acids is an ACC1 (S659A, S1157A) polypeptide and comprises the amino acid sequence set forth in SEQ ID NO:207. In some embodiments, the ACC polypeptide encoded by the one or more heterologous nucleic acids is an ACC1 (S659A, S1157A) polypeptide and comprises the amino acid sequence set forth in SEQ ID NO:207, or a conservatively substituted amino acid sequence thereof. In some embodiments, the ACC polypeptide encoded by the one or more heterologous nucleic acids is an ACC1 (S659A, S1157A) polypeptide and comprises an amino acid sequence having at least 50%, at least 55%, at least 60%, at least 65%, at least 70%, or at least 75% amino acid sequence identity to SEQ ID NO:207. In some embodiments, the ACC polypeptide encoded by the one or more heterologous nucleic acids is an ACC1 (S659A, S1157A) polypeptide and comprises an amino acid sequence having at least 80%, at least 81%, at least 82%, at least 83%, or at least 84% amino acid sequence identity to SEQ ID NO:207. In some embodiments, the ACC polypeptide encoded by the one or more heterologous nucleic acids is an ACC1 (S659A, S1157A) polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:207.

Exemplary ACC heterologous nucleic acids disclosed herein may include nucleic acids that encode an ACC polypeptide, such as, a full-length ACC polypeptide, a fragment of an ACC polypeptide, a variant of an ACC polypeptide, a truncated ACC polypeptide, or a fusion polypeptide that has at least one activity of an ACC polypeptide.

In some embodiments, the ACC polypeptide is overexpressed in the genetically modified host cell. See, e.g., Runguphan and Keasling (2014) *Metabolic Engineering* 21:103. Overexpression may be achieved by increasing the copy number of the ACC polypeptide-encoding heterologous nucleic acid, e.g., through use of a high copy number expression vector (e.g., a plasmid that exists at 10-40 copies per cell) and/or by operably linking the ACC polypeptide-encoding heterologous nucleic acid to a strong promoter. In some embodiments, the genetically modified host cell has one copy of an ACC polypeptide-encoding heterologous nucleic acid. In some embodiments, the genetically modified host cell has two copies of an ACC polypeptide-encoding heterologous nucleic acid. In some embodiments, the genetically modified host cell has three copies of an ACC polypeptide-encoding heterologous nucleic acid. In some embodiments, the genetically modified host cell has four copies of an ACC polypeptide-encoding heterologous nucleic acid. In some embodiments, the genetically modified host cell has five copies of an ACC polypeptide-encoding heterologous nucleic acid. In some embodiments, the genetically modified host cell has six copies of an ACC polypeptide-encoding heterologous nucleic acid. In some embodiments, the genetically modified host cell has seven copies of an ACC polypeptide-encoding heterologous nucleic acid. In some embodiments, the genetically modified host cell has eight copies of an ACC polypeptide-encoding heterologous nucleic acid.

In some embodiments, the one or more heterologous nucleic acids encoding an ACC polypeptide comprise the nucleotide sequence set forth in SEQ ID NO:201. In some embodiments, the one or more heterologous nucleic acids encoding an ACC polypeptide comprise the nucleotide sequence set forth in SEQ ID NO:201, or a codon degenerate nucleotide sequence thereof. In some embodiments, the one or more heterologous nucleic acids encoding an ACC polypeptide comprise a nucleotide sequence having at least 80%, at least 81%, at least 82%, at least 83%, or at least 84% sequence identity to SEQ ID NO:201. In some embodiments, the one or more heterologous nucleic acids encoding an ACC polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:201. In some embodiments, the one or more heterologous nucleic acids encoding an ACC polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:201.

Polypeptides that Condense an Acyl-CoA Compound or an Acyl-CoA Compound Derivative with Malonyl-CoA to Generate Olivetolic Acid or Derivatives of Olivetolic Acid, Nucleic Acids Comprising Said Polypeptides, and Genetically Modified Host Cells Expressing Said Polypeptides In some embodiments, a genetically modified host cell of the present disclosure is genetically modified with one or more heterologous nucleic acids encoding one or more polypeptides that condense an acyl-CoA compound, such as hexanoyl-CoA, or an acyl-CoA compound derivative, such as a hexanoyl-CoA derivative, with malonyl-CoA to generate olivetolic acid, or a derivative of olivetolic acid. Polypeptides that react an acyl-CoA compound or an acyl-CoA compound derivative with malonyl-CoA to generate olivetolic acid, or a derivative of olivetolic acid, may include TKS and OAC polypeptides. TKS and OAC polypeptides have been found to have broad substrate specificity, enabling production of cannabinoid derivatives or cannabinoid precursor derivatives, in addition to cannabinoids and cannabinoid precursors.

In some embodiments, a genetically modified host cell of the present disclosure is genetically modified with one or more heterologous nucleic acids encoding a TKS polypeptide. In some embodiments, a genetically modified host cell of the present disclosure is genetically modified with one or more heterologous nucleic acids encoding more than one TKS polypeptide. In some embodiments, a genetically modified host cell of the present disclosure is genetically modified with one or more heterologous nucleic acids encoding more than two TKS polypeptides. In some embodiments, a genetically modified host cell of the present disclosure is genetically modified with one or more heterologous nucleic acids encoding more than three TKS polypeptides. In some embodiments, a genetically modified host cell of the present disclosure is genetically modified with one or more heterologous nucleic acids encoding two TKS polypeptides. In some embodiments, a genetically modified host cell of the present disclosure is genetically modified with one or more heterologous nucleic acids encoding three TKS polypeptides. In some embodiments, a genetically modified host cell of the present disclosure is genetically modified with one or more heterologous nucleic acids encoding 1, 2, 3, or more TKS polypeptides. In some embodiments, a genetically modified host cell of the present disclosure is genetically modified with one or more heterologous nucleic acids encoding 1, 2, or 3 TKS polypeptides.

In some embodiments, a genetically modified host cell of the present disclosure is genetically modified with one or more heterologous nucleic acids encoding an OAC polypeptide. In some embodiments, a genetically modified host cell of the present disclosure is genetically modified with one or more heterologous nucleic acids encoding more than one OAC polypeptide. In some embodiments, a genetically modified host cell of the present disclosure is genetically modified with one or more heterologous nucleic acids encoding more than two OAC polypeptides. In some embodiments, a genetically modified host cell of the present disclosure is genetically modified with one or more heterologous nucleic acids encoding more than three OAC polypeptides. In some embodiments, a genetically modified host cell of the present disclosure is genetically modified with one or more heterologous nucleic acids encoding two OAC polypeptides. In some embodiments, a genetically modified host cell of the present disclosure is genetically modified with one or more heterologous nucleic acids encoding three OAC polypeptides. In some embodiments, a genetically modified host cell of the present disclosure is genetically modified with one or more heterologous nucleic acids encoding 1, 2, 3, or more OAC polypeptides. In some embodiments, a genetically modified host cell of the present disclosure is genetically modified with one or more heterologous nucleic acids encoding 1, 2, or 3 OAC polypeptides.

Exemplary TKS or OAC polypeptides disclosed herein may include a full-length TKS or OAC polypeptide, a fragment of a TKS or OAC polypeptide, a variant of a TKS or OAC polypeptide, a truncated TKS or OAC polypeptide, or a fusion polypeptide that has at least one activity of a TKS or OAC polypeptide.

In some embodiments, the TKS polypeptide encoded by the one or more heterologous nucleic acids comprises the amino acid sequence set forth in SEQ ID NO:11 or SEQ ID NO:76. In some embodiments, the TKS polypeptide encoded by the one or more heterologous nucleic acids comprises the amino acid sequence set forth in SEQ ID NO:11 or SEQ ID NO:76, or a conservatively substituted amino acid sequence thereof. In some embodiments, the TKS polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:11 or SEQ ID NO:76.

In some embodiments, the OAC polypeptide encoded by the one or more heterologous nucleic acids comprises the amino acid sequence set forth in SEQ ID NO:10 or SEQ ID NO:78. In some embodiments, the OAC polypeptide encoded by the one or more heterologous nucleic acids comprises the amino acid sequence set forth in SEQ ID NO:10 or SEQ ID NO:78, or a conservatively substituted amino acid sequence thereof. In some embodiments, the OAC polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:10 or SEQ ID NO:78.

In some embodiments, the TKS polypeptide encoded by the one or more heterologous nucleic acids comprises the amino acid sequence set forth in SEQ ID NO:11. In some embodiments, the TKS polypeptide encoded by the one or more heterologous nucleic acids comprises the amino acid sequence set forth in SEQ ID NO:11, or a conservatively substituted amino acid sequence thereof. In some embodiments, the TKS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:11. In some embodiments, the TKS polypeptide encoded by the one or more heterologous nucleic acids comprises an amino acid sequence having at least 80%, at least 81%, at least 82%, at least 83%, or at least 84% amino acid sequence identity to SEQ ID NO:11. In some embodiments, the TKS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:11.

In some embodiments, the TKS polypeptide encoded by the one or more heterologous nucleic acids comprises the amino acid sequence set forth in SEQ ID NO:76. In some embodiments, the TKS polypeptide encoded by the one or more heterologous nucleic acids comprises the amino acid sequence set forth in SEQ ID NO:76, or a conservatively substituted amino acid sequence thereof. In some embodiments, the TKS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:76. In some embodiments, the TKS polypeptide encoded by the one or more heterologous nucleic acids comprises an amino acid sequence having at least 80%, at least 81%, at least 82%, at least 83%, or at least 84% amino acid sequence identity to SEQ ID NO:76. In some embodiments, the TKS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:76.

In some embodiments, the OAC polypeptide encoded by the one or more heterologous nucleic acids comprises the amino acid sequence set forth in SEQ ID NO:10. In some embodiments, the OAC polypeptide encoded by the one or more heterologous nucleic acids comprises the amino acid sequence set forth in SEQ ID NO:10, or a conservatively substituted amino acid sequence thereof. In some embodiments, the OAC polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:10. In some embodiments, the OAC polypeptide encoded by the one or more heterologous nucleic acids comprises an amino acid sequence having at least 80%, at least 81%, at least 82%, at least 83%, or at least 84% amino acid sequence identity to SEQ ID NO:10. In some embodiments, the OAC polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:10.

In some embodiments, the OAC polypeptide encoded by the one or more heterologous nucleic acids comprises the amino acid sequence set forth in SEQ ID NO:78. In some embodiments, the OAC polypeptide encoded by the one or more heterologous nucleic acids comprises the amino acid sequence set forth in SEQ ID NO:78, or a conservatively substituted amino acid sequence thereof. In some embodiments, the OAC polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:78. In some embodiments, the OAC polypeptide encoded by the one or more heterologous nucleic acids comprises an amino acid sequence having at least 80%, at least 81%, at least 82%, at least 83%, or at least 84% amino acid sequence identity to SEQ ID NO:78. In some embodiments, the OAC polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:78.

In some embodiments, the TKS and OAC polypeptides are fused into a single polypeptide chain (a TKS/OAC fusion polypeptide). In some embodiments, the TKS/OAC polypeptide encoded by the one or more heterologous nucleic acids comprises the amino acid sequence set forth in SEQ ID NO:80. In some embodiments, the TKS/OAC polypeptide encoded by the one or more heterologous nucleic acids comprises the amino acid sequence set forth in SEQ ID NO:80, or a conservatively substituted amino acid sequence thereof. In some embodiments, the TKS/OAC polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:80. In some embodiments, the TKS/OAC polypeptide encoded by the one or more heterologous nucleic acids comprises an amino acid sequence having at least 80%, at least 81%, at least 82%, at least 83%, or at least 84% amino acid sequence identity to SEQ ID NO:80. In some embodiments, the TKS/OAC polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:80. In some embodiments, the TKS/OAC polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:80.

Exemplary TKS or OAC heterologous nucleic acids disclosed herein may include nucleic acids that encode a TKS or OAC polypeptide, such as, a full-length TKS or OAC polypeptide, a fragment of a TKS or OAC polypeptide, a variant of a TKS or OAC polypeptide, a truncated TKS or OAC polypeptide, or a fusion polypeptide that has at least one activity of a TKS or OAC polypeptide.

In some embodiments, the TKS or OAC polypeptide is overexpressed in the genetically modified host cell. Overexpression may be achieved by increasing the copy number of the TKS and/or OAC polypeptide-encoding heterologous nucleic acid, e.g., through use of a high copy number expression vector (e.g., a plasmid that exists at 10-40 copies per cell) and/or by operably linking the TKS and/or OAC polypeptide-encoding heterologous nucleic acid to a strong promoter. In some embodiments, the genetically modified host cell has one copy of a TKS and/or OAC polypeptide-encoding heterologous nucleic acid. In some embodiments, the genetically modified host cell has two copies of a TKS and/or OAC polypeptide-encoding heterologous nucleic acid. In some embodiments, the genetically modified host cell has three copies of a TKS and/or OAC polypeptide-encoding heterologous nucleic acid. In some embodiments, the genetically modified host cell has four copies of a TKS and/or OAC polypeptide-encoding heterologous nucleic acid. In some embodiments, the genetically modified host cell has five copies of a TKS and/or OAC polypeptide-encoding heterologous nucleic acid. In some embodiments, the genetically modified host cell has six copies of a TKS and/or OAC polypeptide-encoding heterologous nucleic acid. In some embodiments, the genetically modified host cell has seven copies of a TKS and/or OAC polypeptide-encoding heterologous nucleic acid. In some embodiments, the genetically modified host cell has eight copies of a TKS and/or OAC polypeptide-encoding heterologous nucleic acid. In some embodiments, the genetically modified host cell has nine copies of a TKS and/or OAC polypeptide-encoding heterologous nucleic acid. In some embodiments, the genetically modified host cell has 10 copies of a TKS and/or OAC polypeptide-encoding heterologous nucleic acid. In some embodiments, the genetically modified host cell has 11 copies of a TKS and/or OAC polypeptide-encoding heterologous nucleic acid. In some embodiments, the genetically modified host cell has 12 copies of a TKS and/or OAC polypeptide-encoding heterologous nucleic acid.

In some embodiments, the one or more heterologous nucleic acids encoding an OAC polypeptide comprise the nucleotide sequence set forth in SEQ ID NO:77 or SEQ ID NO:163. In some embodiments, the one or more heterologous nucleic acids encoding an OAC polypeptide comprise the nucleotide sequence set forth in SEQ ID NO:77 or SEQ ID NO:163, or a codon degenerate nucleotide sequence thereof. In some embodiments, the one or more heterologous nucleic acids encoding an OAC polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:77 or SEQ ID NO:163.

In some embodiments, the one or more heterologous nucleic acids encoding a TKS polypeptide comprise the nucleotide sequence set forth in SEQ ID NO:75. In some embodiments, the one or more heterologous nucleic acids encoding a TKS polypeptide comprise the nucleotide sequence set forth in SEQ ID NO:75, or a codon degenerate nucleotide sequence thereof. In some embodiments, the one or more heterologous nucleic acids encoding a TKS polypeptide comprise a nucleotide sequence having at least 80%, at least 81%, at least 82%, at least 83%, or at least 84% sequence identity to SEQ ID NO:75. In some embodiments, the one or more heterologous nucleic acids encoding a TKS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:75.

In some embodiments, the one or more heterologous nucleic acids encoding a TKS polypeptide comprise the nucleotide sequence set forth in SEQ ID NO:162. In some embodiments, the one or more heterologous nucleic acids encoding a TKS polypeptide comprise the nucleotide sequence set forth in SEQ ID NO:162, or a codon degenerate nucleotide sequence thereof. In some embodiments, the one or more heterologous nucleic acids encoding a TKS polypeptide comprise a nucleotide sequence having at least 80%, at least 81%, at least 82%, at least 83%, or at least 84% sequence identity to SEQ ID NO:162. In some embodiments, the one or more heterologous nucleic acids encoding a TKS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:162. In some embodiments, the one or more heterologous nucleic acids encoding a TKS polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:162.

In some embodiments, the one or more heterologous nucleic acids encoding an OAC polypeptide comprise the nucleotide sequence set forth in SEQ ID NO:77. In some embodiments, the one or more heterologous nucleic acids encoding an OAC polypeptide comprise the nucleotide sequence set forth in SEQ ID NO:77, or a codon degenerate nucleotide sequence thereof. In some embodiments, the one or more heterologous nucleic acids encoding an OAC polypeptide comprise a nucleotide sequence having at least 80%, at least 81%, at least 82%, at least 83%, or at least 84% sequence identity to SEQ ID NO:77. In some embodiments, the one or more heterologous nucleic acids encoding an OAC polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:77.

In some embodiments, the one or more heterologous nucleic acids encoding an OAC polypeptide comprise the nucleotide sequence set forth in SEQ ID NO:163. In some embodiments, the one or more heterologous nucleic acids encoding an OAC polypeptide comprise the nucleotide sequence set forth in SEQ ID NO:163, or a codon degenerate nucleotide sequence thereof. In some embodiments, the one or more heterologous nucleic acids encoding an OAC polypeptide comprise a nucleotide sequence having at least 80%, at least 81%, at least 82%, at least 83%, or at least 84% sequence identity to SEQ ID NO:163. In some embodiments, the one or more heterologous nucleic acids encoding an OAC polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:163.

In some embodiments, the one or more heterologous nucleic acids encoding a TKS/OAC polypeptide comprise the nucleotide sequence set forth in SEQ ID NO:79. In some embodiments, the one or more heterologous nucleic acids encoding a TKS/OAC polypeptide comprise the nucleotide sequence set forth in SEQ ID NO:79, or a codon degenerate nucleotide sequence thereof. In some embodiments, the one or more heterologous nucleic acids encoding a TKS/OAC polypeptide comprise a nucleotide sequence having at least 80%, at least 81%, at least 82%, at least 83%, or at least 84% sequence identity to SEQ ID NO:79. In some embodiments, the one or more heterologous nucleic acids encoding a TKS/OAC polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:79. In some embodiments, the one or more heterologous nucleic acids encoding a TKS/OAC polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:79.

Polypeptides that Generate Geranyl Pyrophosphate, Nucleic Acids Comprising Said Polypeptides, and Genetically Modified Host Cells Expressing Said Polypeptides In some embodiments, a genetically modified host cell of the present disclosure is genetically modified with one or more heterologous nucleic acids encoding a polypeptide that generates GPP. In some embodiments, the polypeptide that generates GPP is a geranyl diphosphate synthase (GPPS) polypeptide. In some embodiments, the GPPS polypeptide also has a farnesyl diphosphate synthase (FPPS) polypeptide activity. In some embodiments, the GPPS polypeptide is modified such that it has reduced FPPS polypeptide activity (e.g., at least 10%, 20%, 30%, 40%, 50%, 60%, 70%, 80%, 90%, or more than 90%, less FPPS polypeptide activity) than the corresponding wild-type or parental GPPS polypeptide from which the modified GPPS polypeptide is derived. In some embodiments, the GPPS polypeptide is modified such that it has substantially no FPPS polypeptide activity. In some embodiments, a genetically modified host cell of the present disclosure is genetically modified with one or more heterologous nucleic acids encoding a GPPS polypeptide.

Exemplary GPPS polypeptides disclosed herein may include a full-length GPPS polypeptide, a fragment of a GPPS polypeptide, a variant of a GPPS polypeptide, a truncated GPPS polypeptide, or a fusion polypeptide that has at least one activity of a GPPS polypeptide. In some embodiments, the one or more polypeptides that generate GPP or are part of a biosynthetic pathway that generates GPP are one or more polypeptides having at least one activity of a polypeptide present in the mevalonate (MEV) pathway. In some embodiments, the one or more polypeptides that generate GPP or are part of a biosynthetic pathway that generates GPP are one or more polypeptides having at least one activity of a polypeptide present in the DXP pathway.

In some embodiments, the GPPS polypeptide encoded by the one or more heterologous nucleic acids comprises the amino acid sequence set forth in SEQ ID NO:7, SEQ ID NO:8, or SEQ ID NO:60. In some embodiments, the GPPS polypeptide encoded by the one or more heterologous nucleic acids comprises the amino acid sequence set forth in SEQ ID NO:7, SEQ ID NO:8, or SEQ ID NO:60, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:7, SEQ ID NO:8, or SEQ ID NO:60.

In some embodiments, the GPPS polypeptide encoded by the one or more heterologous nucleic acids comprises the amino acid sequence set forth in SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, or SEQ ID NO:203. In some embodiments, the GPPS polypeptide encoded by the one or more heterologous nucleic acids comprises the amino acid sequence set forth in SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, or SEQ ID NO:203, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, or SEQ ID NO:203.

In some embodiments, the GPPS polypeptide encoded by the one or more heterologous nucleic acids comprises the amino acid sequence set forth in SEQ ID NO:5 or SEQ ID NO:6. In some embodiments, the GPPS polypeptide encoded by the one or more heterologous nucleic acids comprises the amino acid sequence set forth in SEQ ID NO:5 or SEQ ID NO:6, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:5 or SEQ ID NO:6.

In some embodiments, a genetically modified host cell of the present disclosure is genetically modified with: i) one or more heterologous nucleic acids that encode a GPPS polypeptide comprising an amino acid sequence as set forth in SEQ ID NO:5; and ii) one or more heterologous nucleic acids that encode a GPPS polypeptide comprising an amino acid sequence as set forth in SEQ ID NO:6.

In some embodiments, the GPPS (Erg20) polypeptide encoded by the one or more heterologous nucleic acids comprises the amino acid sequence set forth in SEQ ID NO:7. In some embodiments, the GPPS (Erg20) polypeptide encoded by the one or more heterologous nucleic acids comprises the amino acid sequence set forth in SEQ ID NO:7, or a conservatively substituted amino acid sequence thereof. In some embodiments, the GPPS (Erg20) polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:7. In some embodiments, the GPPS (Erg20) polypeptide encoded by the one or more heterologous nucleic acids comprises an amino acid sequence having at least 80%, at least 81%, at least 82%, at least 83%, or at least 84% amino acid sequence identity to SEQ ID NO:7. In some embodiments, the GPPS (Erg20) polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:7.

In some embodiments, the GPPS (Erg20 (K197G)) polypeptide encoded by the one or more heterologous nucleic acids comprises the amino acid sequence set forth in SEQ ID NO:8. In some embodiments, the GPPS (Erg20 (K197G)) polypeptide encoded by the one or more heterologous nucleic acids comprises the amino acid sequence set forth in SEQ ID NO:8, or a conservatively substituted amino acid sequence thereof. In some embodiments, the GPPS (Erg20 (K197G)) polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:8. In some embodiments, the GPPS (Erg20 (K197G)) polypeptide encoded by the one or more heterologous nucleic acids comprises an amino acid sequence having at least 80%, at least 81%, at least 82%, at least 83%, or at least 84% amino acid sequence identity to SEQ ID NO:8. In some embodiments, the GPPS (Erg20 (K197G)) polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:8. The GPPS (Erg20

(K197G)) polypeptide encoded by the one or more heterologous nucleic acids comprises the amino acid sequence set forth in SEQ ID NO:8 comprises a K197G amino acid substitution relative to the GPPS amino acid sequence set forth in SEQ ID NO:7. This mutation shifts the ratio of GPP to farnesyl diphosphate (FPP), increasing the production of the GPP required to produce CBDA.

In some embodiments, a genetically modified host cell of the present disclosure is genetically modified with one or more heterologous nucleic acids encoding a GPPS large subunit polypeptide and a GPPS small subunit polypeptide, where the GPPS large subunit polypeptide and the GPPS small subunit polypeptide together form a heterodimeric GPPS polypeptide. In some embodiments, the GPPS large subunit polypeptide encoded by the one or more heterologous nucleic acids comprises the amino acid sequence set forth in SEQ ID NO:72. In some embodiments, the GPPS large subunit polypeptide encoded by the one or more heterologous nucleic acids comprises the amino acid sequence set forth in SEQ ID NO:72, or a conservatively substituted amino acid sequence thereof. In some embodiments, the GPPS large subunit polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:72. In some embodiments, the GPPS small subunit polypeptide encoded by the one or more heterologous nucleic acids comprises the amino acid sequence set forth in SEQ ID NO:74. In some embodiments, the GPPS small subunit polypeptide encoded by the one or more heterologous nucleic acids comprises the amino acid sequence set forth in SEQ ID NO:74, or a conservatively substituted amino acid sequence thereof. In some embodiments, the GPPS small subunit polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:74.

In some embodiments, the GPPS polypeptide encoded by the one or more heterologous nucleic acids is an ERG20mut (F96W, N127W) polypeptide and comprises the amino acid sequence set forth in SEQ ID NO:60. In some embodiments, the GPPS polypeptide encoded by the one or more heterologous nucleic acids is an ERG20mut (F96W, N127W) polypeptide and comprises the amino acid sequence set forth in SEQ ID NO:60, or a conservatively substituted amino acid sequence thereof. In some embodiments, the GPPS polypeptide encoded by the one or more heterologous nucleic acids is an ERG20mut (F96W, N127W) polypeptide and comprises an amino acid sequence having at least 50%, at least 55%, at least 60%, at least 65%, at least 70%, or at least 75% amino acid sequence identity to SEQ ID NO:60. In some embodiments, the GPPS polypeptide encoded by the one or more heterologous nucleic acids is an ERG20mut (F96W, N127W) polypeptide and comprises an amino acid sequence having at least 80%, at least 81%, at least 82%, at least 83%, or at least 84% amino acid sequence identity to SEQ ID NO:60. In some embodiments, the GPPS polypeptide encoded by the one or more heterologous nucleic acids is an ERG20mut (F96W, N127W) polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:60. This mutation shifts the ratio of GPP to farnesyl diphosphate (FPP), increasing the production of the GPP required to produce CBDA.

In some embodiments, the GPPS polypeptide encoded by the one or more heterologous nucleic acids comprises the amino acid sequence set forth in SEQ ID NO:121. In some embodiments, the GPPS polypeptide encoded by the one or more heterologous nucleic acids comprises the amino acid sequence set forth in SEQ ID NO:121, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:121. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:121. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:121.

In some embodiments, the GPPS polypeptide encoded by the one or more heterologous nucleic acids comprises the amino acid sequence set forth in SEQ ID NO:123. In some embodiments, the GPPS polypeptide encoded by the one or more heterologous nucleic acids comprises the amino acid sequence set forth in SEQ ID NO:123, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:123. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:123. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:123.

In some embodiments, the GPPS polypeptide encoded by the one or more heterologous nucleic acids comprises the amino acid sequence set forth in SEQ ID NO:125. In some embodiments, the GPPS polypeptide encoded by the one or more heterologous nucleic acids comprises the amino acid sequence set forth in SEQ ID NO:125, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:125. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:125. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:125.

In some embodiments, the GPPS polypeptide encoded by the one or more heterologous nucleic acids comprises the amino acid sequence set forth in SEQ ID NO:127. In some embodiments, the GPPS polypeptide encoded by the one or more heterologous nucleic acids comprises the amino acid sequence set forth in SEQ ID NO:127, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:127. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:127. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:127.

In some embodiments, the GPPS polypeptide encoded by the one or more heterologous nucleic acids comprises the amino acid sequence set forth in SEQ ID NO:129. In some embodiments, the GPPS polypeptide encoded by the one or more heterologous nucleic acids comprises the amino acid sequence set forth in SEQ ID NO:129, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:129. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:129. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:129.

In some embodiments, the GPPS polypeptide encoded by the one or more heterologous nucleic acids comprises the amino acid sequence set forth in SEQ ID NO:131. In some embodiments, the GPPS polypeptide encoded by the one or more heterologous nucleic acids comprises the amino acid sequence set forth in SEQ ID NO:131, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:131. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:131. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:131.

In some embodiments, the GPPS polypeptide encoded by the one or more heterologous nucleic acids comprises the amino acid sequence set forth in SEQ ID NO:133. In some embodiments, the GPPS polypeptide encoded by the one or more heterologous nucleic acids comprises the amino acid sequence set forth in SEQ ID NO:133, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:133. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:133. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:133.

In some embodiments, the GPPS polypeptide encoded by the one or more heterologous nucleic acids comprises the amino acid sequence set forth in SEQ ID NO:135. In some embodiments, the GPPS polypeptide encoded by the one or more heterologous nucleic acids comprises the amino acid sequence set forth in SEQ ID NO:135, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:135. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:135. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:135.

In some embodiments, the GPPS polypeptide encoded by the one or more heterologous nucleic acids comprises the amino acid sequence set forth in SEQ ID NO:137. In some embodiments, the GPPS polypeptide encoded by the one or more heterologous nucleic acids comprises the amino acid sequence set forth in SEQ ID NO:137, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:137. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:137. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:137.

In some embodiments, the GPPS polypeptide encoded by the one or more heterologous nucleic acids comprises the amino acid sequence set forth in SEQ ID NO:139. In some embodiments, the GPPS polypeptide encoded by the one or more heterologous nucleic acids comprises the amino acid sequence set forth in SEQ ID NO:139, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:139. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:139. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:139.

In some embodiments, the GPPS polypeptide encoded by the one or more heterologous nucleic acids comprises the amino acid sequence set forth in SEQ ID NO:141. In some embodiments, the GPPS polypeptide encoded by the one or more heterologous nucleic acids comprises the amino acid sequence set forth in SEQ ID NO:141, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:141. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:141. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:141.

In some embodiments, the GPPS polypeptide encoded by the one or more heterologous nucleic acids comprises the amino acid sequence set forth in SEQ ID NO:143. In some embodiments, the GPPS polypeptide encoded by the one or more heterologous nucleic acids comprises the amino acid sequence set forth in SEQ ID NO:143, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:143. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:143. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:143.

In some embodiments, the GPPS polypeptide encoded by the one or more heterologous nucleic acids comprises the amino acid sequence set forth in SEQ ID NO:203. In some embodiments, the GPPS polypeptide encoded by the one or more heterologous nucleic acids comprises the amino acid sequence set forth in SEQ ID NO:203, or a conservatively substituted amino acid sequence thereof. In some embodiments, the GPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:203. In some embodiments, the GPPS polypeptide encoded by the one or more heterologous nucleic acids comprises an amino acid sequence having at least 80%, at least 81%, at least 82%, at least 83%, or at least 84% amino acid sequence identity to SEQ ID NO:203. In some embodiments, the GPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:203.

Exemplary GPPS heterologous nucleic acids disclosed herein may include nucleic acids that encode a GPPS polypeptide, such as, a full-length GPPS polypeptide, a fragment of a GPPS polypeptide, a variant of a GPPS polypeptide, a truncated GPPS polypeptide, or a fusion polypeptide that has at least one activity of a GPPS polypeptide.

In some embodiments, the GPPS polypeptide is overexpressed in the genetically modified host cell. Overexpression may be achieved by increasing the copy number of the GPPS polypeptide-encoding heterologous nucleic acid, e.g., through use of a high copy number expression vector (e.g., a plasmid that exists at 10-40 copies per cell) and/or by operably linking the GPPS polypeptide-encoding heterologous nucleic acid to a strong promoter. In some embodiments, the genetically modified host cell has one copy of a GPPS polypeptide-encoding heterologous nucleic acid. In some embodiments, the genetically modified host cell has two copies of a GPPS polypeptide-encoding heterologous nucleic acid. In some embodiments, the genetically modified host cell has three copies of a GPPS polypeptide-encoding heterologous nucleic acid. In some embodiments, the genetically modified host cell has four copies of a GPPS polypeptide-encoding heterologous nucleic acid. In some embodiments, the genetically modified host cell has five copies of a GPPS polypeptide-encoding heterologous nucleic acid. In some embodiments, the genetically modified host cell has six copies of a GPPS polypeptide-encoding heterologous nucleic acid. In some embodiments, the genetically modified host cell has seven copies of a GPPS polypeptide-encoding heterologous nucleic acid. In some embodiments, the genetically modified host cell has eight copies of a GPPS polypeptide-encoding heterologous nucleic acid.

In some embodiments, the one or more heterologous nucleic acids encoding a GPPS polypeptide comprise the nucleotide sequence set forth in SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, or SEQ ID NO:202. In some embodiments, the one or more heterologous nucleic acids encoding a GPPS polypeptide comprise the nucleotide sequence set forth in SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, or SEQ ID NO:202, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, or SEQ ID NO:202.

In some embodiments, the one or more heterologous nucleic acids encoding a GPPS polypeptide comprise the nucleotide sequence set forth in SEQ ID NO:71 and/or SEQ ID NO:73. In some embodiments, the one or more heterologous nucleic acids encoding a GPPS polypeptide comprise the nucleotide sequence set forth in SEQ ID NO:71 and/or SEQ ID NO:73, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:71 and/or SEQ ID NO:73.

In some embodiments, the one or more heterologous nucleic acids encoding a GPPS polypeptide (ERG20mut (F96W, N127W)) comprise the nucleotide sequence set forth in SEQ ID NO:59. In some embodiments, the one or more heterologous nucleic acids encoding a GPPS polypeptide (ERG20mut (F96W, N127W)) comprise the nucleotide sequence set forth in SEQ ID NO:59, or a codon degenerate nucleotide sequence thereof. In some embodiments, the one or more heterologous nucleic acids encoding a GPPS polypeptide (ERG20mut (F96W, N127W)) comprise a nucleotide sequence having at least 80%, at least 81%, at least 82%, at least 83%, or at least 84% sequence identity to SEQ ID NO:59. In some embodiments, the one or more heterologous nucleic acids encoding a GPPS polypeptide (ERG20mut (F96W, N127W)) comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:59.

In some embodiments, the one or more heterologous nucleic acids encoding a GPPS polypeptide (ERG20mut (F96W, N127W)) comprise the nucleotide sequence set forth in SEQ ID NO:161. In some embodiments, the one or more heterologous nucleic acids encoding a GPPS polypeptide (ERG20mut (F96W, N127W)) comprise the nucleotide sequence set forth in SEQ ID NO:161, or a codon degenerate nucleotide sequence thereof. In some embodiments, the one or more heterologous nucleic acids encoding a GPPS polypeptide (ERG20mut (F96W, N127W)) comprise a nucleotide sequence having at least 80%, at least 81%, at least 82%, at least 83%, or at least 84% sequence identity to SEQ ID NO:161. In some embodiments, the one or more heterologous nucleic acids encoding a GPPS polypeptide (ERG20mut (F96W, N127W)) comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:161. In some embodiments, the one or more heterologous nucleic acids encoding a GPPS polypeptide (ERG20mut (F96W, N127W)) comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:161.

In some embodiments, the one or more heterologous nucleic acids encoding a GPPS polypeptide comprise the nucleotide sequence set forth in SEQ ID NO:122. In some embodiments, the one or more heterologous nucleic acids encoding a GPPS polypeptide comprise the nucleotide sequence set forth in SEQ ID NO:122, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:122. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:122.

In some embodiments, the one or more heterologous nucleic acids encoding a GPPS polypeptide comprise the nucleotide sequence set forth in SEQ ID NO:124. In some embodiments, the one or more heterologous nucleic acids encoding a GPPS polypeptide comprise the nucleotide sequence set forth in SEQ ID NO:124, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:124. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:124.

In some embodiments, the one or more heterologous nucleic acids encoding a GPPS polypeptide comprise the nucleotide sequence set forth in SEQ ID NO:126. In some embodiments, the one or more heterologous nucleic acids encoding a GPPS polypeptide comprise the nucleotide sequence set forth in SEQ ID NO:126, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:126. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:126.

In some embodiments, the one or more heterologous nucleic acids encoding a GPPS polypeptide comprise the nucleotide sequence set forth in SEQ ID NO:128. In some embodiments, the one or more heterologous nucleic acids encoding a GPPS polypeptide comprise the nucleotide sequence set forth in SEQ ID NO:128, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:128. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:128.

In some embodiments, the one or more heterologous nucleic acids encoding a GPPS polypeptide comprise the nucleotide sequence set forth in SEQ ID NO:130. In some embodiments, the one or more heterologous nucleic acids encoding a GPPS polypeptide comprise the nucleotide sequence set forth in SEQ ID NO:130, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:130. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:130.

In some embodiments, the one or more heterologous nucleic acids encoding a GPPS polypeptide comprise the nucleotide sequence set forth in SEQ ID NO:132. In some embodiments, the one or more heterologous nucleic acids encoding a GPPS polypeptide comprise the nucleotide sequence set forth in SEQ ID NO:132, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:132. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:132.

In some embodiments, the one or more heterologous nucleic acids encoding a GPPS polypeptide comprise the nucleotide sequence set forth in SEQ ID NO:134. In some embodiments, the one or more heterologous nucleic acids encoding a GPPS polypeptide comprise the nucleotide sequence set forth in SEQ ID NO:134, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:134. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:134.

In some embodiments, the one or more heterologous nucleic acids encoding a GPPS polypeptide comprise the nucleotide sequence set forth in SEQ ID NO:136. In some embodiments, the one or more heterologous nucleic acids encoding a GPPS polypeptide comprise the nucleotide sequence set forth in SEQ ID NO:136, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:136. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:136.

In some embodiments, the one or more heterologous nucleic acids encoding a GPPS polypeptide comprise the nucleotide sequence set forth in SEQ ID NO:138. In some embodiments, the one or more heterologous nucleic acids encoding a GPPS polypeptide comprise the nucleotide sequence set forth in SEQ ID NO:138, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:138. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:138.

In some embodiments, the one or more heterologous nucleic acids encoding a GPPS polypeptide comprise the nucleotide sequence set forth in SEQ ID NO:140. In some embodiments, the one or more heterologous nucleic acids encoding a GPPS polypeptide comprise the nucleotide sequence set forth in SEQ ID NO:140, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:140. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:140.

In some embodiments, the one or more heterologous nucleic acids encoding a GPPS polypeptide comprise the nucleotide sequence set forth in SEQ ID NO:142. In some embodiments, the one or more heterologous nucleic acids encoding a GPPS polypeptide comprise the nucleotide sequence set forth in SEQ ID NO:142, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:142. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:142.

In some embodiments, the one or more heterologous nucleic acids encoding a GPPS polypeptide comprise the nucleotide sequence set forth in SEQ ID NO:144. In some embodiments, the one or more heterologous nucleic acids encoding a GPPS polypeptide comprise the nucleotide sequence set forth in SEQ ID NO:144, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:144. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:144.

In some embodiments, the one or more heterologous nucleic acids encoding a GPPS polypeptide comprise the nucleotide sequence set forth in SEQ ID NO:202. In some embodiments, the one or more heterologous nucleic acids encoding a GPPS polypeptide comprise the nucleotide sequence set forth in SEQ ID NO:202, or a codon degenerate nucleotide sequence thereof. In some embodiments, the one or more heterologous nucleic acids encoding a GPPS polypeptide comprise a nucleotide sequence having at least 80%, at least 81%, at least 82%, at least 83%, or at least 84% sequence identity to SEQ ID NO:202. In some embodiments, the one or more heterologous nucleic acids encoding a GPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:202.

NphB Polypeptides, Nucleic Acids Comprising Said Polypeptides, and Genetically Modified Host Cells Expressing Said Polypeptides In some embodiments, a NphB polypeptide is used instead of a GOT polypeptide to generate cannabigerolic acid from GPP and olivetolic acid. In some embodiments, a genetically modified host cell of the present disclosure is genetically modified with one or more heterologous nucleic acids encoding a NphB polypeptide.

Exemplary NphB polypeptides disclosed herein may include a full-length NphB polypeptide, a fragment of a NphB polypeptide, a variant of a NphB polypeptide, a truncated NphB polypeptide, or a fusion polypeptide that has at least one activity of a NphB polypeptide.

In some embodiments, the NphB polypeptide encoded by the one or more heterologous nucleic acids comprises the amino acid sequence set forth in SEQ ID NO:84. In some embodiments, the NphB polypeptide encoded by the one or more heterologous nucleic acids comprises the amino acid sequence set forth in SEQ ID NO:84, or a conservatively substituted amino acid sequence thereof. In some embodiments, the NphB polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:84.

Exemplary NphB heterologous nucleic acids disclosed herein may include nucleic acids that encode a NphB polypeptide, such as, a full-length NphB polypeptide, a fragment of a NphB polypeptide, a variant of a NphB polypeptide, a truncated NphB polypeptide, or a fusion polypeptide that has at least one activity of a NphB polypeptide.

In some embodiments, the NphB polypeptide is overexpressed in the genetically modified host cell. Overexpression may be achieved by increasing the copy number of the NphB polypeptide-encoding heterologous nucleic acid, e.g., through use of a high copy number expression vector (e.g., a plasmid that exists at 10-40 copies per cell) and/or by operably linking the NphB polypeptide-encoding heterologous nucleic acid to a strong promoter. In some embodiments, the genetically modified host cell has one copy of a NphB polypeptide-encoding heterologous nucleic acid. In some embodiments, the genetically modified host cell has two copies of a NphB polypeptide-encoding heterologous nucleic acid. In some embodiments, the genetically modified host cell has three copies of a NphB polypeptide-encoding heterologous nucleic acid. In some embodiments, the genetically modified host cell has four copies of a NphB polypeptide-encoding heterologous nucleic acid. In some embodiments, the genetically modified host cell has five copies of a NphB polypeptide-encoding heterologous nucleic acid. In some embodiments, the genetically modified host cell has six copies of a NphB polypeptide-encoding heterologous nucleic acid. In some embodiments, the genetically modified host cell has seven copies of a NphB polypeptide-encoding heterologous nucleic acid. In some embodiments, the genetically modified host cell has eight copies of a NphB polypeptide-encoding heterologous nucleic acid.

In some embodiments, the one or more heterologous nucleic acids encoding a NphB polypeptide comprise the nucleotide sequence set forth in SEQ ID NO:83. In some embodiments, the one or more heterologous nucleic acids encoding a NphB polypeptide comprise the nucleotide sequence set forth in SEQ ID NO:83, or a codon degenerate nucleotide sequence thereof. In some embodiments, the one or more heterologous nucleic acids encoding a NphB polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:83.

Polypeptides that Generate Neryl Pyrophosphate or Cannabinerolic Acid, Nucleic Acids Comprising Said Polypeptides, and Genetically Modified Host Cells Expressing Said Polypeptides In some embodiments, a genetically modified host cell of the present disclosure is genetically modified with one or more heterologous nucleic acids encoding a neryl pyrophosphate (NPP) synthase (NPPS) polypeptide (FIG. 11). NPP and olivetolic acid may be substrates to generate cannabinerolic acid (CBNRA). In some embodiments, a GOT polypeptide acts on NPP and an olivetolic acid derivative (as described elsewhere herein) to generate a CBNRA derivative. Cannabinerolic acid or derivatives thereof can serve as a substrate for a CBDAS or THCAS polypeptide to generate CBDA or THCA, or derivatives thereof, respectively.

Exemplary NPPS polypeptides disclosed herein may include a fragment of a NPPS polypeptide, a variant of a NPPS polypeptide, a full-length NPPS polypeptide, a truncated NPPS polypeptide, or a fusion polypeptide that has at least one activity of a NPPS polypeptide.

In some embodiments, the NPPS polypeptide encoded by the one or more heterologous nucleic acids comprises the amino acid sequence set forth in SEQ ID NO:70. In some embodiments, the NPPS polypeptide encoded by the one or more heterologous nucleic acids comprises the amino acid sequence set forth in SEQ ID NO:70, or a conservatively substituted amino acid sequence thereof. In some embodiments, the NPPS polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:70. In some embodiments, the NPPS polypeptide encoded by the one or more heterologous nucleic acids comprises an amino acid sequence having at least 80%, at least 81%, at least 82%, at least 83%, or at least 84% amino acid sequence identity to SEQ ID NO:70. In some embodiments, the NPPS polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:70. In some embodiments, the NPPS polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:70.

Exemplary NPPS heterologous nucleic acids disclosed herein may include nucleic acids that encode a NPPS polypeptide, such as, a full-length NPPS polypeptide, a fragment of a NPPS polypeptide, a variant of a NPPS polypeptide, a truncated NPPS polypeptide, or a fusion polypeptide that has at least one activity of a NPPS polypeptide.

In some embodiments, the NPPS polypeptide is overexpressed in the genetically modified host cell. Overexpression may be achieved by increasing the copy number of the NPPS polypeptide-encoding heterologous nucleic acid, e.g., through use of a high copy number expression vector (e.g., a plasmid that exists at 10-40 copies per cell) and/or by operably linking the NPPS polypeptide-encoding heterologous nucleic acid to a strong promoter. In some embodiments, the genetically modified host cell has one copy of an NPPS polypeptide-encoding heterologous nucleic acid. In some embodiments, the genetically modified host cell has two copies of an NPPS polypeptide-encoding heterologous nucleic acid. In some embodiments, the genetically modified host cell has three copies of an NPPS polypeptide-encoding heterologous nucleic acid. In some embodiments, the genetically modified host cell has four copies of an NPPS polypeptide-encoding heterologous nucleic acid. In some embodiments, the genetically modified host cell has five copies of an NPPS polypeptide-encoding heterologous nucleic acid. In some embodiments, the genetically modified host cell has six copies of an NPPS polypeptide-encoding heterologous nucleic acid. In some embodiments, the genetically modified host cell has seven copies of an NPPS polypeptide-encoding heterologous nucleic acid. In some embodiments, the genetically modified host cell has eight copies of an NPPS polypeptide-encoding heterologous nucleic acid.

In some embodiments, the one or more heterologous nucleic acids encoding a NPPS polypeptide comprise the nucleotide sequence set forth in SEQ ID NO:69. In some embodiments, the one or more heterologous nucleic acids encoding a NPPS polypeptide comprise the nucleotide sequence set forth in SEQ ID NO:69, or a codon degenerate nucleotide sequence thereof. In some embodiments, the one or more heterologous nucleic acids encoding a NPPS polypeptide comprise a nucleotide sequence having at least 80%, at least 81%, at least 82%, at least 83%, or at least 84% sequence identity to SEQ ID NO:69. In some embodiments, the one or more heterologous nucleic acids encoding a NPPS polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:69. In some embodiments, the one or more heterologous nucleic acids encoding a NPPS polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:69.

Polypeptides that Generate Acetyl-CoA from Pyruvate, Nucleic Acids Comprising Said Polypeptides, and Genetically Modified Host Cells Expressing Said Polypeptides In some embodiments, a genetically modified host cell of the present disclosure is genetically modified with one or more heterologous nucleic acids encoding a polypeptide that generates acetyl-CoA from pyruvate. Polypeptides that generate acetyl-CoA from pyruvate may include a pyruvate decarboxylase (PDC) polypeptide. In some embodiments, a genetically modified host cell of the present disclosure is genetically modified with one or more heterologous nucleic acids encoding a PDC polypeptide.

Exemplary PDC polypeptides disclosed herein may include a full-length PDC polypeptide, a fragment of a PDC polypeptide, a variant of a PDC polypeptide, a truncated PDC polypeptide, or a fusion polypeptide that has at least one activity of a PDC polypeptide.

In some embodiments, the PDC polypeptide encoded by the one or more heterologous nucleic acids comprises the amino acid sequence set forth in SEQ ID NO:117. In some embodiments, the PDC polypeptide encoded by the one or more heterologous nucleic acids comprises the amino acid sequence set forth in SEQ ID NO:117, or a conservatively substituted amino acid sequence thereof. In some embodiments, the PDC polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:117. In some embodiments, the PDC polypeptide encoded by the one or more heterologous nucleic acids comprises an amino acid sequence having at least 80%, at least 81%, at least 82%, at least 83%, or at least 84% amino acid sequence identity to SEQ ID NO:117. In some embodiments, the PDC polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:117. In some embodiments, the PDC polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:117.

Exemplary PDC heterologous nucleic acids disclosed herein may include nucleic acids that encode a PDC polypeptide, such as, a full-length PDC polypeptide, a fragment of a PDC polypeptide, a variant of a PDC polypeptide, a truncated PDC polypeptide, or a fusion polypeptide that has at least one activity of a PDC polypeptide.

In some embodiments, the PDC polypeptide is overexpressed in the genetically modified host cell. Overexpression may be achieved by increasing the copy number of the PDC polypeptide-encoding heterologous nucleic acid, e.g., through use of a high copy number expression vector (e.g., a plasmid that exists at 10-40 copies per cell) and/or by operably linking the PDC polypeptide-encoding heterologous nucleic acid to a strong promoter. In some embodiments, the genetically modified host cell has one copy of a PDC polypeptide-encoding heterologous nucleic acid. In some embodiments, the genetically modified host cell has two copies of a PDC polypeptide-encoding heterologous nucleic acid. In some embodiments, the genetically modified host cell has three copies of a PDC polypeptide-encoding heterologous nucleic acid. In some embodiments, the genetically modified host cell has four copies of a PDC polypeptide-encoding heterologous nucleic acid. In some embodiments, the genetically modified host cell has five copies of a PDC polypeptide-encoding heterologous nucleic acid.

In some embodiments, the one or more heterologous nucleic acids encoding a PDC polypeptide comprise the nucleotide sequence set forth in SEQ ID NO:118. In some embodiments, the one or more heterologous nucleic acids encoding a PDC polypeptide comprise the nucleotide sequence set forth in SEQ ID NO:118, or a codon degenerate nucleotide sequence thereof. In some embodiments, the one or more heterologous nucleic acids encoding a PDC polypeptide comprise a nucleotide sequence having at least 80%, at least 81%, at least 82%, at least 83%, or at least 84% sequence identity to SEQ ID NO:118. In some embodiments, the one or more heterologous nucleic acids encoding a PDC polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:118. In some embodiments, the one or more heterologous nucleic acids encoding a PDC polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:118.

Polypeptides that Condense Two Molecules of Acetyl-CoA to Generate Acetoacetyl-CoA, Nucleic Acids Comprising Said Polypeptides, and Genetically Modified Host Cells Expressing Said Polypeptides In some embodiments, the host cell is genetically modified with one or more heterologous nucleic acids encoding a polypeptide that condenses two molecules of acetyl-CoA to generate acetoacetyl-CoA. In some embodiments, the polypeptide that condenses two molecules of acetyl-CoA to generate acetoacetyl-CoA is an acetoacetyl-CoA thiolase (ERG10p) polypeptide. In some embodiments, a genetically modified host cell of the present disclosure is genetically modified with one or more heterologous nucleic acids encoding an acetoacetyl-CoA thiolase polypeptide.

Exemplary acetoacetyl-CoA thiolase polypeptides disclosed herein may include a full-length acetoacetyl-CoA thiolase polypeptide, a fragment of an acetoacetyl-CoA thiolase polypeptide, a variant of an acetoacetyl-CoA thiolase polypeptide, a truncated acetoacetyl-CoA thiolase polypeptide, or a fusion polypeptide that has at least one activity of an acetoacetyl-CoA thiolase polypeptide.

In some embodiments, the acetoacetyl-CoA thiolase (ERG10p) polypeptide encoded by the one or more heterologous nucleic acids comprises the amino acid sequence set forth in SEQ ID NO:25. In some embodiments, the acetoacetyl-CoA thiolase (ERG10p) polypeptide encoded by the one or more heterologous nucleic acids comprises the amino acid sequence set forth in SEQ ID NO:25, or a conservatively substituted amino acid sequence thereof. In some embodiments, the acetoacetyl-CoA thiolase (ERG10p) polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:25. In some embodiments, the acetoacetyl-CoA thiolase (ERG10p) polypeptide encoded by the one or more heterologous nucleic acids comprises an amino acid sequence having at least 80%, at least 81%, at least 82%, at least 83%, or at least 84% amino acid sequence identity to SEQ ID NO:25. In some embodiments, the acetoacetyl-CoA thiolase (ERG10p) polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:25. In some embodiments, the acetoacetyl-CoA thiolase (ERG10p) polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:25.

Exemplary acetoacetyl-CoA thiolase heterologous nucleic acids disclosed herein may include nucleic acids that encode an acetoacetyl-CoA thiolase polypeptide, such as, a full-length acetoacetyl-CoA thiolase polypeptide, a fragment of an acetoacetyl-CoA thiolase polypeptide, a variant of an acetoacetyl-CoA thiolase polypeptide, a truncated acetoacetyl-CoA thiolase polypeptide, or a fusion polypeptide that has at least one activity of an acetoacetyl-CoA thiolase polypeptide.

In some embodiments, the acetoacetyl-CoA thiolase polypeptide is overexpressed in the genetically modified host cell. Overexpression may be achieved by increasing the copy number of the acetoacetyl-CoA thiolase polypeptide-encoding heterologous nucleic acid, e.g., through use of a high copy number expression vector (e.g., a plasmid that exists at 10-40 copies per cell) and/or by operably linking the acetoacetyl-CoA thiolase polypeptide-encoding heterologous nucleic acid to a strong promoter. In some embodiments, the genetically modified host cell has one copy of an acetoacetyl-CoA thiolase polypeptide-encoding heterologous nucleic acid. In some embodiments, the genetically modified host cell has two copies of an acetoacetyl-CoA thiolase polypeptide-encoding heterologous nucleic acid. In some embodiments, the genetically modified host cell has three copies of an acetoacetyl-CoA thiolase polypeptide-encoding heterologous nucleic acid. In some embodiments, the genetically modified host cell has four copies of an acetoacetyl-CoA thiolase polypeptide-encoding heterologous nucleic acid. In some embodiments, the genetically modified host cell has five copies of an acetoacetyl-CoA thiolase polypeptide-encoding heterologous nucleic acid.

In some embodiments, the one or more heterologous nucleic acids encoding an acetoacetyl-CoA thiolase (ERG10p) polypeptide comprise the nucleotide sequence set forth in SEQ ID NO:157. In some embodiments, the one or more heterologous nucleic acids encoding a ERG10p polypeptide comprise the nucleotide sequence set forth in SEQ ID NO:157, or a codon degenerate nucleotide sequence thereof. In some embodiments, the one or more heterologous nucleic acids encoding an acetoacetyl-CoA thiolase (ERG10p) polypeptide comprise a nucleotide sequence having at least 80%, at least 81%, at least 82%, at least 83%, or at least 84% sequence identity to SEQ ID NO:157. In some embodiments, the one or more heterologous nucleic acids encoding an acetoacetyl-CoA thiolase (ERG10p) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:157. In some embodiments, the one or more heterologous nucleic acids encoding an acetoacetyl-CoA thiolase (ERG10p) polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:157.

In some embodiments, the one or more heterologous nucleic acids encoding an acetoacetyl-CoA thiolase (ERG10p) polypeptide comprise the nucleotide sequence set forth in SEQ ID NO:209. In some embodiments, the one or more heterologous nucleic acids encoding a ERG10p polypeptide comprise the nucleotide sequence set forth in SEQ ID NO:209, or a codon degenerate nucleotide sequence thereof. In some embodiments, the one or more heterologous nucleic acids encoding an acetoacetyl-CoA thiolase (ERG10p) polypeptide comprise a nucleotide sequence having at least 80%, at least 81%, at least 82%, at least 83%, or at least 84% sequence identity to SEQ ID NO:209. In some embodiments, the one or more heterologous nucleic acids encoding an acetoacetyl-CoA thiolase (ERG10p) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:209. In some embodiments, the one or more heterologous nucleic acids encoding an acetoacetyl-CoA thiolase (ERG10p) polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:209.

Mevalonate Pathway Polypeptides, Nucleic Acids Comprising Said Polypeptides, and Genetically Modified Host Cells Expressing Said Polypeptides In some embodiments, a genetically modified host cell of the present disclosure is genetically modified with one or more heterologous nucleic acids encoding one or more polypeptides having at least one activity of a polypeptide present in the mevalonate (MEV) pathway.

In some embodiments, the one or more polypeptides that generate GPP or are part of a biosynthetic pathway that generates GPP are one or more polypeptides having at least one activity of a polypeptide present in the mevalonate pathway. The mevalonate pathway may comprise polypeptides that catalyze the following steps: (a) condensing two molecules of acetyl-CoA to generate acetoacetyl-CoA (e.g., by action of an acetoacetyl-CoA thiolase polypeptide); (b) condensing acetoacetyl-CoA with acetyl-CoA to form hydroxymethylglutaryl-CoA (HMG-CoA) (e.g., by action of a HMGS polypeptide); (c) converting HMG-CoA to mevalonate (e.g., by action of an HMGR polypeptide); (d) phosphorylating mevalonate to mevalonate 5-phosphate (e.g., by action of a MK polypeptide); (e) converting mevalonate 5-phosphate to mevalonate 5-pyrophosphate (e.g., by action of a PMK polypeptide); (f) converting mevalonate 5-pyrophosphate to isopentenyl pyrophosphate (e.g., by action of a mevalonate pyrophosphate decarboxylase (MPD or MVD) polypeptide); and (g) converting isopentenyl pyrophosphate to dimethylallyl pyrophosphate (e.g., by action of an isopentenyl pyrophosphate isomerase (IDI) polypeptide).

In some embodiments, a genetically modified host cell of the present disclosure is genetically modified with one or more heterologous nucleic acids encoding a MEV pathway polypeptide. In some embodiments, a genetically modified host cell of the present disclosure is genetically modified with one or more heterologous nucleic acids encoding more than one MEV pathway polypeptide. In some embodiments, a genetically modified host cell of the present disclosure is genetically modified with one or more heterologous nucleic acids encoding more than two MEV pathway polypeptides. In some embodiments, a genetically modified host cell of the present disclosure is genetically modified with one or more heterologous nucleic acids encoding more than three MEV pathway polypeptides. In some embodiments, a genetically modified host cell of the present disclosure is genetically modified with one or more heterologous nucleic acids encoding more than four MEV pathway polypeptides. In some embodiments, a genetically modified host cell of the present disclosure is genetically modified with one or more heterologous nucleic acids encoding more than five MEV pathway polypeptides. In some embodiments, a genetically modified host cell of the present disclosure is genetically modified with one or more heterologous nucleic acids encoding more than six MEV pathway polypeptides. In some embodiments, a genetically modified host cell of the present disclosure is genetically modified with one or more heterologous nucleic acids encoding all MEV pathway polypeptides.

In some embodiments, a genetically modified host cell of the present disclosure is genetically modified with one or more heterologous nucleic acids encoding two MEV pathway polypeptides. In some embodiments, a genetically modified host cell of the present disclosure is genetically modified with one or more heterologous nucleic acids encoding three MEV pathway polypeptides. In some embodiments, a genetically modified host cell of the present disclosure is genetically modified with one or more heterologous nucleic acids encoding four MEV pathway polypeptides. In some embodiments, a genetically modified host cell of the present disclosure is genetically modified with one or more heterologous nucleic acids encoding five MEV pathway polypeptides. In some embodiments, a genetically modified host cell of the present disclosure is genetically modified with one or more heterologous nucleic acids encoding six MEV pathway polypeptides. In some embodiments, a genetically modified host cell of the present disclosure is genetically modified with one or more heterologous nucleic acids encoding 1, 2, 3, 4, 5, 6, or more MEV pathway polypeptides. In some embodiments, a genetically modified host cell of the present disclosure is genetically modified with one or more heterologous nucleic acids encoding 1, 2, 3, 4, 5, or 6 MEV pathway polypeptides.

Exemplary MEV pathway polypeptides disclosed herein may include a full-length MEV pathway polypeptide, a fragment of a MEV pathway polypeptide, a variant of a MEV pathway polypeptide, a truncated MEV pathway polypeptide, or a fusion polypeptide that has at least one activity of a MEV pathway polypeptide. In some embodiments, the one or more MEV pathway polypeptides are selected from the group consisting of an acetoacetyl-CoA thiolase polypeptide, a HMGS polypeptide, an HMGR polypeptide, an MK polypeptide, a PMK polypeptide, an MVD polypeptide, and an IDI polypeptide.

In some embodiments, the HMGS polypeptide encoded by the one or more heterologous nucleic acids comprises the amino acid sequence set forth in SEQ ID NO:23, SEQ ID NO:24, or SEQ ID NO:115. In some embodiments, the HMGS polypeptide encoded by the one or more heterologous nucleic acids comprises the amino acid sequence set forth in SEQ ID NO:23, SEQ ID NO:24, or SEQ ID NO:115, or a conservatively substituted amino acid sequence thereof. In some embodiments, the HMGS polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:23, SEQ ID NO:24, or SEQ ID NO:115.

In some embodiments, the HMGS polypeptide encoded by the one or more heterologous nucleic acids is a MvaS polypeptide and comprises the amino acid sequence set forth in SEQ ID NO:23. In some embodiments, the HMGS polypeptide encoded by the one or more heterologous nucleic acids is a MvaS polypeptide and comprises the amino acid sequence set forth in SEQ ID NO:23, or a conservatively substituted amino acid sequence thereof. In some embodiments, the HMGS polypeptide encoded by the one or more heterologous nucleic acids is a MvaS polypeptide and comprises an amino acid sequence having at least 50%, at least 55%, at least 60%, at least 65%, at least 70%, or at least 75% amino acid sequence identity to SEQ ID NO:23. In some embodiments, the HMGS polypeptide encoded by the one or more heterologous nucleic acids is a MvaS polypeptide and comprises an amino acid sequence having at least 80%, at least 81%, at least 82%, at least 83%, or at least 84% amino acid sequence identity to SEQ ID NO:23. In some embodiments, the HMGS polypeptide encoded by the one or more heterologous nucleic acids is a MvaS polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:23.

In some embodiments, the HMGS polypeptide encoded by the one or more heterologous nucleic acids is a MvaS polypeptide and comprises the amino acid sequence set forth in SEQ ID NO:56. In some embodiments, the HMGS polypeptide encoded by the one or more heterologous nucleic acids is a MvaS polypeptide and comprises the amino acid sequence set forth in SEQ ID NO:56, or a conservatively substituted amino acid sequence thereof. In some embodiments, the HMGS polypeptide encoded by the one or more heterologous nucleic acids is a MvaS polypeptide and comprises an amino acid sequence having at least 50%, at least 55%, at least 60%, at least 65%, at least 70%, or at least 75% amino acid sequence identity to SEQ ID NO:56. In some embodiments, the HMGS polypeptide encoded by the one or more heterologous nucleic acids is a MvaS polypeptide and comprises an amino acid sequence having at least 80%, at least 81%, at least 82%, at least 83%, or at least 84% amino acid sequence identity to SEQ ID NO:56. In some embodiments, the HMGS polypeptide encoded by the one or more heterologous nucleic acids is a MvaS polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:56.

In some embodiments, the HMGS polypeptide encoded by the one or more heterologous nucleic acids is an ERG13 polypeptide and comprises the amino acid sequence set forth in SEQ ID NO:24. In some embodiments, the HMGS polypeptide encoded by the one or more heterologous nucleic acids is an ERG13 polypeptide and comprises the amino acid sequence set forth in SEQ ID NO:24, or a conservatively substituted amino acid sequence thereof. In some embodiments, the HMGS polypeptide encoded by the one or more heterologous nucleic acids is an ERG13 polypeptide and comprises an amino acid sequence having at least 50%, at least 55%, at least 60%, at least 65%, at least 70%, or at least 75% amino acid sequence identity to SEQ ID NO:24. In some embodiments, the HMGS polypeptide encoded by the one or more heterologous nucleic acids is an ERG13 polypeptide and comprises an amino acid sequence having at least 80%, at least 81%, at least 82%, at least 83%, or at least 84% amino acid sequence identity to SEQ ID NO:24. In some embodiments, the HMGS polypeptide encoded by the one or more heterologous nucleic acids is an ERG13 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:24.

In some embodiments, the HMGS polypeptide encoded by the one or more heterologous nucleic acids is an ERG13 polypeptide and comprises the amino acid sequence set forth in SEQ ID NO:115. In some embodiments, the HMGS polypeptide encoded by the one or more heterologous nucleic acids is an ERG13 polypeptide and comprises the amino acid sequence set forth in SEQ ID NO:115, or a conservatively substituted amino acid sequence thereof. In some embodiments, the HMGS polypeptide encoded by the one or more heterologous nucleic acids is an ERG13 polypeptide and comprises an amino acid sequence having at least 50%, at least 55%, at least 60%, at least 65%, at least 70%, or at least 75% amino acid sequence identity to SEQ ID NO:115. In some embodiments, the HMGS polypeptide encoded by the one or more heterologous nucleic acids is an ERG13 polypeptide and comprises an amino acid sequence having at least 80%, at least 81%, at least 82%, at least 83%, or at least 84% amino acid sequence identity to SEQ ID NO:115. In some embodiments, the HMGS polypeptide encoded by the one or more heterologous nucleic acids is an ERG13 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:115.

In some embodiments, the HMGR polypeptide encoded by the one or more heterologous nucleic acids is a MvaE polypeptide and comprises the amino acid sequence set forth in SEQ ID NO:22. In some embodiments, the HMGR polypeptide encoded by the one or more heterologous nucleic acids is a MvaE polypeptide and comprises the amino acid sequence set forth in SEQ ID NO:22, or a conservatively substituted amino acid sequence thereof. In some embodiments, the HMGR polypeptide encoded by the one or more heterologous nucleic acids is a MvaE polypeptide and comprises an amino acid sequence having at least 50%, at least 55%, at least 60%, at least 65%, at least 70%, or at least 75% amino acid sequence identity to SEQ ID NO:22. In some embodiments, the HMGR polypeptide encoded by the one or more heterologous nucleic acids is a MvaE polypeptide and comprises an amino acid sequence having at least 80%, at least 81%, at least 82%, at least 83%, or at least 84% amino acid sequence identity to SEQ ID NO:22. In some embodiments, the HMGR polypeptide encoded by the one or more heterologous nucleic acids is a MvaE polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:22. In some embodiments, the HMGR polypeptide encoded by the one or more heterologous nucleic acids is a MvaE polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:22.

In some embodiments, the HMGR polypeptide encoded by the one or more heterologous nucleic acids is a MvaE polypeptide and comprises the amino acid sequence set forth in SEQ ID NO:54. In some embodiments, the HMGR polypeptide encoded by the one or more heterologous nucleic acids is a MvaE polypeptide and comprises the amino acid sequence set forth in SEQ ID NO:54, or a conservatively substituted amino acid sequence thereof. In some embodiments, the HMGR polypeptide encoded by the one or more heterologous nucleic acids is a MvaE polypeptide and comprises an amino acid sequence having at least 50%, at least 55%, at least 60%, at least 65%, at least 70%, or at least 75% amino acid sequence identity to SEQ ID NO:54. In some embodiments, the HMGR polypeptide encoded by the one or more heterologous nucleic acids is a MvaE polypeptide and comprises an amino acid sequence having at least 80%, at least 81%, at least 82%, at least 83%, or at least 84% amino acid sequence identity to SEQ ID NO:54. In some embodiments, the HMGR polypeptide encoded by the one or more heterologous nucleic acids is a MvaE polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:54.

In some embodiments, the HMGR polypeptide is a truncated HMGR (tHMGR) polypeptide. In some embodiments, the tHMGR polypeptide encoded by the one or more heterologous nucleic acids comprises the amino acid sequence set forth in SEQ ID NO:17, SEQ ID NO:52, SEQ ID NO:113, or SEQ ID NO:208. In some embodiments, the tHMGR polypeptide encoded by the one or more heterologous nucleic acids comprises the amino acid sequence set forth in SEQ ID NO:17, SEQ ID NO:52, SEQ ID NO:113, or SEQ ID NO:208, or a conservatively substituted amino acid sequence thereof. In some embodiments, the tHMGR polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:17, SEQ ID NO:52, SEQ ID NO:113, or SEQ ID NO:208.

In some embodiments, the tHMGR polypeptide encoded by the one or more heterologous nucleic acids comprises the amino acid sequence set forth in SEQ ID NO:17. In some embodiments, the tHMGR polypeptide encoded by the one or more heterologous nucleic acids comprises the amino acid sequence set forth in SEQ ID NO:17, or a conservatively substituted amino acid sequence thereof. In some embodiments, the tHMGR polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:17. In some embodiments, the tHMGR polypeptide encoded by the one or more heterologous nucleic acids comprises an amino acid sequence having at least 80%, at least 81%, at least 82%, at least 83%, or at least 84% amino acid sequence identity to SEQ ID NO:17. In some embodiments, the tHMGR polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:17.

In some embodiments, the tHMGR polypeptide encoded by the one or more heterologous nucleic acids comprises the amino acid sequence set forth in SEQ ID NO:52. In some embodiments, the tHMGR polypeptide encoded by the one or more heterologous nucleic acids comprises the amino acid sequence set forth in SEQ ID NO:52, or a conservatively substituted amino acid sequence thereof. In some embodiments, the tHMGR polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:52. In some embodiments, the tHMGR polypeptide encoded by the one or more heterologous nucleic acids comprises an amino acid sequence having at least 80%, at least 81%, at least 82%, at least 83%, or at least 84% amino acid sequence identity to SEQ ID NO:52. In some embodiments, the tHMGR polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:52.

In some embodiments, the tHMGR polypeptide encoded by the one or more heterologous nucleic acids comprises the amino acid sequence set forth in SEQ ID NO:113. In some embodiments, the tHMGR polypeptide encoded by the one or more heterologous nucleic acids comprises the amino acid sequence set forth in SEQ ID NO:113, or a conservatively substituted amino acid sequence thereof. In some embodiments, the tHMGR polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:113. In some embodiments, the tHMGR polypeptide encoded by the one or more heterologous nucleic acids comprises an amino acid sequence having at least 80%, at least 81%, at least 82%, at least 83%, or at least 84% amino acid sequence identity to SEQ ID NO:113. In some embodiments, the tHMGR polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:113.

In some embodiments, the tHMGR polypeptide encoded by the one or more heterologous nucleic acids comprises the amino acid sequence set forth in SEQ ID NO:208. In some embodiments, the tHMGR polypeptide encoded by the one or more heterologous nucleic acids comprises the amino acid sequence set forth in SEQ ID NO:208, or a conservatively substituted amino acid sequence thereof. In some embodiments, the tHMGR polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:208. In some embodiments, the tHMGR polypeptide encoded by the one or more heterologous nucleic acids comprises an amino acid sequence having at least 80%, at least 81%, at least 82%, at least 83%, or at least 84% amino acid sequence identity to SEQ ID NO:208. In some embodiments, the tHMGR polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:208.

In some embodiments, the MK (ERG12) polypeptide encoded by the one or more heterologous nucleic acids comprises the amino acid sequence set forth in SEQ ID NO:64. In some embodiments, the MK (ERG12) polypeptide encoded by the one or more heterologous nucleic acids comprises the amino acid sequence set forth in SEQ ID NO:64, or a conservatively substituted amino acid sequence thereof. In some embodiments, the MK (ERG12) polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:64. In some embodiments, the MK (ERG12) polypeptide encoded by the one or more heterologous nucleic acids comprises an amino acid sequence having at least 80%, at least 81%, at least 82%, at least 83%, or at least 84% amino acid sequence identity to SEQ ID NO:64. In some embodiments, the MK (ERG12) polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:64. In some embodiments, the MK (ERG12) polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:64.

In some embodiments, the PMK polypeptide encoded by the one or more heterologous nucleic acids comprises the amino acid sequence set forth in SEQ ID NO:62 or SEQ ID NO:205. In some embodiments, the PMK polypeptide encoded by the one or more heterologous nucleic acids comprises the amino acid sequence set forth in SEQ ID NO:62 or SEQ ID NO:205, or a conservatively substituted amino acid sequence thereof. In some embodiments, the PMK polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:62 or SEQ ID NO:205.

In some embodiments, the PMK polypeptide encoded by the one or more heterologous nucleic acids comprises the amino acid sequence set forth in SEQ ID NO:62. In some embodiments, the PMK polypeptide encoded by the one or more heterologous nucleic acids comprises the amino acid sequence set forth in SEQ ID NO:62, or a conservatively substituted amino acid sequence thereof. In some embodiments, the PMK polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:62. In some embodiments, the PMK polypeptide encoded by the one or more heterologous nucleic acids comprises an amino acid sequence having at least 80%, at least 81%, at least 82%, at least 83%, or at least 84% amino acid sequence identity to SEQ ID NO:62. In some embodiments, the PMK polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:62.

In some embodiments, the PMK polypeptide encoded by the one or more heterologous nucleic acids is an ERG8 polypeptide and comprises the amino acid sequence set forth in SEQ ID NO:205. In some embodiments, the PMK polypeptide encoded by the one or more heterologous nucleic acids is an ERG8 polypeptide and comprises the amino acid sequence set forth in SEQ ID NO:205, or a conservatively substituted amino acid sequence thereof. In some embodiments, the PMK polypeptide encoded by the one or more heterologous nucleic acids is an ERG8 polypeptide and comprises an amino acid sequence having at least 50%, at least 55%, at least 60%, at least 65%, at least 70%, or at least 75% amino acid sequence identity to SEQ ID NO:205. In some embodiments, the PMK polypeptide encoded by the one or more heterologous nucleic acids is an ERG8 polypeptide and comprises an amino acid sequence having at least 80%, at least 81%, at least 82%, at least 83%, or at least 84% amino acid sequence identity to SEQ ID NO:205. In some embodiments, the PMK polypeptide encoded by the one or more heterologous nucleic acids is an ERG8 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:205.

In some embodiments, a PMK polypeptide and MK polypeptide are fused into a single polypeptide chain (a PMK/MK fusion polypeptide). In some embodiments, the PMK/MK polypeptide encoded by the one or more heterologous nucleic acids comprises the amino acid sequence set forth in SEQ ID NO:68. In some embodiments, the PMK/MK polypeptide encoded by the one or more heterologous nucleic acids comprises the amino acid sequence set forth in SEQ ID NO:68, or a conservatively substituted amino acid sequence thereof. In some embodiments, the PMK/MK polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:68. In some embodiments, the PMK/MK polypeptide encoded by the one or more heterologous nucleic acids comprises an amino acid sequence having at least 80%, at least 81%, at least 82%, at least 83%, or at least 84% amino acid sequence identity to SEQ ID NO:68. In some embodiments, the PMK/MK polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:68. In some embodiments, the PMK/MK polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:68.

In some embodiments, the MVD polypeptide encoded by the one or more heterologous nucleic acids is an ERG19 polypeptide and comprises the amino acid sequence set forth in SEQ ID NO:66. In some embodiments, the MVD polypeptide encoded by the one or more heterologous nucleic acids is an ERG19 polypeptide and comprises the amino acid sequence set forth in SEQ ID NO:66, or a conservatively substituted amino acid sequence thereof. In some embodiments, the MVD polypeptide encoded by the one or more heterologous nucleic acids is an ERG19 polypeptide and comprises an amino acid sequence having at least 50%, at least 55%, at least 60%, at least 65%, at least 70%, or at least 75% amino acid sequence identity to SEQ ID NO:66. In some embodiments, the MVD polypeptide encoded by the one or more heterologous nucleic acids is an ERG19 polypeptide and comprises an amino acid sequence having at least 80%, at least 81%, at least 82%, at least 83%, or at least 84% amino acid sequence identity to SEQ ID NO:66. In some embodiments, the MVD polypeptide encoded by the one or more heterologous nucleic acids is an ERG19 polypeptide and comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:66. In some embodiments, the MVD polypeptide encoded by the one or more heterologous nucleic acids is an ERG19 polypeptide and comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:66.

In some embodiments, the IDI1 polypeptide encoded by the one or more heterologous nucleic acids comprises the amino acid sequence set forth in SEQ ID NO:58. In some embodiments, the IDI1 polypeptide encoded by the one or more heterologous nucleic acids comprises the amino acid sequence set forth in SEQ ID NO:58, or a conservatively substituted amino acid sequence thereof. In some embodiments, the IDI1 polypeptide encoded by the one or more heterologous nucleic acids comprises an amino acid sequence having at least 50%, at least 55%, at least 60%, at least 65%, at least 70%, or at least 75% amino acid sequence identity to SEQ ID NO:58. In some embodiments, the IDI1 polypeptide encoded by the one or more heterologous nucleic acids comprises an amino acid sequence having at least 80%, at least 81%, at least 82%, at least 83%, or at least 84% amino acid sequence identity to SEQ ID NO:58. In some embodiments, the IDI1 polypeptide encoded by the one or more heterologous nucleic acids comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:58. In some embodiments, the IDI1 polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:58.

Exemplary MEV pathway heterologous nucleic acids disclosed herein may include nucleic acids that encode a MEV pathway polypeptide, such as, a full-length MEV pathway polypeptide, a fragment of a MEV pathway polypeptide, a variant of a MEV pathway polypeptide, a truncated MEV pathway polypeptide, or a fusion polypeptide that has at least one activity of a polypeptide that is part of the MEV pathway.

In some embodiments, the MEV pathway polypeptide is overexpressed in the genetically modified host cell. Overexpression may be achieved by increasing the copy number of a MEV pathway polypeptide-encoding heterologous nucleic acid, e.g., through use of a high copy number expression vector (e.g., a plasmid that exists at 10-40 copies per cell) and/or by operably linking the MEV pathway polypeptide-encoding heterologous nucleic acid to a strong promoter. In some embodiments, the genetically modified host cell has one copy of a MEV pathway polypeptide-encoding heterologous nucleic acid. In some embodiments, the genetically modified host cell has two copies of a MEV pathway polypeptide-encoding heterologous nucleic acid. In some embodiments, the genetically modified host cell has three copies of a MEV pathway polypeptide-encoding heterologous nucleic acid. In some embodiments, the genetically modified host cell has four copies of a MEV pathway polypeptide-encoding heterologous nucleic acid. In some embodiments, the genetically modified host cell has five copies of a MEV pathway polypeptide-encoding heterologous nucleic acid.

In some embodiments, the one or more heterologous nucleic acids encoding a HMGS (mvaS) polypeptide comprise the nucleotide sequence set forth in SEQ ID NO:55. In some embodiments, the one or more heterologous nucleic acids encoding a HMGS (mvaS) polypeptide comprise the nucleotide sequence set forth in SEQ ID NO:55, or a codon degenerate nucleotide sequence thereof. In some embodiments, the one or more heterologous nucleic acids encoding a HMGS (mvaS) polypeptide comprise a nucleotide sequence having at least 80%, at least 81%, at least 82%, at least 83%, or at least 84% sequence identity to SEQ ID NO:55. In some embodiments, the one or more heterologous nucleic acids encoding a HMGS (mvaS) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:55.

In some embodiments, the one or more heterologous nucleic acids encoding a HMGS (ERG13) polypeptide comprise the nucleotide sequence set forth in SEQ ID NO:116 or SEQ ID NO:120. In some embodiments, the one or more heterologous nucleic acids encoding a HMGS (ERG13) polypeptide comprise the nucleotide sequence set forth in SEQ ID NO:116 or SEQ ID NO:120, or a codon degenerate nucleotide sequence thereof. In some embodiments, the one or more heterologous nucleic acids encoding a HMGS (ERG13) polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:116 or SEQ ID NO:120.

In some embodiments, the one or more heterologous nucleic acids encoding a HMGS (ERG13) polypeptide comprise the nucleotide sequence set forth in SEQ ID NO:116. In some embodiments, the one or more heterologous nucleic acids encoding a HMGS (ERG13) polypeptide comprise the nucleotide sequence set forth in SEQ ID NO:116, or a codon degenerate nucleotide sequence thereof. In some embodiments, the one or more heterologous nucleic acids encoding a HMGS (ERG13) polypeptide comprise a nucleotide sequence having at least 80%, at least 81%, at least 82%, at least 83%, or at least 84% sequence identity to SEQ ID NO:116. In some embodiments, the one or more heterologous nucleic acids encoding a HMGS (ERG13) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:116.

In some embodiments, the one or more heterologous nucleic acids encoding a HMGS (ERG13) polypeptide comprise the nucleotide sequence set forth in SEQ ID NO:120. In some embodiments, the one or more heterologous nucleic acids encoding a HMGS (ERG13) polypeptide comprise the nucleotide sequence set forth in SEQ ID NO:120, or a codon degenerate nucleotide sequence thereof. In some embodiments, the one or more heterologous nucleic acids encoding a HMGS (ERG13) polypeptide comprise a nucleotide sequence having at least 80%, at least 81%, at least 82%, at least 83%, or at least 84% sequence identity to SEQ ID NO:120. In some embodiments, the one or more heterologous nucleic acids encoding a HMGS (ERG13) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:120.

In some embodiments, the one or more heterologous nucleic acids encoding an HMGR (mvaE) polypeptide comprise the nucleotide sequence set forth in SEQ ID NO:53. In some embodiments, the one or more heterologous nucleic acids encoding an HMGR (mvaE) polypeptide comprise the nucleotide sequence set forth in SEQ ID NO:53, or a codon degenerate nucleotide sequence thereof. In some embodiments, the one or more heterologous nucleic acids encoding an HMGR (mvaE) polypeptide comprise a nucleotide sequence having at least 80%, at least 81%, at least 82%, at least 83%, or at least 84% sequence identity to SEQ ID NO:53. In some embodiments, the one or more heterologous nucleic acids encoding an HMGR (mvaE) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:53.

In some embodiments, the one or more heterologous nucleic acids encoding a tHMGR polypeptide comprise the nucleotide sequence set forth in SEQ ID NO:51, SEQ ID NO:114, or SEQ ID NO:119. In some embodiments, the one or more heterologous nucleic acids encoding a tHMGR polypeptide comprise the nucleotide sequence set forth in SEQ ID NO:51, SEQ ID NO:114, or SEQ ID NO:119, or a codon degenerate nucleotide sequence thereof. In some embodiments, the one or more heterologous nucleic acids encoding a tHMGR polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:51, SEQ ID NO:114, or SEQ ID NO:119.

In some embodiments, the one or more heterologous nucleic acids encoding a tHMGR polypeptide comprise the nucleotide sequence set forth in SEQ ID NO:51. In some embodiments, the one or more heterologous nucleic acids encoding a tHMGR polypeptide comprise the nucleotide sequence set forth in SEQ ID NO:51, or a codon degenerate nucleotide sequence thereof. In some embodiments, the one or more heterologous nucleic acids encoding a tHMGR polypeptide comprise a nucleotide sequence having at least 80%, at least 81%, at least 82%, at least 83%, or at least 84% sequence identity to SEQ ID NO:51. In some embodiments, the one or more heterologous nucleic acids encoding a tHMGR polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:51.

In some embodiments, the one or more heterologous nucleic acids encoding a tHMGR polypeptide comprise the nucleotide sequence set forth in SEQ ID NO:114. In some embodiments, the one or more heterologous nucleic acids encoding a tHMGR polypeptide comprise the nucleotide sequence set forth in SEQ ID NO:114, or a codon degenerate nucleotide sequence thereof. In some embodiments, the one or more heterologous nucleic acids encoding a tHMGR polypeptide comprise a nucleotide sequence having at least 80%, at least 81%, at least 82%, at least 83%, or at least 84% sequence identity to SEQ ID NO:114. In some embodiments, the one or more heterologous nucleic acids encoding a tHMGR polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:114.

In some embodiments, the one or more heterologous nucleic acids encoding a tHMGR polypeptide comprise the nucleotide sequence set forth in SEQ ID NO:119. In some embodiments, the one or more heterologous nucleic acids encoding a tHMGR polypeptide comprise the nucleotide sequence set forth in SEQ ID NO:119, or a codon degenerate nucleotide sequence thereof. In some embodiments, the one or more heterologous nucleic acids encoding a tHMGR polypeptide comprise a nucleotide sequence having at least 80%, at least 81%, at least 82%, at least 83%, or at least 84% sequence identity to SEQ ID NO:119. In some embodiments, the one or more heterologous nucleic acids encoding a tHMGR polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:119.

In some embodiments, a genetically modified host cell of the present disclosure is genetically modified with two or more heterologous nucleic acids that encode a tHMGR polypeptide. In some embodiments, a genetically modified host cell of the present disclosure is genetically modified with two heterologous nucleic acids that encode a tHMGR polypeptide. In some embodiments, a genetically modified host cell of the present disclosure is genetically modified with two or more heterologous nucleic acids that encode an HMGR polypeptide. In some embodiments, a genetically modified host cell of the present disclosure is genetically modified with two heterologous nucleic acids that encode an HMGR polypeptide.

In some embodiments, the one or more heterologous nucleic acids encoding an MK (ERG12) polypeptide comprise the nucleotide sequence set forth in SEQ ID NO:63 or SEQ ID NO:206. In some embodiments, the one or more heterologous nucleic acids encoding an MK (ERG12) polypeptide comprise the nucleotide sequence set forth in SEQ ID NO:63 or SEQ ID NO:206, or a codon degenerate nucleotide sequence thereof. In some embodiments, the one or more heterologous nucleic acids encoding an MK (ERG12) polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:63 or SEQ ID NO:206.

In some embodiments, the one or more heterologous nucleic acids encoding an MK (ERG12) polypeptide comprise the nucleotide sequence set forth in SEQ ID NO:63. In some embodiments, the one or more heterologous nucleic acids encoding an MK (ERG12) polypeptide comprise the nucleotide sequence set forth in SEQ ID NO:63, or a codon degenerate nucleotide sequence thereof. In some embodiments, the one or more heterologous nucleic acids encoding an MK (ERG12) polypeptide comprise a nucleotide sequence having at least 80%, at least 81%, at least 82%, at least 83%, or at least 84% sequence identity to SEQ ID NO:63. In some embodiments, the one or more heterologous nucleic acids encoding an MK (ERG12) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:63.

In some embodiments, the one or more heterologous nucleic acids encoding an MK (ERG12) polypeptide comprise the nucleotide sequence set forth in SEQ ID NO:206. In some embodiments, the one or more heterologous nucleic acids encoding an MK (ERG12) polypeptide comprise the nucleotide sequence set forth in SEQ ID NO:206, or a codon degenerate nucleotide sequence thereof. In some embodiments, the one or more heterologous nucleic acids encoding an MK (ERG12) polypeptide comprise a nucleotide sequence having at least 80%, at least 81%, at least 82%, at least 83%, or at least 84% sequence identity to SEQ ID NO:206. In some embodiments, the one or more heterologous nucleic acids encoding an MK (ERG12) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:206.

In some embodiments, the one or more heterologous nucleic acids encoding a PMK (ERG8) polypeptide comprise the nucleotide sequence set forth in SEQ ID NO:61, SEQ ID NO:160, or SEQ ID NO:204. In some embodiments, the one or more heterologous nucleic acids encoding a PMK (ERG8) polypeptide comprise the nucleotide sequence set forth in SEQ ID NO:61, SEQ ID NO:160, or SEQ ID NO:204, or a codon degenerate nucleotide sequence thereof. In some embodiments, the one or more heterologous nucleic acids encoding a PMK (ERG8) polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:61, SEQ ID NO:160, or SEQ ID NO:204.

In some embodiments, the one or more heterologous nucleic acids encoding a PMK (ERG8) polypeptide comprise the nucleotide sequence set forth in SEQ ID NO:61. In some embodiments, the one or more heterologous nucleic acids encoding a PMK (ERG8) polypeptide comprise the nucleotide sequence set forth in SEQ ID NO:61, or a codon degenerate nucleotide sequence thereof. In some embodiments, the one or more heterologous nucleic acids encoding a PMK (ERG8) polypeptide comprise a nucleotide sequence having at least 80%, at least 81%, at least 82%, at least 83%, or at least 84% sequence identity to SEQ ID NO:61. In some embodiments, the one or more heterologous nucleic acids encoding a PMK (ERG8) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:61.

In some embodiments, the one or more heterologous nucleic acids encoding a PMK (ERG8) polypeptide comprise the nucleotide sequence set forth in SEQ ID NO:160. In some embodiments, the one or more heterologous nucleic acids encoding a PMK (ERG8) polypeptide comprise the nucleotide sequence set forth in SEQ ID NO:160, or a codon degenerate nucleotide sequence thereof. In some embodiments, the one or more heterologous nucleic acids encoding a PMK (ERG8) polypeptide comprise a nucleotide sequence having at least 80%, at least 81%, at least 82%, at least 83%, or at least 84% sequence identity to SEQ ID NO:160. In some embodiments, the one or more heterologous nucleic acids encoding a PMK (ERG8) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:160.

In some embodiments, the one or more heterologous nucleic acids encoding a PMK (ERG8) polypeptide comprise the nucleotide sequence set forth in SEQ ID NO:204. In some embodiments, the one or more heterologous nucleic acids encoding a PMK (ERG8) polypeptide comprise the nucleotide sequence set forth in SEQ ID NO:204, or a codon degenerate nucleotide sequence thereof. In some embodiments, the one or more heterologous nucleic acids encoding a PMK (ERG8) polypeptide comprise a nucleotide sequence having at least 80%, at least 81%, at least 82%, at least 83%, or at least 84% sequence identity to SEQ ID NO:204. In some embodiments, the one or more heterologous nucleic acids encoding a PMK (ERG8) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:204.

In some embodiments, the one or more heterologous nucleic acids encoding a PMK/MK polypeptide comprise the nucleotide sequence set forth in SEQ ID NO:67. In some embodiments, the one or more heterologous nucleic acids encoding a PMK/MK polypeptide comprise the nucleotide sequence set forth in SEQ ID NO:67, or a codon degenerate nucleotide sequence thereof. In some embodiments, the one or more heterologous nucleic acids encoding a PMK/MK polypeptide comprise a nucleotide sequence having at least 80%, at least 81%, at least 82%, at least 83%, or at least 84% sequence identity to SEQ ID NO:67. In some embodiments, the one or more heterologous nucleic acids encoding a PMK/MK polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:67. In some embodiments, the one or more heterologous nucleic acids encoding a PMK/MK polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:67.

In some embodiments, the one or more heterologous nucleic acids encoding an MVD (ERG19) polypeptide comprise the nucleotide sequence set forth in SEQ ID NO:65 or SEQ ID NO:158. In some embodiments, the one or more heterologous nucleic acids encoding an MVD (ERG19) polypeptide comprise the nucleotide sequence set forth in SEQ ID NO:65 or SEQ ID NO:158, or a codon degenerate nucleotide sequence thereof. In some embodiments, the one or more heterologous nucleic acids encoding an MVD (ERG19) polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:65 or SEQ ID NO:158.

In some embodiments, the one or more heterologous nucleic acids encoding an MVD (ERG19) polypeptide comprise the nucleotide sequence set forth in SEQ ID NO:65. In some embodiments, the one or more heterologous nucleic acids encoding an MVD (ERG19) polypeptide comprise the nucleotide sequence set forth in SEQ ID NO:65, or a codon degenerate nucleotide sequence thereof. In some embodiments, the one or more heterologous nucleic acids encoding an MVD (ERG19) polypeptide comprise a nucleotide sequence having at least 80%, at least 81%, at least 82%, at least 83%, or at least 84% sequence identity to SEQ ID NO:65. In some embodiments, the one or more heterologous nucleic acids encoding an MVD (ERG19) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:65.

In some embodiments, the one or more heterologous nucleic acids encoding an MVD (ERG19) polypeptide comprise the nucleotide sequence set forth in SEQ ID NO:158. In some embodiments, the one or more heterologous nucleic acids encoding an MVD (ERG19) polypeptide comprise the nucleotide sequence set forth in SEQ ID NO:158, or a codon degenerate nucleotide sequence thereof. In some embodiments, the one or more heterologous nucleic acids encoding an MVD (ERG19) polypeptide comprise a nucleotide sequence having at least 80%, at least 81%, at least 82%, at least 83%, or at least 84% sequence identity to SEQ ID NO:158. In some embodiments, the one or more heterologous nucleic acids encoding an MVD (ERG19) polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:158.

In some embodiments, the one or more heterologous nucleic acids encoding an IDI1 polypeptide comprise the nucleotide sequence set forth in SEQ ID NO:57 or SEQ ID NO:159. In some embodiments, the one or more heterologous nucleic acids encoding an IDI1 polypeptide comprise the nucleotide sequence set forth in SEQ ID NO:57 or SEQ ID NO:159, or a codon degenerate nucleotide sequence thereof. In some embodiments, the one or more heterologous nucleic acids encoding an IDI1 polypeptide comprise a nucleotide sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:57 or SEQ ID NO:159.

In some embodiments, the one or more heterologous nucleic acids encoding an IDI1 polypeptide comprise the nucleotide sequence set forth in SEQ ID NO:57. In some embodiments, the one or more heterologous nucleic acids encoding an IDI1 polypeptide comprise the nucleotide sequence set forth in SEQ ID NO:57, or a codon degenerate nucleotide sequence thereof. In some embodiments, the one or more heterologous nucleic acids encoding an IDI1 polypeptide comprise a nucleotide sequence having at least 80%, at least 81%, at least 82%, at least 83%, or at least 84% sequence identity to SEQ ID NO:57. In some embodiments, the one or more heterologous nucleic acids encoding an IDI1 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:57.

In some embodiments, the one or more heterologous nucleic acids encoding an IDI1 polypeptide comprise the nucleotide sequence set forth in SEQ ID NO:159. In some embodiments, the one or more heterologous nucleic acids encoding an IDI1 polypeptide comprise the nucleotide sequence set forth in SEQ ID NO:159, or a codon degenerate nucleotide sequence thereof. In some embodiments, the one or more heterologous nucleic acids encoding an IDI1 polypeptide comprise a nucleotide sequence having at least 80%, at least 81%, at least 82%, at least 83%, or at least 84% sequence identity to SEQ ID NO:159. In some embodiments, the one or more heterologous nucleic acids encoding an IDI1 polypeptide comprise a nucleotide sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% sequence identity to SEQ ID NO:159.

Polypeptides that Modulate NADH or NADPH Redox Balance, Nucleic Acids Comprising Said Polypeptides, and Genetically Modified Host Cells Expressing Said Polypeptides In some embodiments, the host cell is genetically modified with one or more heterologous nucleic acids encoding a polypeptide that modulates NADH or NADPH redox balance. GPP production has a redox imbalance in it that can be modulated by changing NADPH-using enzymes to NADH-using enzymes, bringing redox into better balance.

In some embodiments, a genetically modified host cell of the present disclosure is genetically modified with one or more heterologous nucleic acids encoding a polypeptide that modulates NADH or NADPH redox balance. In some embodiments, a genetically modified host cell of the present disclosure is genetically modified with one or more heterologous nucleic acids encoding more than one polypeptide that modulates NADH or NADPH redox balance. In some embodiments, a genetically modified host cell of the present disclosure is genetically modified with one or more heterologous nucleic acids encoding more than two polypeptides that modulate NADH or NADPH redox balance. In some embodiments, a genetically modified host cell of the present disclosure is genetically modified with one or more heterologous nucleic acids encoding more than three polypeptides that modulate NADH or NADPH redox balance. In some embodiments, a genetically modified host cell of the present disclosure is genetically modified with one or more heterologous nucleic acids encoding two polypeptides that modulate NADH or NADPH redox balance. In some embodiments, a genetically modified host cell of the present disclosure is genetically modified with one or more heterologous nucleic acids encoding three polypeptides that modulate NADH or NADPH redox balance. In some embodiments, a genetically modified host cell of the present disclosure is genetically modified with one or more heterologous nucleic acids encoding 1, 2, 3, or more polypeptides that modulate NADH or NADPH redox balance. In some embodiments, a genetically modified host cell of the present disclosure is genetically modified with one or more heterologous nucleic acids encoding 1, 2, or 3 polypeptides that modulate NADH or NADPH redox balance.

Exemplary polypeptides that modulate NADH or NADPH redox balance disclosed herein may include a full-length polypeptide that modulates NADH or NADPH redox balance, a fragment of a polypeptide that modulates NADH or NADPH redox balance, a variant of a polypeptide that modulates NADH or NADPH redox balance, a truncated polypeptide that modulates NADH or NADPH redox balance, or a fusion polypeptide that has at least one activity of a polypeptide that modulates NADH or NADPH redox balance.

Exemplary heterologous nucleic acids disclosed herein may include nucleic acids that encode a polypeptide that modulates NADH or NADPH redox balance, such as, a full-length polypeptide that modulates NADH or NADPH redox balance, a fragment of a polypeptide that modulates NADH or NADPH redox balance, a variant of a polypeptide that modulates NADH or NADPH redox balance, a truncated polypeptide that modulates NADH or NADPH redox balance, or a fusion polypeptide that has at least one activity of a polypeptide that modulates NADH or NADPH redox balance.

In some embodiments, the polypeptide that modulates NADH or NADPH redox balance is overexpressed in the genetically modified host cell. Overexpression may be achieved by increasing the copy number of the heterologous nucleic acid encoding a polypeptide that modulates NADH or NADPH redox balance, e.g., through use of a high copy number expression vector (e.g., a plasmid that exists at 10-40 copies per cell) and/or by operably linking the polypeptide that modulates NADH or NADPH redox balance encoding heterologous nucleic acid to a strong promoter. In some embodiments, the genetically modified host cell has one copy of a heterologous nucleic acid encoding a polypeptide that modulates NADH or NADPH redox balance. In some embodiments, the genetically modified host cell has two copies of a heterologous nucleic acid encoding a polypeptide that modulates NADH or NADPH redox balance. In some embodiments, the genetically modified host cell has three copies of a heterologous nucleic acid encoding a polypeptide that modulates NADH or NADPH redox balance. In some embodiments, the genetically modified host cell has four copies of a heterologous nucleic acid encoding a polypeptide that modulates NADH or NADPH redox balance. In some embodiments, the genetically modified host cell has five copies of a heterologous nucleic acid encoding a polypeptide that modulates NADH or NADPH redox balance.

DXP Pathway Polypeptides, Nucleic Acids Comprising Said Polypeptides, and Genetically Modified Host Cells Expressing Said Polypeptides In some embodiments, a genetically modified host cell of the present disclosure is genetically modified with one or more heterologous nucleic acids encoding one or more polypeptides having at least one activity of a polypeptide present in the deoxyxylulose-5-phosphate (DXP) pathway.

In some embodiments, the one or more polypeptides that generate GPP or are part of a biosynthetic pathway that generates GPP are polypeptides of the DXP pathway. The term "1-deoxy-D-xylulose 5-diphosphate pathway" or "DXP pathway" as used herein may refer to the pathway that converts glyceraldehyde-3-phosphate and pyruvate to IPP and DMAPP through a DXP pathway intermediate.

In the DXP pathway, pyruvate and D-glyceraldehyde-3-phosphate are converted via a series of reactions to IPP and DMAPP. The pathway involves action of the following polypeptides: a 1-deoxy-D-xylulose-5-phosphate synthase (Dxs) polypeptide, a 1-deoxy-D-xylulose-5-phosphate reductoisomerase (IspC) polypeptide, a 4-diphosphocytidyl-2-C-methyl-D-erythritol synthase (IspD) polypeptide, a 4-diphosphocytidyl-2-C-methyl-D-erythritol kinase (IspE) polypeptide, a 2C-methyl-D-erythritol 2,4-cyclodiphosphate synthase (IspF) polypeptide, a 1-hydroxy-2-methyl-2-(E)-butenyl 4-diphosphate synthase (IspG) polypeptide, and an isopentenyl diphosphate isomerase (IspH) polypeptide.

In some embodiments, a genetically modified host cell of the present disclosure is genetically modified with one or more heterologous nucleic acids encoding a DXP pathway polypeptide. In some embodiments, a genetically modified host cell of the present disclosure is genetically modified with one or more heterologous nucleic acids encoding more than one DXP pathway polypeptide. In some embodiments, a genetically modified host cell of the present disclosure is genetically modified with one or more heterologous nucleic acids encoding more than two DXP pathway polypeptides. In some embodiments, a genetically modified host cell of the present disclosure is genetically modified with one or more heterologous nucleic acids encoding more than three DXP pathway polypeptides. In some embodiments, a genetically modified host cell of the present disclosure is genetically modified with one or more heterologous nucleic acids encoding more than four DXP pathway polypeptides. In some embodiments, a genetically modified host cell of the present disclosure is genetically modified with one or more heterologous nucleic acids encoding more than five DXP pathway polypeptides. In some embodiments, a genetically modified host cell of the present disclosure is genetically modified with one or more heterologous nucleic acids encoding more than six DXP pathway polypeptides. In some embodiments, a genetically modified host cell of the present disclosure is genetically modified with one or more heterologous nucleic acids encoding all DXP pathway polypeptides.

In some embodiments, a genetically modified host cell of the present disclosure is genetically modified with one or more heterologous nucleic acids encoding two DXP pathway polypeptides. In some embodiments, a genetically modified host cell of the present disclosure is genetically modified with one or more heterologous nucleic acids encoding three DXP pathway polypeptides. In some embodiments, a genetically modified host cell of the present disclosure is genetically modified with one or more heterologous nucleic acids encoding four DXP pathway polypeptides. In some embodiments, a genetically modified host cell of the present disclosure is genetically modified with one or more heterologous nucleic acids encoding five DXP pathway polypeptides. In some embodiments, a genetically modified host cell of the present disclosure is genetically modified with one or more heterologous nucleic acids encoding six DXP pathway polypeptides. In some embodiments, a genetically modified host cell of the present disclosure is genetically modified with one or more heterologous nucleic acids encoding 1, 2, 3, 4, 5, 6, or more DXP pathway polypeptides. In some embodiments, a genetically modified host cell of the present disclosure is genetically modified with one or more heterologous nucleic acids encoding 1, 2, 3, 4, 5, or 6 DXP pathway polypeptides.

Exemplary polypeptides disclosed herein that are part of the DXP pathway may include a full-length DXP pathway polypeptide, a fragment of a DXP pathway polypeptide, a variant of a DXP pathway polypeptide, a truncated DXP pathway polypeptide, or a fusion polypeptide that has at least one activity of a polypeptide that is part of the DXP pathway.

Examples of polypeptides of the DXP pathway are set forth in SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40.

In some embodiments, the 1-deoxy-D-xylulose-5-phosphate synthase (Dxs) polypeptide encoded by the one or more heterologous nucleic acids comprises the amino acid sequence set forth in SEQ ID NO:32. In some embodiments, the 1-deoxy-D-xylulose-5-phosphate synthase (Dxs) polypeptide encoded by the one or more heterologous nucleic acids comprises the amino acid sequence set forth in SEQ ID NO:32, or a conservatively substituted amino acid sequence thereof. In some embodiments, the 1-deoxy-D-xylulose-5-phosphate synthase (Dxs) polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:32.

In some embodiments, the 1-deoxy-D-xylulose 5-phosphate reductoisomerase polypeptide encoded by the one or more heterologous nucleic acids comprises the amino acid sequence set forth in SEQ ID NO:33. In some embodiments, the 1-deoxy-D-xylulose 5-phosphate reductoisomerase polypeptide encoded by the one or more heterologous nucleic acids comprises the amino acid sequence set forth in SEQ ID NO:33, or a conservatively substituted amino acid sequence thereof. In some embodiments, the 1-deoxy-D- xylulose 5-phosphate reductoisomerase polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:33.

In some embodiments, the 2-C-methyl-D-erythritol 4-phosphate cytidylyltransferase polypeptide encoded by the one or more heterologous nucleic acids comprises the amino acid sequence set forth in SEQ ID NO:34. In some embodiments, the 2-C-methyl-D-erythritol 4-phosphate cytidylyltransferase polypeptide encoded by the one or more heterologous nucleic acids comprises the amino acid sequence set forth in SEQ ID NO:34, or a conservatively substituted amino acid sequence thereof. In some embodiments, the 2-C-methyl-D-erythritol 4-phosphate cytidylyltransferase polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:34.

In some embodiments, the 4-diphosphocytidyl-2-C-methylerythritol kinase polypeptide encoded by the one or more heterologous nucleic acids comprises the amino acid sequence set forth in SEQ ID NO:35. In some embodiments, the 4-diphosphocytidyl-2-C-methylerythritol kinase polypeptide encoded by the one or more heterologous nucleic acids comprises the amino acid sequence set forth in SEQ ID NO:35, or a conservatively substituted amino acid sequence thereof. In some embodiments, the 4-diphosphocytidyl-2-C-methylerythritol kinase polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:35.

In some embodiments, the 2C-methyl-D-erythritol 2,4-cyclodiphosphate synthase polypeptide encoded by the one or more heterologous nucleic acids comprises the amino acid sequence set forth in SEQ ID NO:36. In some embodiments, the 2C-methyl-D-erythritol 2,4-cyclodiphosphate synthase polypeptide encoded by the one or more heterologous nucleic acids comprises the amino acid sequence set forth in SEQ ID NO:36, or a conservatively substituted amino acid sequence thereof. In some embodiments, the 2C-methyl-D-erythritol 2,4-cyclodiphosphate synthase polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:36.

In some embodiments, the 4-hydroxy-3-methylbut-2-en-1-yl diphosphate synthase polypeptide encoded by the one or more heterologous nucleic acids comprises the amino acid sequence set forth in SEQ ID NO:37. In some embodiments, the 4-hydroxy-3-methylbut-2-en-1-yl diphosphate synthase polypeptide encoded by the one or more heterologous nucleic acids comprises the amino acid sequence set forth in SEQ ID NO:37, or a conservatively substituted amino acid sequence thereof. In some embodiments, the 4-hydroxy-3-methylbut-2-en-1-yl diphosphate synthase polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:37.

In some embodiments, the 4-hydroxy-3-methylbut-2-enyl diphosphate reductase polypeptide encoded by the one or more heterologous nucleic acids comprises the amino acid sequence set forth in SEQ ID NO:38. In some embodiments, the 4-hydroxy-3-methylbut-2-enyl diphosphate reductase polypeptide encoded by the one or more heterologous nucleic acids comprises the amino acid sequence set forth in SEQ ID NO:38, or a conservatively substituted amino acid sequence thereof. In some embodiments, the 4-hydroxy-3-methylbut-2-enyl diphosphate reductase polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:38.

In some embodiments, the isopentenyl diphosphate (IPP) isomerase polypeptide encoded by the one or more heterologous nucleic acids comprises the amino acid sequence set forth in SEQ ID NO:39. In some embodiments, the isopentenyl diphosphate (IPP) isomerase polypeptide encoded by the one or more heterologous nucleic acids comprises the amino acid sequence set forth in SEQ ID NO:39, or a conservatively substituted amino acid sequence thereof. In some embodiments, the isopentenyl diphosphate (IPP) isomerase polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:39.

In some embodiments, the DXP pathway polypeptide is a mutated FPP synthase polypeptide. In some embodiments, the mutated FPP synthase polypeptide encoded by the one or more heterologous nucleic acids comprises the amino acid sequence set forth in SEQ ID NO:40. In some embodiments, the mutated FPP synthase polypeptide encoded by the one or more heterologous nucleic acids comprises the amino acid sequence set forth in SEQ ID NO:40, or a conservatively substituted amino acid sequence thereof. In some embodiments, the mutated FPP synthase isomerase polypeptide encoded by the one or more heterologous nucleic acids comprises an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:40.

Exemplary DXP pathway heterologous nucleic acids disclosed herein may include nucleic acids that encode a DXP pathway polypeptide, such as, a full-length DXP pathway polypeptide, a fragment of a DXP pathway polypeptide, a variant of a DXP pathway polypeptide, a truncated DXP pathway polypeptide, or a fusion polypeptide that has at least one activity of a polypeptide that is part of the DXP pathway.

In some embodiments, the DXP pathway polypeptide is overexpressed in the genetically modified host cell. Overexpression may be achieved by increasing the copy number of the DXP pathway polypeptide-encoding heterologous nucleic acid, e.g., through use of a high copy number expression vector (e.g., a plasmid that exists at 10-40 copies per cell) and/or by operably linking the DXP pathway polypeptide-encoding heterologous nucleic acid to a strong promoter. In some embodiments, the genetically modified host cell has one copy of a DXP pathway polypeptide-encoding heterologous nucleic acid. In some embodiments, the genetically modified host cell has two copies of a DXP pathway polypeptide-encoding heterologous nucleic acid. In some embodiments, the genetically modified host cell has three copies of a DXP pathway polypeptide-encoding heterologous nucleic acid. In some embodiments, the genetically modified host cell has four copies of a DXP pathway polypeptide-encoding heterologous nucleic acid. In some embodiments, the genetically modified host cell has five copies of a DXP pathway polypeptide-encoding heterologous nucleic acid.

Genetically Modified Host Cells to Generate Cannabinoids, Cannabinoid Derivatives, Cannabinoid Precursors, or Cannabinoid Precursor Derivatives The disclosure provides for genetically modified host cells for producing cannabinoids, cannabinoid derivatives, cannabinoid precursors, or cannabinoid precursor derivatives. For producing cannabinoids, cannabinoid derivatives, cannabinoid precursors, or cannabinoid precursor derivatives, genetically modified host cells disclosed herein may be genetically modified to express or overexpress one or more heterologous nucleic acids disclosed herein that encode one or more polypeptides disclosed herein. In some embodiments, the genetically modified host cell of the disclosure produces a cannabinoid or a cannabinoid derivative. The disclosure also provides genetically modified host cells genetically modified to express or overexpress one or more heterologous nucleic acids disclosed herein that encode one or more polypeptides disclosed herein.

In some embodiments, to produce cannabinoids, cannabinoid derivatives, cannabinoid precursors, or cannabinoid precursor derivatives, expression or overexpression of one or more heterologous nucleic acids disclosed herein that encode one or more polypeptides disclosed herein in a genetically modified host cell may be done in combination with expression or overexpression by the genetically modified host cell of one or more other heterologous nucleic acids disclosed herein that encode one or more polypeptides disclosed herein. In certain such embodiments, the genetically modified host cell produces a cannabinoid or a cannabinoid derivative.

Exemplary Genetically Modified Host Cells Expressing a GOT Polypeptide, Wherein Said GOT Polypeptide Can Catalyze Production of Cannabigerolic Acid from Geranyl Pyrophosphate and Olivetolic Acid in an Amount at Least Ten Times Higher than a Polypeptide Comprising an Amino Acid Sequence Set Forth in SEQ ID NO:82

Some embodiments of the disclosure relate to a genetically modified host cell for producing a cannabinoid or a cannabinoid derivative, the genetically modified host cell comprising one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82.

The disclosure also provides genetically modified host cells genetically modified to express or overexpress one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82.

In some embodiments, the genetically modified host cell comprising one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, further comprises one or more heterologous nucleic acids encoding a TKS polypeptide and one or more heterologous nucleic acids encoding an OAC polypeptide. In certain such embodiments, the TKS polypeptide comprises an amino acid sequence having at least 50% sequence identity to SEQ ID NO:11 or SEQ ID NO:76, and the OAC polypeptide comprises an amino acid sequence having at least 50% sequence identity to SEQ ID NO:10 or SEQ ID NO:78.

In some embodiments, a genetically modified host cell comprising one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, further comprises one or more of the following: a) one or more heterologous nucleic acids encoding a polypeptide that generates an acyl-CoA compound or an acyl-CoA compound derivative; b) one or more heterologous nucleic acids encoding a polypeptide that generates GPP; or c) one or more heterologous nucleic acids encoding a polypeptide that generates malonyl-CoA. In certain such embodiments, the polypeptide that generates an acyl-CoA compound or an acyl-CoA compound derivative is an acyl-activating enzyme (AAE) polypeptide. In certain such embodiments, the AAE polypeptide comprises an amino acid sequence having at least 50% sequence identity to SEQ ID NO:90. In some embodiments, the AAE polypeptide comprises an amino acid sequence having at least 50% sequence identity to SEQ ID NO:92 or SEQ ID NO:149. In some embodiments, the polypeptide that generates an acyl-CoA compound or an acyl-CoA compound derivative is a fatty acyl-CoA ligase polypeptide. In certain such embodiments, the fatty acyl-CoA ligase polypeptide comprises an amino acid sequence having at least 50% sequence identity to SEQ ID NO:145 or SEQ ID NO:147. In some embodiments, the polypeptide that generates an acyl-CoA compound or an acyl-CoA compound derivative is a fatty acyl-CoA synthetase (FAA) polypeptide. In certain such embodiments, the FAA polypeptide comprises an amino acid sequence having at least 50% sequence identity to SEQ ID NO:169, SEQ ID NO:192, SEQ ID NO:194, SEQ ID NO:196, SEQ ID NO:198, or SEQ ID NO:200. In some embodiments, the polypeptide that generates GPP is a GPPS polypeptide. In certain such embodiments, the GPPS polypeptide comprises an amino acid sequence having at least 50% sequence identity to SEQ ID NO:7, SEQ ID NO:8, or SEQ ID NO:60. In some embodiments, the polypeptide that generates malonyl-CoA is an ACC polypeptide. In certain such embodiments, the ACC polypeptide comprises an amino acid sequence having at least 50% sequence identity to SEQ ID NO:9, SEQ ID NO:97, or SEQ ID NO:207.

In some embodiments, a genetically modified host cell comprising one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, further comprises one or more of the following: a) one or more heterologous nucleic acids encoding a HMGS polypeptide; b) one or more heterologous nucleic acids encoding a 3-hydroxy-3-methyl-glutaryl-CoA reductase (HMGR) polypeptide; c) one or more heterologous nucleic acids encoding a MK polypeptide; d) a PMK polypeptide; e) one or more heterologous nucleic acids encoding a MVD polypeptide; or f) one or more heterologous nucleic acids encoding an IDI polypeptide. In certain such embodiments, the genetically modified host cell further comprises one or more heterologous nucleic acids encoding an IDI polypeptide. In certain such embodiments, the IDI polypeptide comprises an amino acid sequence having at least 50% sequence identity to SEQ ID NO:58. In some embodiments, the genetically modified host cell further comprises one or more heterologous nucleic acids encoding an HMGR polypeptide. In certain such embodiments, the HMGR polypeptide comprises an amino acid sequence having at least 50% sequence identity to SEQ ID NO:22. In some embodiments, the HMGR polypeptide is a truncated HMGR (tHMGR) polypeptide. In certain such embodiments, the tHMGR polypeptide comprises an amino acid sequence having at least 50% sequence identity to SEQ ID NO:17, SEQ ID NO:52, SEQ ID NO:113, or SEQ ID NO:208. In some embodiments, the genetically modified host cell further comprises one or more heterologous nucleic acids encoding an HMGS polypeptide. In certain such embodiments, the HMGS polypeptide comprises an amino acid sequence having at least 50% sequence identity to SEQ ID NO:23, SEQ ID NO:24, or SEQ ID NO:115. In some embodiments, the genetically modified host cell further comprises one or more heterologous nucleic acids encoding an MK polypeptide. In certain such embodiments, the MK polypeptide comprises an amino acid sequence having at least 50% sequence identity to SEQ ID NO:64. In some embodiments, the genetically modified host cell further comprises one or more heterologous nucleic acids encoding a PMK polypeptide. In certain such embodiments, the PMK polypeptide comprises an amino acid sequence having at least 50% sequence identity to SEQ ID NO:62 or SEQ ID NO:205. In some embodiments, the genetically modified host cell further comprises one or more heterologous nucleic acids encoding a MVD polypeptide. In certain such embodiments, the MVD polypeptide comprises an amino acid sequence having at least 50% sequence identity to SEQ ID NO:66.

In some embodiments, a genetically modified host cell comprising one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, further comprises one or more heterologous nucleic acids encoding a polypeptide that condenses two molecules of acetyl-CoA to generate acetoacetyl-CoA. In certain such embodiments, the polypeptide that condenses two molecules of acetyl-CoA to generate acetoacetyl-CoA is an acetoacetyl-CoA thiolase polypeptide. In certain such embodiments, the acetoacetyl-CoA thiolase polypeptide comprises an amino acid sequence having at least 50% sequence identity to SEQ ID NO:25.

In some embodiments, a genetically modified host cell comprising one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, further comprises one or more heterologous nucleic acids encoding a PDC polypeptide. In certain such embodiments, the PDC polypeptide comprises an amino acid sequence having at least 50% sequence identity to SEQ ID NO:117.

In some embodiments, a genetically modified host cell comprising one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, further comprises one or more heterologous nucleic acids encoding a cannabinoid synthase polypeptide. In certain such embodiments, the cannabinoid synthase polypeptide is a THCA synthase polypeptide. In certain such embodiments, the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155. In some embodiments, the cannabinoid synthase polypeptide is a CBDA synthase polypeptide. In certain such embodiments, the CBDA synthase polypeptide comprises an amino acid sequence having at least 50% sequence identity to SEQ ID NO:88 or SEQ ID NO:151.

Exemplary Genetically Modified Host Cells Expressing a Polypeptide Comprising an Amino Acid Sequence Having Sequence Identity to SEQ ID NO:110

Some embodiments of the disclosure relate to a genetically modified host cell for producing a cannabinoid or a cannabinoid derivative, the genetically modified host cell comprising one or more heterologous nucleic acids encoding a GOT polypeptide comprising an amino acid sequence having at least 65% sequence identity to SEQ ID NO:110. In certain such embodiments, the GOT polypeptide encoded by the one or more heterologous nucleic acids comprises an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110. In some embodiments, the GOT polypeptide encoded by the one or more heterologous nucleic acids comprises the amino acid sequence set forth in SEQ ID NO:110. In some embodiments, the GOT polypeptide encoded by the one or more heterologous nucleic acids comprises the amino acid sequence set forth in SEQ ID NO:110, or a conservatively substituted amino acid sequence thereof.

The disclosure also provides genetically modified host cells genetically modified to express or overexpress one or more heterologous nucleic acids encoding a GOT polypeptide comprising an amino acid sequence having at least 65% sequence identity to SEQ ID NO:110. In certain such embodiments, the GOT polypeptide encoded by the one or more heterologous nucleic acids comprises an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:110. In some embodiments, the GOT polypeptide encoded by the one or more heterologous nucleic acids comprises the amino acid sequence set forth in SEQ ID NO:110. In some embodiments, the GOT polypeptide encoded by the one or more heterologous nucleic acids comprises the amino acid sequence set forth in SEQ ID NO:110, or a conservatively substituted amino acid sequence thereof.

In some embodiments, the genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110 further comprises one or more heterologous nucleic acids encoding a TKS polypeptide and one or more heterologous nucleic acids encoding an OAC polypeptide. In certain such embodiments, the TKS polypeptide comprises an amino acid sequence having at least 50% sequence identity to SEQ ID NO:11 or SEQ ID NO:76, and the OAC polypeptide comprises an amino acid sequence having at least 50% sequence identity to SEQ ID NO:10 or SEQ ID NO:78.

In some embodiments, a genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110 further comprises one or more of the following: a) one or more heterologous nucleic acids encoding a polypeptide that generates an acyl-CoA compound or an acyl-CoA compound derivative; b) one or more heterologous nucleic acids encoding a polypeptide that generates GPP; or c) one or more heterologous nucleic acids encoding a polypeptide that generates malonyl-CoA. In certain such embodiments, the polypeptide that generates an acyl-CoA compound or an acyl-CoA compound derivative is an acyl-activating enzyme (AAE) polypeptide. In certain such embodiments, the AAE polypeptide comprises an amino acid sequence having at least 50% sequence identity to SEQ ID NO:90. In some embodiments, the AAE polypeptide comprises an amino acid sequence having at least 50% sequence identity to SEQ ID NO:92 or SEQ ID NO:149. In some embodiments, the polypeptide that generates an acyl-CoA compound or an acyl-CoA compound derivative is a fatty acyl-CoA ligase polypeptide. In certain such embodiments, the fatty acyl-CoA ligase polypeptide comprises an amino acid sequence having at least 50% sequence identity to SEQ ID NO:145 or SEQ ID NO:147. In some embodiments, the polypeptide that generates an acyl-CoA compound or an acyl-CoA compound derivative is a fatty acyl-CoA synthetase (FAA) polypeptide. In certain such embodiments, the FAA polypeptide comprises an amino acid sequence having at least 50% sequence identity to SEQ ID NO:169, SEQ ID NO:192, SEQ ID NO:194, SEQ ID NO:196, SEQ ID NO:198, or SEQ ID NO:200. In some embodiments, the polypeptide that generates GPP is a GPPS polypeptide. In certain such embodiments, the GPPS polypeptide comprises an amino acid sequence having at least 50% sequence identity to SEQ ID NO:7, SEQ ID NO:8, or SEQ ID NO:60. In some embodiments, the polypeptide that generates malonyl-CoA is an ACC polypeptide. In certain such embodiments, the ACC polypeptide comprises an amino acid sequence having at least 50% sequence identity to SEQ ID NO:9, SEQ ID NO:97, or SEQ ID NO:207.

In some embodiments, a genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110 further comprises one or more of the following: a) one or more heterologous nucleic acids encoding a HMGS polypeptide; b) one or more heterologous nucleic acids encoding a 3-hydroxy-3-methyl-glutaryl-CoA reductase (HMGR) polypeptide; c) one or more heterologous nucleic acids encoding a MK polypeptide; d) one or more heterologous nucleic acids encoding a PMK polypeptide; e) one or more heterologous nucleic acids encoding a MVD polypeptide; or f) one or more heterologous nucleic acids encoding an IDI polypeptide. In certain such embodiments, the genetically modified host cell further comprises one or more heterologous nucleic acids encoding an IDI polypeptide. In certain such embodiments, the IDI polypeptide comprises an amino acid sequence having at least 50% sequence identity to SEQ ID NO:58. In some embodiments, the genetically modified host cell further comprises one or more heterologous nucleic acids encoding an HMGR polypeptide. In certain such embodiments, the HMGR polypeptide comprises an amino acid sequence having at least 50% sequence identity to SEQ ID NO:22. In some embodiments, the HMGR polypeptide is a truncated HMGR (tHMGR) polypeptide. In certain such embodiments, the tHMGR polypeptide comprises an amino acid sequence having at least 50% sequence identity to SEQ ID NO:17, SEQ ID NO:52, SEQ ID NO:113, or SEQ ID NO:208. In some embodiments, the genetically modified host cell further comprises one or more heterologous nucleic acids encoding an HMGS polypeptide. In certain such embodiments, the HMGS polypeptide comprises an amino acid sequence having at least 50% sequence identity to SEQ ID NO:23, SEQ ID NO:24, or SEQ ID NO:115. In some embodiments, the genetically modified host cell further comprises one or more heterologous nucleic acids encoding an MK polypeptide. In certain such embodiments, the MK polypeptide comprises an amino acid sequence having at least 50% sequence identity to SEQ ID NO:64. In some embodiments, the genetically modified host cell further comprises one or more heterologous nucleic acids encoding a PMK polypeptide. In certain such embodiments, the PMK polypeptide comprises an amino acid sequence having at least 50% sequence identity to SEQ ID NO:62 or SEQ ID NO:205. In some embodiments, the genetically modified host cell further comprises one or more heterologous nucleic acids encoding a MVD polypeptide. In certain such embodiments, the MVD polypeptide comprises an amino acid sequence having at least 50% sequence identity to SEQ ID NO:66.

In some embodiments, a genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110 further comprises one or more heterologous nucleic acids encoding a polypeptide that condenses two molecules of acetyl-CoA to generate acetoacetyl-CoA. In certain such embodiments, the polypeptide that condenses two molecules of acetyl-CoA to generate acetoacetyl-CoA is an acetoacetyl-CoA thiolase polypeptide. In certain such embodiments, the acetoacetyl-CoA thiolase polypeptide comprises an amino acid sequence having at least 50% sequence identity to SEQ ID NO:25.

In some embodiments, a genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110 further comprises one or more heterologous nucleic acids encoding a PDC polypeptide. In certain such embodiments, the PDC polypeptide comprises an amino acid sequence having at least 50% sequence identity to SEQ ID NO:117.

In some embodiments, a genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110 further comprises one or more heterologous nucleic acids encoding a cannabinoid synthase polypeptide. In certain such embodiments, the cannabinoid synthase polypeptide is a THCA synthase polypeptide. In certain such embodiments, the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155. In some embodiments, the cannabinoid synthase polypeptide is a CBDA synthase polypeptide. In certain such embodiments, the CBDA synthase polypeptide comprises an amino acid sequence having at least 50% sequence identity to SEQ ID NO:88 or SEQ ID NO:151.

Exemplary Genetically Modified Host Cells Expressing a Polypeptide Comprising an Amino Acid Sequence Having Sequence Identity to SEQ ID NO:100

The disclosure provides a genetically modified host cell for producing a cannabinoid or a cannabinoid derivative, the genetically modified host cell comprising one or more heterologous nucleic acids encoding a GOT polypeptide comprising an amino acid sequence having at least 65% sequence identity to SEQ ID NO:100. In certain such embodiments, the GOT polypeptide encoded by the one or more heterologous nucleic acids comprises an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100. In some embodiments, the GOT polypeptide encoded by the one or more heterologous nucleic acids comprises the amino acid sequence set forth in SEQ ID NO:100. In some embodiments, the GOT polypeptide encoded by the one or more heterologous nucleic acids comprises the amino acid sequence set forth in SEQ ID NO:100, or a conservatively substituted amino acid sequence thereof.

The disclosure also provides genetically modified host cells genetically modified to express or overexpress one or more heterologous nucleic acids encoding GOT a polypeptide comprising an amino acid sequence having at least 65% sequence identity to SEQ ID NO:100. In certain such embodiments, the GOT polypeptide encoded by the one or more heterologous nucleic acids comprises an amino acid sequence having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:100. In some embodiments, the GOT polypeptide encoded by the one or more heterologous nucleic acids comprises the amino acid sequence set forth in SEQ ID NO:100. In some embodiments, the GOT polypeptide encoded by the one or more heterologous nucleic acids comprises the amino acid sequence set forth in SEQ ID NO:100, or a conservatively substituted amino acid sequence thereof.

In some embodiments, the genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 further comprises one or more heterologous nucleic acids encoding a TKS polypeptide and one or more heterologous nucleic acids encoding an OAC polypeptide. In certain such embodiments, the TKS polypeptide comprises an amino acid sequence having at least 50% sequence identity to SEQ ID NO:11 or SEQ ID NO:76, and the OAC polypeptide comprises an amino acid sequence having at least 50% sequence identity to SEQ ID NO:10 or SEQ ID NO:78.

In some embodiments, a genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 further comprises one or more of the following: a) one or more heterologous nucleic acids encoding a polypeptide that generates an acyl-CoA compound or an acyl-CoA compound derivative; b) one or more heterologous nucleic acids encoding a polypeptide that generates GPP; or c) one or more heterologous nucleic acids encoding a polypeptide that generates malonyl-CoA. In certain such embodiments, the polypeptide that generates an acyl-CoA compound or an acyl-CoA compound derivative is an acyl-activating enzyme (AAE) polypeptide. In certain such embodiments, the AAE polypeptide comprises an amino acid sequence having at least 50% sequence identity to SEQ ID NO:90. In some embodiments, the AAE polypeptide comprises an amino acid sequence having at least 50% sequence identity to SEQ ID NO:92 or SEQ ID NO:149. In some embodiments, the polypeptide that generates an acyl-CoA compound or an acyl-CoA compound derivative is a fatty acyl-CoA ligase polypeptide. In certain such embodiments, the fatty acyl-CoA ligase polypeptide comprises an amino acid sequence having at least 50% sequence identity to SEQ ID NO:145 or SEQ ID NO:147. In some embodiments, the polypeptide that generates an acyl-CoA compound or an acyl-CoA compound derivative is a fatty acyl-CoA synthetase (FAA) polypeptide. In certain such embodiments, the FAA polypeptide comprises an amino acid sequence having at least 50% sequence identity to SEQ ID NO:169, SEQ ID NO:192, SEQ ID NO:194, SEQ ID NO:196, SEQ ID NO:198, or SEQ ID NO:200. In some embodiments, the polypeptide that generates GPP is a GPPS polypeptide. In certain such embodiments, the GPPS polypeptide comprises an amino acid sequence having at least 50% sequence identity to SEQ ID NO:7, SEQ ID NO:8, or SEQ ID NO:60. In some embodiments, the polypeptide that generates malonyl-CoA is an ACC polypeptide. In certain such embodiments, the ACC polypeptide comprises an amino acid sequence having at least 50% sequence identity to SEQ ID NO:9, SEQ ID NO:97, or SEQ ID NO:207.

In some embodiments, a genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 further comprises one or more of the following: a) one or more heterologous nucleic acids encoding a HMGS polypeptide; b) one or more heterologous nucleic acids encoding a 3-hydroxy-3-methyl-glutaryl-CoA reductase (HMGR) polypeptide; c) one or more heterologous nucleic acids encoding a MK polypeptide; d) one or more heterologous nucleic acids encoding a PMK polypeptide; e) one or more heterologous nucleic acids encoding a MVD polypeptide; or f) one or more heterologous nucleic acids encoding an IDI polypeptide. In certain such embodiments, the genetically modified host cell further comprises one or more heterologous nucleic acids encoding an IDI polypeptide. In certain such embodiments, the IDI polypeptide comprises an amino acid sequence having at least 50% sequence identity to SEQ ID NO:58. In some embodiments, the genetically modified host cell further comprises one or more heterologous nucleic acids encoding an HMGR polypeptide. In certain such embodiments, the HMGR polypeptide comprises an amino acid sequence having at least 50% sequence identity to SEQ ID NO:22. In some embodiments, the HMGR polypeptide is a truncated HMGR (tHMGR) polypeptide. In certain such embodiments, the tHMGR polypeptide comprises an amino acid sequence having at least 50% sequence identity to SEQ ID NO:17, SEQ ID NO:52, SEQ ID NO:113, or SEQ ID NO:208. In some embodiments, the genetically modified host cell further comprises one or more heterologous nucleic acids encoding an HMGS polypeptide. In certain such embodiments, the HMGS polypeptide comprises an amino acid sequence having at least 50% sequence identity to SEQ ID NO:23, SEQ ID NO:24, or SEQ ID NO:115. In some embodiments, the genetically modified host cell further comprises one or more heterologous nucleic acids encoding an MK polypeptide. In certain such embodiments, the MK polypeptide comprises an amino acid sequence having at least 50% sequence identity to SEQ ID NO:64. In some embodiments, the genetically modified host cell further comprises one or more heterologous nucleic acids encoding a PMK polypeptide. In certain such embodiments, the PMK polypeptide comprises an amino acid sequence having at least 50% sequence identity to SEQ ID NO:62 or SEQ ID NO:205. In some embodiments, the genetically modified host cell further comprises one or more heterologous nucleic acids encoding a MVD polypeptide. In certain such embodiments, the MVD polypeptide comprises an amino acid sequence having at least 50% sequence identity to SEQ ID NO:66.

In some embodiments, a genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 further comprises one or more heterologous nucleic acids encoding a polypeptide that condenses two molecules of acetyl-CoA to generate acetoacetyl-CoA. In certain such embodiments, the polypeptide that condenses two molecules of acetyl-CoA to generate acetoacetyl-CoA is an acetoacetyl-CoA thiolase polypeptide. In certain such embodiments, the acetoacetyl-CoA thiolase polypeptide comprises an amino acid sequence having at least 50% sequence identity to SEQ ID NO:25.

In some embodiments, a genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 further comprises one or more heterologous nucleic acids encoding a PDC polypeptide. In certain such embodiments, the PDC polypeptide comprises an amino acid sequence having at least 50% sequence identity to SEQ ID NO:117.

In some embodiments, a genetically modified host cell comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 further comprises one or more heterologous nucleic acids encoding a cannabinoid synthase polypeptide. In certain such embodiments, the cannabinoid synthase polypeptide is a THCA synthase polypeptide. In certain such embodiments, the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155. In some embodiments, the cannabinoid synthase polypeptide is a CBDA synthase polypeptide. In certain such embodiments, the CBDA synthase polypeptide comprises an amino acid sequence having at least 50% sequence identity to SEQ ID NO:88 or SEQ ID NO:151.

Exemplary Genetically Modified Host Cells Expressing GOT Polypeptides

The present disclosure provides a genetically modified host cell that produces a cannabinoid or a cannabinoid derivative, wherein the genetically modified host cell is genetically modified with: a) one or more heterologous nucleic acids that encode a GOT polypeptide and b) one or more heterologous nucleic acids that encode a THCA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155.

The present disclosure provides a genetically modified host cell that produces a cannabinoid or a cannabinoid derivative, wherein the genetically modified host cell is genetically modified with: a) one or more heterologous nucleic acids that encode a GOT polypeptide and b) one or more heterologous nucleic acids that encode a CBDA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the CBDA synthase polypeptide comprises an amino acid sequence having at least 50% sequence identity to SEQ ID NO:88 or SEQ ID NO:151.

The present disclosure provides a genetically modified host cell for producing a cannabinoid or a cannabinoid derivative, wherein the genetically modified host cell is genetically modified with: a) one or more heterologous nucleic acids that encode a GOT polypeptide and b) one or more heterologous nucleic acids that encode a TKS polypeptide and one or more heterologous nucleic acids that encode an OAC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide, b) one or more heterologous nucleic acids that encode a TKS polypeptide and one or more heterologous nucleic acids that encode an OAC polypeptide, and c) one or more heterologous nucleic acids that encode a THCA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; and the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155.

The present disclosure provides a genetically modified host cell for producing a cannabinoid or a cannabinoid derivative, wherein the genetically modified host cell is genetically modified with: a) one or more heterologous nucleic acids that encode a GOT polypeptide, b) one or more heterologous nucleic acids that encode a TKS polypeptide and one or more heterologous nucleic acids that encode an OAC polypeptide, and c) one or more heterologous nucleic acids that encode a CBDA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; and the CBDA synthase polypeptide comprises an amino acid sequence having at least 50% sequence identity to SEQ ID NO:88 or SEQ ID NO:151.

The present disclosure provides a genetically modified host cell for producing a cannabinoid or a cannabinoid derivative, wherein the genetically modified host cell is genetically modified with: a) one or more heterologous nucleic acids that encode a GOT polypeptide and b) one or more heterologous nucleic acids that encode a polypeptide that generates GPP. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60.

The present disclosure provides a genetically modified host cell for producing a cannabinoid or a cannabinoid derivative, wherein the genetically modified host cell is genetically modified with: a) one or more heterologous nucleic acids that encode a GOT polypeptide, b) one or more heterologous nucleic acids that encode a polypeptide that generates GPP, and c) one or more heterologous nucleic acids that encode a THCA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; and the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155.

The present disclosure provides a genetically modified host cell for producing a cannabinoid or a cannabinoid derivative, wherein the genetically modified host cell is genetically modified with: a) one or more heterologous nucleic acids that encode a GOT polypeptide, b) one or more heterologous nucleic acids that encode a polypeptide that generates GPP, and c) one or more heterologous nucleic acids that encode a CBDA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; and the CBDA synthase polypeptide comprises an amino acid sequence having at least 50% sequence identity to SEQ ID NO:88 or SEQ ID NO:151.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; and c) one or more heterologous nucleic acids that encode a TKS polypeptide and one or more heterologous nucleic acids that encode an OAC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; c) one or more heterologous nucleic acids that encode a TKS polypeptide and one or more heterologous nucleic acids that encode an OAC polypeptide; and d) one or more heterologous nucleic acids that encode a THCA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; and the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; c) one or more heterologous nucleic acids that encode a TKS polypeptide and one or more heterologous nucleic acids that encode an OAC polypeptide; and d) one or more heterologous nucleic acids that encode a CBDA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; and the CBDA synthase polypeptide comprises an amino acid sequence having at least 50% sequence identity to SEQ ID NO:88 or SEQ ID NO:151.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; c) one or more heterologous nucleic acids that encode a TKS polypeptide and one or more heterologous nucleic acids that encode an OAC polypeptide; and d) one or more heterologous nucleic acids that encode a polypeptide that generates malonyl-CoA. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; and the polypeptide that generates malonyl-CoA is an ACC polypeptide and comprises an amino acid sequence having at least 50% sequence identity to SEQ ID NO:9, SEQ ID NO:97, or SEQ ID NO:207.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; c) one or more heterologous nucleic acids that encode a TKS polypeptide and one or more heterologous nucleic acids that encode an OAC polypeptide; d) one or more heterologous nucleic acids that encode a polypeptide that generates malonyl-CoA; and e) one or more heterologous nucleic acids that encode a THCA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; the polypeptide that generates malonyl-CoA is an ACC polypeptide and comprises an amino acid sequence having at least 50% sequence identity to SEQ ID NO:9, SEQ ID NO:97, or SEQ ID NO:207; and the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; c) one or more heterologous nucleic acids that encode a TKS polypeptide and one or more heterologous nucleic acids that encode an OAC polypeptide; d) one or more heterologous nucleic acids that encode a polypeptide that generates malonyl-CoA; and e) one or more heterologous nucleic acids that encode a CBDA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; the polypeptide that generates malonyl-CoA is an ACC polypeptide and comprises an amino acid sequence having at least 50% sequence identity to SEQ ID NO:9, SEQ ID NO:97, or SEQ ID NO:207; and the CBDA synthase polypeptide comprises an amino acid sequence having at least 50% sequence identity to SEQ ID NO:88 or SEQ ID NO:151.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; c) one or more heterologous nucleic acids that encode a polypeptide that generates GPP; and d) one or more heterologous nucleic acids that encode a TKS polypeptide and one or more heterologous nucleic acids that encode an OAC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the polypeptide that generates GPP is a GPPS polypeptide and comprises an amino acid sequence having at least 50% sequence identity to SEQ ID NO:7, SEQ ID NO:8, or SEQ ID NO:60; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; c) one or more heterologous nucleic acids that encode a TKS polypeptide and one or more heterologous nucleic acids that encode an OAC polypeptide; d) one or more heterologous nucleic acids that encode a polypeptide that generates GPP; and e) one or more heterologous nucleic acids that encode a THCA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; the polypeptide that generates GPP is a GPPS polypeptide and comprises an amino acid sequence having at least 50% sequence identity to SEQ ID NO:7, SEQ ID NO:8, or SEQ ID NO:60; and the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; c) one or more heterologous nucleic acids that encode a TKS polypeptide and one or more heterologous nucleic acids that encode an OAC polypeptide; d) one or more heterologous nucleic acids that encode a polypeptide that generates GPP; and e) one or more heterologous nucleic acids that encode a CBDA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; the polypeptide that generates GPP is a GPPS polypeptide and comprises an amino acid sequence having at least 50% sequence identity to SEQ ID NO:7, SEQ ID NO:8, or SEQ ID NO:60; and the CBDA synthase polypeptide comprises an amino acid sequence having at least 50% sequence identity to SEQ ID NO:88 or SEQ ID NO:151.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; c) one or more heterologous nucleic acids that encode a TKS polypeptide and one or more heterologous nucleic acids that encode an OAC polypeptide; d) one or more heterologous nucleic acids that encode a polypeptide that generates GPP; and e) one or more heterologous nucleic acids that encode a polypeptide that generates malonyl-CoA. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; the polypeptide that generates GPP is a GPPS polypeptide and comprises an amino acid sequence having at least 50% sequence identity to SEQ ID NO:7, SEQ ID NO:8, or SEQ ID NO:60; and the polypeptide that generates malonyl-CoA is an ACC polypeptide and comprises an amino acid sequence having at least 50% sequence identity to SEQ ID NO:9, SEQ ID NO:97, or SEQ ID NO:207.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; c) one or more heterologous nucleic acids that encode a TKS polypeptide and one or more heterologous nucleic acids that encode an OAC polypeptide; d) one or more heterologous nucleic acids that encode a polypeptide that generates malonyl-CoA; e) one or more heterologous nucleic acids that encode a polypeptide that generates GPP; and f) one or more heterologous nucleic acids that encode a THCA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; the polypeptide that generates malonyl-CoA is an ACC polypeptide and comprises an amino acid sequence having at least 50% sequence identity to SEQ ID NO:9, SEQ ID NO:97, or SEQ ID NO:207; the polypeptide that generates GPP is a GPPS polypeptide and comprises an amino acid sequence having at least 50% sequence identity to SEQ ID NO:7, SEQ ID NO:8, or SEQ ID NO:60; and the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates an acyl-CoA compound or an acyl-CoA compound derivative; c) one or more heterologous nucleic acids that encode a TKS polypeptide and one or more heterologous nucleic acids that encode an OAC polypeptide; d) one or more heterologous nucleic acids that encode a polypeptide that generates malonyl-CoA; e) one or more heterologous nucleic acids that encode a polypeptide that generates GPP; and f) one or more heterologous nucleic acids that encode a CBDA synthase polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; the OAC polypeptide comprises an amino acid sequence having at least 50% sequence identity to SEQ ID NO:10 or SEQ ID NO:78; the polypeptide that generates malonyl-CoA is an ACC polypeptide and comprises an amino acid sequence having at least 50% sequence identity to SEQ ID NO:9, SEQ ID NO:97, or SEQ ID NO:207; the polypeptide that generates GPP is a GPPS polypeptide and comprises an amino acid sequence having at least 50% sequence identity to SEQ ID NO:7, SEQ ID NO:8, or SEQ ID NO:60; and the CBDA synthase polypeptide comprises an amino acid sequence having at least 50% sequence identity to SEQ ID NO:88 or SEQ ID NO:151.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; d) one or more heterologous nucleic acids that encode a polypeptide that condenses two molecules of acetyl-CoA to generate acetoacetyl-CoA; and e) one or more heterologous nucleic acids that encode a PDC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; and the PDC polypeptide comprises an amino acid sequence having at least 50% sequence identity to SEQ ID NO:117.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a THCA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; and f) one or more heterologous nucleic acids that encode a PDC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; and the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a CBDA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; and f) one or more heterologous nucleic acids that encode a PDC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; and the CBDA synthase polypeptide comprises an amino acid sequence having at least 50% sequence identity to SEQ ID NO:88 or SEQ ID NO:151.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; d) one or more heterologous nucleic acids that encode a polypeptide that condenses two molecules of acetyl-CoA to generate acetoacetyl-CoA; e) one or more heterologous nucleic acids that encode a PDC polypeptide; and f) one or more heterologous nucleic acids that encode a polypeptide that generates an acyl-CoA compound or an acyl-CoA compound derivative. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; and the PDC polypeptide comprises an amino acid sequence having at least 50% sequence identity to SEQ ID NO:117.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a THCA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; f) one or more heterologous nucleic acids that encode a PDC polypeptide; and g) one or more heterologous nucleic acids that encode a polypeptide that generates an acyl-CoA compound or an acyl-CoA compound derivative. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; and the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a CBDA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; f) one or more heterologous nucleic acids that encode a PDC polypeptide; and g) one or more heterologous nucleic acids that encode a polypeptide that generates an acyl-CoA compound or an acyl-CoA compound derivative. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; and the CBDA synthase polypeptide comprises an amino acid sequence having at least 50% sequence identity to SEQ ID NO:88 or SEQ ID NO:151.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; d) one or more heterologous nucleic acids that encode a polypeptide that condenses two molecules of acetyl-CoA to generate acetoacetyl-CoA; e) one or more heterologous nucleic acids that encode a PDC polypeptide; f) one or more heterologous nucleic acids that encode a TKS polypeptide and one or more heterologous nucleic acids that encode an OAC polypeptide; and g) one or more heterologous nucleic acids that encode a polypeptide that generates an acyl-CoA compound or an acyl-CoA compound derivative. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the PDC polypeptide comprises an amino acid sequence having at least 50% sequence identity to SEQ ID NO:117; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a THCA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; f) one or more heterologous nucleic acids that encode a PDC polypeptide; g) one or more heterologous nucleic acids that encode a TKS polypeptide and one or more heterologous nucleic acids that encode an OAC polypeptide; and h) one or more heterologous nucleic acids that encode a polypeptide that generates an acyl-CoA compound or an acyl-CoA compound derivative. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a CBDA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; f) one or more heterologous nucleic acids that encode a PDC polypeptide; g) one or more heterologous nucleic acids that encode a TKS polypeptide and one or more heterologous nucleic acids that encode an OAC polypeptide; and h) one or more heterologous nucleic acids that encode a polypeptide that generates an acyl-CoA compound or an acyl-CoA compound derivative. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%)

sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the CBDA synthase polypeptide comprises an amino acid sequence having at least 50% sequence identity to SEQ ID NO:88 or SEQ ID NO:151; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; d) one or more heterologous nucleic acids that encode a polypeptide that condenses two molecules of acetyl-CoA to generate acetoacetyl-CoA; e) one or more heterologous nucleic acids that encode a PDC polypeptide; and f) one or more heterologous nucleic acids that encode a TKS polypeptide and one or more heterologous nucleic acids that encode an OAC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a THCA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; f) a PDC polypeptide; and g) one or more heterologous nucleic acids that encode a TKS polypeptide and one or more heterologous nucleic acids that encode an OAC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a CBDA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; f) one or more heterologous nucleic acids that encode a PDC polypeptide; and g) one or more heterologous nucleic acids that encode a TKS polypeptide and one or more heterologous nucleic acids that encode an OAC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the CBDA synthase polypeptide comprises an amino acid sequence having at least 50% sequence identity to SEQ ID NO:88 or SEQ ID NO:151; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; d) one or more heterologous nucleic acids that encode a polypeptide that condenses two molecules of acetyl-CoA to generate acetoacetyl-CoA; e) one or more heterologous nucleic acids that encode a PDC polypeptide; f) one or more heterologous nucleic acids that encode a TKS polypeptide and one or more heterologous nucleic acids that encode an OAC polypeptide; g) one or more heterologous nucleic acids that encode a polypeptide that generates malonyl-CoA; and h) one or more heterologous nucleic acids that encode a polypeptide that generates an acyl-CoA compound or an acyl-CoA compound derivative. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the PDC polypeptide comprises an amino acid sequence having at least 50% sequence identity to SEQ ID NO:117; the polypeptide that generates malonyl-CoA is an ACC polypeptide and comprises an amino acid sequence having at least 50% sequence identity to SEQ ID NO:9, SEQ ID NO:97, or SEQ ID NO:207; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a THCA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; f) one or more heterologous nucleic acids that encode a PDC polypeptide; g) one or more heterologous nucleic acids that encode a TKS polypeptide and one or more heterologous nucleic acids that encode an OAC polypeptide; h) one or more heterologous nucleic acids that encode a polypeptide that generates malonyl-CoA; and i) one or more heterologous nucleic acids that encode a polypeptide that generates an acyl-CoA compound or an acyl-CoA compound derivative. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155; the polypeptide that generates malonyl-CoA is an ACC polypeptide and comprises an amino acid sequence having at least 50% sequence identity to SEQ ID NO:9, SEQ ID NO:97, or SEQ ID NO:207; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a CBDA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; f) one or more heterologous nucleic acids that encode a PDC polypeptide; g) one or more heterologous nucleic acids that encode a TKS polypeptide and one or more heterologous nucleic acids that encode an OAC polypeptide; h) one or more heterologous nucleic acids that encode a polypeptide that generates malonyl-CoA; and i) one or more heterologous nucleic acids that encode a polypeptide that generates an acyl-CoA compound or an acyl-CoA compound derivative. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the CBDA synthase polypeptide comprises an amino acid sequence having at least 50% sequence identity to SEQ ID NO:88 or SEQ ID NO:151; the polypeptide that generates malonyl-CoA is an ACC polypeptide and comprises an amino acid sequence having at least 50% sequence identity to SEQ ID NO:9, SEQ ID NO:97, or SEQ ID NO:207; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; d) one or more heterologous nucleic acids that encode a polypeptide that condenses two molecules of acetyl-CoA to generate acetoacetyl-CoA; e) one or more heterologous nucleic acids that encode a PDC polypeptide; f) one or more heterologous nucleic acids that encode a polypeptide that generates malonyl-CoA; and g) one or more heterologous nucleic acids that encode a TKS polypeptide and one or more heterologous nucleic acids that encode an OAC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the polypeptide that generates malonyl-CoA is an ACC polypeptide and comprises an amino acid sequence having at least 50% sequence identity to SEQ ID NO:9, SEQ ID NO:97, or SEQ ID NO:207; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a THCA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; f) one or more heterologous nucleic acids that encode a PDC polypeptide; g) one or more heterologous nucleic acids that encode a polypeptide that generates malonyl-CoA; and h) one or more heterologous nucleic acids that encode a TKS polypeptide and one or more heterologous nucleic acids that encode an OAC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155; the polypeptide that generates malonyl-CoA is an ACC polypeptide and comprises an amino acid sequence having at least 50% sequence identity to SEQ ID NO:9, SEQ ID NO:97, or SEQ ID NO:207; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a GOT polypeptide; b) one or more heterologous nucleic acids that encode a polypeptide that generates GPP; c) one or more heterologous nucleic acids that encode a CBDA synthase polypeptide; d) one or more heterologous nucleic acids that encode one or more of the following polypeptides: a HMGS polypeptide, a tHMGR polypeptide, a MK polypeptide, a PMK polypeptide, a MVD polypeptide, or an IDI polypeptide; e) one or more heterologous nucleic acids that encode a polypeptide that condenses two molecules of acetyl-CoA to generate acetoacetyl-CoA; f) one or more heterologous nucleic acids that encode a PDC polypeptide; g) one or more heterologous nucleic acids that encode a polypeptide that generates malonyl-CoA; and h) one or more heterologous nucleic acids that encode a TKS polypeptide and one or more heterologous nucleic acids that encode an OAC polypeptide. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In certain such embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110. In some embodiments, the polypeptide that generates GPP is a GPPS polypeptide and comprises an amino acid sequence having at least 50% sequence identity to SEQ ID NO:7, SEQ ID NO:8, or SEQ ID NO:60; the IDI polypeptide comprises an amino acid sequence having at least 50% sequence identity to SEQ ID NO:58; the tHMGR polypeptide comprises an amino acid sequence having at least 50% sequence identity to SEQ ID NO:17, SEQ ID NO:52, SEQ ID NO:113, or SEQ ID NO:208; the HMGS polypeptide comprises an amino acid sequence having at least 50% sequence identity to SEQ ID NO:23, SEQ ID NO:24, or SEQ ID NO:115; the MK polypeptide comprises an amino acid sequence having at least 50% sequence identity to SEQ ID NO:64; the PMK polypeptide comprises an amino acid sequence having at least 50% sequence identity to SEQ ID NO:62 or SEQ ID NO:205; the MVD polypeptide comprises an amino acid sequence having at least 50% sequence identity to SEQ ID NO:66; the polypeptide that condenses two molecules of acetyl-CoA to generate acetoacetyl-CoA is an acetoacetyl-CoA thiolase polypeptide and comprises an amino acid sequence having at least 50% sequence identity to SEQ ID NO:25; the PDC polypeptide comprises an amino acid sequence having at least 50% sequence identity to SEQ ID NO:117; the CBDA synthase polypeptide comprises an amino acid sequence having at least 50% sequence identity to SEQ ID NO:88 or SEQ ID NO:151; the polypeptide that generates malonyl-CoA is an ACC polypeptide and comprises an amino acid sequence having at least 50% sequence identity to SEQ ID NO:9, SEQ ID NO:97, or SEQ ID NO:207; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78.

The present disclosure provides a genetically modified host cell for producing a cannabinoid or a cannabinoid derivative, wherein the genetically modified host cell is genetically modified with: a) one or more heterologous nucleic acids that encode a polypeptide that generates an acyl-CoA compound or an acyl-CoA compound derivative; b) one or more heterologous nucleic acids that encode a polypeptide that generates GPP; c) one or more heterologous nucleic acids that encode a polypeptide that generates malonyl-CoA; d) one or more heterologous nucleic acids that encode one or more polypeptides that condense an acyl-CoA compound or an acyl-CoA compound derivative with malonyl-CoA to generate olivetolic acid or derivatives of olivetolic acid; e) one or more heterologous nucleic acids that encode a geranyl pyrophosphate:olivetolic acid transferase (GOT) polypeptide or an aromatic prenyltransferase polypeptide such as a NphB polypeptide; and f) one or more heterologous nucleic acids that encode a cannabinoid synthase polypeptide.

The present disclosure also provides a genetically modified host cell for producing a cannabinoid or a cannabinoid derivative, wherein the genetically modified host cell is genetically modified with: a) one or more heterologous nucleic acids that encode a polypeptide that generates an acyl-CoA compound or an acyl-CoA compound derivative; b) one or more heterologous nucleic acids that encode a polypeptide that generates neryl pyrophosphate (NPP); c) one or more heterologous nucleic acids that encode a polypeptide that generates malonyl-CoA; d) one or more heterologous nucleic acids that encode one or more polypeptides that condense an acyl-CoA compound or an acyl-CoA compound derivative and malonyl-CoA to generate olivetolic acid or derivatives of olivetolic acid; e) one or more heterologous nucleic acids that encode a GOT polypeptide or a NphB polypeptide; and f) one or more heterologous nucleic acids that encode a cannabinoid synthase polypeptide. In certain such embodiments, culturing of the genetically modified host cell in a suitable medium provides for synthesis of the cannabinoid or the cannabinoid derivative in a recoverable amount.

The present disclosure provides a genetically modified host cell for producing a cannabinoid or a cannabinoid derivative, wherein the genetically modified host cell is genetically modified with: a) one or more heterologous nucleic acids that encode a polypeptide that generates an acyl-CoA compound or an acyl-CoA compound derivative; b) one or more heterologous nucleic acids that encode a TKS/OAC fusion polypeptide; and c) one or more heterologous nucleic acids that encode a GOT polypeptide or a NphB polypeptide. In certain such embodiments, culturing the genetically modified host cell in a medium comprising a carboxylic acid provides for synthesis of a cannabinoid derivative or cannabinoid in a recoverable amount. In some embodiments, the genetically modified host cell is further genetically modified with one or more heterologous nucleic acids that encode a THCAS or CBDAS polypeptide. In certain such embodiments, culturing the genetically modified host cell in a medium comprising a carboxylic acid provides for synthesis of a cannabinoid derivative or a cannabinoid in a recoverable amount.

Exemplary Genetically Modified Host Cells Expressing NPPS Polypeptides

In some embodiments, a genetically modified host cell of the present disclosure is genetically modified with: a) one or more heterologous nucleic acids encoding a polypeptide that condenses 2 molecules of acetyl-CoA to generate acetoacetyl-CoA; b) one or more heterologous nucleic acids encoding one or more mevalonate pathway polypeptides; and c) one or more heterologous nucleic acids encoding a NPPS polypeptide.

In some embodiments, a genetically modified host cell of the present disclosure is genetically modified with: a) one or more heterologous nucleic acids encoding a polypeptide that condenses 2 molecules of acetyl-CoA to generate acetoacetyl-CoA; b) one or more heterologous nucleic acids encoding one or more mevalonate pathway polypeptides; c) one or more heterologous nucleic acids encoding a NPPS polypeptide; and d) one or more heterologous nucleic acids encoding a TKS polypeptide and one or more heterologous nucleic acids encoding an OAC polypeptide.

In some embodiments, a genetically modified host cell of the present disclosure is genetically modified with: a) one or more heterologous nucleic acids encoding a polypeptide that condenses 2 molecules of acetyl-CoA to generate acetoacetyl-CoA; b) one or more heterologous nucleic acids encoding one or more mevalonate pathway polypeptides; c) one or more heterologous nucleic acids encoding a NPPS polypeptide; d) one or more heterologous nucleic acids encoding a polypeptide that generates an acyl-CoA compound or an acyl-CoA compound derivative; and e) one or more heterologous nucleic acids encoding a TKS polypeptide and one or more heterologous nucleic acids encoding an OAC polypeptide.

A GOT polypeptide, using NPP and olivetolic acid as substrates, can generate cannabinerolic acid (CBNRA). In some embodiments, a GOT polypeptide acts on NPP and an olivetolic acid derivative (as described elsewhere herein) to generate a CBNRA derivative. Cannabinerolic acid or derivatives thereof can serve as a substrate for a CBDAS or THCAS polypeptide to generate CBDA or THCA, or derivatives thereof, respectively.

In some embodiments, a genetically modified host cell of the present disclosure is genetically modified with: a) one or more heterologous nucleic acids encoding a polypeptide that condenses one molecule of acetyl-CoA and one molecule of malonyl-CoA to generate acetoacetyl-CoA; b) one or more heterologous nucleic acids encoding one or more mevalonate pathway polypeptides; c) one or more heterologous nucleic acids encoding a NPPS polypeptide; and d) one or more heterologous nucleic acids encoding a GOT polypeptide. In certain such embodiments, the GOT polypeptide encoded by one or more heterologous nucleic acids can catalyze production of cannabigerolic acid from GPP and olivetolic acid in an amount at least ten times higher than a polypeptide comprising an amino acid sequence set forth in SEQ ID NO:82. In some embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:100 or SEQ ID NO:110. In certain such embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:110.

In some embodiments, a genetically modified host cell of the present disclosure is genetically modified with: a) one or more heterologous nucleic acids encoding a polypeptide that condenses 2 molecules of acetyl-CoA to generate acetoacetyl-CoA; b) one or more heterologous nucleic acids encoding one or more mevalonate pathway polypeptides; c) one or more heterologous nucleic acids encoding a NPPS polypeptide; and d) one or more heterologous nucleic acids encoding a GOT polypeptide or a NphB polypeptide. In certain such embodiments, the GOT polypeptide encoded by one or more heterologous nucleic acids can catalyze production of cannabigerolic acid from GPP and olivetolic acid in an amount at least ten times higher than a polypeptide comprising an amino acid sequence set forth in SEQ ID NO:82. In some embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:100 or SEQ ID NO:110. In certain such embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:110.

In some embodiments, a genetically modified host cell of the present disclosure is genetically modified with: a) one or more heterologous nucleic acids encoding a polypeptide that condenses 2 molecules of acetyl-CoA to generate acetoacetyl-CoA; b) one or more heterologous nucleic acids encoding one or more mevalonate pathway polypeptides; c) one or more heterologous nucleic acids encoding a NPPS polypeptide; d) one or more heterologous nucleic acids encoding a GOT polypeptide or a NphB polypeptide; and e) one or more heterologous nucleic acids encoding a CBDAS or THCAS polypeptide. In certain such embodiments, the GOT polypeptide encoded by one or more heterologous nucleic acids can catalyze production of cannabigerolic acid from GPP and olivetolic acid in an amount at least ten times higher than a polypeptide comprising an amino acid sequence set forth in SEQ ID NO:82. In some embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:100 or SEQ ID NO:110. In certain such embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:110.

In some embodiments, a genetically modified host cell of the present disclosure is genetically modified with: a) one or more heterologous nucleic acids encoding a polypeptide that condenses one molecule of acetyl-CoA and one molecule of malonyl-CoA to generate acetoacetyl-CoA; b) one or more heterologous nucleic acids encoding one or more mevalonate pathway polypeptides; c) one or more heterologous nucleic acids encoding a NPPS polypeptide; d) one or more heterologous nucleic acids encoding a TKS polypeptide and one or more heterologous nucleic acids encoding an OAC polypeptide; and e) one or more heterologous nucleic acids encoding a GOT polypeptide. In certain such embodiments, the GOT polypeptide encoded by one or more heterologous nucleic acids can catalyze production of cannabigerolic acid from GPP and olivetolic acid in an amount at least ten times higher than a polypeptide comprising an amino acid sequence set forth in SEQ ID NO:82. In some embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:100 or SEQ ID NO:110. In certain such embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:110.

In some embodiments, a genetically modified host cell of the present disclosure is genetically modified with: a) one or more heterologous nucleic acids encoding a polypeptide that condenses 2 molecules of acetyl-CoA to generate acetoacetyl-CoA; b) one or more heterologous nucleic acids encoding one or more mevalonate pathway polypeptides; c) one or more heterologous nucleic acids encoding a NPPS polypeptide; d) one or more heterologous nucleic acids encoding a TKS polypeptide and one or more heterologous nucleic acids encoding an OAC polypeptide; and e) one or more heterologous nucleic acids encoding a GOT polypeptide or a NphB polypeptide. In certain such embodiments, the GOT polypeptide encoded by one or more heterologous nucleic acids can catalyze production of cannabigerolic acid from GPP and olivetolic acid in an amount at least ten times higher than a polypeptide comprising an amino acid sequence set forth in SEQ ID NO:82. In some embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:100 or SEQ ID NO:110. In certain such embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:110.

In some embodiments, a genetically modified host cell of the present disclosure is genetically modified with: a) one or more heterologous nucleic acids encoding a polypeptide that condenses 2 molecules of acetyl-CoA to generate acetoacetyl-CoA; b) one or more heterologous nucleic acids encoding one or more mevalonate pathway polypeptides; c) one or more heterologous nucleic acids encoding a NPPS polypeptide; d) one or more heterologous nucleic acids encoding a TKS polypeptide and one or more heterologous nucleic acids encoding an OAC polypeptide; e) one or more heterologous nucleic acids encoding a GOT polypeptide or a NphB polypeptide; and f) one or more heterologous nucleic acids encoding a CBDAS or THCAS polypeptide. In certain such embodiments, the GOT polypeptide encoded by one or more heterologous nucleic acids can catalyze production of cannabigerolic acid from GPP and olivetolic acid in an amount at least ten times higher than a polypeptide comprising an amino acid sequence set forth in SEQ ID NO:82. In some embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:100 or SEQ ID NO:110. In certain such embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:110.

In some embodiments, a genetically modified host cell of the present disclosure is genetically modified with: a) one or more heterologous nucleic acids encoding a polypeptide that condenses one molecule of acetyl-CoA and one molecule of malonyl-CoA to generate acetoacetyl-CoA; b) one or more heterologous nucleic acids encoding one or more mevalonate pathway polypeptides; c) one or more heterologous nucleic acids encoding a NPPS polypeptide; d) one or more heterologous nucleic acids encoding a TKS polypeptide and one or more heterologous nucleic acids encoding an OAC polypeptide; e) one or more heterologous nucleic acids encoding a polypeptide that generates an acyl-CoA compound or an acyl-CoA compound derivative; and f) one or more heterologous nucleic acids encoding a GOT polypeptide. In certain such embodiments, the GOT polypeptide encoded by one or more heterologous nucleic acids can catalyze production of cannabigerolic acid from GPP and olivetolic acid in an amount at least ten times higher than a polypeptide comprising an amino acid sequence set forth in SEQ ID NO:82. In some embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:100 or SEQ ID NO:110. In certain such embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:110.

In some embodiments, a genetically modified host cell of the present disclosure is genetically modified: a) with one or more heterologous nucleic acids encoding a polypeptide that condenses 2 molecules of acetyl-CoA to generate acetoacetyl-CoA; b) with one or more heterologous nucleic acids encoding one or more mevalonate pathway polypeptides; c) with one or more heterologous nucleic acids encoding a NPPS polypeptide; d) with one or more heterologous nucleic acids encoding a TKS polypeptide and with one or more heterologous nucleic acids encoding an OAC polypeptide; e) with one or more heterologous nucleic acids encoding a polypeptide that generates an acyl-CoA compound or an acyl-CoA compound derivative; and f) with one or more heterologous nucleic acids encoding a GOT polypeptide or a NphB polypeptide. In certain such embodiments, the GOT polypeptide encoded by one or more heterologous nucleic acids can catalyze production of cannabigerolic acid from GPP and olivetolic acid in an amount at least ten times higher than a polypeptide comprising an amino acid sequence set forth in SEQ ID NO:82. In some embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:100 or SEQ ID NO:110. In certain such embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:110.

In some embodiments, a genetically modified host cell of the present disclosure is genetically modified with: a) one or more heterologous nucleic acids encoding a polypeptide that condenses 2 molecules of acetyl-CoA to generate acetoacetyl-CoA; b) one or more heterologous nucleic acids encoding one or more mevalonate pathway polypeptides; c) one or more heterologous nucleic acids encoding a NPPS polypeptide; d) one or more heterologous nucleic acids encoding a TKS polypeptide and one or more heterologous nucleic acids encoding an OAC polypeptide; e) one or more heterologous nucleic acids encoding a polypeptide that generates an acyl-CoA compound or an acyl-CoA compound derivative; f) one or more heterologous nucleic acids encoding a GOT polypeptide or a NphB polypeptide; and g) one or more heterologous nucleic acids encoding a CBDAS or THCAS polypeptide. In certain such embodiments, the GOT polypeptide encoded by one or more heterologous nucleic acids can catalyze production of cannabigerolic acid from GPP and olivetolic acid in an amount at least ten times higher than a polypeptide comprising an amino acid sequence set forth in SEQ ID NO:82. In some embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:100 or SEQ ID NO:110. In certain such embodiments, the GOT polypeptide encoded by the one or more heterologous nucleic acids comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) amino acid sequence identity to SEQ ID NO:110.

Exemplary Genetically Modified Host Cells for Making Olivetolic Acid or Olivetolic Acid Derivatives The present disclosure provides a genetically modified host cell for producing olivetolic acid or an olivetolic acid derivative, wherein the genetically modified host cell is genetically modified with: a) one or more heterologous nucleic acids that encode a polypeptide that generates an acyl-CoA compound or an acyl-CoA compound derivative and b) one or more heterologous nucleic acids that encode a TKS polypeptide and one or more heterologous nucleic acids encoding an OAC polypeptide. In certain such embodiments, the polypeptide that generates an acyl-CoA compound or an acyl-CoA compound derivative comprises an amino acid sequence having at least 50% sequence identity to SEQ ID NO:90, SEQ ID NO:92, SEQ ID NO:145, SEQ ID NO:147, SEQ ID NO:149, SEQ ID NO:169, SEQ ID NO:192, SEQ ID NO:194, SEQ ID NO:196, SEQ ID NO:198, or SEQ ID NO:200; the TKS polypeptide comprises an amino acid sequence having at least 50% sequence identity to SEQ ID NO:11 or SEQ ID NO:76; and the OAC polypeptide comprises an amino acid sequence having at least 50% sequence identity to SEQ ID NO:10 or SEQ ID NO:78. In certain such embodiments, culturing the genetically modified host cell disclosed herein in a medium comprising a carboxylic acid provides for synthesis of an olivetolic acid or olivetolic acid derivative in a recoverable amount.

The present disclosure provides a genetically modified host cell for producing olivetolic acid or an olivetolic acid derivative, wherein the genetically modified host cell is genetically modified with: a) one or more heterologous nucleic acids that encode a polypeptide that generates an acyl-CoA compound or an acyl-CoA compound derivative; and b) one or more heterologous nucleic acids that encode a TKS/OAC fusion polypeptide. In certain such embodiments, culturing the genetically modified host cell in a medium comprising a carboxylic acid provides for synthesis of the olivetolic acid or olivetolic acid derivative in a recoverable amount.

Suitable Host Cells

Parent host cells that are suitable for use in generating a genetically modified host cell of the present disclosure may include prokaryotic cells and eukaryotic cells. In some embodiments, the eukaryotic cells are yeast cells. In some embodiments, the eukaryotic cells are plant cells.

Host cells (including parent host cells and genetically modified host cells) are in some embodiments unicellular organisms, or are grown in culture as single cells. In some embodiments, the host cell is a eukaryotic cell. Suitable eukaryotic host cells may include, but are not limited to, yeast cells, insect cells, plant cells, fungal cells, and algal cells. Suitable eukaryotic host cells may include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha* (now known as *Pichia angusta*), *Kluyveromyces* sp., *Kluyveromyces lactis, Kluyveromyces marxianus, Schizosaccharomyces pombe, Dekkera bruxellensis, Arxula adeninivorans, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. In some embodiments, the host cell is a protease-deficient strain of *Saccharomyces cerevisiae*. In some embodiments, the host cell is a eukaryotic cell other than a plant cell. In some embodiments, the eukaryotic cell is a plant cell. In some embodiments, the eukaryotic cell is a plant cell, where the plant cell is one that does not normally produce a cannabinoid, a cannabinoid derivative, a cannabinoid precursor, or a cannabinoid precursor derivative. In some embodiments, the host cell is *Saccharomyces cerevisiae*. In some embodiments, the genetically modified host cell disclosed herein is cultured in vitro.

In some embodiments, the host cell is a prokaryotic cell. Suitable prokaryotic cells may include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed may include, but are not limited to, *Salmonella typhi* and *S. typhimurium*. Suitable *Shigella* strains may include, but are not limited to, *Shigella flexneri, Shigella sonnei*, and *Shigella disenteriae*. Typically, the laboratory strain is one that is non-pathogenic. Non-limiting examples of other suitable bacteria may include, but are not limited to, *Bacillus subtilis, Pseudomonas putida, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

Genetic Modification of Host Cells

The present disclosure provides for a method of making a genetically modified host cell for producing a cannabinoid, a cannabinoid derivative, a cannabinoid precursor derivative, or a cannabinoid precursor, comprising introducing into the genetically modified host cell one or more heterologous nucleic acids disclosed herein. In some embodiments, the genetically modified host cell produces a cannabinoid or a cannabinoid derivative. The disclosure also provides a method for making a genetically modified host cell genetically modified to express or overexpress one or more heterologous nucleic acids disclosed herein that encode one or more polypeptides disclosed herein, comprising introducing into the genetically modified host cell one or more heterologous nucleic acids disclosed herein.

In some embodiments, the disclosure provides for a method of making a genetically modified host cell for producing a cannabinoid or a cannabinoid derivative, comprising introducing one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, into the genetically modified host cell. In some embodiments, the present disclosure provides for a method of making a genetically modified host cell genetically modified to express or overexpress one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, comprising introducing one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, into the genetically modified host cell.

In some embodiments, the disclosure provides for a method of making a genetically modified host cell for producing a cannabinoid or a cannabinoid derivative, comprising introducing one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110 into the genetically modified host cell. In some embodiments, the present disclosure provides for a method of making a genetically modified host cell genetically modified to express or overexpress one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110 comprising introducing one or more heterologous nucleic acids encoding the GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110 into the genetically modified host cell.

The disclosure provides for a method of making a genetically modified host cell for producing a cannabinoid or a cannabinoid derivative, comprising introducing one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 into the genetically modified host cell. In some embodiments, the present disclosure provides for a method of making a genetically modified host cell genetically modified to express or overexpress one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 comprising introducing one or more heterologous nucleic acids encoding the GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 into the genetically modified host cell.

To genetically modify a parent host cell to produce a genetically modified host cell of the present disclosure, one or more heterologous nucleic acids disclosed herein is introduced stably or transiently into a host cell, using established techniques. Such techniques may include, but are not limited to, electroporation, calcium phosphate precipitation, DEAE-dextran mediated transfection, liposome-mediated transfection, and the like. For stable transformation, a heterologous nucleic acid will generally further include a selectable marker, e.g., any of several well-known selectable markers such as neomycin resistance, ampicillin resistance, tetracycline resistance, chloramphenicol resistance, kanamycin resistance, and the like. In some embodiments, a parent host cell is genetically modified to produce a genetically modified host cell of the present disclosure using a CRISPR/Cas9 system to genetically modify a parent host cell with one or more heterologous nucleic acids disclosed herein.

One or more nucleic acids disclosed herein can be present in an expression vector or construct. Suitable expression vectors may include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as E. coli and yeast). Thus, for example, one or more nucleic acids encoding a mevalonate pathway gene product(s) is included in any one of a variety of expression vectors for expressing the mevalonate pathway gene product(s). Such vectors may include chromosomal, non-chromosomal, and synthetic DNA sequences.

Numerous additional suitable expression vectors are known to those of skill in the art, and many are commercially available. The following vectors are provided by way of example; for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

In some embodiments, one or more of the nucleic acids disclosed herein are present in a single expression vector. In some embodiments, two or more of the nucleic acids disclosed herein are present in a single expression vector. In some embodiments, three or more of the nucleic acids disclosed herein are present in a single expression vector. In some embodiments, four or more of the nucleic acids disclosed herein are present in a single expression vector. In some embodiments, five or more of the nucleic acids disclosed herein are present in a single expression vector. In some embodiments, six or more of the nucleic acids disclosed herein are present in a single expression vector. In some embodiments, seven or more of the nucleic acids disclosed herein are present in a single expression vector.

In some embodiments, two or more nucleic acids disclosed herein are in separate expression vectors. In some embodiments, three or more nucleic acids disclosed herein are in separate expression vectors. In some embodiments, four or more nucleic acids disclosed herein are in separate expression vectors. In some embodiments, five or more nucleic acids disclosed herein are in separate expression vectors. In some embodiments, six or more nucleic acids disclosed herein are in separate expression vectors. In some embodiments, seven or more nucleic acids disclosed herein are in separate expression vectors. In some embodiments, eight or more nucleic acids disclosed herein are in separate expression vectors. In some embodiments, nine or more nucleic acids disclosed herein are in separate expression vectors. In some embodiments, ten or more nucleic acids disclosed herein are in separate expression vectors.

In some embodiments, one or more of the nucleic acids disclosed herein are present in a single expression construct. In some embodiments, two or more of the nucleic acids disclosed herein are present in a single expression construct. In some embodiments, three or more of the nucleic acids disclosed herein are present in a single expression construct. In some embodiments, four or more of the nucleic acids disclosed herein are present in a single expression construct. In some embodiments, five or more of the nucleic acids disclosed herein are present in a single expression construct. In some embodiments, six or more of the nucleic acids disclosed herein are present in a single expression construct.

In some embodiments, seven or more of the nucleic acids disclosed herein are present in a single expression construct.

In some embodiments, two or more nucleic acids disclosed herein are in separate expression constructs. In some embodiments, three or more nucleic acids disclosed herein are in separate expression constructs. In some embodiments, four or more nucleic acids disclosed herein are in separate expression constructs. In some embodiments, five or more nucleic acids disclosed herein are in separate expression constructs. In some embodiments, six or more nucleic acids disclosed herein are in separate expression constructs. In some embodiments, seven or more nucleic acids disclosed herein are in separate expression constructs. In some embodiments, eight or more nucleic acids disclosed herein are in separate expression constructs. In some embodiments, nine or more nucleic acids disclosed herein are in separate expression constructs. In some embodiments, ten or more nucleic acids disclosed herein are in separate expression constructs.

The disclosure provides a method of making a genetically modified host cell for producing a cannabinoid or a cannabinoid derivative, comprising introducing a vector comprising one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, into the genetically modified host cell. The disclosure provides a method of making a genetically modified host cell for producing a cannabinoid or a cannabinoid derivative, comprising introducing a vector comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110 into the genetically modified host cell. The disclosure also provides a method of making a genetically modified host cell for producing a cannabinoid or a cannabinoid derivative, comprising introducing a vector comprising one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 into the genetically modified host cell.

The disclosure also provides a method of making a genetically modified host cell for producing a cannabinoid or a cannabinoid derivative, comprising introducing a vector comprising a CsPT4 heterologous nucleic acid comprising a nucleotide sequence having at least 80% sequence identity to SEQ ID NO:111 into the genetically modified host cell. The disclosure also provides a method of making a genetically modified host cell for producing a cannabinoid or a cannabinoid derivative, comprising introducing a vector comprising a CsPT4 heterologous nucleic acid comprising a nucleotide sequence having at least 80% sequence identity to SEQ ID NO:225 into the genetically modified host cell. The disclosure also provides a method of making a genetically modified host cell for producing a cannabinoid or a cannabinoid derivative, comprising introducing a vector comprising a CsPT4t heterologous nucleic acid comprising a nucleotide sequence having at least 80% sequence identity to SEQ ID NO:221 into the genetically modified host cell. The disclosure also provides a method of making a genetically modified host cell for producing a cannabinoid or a cannabinoid derivative, comprising introducing a vector comprising a CsPT4t heterologous nucleic acid comprising a nucleotide sequence having at least 80% sequence identity to SEQ ID NO:224 into the genetically modified host cell.

The disclosure provides a method of making a genetically modified host cell genetically modified to express or overexpress one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, comprising introducing a vector comprising one or more heterologous nucleic acids encoding a GOT polypeptide, wherein said GOT polypeptide can catalyze production of cannabigerolic acid from GPP and olivetolic acid in an amount at least ten times higher than a polypeptide comprising an amino acid sequence set forth in SEQ ID NO:82, into the genetically modified host cell. The disclosure provides a method of making a genetically modified host cell genetically modified to express or overexpress one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110, comprising introducing a vector comprising one or more heterologous nucleic acids encoding the GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:110 into the genetically modified host cell. The disclosure provides a method of making a genetically modified host cell genetically modified to express or overexpress one or more heterologous nucleic acids encoding a GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100, comprising introducing a vector comprising one or more heterologous nucleic acids encoding the GOT polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 into the genetically modified host cell.

The disclosure also provides a method of making a genetically modified host cell genetically modified to express or overexpress a CsPT4 heterologous nucleic acid comprising a nucleotide sequence having at least 80% sequence identity to SEQ ID NO:111, comprising introducing a vector comprising a CsPT4 heterologous nucleic acid comprising a nucleotide sequence having at least 80% sequence identity to SEQ ID NO:111 into the genetically modified host cell. The disclosure also provides a method of making a genetically modified host cell genetically modified to express or overexpress a CsPT4 heterologous nucleic acid comprising a nucleotide sequence having at least 80% sequence identity to SEQ ID NO:225, comprising introducing a vector comprising a CsPT4 heterologous nucleic acid comprising a nucleotide sequence having at least 80% sequence identity to SEQ ID NO:225 into the genetically modified host cell. The disclosure also provides a method of making a genetically modified host cell genetically modified to express or overexpress a CsPT4t heterologous nucleic acid comprising a nucleotide sequence having at least 80% sequence identity to SEQ ID NO:221, comprising introducing a vector comprising a CsPT4t heterologous nucleic acid comprising a nucleotide sequence having at least 80% sequence identity to SEQ ID NO:221 into the genetically modified host cell. The disclosure also provides a method of making a genetically modified host cell genetically modified to express or overexpress a CsPT4t heterologous nucleic acid comprising a nucleotide sequence having at least 80% sequence identity to SEQ ID NO:224, comprising introducing a vector comprising a CsPT4t heterologous nucleic acid comprising a nucleotide sequence having at least 80% sequence identity to SEQ ID NO:224 into the genetically modified host cell.

In some embodiments, one or more of the heterologous nucleic acids disclosed herein is present in a high copy number plasmid, e.g., a plasmid that exists in about 10-50 copies per cell, or more than 50 copies per cell. In some embodiments, one or more of the heterologous nucleic acids disclosed herein is present in a low copy number plasmid. In some embodiments, one or more of the heterologous nucleic acids disclosed herein is present in a medium copy number plasmid.

Depending on the host/vector or host/construct system utilized, any of a number of suitable transcription and translation control elements, including constitutive and inducible promoters, transcription enhancer elements, transcription terminators, etc. may be used in the expression vector or construct (see e.g., Bitter et al. (1987) *Methods in Enzymology*, 153:516-544).

In some embodiments, heterologous nucleic acids disclosed herein are operably linked to a promoter. In some embodiments, the promoter is a constitutive promoter. In some embodiments, the promoter is an inducible promoter. In some embodiments, the promoter is functional in a prokaryotic cell. In some embodiments, the promoter is functional in a eukaryotic cell. In some embodiments, the promoter can be a strong driver of expression. In some embodiments, the promoter can be a weak driver of expression. In some embodiments, the promoter can be a medium driver of expression.

Suitable promoters for use in prokaryotic host cells may include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, a spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein—Nucleic Acid Interaction*. Macmillan, London, UK, Vol. 10, pp. 143-162); an SP6 promoter (see, e.g., Melton et al. (1984) *Nucl. Acids Res.* 12:7035); and the like.

Suitable constitutive promoters for use in prokaryotic cells are known in the art and may also include, but are not limited to, a sigma70 promoter, e.g., a consensus sigma70 promoter.

Non-limiting examples of suitable eukaryotic promoters may include CMV immediate early, HSV thymidine kinase, early and late SV40, LTRs from retrovirus, and mouse metallothionein-I. Selection of the appropriate vector, construct, and promoter is well within the level of ordinary skill in the art. The expression vector or construct may also contain a ribosome binding site for translation initiation and a transcription terminator. The expression vector or construct may also include appropriate sequences for amplifying expression.

In yeast, a number of vectors or constructs containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

Generally, recombinant expression vectors will include origins of replication and selectable markers permitting transformation of the host cell, e.g., the ampicillin resistance gene of *E. coli*, the *S. cerevisiae* TRP1 gene, etc.; and a promoter derived from a highly-expressed gene to direct transcription of the coding sequence. Such promoters can be derived from operons encoding glycolytic enzymes such as 3-phosphoglycerate kinase (PGK), α-factor, acid phosphatase, or heat shock proteins, among others.

Inducible promoters are well known in the art. Suitable inducible promoters may include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) *J. Bacteriol.* 177:4121-4130); a xylose-inducible promoter, e.g., Pxyl (see, e.g., Kim et al. (1996) *Gene* 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) *FEMS Microbiol Lett.* 177(2):327-34); and the like.

In addition, the expression vectors or constructs will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as *E. coli*.

In some embodiments, one or more heterologous nucleic acids disclosed herein is integrated into the genome of the genetically modified host cell disclosed herein. In some embodiments, one or more heterologous nucleic acids disclosed herein remains episomal (i.e., is not integrated into the genome of the genetically modified host cell). In some embodiments, at least one of the one or more heterologous nucleic acids disclosed herein is maintained extrachromosomally.

In some embodiments, a subject heterologous nucleic acid or a subject recombinant expression vector or construct comprises a promoter or other regulatory element(s) for expression in a plant cell. Non-limiting examples of suitable constitutive promoters that are functional in a plant cell is the cauliflower mosaic virus 35S promoter, a tandem 35S promoter (Kay et al., *Science* 236:1299 (1987)), a cauliflower mosaic virus 19S promoter, a nopaline synthase gene promoter (Singer et al., *Plant Mol. Biol.* 14:433 (1990); An, *Plant Physiol.* 81:86 (1986), an octopine synthase gene promoter, and a ubiquitin promoter. Suitable inducible promoters that are functional in a plant cell may include, but are not limited to, a phenylalanine ammonia-lyase gene promoter, a chalcone synthase gene promoter, a pathogenesis-related protein gene promoter, a copper-inducible regulatory element (Mett et al., *Proc. Natl. Acad. Sci. USA* 90:4567-4571 (1993); Furst et al., Cell 55:705-717 (1988)); tetracycline and chlor-tetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992); a nitrate-inducible promoter derived from the spinach nitrite reductase gene (Back et al., *Plant Mol. Biol.* 17:9 (1991)); a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)); a light-responsive regulatory element as described in U.S. Patent Publication No. 20040038400; a salicylic acid inducible regulatory elements (Uknes et al., *Plant Cell* 5:159-169 (1993); Bi et al., *Plant J.* 8:235-245 (1995)); plant hormone-inducible regulatory elements (Yamaguchi-Shinozaki et al., *Plant Mol. Biol.* 15:905 (1990); Kares et al., *Plant Mol. Biol.* 15:225 (1990)); and human hormone-inducible regulatory elements such as the human glucocorticoid response element (Schena et al., *Proc. Natl. Acad. Sci. USA* 88:10421 (1991).

Plant tissue-selective regulatory elements also can be included in a subject heterologous nucleic acid or a subject vector or construct. Suitable tissue-selective regulatory elements, which can be used to ectopically express a heterologous nucleic acid in a single tissue or in a limited number of tissues, may include, but are not limited to, a xylem-selective regulatory element, a tracheid-selective regulatory element, a fiber-selective regulatory element, a trichome-selective regulatory element (see, e.g., Wang et al. (2002) *J. Exp. Botany* 53:1891-1897), a glandular trichome-selective regulatory element, and the like.

Vectors that are suitable for use in plant cells are known in the art, and any such vector can be used to introduce a subject heterologous nucleic acid into a plant host cell. Suitable vectors may include, e.g., a Ti plasmid of *Agrobacterium tumefaciens* or an $Ri_1$ plasmid of *A. rhizogenes*. The Ti or $Ri_1$ plasmid is transmitted to plant cells on infection by *Agrobacterium* and is stably integrated into the plant genome. J. Schell, *Science*, 237:1176-83 (1987). Also suitable for use is a plant artificial chromosome, as described in, e.g., U.S. Pat. No. 6,900,012.

As will be appreciated by the skilled artisan, slight changes in nucleotide sequence do not necessarily alter the amino acid sequence of the encoded polypeptide. It will be appreciated by persons skilled in the art that changes in the identities of nucleotides in a specific gene sequence that change the amino acid sequence of the encoded polypeptide may result in reduced or enhanced effectiveness of the genes and that, in some applications (e.g., anti-sense, co-suppression, or RNAi), partial sequences often work as effectively as full length versions. The ways in which the nucleotide sequence can be varied or shortened are well known to persons skilled in the art, as are ways of testing the effectiveness of the altered genes. In certain embodiments, effectiveness may easily be tested by, for example, conventional gas chromatography. All such variations of the genes are therefore included as part of the present disclosure.

Codon Usage

As is well known to those of skill in the art, it is possible to improve the expression of a heterologous nucleic acid in a host organism by replacing the nucleotide sequences coding for a particular amino acid (i.e., a codon) with another codon which is better expressed in the host organism (i.e., codon optimization). One reason that this effect arises due to the fact that different organisms show preferences for different codons. In some embodiments, a heterologous nucleic acid disclosed herein is modified or optimized such that the nucleotide sequence reflects the codon preference for the particular host cell. For example, the nucleotide sequence will in some embodiments be modified or optimized for yeast codon preference. See, e.g., Bennetzen and Hall (1982) *J. Biol. Chem.* 257(6): 3026-3031. As another non-limiting example, the nucleotide sequence will in some embodiments be modified or optimized for *E. coli* codon preference. See, e.g., Gouy and Gautier (1982) *Nucleic Acids Res.* 10(22):7055-7074; Eyre-Walker (1996) *Mol. Biol. Evol.* 13(6):864-872. See also Nakamura et al. (2000) *Nucleic Acids Res.* 28(1):292.

Statistical methods have been generated to analyze codon usage bias in various organisms and many computer algorithms have been developed to implement these statistical analyses in the design of codon optimized gene sequences (Lithwick G, Margalit H (2003) Hierarchy of sequence-dependent features associated with prokaryotic translation. Genome Research 13: 2665-73). Other modifications in codon usage to increase protein expression that are not dependent on codon bias have also been described (Welch et al. (2009). Design parameters to control synthetic gene expression in *Escherichia coli*. PLoS ONE 4: e7002).

In some embodiments, the codon usage of a coding sequence is modified such that the level of translation of the encoded mRNA is decreased. Reducing the level of translation of an mRNA by modifying codon usage is achieved by modifying the sequence to include codons that are rare or not commonly used by the host cell. Codon usage tables for many organisms are available that summarize the percentage of time a specific organism uses a specific codon to encode for an amino acid. Certain codons are used more often than other, "rare" codons. The use of "rare" codons in a sequence generally decreases its rate of translation. Thus, e.g., the coding sequence is modified by introducing one or more rare codons, which affect the rate of translation, but not the amino acid sequence of the polypeptide translated. For example, there are 6 codons that encode for arginine: CGT, CGC, CGA, CGG, AGA, and AGG. In *E. coli* the codons CGT and CGC are used far more often (encoding approximately 40% of the arginines in *E. coli* each) than the codon AGG (encoding approximately 2% of the arginines in *E. coli*). Modifying a CGT codon within the sequence of a gene to an AGG codon would not change the sequence of the polypeptide, but would likely decrease the gene's rate of translation.

Further, it will be appreciated that this disclosure embraces the degeneracy of codon usage as would be understood by one of ordinary skill in the art and illustrated in the following table.

Codon Degeneracies

| Amino Acid | Codons |
| --- | --- |
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

Genetically Modified Plants

The present disclosure provides genetically modified plants, where the genetically modified plants are genetically modified with one or more heterologous nucleic acids disclosed herein to generate a cannabinoid, a cannabinoid derivative, a cannabinoid precursor, or a cannabinoid precursor derivative. In some embodiments, the genetically modified plant is a plant of a genus other than *Cannabis*.

The present disclosure provides a genetically modified plant, wherein the genetically modified plant is genetically modified with: a) one or more heterologous nucleic acids that encode a polypeptide that generates an acyl-CoA compound or an acyl-CoA compound derivative; b) one or more heterologous nucleic acids that encode a polypeptide that generates GPP; c) one or more heterologous nucleic acids that encode a polypeptide that generates malonyl-CoA; d) one or more heterologous nucleic acids that encode one or more polypeptides that condense an acyl-CoA compound or an acyl-CoA compound derivative and malonyl-CoA to generate olivetolic acid or derivatives of olivetolic acid; e) one or more heterologous nucleic acids that encode a polypeptide that condenses GPP and olivetolic acid to generate cannabigerolic acid or derivatives thereof; or f) one or more heterologous nucleic acids that encode a cannabinoid synthase polypeptide, wherein the polypeptides are produced in the plant, and wherein production of the polypeptides results in production of a cannabinoid, a cannabinoid derivative, a cannabinoid precursor, or a cannabinoid precursor derivative by the genetically modified plant. In some embodiments, the plant is a monocot. In some embodiments, the plant is a dicot. In some embodiments, one or more of the polypeptide-encoding heterologous nucleic acids is operably linked to a constitutive promoter. In some embodiments, one or more of the polypeptide-encoding heterologous nucleic acids is operably linked to an inducible promoter. In some embodiments, one or more of the polypeptide-encoding heterologous nucleic acids is operably linked to a tissue-specific promoter. In some embodiments, the tissue-specific promoter is a trichome-specific promoter.

The present disclosure provides a method of producing a cannabinoid, a cannabinoid derivative, a cannabinoid precursor, or a cannabinoid precursor derivative, the method comprising maintaining a transgenic plant under conditions that favor production of the encoded one or more polypeptides, wherein production of the encoded one or more polypeptides results in production of the cannabinoid, the cannabinoid derivative, the cannabinoid precursor, or the cannabinoid precursor derivative.

In some embodiments, the genome of the transgenic plant comprises a subject heterologous nucleic acid. In some embodiments, the transgenic plant is homozygous for the genetic modification. In some embodiments, the transgenic plant is heterozygous for the genetic modification.

In some embodiments, a subject transgenic plant produces one or more transgene-encoded polypeptides disclosed herein that result in the production of a cannabinoid, a cannabinoid derivative, a cannabinoid precursor, or a cannabinoid precursor derivative in an amount that is at least about 50%, at least about 2-fold, at least about 5-fold, at least about 10-fold, at least about 25-fold, at least about 50-fold, or at least about 100-fold, or higher, than the amount of the cannabinoid, a cannabinoid derivative, a cannabinoid precursor, or a cannabinoid precursor derivative produced by a control plant, e.g., a non-transgenic plant (a plant that does not include the transgene encoding the one or more polypeptides) of the same species.

In some embodiments, a subject transgenic plant is a transgenic version of a control, non-transgenic plant that normally produces a cannabinoid, a cannabinoid derivative, a cannabinoid precursor, or a cannabinoid precursor derivative that is generated by, or is a downstream product of, transgene-encoded one or more polypeptides that produce a cannabinoid, a cannabinoid derivative, a cannabinoid precursor, or a cannabinoid precursor derivative; where the transgenic plant produces the cannabinoid, a cannabinoid derivative, a cannabinoid precursor, or a cannabinoid precursor derivative in an amount that is at least about 50%, at least about 2-fold, at least about 5-fold, at least about 10-fold, at least about 25-fold, at least about 50-fold, or at least about 100-fold, or higher, than the amount of the cannabinoid, a cannabinoid derivative, a cannabinoid precursor, or a cannabinoid precursor derivative produced by the control plant, e.g., a non-transgenic plant (a plant that does not include the transgene encoding the one or more polypeptides) of the same species.

Methods of introducing exogenous nucleic acids into plant cells are well known in the art. Such plant cells are considered "transformed." Suitable methods may include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation, CRISPR/Cas9-mediated genome editing, and the like. The choice of method is generally dependent on the type of cell being transformed and the circumstances under which the transformation is taking place (e.g., in vitro, ex vivo, or in vivo).

A CRISPR/Cas9 system can be used to generate a transgenic (genetically modified) plant of the present disclosure. CRISPR/Cas9 systems and methods are known in the art. See, e.g., Bortesi and Fischer (2015) *Biotechnol. Advances* 33:41; and Fan et al. (2015) *Sci. Reports* 5:12217.

Transformation methods based upon the soil bacterium *Agrobacterium tumefaciens* can be used for introducing an exogenous nucleic acid into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleotide sequence of interest to be introduced into the plant host.

*Agrobacterium*-mediated transformation generally employs cointegrate vectors or, e.g., binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors are well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See, e.g., Glick and Thompson, (eds.), *Methods in Plant Molecular Biology and Biotechnology*, Boca Raton, Fla.: CRC Press (1993).

*Agrobacterium*-mediated transformation is useful for producing a variety of transgenic vascular plants (Wang et al., supra, 1995) including at least one species of *Eucalyptus* and forage legumes such as alfalfa (lucerne); birdsfoot trefoil, white clover, *Stylosanthes, Lotononis bainessii* and sainfoin.

Microprojectile-mediated transformation also can be used to produce a subject transgenic plant. This method, first described by Klein et al. (*Nature* 327:70-73 (1987)), relies on microprojectiles such as gold or tungsten that are coated with the desired heterologous nucleic acid by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A subject heterologous nucleic acid may be introduced into a plant in a manner such that the heterologous nucleic acid is able to enter a plant cell(s), e.g., via an in vivo or ex vivo protocol. By "in vivo," it may mean that the heterologous nucleic acid is administered to a living body of a plant e.g. infiltration. By "ex vivo" it may mean that cells or explants are modified outside of the plant, and then such cells or organs are regenerated to a plant. A number of vectors or constructs suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples may include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-962) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545, 817, 5,545,818, and 5,576,198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified may include grains, forage crops, fruits, vegetables, oil seed crops, palms, forestry, and vines. Specific examples of plants which can be modified may include, but are not limited to, maize, banana, peanut, field peas, sunflower, tobacco, tomato, canola, tobacco, wheat, barley, oats, potato, soybeans, cotton, sorghum, lupin, and rice. Plants which can be genetically modified may include *Theobroma cacao*.

Also provided by the present disclosure are transformed plant cells, tissues, plants and products that contain the transformed plant cells. A feature of the subject transformed cells, and tissues and products that include the same is the presence of a subject heterologous nucleic acid integrated into the genome, and production by plant cells of one or more polypeptides that are utilized to generate a cannabinoid, a cannabinoid derivative, a cannabinoid precursor, or a cannabinoid precursor derivative. Recombinant plant cells of the present disclosure are useful as populations of recombinant cells, or as a tissue, seed, whole plant, stem, fruit, leaf, root, flower, stem, tuber, grain, animal feed, a field of plants, and the like.

Also provided by the present disclosure is reproductive material of a subject transgenic plant, where reproductive material may include seeds, progeny plants and clonal material, where such material can give rise to a plant that produces a cannabinoid, a cannabinoid derivative, a cannabinoid precursor, or a cannabinoid precursor derivative.

Methods of Producing a Cannabinoid, a Cannabinoid Precursor, a Cannabinoid Derivative, or a Cannabinoid Precursor Derivative The present disclosure provides methods of producing a cannabinoid, a cannabinoid derivative, a cannabinoid precursor, or a cannabinoid precursor derivative. The methods may involve culturing a genetically modified host cell of the present disclosure in a suitable medium and recovering the produced cannabinoid, the cannabinoid precursor, the cannabinoid precursor derivative, or the cannabinoid derivative. The methods may also involve cell-free production of cannabinoids, cannabinoid precursors, cannabinoid precursor derivatives, or cannabinoid derivatives using one or more polypeptides disclosed herein expressed or overexpressed by a genetically modified host cell of the disclosure.

The present disclosure provides methods of producing a cannabinoid or a cannabinoid derivative. The methods may involve culturing a genetically modified host cell of the present disclosure in a suitable medium and recovering the produced cannabinoid or cannabinoid derivative. The methods may also involve cell-free production of cannabinoids or cannabinoid derivatives using one or more polypeptides disclosed herein expressed or overexpressed by a genetically modified host cell of the disclosure.

Cannabinoids, cannabinoid derivatives, cannabinoid precursors, or cannabinoid precursor derivatives that can be produced with the methods or genetically modified host cells of the present disclosure may include, but are not limited to, cannabichromene (CBC) type (e.g. cannabichromenic acid), cannabigerol (CBG) type (e.g. cannabigerolic acid), cannabidiol (CBD) type (e.g. cannabidiolic acid), $\Delta^9$-trans-tetrahydrocannabinol ($\Delta^9$-THC) type (e.g. $\Delta^9$-tetrahydrocannabinolic acid), $\Delta^8$-trans-tetrahydrocannabinol ($\Delta^8$-THC) type, cannabicyclol (CBL) type, cannabielsoin (CBE) type, cannabinol (CBN) type, cannabinodiol (CBND) type, cannabitriol (CBT) type, olivetolic acid, GPP, derivatives of any of the foregoing, and others as listed in Elsohly M. A. and Slade D., Life Sci. 2005 Dec. 22; 78(5):539-48. Epub 2005 Sep. 30.

Cannabinoids or cannabinoid derivatives that can be produced with the methods or genetically modified host cells of the present disclosure may also include, but are not limited to, cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CBD), cannabidiol monomethylether (CBDM), cannabidiol-$C_4$ (CBD-$C_4$), cannabidivarinic acid (CBDVA), cannabidivarin (CBDV), cannabidiorcol (CBD-$C_1$), $\Delta^9$-tetrahydrocannabinolic acid A (THCA-A), $\Delta^9$-tetrahydrocannabinolic acid B (THCA-B), $\Delta^9$-tetrahydrocannabinol (THC), $\Delta^9$-tetrahydrocannabinolic acid-$C_4$ (THCA-$C_4$), $\Delta^9$-tetrahydrocannabinol-$C_4$ (THC-$C_4$), $\Delta^9$-tetrahydrocannabivarinic acid (THCVA), $\Delta^9$-tetrahydrocannabivarin (THCV), $\Delta^9$-tetrahydrocannabiorcolic acid (THCA-$C_1$), $\Delta^9$-tetrahydrocannabiorcol (THC-$C_1$), $\Delta^7$-cis-iso-tetrahydrocannabivarin, $\Delta^8$-tetrahydrocannabinolic acid ($\Delta^8$-THCA), $\Delta^8$-tetrahydrocannabinol ($\Delta^8$-THC), cannabicyclolic acid (CBLA), cannabicyclol (CBL), cannabicyclovarin (CBLV), cannabielsoic acid A (CBEA-A), cannabielsoic acid B (CBEA-B), cannabielsoin (CBE), cannabielsoinic acid, cannabicitranic acid, cannabinolic acid (CBNA), cannabinol (CBN), cannabinol methylether (CBNM), cannabinol-$C_4$, (CBN-$C_4$), cannabivarin (CBV), cannabinol-$C_2$ (CNB-$C_2$), cannabiorcol (CBN-$C_1$), cannabinodiol (CBND), cannabinodivarin (CBVD), cannabitriol (CBT), 10-ethyoxy-9-hydroxy-delta-6a-tetrahydrocannabinol, 8,9-dihydroxyl-delta-6a-tetrahydrocannabinol, cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahydro-7-hydroxy-alpha-alpha-2-trimethyl-9-n-propyl-2,6-methano-2H-1-benzoxocin-5-methanol (OH-iso-HHCV), cannabiripsol (CBR), trihydroxy-delta-9-tetrahydrocannabinol (triOH-THC), and derivatives of any of the foregoing.

Additional cannabinoid derivatives that can be produced with the methods or genetically modified host cells of the present disclosure may also include, but are not limited to, 2-geranyl-5-pentyl-resorcylic acid, 2-geranyl-5-(4-pentynyl)-resorcylic acid, 2-geranyl-5-(trans-2-pentenyl)-resorcylic acid, 2-geranyl-5-(4-methylhexyl)-resorcylic acid, 2-geranyl-5-(5-hexynyl) resorcylic acid, 2-geranyl-5-(trans-2-hexenyl)-resorcylic acid, 2-geranyl-5-(5-hexenyl)-resorcylic acid, 2-geranyl-5-heptyl-resorcylic acid, 2-geranyl-5-(6-heptynoic)-resorcylic acid, 2-geranyl-5-octyl-resorcylic acid, 2-geranyl-5-(trans-2-octenyl)-resorcylic acid, 2-geranyl-5-nonyl-resorcylic acid, 2-geranyl-5-(trans-2-nonenyl) resorcylic acid, 2-geranyl-5-decyl-resorcylic acid, 2-geranyl-5-(4-phenylbutyl)-resorcylic acid, 2-geranyl-5-(5-phenylpentyl)-resorcylic acid, 2-geranyl-5-(6-phenylhexyl)-resorcylic acid, 2-geranyl-5-(7-phenylheptyl)-resorcylic acid, (6aR,10aR)-1-hydroxy-6,6,9-trimethyl-3-propyl-6a,7,8,10a-tetrahydro-6H-dibenzo[b,d]pyran-2-carboxylic acid, (6aR,10aR)-1-hydroxy-6,6,9-trimethyl-3-(4-methylhexyl)-6a,7,8,10a-tetrahydro-6H-dibenzo[b,d]pyran-2-carboxylic acid, (6aR,10aR)-1-hydroxy-6,6,9-trimethyl-3-(5-hexenyl)-6a,7,8,10a-tetrahydro-6H-dibenzo[b,d]pyran-2-carboxylic acid, (6aR,10aR)-1-hydroxy-6,6,9-trimethyl-3-(5-hexenyl)-6a,7,8,10a-tetrahydro-6H-dibenzo[b,d]pyran-2-carboxylic acid, (6aR,10aR)-1-hydroxy-6,6,9-trimethyl-3-(6-heptynyl)-6a,7,8,10a-tetrahydro-6H-dibenzo[b,d]pyran-2-carboxylic acid, 3-[(2E)-3,7-dimethylocta-2,6-dien-1-yl]-6-(hexan-2-yl)-2,4-dihydroxybenzoic acid, 3-[(2E)-3,7-dimethylocta-2,6-dien-1-yl]-2,4-dihydroxy-6-(2-methylpentyl)benzoic acid, 3-[(2E)-3,7-dimethylocta-2,6-dien-1-yl]-2,4-dihydroxy-6-(3-methylpentyl)benzoic acid, 3-[(2E)-3,7-dimethylocta-2,6-dien-1-yl]-2,4-dihydroxy-6-(4-methylpentyl)benzoic acid, 3-[(2E)-3,7-dimethylocta-2,6-dien-1-yl]-2,4-dihydroxy-6-[(IE)-pent-1-en-1-yl]benzoic acid, 3-[(2E)-3,7-dimethylocta-2,6-dien-1-yl]-2,4-dihydroxy-6-[(2E)-pent-2-en-1-yl]benzoic acid, 3-[(2E)-3,7-dimethylocta-2,6-dien-1-yl]-2,4-dihydroxy-6-[(2E)-pent-3-en-1-yl]benzoic acid, 3-[(2E)-3,7-dimethylocta-2,6-dien-1-yl]-2,4-dihydroxy-6-(pent-4-en-1-yl)benzoic acid, 3-[(2E)-

3,7-dimethylocta-2,6-dien-1-yl]-2,4-dihydroxy-6-propylbenzoic acid, 3-[(2E)-3,7-dimethylocta-2,6-dien-1-yl]-2,4-dihydroxy-6-butylbenzoic acid, 3-[(2E)-3,7-dimethylocta-2,6-dien-1-yl]-2,4-dihydroxy-6-hexylbenzoic acid, 3-[(2E)-3,7-dimethylocta-2,6-dien-1-yl]-2,4-dihydroxy-6-heptylbenzoic acid, 3-[(2E)-3,7-dimethylocta-2,6-dien-1-yl]-2,4-dihydroxy-6-octylbenzoic acid, 3-[(2E)-3,7-dimethylocta-2,6-dien-1-yl]-2,4-dihydroxy-6-nonanylbenzoic acid, 3-[(2E)-3,7-dimethylocta-2,6-dien-1-yl]-2,4-dihydroxy-6-decanylbenzoic acid, 3-[(2E)-3,7-dimethylocta-2,6-dien-1-yl]-2,4-dihydroxy-6-undecanylbenzoic acid, 6-(4-chlorobutyl)-3-[(2E)-3,7-dimethylocta-2,6-dien-1-yl]-2,4-dihydroxybenzoic acid, 3-[(2E)-3,7-dimethylocta-2,6-dien-1-yl]-2,4-dihydroxy-6-[4-(methylsulfanyl)butyl]benzoic acid, and others as listed in Bow, E. W. and Rimoldi, J. M., "The Structure-Function Relationships of Classical Cannabinoids: CB1/CB2 Modulation," *Perspectives in Medicinal Chemistry* 2016:8 17-39 doi: 10.4137/PMC.S32171, incorporated by reference herein.

Cannabinoid precursor derivatives that can be produced with the methods or genetically modified host cells of the present disclosure may also include, but are not limited to, divarinolic acid, 5-pentyl-resorcylic acid, 5-(4-pentynyl)-resorcylic acid, 5-(trans-2-pentenyl)-resorcylic acid, 5-(4-methylhexyl)-resorcylic acid, 5-(5-hexynyl)-resorcylic acid, 5-(trans-2-hexenyl)-resorcylic acid, 5-(5-hexenyl)-resorcylic acid, 5-heptyl-resorcylic acid, 5-(6-heptynoic)-resorcylic acid, 5-octyl-resorcylic acid, 5-(trans-2-octenyl)-resorcylic acid, 5-nonyl-resorcylic acid, 5-(trans-2-nonenyl)-resorcylic acid, 5-decyl-resorcylic acid, 5-(4-phenylbutyl)-resorcylic acid, 5-(5-phenylpentyl)-resorcylic acid, 5-(6-phenylhexyl)-resorcylic acid, and 5-(7-phenylheptyl)-resorcylic acid.

Cannabinoids, cannabinoid derivatives, cannabinoid precursors, or cannabinoid precursor derivatives that can be produced with the methods or genetically modified host cells of the present disclosure may also include, but are not limited to, polyketides or polyketide derivatives.

A cannabinoid derivative or cannabinoid precursor derivative may lack one or more chemical moieties found in a naturally-occurring cannabinoid or naturally-occurring cannabinoid precursor. Such chemical moieties may include, but are not limited to, methyl, alkyl, alkenyl, methoxy, alkoxy, acetyl, carboxyl, carbonyl, oxo, ester, hydroxyl, aryl, heteroaryl, cycloalkyl, cycloalkenyl, cycloalkylalkenyl, cycloalkenylalkyl, cycloalkenylalkenyl, heterocyclylalkenyl, heteroarylalkenyl, arylalkenyl, heterocyclyl, aralkyl, cycloalkylalkyl, heterocyclylalkyl, heteroarylalkyl, and the like. In some embodiments, a cannabinoid derivative or cannabinoid precursor derivative lacking one or more chemical moieties found in a naturally-occurring cannabinoid or naturally-occurring cannabinoid precursor, and produced by a genetically modified host cell disclosed herein or in a cell-free reaction mixture comprising one or more of the polypeptides disclosed herein, may also comprise one or more of any of the functional and/or reactive groups described herein. Functional and reactive groups may be optionally substituted with one or more additional functional or reactive groups.

A cannabinoid derivative or cannabinoid precursor derivative may be a cannabinoid or cannabinoid precursor comprising one or more functional and/or reactive groups and is produced by a genetically modified host cell disclosed herein or in a cell-free reaction mixture comprising one or more of the polypeptides disclosed herein. Functional groups may include, but are not limited to, azido, halo (e.g., chloride, bromide, iodide, fluorine), methyl, alkyl, alkynyl, alkenyl, methoxy, alkoxy, acetyl, amino, carboxyl, carbonyl, oxo, ester, hydroxyl, thio, cyano, aryl, heteroaryl, cycloalkyl, cycloalkenyl, cycloalkylalkenyl, cycloalkylalkynyl, cycloalkenylalkyl, cycloalkenylalkenyl, cycloalkenylalkynyl, heterocyclylalkenyl, heterocyclylalkynyl, heteroarylalkenyl, heteroarylalkynyl, arylalkenyl, arylalkynyl, spirocyclyl, heterospirocyclyl, heterocyclyl, thioalkyl, sulfone, sulfonyl, sulfoxide, amido, alkylamino, dialkylamino, arylamino, alkylarylamino, diarylamino, N-oxide, imide, enamine, imine, oxime, hydrazone, nitrile, aralkyl, cycloalkylalkyl, haloalkyl, heterocyclylalkyl, heteroarylalkyl, nitro, thioxo, and the like. See, e.g., FIGS. 12 and 13. Suitable reactive groups may include, but are not necessarily limited to, azide, carboxyl, carbonyl, amine, (e.g., alkyl amine (e.g., lower alkyl amine), aryl amine), halide, ester (e.g., alkyl ester (e.g., lower alkyl ester, benzyl ester), aryl ester, substituted aryl ester), cyano, thioester, thioether, sulfonyl halide, alcohol, thiol, succinimidyl ester, isothiocyanate, iodoacetamide, maleimide, hydrazine, alkynyl, alkenyl, acetyl, and the like. In some embodiments, the reactive group is selected from a carboxyl, a carbonyl, an amine, an ester, a thioester, a thioether, a sulfonyl halide, an alcohol, a thiol, an alkyne, alkene, an azide, a succinimidyl ester, an isothiocyanate, an iodoacetamide, a maleimide, and a hydrazine. Functional and reactive groups may be optionally substituted with one or more additional functional or reactive groups.

A reactive group may facilitate covalent attachment of a molecule of interest. Suitable molecules of interest may include, but are not limited to, a detectable label; imaging agents; a toxin (including cytotoxins); a linker; a peptide; a drug (e.g., small molecule drugs); a member of a specific binding pair; an epitope tag; ligands for binding by a target receptor; tags to aid in purification; molecules that increase solubility; and the like. A linker may be a peptide linker or a non-peptide linker.

In some embodiments, a cannabinoid derivative or a cannabinoid precursor derivative comprising an azide may be reacted with a compound comprising an alkyne group via "click chemistry" to generate a product comprising a heterocycle, also known as an azide-alkyne cycloaddition. In some embodiments, a cannabinoid derivative or a cannabinoid precursor derivative comprising an alkyne may be reacted with a compound comprising an azide group via click chemistry to generate a product comprising a heterocycle.

Additional molecules that may be desirable for attachment to a cannabinoid derivative or cannabinoid precursor derivative may include, but are not necessarily limited to, detectable labels (e.g., spin labels, fluorescence resonance energy transfer (FRET)-type dyes, e.g., for studying structure of biomolecules in vivo); small molecule drugs; cytotoxic molecules (e.g., drugs); imaging agents; ligands for binding by a target receptor; tags to aid in purification by, for example, affinity chromatography (e.g., attachment of a FLAG epitope); molecules that increase solubility (e.g., poly(ethylene glycol); molecules that enhance bioavailability; molecules that increase in vivo half-life; molecules that target to a particular cell type (e.g., an antibody specific for an epitope on a target cell); molecules that target to a particular tissue; molecules that provide for crossing the blood-brain barrier; and molecules to facilitate selective attachment to a surface, and the like.

In some embodiments, a molecule of interest comprises an imaging agent. Suitable imaging agents may include positive contrast agents and negative contrast agents. Suitable positive contrast agents may include, but are not limited to, gadolinium tetraazacyclododecanetetraacetic acid (Gd-DOTA); gadolinium-diethylenetriaminepentaacetic acid (Gd-DTPA); gadolinium-1,4,7-tris(carbonylmethyl)-10-(2'-hydroxypropyl)-1,4,7,10-tetraazacyclododecane (Gd-HP-DO3A); Manganese(II)-dipyridoxal diphosphate (Mn-DPDP); Gd-diethylenetriaminepentaacetate-bis (methylamide) (Gd-DTPA-BMA); and the like. Suitable negative contrast agents may include, but are not limited to, a superparamagnetic iron oxide (SPIO) imaging agent; and a perfluorocarbon, where suitable perfluorocarbons may include, but are not limited to, fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotriethylamines, perfluorohexanes, perfluoropentanes, perfluorobutanes, perfluoropropanes, sulfur hexafluoride, and the like.

Additional cannabinoid derivatives and cannabinoid precursor derivatives that can be produced with a method or genetically modified host cell of the present disclosure may include derivatives that have been modified via organic synthesis or an enzymatic route to modify drug metabolism and pharmacokinetics (e.g. solubility, bioavailability, absorption, distribution, plasma half-life and metabolic clearance). Modification examples may include, but are not limited to, halogenation, acetylation and methylation.

The cannabinoids, cannabinoid derivatives, cannabinoid precursors, and cannabinoid precursor derivatives described herein further include all pharmaceutically acceptable isotopically labeled cannabinoids, cannabinoid derivatives, cannabinoid precursors, and cannabinoid precursor derivatives. An "isotopically-" or "radio-labeled" compound is a compound where one or more atoms are replaced or substituted by an atom having an atomic mass or mass number different from the atomic mass or mass number typically found in nature (i.e., naturally occurring). For example, in some embodiments, in the cannabinoids, cannabinoid derivatives, cannabinoid precursors, and cannabinoid precursor derivatives described herein hydrogen atoms are replaced or substituted by one or more deuterium or tritium. Certain isotopically labeled cannabinoids, cannabinoid derivatives, cannabinoid precursors, and cannabinoid precursor derivatives of this disclosure, for example, those incorporating a radioactive isotope, are useful in drug and/or substrate tissue distribution studies. The radioactive isotopes tritium, i.e., $^3$H, and carbon $^{14}$C, i.e., $^{14}$C, are particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances. Suitable isotopes that may be incorporated in cannabinoids, cannabinoid derivatives, cannabinoid precursors, and cannabinoid precursor derivatives described herein include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. Substitution with positron emitting isotopes, such as $^{11}$C, $^{18}$F, $^{15}$, and $^{13}$N, can be useful in Positron Emission Topography (PET) studies.

The methods of bioproduction disclosed herein enable synthesis of cannabinoids, cannabinoid derivatives, cannabinoid precursors, or cannabinoid precursor derivatives with defined stereochemistries, which is challenging to do using chemical synthesis. Cannabinoids, cannabinoid derivatives, cannabinoid precursors, or cannabinoid precursor derivatives disclosed herein may be enantiomers or disastereomers. The term "enantiomers" may refer to a pair of stereoisomers which are non-superimposable mirror images of one another. In some embodiments the cannabinoids, cannabinoid derivatives, cannabinoid precursors, or cannabinoid precursor derivatives may be the (S)-enantiomer. In some embodiments the cannabinoids, cannabinoid derivatives, cannabinoid precursors, or cannabinoid precursor derivatives may be the (R)-enantiomer. In some embodiments, the cannabinoids, cannabinoid derivatives, cannabinoid precursors, or cannabinoid precursor derivatives may be the (+) or (−) enantiomers. The term "diastereomers" may refer to the set of stereoisomers which cannot be made superimposable by rotation around single bonds. For example, cis- and trans-double bonds, endo- and exo-substitution on bicyclic ring systems, and compounds containing multiple stereogenic centers with different relative configurations may be considered to be diastereomers. The term "diastereomer" may refer to any member of this set of compounds. Cannabinoids, cannabinoid derivatives, cannabinoid precursors, or cannabinoid precursor derivatives disclosed herein may include a double bond or a fused ring. In certain such embodiments, the double bond or fused ring may be cis or trans, unless the configuration is specifically defined. If the cannabinoid, cannabinoid derivative, cannabinoid precursor, or cannabinoid precursor derivative contains a double bond, the substituent may be in the E or Z configuration, unless the configuration is specifically defined.

In some embodiments when the cannabinoid, cannabinoid precursor, cannabinoid precursor derivative, or cannabinoid derivative is recovered from the cell lysate, from the culture medium, from both the cell lysate and the culture medium, or from a cell-free reaction mixture comprising one or more polypeptides disclosed herein, the recovered cannabinoid, cannabinoid precursor, cannabinoid precursor derivative, or cannabinoid derivative is in the form of a salt. In certain such embodiments, the salt is a pharmaceutically acceptable salt. In some embodiments, the salt of the recovered cannabinoid, cannabinoid precursor, cannabinoid precursor derivative, or cannabinoid derivative is then purified as disclosed herein.

The disclosure includes pharmaceutically acceptable salts of the cannabinoids, cannabinoid derivatives, cannabinoid precursors, and cannabinoid precursor derivatives described herein. "Pharmaceutically acceptable salts" refer to those salts which retain the biological effectiveness and properties of the free bases, which are not biologically or otherwise undesirable. Representative pharmaceutically acceptable salts include, but are not limited to, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

"Pharmaceutically acceptable salt" also includes both acid and base addition salts. "Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. For example, inorganic salts include, but are not limited to, ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

Methods of Using Host Cells to Generate Cannabinoids, Cannabinoid Precursors, Cannabinoid Derivatives, or Cannabinoid Precursor Derivatives The disclosure provides methods of producing a cannabinoid, a cannabinoid precursor, a cannabinoid precursor derivative, or a cannabinoid derivative in a genetically modified host cell, the method comprising: culturing a genetically modified host cell of the disclosure in a suitable medium and recovering the produced cannabinoid, cannabinoid precursor, cannabinoid precursor derivative, or cannabinoid derivative. In certain such embodiments, the produced cannabinoid, cannabinoid precursor, cannabinoid precursor derivative, or cannabinoid derivative is then purified as disclosed herein.

In some embodiments, culturing of the genetically modified host cells of the disclosure in a suitable medium provides for synthesis of a cannabinoid, a cannabinoid derivative, a cannabinoid precursor, or a cannabinoid precursor derivative in an increased amount compared to a non-genetically modified host cell cultured under similar conditions.

The disclosure provides methods of producing a cannabinoid, a cannabinoid precursor, a cannabinoid precursor derivative, or a cannabinoid derivative, the method comprising: culturing a genetically modified host cell of the disclosure in a suitable medium comprising a carboxylic acid and recovering the produced cannabinoid, cannabinoid precursor, cannabinoid precursor derivative, or cannabinoid derivative. In certain such embodiments, the produced cannabinoid, cannabinoid precursor, cannabinoid precursor derivative, or cannabinoid derivative is then purified as disclosed herein.

In some embodiments, the cannabinoid, cannabinoid precursor, cannabinoid precursor derivative, or cannabinoid derivative is recovered from the cell lysate, from the culture medium, or from both the cell lysate and the culture medium. In certain such embodiments, the recovered cannabinoid, cannabinoid precursor, cannabinoid precursor derivative, or cannabinoid derivative is then purified as disclosed herein.

The disclosure provides methods of producing a cannabinoid or a cannabinoid derivative in a genetically modified host cell, the method comprising: culturing a genetically modified host cell of the disclosure in a suitable medium and recovering the produced cannabinoid or cannabinoid derivative. In certain such embodiments, the produced cannabinoid or cannabinoid derivative is then purified as disclosed herein.

In some embodiments, culturing of the genetically modified host cells of the disclosure in a suitable medium provides for synthesis of a cannabinoid or a cannabinoid derivative in an increased amount compared to a non-genetically modified host cell cultured under similar conditions.

The disclosure provides methods of producing a cannabinoid or a cannabinoid derivative, the method comprising: culturing a genetically modified host cell of the disclosure in a suitable medium comprising a carboxylic acid and recovering the produced cannabinoid or cannabinoid derivative. In certain such embodiments, the produced cannabinoid or cannabinoid derivative is then purified as disclosed herein.

In some embodiments, the cannabinoid or cannabinoid derivative is recovered from the cell lysate, from the culture medium, or from both the cell lysate and the culture medium. In certain such embodiments, the recovered cannabinoid or cannabinoid derivative is then purified as disclosed herein.

In some embodiments, the genetically modified host cell of the present disclosure is cultured in a suitable medium comprising a carboxylic acid to generate an acyl-CoA compound or an acyl-CoA compound derivative. In certain such embodiments, the genetically modified host cell is genetically modified with one or more heterologous nucleic acids encoding an AAE polypeptide, a FAA polypeptide, or a fatty acyl-CoA ligase polypeptide, as described herein. In some embodiments, the genetically modified host cells of the present disclosure may further convert an acyl-CoA compound or an acyl-CoA compound derivative to cannabinoids, cannabinoid precursors, cannabinoid precursor derivatives, or cannabinoid derivatives.

Carboxylic acids may include, but are not limited to, $C_3$-$C_{18}$ fatty acids, butyric acid, isobutyric acid, valeric acid, hexanoic acid, heptanoic acid, octanoic acid, nonanoic acid, decanoic acid, undecanoic acid, lauric acid, myristic acid, $C_{15}$-$C_{18}$ fatty acids, fumaric acid, itaconic acid, malic acid, succinic acid, maleic acid, malonic acid, glutaric acid, glucaric acid, oxalic acid, adipic acid, pimelic acid, suberic acid, azelaic acid, sebacic acid, dodecanedioic acid, glutaconic acid, ortho-phthalic acid, isophthalic acid, terephthalic acid, citric acid, isocitric acid, aconitic acid, tricarballylic acid, and trimesic acid. Carboxylic acids may include $C_4$-$C_{10}$ carboxylic acids. In some embodiments, the carboxylic acid is a $C_4$ carboxylic acid. In some embodiments, the carboxylic acid is a $C_5$ carboxylic acid. In some embodiments, the carboxylic acid is a $C_6$ carboxylic acid. In some embodiments, the carboxylic acid is a $C_7$ carboxylic acid. In some embodiments, the carboxylic acid is a $C_8$ carboxylic acid. In some embodiments, the carboxylic acid is a $C_9$ carboxylic acid. In some embodiments, the carboxylic acid is a $C_{10}$ carboxylic acid. In some embodiments, the carboxylic acid is butyric acid. In some embodiments, the carboxylic acid is valeric acid. In some embodiments, the carboxylic acid is hexanoic acid. In some embodiments, the carboxylic acid is heptanoic acid. In some embodiments, the carboxylic acid is octanoic acid. In some embodiments, the carboxylic acid is nonanoic acid. In some embodiments, the carboxylic acid is decanoic acid. See, e.g., FIG. 12.

In some embodiments, the carboxylic acid comprises one or more functional and/or reactive groups to generate derivatives of hexanoyl-CoA or derivatives of acyl-CoA compounds. Functional groups may include, but are not limited to, azido, halo (e.g., chloride, bromide, iodide, fluorine), methyl, alkyl, alkynyl, alkenyl, methoxy, alkoxy, acetyl, amino, carboxyl, carbonyl, oxo, ester, hydroxyl, thio, cyano, aryl, heteroaryl, cycloalkyl, cycloalkenyl, cycloalkylalkenyl, cycloalkylalkynyl, cycloalkenylalkyl, cycloalkenylalkenyl, cycloalkenylalkynyl, heterocyclylalkenyl, heterocyclylalkynyl, heteroarylalkenyl, heteroarylalkynyl, arylalkenyl, arylalkynyl, spirocyclyl, heterospirocyclyl, heterocyclyl, thioalkyl, sulfone, sulfonyl, sulfoxide, amido, alkylamino, dialkylamino, arylamino, alkylarylamino, diarylamino, N-oxide, imide, enamine, imine, oxime, hydrazone, nitrile, aralkyl, cycloalkylalkyl, haloalkyl, heterocyclylalkyl, heteroarylalkyl, nitro, thioxo, and the like. See, e.g., FIGS. 12 and 13. Reactive groups may include, but are not necessarily limited to, azide, halogen, carboxyl, carbonyl, amine, (e.g., alkyl amine (e.g., lower alkyl amine), aryl amine), ester (e.g., alkyl ester (e.g., lower alkyl ester, benzyl ester), aryl ester, substituted aryl ester), cyano, thioester, thioether, sulfonyl halide, alcohol, thiol, succinimidyl ester, isothiocyanate, iodoacetamide, maleimide, hydrazine, alkynyl, alkenyl, and the like. In some embodiments, the reactive group is selected from a carboxyl, a carbonyl, an amine, an ester, thioester, thioether, a sulfonyl halide, an alcohol, a thiol, a succinimidyl ester, an isothiocyanate, an iodoacetamide, a maleimide, an azide, an alkyne, an alkene, and a hydrazine. Functional and reactive groups may be optionally substituted with one or more additional functional or reactive groups.

In some embodiments, the carboxylic acid is isotopically- or radio-labeled. In some embodiments, the carboxylic acid may be an enantiomer or diastereomer. In some embodiments the carboxylic acid may be the (S)-enantiomer. In some embodiments the carboxylic acid may be the (R)-enantiomer. In some embodiments, the carboxylic acid may be the (+) or (−) enantiomer. In some embodiments, the carboxylic acid may include a double bond or a fused ring. In certain such embodiments, the double bond or fused ring may be cis or trans, unless the configuration is specifically defined. If the carboxylic acid contains a double bond, the substituent may be in the E or Z configuration, unless the configuration is specifically defined.

In some embodiments, the carboxylic acid comprises a C=C group. In some embodiments, the carboxylic acid comprises an alkyne group. In some embodiments, the carboxylic acid comprises an $N_3$ group. In some embodiments, the carboxylic acid comprises a halogen. In some embodiments, the carboxylic acid comprises a CN group. In some embodiments, the carboxylic acid comprises an iodide. In some embodiments, the carboxylic acid comprises a bromide. In some embodiments, the carboxylic acid comprises chloride. In some embodiments, the carboxylic acid comprises fluoride. In some embodiments, the carboxylic acid comprises a carbonyl. In some embodiments, the carboxylic acid comprises an acetyl. In some embodiments, the carboxylic acid comprises an alkyl group.

Carboxylic acids may include, but are not limited to, 2-methylhexanoic acid, 3-methylhexanoic acid, 4-methylhexanoic acid, 5-methylhexanoic acid, 2-hexenoic acid, 3-hexenoic acid, 4-hexenoic acid, 5-hexenoic acid, 5-chlorovaleric acid, 5-aminovaleric acid, 5-cyanovaleric acid, 5-(methylsulfanyl)valeric acid, 5-hydroxyvaleric acid, 5-phenylvaleric acid, 2,3-dimethylhexanoic acid, $d_3$-hexanoic acid, 5-chloropentanoic acid, 5-(methylsulfanyl)pentanoic acid, 4-pentynoic acid, trans-2-pentenoic acid, 5-hexynoic acid, trans-2-hexenoic acid, 6-heptynoic acid, trans-2-octenoic acid, trans-2-nonenoic acid, 4-phenylbutyric acid, 6-phenylhexanoic acid, 7-phenylheptanoic acid, and the like. In some embodiments, the carboxylic acid is 2-methylhexanoic acid. In some embodiments, the carboxylic acid is 3-methylhexanoic acid. In some embodiments, the carboxylic acid is 4-methylhexanoic acid. In some embodiments, the carboxylic acid is 5-methylhexanoic acid. In some embodiments, the carboxylic acid is 2-hexenoic acid. In some embodiments, the carboxylic acid is 3-hexenoic acid. In some embodiments, the carboxylic acid is 4-hexenoic acid. In some embodiments, the carboxylic acid is 5-hexenoic acid. In some embodiments, the carboxylic acid is 5-chlorovaleric acid. In some embodiments, the carboxylic acid is 5-aminovaleric acid. In some embodiments, the carboxylic acid is 5-cyanovaleric acid. In some embodiments, the carboxylic acid is 5-(methylsulfanyl)valeric acid. In some embodiments, the carboxylic acid is 5-hydroxyvaleric acid. In some embodiments, the carboxylic acid is 5-phenylvaleric acid. In some embodiments, the carboxylic acid is 2,3-dimethylhexanoic acid. In some embodiments, the carboxylic acid is $d_3$-hexanoic acid. In some embodiments, the carboxylic acid is 5-chloropentanoic acid. In some embodiments, the carboxylic acid is 5-(methylsulfanyl)pentanoic acid. In some embodiments, the carboxylic acid is 4-pentynoic acid. In some embodiments, the carboxylic acid is trans-2-pentenoic acid. In some embodiments, the carboxylic acid is 5-hexynoic acid. In some embodiments, the carboxylic acid is trans-2-hexenoic acid. In some embodiments, the carboxylic acid is 6-heptynoic acid. In some embodiments, the carboxylic acid is trans-2-octenoic acid. In some embodiments, the carboxylic acid is trans-2-nonenoic acid. In some embodiments, the carboxylic acid is 4-phenylbutyric acid. In some embodiments, the carboxylic acid is 6-phenylhexanoic acid. In some embodiments, the carboxylic acid is 7-phenylheptanoic acid.

The disclosure also provides methods of producing the following cannabinoid precursor or precursor derivatives: olivetolic acid or olivetolic acid derivatives. In certain such embodiments, the method comprises: culturing a genetically modified host cell of the disclosure in a suitable medium comprising a carboxylic acid, and recovering the produced olivetolic acid or olivetolic acid derivative. In certain such embodiments, the genetically modified host cell of the disclosure is genetically modified with: a) one or more heterologous nucleic acids encoding a polypeptide that generates an acyl-CoA compound or an acyl-CoA compound derivative, such as an AAE polypeptide, a FAA polypeptide, or a fatty acyl-CoA ligase polypeptide; b) one or more heterologous nucleic acids encoding a TKS polypeptide; and c) one or more heterologous nucleic acids encoding an OAC polypeptide. In some embodiments, the genetically modified host cell is genetically modified with: a) one or more heterologous nucleic acids encoding a polypeptide that generates an acyl-CoA compound or an acyl-CoA compound derivative, such as an AAE polypeptide, a FAA polypeptide, or a fatty acyl-CoA ligase polypeptide; and b) one or more heterologous nucleic acids encoding a TKS/OAC fusion polypeptide.

In some embodiments, the olivetolic acid derivative produced by the methods or genetically modified host cells of the disclosure has the following formula:

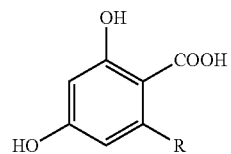

where R is alkyl (e.g., $C_1$-$C_{10}$ alkyl), substituted alkyl, alkyl ester, or alkyl-X, where X is a reactive or functional group, as disclosed herein. In some embodiments, the olivetolic acid or olivetolic acid derivative is recovered from the cell lysate, from the culture medium, or from both the cell lysate and the culture medium. In certain such embodiments, the recovered olivetolic acid or olivetolic acid derivative is then purified as disclosed herein. In some embodiments, the olivetolic acid or olivetolic acid derivative is further converted by the genetically modified host cell to a cannabinoid derivative or a cannabinoid.

The disclosure also provides methods of producing a cannabinoid or a cannabinoid derivative, the method comprising: culturing a genetically modified host cell of the disclosure in a suitable medium comprising olivetolic acid or an olivetolic acid derivative and recovering the produced cannabinoid or cannabinoid derivative. In certain such embodiments, the produced cannabinoid or cannabinoid derivative is then purified as disclosed herein. The disclosure also provides methods of producing a cannabinoid derivative, the method comprising: culturing a genetically modified host cell of the disclosure in a suitable medium comprising olivetolic acid or an olivetolic acid derivative and recovering the produced cannabinoid derivative. In certain such embodiments, the produced cannabinoid derivative is then purified as disclosed herein.

In some embodiments, the genetically modified host cell is genetically modified with: a) one or more heterologous nucleic acids that encode a GOT polypeptide and b) one or more heterologous nucleic acids that encode a polypeptide that generates GPP (e.g., a GPPS polypeptide). In some embodiments, the olivetolic acid or olivetolic acid derivative is further converted to a cannabinoid derivative or a cannabinoid.

Olivetolic acid derivatives used herein may comprise one or more reactive and/or functional groups as disclosed herein. In some embodiments when the suitable medium comprises an olivetolic acid derivative, the olivetolic acid derivative is orsellinic acid. In some embodiments when the suitable medium comprises an olivetolic acid derivative, the olivetolic acid derivative is divarinic acid.

In some embodiments, a method of producing a cannabinoid, a cannabinoid derivative, a cannabinoid precursor, or a cannabinoid precursor derivative may involve growing a transgenic (genetically modified) plant of the present disclosure under conditions that favor production of the cannabinoid, cannabinoid derivative, cannabinoid precursor, or cannabinoid precursor derivative. The cannabinoid, cannabinoid derivative, cannabinoid precursor, or cannabinoid precursor derivative can be purified from the plant, or a part of the plant. The present disclosure provides food products made from a transgenic (genetically modified) plant of the present disclosure.

Exemplary Cell Culture Conditions

Suitable media may include standard culture media (e.g., Luria-Bertani broth, optionally supplemented with one or more additional agents, such as an inducer (e.g., where heterologous nucleic acids disclosed herein is under the control of an inducible promoter, etc.); standard yeast culture media; and the like). In some embodiments, the culture medium can be supplemented with a fermentable sugar (e.g., a hexose sugar, e.g., glucose, xylose, and the like). In some embodiments, the culture medium can be supplemented with hexanoate, carboxylic acids other than hexanoate, olivetolic acid, or olivetolic acid derivatives. In some embodiments, the culture medium can be supplemented with pretreated cellulosic feedstock (e.g., wheat grass, wheat straw, barley straw, sorghum, rice grass, sugarcane straw, bagasse, switchgrass, corn stover, corn fiber, grains, or any combination thereof). In some embodiments, the culture medium can be supplemented with oleic acid. In some embodiments, the suitable medium comprises a non-fermentable carbon source. In certain such embodiments, the non-fermentable carbon source comprises ethanol. In some embodiments, the suitable media comprises an inducer. In certain such embodiments, the inducer comprises galactose.

The carbon source in the suitable media can vary significantly, from simple sugars like glucose to more complex hydrolysates of other biomass, such as yeast extract. The addition of salts generally provide essential elements such as magnesium, nitrogen, phosphorus, and sulfur to allow the cells to synthesize polypeptides and nucleic acids. The suitable media can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. The suitable media can be supplemented with other compounds as necessary to select for desired physiological or biochemical characteristics, such as particular amino acids and the like.

In some embodiments, genetically modified host cells disclosed herein are grown in minimal medium. As used herein, the terms "minimal medium" or "minimal media" may refer to growth medium containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for cellular (e.g. bacterial or yeast) growth; (2) various salts, which can vary among cellular (e.g. bacterial or yeast) species and growing conditions; and (3) water.

In some embodiments, genetically modified host cells disclosed herein are grown in rich medium or rich media. In certain such embodiments, the rich medium or rich media comprises yeast extract peptone dextrose (YPD) media comprising water, 10 g/L yeast extract, 20 g/L Bacto peptone, and 20 g/L dextrose (glucose). In some embodiments, the rich medium or rich media comprises YP+20 g/L galactose and 1 g/L glucose. In some embodiments, the rich medium or rich media further comprises a carboxylic acid (e.g., 1 mM olivetolic acid, 1 mM olivetolic acid derivative, 2 mM hexanoic acid, or 2 mM of a carboxylic acid other than hexanoic acid). In some embodiments, rich medium or rich media affords more rapid cell growth compared to minimal media or minimal medium.

Materials and methods suitable for the maintenance and growth of the recombinant cells of the disclosure are described herein, e.g., in the Examples section. Other materials and methods suitable for the maintenance and growth of cell (e.g. bacterial or yeast) cultures are well known in the art. Exemplary techniques can be found in International Publication No. WO2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716, Manual of Methods for General Bacteriology Gerhardt et al, eds), American Society for Microbiology, Washington, D.C. (1994) or Brock in Biotechnology: A Textbook of Industrial Microbiology, Second Edition (1989) Sinauer Associates, Inc., Sunderland, MA.

Standard cell culture conditions can be used to culture the genetically modified host cells disclosed herein (see, for example, WO 2004/033646 and references cited therein). In some embodiments, cells are grown and maintained at an appropriate temperature, gas mixture, and pH (such as at about 20° C. to about 37° C., at about 0.04% to about 84% $CO_2$, at about 0% to about 100% dissolved oxygen, and at a pH between about 2 to about 9). In some embodiments, genetically modified host cells disclosed herein are grown at about 34° C. in a suitable cell culture medium. In some embodiments, genetically modified host cells disclosed herein are grown at about 20° C. to about 37° C. in a suitable cell culture medium. In some embodiments, genetically modified host cells disclosed herein are grown at about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., or about 37° C. in a suitable cell culture medium. In some embodiments, the pH ranges for fermentation are between about pH 3.0 to about pH 9.0 (such as about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 6.0 to about pH 8.0 or about 6.5 to about 7.0). In some embodiments, the pH ranges for fermentation are between about pH 4.5 to about pH 5.5. In some embodiments, the pH ranges for fermentation are between about pH 4.0 to about pH 6.0. In some embodiments, the pH ranges for fermentation are between about pH 3.0 to about pH 6.0. In some embodiments, the pH ranges for fermentation are between about pH 3.0 to about pH 5.5. In some embodiments, the pH ranges for fermentation are between about pH 3.0 to about pH 5.0. In some embodiments, the dissolved oxygen is between about 0% to about 10%, about 0% to about 20%, about 0% to about 30%, about 0% to about 40%, about 0% to about 50%, about 0% to about 60%, about 0% to about 70%, about 0% to about 80%, about 0% to about 90%, about 5% to about 10%, about 5% to about 20%, about 5% to about 30%, about 5% to about 40%, about 5% to about 50%, about 5% to about 60%, about 5% to about 70%, about 5% to about 80%, about 5% to about 90%, about 10% to about 20%, about 10% to about 30%, about 10% to about 40% or about 10% to about 50%. In some embodiments, the $CO_2$ level is between about 0.04% to about 0.1% $CO_2$, about 0.04% to about 1% $CO_2$, about 0.04% to about 5% $CO_2$, about 0.04% to about 10% $CO_2$, about 0.04% to about 20% $CO_2$, about 0.04% to about 30% $CO_2$, about 0.04% to about 40% $CO_2$, about 0.04% to about 50% $CO_2$, about 0.04% to about 60% $CO_2$, about 0.04% to about 70% $CO_2$, about 0.1% to about 5% $CO_2$, about 0.1% to about 10% $CO_2$, about 0.1% to about 20% $CO_2$, about 0.1% to about 30% $CO_2$, about 0.1% to about 40% $CO_2$, about 0.1% to about 50% $CO_2$, about 1% to about 5% $CO_2$, about 1% to about 10% $CO_2$, about 1% to about 20% $CO_2$, about 1% to about 30% $CO_2$, about 1% to about 40% $CO_2$, about 1% to about 50% $CO_2$, about 5% to about 10% $CO_2$, about 10% to about 20% $CO_2$, about 10% to about 30% $CO_2$, about 10% to about 40% $CO_2$, about 10% to about 50% $CO_2$, about 10% to about 60% $CO_2$, about 10% to about 70% $CO_2$, about 10% to about 80% $CO_2$, about 50% to about 60% $CO_2$, about 50% to about 70% $CO_2$, or about 50% to about 80% $CO_2$, genetically modified host cells disclosed herein disclosed herein can be grown under aerobic, anoxic, microaerobic, or anaerobic conditions based on the requirements of the cells.

Standard culture conditions and modes of fermentation, such as batch, fed-batch, or continuous fermentation that can be used are described in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716, the contents of each of which are incorporated by reference herein in their entireties. Batch and Fed-Batch fermentations are common and well known in the art and examples can be found in Brock, Biotechnology: A Textbook of Industrial Microbiology, Second Edition (1989) Sinauer Associates, Inc.

Production and Recovery of Produced Cannabinoids, Cannabinoid Precursors, Cannabinoid Derivatives or Cannabinoid Precursor Derivatives In some embodiments, a method of the present disclosure provides for production of a cannabinoid, a cannabinoid derivative, a cannabinoid precursor, or a cannabinoid precursor derivative by genetically modified host cells of the disclosure in a recoverable amount of from about 1 mg/L culture medium to about 1 g/L culture medium. In some embodiments, a method of the present disclosure provides for production of a cannabinoid, a cannabinoid derivative, a cannabinoid precursor, or a cannabinoid precursor derivative in a recoverable amount of from about 1 mg/L culture medium to about 500 mg/L culture medium. In some embodiments, a method of the present disclosure provides for production of a cannabinoid, a cannabinoid derivative, a cannabinoid precursor, or a cannabinoid precursor derivative in a recoverable amount of from about 1 mg/L culture medium to about 100 mg/L culture medium. For example, in some embodiments, a method of the present disclosure provides for production of a cannabinoid, a cannabinoid derivative, a cannabinoid precursor, or a cannabinoid precursor derivative in a recoverable amount of from about 1 mg/L culture medium to about 5 mg/L culture medium, from about 5 mg/L culture medium to about 10 mg/L culture medium, from about 10 mg/L culture medium to about 25 mg/L culture medium, from about 25 mg/L culture medium to about 50 mg/L culture medium, from about 50 mg/L culture medium to about 75 mg/L culture medium, or from about 75 mg/L culture medium to about 100 mg/L culture medium. In some embodiments, a method of the present disclosure provides for production of a cannabinoid, a cannabinoid derivative, a cannabinoid precursor, or a cannabinoid precursor derivative in a recoverable amount of from about 100 mg/L culture medium to about 150 mg/L culture medium, from about 150 mg/L culture medium to about 200 mg/L culture medium, from about 200 mg/L culture medium to about 250 mg/L culture medium, from about 250 mg/L culture medium to about 500 mg/L culture medium, from about 500 mg/L culture medium to about 750 mg/L culture medium, or from about 750 mg/L culture medium to about 1 g/L culture medium. In some embodiments, a method of the present disclosure provides for production of a cannabinoid, a cannabinoid derivative, a cannabinoid precursor, or a cannabinoid precursor derivative in a recoverable amount of from about from about 50 mg/L culture medium to about 100 mg/L culture medium, 50 mg/L culture medium to about 150 mg/L culture medium, from about 50 mg/L culture medium to about 200 mg/L culture medium, from about 50 mg/L culture medium to about 250 mg/L culture medium, from about 50 mg/L culture medium to about 500 mg/L culture medium, or from about 50 mg/L culture medium to about 750 mg/L culture medium.

In some embodiments, a method of the present disclosure provides for production of a cannabinoid, a cannabinoid derivative, a cannabinoid precursor, or a cannabinoid precursor derivative in a recoverable amount of from about 100 mg/L culture medium to about 500 mg/L culture medium, or more than 500 mg/L culture medium. In some embodiments, a method of the present disclosure provides for production of a cannabinoid, a cannabinoid derivative, a cannabinoid precursor, or a cannabinoid precursor derivative in a recoverable amount of from about 500 mg/L culture medium to about 1 g/L culture medium, or more than 1 g/L culture medium. In some embodiments, a method of the present disclosure provides for production of a cannabinoid, a cannabinoid derivative, a cannabinoid precursor, or a cannabinoid precursor derivative in a recoverable amount of from about 1 g/L culture medium to about 10 g/L culture medium, or more than 10 g/L culture medium. In some embodiments, a method of the present disclosure provides for production of a cannabinoid, a cannabinoid derivative, a cannabinoid precursor, or a cannabinoid precursor derivative in a recoverable amount of from about 10 g/L culture medium to about 100 g/L culture medium, or more than 100 g/L culture medium. In some embodiments, a method of the present disclosure provides for production of a cannabinoid, a cannabinoid derivative, a cannabinoid precursor, or a cannabinoid precursor derivative in a recoverable amount of from about 1 g/L culture medium to about 20 g/L culture medium, or more than 20 g/L culture medium. In some embodiments, a method of the present disclosure provides for production of a cannabinoid, a cannabinoid derivative, a cannabinoid precursor, or a cannabinoid precursor derivative in a recoverable amount of from about 1 g/L culture medium to about 30 g/L culture medium, or more than 30 g/L culture medium. In some embodiments, a method of the present disclosure provides for production of a cannabinoid, a cannabinoid derivative, a cannabinoid precursor, or a cannabinoid precursor derivative in a recoverable amount of from about 1 g/L culture medium to about 40 g/L culture medium, or more than 40 g/L culture medium. In some embodiments, a method of the present disclosure provides for production of a cannabinoid, a cannabinoid derivative, a cannabinoid precursor, or a cannabinoid precursor derivative in a recoverable amount of from about 1 g/L culture medium to about 50 g/L culture medium, or more than 50 g/L culture medium. In some embodiments, a method of the present disclosure provides for production of a cannabinoid, a cannabinoid derivative, a cannabinoid precursor, or a cannabinoid precursor derivative in a recoverable amount of from about 1 g/L culture medium to about 60 g/L culture medium, or more than 60 g/L culture medium. In some embodiments, a method of the present disclosure provides for production of a cannabinoid, a cannabinoid derivative, a cannabinoid precursor, or a cannabinoid precursor derivative in a recoverable amount of from about 1 g/L culture medium to about 70 g/L culture medium, or more than 70 g/L culture medium. In some embodiments, a method of the present disclosure provides for production of a cannabinoid, a cannabinoid derivative, a cannabinoid precursor, or a cannabinoid precursor derivative in a recoverable amount of from about 1 g/L culture medium to about 80 g/L culture medium, or more than 80 g/L culture medium. In some embodiments, a method of the present disclosure provides for production of a cannabinoid, a cannabinoid derivative, a cannabinoid precursor, or a cannabinoid precursor derivative in a recoverable amount of from about 1 g/L culture medium to about 90 g/L culture medium, or more than 90 g/L culture medium. In some embodiments, a method of the present disclosure provides for production of a cannabinoid, a cannabinoid derivative, a cannabinoid precursor, or a cannabinoid precursor derivative in a recoverable amount of from about 10 g/L culture medium to about 20 g/L culture medium, or more than 20 g/L culture medium. In some embodiments, a method of the present disclosure provides for production of a cannabinoid, a cannabinoid derivative, a cannabinoid precursor, or a cannabinoid precursor derivative in a recoverable amount of from about 10 g/L culture medium to about 30 g/L culture medium, or more than 30 g/L culture medium. In some embodiments, a method of the present disclosure provides for production of a cannabinoid, a cannabinoid derivative, a cannabinoid precursor, or a cannabinoid precursor derivative in a recoverable amount of from about 10 g/L culture medium to about 40 g/L culture medium, or more than 40 g/L culture medium. In some embodiments, a method of the present disclosure provides for production of a cannabinoid, a cannabinoid derivative, a cannabinoid precursor, or a cannabinoid precursor derivative in a recoverable amount of from about 10 g/L culture medium to about 50 g/L culture medium, or more than 50 g/L culture medium. In some embodiments, a method of the present disclosure provides for production of a cannabinoid, a cannabinoid derivative, a cannabinoid precursor, or a cannabinoid precursor derivative in a recoverable amount of from about 10 g/L culture medium to about 60 g/L culture medium, or more than 60 g/L culture medium. In some embodiments, a method of the present disclosure provides for production of a cannabinoid, a cannabinoid derivative, a cannabinoid precursor, or a cannabinoid precursor derivative in a recoverable amount of from about 10 g/L culture medium to about 70 g/L culture medium, or more than 70 g/L culture medium. In some embodiments, a method of the present disclosure provides for production of a cannabinoid, a cannabinoid derivative, a cannabinoid precursor, or a cannabinoid precursor derivative in a recoverable amount of from about 10 g/L culture medium to about 80 g/L culture medium, or more than 80 g/L culture medium. In some embodiments, a method of the present disclosure provides for production of a cannabinoid, a cannabinoid derivative, a cannabinoid precursor, or a cannabinoid precursor derivative in a recoverable amount of from about 10 g/L culture medium to about 90 g/L culture medium, or more than 90 g/L culture medium. In some embodiments, a method of the present disclosure provides for production of a cannabinoid, a cannabinoid derivative, a cannabinoid precursor, or a cannabinoid precursor derivative in a recoverable amount of from about 50 g/L culture medium to about 100 g/L culture medium, or more than 100 g/L culture medium. In some embodiments, a method of the present disclosure provides for production of a cannabinoid, a cannabinoid derivative, a cannabinoid precursor, or a cannabinoid precursor derivative in a recoverable amount of from about 50 g/L culture medium to about 60 g/L culture medium, or more than 60 g/L culture medium. In some embodiments, a method of the present disclosure provides for production of a cannabinoid, a cannabinoid derivative, a cannabinoid precursor, or a cannabinoid precursor derivative in a recoverable amount of from about 50 g/L culture medium to about 70 g/L culture medium, or more than 70 g/L culture medium. In some embodiments, a method of the present disclosure provides for production of a cannabinoid, a cannabinoid derivative, a cannabinoid precursor, or a cannabinoid precursor derivative in a recoverable amount of from about 50 g/L culture medium to about 80 g/L culture medium, or more than 80 g/L culture medium. In some embodiments, a method of the present disclosure provides for production of a cannabinoid, a cannabinoid derivative, a cannabinoid precursor, or a cannabinoid precursor derivative in a recoverable amount of from about 50 g/L culture medium to about 90 g/L culture medium, or more than 90 g/L culture medium. In some embodiments, a method of the present disclosure provides for production of a cannabinoid, a cannabinoid derivative, a cannabinoid precursor, or a cannabinoid precursor derivative in a recoverable amount of from about 20 g/L culture medium to about 100 g/L culture medium, or more than 100 g/L culture medium. In some embodiments, a method of the present disclosure provides for production of a cannabinoid, a cannabinoid derivative, a cannabinoid precursor, or a cannabinoid precursor derivative in a recoverable amount of from about 20 g/L culture medium to about 30 g/L culture medium, or more than 30 g/L culture medium. In some embodiments, a method of the present disclosure provides for production of a cannabinoid, a cannabinoid derivative, a cannabinoid precursor, or a cannabinoid precursor derivative in a recoverable amount of from about 20 g/L culture medium to about 40 g/L culture medium, or more than 40 g/L culture medium. In some embodiments, a method of the present disclosure provides for production of a cannabinoid, a cannabinoid derivative, a cannabinoid precursor, or a cannabinoid precursor derivative in a recoverable amount of from about 20 g/L culture medium to about 50 g/L culture medium, or more than 50 g/L culture medium. In some embodiments, a method of the present disclosure provides for production of a cannabinoid, a cannabinoid derivative, a cannabinoid precursor, or a cannabinoid precursor derivative in a recoverable amount of from about 20 g/L culture medium to about 60 g/L culture medium, or more than 60 g/L culture medium. In some embodiments, a method of the present disclosure provides for production of a cannabinoid, a cannabinoid derivative, a cannabinoid precursor, or a cannabinoid precursor derivative in a recoverable amount of from about 20 g/L culture medium to about 70 g/L culture medium, or more than 70 g/L culture medium. In some embodiments, a method of the present disclosure provides for production of a cannabinoid, a cannabinoid derivative, a cannabinoid precursor, or a cannabinoid precursor derivative in a recoverable amount of from about 20 g/L culture medium to about 80 g/L culture medium, or more than 80 g/L culture medium. In some embodiments, a method of the present disclosure provides for production of a cannabinoid, a cannabinoid derivative, a cannabinoid precursor, or a cannabinoid precursor derivative in a recoverable amount of from about 20 g/L culture medium to about 90 g/L culture medium, or more than 90 g/L culture medium.

In some embodiments, the genetically modified host cell disclosed herein is cultured in a liquid medium comprising a precursor acid to generate acyl-CoA compounds or acyl-CoA compound derivatives. Suitable precursor acids may include, but are not limited to, carboxylic acids.

In some embodiments, a method of producing a cannabinoid, a cannabinoid derivative, cannabinoid precursor, cannabinoid precursor derivative, or cannabinoid precursor derivative may involve culturing a genetically modified yeast cell of the present disclosure under conditions that favor production of the cannabinoid, cannabinoid derivative, cannabinoid precursor, or cannabinoid precursor derivative; where the cannabinoid, cannabinoid derivative, cannabinoid precursor, or cannabinoid precursor derivative is produced by the genetically modified yeast cell and is present in the culture medium (e.g., a liquid culture medium) in which the genetically modified yeast cell is cultured. In some embodiments, the culture medium in which the genetically modified yeast cell is cultured comprises a cannabinoid, a cannabinoid derivative, a cannabinoid precursor, or a cannabinoid precursor derivative in an amount of from 1 ng/L to 1 g/L (e.g., from 1 ng/L to 50 ng/L, from 50 ng/L to 100 ng/L, from 100 ng/L to 500 ng/L, from 500 ng/L to 1 µg/L, from 1 µg/L to 50 µg/L, from 50 µg/L to 100 µg/L, from 100 µg/L to 500 µg/L, from 500 µg/L to 1 mg/L, from 1 mg/L to 50 mg/L, from 50 mg/L to 100 mg/L, from 100 mg/L to 500 mg/L, or from 500 mg/L to 1 g/L). In some embodiments, the culture medium in which the genetically modified yeast cell is cultured comprises a cannabinoid, a cannabinoid derivative, a cannabinoid precursor, or a cannabinoid precursor derivative in an amount more than 1 g/L.

In some embodiments, a method of producing a cannabinoid, a cannabinoid derivative, a cannabinoid precursor, or a cannabinoid precursor derivative may involve culturing a genetically modified yeast cell of the present disclosure under conditions that favor fermentation of a sugar, and under conditions that favor production of the cannabinoid, cannabinoid derivative, cannabinoid precursor, or cannabinoid precursor derivative; wherein the cannabinoid, cannabinoid derivative, cannabinoid precursor, or cannabinoid precursor derivative is produced by the genetically modified yeast cell and is present in alcohol produced by the genetically modified yeast cell. The present disclosure provides an alcoholic beverage produced by the genetically modified yeast cell, where the alcoholic beverage comprises the cannabinoid, cannabinoid derivative, cannabinoid precursor, or cannabinoid precursor derivative produced by the genetically modified yeast cell. Alcoholic beverages may include beer, wine, and distilled alcoholic beverages. In some embodiments, an alcoholic beverage of the present disclosure comprises a cannabinoid, cannabinoid derivative, cannabinoid precursor, or cannabinoid precursor derivative in an amount of from 1 ng/L to 1 g/L (e.g., from 1 ng/L to 50 ng/L, from 50 ng/L to 100 ng/L, from 100 ng/L to 500 ng/L, from 500 ng/L to 1 µg/L, from 1 µg/L to 50 µg/L, from 50

µg/L to 100 µg/L, from 100 µg/L to 500 µg/L, from 500 µg/L to 1 mg/L, from 1 mg/L to 50 mg/L, from 50 mg/L to 100 mg/L, from 100 mg/L to 500 mg/L, or from 500 mg/L to 1 g/L). In some embodiments, an alcoholic beverage of the present disclosure comprises a cannabinoid, cannabinoid derivative, cannabinoid precursor, or cannabinoid precursor derivative in an amount more than 1 g/L In some embodiments, a method of the present disclosure provides for increased production of a cannabinoid, a cannabinoid derivative, a cannabinoid precursor, or a cannabinoid precursor derivative. In certain such embodiments, culturing of the genetically modified host cell disclosed herein in a suitable medium provides for synthesis of the cannabinoid, the cannabinoid derivative, the cannabinoid precursor, or the cannabinoid precursor derivative in an increased amount compared to a non-genetically modified host cell cultured under similar conditions. The production of a cannabinoid, a cannabinoid derivative, a cannabinoid precursor, or a cannabinoid precursor derivative by the genetically modified host cells disclosed herein may be increased by about 5% to about 1,000,000 folds compared to a non-genetically modified host cell cultured under similar conditions. The production of a cannabinoid, a cannabinoid derivative, a cannabinoid precursor, or a cannabinoid precursor derivative by the genetically modified host cells disclosed herein may be increased by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of a cannabinoid, a cannabinoid derivative, a cannabinoid precursor, or a cannabinoid precursor derivative by non-genetically modified host cells cultured under similar conditions. The production of a cannabinoid, a cannabinoid derivative, a cannabinoid precursor, or a cannabinoid precursor derivative by genetically modified host cells disclosed herein may also be increased by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of a cannabinoid, a cannabinoid derivative, a cannabinoid precursor, or a cannabinoid precursor derivative by non-genetically modified host cells cultured under similar conditions.

In some embodiments, the production of a cannabinoid, a cannabinoid derivative, a cannabinoid precursor, or a cannabinoid precursor derivative by genetically modified host cells of the disclosure may also be increased by at least about any of 10%, 20%, 30%, 40%, 50%, 60%, 70%, 80%, or 90% compared to the production of a cannabinoid, a cannabinoid derivative, a cannabinoid precursor, or a cannabinoid precursor derivative by non-genetically modified host cells cultured under similar conditions. In some embodiments, the production of a cannabinoid, a cannabinoid derivative, a cannabinoid precursor, or a cannabinoid precursor derivative by genetically modified host cells disclosed herein may also be increased by at least about any of 1-20%, 2-20%, 5-20%, 10-20%, 15-20%, 1-15%, 1-10%, 2-15%, 2-10%, 5-15%, 10-15%, 1-50%, 10-50%, 20-50%, 30-50%, 40-50%, 50-100%, 50-60%, 50-70%, 50-80%, or 50-90% compared to the production of a cannabinoid, a cannabinoid derivative, a cannabinoid precursor, or a cannabinoid precursor derivative by non-genetically modified host cells cultured under similar conditions.

In some embodiments, production of a cannabinoid, a cannabinoid derivative, a cannabinoid precursor, or a cannabinoid precursor derivative by genetically modified host cells of the disclosure is determined by LC-MS analysis. In certain such embodiments, each cannabinoid, cannabinoid precursor, cannabinoid derivative, or cannabinoid precursor derivative is identified by retention time, determined from an authentic standard, and multiple reaction monitoring (MRM) transition.

In some embodiments, the genetically modified host cell of the disclosure is yeast cell. In certain such embodiments, the genetically modified host cell disclosed herein is cultured in a bioreactor. In some embodiments, the genetically modified host cell is cultured in a suitable medium supplemented with hexanoic acid, a carboxylic acid other than hexanoic acid, olivetolic acid, or an olivetolic acid derivative.

In some embodiments, the cannabinoid, cannabinoid derivative, cannabinoid precursor, or cannabinoid precursor derivative is recovered from a cell lysate, e.g., by lysing the genetically modified host cell disclosed herein and recovering the cannabinoid, cannabinoid derivative, cannabinoid precursor, or cannabinoid precursor derivative from the lysate. In other cases, the cannabinoid, cannabinoid derivative, cannabinoid precursor, or cannabinoid precursor derivative is recovered from the culture medium in which the genetically modified host cell disclosed herein is cultured. In other cases, the cannabinoid, cannabinoid derivative, cannabinoid precursor, or cannabinoid precursor derivative is recovered from both the cell lysate and the culture medium.

In some embodiments, the recovered cannabinoid, cannabinoid derivative, cannabinoid precursor, or cannabinoid precursor derivative is then purified. In some embodiments, whole-cell broth from cultures comprising genetically modified host cells of the disclosure may be extracted with a suitable organic solvent to afford cannabinoids, cannabinoid precursors, cannabinoid derivatives, or cannabinoid precursor derivatives. Suitable organic solvents include, but are not limited to, hexane, heptane, ethyl acetate, petroleum ether, and di-ethyl ether, chloroform, and ethyl acetate. In some embodiments, the suitable organic solvent comprises hexane. In some embodiments, the suitable organic solvent may be added to the whole-cell broth from fermentations comprising genetically modified host cells of the disclosure at a 10:1 ratio (10 parts whole-cell broth-1 part organic solvent) and stirred for 30 minutes. In certain such embodiments, the organic fraction may be separated and extracted twice with an equal volume of acidic water (pH 2.5). The organic layer may then be separated and dried in a concentrator (rotary evaporator or thin film evaporator under reduced pressure) to obtain crude cannabinoid, cannabinoid precursor, cannabinoid derivative, or cannabinoid precursor derivative crystals. In certain such embodiments, the crude crystals may be heated to 105° C. for 15 minutes followed by 145° C. for 55 minutes to decarboxylate a crude cannabinoid or cannabinoid derivative. In certain such embodiments, the crude crystalline product may be re-dissolved and recrystallized in a suitable solvent (e.g., n-pentane) and filtered to remove any insoluble material. In certain such embodiments, the solvent may then be removed e.g. by rotary evaporation, to produce pure crystalline product.

In some embodiments, the cannabinoid, cannabinoid derivative, cannabinoid precursor, or cannabinoid precursor derivative is pure, e.g., at least about 40% pure, at least about 50% pure, at least about 60% pure, at least about 70% pure, at least about 80% pure, at least about 90% pure, at least about 95% pure, at least about 98%, or more than 98% pure, where "pure" in the context of a cannabinoid, cannabinoid derivative, cannabinoid precursor, or cannabinoid precursor derivative may refer to a cannabinoid, cannabinoid derivative, cannabinoid precursor, or cannabinoid precursor derivative that is free from other cannabinoids, cannabinoid derivatives, cannabinoid precursors, cannabinoid precursor derivatives macromolecules, contaminants, etc.

Cell-Free Methods of Generating Cannabinoids, Cannabinoid Precursors, Olivetolic Acid Derivatives, Olivetolic Acid, Cannabinoid Derivatives, or Cannabinoid Precursor Derivatives The methods of the disclosure may involve cell-free production of cannabinoids, cannabinoid precursors, cannabinoid precursor derivatives, or cannabinoid derivatives using one or more polypeptides disclosed herein expressed or overexpressed by a genetically modified host cell of the disclosure. In some embodiments, one or more polypeptides disclosed herein expressed or overexpressed by a genetically modified host cell of the disclosure are used in a cell-free system for the production of cannabinoids, cannabinoid precursors, cannabinoid precursor derivatives, or cannabinoid derivatives. In certain such embodiments, appropriate starting materials for use in producing cannabinoids, cannabinoid precursors, cannabinoid precursor derivatives, or cannabinoid derivatives may be mixed together with one or more polypeptides disclosed herein expressed or overexpressed by a genetically modified host cell of the disclosure in a suitable reaction vessel to effect the reaction. The one or more polypeptides disclosed herein expressed or overexpressed by a genetically modified host cell of the disclosure may be used in combination to effect a complete synthesis of a cannabinoid, cannabinoid precursor, cannabinoid precursor derivative, or cannabinoid derivative from the appropriate starting materials. In some embodiments, the cannabinoid, cannabinoid precursor, the cannabinoid precursor derivative, or cannabinoid derivative is recovered from a cell-free reaction mixture comprising one or more of the polypeptides disclosed herein.

In some embodiments, the recovered cannabinoids, cannabinoid precursors, cannabinoid precursor derivatives, or cannabinoid derivatives are then purified. In certain such embodiments, a cell-free reaction mixture comprising one or more of the polypeptides disclosed herein may be extracted with a suitable organic solvent to afford cannabinoids, cannabinoid precursors, cannabinoid derivatives, or cannabinoid precursor derivatives. Suitable organic solvents include, but are not limited to, hexane, heptane, ethyl acetate, petroleum ether, and di-ethyl ether, chloroform, and ethyl acetate. In some embodiments, the suitable organic solvent comprises hexane. In some embodiments, the suitable organic solvent may be added to the cell-free reaction mixture comprising one or more of the polypeptides disclosed herein at a 10:1 ratio (10 parts reaction mixture-1 part organic solvent) and stirred for 30 minutes. In certain such embodiments, the organic fraction may be separated and extracted twice with an equal volume of acidic water (pH 2.5). The organic layer may then be separated and dried in a concentrator (rotary evaporator or thin film evaporator under reduced pressure) to obtain crude cannabinoid, cannabinoid precursor, cannabinoid derivative, or cannabinoid precursor derivative crystals. In certain such embodiments, the crude crystals may be heated to 105° C. for 15 minutes followed by 145° C. for 55 minutes to decarboxylate a crude cannabinoid or cannabinoid derivative. In certain such embodiments, the crude crystalline product may be re-dissolved and recrystallized in a suitable solvent (e.g., n-pentane) and filtered to remove any insoluble material. In certain such embodiments, the solvent may then be removed e.g. by rotary evaporation, to produce pure crystalline product.

In some embodiments, a prenyl group acceptor molecule, a prenyl group donor molecule and a GOT polypeptide may be mixed together in a suitable reaction vessel to effect the reaction. In certain such embodiments, the GOT polypeptide can catalyze production of cannabigerolic acid from GPP and olivetolic acid in an amount at least ten times higher than a polypeptide comprising an amino acid sequence set forth in SEQ ID NO:82. In some embodiments, the GOT polypeptide comprises an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110. In some embodiments, the prenyl group acceptor molecule is olivetolic acid or a derivative thereof. In some embodiments, the prenyl group donor molecule is GPP or a derivative thereof. In some embodiments, the reaction produces cannabigerolic acid or a derivative thereof.

In some embodiments, cell-free production of a cannabinoid, a cannabinoid derivative, a cannabinoid precursor, or a cannabinoid precursor derivative by one or more polypeptides disclosed herein expressed or overexpressed by a genetically modified host cell of the disclosure is determined by LC-MS analysis. In certain such embodiments, each cannabinoid, cannabinoid precursor, cannabinoid derivative, or cannabinoid precursor derivative is identified by retention time, determined from an authentic standard, and multiple reaction monitoring (MRM) transition.

EXAMPLES OF NON-LIMITING EMBODIMENTS OF THE DISCLOSURE

Embodiments, of the present subject matter disclosed herein may be beneficial alone or in combination, with one or more other embodiments. Without limiting the foregoing description, certain non-limiting embodiments of the disclosure, numbered I-1 to I-54, II-1 to II-55, and III-1 to III-81 are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiments explicitly provided below. Some embodiments of the disclosure are of Embodiment I:

Embodiment I-1. A genetically modified host cell that produces a cannabinoid compound or a cannabinoid precursor, wherein the genetically modified host cell is genetically modified with: a) one or more heterologous nucleic acids that encode one or more polypeptides that generate hexanoyl-CoA or derivatives of hexanoyl-CoA; b) one or more heterologous nucleic acids that encode one or more polypeptides that generate geranyl pyrophosphate; c) one or more heterologous nucleic acids that encode one or more polypeptides that generate malonyl-CoA; d) one or more heterologous nucleic acids that encode a fusion TKS/OAC polypeptide that condenses hexanoyl-CoA or its derivatives and malonyl-CoA to generate olivetolic acid or derivatives of olivetolic acid; e) one or more heterologous nucleic acids that encode a truncated geranyl pyrophosphate:olivetolic acid geranyltransferase (GOT) polypeptide or an NphB polypeptide; and f) one or more heterologous nucleic acids that encode a cannabinoid synthase polypeptide, wherein culturing of the genetically modified host cell in a suitable medium provides for synthesis of the cannabinoid compound or the cannabinoid precursor in a recoverable amount.

Embodiment I-2. The genetically modified host cell of Embodiment I-1, wherein the host cell is a eukaryotic cell.

Embodiment I-3. The genetically modified host cell of Embodiment I-2, wherein the host cell is a yeast cell.

Embodiment I-4. The genetically modified host cell of Embodiment I-3, wherein the host cell is *Saccharomyces cerevisiae*.

Embodiment I-5. The genetically modified host cell of Embodiment I-4, wherein the host cell is a protease-deficient strain of *Saccharomyces cerevisiae*.

Embodiment I-6. The genetically modified host cell of Embodiment I-2, wherein the host cell is a plant cell.

Embodiment I-7. The genetically modified host cell of Embodiment I-1, wherein the host cell is a prokaryotic cell.

Embodiment I-8. The genetically modified host cell of Embodiment I-1, wherein the one or more polypeptides that generate hexanoyl-CoA or a hexanoyl-CoA derivative is hexanoyl-CoA synthetase (HCS) polypeptide, and wherein the medium comprises hexanoate.

Embodiment I-9. The genetically modified host cell of Embodiment I-6, wherein the HCS polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:1, SEQ ID NO:2, SEQ ID NO:3, or SEQ ID NO:4.

Embodiment I-10. The genetically modified host cell of Embodiment I-1, wherein the one or more polypeptides that generate geranyl pyrophosphate comprise geranyl pyrophosphate synthetase (GPPS) polypeptide.

Embodiment I-11. The genetically modified host cell of Embodiment I-11, wherein the GPPS polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to one of the amino acid sequences set forth in SEQ ID NO:5, SEQ ID NO:6, SEQ ID NO:7, or SEQ ID NO:8.

Embodiment I-12. The genetically modified host cell of Embodiment I-10, wherein the GPPS polypeptide is a dominant negative variant that reduces the ability of an endogenous GPPS polypeptide to function as a farnesyl pyrophosphate synthetase (FPPS) polypeptide.

Embodiment I-13. The genetically modified host cell of Embodiment I-10, wherein the GPPS polypeptide comprises a K197G amino acid substitution.

Embodiment I-14. The genetically modified host cell of Embodiment I-10, wherein the GPPS polypeptide is a heterodimeric protein comprising a GPPS large subunit polypeptide and a GPPS small subunit polypeptide, or a homodimeric or monomeric GPPS polypeptide.

Embodiment I-15. The genetically modified host cell of Embodiment I-1, wherein the one or more polypeptides that generate malonyl-CoA comprises acetyl-CoA carboxylase-1 (ACC1) polypeptide.

Embodiment I-16. The genetically modified host cell of Embodiment I-15, wherein the ACC1 polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:9.

Embodiment I-17. The genetically modified host cell of Embodiment I-1, wherein the one or more polypeptides that generate hexanoyl-CoA comprise an MCT1 polypeptide, a PaaH1 polypeptide, a Crt polypeptide, a Ter polypeptide, and a BktB polypeptide.

Embodiment I-18. The genetically modified host cell of Embodiment I-1, wherein the one or more polypeptides that generate hexanoyl-CoA comprise a MCT1 polypeptide, a PhaB polypeptide, a PhaJ polypeptide, a Ter polypeptide, and a BktB polypeptide.

Embodiment I-19. The genetically modified host cell of Embodiment I-17, wherein: i) the PaaH1 polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:18 or SEQ ID NO:46; ii) the Crt polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:19 or SEQ ID NO:48; iii) the Ter polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:20 or SEQ ID NO:50; and iv) the BktB polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:21 or SEQ ID NO:44.

Embodiment I-20. The genetically modified host cell of Embodiment I-18, wherein: i) the PhaB polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:94; ii) the PhaJ polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:96; iii) the Ter polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:20 or SEQ ID NO:50; and iv) the BktB polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:21 or SEQ ID NO:44.

Embodiment I-21. The genetically modified host cell of Embodiment I-1, wherein the host cell is genetically modified with a heterologous nucleic acid encoding one or more polypeptides that modulate NADH redox balance.

Embodiment I-22. The genetically modified host cell of Embodiment I-1, wherein the host cell is genetically modified with one or more of: i) one or more heterologous nucleic acids encoding a HMG-CoA synthase polypeptide; ii) one or more heterologous nucleic acids encoding a 3-hydroxy-3-methyl-glutaryl-CoA reductase (HMGR) polypeptide; iii) one or more heterologous nucleic acids encoding an MK polypeptide; and iv) one or more heterologous nucleic acids encoding an isopentenyl diphosphate isomerase (IDI) polypeptide.

Embodiment I-23. The genetically modified host cell of Embodiment I-22, wherein the host cell is genetically modified to overexpress a heterologous IDI polypeptide.

Embodiment I-24. The genetically modified host cell of Embodiment I-23, wherein the IDI polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:58.

Embodiment I-25. The genetically modified host cell of Embodiment I-22, wherein the host cell is genetically modified to overexpress a truncated HMGR (tHMGR) polypeptide.

Embodiment I-26. The genetically modified host cell of Embodiment I-25, wherein the tHMGR polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:17.

Embodiment I-27. The genetically modified host cell of Embodiment I-22, wherein the HMGR polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:22.

Embodiment I-28. The genetically modified host cell of Embodiment I-22, wherein the HMGS polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the MvaS polypeptide amino acid sequence set forth in SEQ ID NO:23, or wherein the HMGS polypeptide comprises an amino acid having at least 50% amino acid sequence identity to the ERG13 polypeptide amino acid sequence set forth in SEQ ID NO:24.

Embodiment I-29. The genetically modified host cell of Embodiment I-22, wherein the MK polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the ERG12 polypeptide amino acid sequence set forth in SEQ ID NO:64.

Embodiment I-30. The genetically modified host cell of Embodiment I-1, wherein the host cell is genetically modified with a heterologous nucleic acid encoding one or more polypeptides that condense two molecules of acetyl-CoA to generate acetoacetyl-CoA.

Embodiment I-31. The genetically modified host cell of Embodiment I-30, wherein the polypeptide that condenses two molecules of acetyl-CoA to generate acetoacetyl-CoA is an acetoacetyl-CoA thiolase polypeptide.

Embodiment I-32. The genetically modified host cell of Embodiment I-31, wherein the acetoacetyl-CoA thiolase polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to the amino acid sequence set forth in SEQ ID NO:25.

Embodiment I-33. The genetically modified host cell of Embodiment I-1, wherein the host cell is genetically modified with a heterologous nucleic acid encoding one or more polypeptides that condense one molecule of acetyl-CoA and one molecule of malonyl-CoA to generate acetoacetyl-CoA.

Embodiment I-34. The genetically modified host cell of any one of Embodiments I-1 to I-33, wherein at least one of the one or more heterologous nucleic acids is integrated into the chromosome of the host cell.

Embodiment I-35. The genetically modified host cell of any one of Embodiments I-1 to I-33, wherein at least one of the one or more heterologous nucleic acids is maintained extrachromosomally.

Embodiment I-36. The genetically modified host cell of any one of Embodiments I-1 to I-33, wherein two or more of the one or more heterologous nucleic acids are present in a single expression vector.

Embodiment I-37. The genetically modified host cell of any one of Embodiments I-1 to I-36, wherein the cannabinoid compound is cannabigerolic acid.

Embodiment I-38. The genetically modified host cell of Embodiment I-1, wherein the genetically modified host cell is genetically modified with a heterologous nucleic acid encoding a $\Delta^9$-THCA synthase polypeptide.

Embodiment I-39. The genetically modified host cell of Embodiment I-38, wherein the THCA synthase polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to SEQ ID NO:14 or SEQ ID NO:15.

Embodiment I-40. The genetically modified host cell of Embodiment I-1, wherein the genetically modified host cell is genetically modified with a heterologous nucleic acid encoding a CBDA synthase polypeptide.

Embodiment I-41. The genetically modified host cell of Embodiment I-40, wherein the CBDA synthase polypeptide comprises an amino acid having at least 50% (at least 50%, at least 60%, at least 70%, at least 75%, at least 80%, at least 85%, at least 90%, at least 95%, at least 98%, at least 99%, or 100%) amino acid sequence identity to SEQ ID NO:88 or SEQ ID NO:16.

Embodiment I-42. The genetically modified host cell of any one of Embodiments I-1 to I-41, wherein at least one of the heterologous nucleic acids is operably linked to an inducible promoter.

Embodiment I-43. The genetically modified host cell of any one of Embodiments I-1 to I-41, wherein at least one of the heterologous nucleic acids is operably linked to a constitutive promoter.

Embodiment I-44. The genetically modified host cell of Embodiment I-1, wherein the cannabinoid compound is cannabichromenic acid, cannabigerolic acid, $\Delta^9$-tetrahydrocannabinolic acid, cannabidiolic acid, $\Delta^9$-tetrahydrocannabinol, cannabidiol, or cannabichromene.

Embodiment I-45. A method of synthesizing a cannabinoid compound or cannabinoid precursor in a host cell, the method comprising: a) culturing a host cell of any one of Embodiments I-1 to I-40 in a suitable medium; and b) recovering the produced cannabinoid compound or cannabinoid precursor.

Embodiment I-46. The method of Embodiment I-45, wherein the medium comprises a fermentable sugar.

Embodiment I-47. The method of Embodiment I-45, wherein the medium comprises a pretreated cellulosic feedstock.

Embodiment I-48. A genetically modified host cell that produces an olivetolic acid derivative, wherein the genetically modified host cell is genetically modified with: a) one or more heterologous nucleic acids that encode an acyl-activating enzyme (AAE) polypeptide; and b) one or more heterologous nucleic acids that encode a TKS/OAC fusion polypeptide.

Embodiment I-49. The genetically modified host cell of Embodiment I-48, wherein the AAE polypeptide comprises an amino acid sequence having at least 50% (at least 50%, at least 60%, at least 70%, at least 75%, at least 80%, at least 85%, at least 90%, at least 95%, at least 98%, at least 99%, or 100%) amino acid sequence identity to an AAE amino acid sequence set forth in SEQ ID NO:90 or SEQ ID NO:91.

Embodiment I-50. A genetically modified host cell that produces a cannabinoid derivative, wherein the genetically modified host cell is genetically modified with: a) one or more heterologous nucleic acids that encode an acyl-activating enzyme (AAE) polypeptide; b) one or more heterologous nucleic acids that encode a TKS/OAC fusion polypeptide; and c) one or more heterologous nucleic acids that encode a GOT polypeptide or an NphB polypeptide.

Embodiment I-51. The genetically modified host cell of Embodiment I-50, wherein the genetically modified host cell is genetically modified with a heterologous nucleic acid encoding a THCAS polypeptide.

Embodiment I-52. The genetically modified host cell of Embodiment I-50, wherein the genetically modified host cell is genetically modified with a heterologous nucleic acid encoding a CBDAS polypeptide.

Embodiment I-53. A method of producing an olivetolic acid derivative, the method comprising culturing the genetically modified host cell of Embodiment I-48 or Embodiment I-49 in a culture medium comprising a carboxylic acid.

Embodiment I-54. A method of producing a cannabinoid derivative, the method comprising culturing the genetically modified host cell of any one of Embodiments I-50 to I-52 in a culture medium comprising a carboxylic acid.

Some embodiments of the disclosure are of Embodiment II:

Embodiment II-1. A genetically modified host cell that produces a cannabinoid compound, a cannabinoid derivative, or a cannabinoid precursor, wherein the genetically modified host cell is genetically modified with: a) one or more heterologous nucleic acids that encode one or more polypeptides that generate hexanoyl-CoA or derivatives of hexanoyl-CoA; b) one or more heterologous nucleic acids that encode one or more polypeptides that generate geranyl pyrophosphate; c) one or more heterologous nucleic acids that encode one or more polypeptides that generate malonyl-CoA; d) one or more heterologous nucleic acids that encode a TKS polypeptide and an OAC polypeptide, or a fusion TKS and OAC polypeptide, that converts hexanoyl-CoA or its derivatives and malonyl-CoA to olivetolic acid or derivatives of olivetolic acid; e) one or more heterologous nucleic acids that encode a geranyl pyrophosphate:olivetolic acid geranyltransferase (GOT) polypeptide or an NphB polypeptide; and f) one or more heterologous nucleic acids that encode a cannabinoid synthase polypeptide, wherein culturing of the genetically modified host cell in a suitable medium provides for synthesis of the cannabinoid compound, cannabinoid derivative, or the cannabinoid precursor in a recoverable amount.

Embodiment II-2. The genetically modified host cell of Embodiment II-1, wherein the host cell is a eukaryotic cell.

Embodiment II-3. The genetically modified host cell of Embodiment II-2, wherein the host cell is a yeast cell.

Embodiment II-4. The genetically modified host cell of Embodiment II-3, wherein the host cell is *Saccharomyces cerevisiae*.

Embodiment II-5. The genetically modified host cell of Embodiment II-4, wherein the host cell is a protease-deficient strain of *Saccharomyces cerevisiae*.

Embodiment II-6. The genetically modified host cell of Embodiment II-2, wherein the host cell is a plant cell.

Embodiment II-7. The genetically modified host cell of Embodiment II-1, wherein the host cell is a prokaryotic cell.

Embodiment II-8. The genetically modified host cell of Embodiment II-1, wherein the one or more polypeptides that generate hexanoyl-CoA or a hexanoyl-CoA derivative is a hexanoyl-CoA synthetase (HCS) polypeptide, and wherein the medium comprises hexanoate.

Embodiment II-9. The genetically modified host cell of Embodiment II-8, wherein the HCS polypeptide comprises an amino acid having at least 50% amino acid sequence identity to the amino acid sequence set forth in SEQ ID NO:1, SEQ ID NO:2, SEQ ID NO:3, or SEQ ID NO:4.

Embodiment II-10. The genetically modified host cell of Embodiment II-1, wherein the one or more polypeptides that generate geranyl pyrophosphate comprise a geranyl pyrophosphate synthetase (GPPS) polypeptide.

Embodiment II-11. The genetically modified host cell of Embodiment II-11, wherein the GPPS polypeptide comprises an amino acid having at least 50% amino acid sequence identity to one of the amino acid sequences set forth in SEQ ID NO:5, SEQ ID NO:6, SEQ ID NO:7, or SEQ ID NO:8.

Embodiment II-12. The genetically modified host cell of Embodiment II-10, wherein the GPPS polypeptide is a dominant negative variant that reduces the ability of an endogenous GPPS polypeptide to function as a farnesyl pyrophosphate synthetase (FPPS) polypeptide.

Embodiment II-13. The genetically modified host cell of Embodiment II-10, wherein the GPPS polypeptide comprises a K197G amino acid substitution.

Embodiment II-14. The genetically modified host cell of Embodiment II-10, wherein the GPPS polypeptide is a heterodimeric protein comprising a GPPS large subunit polypeptide and a GPPS small subunit polypeptide, or a homodimeric or monomeric GPPS polypeptide.

Embodiment II-15. The genetically modified host cell of Embodiment II-1, wherein the one or more polypeptides that generate malonyl-CoA comprises an acetyl-CoA carboxylase-1 (ACC1) polypeptide.

Embodiment II-16. The genetically modified host cell of Embodiment II-15, wherein the ACC1 polypeptide comprises an amino acid having at least 50% amino acid sequence identity to the amino acid sequence set forth in SEQ ID NO:9.

Embodiment II-17. The genetically modified host cell of Embodiment II-1, wherein the one or more polypeptides that generate hexanoyl-CoA comprise a MCT1 polypeptide, a PaaH1 polypeptide, a Crt polypeptide, a Ter polypeptide, and a BktB polypeptide.

Embodiment II-18. The genetically modified host cell of Embodiment II-1, wherein the one or more polypeptides that generate hexanoyl-CoA comprise a MCT1 polypeptide, a PhaB polypeptide, a PhaJ polypeptide, a Ter polypeptide, and a BktB polypeptide.

Embodiment II-19 The genetically modified host cell of Embodiment II-17, wherein: i) the PaaH1 polypeptide comprises an amino acid having at least 50% amino acid sequence identity to the amino acid sequence set forth in SEQ ID NO:18 or SEQ ID NO:46; ii) the Crt polypeptide comprises an amino acid having at least 50% amino acid sequence identity to the amino acid sequence set forth in SEQ ID NO:19 or SEQ ID NO:48; iii) the Ter polypeptide comprises an amino acid having at least 50% amino acid sequence identity to the amino acid sequence set forth in SEQ ID NO:20 or SEQ ID NO:50; and iv) the BktB polypeptide comprises an amino acid having at least 50% amino acid sequence identity to the amino acid sequence set forth in SEQ ID NO:21 or SEQ ID NO:44.

Embodiment II-20. The genetically modified host cell of Embodiment II-18, wherein: i) the PhaB polypeptide comprises an amino acid having at least 50% amino acid sequence identity to the amino acid sequence set forth in SEQ ID NO:94; ii) the PhaJ polypeptide comprises an amino acid having at least 50% amino acid sequence identity to the amino acid sequence set forth in SEQ ID NO:96; iii) the Ter polypeptide comprises an amino acid having at least 50% amino acid sequence identity to the amino acid sequence set forth in SEQ ID NO:20 or SEQ ID NO:50; and iv) the BktB polypeptide comprises an amino acid having at least 50% amino acid sequence identity to the amino acid sequence set forth in SEQ ID NO:21 or SEQ ID NO:44.

Embodiment II-21. The genetically modified host cell of Embodiment II-1, wherein the host cell is genetically modified with a heterologous nucleic acid encoding one or more polypeptides that modulate NADH redox balance.

Embodiment II-22. The genetically modified host cell of Embodiment II-1, wherein the host cell is genetically modified with one or more of: i) one or more heterologous nucleic acids that encode an HMG-CoA synthase polypeptide; ii) one or more heterologous nucleic acids that encode a 3-hydroxy-3-methyl-glutaryl-CoA reductase (HMGR) polypeptide; iii) one or more heterologous nucleic acids that encode an MK polypeptide; and iv) one or more heterologous nucleic acids that encode an isopentenyl diphosphate isomerase (IDI) polypeptide.

Embodiment II-23. The genetically modified host cell of Embodiment II-22, wherein the host cell is genetically modified to overexpress a heterologous IDI polypeptide.

Embodiment II-24. The genetically modified host cell of Embodiment II-23, wherein the IDI polypeptide comprises an amino acid having at least 50% amino acid sequence identity to the amino acid sequence set forth in SEQ ID NO:58.

Embodiment II-25. The genetically modified host cell of Embodiment II-22, wherein the host cell is genetically modified to overexpress a truncated HMGR (tHMGR) polypeptide.

Embodiment II-26. The genetically modified host cell of Embodiment II-25, wherein the tHMGR polypeptide comprises an amino acid having at least 50% amino acid sequence identity to the amino acid sequence set forth in SEQ ID NO:17.

Embodiment II-27. The genetically modified host cell of Embodiment II-22, wherein the HMGR polypeptide comprises an amino acid having at least 50% amino acid sequence identity to the amino acid sequence set forth in SEQ ID NO:22.

Embodiment II-28. The genetically modified host cell of Embodiment II-22, wherein the HMGS polypeptide comprises an amino acid having at least 50% amino acid sequence identity to the MvaS polypeptide amino acid sequence set forth in SEQ ID NO:23, or wherein the HMGS polypeptide comprises an amino acid having at least 50% amino acid sequence identity to the ERG13 polypeptide amino acid sequence set forth in SEQ ID NO:24.

Embodiment II-29. The genetically modified host cell of Embodiment II-22, wherein the MK polypeptide comprises an amino acid having at least 50% amino acid sequence identity to the ERG12 polypeptide amino acid sequence set forth in SEQ ID NO:64.

Embodiment II-30. The genetically modified host cell of Embodiment II-1, wherein the host cell is genetically modified with a heterologous nucleic acid encoding one or more polypeptides that condense two molecules of acetyl-CoA to generate acetoacetyl-CoA.

Embodiment II-31. The genetically modified host cell of Embodiment II-30, wherein the polypeptide that condenses two molecules of acetyl-CoA to generate acetoacetyl-CoA is an acetoacetyl-CoA thiolase polypeptide.

Embodiment II-32. The genetically modified host cell of Embodiment II-31, wherein the acetoacetyl-CoA thiolase polypeptide comprises an amino acid sequence having at least 50% sequence identity to SEQ ID NO:25.

Embodiment II-33. The genetically modified host cell of Embodiment II-1, wherein the host cell is genetically modified with a heterologous nucleic acid encoding one or more polypeptides that condense one molecule of acetyl-CoA and one molecule of malonyl-CoA to generate acetoacetyl-CoA.

Embodiment II-34. The genetically modified host cell of any one of Embodiments II-1 to II-33, wherein at least one of the one or more heterologous nucleic acids is integrated into the chromosome of the host cell.

Embodiment II-35. The genetically modified host cell of any one of Embodiments II-1 to II-33, wherein at least one of the one or more heterologous nucleic acids is maintained extrachromosomally.

Embodiment II-36. The genetically modified host cell of any one of Embodiments II-1 to II-33, wherein two or more of the one or more heterologous nucleic acids are present in a single expression vector.

Embodiment II-37. The genetically modified host cell of any one of Embodiments II-1 to II-36, wherein the cannabinoid compound is cannabigerolic acid.

Embodiment II-38. The genetically modified host cell of Embodiment II-1, wherein the genetically modified host cell is genetically modified with a heterologous nucleic acid encoding a $\Delta^9$-THCA synthase polypeptide.

Embodiment II-39. The genetically modified host cell of Embodiment II-38, wherein the THCA synthase polypeptide comprises an amino acid having at least 50% amino acid sequence identity to SEQ ID NO:14 or SEQ ID NO:15.

Embodiment II-40. The genetically modified host cell of Embodiment II-1, wherein the genetically modified host cell is genetically modified with a heterologous nucleic acid encoding a CBDA synthase polypeptide.

Embodiment II-41. The genetically modified host cell of Embodiment II-40, wherein the CBDA synthase polypeptide comprises an amino acid having at least 50% amino acid sequence identity to SEQ ID NO:88 or SEQ ID NO:16.

Embodiment II-42. The genetically modified host cell of any one of Embodiments II-1 to II-41, wherein at least one of the heterologous nucleic acids is operably linked to an inducible promoter.

Embodiment II-43. The genetically modified host cell of any one of Embodiments II-1 to II-41, wherein at least one of the heterologous nucleic acids is operably linked to a constitutive promoter.

Embodiment II-44. The genetically modified host cell of Embodiment II-1, wherein the cannabinoid compound is cannabichromenic acid, cannabigerolic acid, $\Delta^9$-tetrahydrocannabinolic acid, cannabidiolic acid, $\Delta^9$-tetrahydrocannabinol, cannabidiol, or cannabichromene.

Embodiment II-45. A method of synthesizing a cannabinoid compound or cannabinoid precursor in a host cell, the method comprising: a) culturing a host cell of any one of Embodiments II-1 to II-40 in a suitable medium; and b) recovering the produced cannabinoid compound or cannabinoid precursor.

Embodiment II-46. The method of Embodiment II-45, wherein the medium comprises a fermentable sugar.

Embodiment II-47. The method of Embodiment II-45, wherein the medium comprises a pretreated cellulosic feedstock.

Embodiment II-48. A genetically modified host cell that produces an olivetolic acid derivative, wherein the genetically modified host cell is genetically modified with: a) one or more heterologous nucleic acids that encode an acyl-activating enzyme (AAE) polypeptide; and b) one or more heterologous nucleic acids that encode a TKS/OAC fusion polypeptide.

Embodiment II-49. The genetically modified host cell of Embodiment II-48, wherein the AAE polypeptide comprises an amino acid sequence having at least 50% amino acid sequence identity to an AAE amino acid sequence set forth in SEQ ID NO:90 or SEQ ID NO:91.

Embodiment II-50. A genetically modified host cell that produces a cannabinoid derivative, wherein the genetically modified host cell is genetically modified with: a) one or more heterologous nucleic acids that encode an acyl-activating enzyme (AAE) polypeptide; b) one or more heterologous nucleic acids that encode a TKS/OAC fusion polypeptide; and c) one or more heterologous nucleic acids that encode a GOT polypeptide or an NphB polypeptide.

Embodiment II-51. The genetically modified host cell of Embodiment II-50, wherein the genetically modified host cell is genetically modified with a heterologous nucleic acid encoding a THCAS polypeptide.

Embodiment II-52. The genetically modified host cell of Embodiment II-50, wherein the genetically modified host cell is genetically modified with a heterologous nucleic acid encoding a CBDAS polypeptide.

Embodiment II-53. A method of producing an olivetolic acid derivative, the method comprising culturing the genetically modified host cell of Embodiment II-48 or II-49 in a culture medium comprising a carboxylic acid.

Embodiment II-54. A method of producing a cannabinoid derivative, the method comprising culturing the genetically modified host cell of any one of Embodiments II-50 to II-52 in a culture medium comprising a carboxylic acid.

Embodiment II-55. The genetically modified host cell of Embodiment II-1, wherein the geranyl pyrophosphate olivetolic acid geranyltransferase (GOT) polypeptide or the NphB polypeptide comprises an amino acid having at least 50% amino acid sequence identity to the amino acid sequence of a GOT polypeptide, including CsPT4t polypeptide, or NphB polypeptide sequence, respectively, disclosed herein.

Some embodiments of the disclosure are of Embodiment III:

Embodiment III-1. A genetically modified host cell for producing a cannabinoid or a cannabinoid derivative, the genetically modified host cell comprising one or more heterologous nucleic acids encoding a geranyl pyrophosphate:olivetolic acid geranyltransferase polypeptide, wherein said geranyl pyrophosphate:olivetolic acid geranyltransferase polypeptide can catalyze production of cannabigerolic acid from geranyl pyrophosphate and olivetolic acid in an amount at least ten times higher than a polypeptide comprising an amino acid sequence set forth in SEQ ID NO:82.

Embodiment III-2. A genetically modified host cell for producing a cannabinoid or a cannabinoid derivative, the genetically modified host cell comprising one or more heterologous nucleic acids encoding a geranyl pyrophosphate:olivetolic acid geranyltransferase polypeptide comprising an amino acid sequence having at least 65% sequence identity to SEQ ID NO:110.

Embodiment III-3. A genetically modified host cell for producing a cannabinoid or a cannabinoid derivative, the genetically modified host cell comprising one or more heterologous nucleic acids encoding a geranyl pyrophosphate:olivetolic acid geranyltransferase polypeptide comprising an amino acid sequence having at least 65% sequence identity to SEQ ID NO:100.

Embodiment III-4. The genetically modified host cell of any one of Embodiments III-1 to III-3, wherein the genetically modified host cell further comprises one or more heterologous nucleic acids encoding a tetraketide synthase (TKS) polypeptide and one or more heterologous nucleic acids encoding an olivetolic acid cyclase (OAC) polypeptide, or one or more heterologous nucleic acids encoding a fusion TKS and OAC polypeptide.

Embodiment III-5. The genetically modified host cell of Embodiment III-4, wherein the TKS polypeptide comprises an amino acid sequence having at least 50% sequence identity to SEQ ID NO:11 or SEQ ID NO:76.

Embodiment III-6. The genetically modified host cell of Embodiment III-4 or III-5, wherein the OAC polypeptide comprises an amino acid sequence having at least 50% sequence identity to SEQ ID NO:10 or SEQ ID NO:78.

Embodiment III-7. The genetically modified host cell of any one of Embodiments III-1 to III-6, wherein the genetically modified host cell further comprises one or more of the following: a) one or more heterologous nucleic acids encoding a polypeptide that generates an acyl-CoA compound or an acyl-CoA compound derivative; b) one or more heterologous nucleic acids encoding a polypeptide that generates geranyl pyrophosphate; or c) one or more heterologous nucleic acids encoding a polypeptide that generates malonyl-CoA.

Embodiment III-8. The genetically modified host cell of Embodiment III-7, wherein the genetically modified host cell further comprises one or more heterologous nucleic acids encoding a polypeptide that generates an acyl-CoA compound or an acyl-CoA compound derivative, wherein the polypeptide that generates an acyl-CoA compound or an acyl-CoA compound derivative is an acyl-activating enzyme (AAE) polypeptide.

Embodiment III-9. The genetically modified host cell of Embodiment III-8, wherein the AAE polypeptide comprises an amino acid sequence having at least 50% sequence identity to SEQ ID NO:90.

Embodiment III-10. The genetically modified host cell of Embodiment III-8, wherein the AAE polypeptide comprises an amino acid sequence having at least 50% sequence identity to SEQ ID NO:92 or SEQ ID NO:149.

Embodiment III-11. The genetically modified host cell of Embodiment III-7, wherein the genetically modified host cell further comprises one or more heterologous nucleic acids encoding a polypeptide that generates an acyl-CoA compound or an acyl-CoA compound derivative, wherein the polypeptide that generates an acyl-CoA compound or an acyl-CoA compound derivative is a fatty acyl-CoA ligase polypeptide.

Embodiment III-12. The genetically modified host cell of Embodiment III-11, wherein the fatty acyl-CoA ligase polypeptide comprises an amino acid sequence having at least 50% sequence identity to SEQ ID NO:145 or SEQ ID NO:147.

Embodiment III-13. The genetically modified host cell of Embodiment III-7, wherein the genetically modified host cell further comprises one or more heterologous nucleic acids encoding a polypeptide that generates an acyl-CoA compound or an acyl-CoA compound derivative, wherein the polypeptide that generates an acyl-CoA compound or an acyl-CoA compound derivative is a fatty acyl-CoA synthetase (FAA) polypeptide.

Embodiment III-14. The genetically modified host cell of Embodiment III-13, wherein the FAA polypeptide comprises an amino acid sequence having at least 50% sequence identity to SEQ ID NO:169, SEQ ID NO:192, SEQ ID NO:194, SEQ ID NO:196, SEQ ID NO:198, or SEQ ID NO:200.

Embodiment III-15. The genetically modified host cell of any one of Embodiments III-7 to III-14, wherein the genetically modified host cell further comprises one or more heterologous nucleic acids encoding a polypeptide that generates geranyl pyrophosphate, wherein the polypeptide that generates geranyl pyrophosphate is a geranyl pyrophosphate synthetase (GPPS) polypeptide.

Embodiment III-16. The genetically modified host cell of Embodiment III-15, wherein the GPPS polypeptide comprises an amino acid sequence having at least 50% sequence identity to SEQ ID NO:7, SEQ ID NO:8, or SEQ ID NO:60.

Embodiment III-17. The genetically modified host cell of any one of Embodiments III-7 to III-16, wherein the genetically modified host cell further comprises one or more heterologous nucleic acids encoding a polypeptide that generates malonyl-CoA, wherein the polypeptide that generates malonyl-CoA is an acetyl-CoA carboxylase-1 (ACC1) polypeptide.

Embodiment III-18. The genetically modified host cell of Embodiment III-17, wherein the ACC1 polypeptide comprises an amino acid sequence having at least 50% sequence identity to SEQ ID NO:9, SEQ ID NO:97, or SEQ ID NO:207.

Embodiment III-19. The genetically modified host cell of any one of Embodiments III-1 to III-18, wherein the genetically modified host cell further comprises one or more of the following: a) one or more heterologous nucleic acids encoding a HMG-CoA synthase (HMGS) polypeptide; b) one or more heterologous nucleic acids encoding a 3-hydroxy-3-methyl-glutaryl-CoA reductase (HMGR) polypeptide; c) one or more heterologous nucleic acids encoding a mevalonate kinase (MK) polypeptide; d) one or more heterologous nucleic acids encoding a phosphomevalonate kinase (PMK) polypeptide; e) one or more heterologous nucleic acids encoding a mevalonate pyrophosphate decarboxylase (MVD) polypeptide; or f) one or more heterologous nucleic acids encoding a isopentenyl diphosphate isomerase (IDI) polypeptide.

Embodiment III-20. The genetically modified host cell of Embodiment III-19, wherein the genetically modified host cell further comprises one or more heterologous nucleic acids encoding an IDI polypeptide.

Embodiment III-21. The genetically modified host cell of Embodiment III-20, wherein the IDI polypeptide comprises an amino acid sequence having at least 50% sequence identity to SEQ ID NO:58.

Embodiment III-22. The genetically modified host cell of any one of Embodiments III-19 to III-21, wherein the genetically modified host cell further comprises one or more heterologous nucleic acids encoding an HMGR polypeptide.

Embodiment III-23. The genetically modified host cell of Embodiment III-22, wherein the HMGR polypeptide comprises an amino acid sequence having at least 50% sequence identity to SEQ ID NO:22.

Embodiment III-24. The genetically modified host cell of any one of Embodiments III-19 to III-21, wherein the genetically modified host cell further comprises one or more heterologous nucleic acids encoding an HMGR polypeptide, wherein the HMGR polypeptide is a truncated HMGR (tHMGR) polypeptide.

Embodiment III-25. The genetically modified host cell of Embodiment III-24, wherein the tHMGR polypeptide comprises an amino acid sequence having at least 50% sequence identity to SEQ ID NO:17, SEQ ID NO:52, SEQ ID NO:113, or SEQ ID NO:208.

Embodiment III-26. The genetically modified host cell of any one of Embodiments III-19 to III-25, wherein the genetically modified host cell further comprises one or more heterologous nucleic acids encoding an HMGS polypeptide.

Embodiment III-27. The genetically modified host cell of Embodiment III-26, wherein the HMGS polypeptide comprises an amino acid sequence having at least 50% sequence identity to SEQ ID NO:23, SEQ ID NO:24, or SEQ ID NO:115.

Embodiment III-28. The genetically modified host cell of any one of Embodiments III-19 to III-27, wherein the genetically modified host cell further comprises one or more heterologous nucleic acids encoding an MK polypeptide.

Embodiment III-29. The genetically modified host cell of Embodiment III-28, wherein the MK polypeptide comprises an amino acid sequence having at least 50% sequence identity to SEQ ID NO:64.

Embodiment III-30. The genetically modified host cell of any one of Embodiments III-19 to III-29, wherein the genetically modified host cell further comprises one or more heterologous nucleic acids encoding a PMK polypeptide.

Embodiment III-31. The genetically modified host cell of Embodiment III-30, wherein the PMK polypeptide comprises an amino acid sequence having at least 50% sequence identity to SEQ ID NO:62 or SEQ ID NO:205.

Embodiment III-32. The genetically modified host cell of any one of Embodiments III-19 to III-31, wherein the genetically modified host cell further comprises one or more heterologous nucleic acids encoding a MVD polypeptide.

Embodiment III-33. The genetically modified host cell of Embodiment III-32, wherein the MVD polypeptide comprises an amino acid sequence having at least 50% sequence identity to SEQ ID NO:66.

Embodiment III-34. The genetically modified host cell of any one of Embodiments III-1 to III-33, wherein the genetically modified host cell further comprises one or more heterologous nucleic acids encoding a polypeptide that condenses two molecules of acetyl-CoA to generate acetoacetyl-CoA.

Embodiment III-35. The genetically modified host cell of Embodiment III-34, wherein the polypeptide that condenses two molecules of acetyl-CoA to generate acetoacetyl-CoA is an acetoacetyl-CoA thiolase polypeptide.

Embodiment III-36. The genetically modified host cell of Embodiment III-35, wherein the acetoacetyl-CoA thiolase polypeptide comprises an amino acid sequence having at least 50% sequence identity to SEQ ID NO:25.

Embodiment III-37. The genetically modified host cell of any one of Embodiments III-1 to III-36, wherein the genetically modified host cell further comprises one or more heterologous nucleic acids encoding a pyruvate decarboxylase (PDC) polypeptide.

Embodiment III-38. The genetically modified host cell of Embodiment III-37, wherein the PDC polypeptide comprises an amino acid sequence having at least 50% sequence identity to SEQ ID NO:117.

Embodiment III-39. The genetically modified host cell of any one of Embodiments III-1 to III-38, wherein the genetically modified host cell is a eukaryotic cell.

Embodiment III-40. The genetically modified host cell of Embodiment III-39, wherein the eukaryotic cell is a yeast cell.

Embodiment III-41. The genetically modified host cell of Embodiment III-40, wherein the yeast cell is Saccharomyces cerevisiae.

Embodiment III-42. The genetically modified host cell of Embodiment III-41, wherein the Saccharomyces cerevisiae is a protease-deficient strain of Saccharomyces cerevisiae.

Embodiment III-43. The genetically modified host cell of any one of Embodiments I11-1 to III-39, wherein the genetically modified host cell is a plant cell.

Embodiment III-44. The genetically modified host cell of any one of Embodiments III-1 to III-38, wherein the genetically modified host cell is a prokaryotic cell.

Embodiment III-45. The genetically modified host cell of any one of Embodiments III-1 to III-44, wherein at least one of the one or more heterologous nucleic acids is integrated into the chromosome of the genetically modified host cell.

Embodiment III-46. The genetically modified host cell of any one of Embodiments III-1 to III-44, wherein at least one of the one or more heterologous nucleic acids is maintained extrachromosomally.

Embodiment III-47. The genetically modified host cell of any one of Embodiments III-1 to III-44, wherein two or more of the one or more heterologous nucleic acids are present in a single expression vector.

Embodiment III-48. The genetically modified host cell of any one of Embodiments III-1 to III-44, wherein at least one of the heterologous nucleic acids is operably linked to an inducible promoter.

Embodiment III-49. The genetically modified host cell of any one of Embodiments III-1 to III-44, wherein at least one of the heterologous nucleic acids is operably linked to a constitutive promoter.

Embodiment III-50. The genetically modified host cell of any one of Embodiments III-1 to III-49, wherein culturing of the genetically modified host cell in a suitable medium provides for synthesis of the cannabinoid or the cannabinoid derivative in an increased amount compared to a non-genetically modified host cell cultured under similar conditions.

Embodiment III-51. The genetically modified host cell of any one of Embodiments III-1 to III-50, wherein the genetically modified host cell further comprises one or more heterologous nucleic acids encoding a cannabinoid synthase polypeptide.

Embodiment III-52. The genetically modified host cell of Embodiment III-51, wherein the cannabinoid synthase polypeptide is a tetrahydrocannabinolic acid (THCA) synthase polypeptide.

Embodiment III-53. The genetically modified host cell of Embodiment III-52, wherein the THCA synthase polypeptide comprises an amino acid sequence having at least 50% sequence identity to SEQ ID NO:14, SEQ ID NO:86, SEQ ID NO:104, SEQ ID NO:153, or SEQ ID NO:155.

Embodiment III-54. The genetically modified host cell of Embodiment III-51, wherein the cannabinoid synthase polypeptide is a cannabidiolic acid (CBDA) synthase polypeptide.

Embodiment III-55. The genetically modified host cell of Embodiment III-54, wherein the CBDA synthase polypeptide comprises an amino acid sequence having at least 50% sequence identity to SEQ ID NO:88 or SEQ ID NO:151.

Embodiment III-56. The genetically modified host cell of any one of Embodiments III-1 to III-55, wherein the cannabinoid is cannabigerolic acid, cannabigerol, $\Delta^9$-tetrahydrocannabinolic acid, $\Delta^9$-tetrahydrocannabinol, $\Delta^8$-tetrahydrocannabinolic acid, $\Delta^8$-tetrahydrocannabinol, cannabidiolic acid, cannabidiol, cannabichromenic acid, cannabichromene, cannabinolic acid, cannabinol, cannabidivarinic acid, cannabidivarin, tetrahydrocannabivarinic acid, tetrahydrocannabivarin, cannabichromevarinic acid, cannabichromevarin, cannabigerovarinic acid, cannabigerovarin, cannabicyclolic acid, cannabicyclol, cannabielsoinic acid, cannabielsoin, cannabicitranic acid, or cannabicitran.

Embodiment III-57. The genetically modified host cell of Embodiment III-56, wherein the cannabinoid is cannabigerolic acid.

Embodiment III-58. A method of producing a cannabinoid or a cannabinoid derivative in a genetically modified host cell, the method comprising: a) culturing the genetically modified host cell of any one of Embodiments III-1 to III-57 in a suitable medium; and b) recovering the produced cannabinoid or cannabinoid derivative.

Embodiment III-59. A method of producing a cannabinoid or a cannabinoid derivative, the method comprising: a) culturing the genetically modified host cell of any one of Embodiments III-1 to III-57 in a suitable medium comprising a carboxylic acid; b) recovering the produced cannabinoid or cannabinoid derivative.

Embodiment III-60. A method of producing a cannabinoid or a cannabinoid derivative, the method comprising: a) culturing the genetically modified host cell of any one of Embodiments III-1 to III-57 in a suitable medium comprising olivetolic acid or an olivetolic acid derivative; b) recovering the produced cannabinoid or cannabinoid derivative.

Embodiment III-61. A method of producing a cannabinoid or a cannabinoid derivative in a genetically modified host cell, the method comprising: a) culturing a genetically modified host cell comprising one or more heterologous nucleic acids encoding a geranyl pyrophosphate:olivetolic acid geranyltransferase polypeptide, wherein said geranyl pyrophosphate:olivetolic acid geranyltransferase polypeptide can catalyze production of cannabigerolic acid from geranyl pyrophosphate and olivetolic acid in an amount at least ten times higher than a polypeptide comprising an amino acid sequence set forth in SEQ ID NO:82, in a suitable medium; and b) recovering the produced cannabinoid or cannabinoid derivative.

Embodiment III-62. A method of producing a cannabinoid or a cannabinoid derivative in a genetically modified host cell, the method comprising: a) culturing a genetically modified host cell comprising one or more heterologous nucleic acids encoding a geranyl pyrophosphate:olivetolic acid geranyltransferase polypeptide comprising an amino acid sequence having at least 65% sequence identity to SEQ ID NO:110 in a suitable medium; and b) recovering the produced cannabinoid or cannabinoid derivative.

Embodiment III-63. A method of producing a cannabinoid or a cannabinoid derivative in a genetically modified host cell, the method comprising: a) culturing a genetically modified host cell comprising one or more heterologous nucleic acids encoding a geranyl pyrophosphate:olivetolic acid geranyltransferase polypeptide comprising an amino acid sequence having at least 65% sequence identity to SEQ ID NO:100 in a suitable medium; and b) recovering the produced cannabinoid or cannabinoid derivative.

Embodiment III-64. The method of any one of Embodiments III-58 to III-63, wherein the suitable medium comprises a fermentable sugar.

Embodiment III-65. The method of any one of Embodiments III-58 to III-63, wherein the suitable medium comprises a pretreated cellulosic feedstock.

Embodiment III-66. The method of any one of Embodiments III-58 to III-63, wherein the suitable medium comprises a non-fermentable carbon source.

Embodiment III-67. The method of Embodiment III-66, wherein the non-fermentable carbon source comprises ethanol.

Embodiment III-68. The method of any one of Embodiments III-58 to III-67, wherein the cannabinoid is cannabigerolic acid, cannabigerol, $\Delta^9$-tetrahydrocannabinolic acid, $\Delta^9$-tetrahydrocannabinol, $\Delta^8$-tetrahydrocannabinolic acid, $\Delta^8$-tetrahydrocannabinol, cannabidiolic acid, cannabidiol, cannabichromenic acid, cannabichromene, cannabinolic acid, cannabinol, cannabidivarinic acid, cannabidivarin, tetrahydrocannabivarinic acid, tetrahydrocannabivarin, cannabichromevarinic acid, cannabichromevarin, cannabigerovarinic acid, cannabigerovarin, cannabicyclolic acid, cannabicyclol, cannabielsoinic acid, cannabielsoin, cannabicitranic acid, or cannabicitran.

Embodiment III-69. An isolated or purified geranyl pyrophosphate:olivetolic acid geranyltransferase polypeptide, wherein said geranyl pyrophosphate:olivetolic acid geranyltransferase polypeptide can catalyze production of cannabigerolic acid from geranyl pyrophosphate and olivetolic acid in an amount at least ten times higher than a polypeptide comprising an amino acid sequence set forth in SEQ ID NO:82.

Embodiment III-70. An isolated or purified polypeptide comprising an amino acid sequence having at least 65% sequence identity to SEQ ID NO:110.

Embodiment III-71. An isolated or purified polypeptide comprising an amino acid sequence having at least 65% sequence identity to SEQ ID NO:100.

Embodiment III-72. An isolated or purified nucleic acid encoding a geranyl pyrophosphate:olivetolic acid geranyltransferase polypeptide, wherein said geranyl pyrophosphate:olivetolic acid geranyltransferase polypeptide can catalyze production of cannabigerolic acid from geranyl pyrophosphate and olivetolic acid in an amount at least ten times higher than a polypeptide comprising an amino acid sequence set forth in SEQ ID NO:82.

Embodiment III-73. An isolated or purified nucleic acid encoding a polypeptide comprising an amino acid sequence having at least 65% sequence identity to SEQ ID NO:110.

Embodiment III-74. An isolated or purified nucleic acid encoding a polypeptide comprising an amino acid sequence having at least 65% sequence identity to SEQ ID NO:100.

Embodiment III-75. A vector comprising a nucleic acid encoding a geranyl pyrophosphate:olivetolic acid geranyltransferase polypeptide, wherein said geranyl pyrophosphate:olivetolic acid geranyltransferase polypeptide can catalyze production of cannabigerolic acid from geranyl pyrophosphate and olivetolic acid in an amount at least ten times higher than a polypeptide comprising an amino acid sequence set forth in SEQ ID NO:82.

Embodiment III-76. A vector comprising a nucleic acid encoding a polypeptide comprising an amino acid sequence having at least 65% sequence identity to SEQ ID NO:110.

Embodiment III-77. A vector comprising a nucleic acid encoding a polypeptide comprising an amino acid sequence having at least 65% sequence identity to SEQ ID NO:100.

Embodiment III-78. A method of making a genetically modified host cell for producing a cannabinoid or a cannabinoid derivative, comprising introducing one or more heterologous nucleic acids encoding a geranyl pyrophosphate:olivetolic acid geranyltransferase polypeptide, wherein said geranyl pyrophosphate:olivetolic acid geranyltransferase polypeptide can catalyze production of cannabigerolic acid from geranyl pyrophosphate and olivetolic acid in an amount at least ten times higher than a polypeptide comprising an amino acid sequence set forth in SEQ ID NO:82, into a host cell.

Embodiment III-79. A method of making a genetically modified host cell for producing a cannabinoid or a cannabinoid derivative, comprising introducing one or more heterologous nucleic acids encoding a geranyl pyrophosphate:olivetolic acid geranyltransferase polypeptide comprising an amino acid sequence having at least 65% sequence identity to SEQ ID NO:110 into a host cell.

Embodiment III-80. A method of making a genetically modified host cell for producing a cannabinoid or a cannabinoid derivative, comprising introducing one or more heterologous nucleic acids encoding a geranyl pyrophosphate:olivetolic acid geranyltransferase polypeptide comprising an amino acid sequence having at least 65% sequence identity to SEQ ID NO:100 into a host cell.

Embodiment III-81. A method of making a genetically modified host cell for producing a cannabinoid or a cannabinoid derivative, comprising introducing the vector of any one of Embodiments III-75 to I11-77 into a host cell.

The Sequence Listing provides amino acid and nucleotide sequences disclosed herein. Where a genus and/or species is noted, the sequence should not be construed to be limited only to the specified genus and/or species, but also includes other genera and/or species expressing said sequence.

EXAMPLES

The following examples are put forth so as to provide those of ordinary skill in the art with a complete disclosure and description of how to make and use the present disclosure, and are not intended to limit the scope of what the inventors regard as their disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); s or sec, second(s); min, minute(s); h or hr, hour(s); aa, amino acid(s); kb, kilobase(s); bp, base pair(s); nt, nucleotide(s); and the like.

GENERAL METHODS OF THE EXAMPLES

Yeast Transformation Methods

Each DNA construct comprising one or more heterologous nucleic acids disclosed herein (e.g., constructs detailed in Table 11) was integrated into *Saccharomyces cerevisiae* (CEN.PK2) with standard molecular biology techniques in an optimized lithium acetate (LiAc) transformation. Briefly, cells were grown overnight in yeast extract peptone dextrose (YPD) media at 30° C. with shaking (200 rpm), diluted to an OD600 of 0.1 in 100 mL YPD, and grown to an OD600 of 0.6-0.8. For each transformation, 5 mL of culture was harvested by centrifugation, washed in 5 mL of sterile water, spun down again, resuspended in 1 mL of 100 mM LiAc, and transferred to a microcentrifuge tube. Cells were spun down (13,000×g) for 30 seconds, the supernatant was removed, and the cells were resuspended in a transformation mix consisting of 240 µL 50% PEG, 36 µL 1M LiAc, 10 µL boiled salmon sperm DNA, and 74 µL of donor DNA. Following a heat shock at 42° C. for 40 minutes, cells were recovered overnight in YPD media before plating on selective media. DNA integration was confirmed by colony PCR with primers specific to the integrations.

Yeast Culturing Conditions

Yeast colonies verified to contain the expected DNA assembly comprising one or more heterologous nucleic acids disclosed herein, genetically modified host cells, were picked into 96-well microtiter plates containing 360 µL of YPD (10 g/L yeast extract, 20 g/L Bacto peptone, 20 g/L dextrose (glucose)) and sealed with a breathable film seal. Cells were cultured at 30° C. in a high capacity microtiter plate incubator shaking at 1000 rpm and 80% humidity for 3 days until the cultures reached carbon exhaustion. The growth-saturated cultures were subcultured into fresh plates containing YPGAL and either olivetolic acid or hexanoic acid, or an olivetolic acid derivative or a carboxylic acid other than hexanoic acid (10 g/L yeast extract, 20 g/L Bacto peptone, 20 g/L galactose, 1 g/L glucose and either 1 mM olivetolic acid or 2 mM hexanoic acid, or 1 mM of an olivetolic acid derivative or 2 mM of a carboxylic acid other than hexanoic acid), by taking 14.4 µL from the saturated cultures and diluting into 360 µL of fresh media and sealed with a breathable film seal. Genetically modified host cells in the production media were cultured at 30° C. in a high capacity microtiter plate shaker at 1000 rpm and 80% humidity for an additional 3 days prior to extraction and analysis. Upon completion, 100 µL of whole cell broth was diluted into 900 µL of methanol, sealed with a foil seal, and shaken at 1500 rpm for 60 seconds to extract the cannabinoids, cannabinoid derivatives, cannabinoid precursors, or cannabinoid precursor derivatives. After shaking, the plate was centrifuged at 1000×g for 60 seconds to remove any solids. After centrifugation, 12 µL of supernatant was transferred to a fresh assay plate containing 228 µL of methanol, sealed with a foil seal, shaken for 60 seconds at 900 rpm, and analyzed by LC-MS.

Analytical Methods

Samples were analyzed by LC-MS mass spectrometer (Agilent 6470) using an Agilent Poroshell 120 Phenyl Hexyl 2.1×50 mm, 1.9 µm analytical column with the following gradient (Mobile Phase A: LC-MS grade water with 0.1% formic acid; Mobile Phase B: LC-MS grade acetonitrile with 0.1% formic acid):

| Time (minutes) | % B |
|---|---|
| 0 | 40 |
| 0.1 | 40 |
| 0.6 | 60 |
| 1 | 65 |
| 1.01 | 95 |
| 2.01 | 95 |
| 2.02 | 40 |
| 2.5 | 40 |

The mass spectrometer was operated in negative ion multiple reaction monitoring mode. Each cannabinoid, cannabinoid precursor, cannabinoid derivative, or cannabinoid precursor derivative was identified by retention time, determined from an authentic standard, and multiple reaction monitoring (MRM) transition:

| Compound Name | Q1 Mass (Da) | Q3 Mass (Da) |
|---|---|---|
| CBGA | 359.2 | 341.1 |
| CBGA | 359.2 | 315.2 |
| CBDA | 357.2 | 339.1 |
| CBDA | 357.2 | 245.1 |
| THCA | 357.0 | 313.0 |

Recovery and Purifications

Whole-cell broth from cultures comprising genetically modified host cells of the disclosure are extracted with a suitable organic solvent to afford cannabinoids, cannabinoid precursors, cannabinoid derivatives, or cannabinoid precursor derivatives. Suitable organic solvents include, but are not limited to, hexane, heptane, ethyl acetate, petroleum ether, and di-ethyl ether, chloroform, and ethyl acetate. The suitable organic solvent, such as hexane, is added to the whole-cell broth from fermentations comprising genetically modified host cells of the disclosure at a 10:1 ratio (10 parts whole-cell broth-1 part organic solvent) and stirred for 30 minutes. The organic fraction is separated and extracted twice with an equal volume of acidic water (pH 2.5). The organic layer is then separated and dried in a concentrator (rotary evaporator or thin film evaporator under reduced pressure) to obtain crude cannabinoid, cannabinoid precursor, cannabinoid derivative, or cannabinoid precursor derivative crystals. The crude crystals may then be heated to 105° C. for 15 minutes followed by 145° C. for 55 minutes to decarboxylate a crude cannabinoid or cannabinoid derivative. The crude crystalline product is re-dissolved and recrystallized in a suitable solvent (e.g., n-pentane) and filtered through a 1 µm filter to remove any insoluble material. The solvent is then removed e.g. by rotary evaporation, to produce pure crystalline product.

In Vitro Enzyme Assay and Cell-Free Production of Cannabinoids or Cannabinoid Derivatives In some embodiments, genetically modified host cells, e.g., genetically modified yeast cells, verified to comprise one or more heterologous nucleic acids encoding a GOT polypeptide that catalyzes production of cannabigerolic acid from geranyl pyrophosphate and olivetolic acid in an amount at least ten times higher than a polypeptide comprising an amino acid sequence set forth in SEQ ID NO:82 or a polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110, are cultured in 96-well microtiter plates containing 360 μL of YPD (10 g/L yeast extract, 20 g/L Bacto peptone, 20 g/L dextrose (glucose)) and sealed with a breathable film seal. Cells are then cultured at 30° C. in a high capacity microtiter plate incubator shaking at 1000 rpm and 80% humidity for 3 days until the cultures reach carbon exhaustion. The growth-saturated cultures are then subcultured into 200 mL of YPGAL media to an OD600 of 0.2 and incubated with shaking for 20 hours at 30° C. Cells are then harvested by centrifugation at 3000×g for 5 minutes at 4° C. Harvested cells are then resuspended in 50 mL buffer (50 mM Tris-HCl, 1 mM EDTA, 0.1 M KCl, pH 7.4, 125 units Benzonase) and then lysed (Emulsiflex C3, Avestin, INC., 60 bar, 10 min). Cells debris is removed by centrifugation (10,000×g, 10 min, 4° C.). Subsequently, the supernatant is then subjected to ultracentrifugation (150,000×g, 1 h, 4° C., Beckman Coulter L-90K, TI-70). The resulting membrane fractions of the GOT polypeptide that catalyzes production of cannabigerolic acid from geranyl pyrophosphate and olivetolic acid in an amount at least ten times higher than a polypeptide comprising an amino acid sequence set forth in SEQ ID NO:82 or the polypeptide comprising an amino acid sequence having at least 65% (e.g., at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, or 100%) sequence identity to SEQ ID NO:100 or SEQ ID NO:110 are then resuspended in 3.3 mL buffer (10 mM Tris-HCl, 10 mM $MgCl_2$, pH 8.0, 10% glycerol) and solubilized with a tissue grinder. Then, 0.02% (v/v) of the respective membrane preparations are then dissolved in reaction buffer (50 mM Tris-HCl, 10 mM $MgCl_2$, pH 8.5) and substrate (500 μM olivetolic acid, 500 μM GPP) to a total volume of 50 μL and incubated for 1 hour at 30° C. Assays are then extracted by adding two reaction volumes of ethyl acetate followed by vortexing and centrifugation. The organic layer is evaporated for 30 minutes, resuspended in acetonitrile/$H_2O$/formic acid (80:20:0.05%) and filtered with Ultrafree®-MC columns (0.22 μm pore size, PVDF membrane material). Cannabinoids or cannabinoid derivatives are then detected via LC-MS and/or recovered and purified.

Yeast Cultivation in a Bioreactor

Single yeast colonies comprising genetically modified host cells disclosed herein are grown in 15 mL of Verduyn medium (originally described by Verduyn et al, Yeast 8(7): 501-17) with 50 mM succinate (pH 5.0) and 2% glucose in a 125 mL flask at 30° C., with shaking at 200 rpm to an OD600 between 4 to 9. Glycerol is then added to the culture to a concentration of 20% and 1 mL vials of the genetically modified host cell suspension are stored at −80° C. One to two vials of genetically modified host cells are thawed and grown in Verduyn medium with 50 mM succinate (pH 5.0) and 4% sucrose for 24 hours, then sub-cultured to an OD600 reading of 0.1 in the same media. After 24 hours of growth at 30° C. with shaking, 65 mL of culture is used to inoculate a 1.3-liter fermenter (Eppendorf DASGIP Bioreactor) with 585 mL of Verduyn fermentation media containing 20 g/L galactose supplemented with hexanoic acid (2 mM), a carboxylic acid other than hexanoic acid (2 mM), olivetolic acid (1 mM), or an olivetolic acid derivative (1 mM). A poly-alpha-olefin may be added to the fermenter as an extractive agent. The fermenter is maintained at 30° C. and pH 5.0 with addition of $NH_4OH$. In an initial batch phase, the fermenter is aerated at 0.5 volume per volume per minute air (VVM) and agitation ramped to maintain 30% dissolved oxygen. After the initial sugar is consumed, the rise in dissolved oxygen triggers feeding of galactose+hexanoic acid (800 g galactose per liter+9.28 g hexanoic acid per liter) at 10 g galactose per liter per hour in pulses of 10 g galactose per liter doses (alternatively, rather than feeding the genetically modified host cells disclosed herein hexanoic acid, olivetolic acid, an olivetolic acid derivative, or a carboxylic acid other than hexanoic acid is fed to the genetically modified host cells).

Between pulses, the feed rate is lowered to 5 g galactose per liter per hour. Upon a 10% rise in dissolved oxygen, the feed rate is resumed at 10 g $L^{-1}$ $hour^{-1}$. As genetically modified host cell density increases, dissolved oxygen is allowed to reach 0%, and the pulse dose is increased to 50 g galacose per liter. Oxygen transfer rate is maintained at rates representative of full-scale conditions of 100 mM per liter per hour by adjusting agitation as volume increased. Feed rate is adjusted dynamically to meet demand using an algorithm that alternates between a high feed rate and low feed rate. During the low feed rate, genetically modified host cells should consume galactose and hexanoic acid, or, alternatively, olivetolic acid, an olivetolic acid derivative, or a carboxylic acid other than hexanoic acid, and any overflow metabolites accumulated during the high feed rate. A rise in dissolved oxygen triggers the high feed rate to resume. The length of time spent in the low feed rate reflects the extent to which genetically modified host cells are over- or under-fed in the prior high feed rate pulse; this information is then monitored and used to tune the high feed rate up or down, keeping the low feed rate within a defined range.

Over time, the feed rate matches sugar and hexanoic acid, or, alternatively, olivetolic acid, an olivetolic acid derivative, or a carboxylic acid other than hexanoic acid, demand from genetically modified host cells. This algorithm ensures minimal net accumulation of fermentation products other than cannabinoids, cannabinoid derivatives, cannabinoid precursors, or cannabinoid precursor derivatives; biomass; and $CO_2$. In some embodiments, the process continues for 5 to 14 days. In certain such embodiments, accumulated broth is removed daily and assayed for biomass and cannabinoid, cannabinoid derivative, cannabinoid precursor, or cannabinoid precursor derivative concentration. A concentrated solution of $NH_4H_2PO_4$, trace metals and vitamins are added periodically to maintain steady state concentrations.

Example 1—Synthesis of Olivetolic Acid or Derivatives Thereof

The cannabinoid pathway is composed of four biosynthetic steps using the precursors hexanoyl-CoA, malonyl-CoA, and geranyl pyrophosphate (FIG. 1, Box 4). *Saccharomyces cerevisiae* has previously been engineered to produce high levels of malonyl-CoA. To increase geranyl pyrophosphate supply, the engineering strategy as outlined in FIG. 1, Box 3, was carried out. In addition, a heterologous nucleic acid encoding an ACC1 polypeptide was overexpressed to increase flux to malonyl-CoA.

FIG. 1: Diagram illustrating biosynthetic pathways for converting sugar or hexanoate to the cannabinoids $\Delta^9$-THC and CBD To date, engineering biosynthesis of the precursor hexanoyl-CoA in *Saccharomyces cerevisiae* has not been described. Strategies for hexanoyl-CoA biosynthesis in *Saccharomyces cerevisiae*, as outlined in FIG. 1, were conceived: Pathway 1a) hexanoyl-CoA synthetase polypeptide from *C. sativa* converts hexanoate to hexanoyl-CoA (FIG. 1, box 1a). A heterologous nucleic acid encoding a hexanoyl-CoA synthetase polypeptide from *C. sativa* was integrated into *S. cerevisiae*. The resulting cells were fed hexanoate to increase hexanoyl-CoA supply (FIG. 2).

Figure 2:
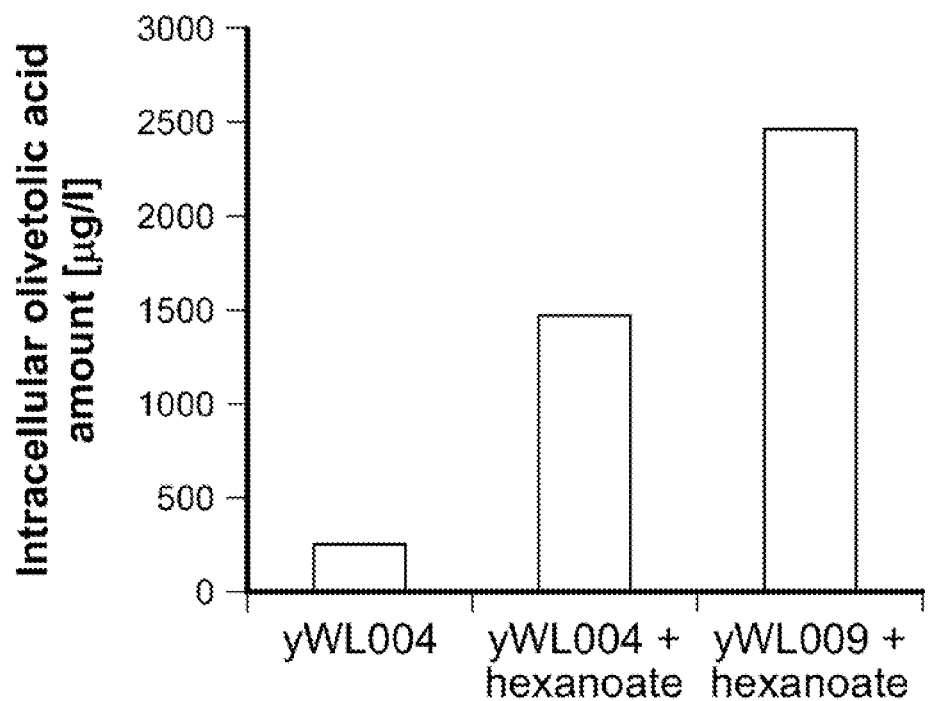
FIG. 2 depicts intracellular olivetolic acid production using pathway 1a and a tetraketide synthase (TKS) polypeptide/olivetolic acid cyclase (OAC) polypeptide.

FIG. 2: Intracellular olivetolic acid production using pathway 1a and TKS/OAC polypeptides. Yeast strains yWL004 expressing a heterologous nucleic acid encoding a TKS polypeptide and a heterologous nucleic acid encoding an OAC polypeptide and yWL009 expressing a heterologous nucleic acid encoding a TKS polypeptide, a heterologous nucleic acid encoding an OAC polypeptide, and a heterologous nucleic acid encoding a HCS polypeptide were grown in YPG and either in the absence or presence of 1 mM hexanoate for olivetolic acid production. Addition of hexanoate leads to six-fold increase in olivetolic acid production in strain yWL004, indicating an endogenous acyl-CoA ligase activity. Chromosomal integration of the heterologous nucleic acid encoding a hexanoyl-CoA synthetase polypeptide leading to strain yWL009 shows an additional two-fold increase in olivetolic acid production due to increased hexanoyl-CoA supply.

Biosynthesis of hexanoyl-CoA from fermentable sugars was increased by integrating pathway 1b, which comprises four enzymes encoding a reverse O-oxidation pathway that has been optimized in *E. coli* for production of hexanol (FIG. 1, box 1b) (Machado et al. 2012). LC-MS analysis confirmed that this pathway was also functional in *S. cerevisiae* and its activity is comparable to pathway 1a, since olivetolic acid yields were similar between the engineered strains yWL009 and yWL0013 (FIG. 3).

Figure 3:
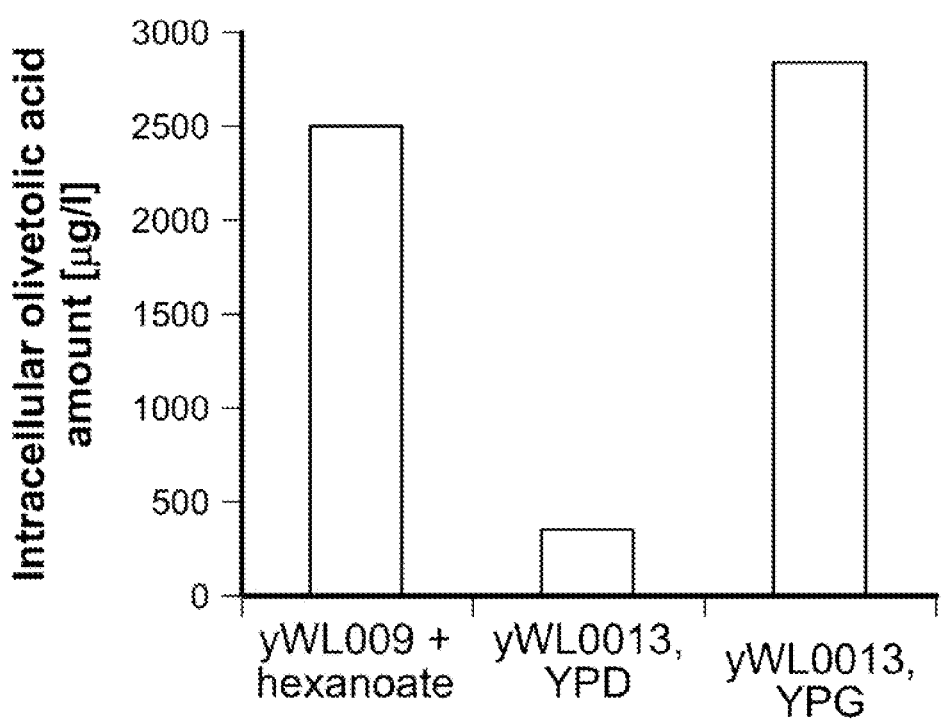
FIG. 3 depicts intracellular olivetolic acid production comparing pathway 1a and 1b.

FIG. 3: Intracellular olivetolic acid production comparing pathway 1a and 1b. Yeast strain yWL009 expressing a heterologous nucleic acid encoding a TKS polypeptide, a heterologous nucleic acid encoding an OAC polypeptide, and a heterologous nucleic acid encoding a HCS polypeptide was grown in producing conditions (YPG with 1 mM hexanoate) and compared to yWL013 expressing a heterologous nucleic acid encoding a TKS polypeptide, a heterologous nucleic acid encoding a OAC polypeptide, and the hexanoyl-CoA supply pathway 1b grown in non-producing (YPD) as well as producing (YPG) conditions. Chromosomal integration of the hexanoyl-CoA pathway yields similar levels in olivetolic acid production as strain yWL009 when grown in YPG with 1 mM hexanoate.

TABLE 2

List of strains used in this study

| | |
|---|---|
| yWL004 | Cen.PK2, ACC1::TKS-OAC, tHMGR::MvaE/S, |
| yWL009 | Cen.PK2, ACC1::TKS-OAC, tHMGR::MvaE/S, URA3::HCS |
| yWL0013 | CenPK2, ACC1::TKS-OAC, URA3::HexCoA |

Codon optimized genes were synthesized and used in this study for the polypeptides listed in Table 3.

TABLE 3

List of polypeptides used in this study

| Polypeptide | Function | Original host |
|---|---|---|
| BktB | β-ketothiolase | *Ralstonia eutropha* |
| PaaH1 | 3-Hydroxyacyl-CoA dehydrogenase | *R. eutropha* |
| Crt | Crotonase | *Clostridium acetobutylicum* |
| Ter | Trans-2-enoyl-CoA reductase | *Treponema denticola* |
| HCS | Hexanoyl-CoA synthetase | *Cannabis sativa* |
| ERG10 | Acetyl-CoA acetyltransferase | *Saccharomyces cerevisiae* |
| ERG13 | HMG-CoA synthase | *S. cerevisiae* |
| tHMG1 | HMG-CoA reductase | *S. cerevisiae* |
| ERG12 | Mevalonate kinase | *S. cerevisiae* |
| IDI1 | Isopentenyl diphosphate:dimethylallyl diphosphate isomerase | *S. cerevisiae* |
| ERG20 | Farnesylpyrophosphate synthetase | *S. cerevisiae* |
| MvaE | acetyl-CoA acetyltransferase/HMG-CoA reductase | *Escherichia coli* |
| MvaS | HMG-CoA synthase | *E. coli* |
| TKS | Tetraketide Synthase (Type III PKS) | *C. sativa* |
| OAC | Olivetolic acid cyclase | *C. sativa* |
| GOT | geranyl pyrophosphate:olivetolate geranyltransferase | *C. sativa* |
| $\Delta^9$-THCAS | $\Delta^9$-tetrahyrdocannabinoidic acid synthase | *C. sativa* |
| CBDAS | cannabidiolic acid synthase | *C. sativa* |
| DXS | 1-deoxy-D-xylulose-5-phosphate synthase gene | *E. coli* |
| IspC | 1-deoxy-D-xylulose 5-phosphate reductoisomerase | *E. coli* |
| IspD | 2-C-methyl-D-erythritol 4-phosphate cytidylyltransferase | *E. coli* |
| IspE | 4-diphosphocytidyl-2-C-methylerythritol kinase | *E. coli* |
| IspF | 2C-methyl-D-erythritol 2,4-cyclodiphosphate synthase | *E. coli* |
| IspG | 4-hydroxy-3-methylbut-2-en-1-yl diphosphate synthase | *E. coli* |
| IspH | 4-hydroxy-3-methylbut-2-enyl diphosphate reductase | *E. coli* |
| IDI | Isopentenyl diphosphate (IPP) isomerase | *E. coli* |
| IspA* | mutated FPP synthase (S81F) for GPP production | *E. coli* |
| AflA | Hexanoyl-CoA synthase, subunit A | *Aspergillus parasiticus* |
| AflB | Hexanoyl-CoA synthase, subunit B | *A. parasiticus* |
| SCFA-TE | Short chain fatty acyl-CoA Thioesterase | Various microbes |

Example 2—Synthesis of Olivetolic Acid or Derivatives Thereof or Cannabinoids or Derivatives Thereof Multiple polypeptides in pathway 1b require NADH as a co-factor. In order to maximize flux through pathway 1b, other biosynthetic pathways that compete for NADH supply are modified (FIG. 1, Box 2). One target can be the ethanol pathway, mediated by various alcohol dehydrogenase polypeptides, but may also include other pathways that consume NADH, such as the glycerol biosynthesis pathway.

Another route conceived towards hexanoyl-CoA is described in pathway 1c: The alfatoxin biosynthetic gene cluster (iterative type I PKS) encodes a fatty acid synthase-based mechanism (FasA and FasB) for production of hexanoyl-CoA. In some embodiments, a heterologous nucleic acid encoding a thioesterase polypeptide and a heterologous nucleic acid encoding a CoA ligase polypeptide similar to a C6-tolerant thioesterase polypeptide (see BMC Biochem. 2011 Aug. 10; 12:44. doi: 10.1186/1471-2091-12-44) and a heterologous nucleic acid encoding a HCS polypeptide are expressed to facilitate release of hexanoyl-ACP and activate free hexanoate to its acyl-CoA compound. Additionally, various type II PKS biosynthetic pathways (e.g. benastatin, R1128) contain a FabH-like KSIII (e.g. BenQ, ZhuH), AT and ACP component, which are crucial for providing and selecting the rare hexanoate PKS starter unit. Lastly, the type I PKS pathway for reveromycin biosynthesis encodes the fatty acyl-CoA ligase RevS polypeptide and the FabH-like KASIII component RevR polypeptide, which are suggested to provide hexanoyl-CoA via fatty acid degradation as well as de novo fatty acid biosynthesis.

To avoid competitive consumption of hexanoyl-CoA via β-oxidation, the fatty acid degradation pathway is engineered to have lowered activity. Alternatively, yeast are grown in presence of oleic acid to avoid competition for fatty acids as energy source.

Figure 4:
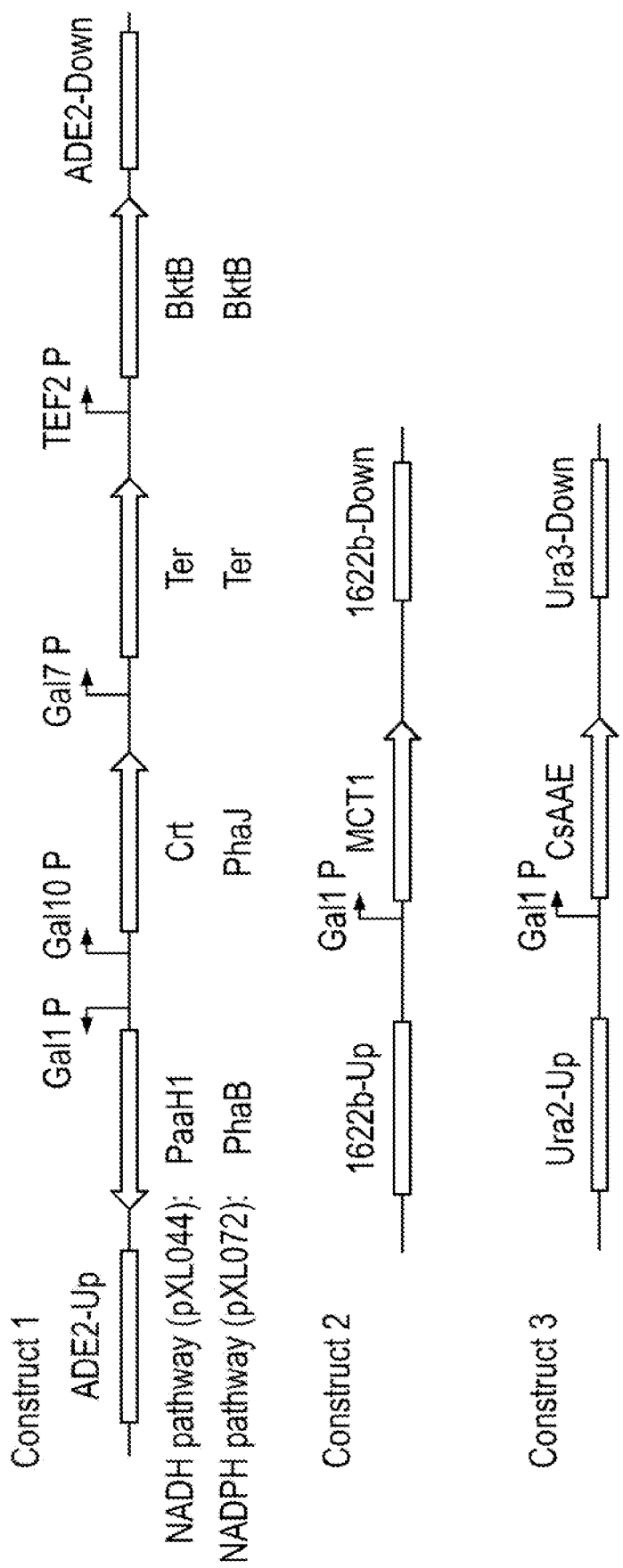
FIG. 4 provides schematic depictions of 3 expression constructs for olivetolic acid production.

The pathway of four genes encoding the NADH pathway for hexanoyl-CoA production, including polypeptides PaaH1, Crt, Ter, and BktB, was constructed under the control of Gal1, Gal10, Gal7, and TEF2 promoters, respectively. FIG. 4. The whole cassette was inserted between the upstream and downstream homology region of ADE2 and was integrated into the genome of S. cerevisiae using CRISPR/Cas9 to generate yXL001 (using Construct 1/pXL044 as shown in FIG. 4). The pathway of four genes encoding the NADPH pathway (including PhaB, PhaJ, Ter, and BktB polypeptides) was introduced into to S. cerevisiae in the same way to generate yXL002 (using Construct 1/pXL072 as shown in FIG. 4). The MCT1 gene under the control of Gal1 promoter flanked by the 1622b homology region (Construct 2; FIG. 4) was introduced into the genome of yXL001 and yXL002 using CRISPR/Cas9 to generate yXL003 and yXL004 (FIG. 4).

Figure 5:
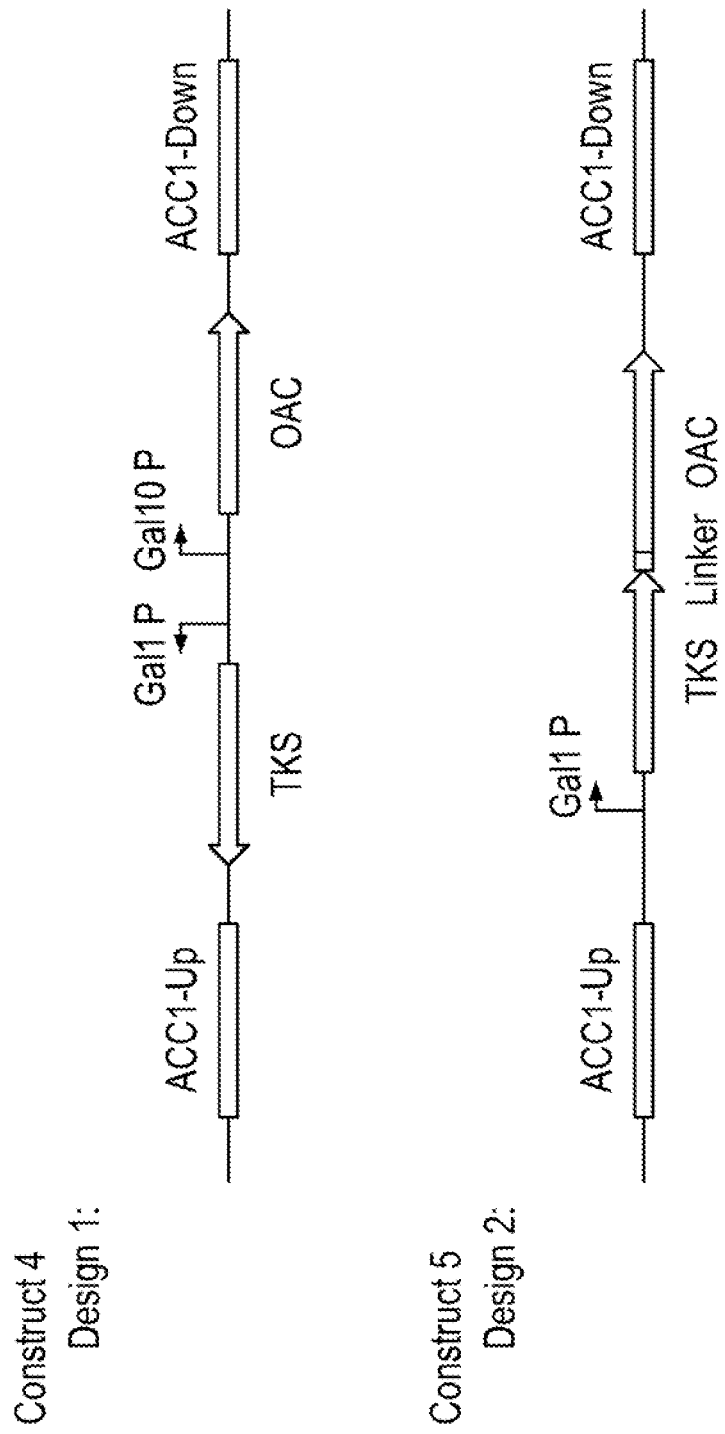
FIG. 5 provides schematic depictions of 2 expression constructs for olivetolic acid production.
Figure 9:
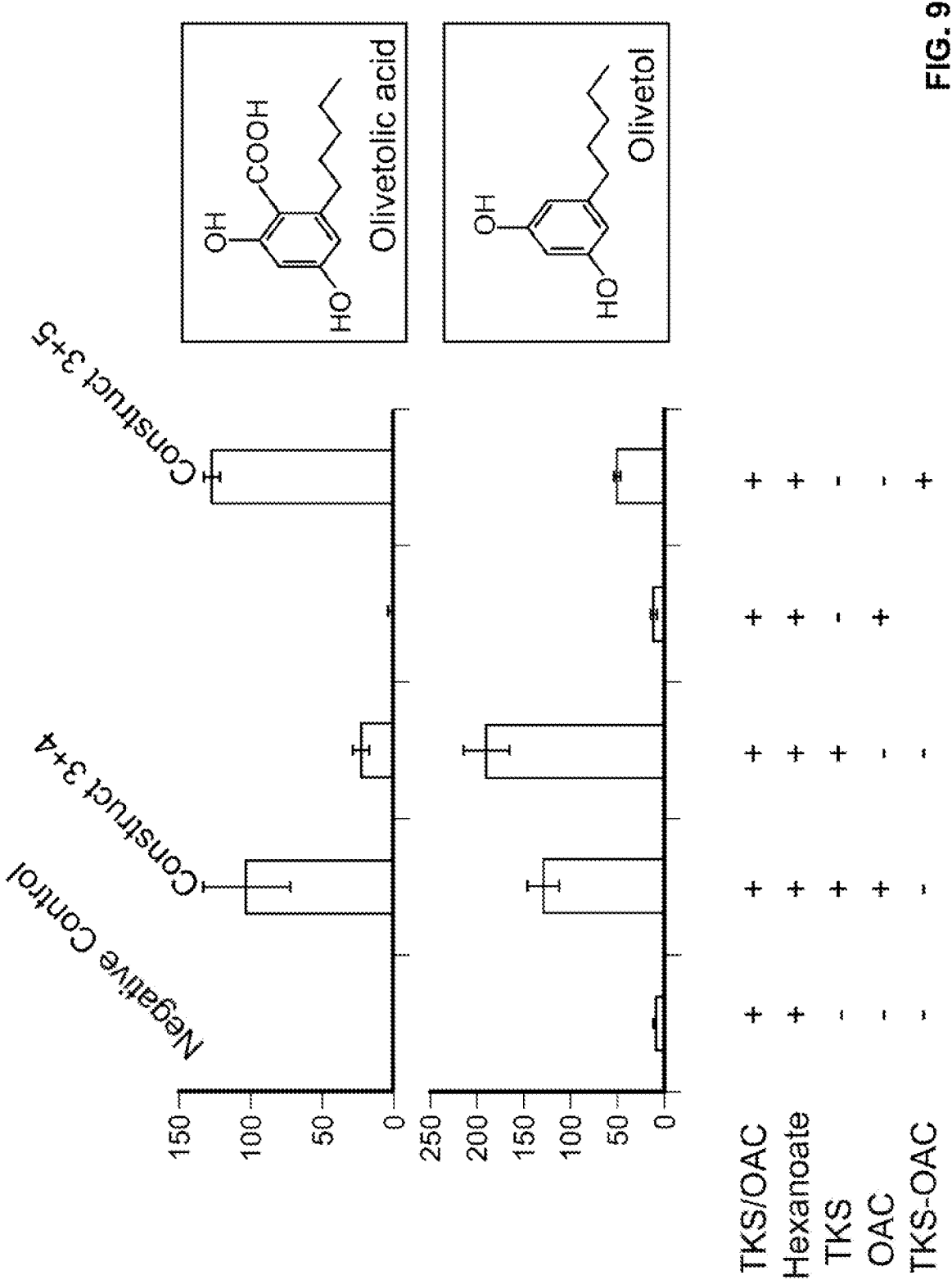
FIG. 9 depicts production of olivetolic acid using expression constructs 3+4 or expression constructs 3+5.
Figure 10:
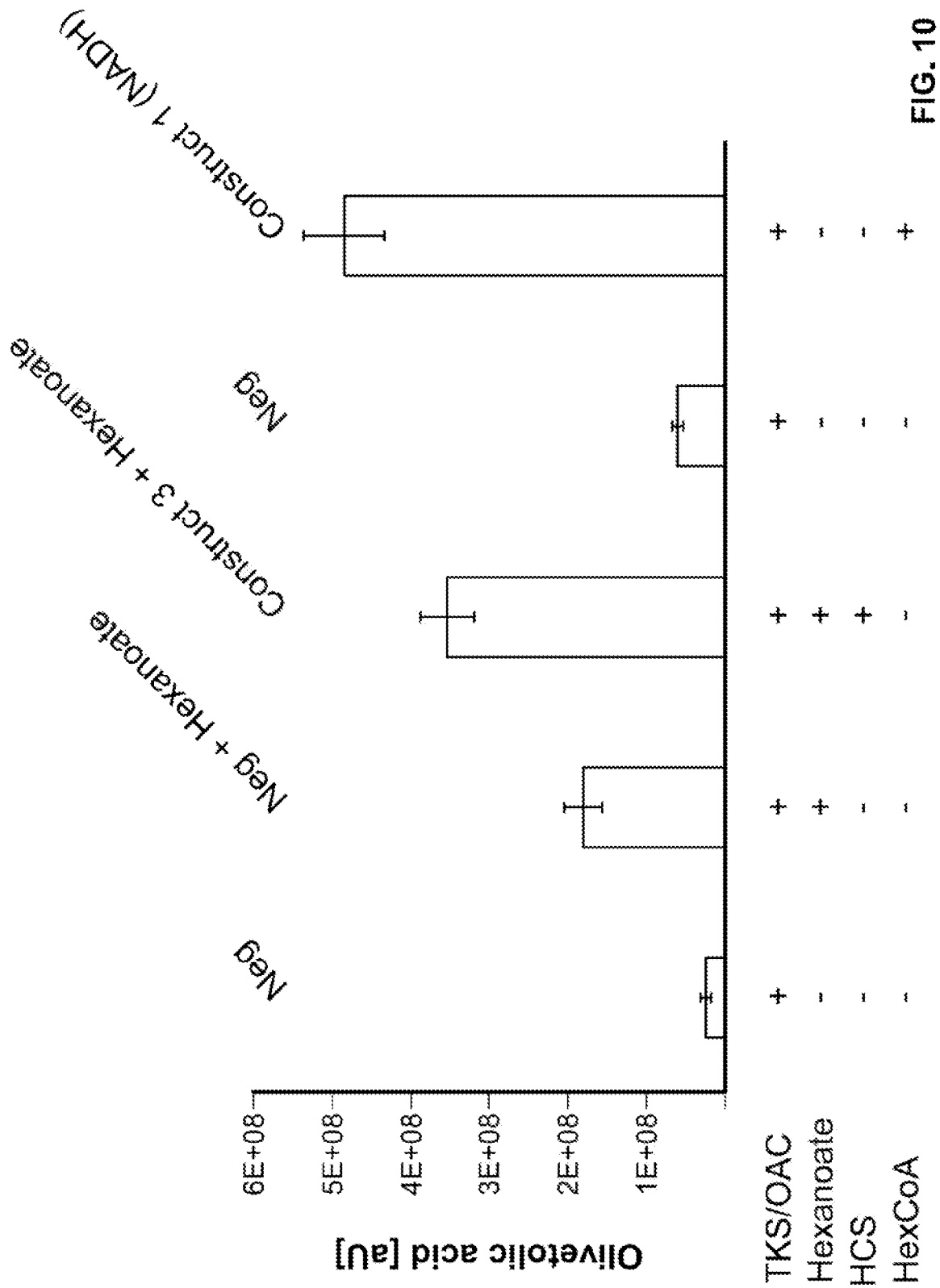
FIG. 10 depicts production of olivetolic acid using Construct 3 and culturing the cells in medium comprising hexanoate; or using Construct 1.

A cassette encoding TKS and OAC genes under the control of Gal1 and Gal10 promoters flanked by ACC1 homology region (Construct 4; FIG. 5) was introduced into the genome of yXL003 and yXL004 using CRISPR/Cas9 to generate yXL005 and yXL006. A heterologous nucleic acid encoding a TKS-OAC fusion polypeptide under the control of a Gal1 promoter (Construct 5; FIG. 5) was introduced into yXL003 and yXL004 to generate yXL007 and yXL008. The resulting strains were inoculated into 10 mL YP medium supplemented with 2% dextrose. After an overnight culture at 30° C. and centrifugation at 3,000×g for 5 mins, the pellet was resuspended into YP medium supplemented with 2% galactose. After two days expression, the culture supernatant was extracted with equal volume of ethyl acetate, and, after evaporation and filtration, the samples were analyzed by LC-MS, which showed the production of a significant amount of olivetolic acid (FIG. 9 and FIG. 10).

CsAAE (Construct 3; FIG. 4), TKS, and OAC genes (Construct 4; FIG. 5) were introduced into the genome of S. cerevisiae using CRISPR/Cas9 to generate yXL009, which can produce higher level of olivetolic acid in the presence of exogenously supplied hexanoate (FIG. 11).

Figure 12:
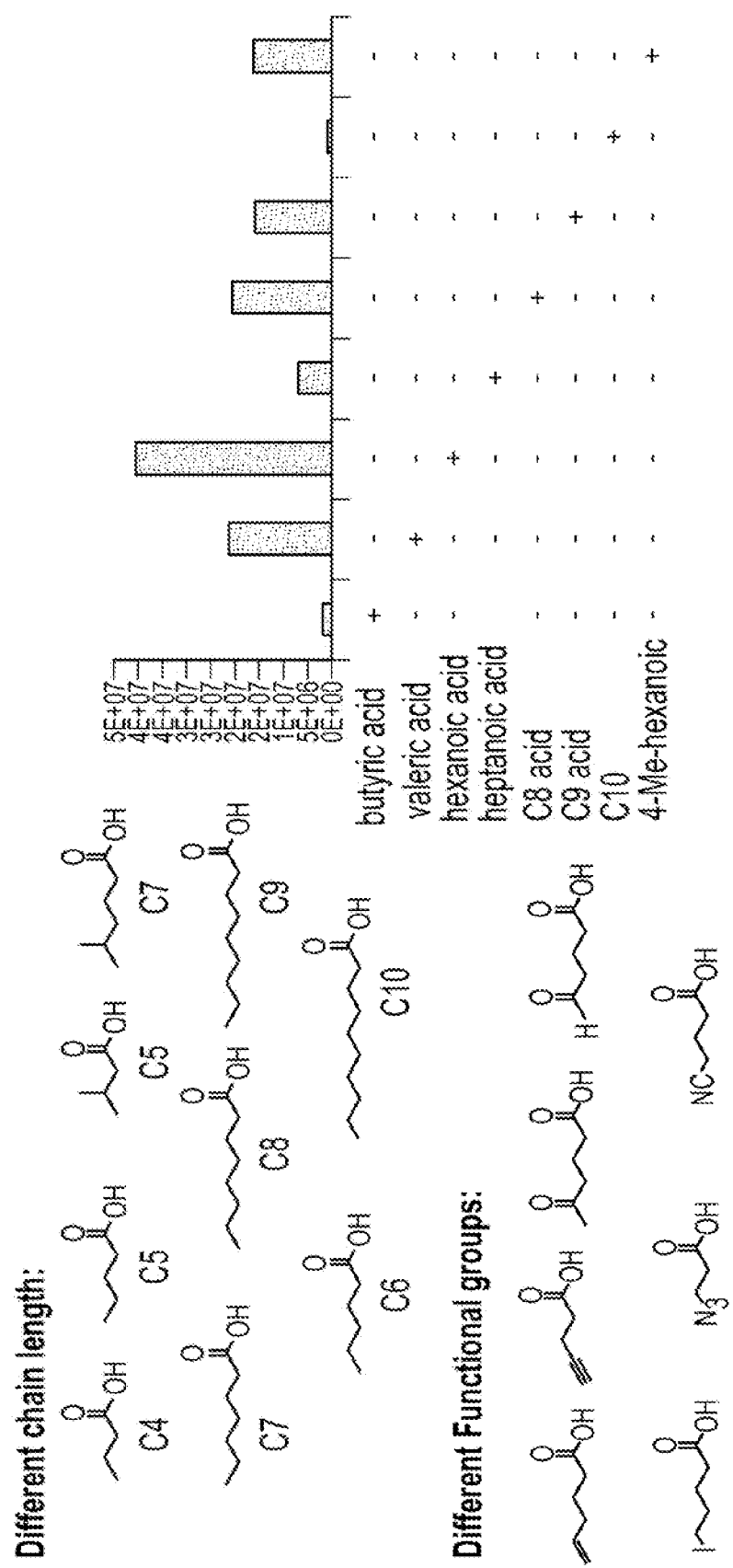
FIG. 12 depicts various representative carboxylic acids with various functional groups that can be used as substrate for the biosynthesis of olivetolic acid or cannabinoid derivatives.

In addition, by supplementing the growth medium with various aliphatic acids, from $C_4$-$C_{10}$, various olivetolic acid derivatives can be produced from yXL009 (FIG. 11 and FIG. 12). Some of the olivetolic acid derivatives can be further modified by biological or chemical means to covalently attach to other compounds. For example, click chemistry can be performed on the olivetolic derivative containing alkyne functional group. The olivetolic derivative is dissolved in biology grade dimethyl sulfoxide (DMSO) and treated with a DMSO solution of crosslinker containing an azide group (1.0 equiv.), TBTA (DMSO: tBuOH 1:1), $CuSO_4$ $5H_2O$, sodium ascorbate and HEPES-KOH pH: 7.0 (final HEPES-KOH≈250 mM). The reaction is placed on a water bath at 37° C. for 12 to 16 hours. Liquid chromatograph-mass spectrometry (LC-MS) analysis of the reaction mixture shows reaction completion after 16 hours to obtain the further modified olivetolic acid.

Figure 7:
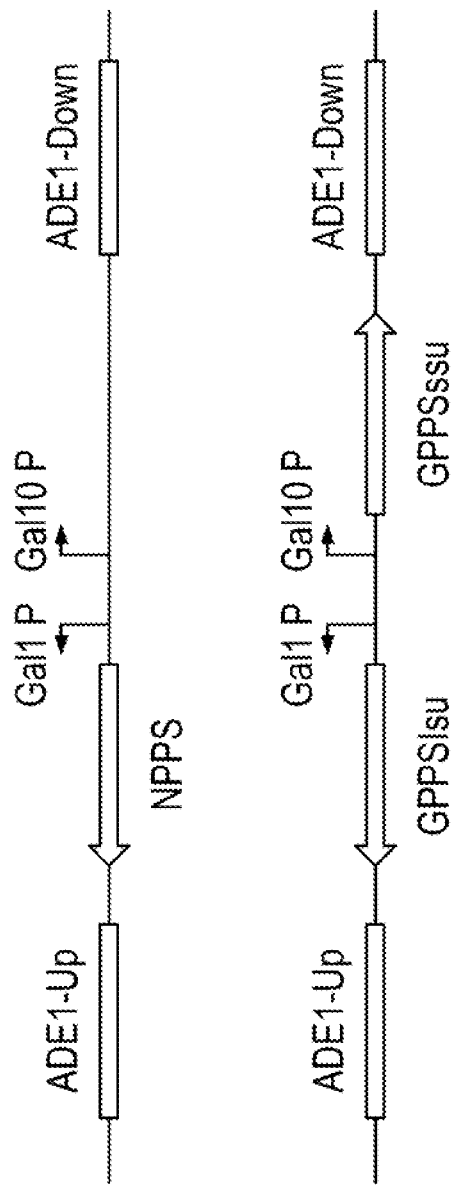
FIG. 7 provides schematic depictions of 2 expression constructs for GPP production.
Figure 8:
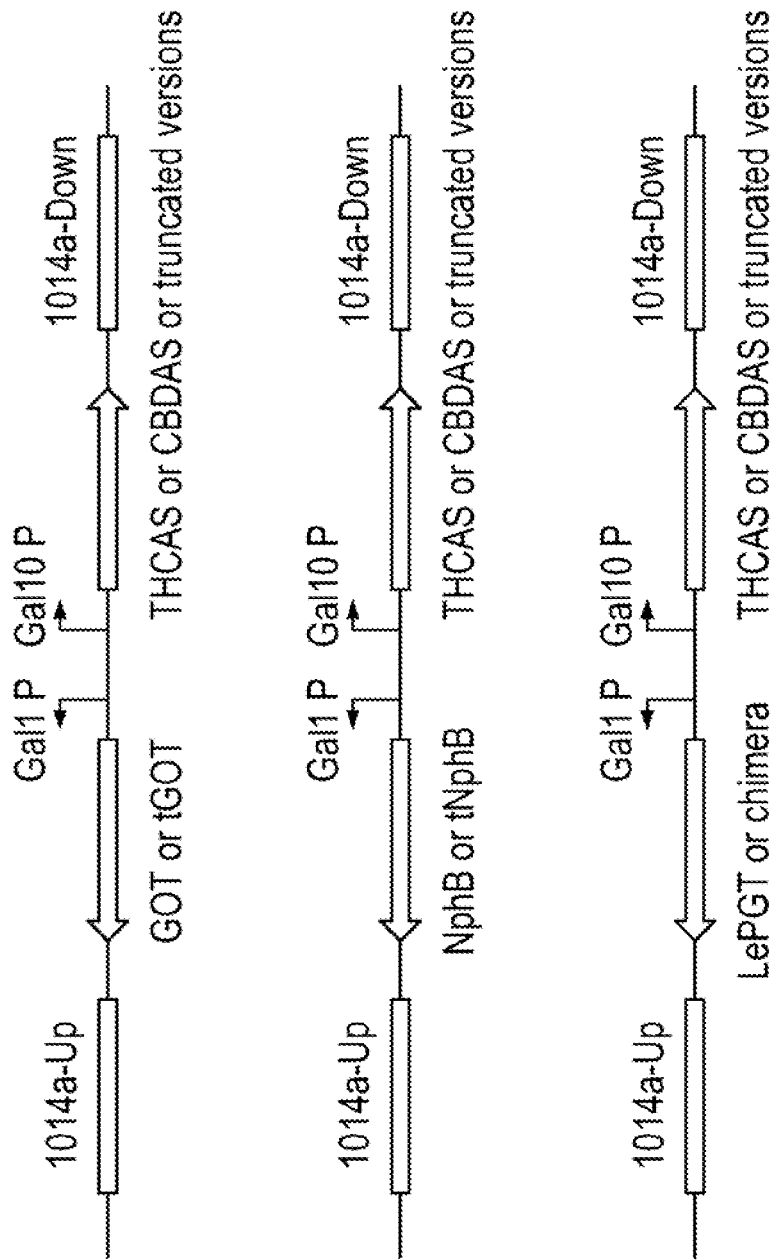
FIG. 8 provides schematic depictions of 3 expression constructs for cannabinoid production.
Figure 13:
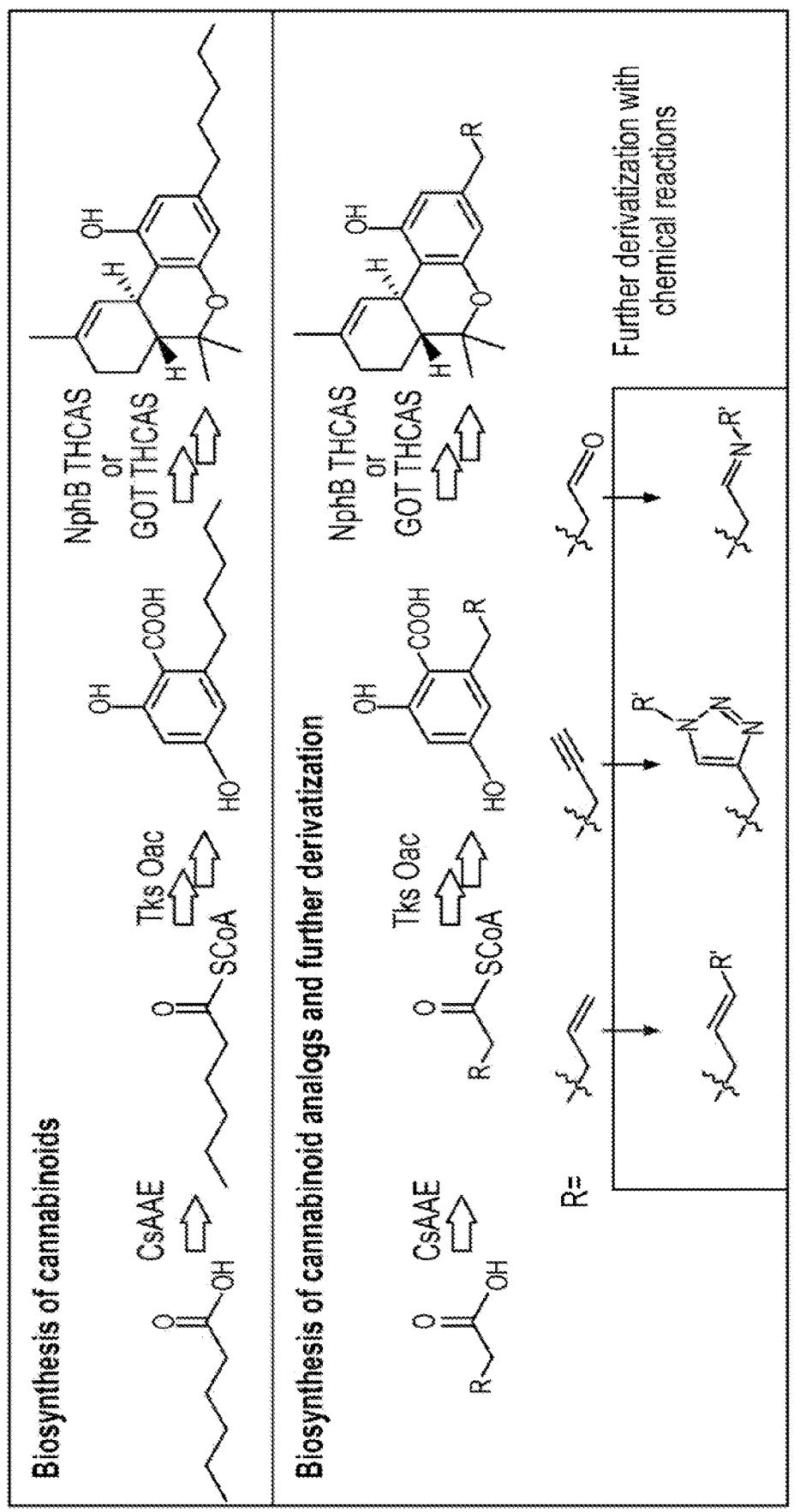
FIG. 13 depicts various representative cannabinoid derivatives that can be generated by feeding different acids and the further derivatization of those derivatives with chemical reactions.
Figure 14:
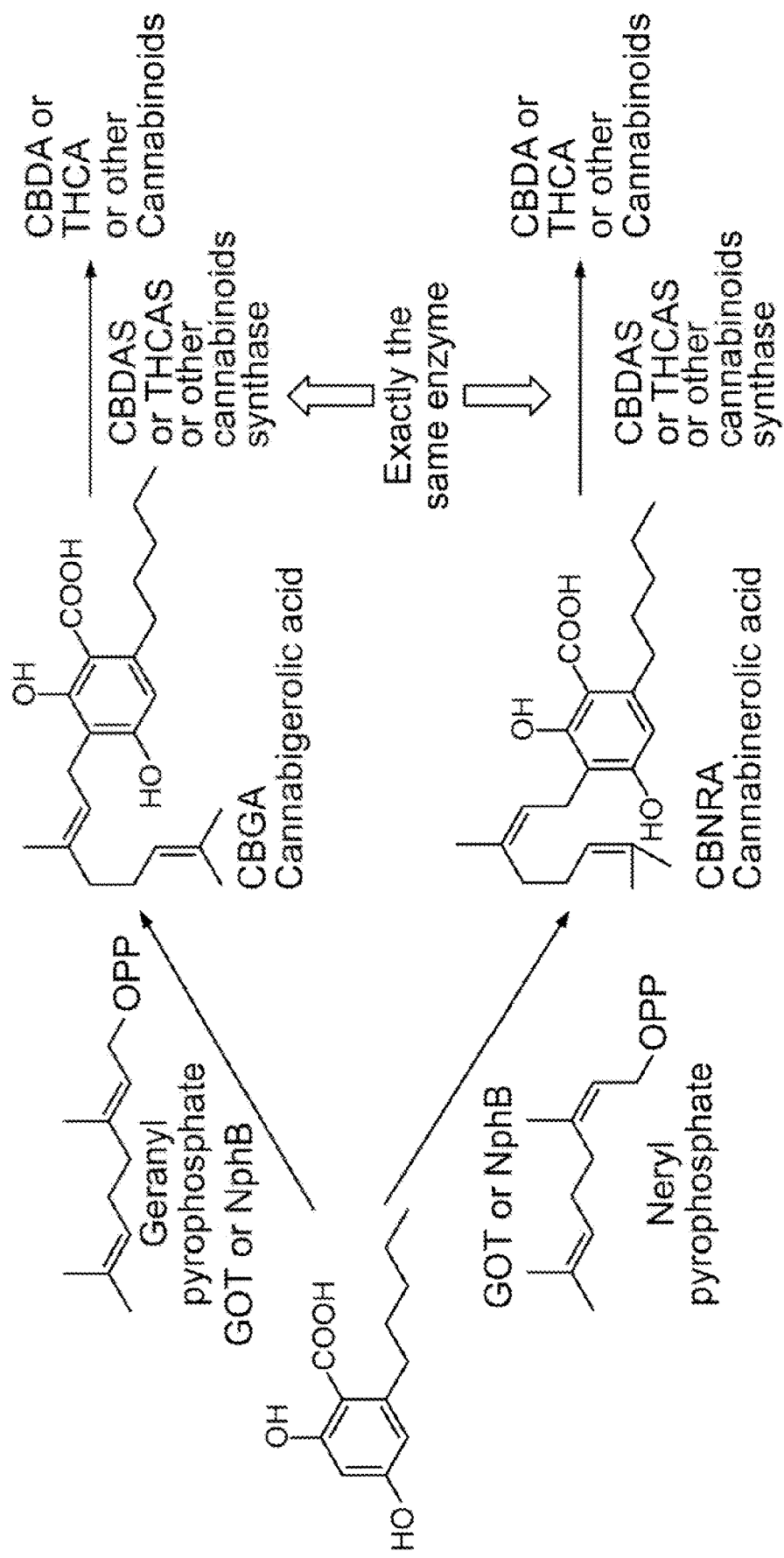
FIG. 14 depicts cannabinoid biosynthetic pathways utilizing neryl pyrophosphate (NPP) or GPP.
Figure 15:
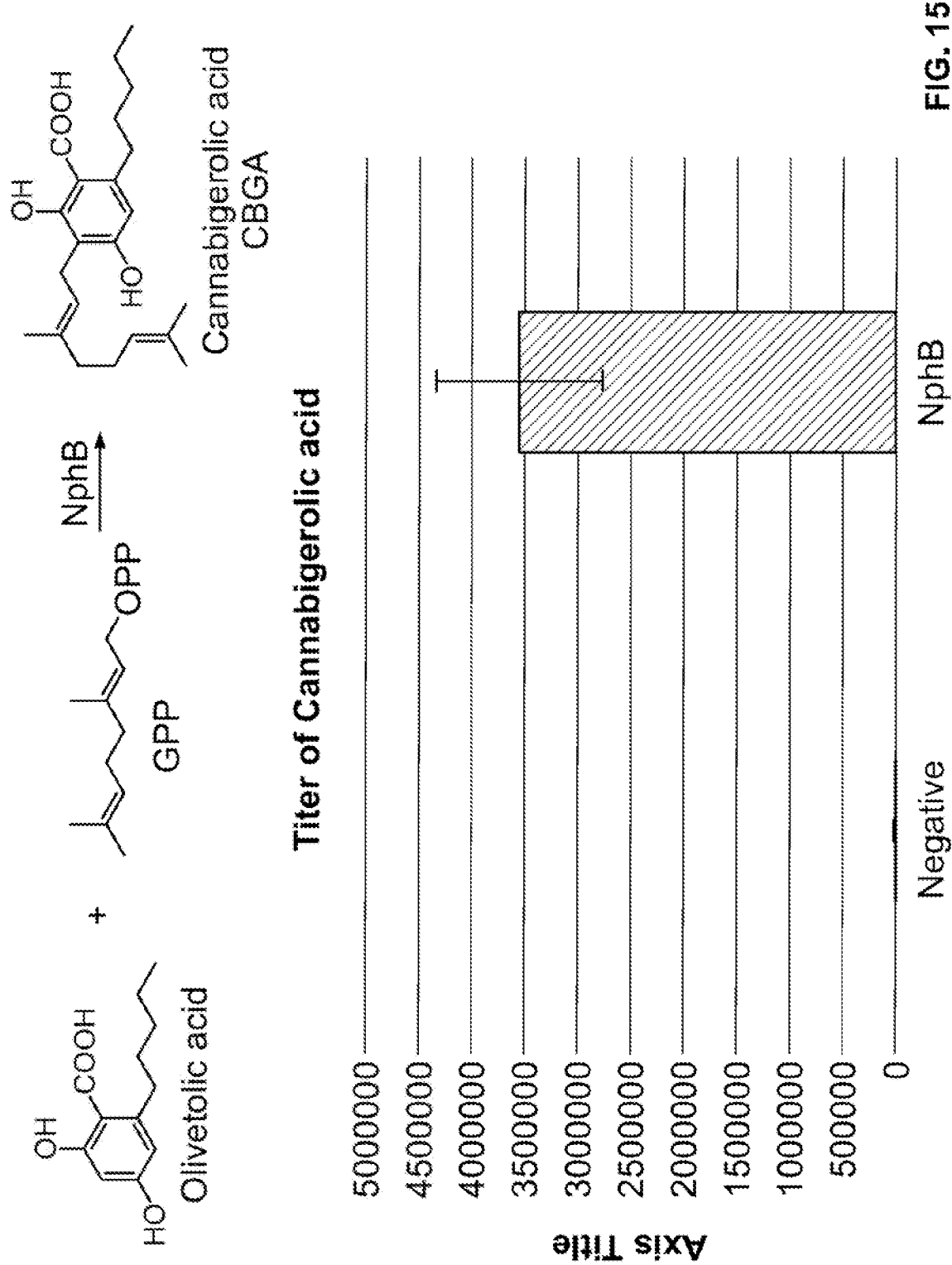
FIG. 15 depicts generation of cannabigerolic acid (CBGA) using a NphB polypeptide and the substrates olivetolic acid and GPP.

The GPPS large subunit (GPPS1su) and small subunit (GPPSssu) genes from Cannabis sativa under the control of Gal1 and Gal10 promoters flanked by ADE1 homology region (Construct 10; FIG. 7) were introduced into yXL008 and yXL009 to generate yXL010 and yXL011. A cassette encoding a NphB polypeptide and a THCAS polypeptide under the control of Gal1 and Gal10 promoters flanked by 1014a homology region (Construct 12; FIG. 8) was introduced into the genome of yXL010 and yXL0l1 to generate yXL012 and yXL013 using CRISPR/Cas9. The resulting strains were inoculated into 10 mL YP medium supplemented with 2% dextrose. After an overnight culture at 30° C. and centrifugation at 3,000×g for 5 mins, the pellet was resuspended into YP medium supplemented with 2% galactose. After two days expression, the culture supernatant was extracted with equal volume of ethyl acetate, and, after evaporation and filtration, the samples were analyzed by LC-MS, which showed that the overexpression of NphB in yXL010 resulted in the production of cannabigerolic acid (FIGS. 14 and 15). In the presence of a THCAS polypeptide, the cannabigerolic acid was transformed into THCA or into THC. With yXL013, $C_4$-$C_{10}$ acids were added to the expression medium, resulting in the production of cannabigerolic acid derivatives, which were then modified by a THCAS polypeptide to produce THCA or THC derivatives. Those derivatives can then be further modified by chemical reactions (FIG. 13).

Example 3—Synthesis of Cannabinoid Precursors, Cannabinoids, or Derivatives of the Foregoing To recreate cannabinoid production in microorganisms, chassis S. cerevisiae strains were developed containing metabolic pathways for the production of (1) GPP through the mevalonate (Mva) pathway, (2), olivetolic acid or derivatives, (3) CBGA or derivatives, and (4) different cannabinoids or cannabinoid derivatives produced by cannabinoid synthase polypeptides.

Production of GPP

Figure 16:
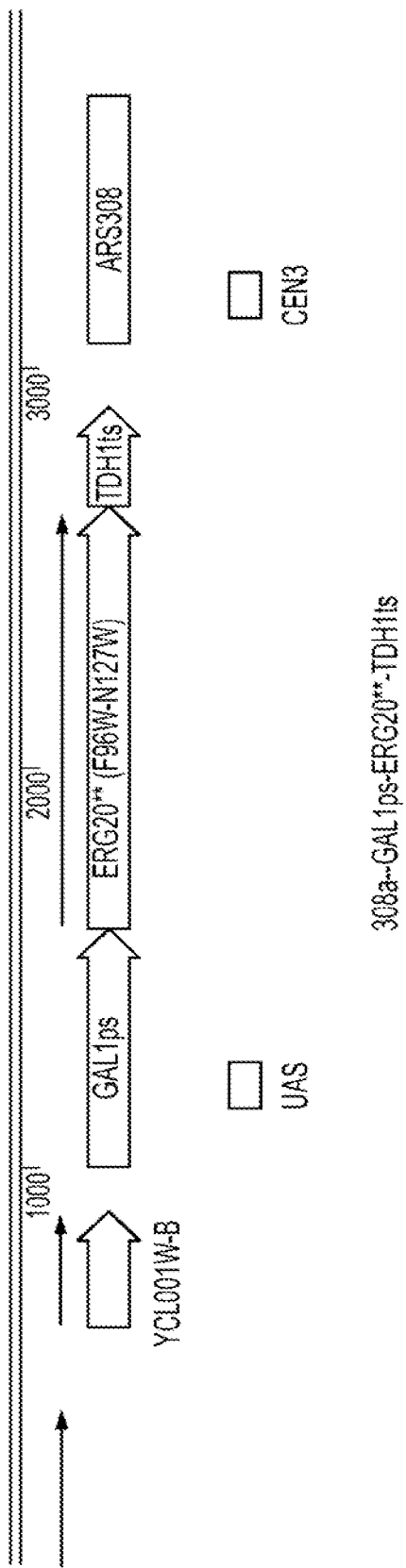
FIG. 16 depicts an expression construct to produce GPP.

A GPP-overproducing strain, GTY23, was produced by overexpressing Mva pathway genes and introducing a repressible promoter on ERG9. A previously described ERG20 F96W-N127W mutant, ERG20mut, was added to provide a source of GPP precursor in the cell (FIG. 16). This strain was used to screen GOT polypeptide candidates.

Production of Olivetolic Acid or Derivatives Thereof

Figure 17:
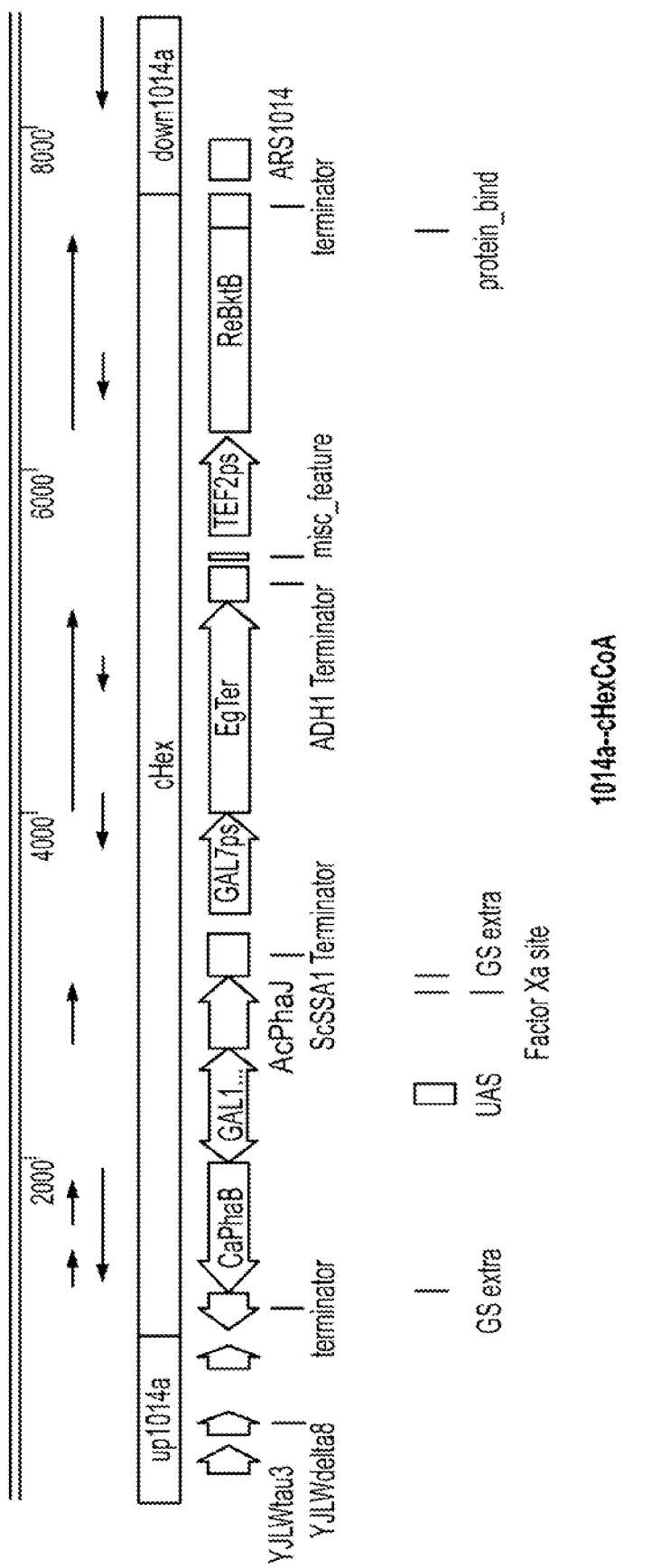
FIG. 17 depicts an expression construct to produce hexanoyl-CoA and/or hexanoate.
Figure 18:
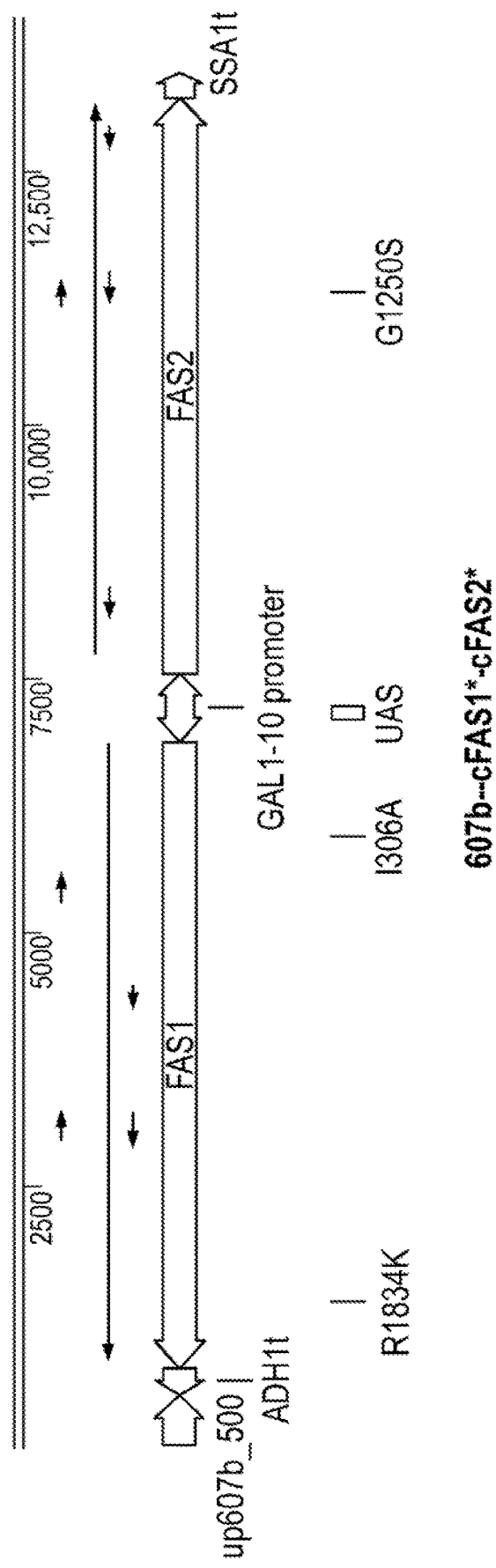
FIG. 18 depicts an expression construct to produce hexanoyl-CoA and/or hexanoate.
Figure 19:
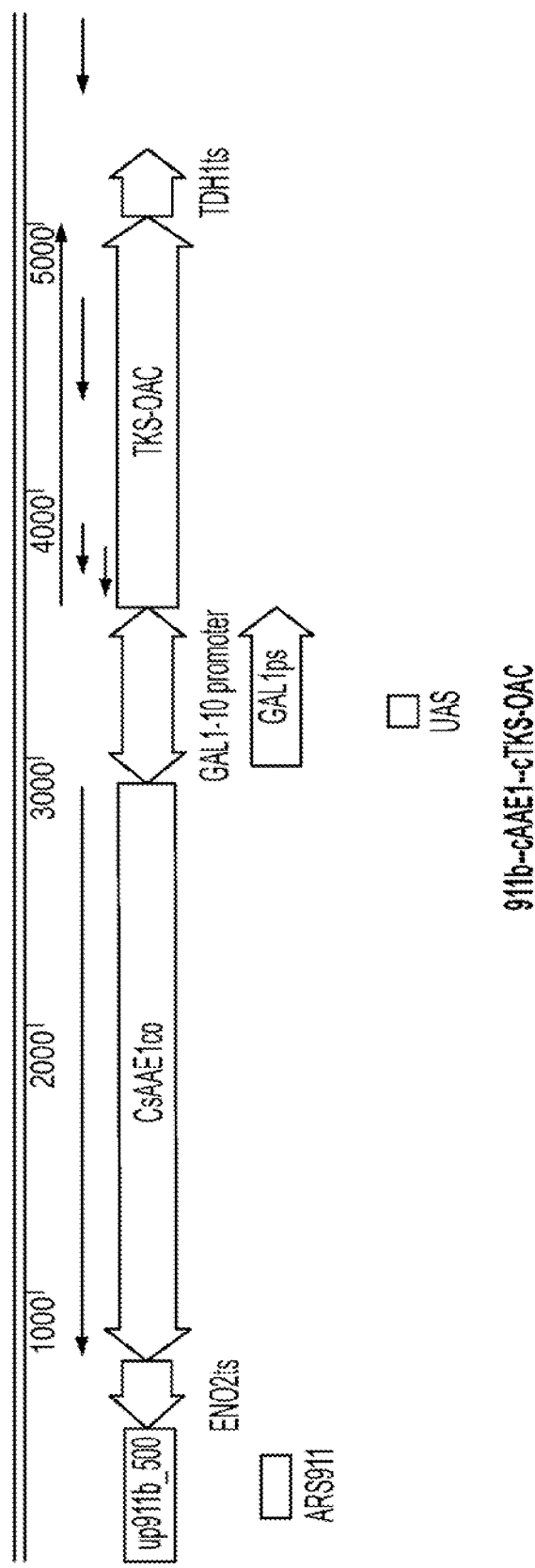
FIG. 19 depicts an expression construct to produce olivetolic acid.

Olivetolic acid was produced from sugar by introducing genes CsTKS and CsOAC, and pathways to produce hexanoyl-CoA. Pathways for the production of hexanoate and hexanoyl-CoA are known in the art (e.g., Gajewski et al, "Engineering fungal de novo fatty acid synthesis for short chain fatty acid production," Nature Communications 2017). To produce olivetolic acid or its derivatives, rather than using hexanoyl-CoA pathways, a previously reported acyl-CoA ligase polypeptide, such as a CsAAE1 or CsAAE3 polypeptide, was introduced and exogenously fed cells hexanoate or a carboxylic acid other than hexanoate (FIGS. 17-19). These pathways allow for the production of non-naturally occurring cannabinoids.

Production of CBGA

Figure 6:
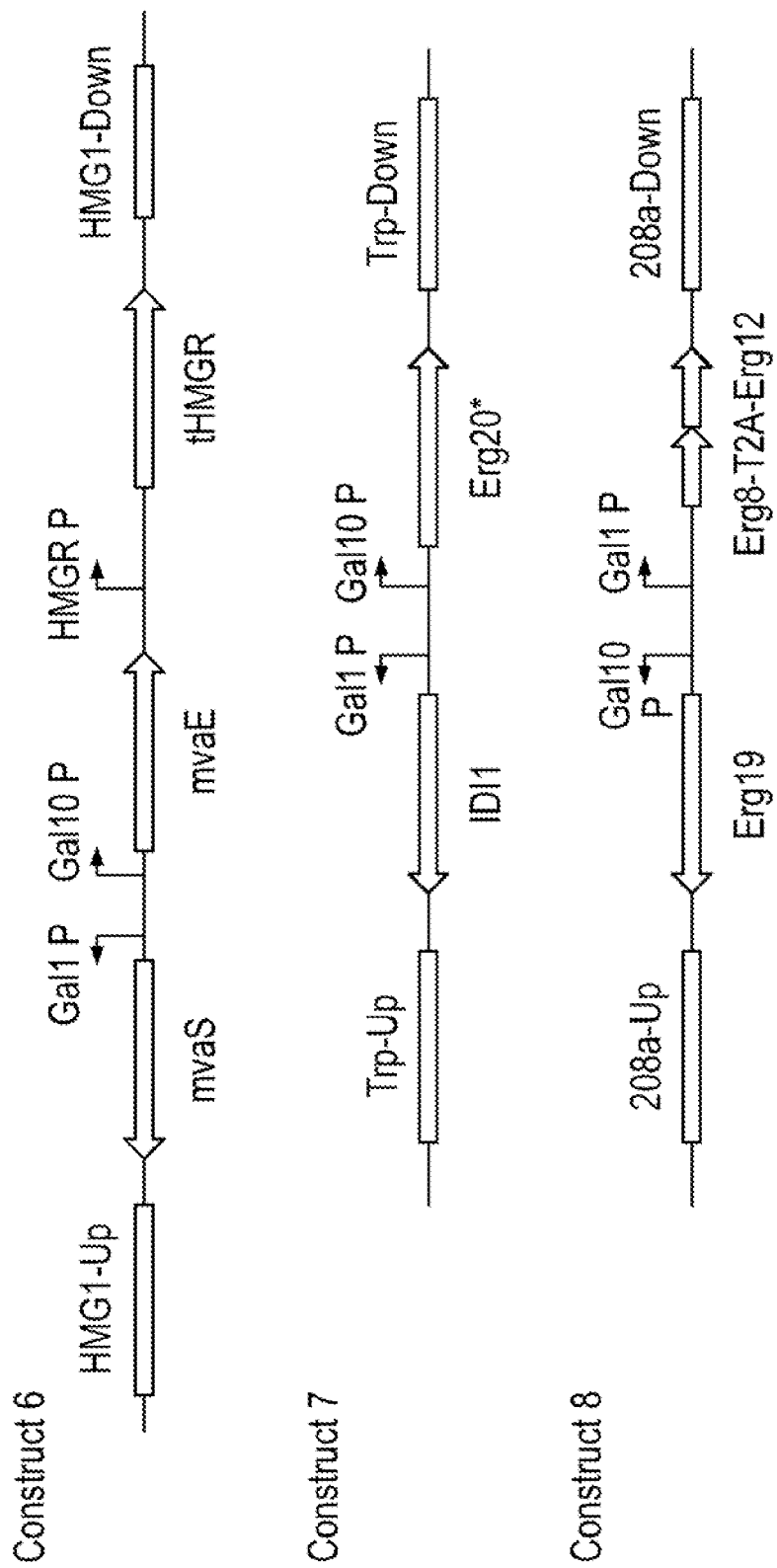
FIG. 6 provides schematic depictions of 3 expression constructs for geranyl pyrophosphate (GPP) production.
Figure 20:
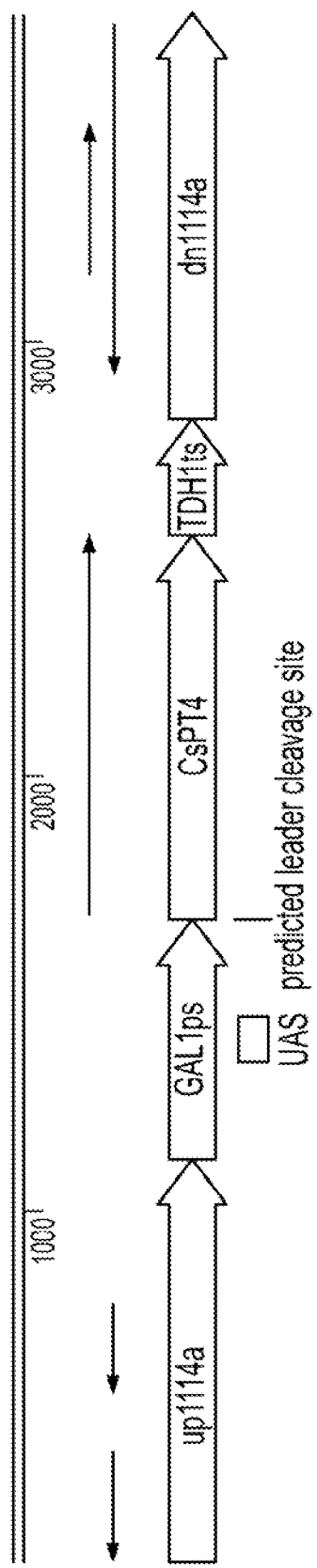
FIG. 20 depicts an expression construct to produce CBGA.
Figure 21:
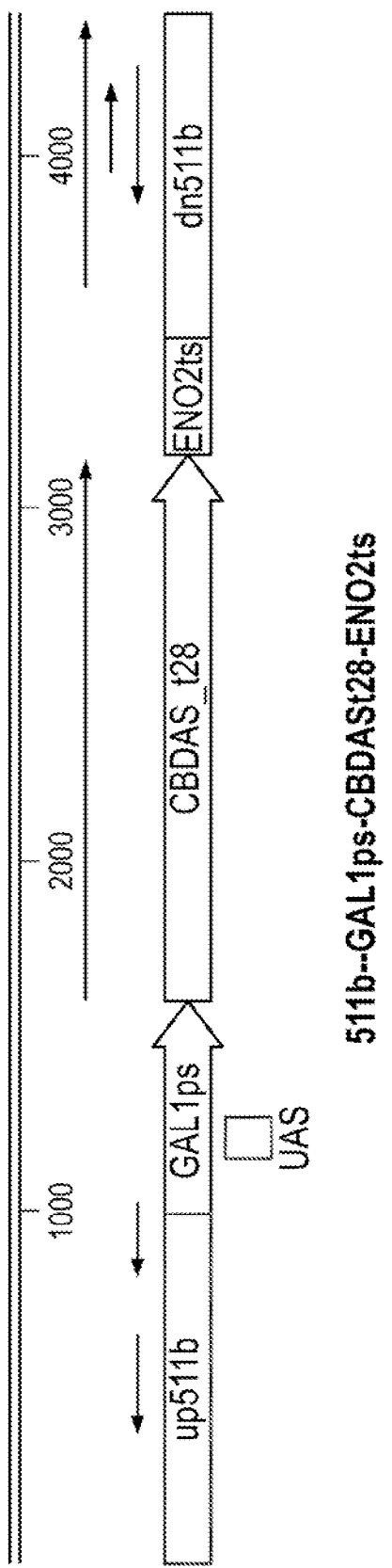
FIG. 21 depicts an expression construct to produce cannabidiolic acid (CBDA).
Figure 22:
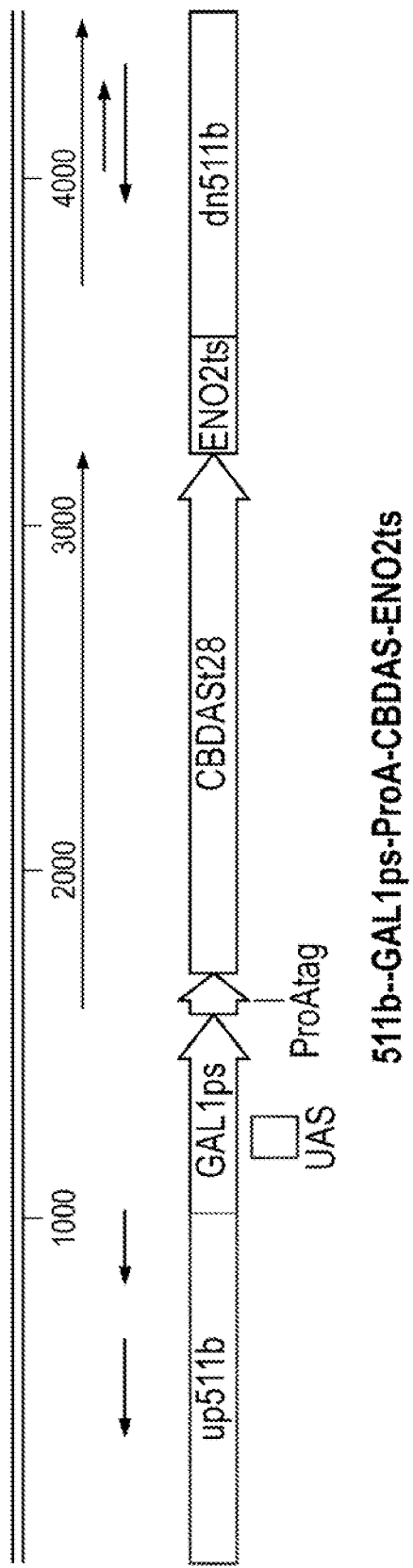
FIG. 22 depicts an expression construct to produce CBDA.
Figure 23:
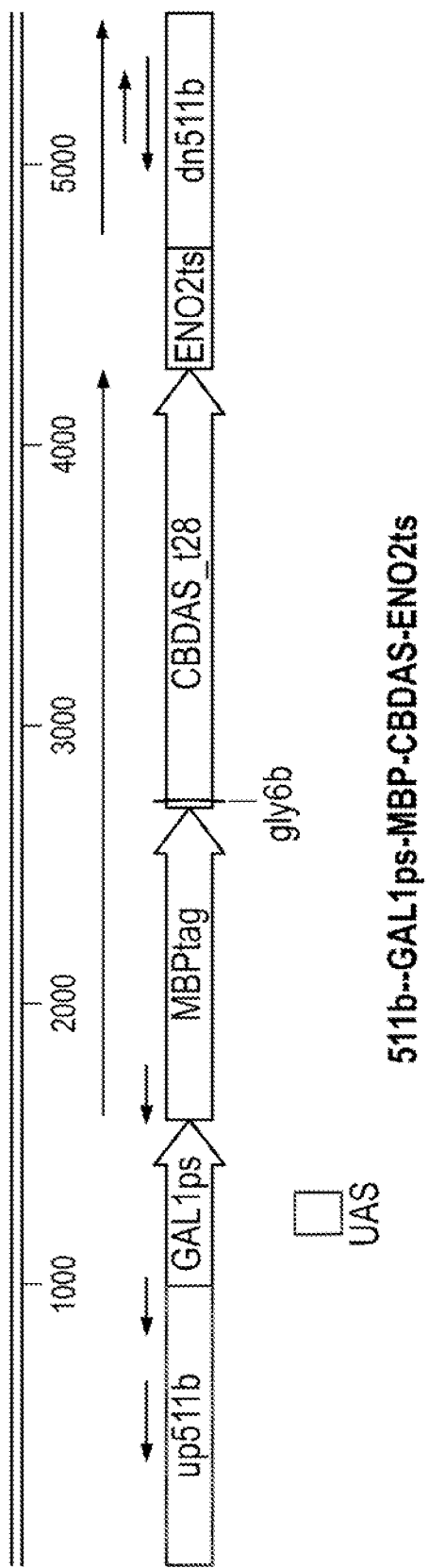
FIG. 23 depicts an expression construct to produce CBDA.
Figure 24:
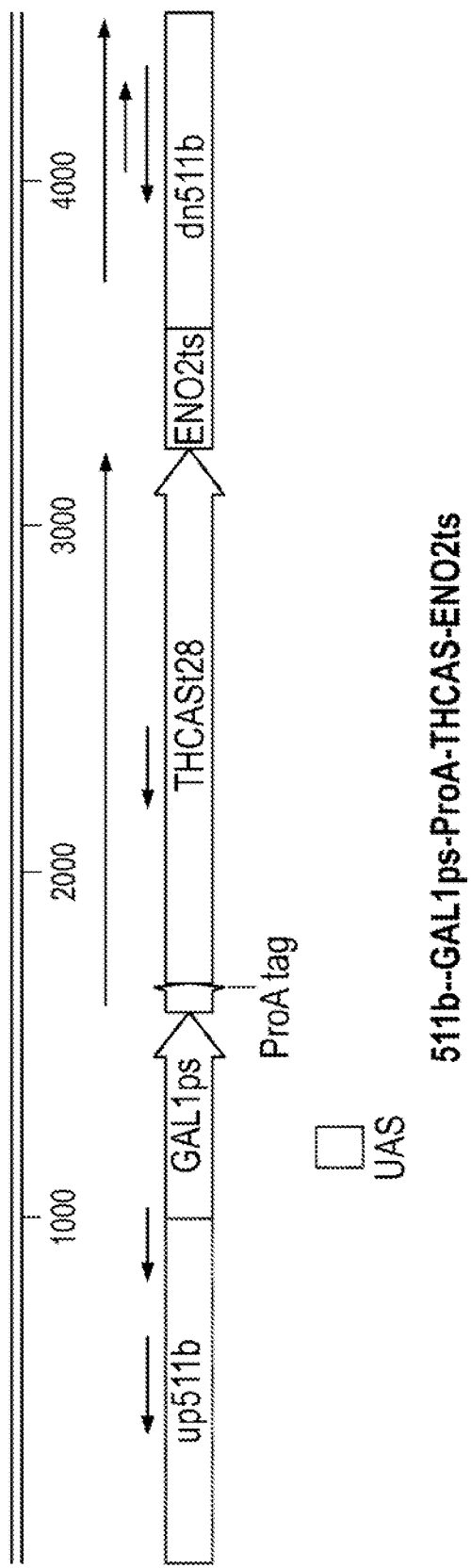
FIG. 24 depicts an expression construct to produce tetrahydrocannabinolic acid (THCA).
Figure 25:
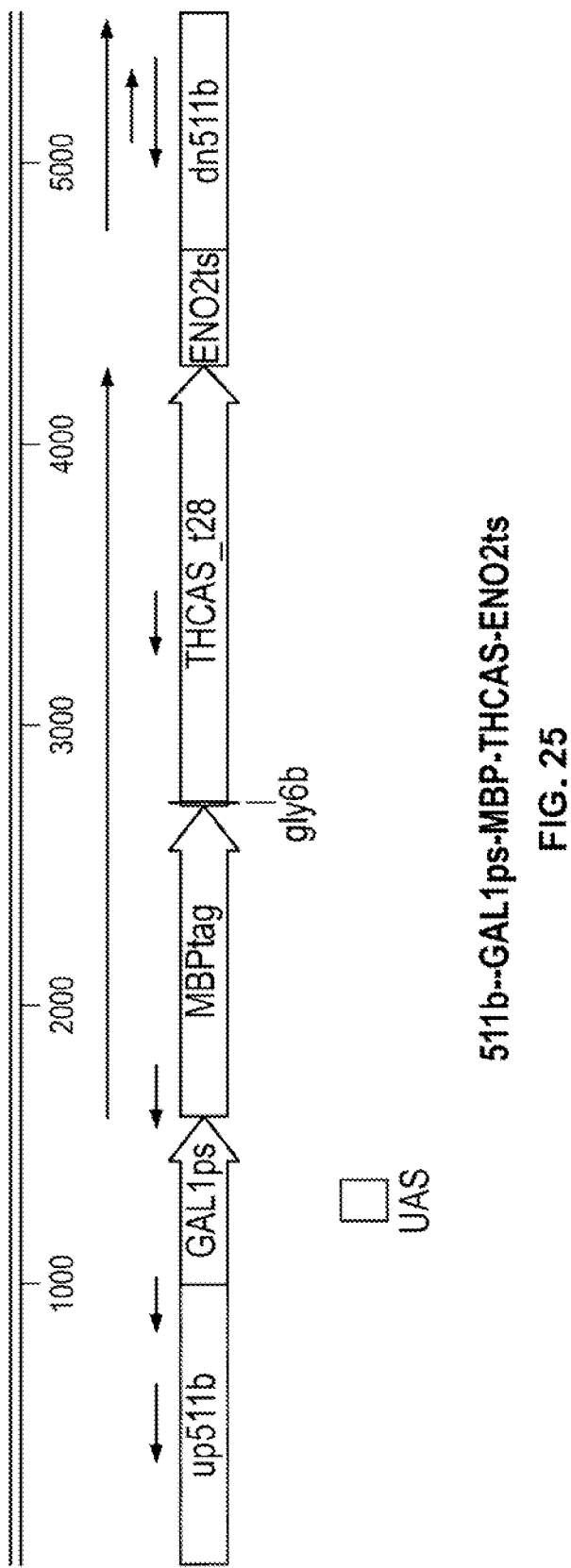
FIG. 25 depicts an expression construct to produce THCA.
Figure 26A:
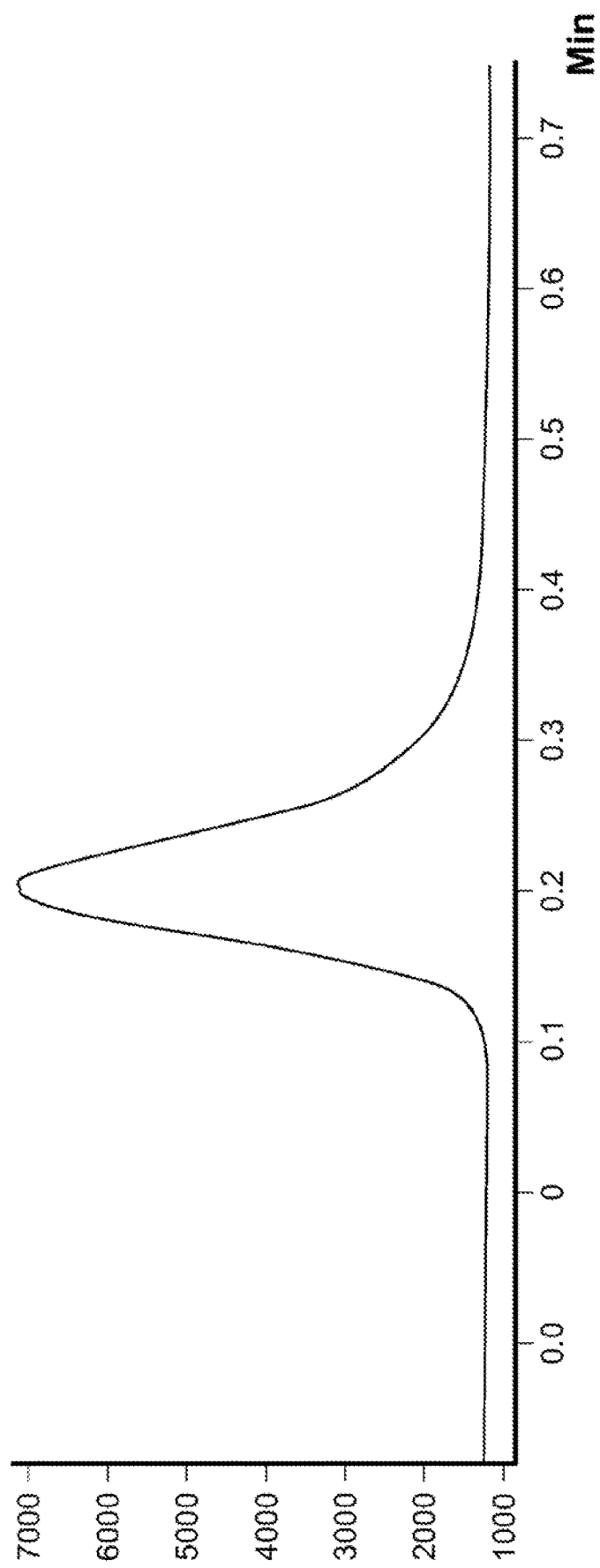
FIGS. 26A, FIG. 26B, and FIG. 26C depict LC-MS traces illustrating the production of CBGA. These figures illustrate an LC-MS trace (m/z=359.2) for ethyl acetate extraction of the yL444 strain (FIG. 26A), a 10 μM CBGA standard (FIG. 26B), and a mixture of ethyl acetate extraction of yL444 and 10 μM CBGA standard (FIG. 26C). Peaks observed at 9.2 minutes indicated the presence of CBGA in the ethyl acetate extraction of yL444.
Figure 26B:
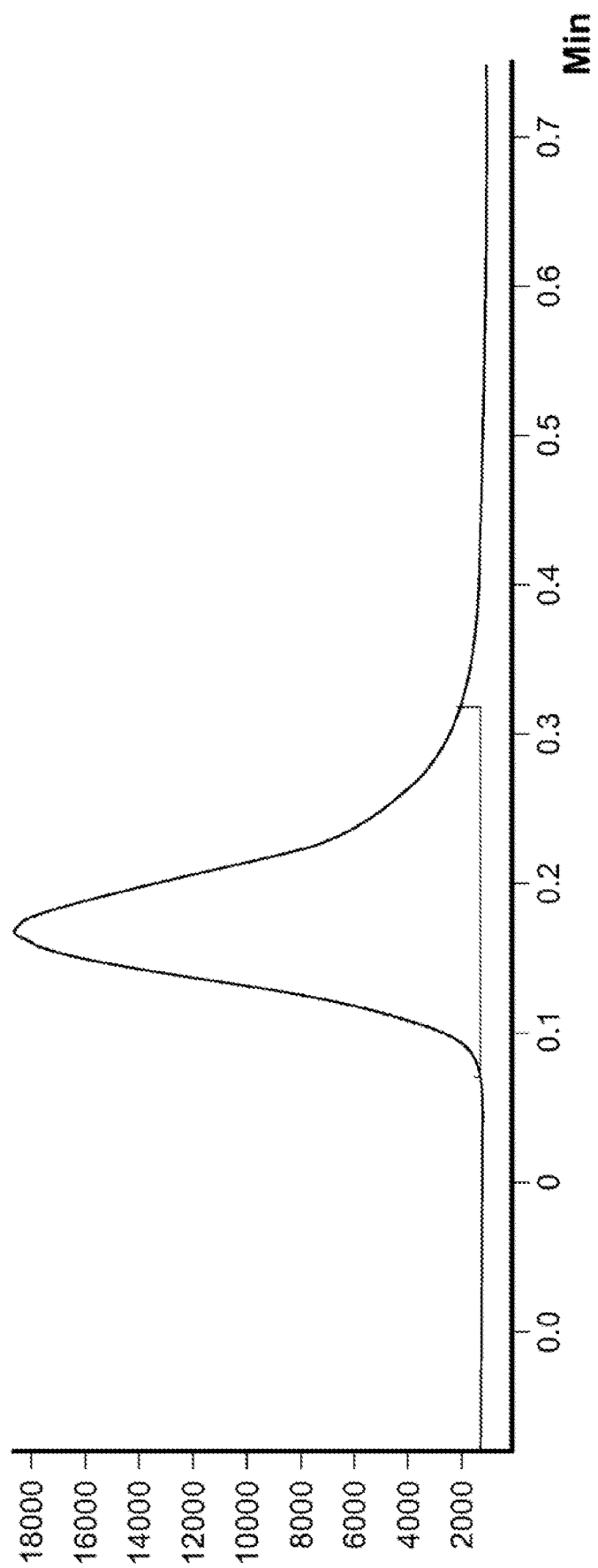
Figure 26C:
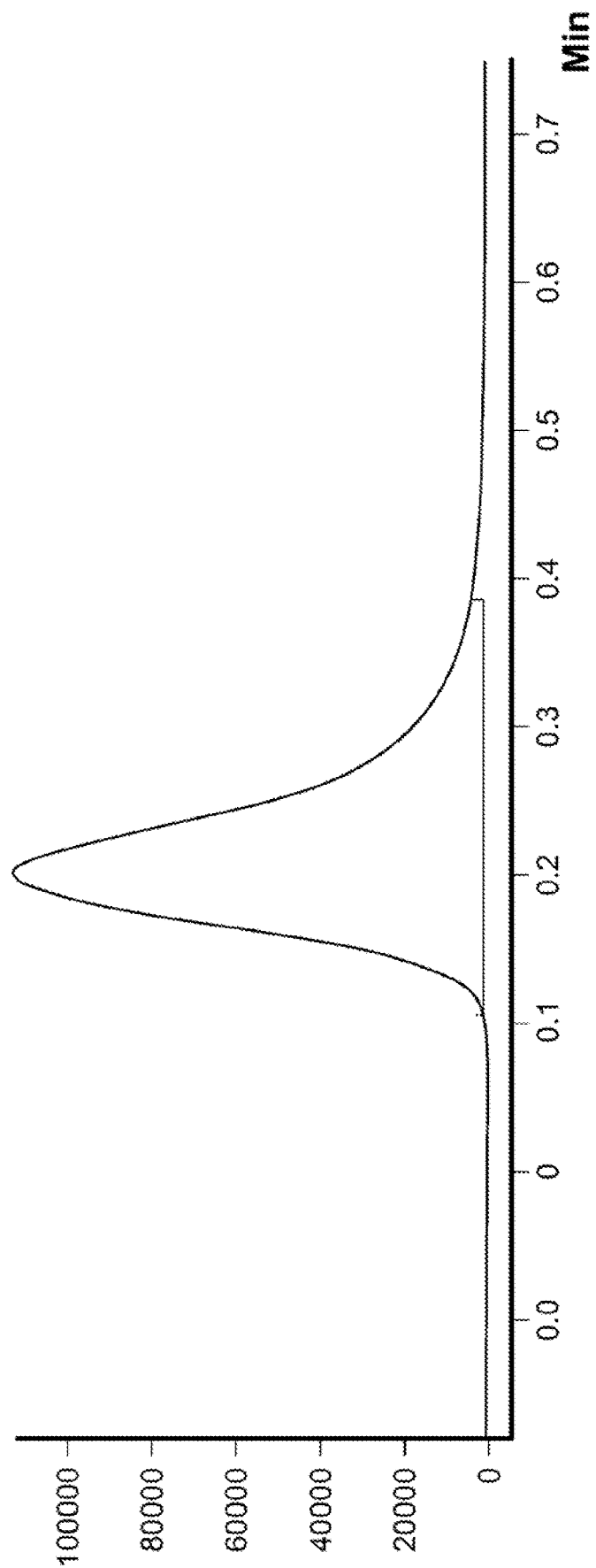

The mother cannabinoid CBGA, or derivatives thereof, was produced by a GOT polypeptide. A *C. sativa* GOT polypeptide was identified in the 1990s, yet no report was identified describing reconstituting GOT polypeptide activity in vivo. Twenty-five polypeptide variants were screened for in vivo production of CBGA in strains containing GPP pathways and exogenously fed olivetolic acid. These genes were all chromosomally integrated driven by GAL1 promoters and screened for activity in yeast extract peptone galactose (YPG) media. GC-MS and LC-MS analysis demonstrated in vivo production of CBGA from a CsPT4t polypeptide (FIGS. 26A-C). The gene sequence of the CsPT4t polypeptide is referred to as a GOT polypeptide (FIG. 20). yL444 was the strain used in the production of CBGA and expresses the following genotype: CEN.PK2-1D {1114a::GAL1p-CsPT4t-TDH1t; 308a::GAL1p-ERG20 (F96W-N127W)-TDH1t; erg9::KanMX_CTR3p-ERG9; leu2-3,112::His3MX6_GAL1p-ERG19/GAL10p-ERG8; ura3-52::ura3/GAL1p-MvaS(A110G)/GAL10p-MvaE; his3_1::hphMX4_GAL1p-ERG12/GAL10p-IDI1; MATa} (FIGS. 6 and 20). LC-MS was carried out as follows (FIGS. 26A-C):

Column info: 2015 Kinetex XB-C18 2.1×100 mm RES6 method 10.6 min
Method info:
  0-5.6 mins, 45%-73% B, 0.2 mL/min
  5.6-6.2 mins, 73%-97% B, 0.2 mL/min
  6.2-11.3 mins, 97% B, 0.3 mL/min
  11.3-12.7, 97-45% B, 0.3 m/min
  12.7-15.5, 45% B, 0.3 mL/min
  A: H2O+0.05% TFA Production of THCA and CBDA Cannabinoid synthase genes have been identified from the *Cannabis* genome (including but not limited to THCA synthase (THCAS), CBDA synthase (CBDAS), JP450547, JP454863, JP471546, JP452622). To produce THCA and CBDA, the corresponding THCA synthase and CBDA synthase, respectively, were introduced into a strain producing CBGA containing a heterologous nucleic acid encoding a CsPT4t polypeptide. The synthases were introduced as N-terminal truncated polypeptides with polypeptide tags, e.g., ProA signal sequence (MIFDGTTMSIAIGLLSTLGI-GAEA, from proteinase A with UniProt accession number F2QUG8) attached and the transcription of both synthases were under the control of GAL10 promoter. The final plasmid constructs were named as pESC-ProA-THCAS and pESC-ProA-CBDAS. Both plasmids were transformed individually into the above-mentioned strain, which has high CBGA production in the presence of olivetolic acid, to give strains yXL046 and yXL047 (FIGS. 21-25).

Figure 27:
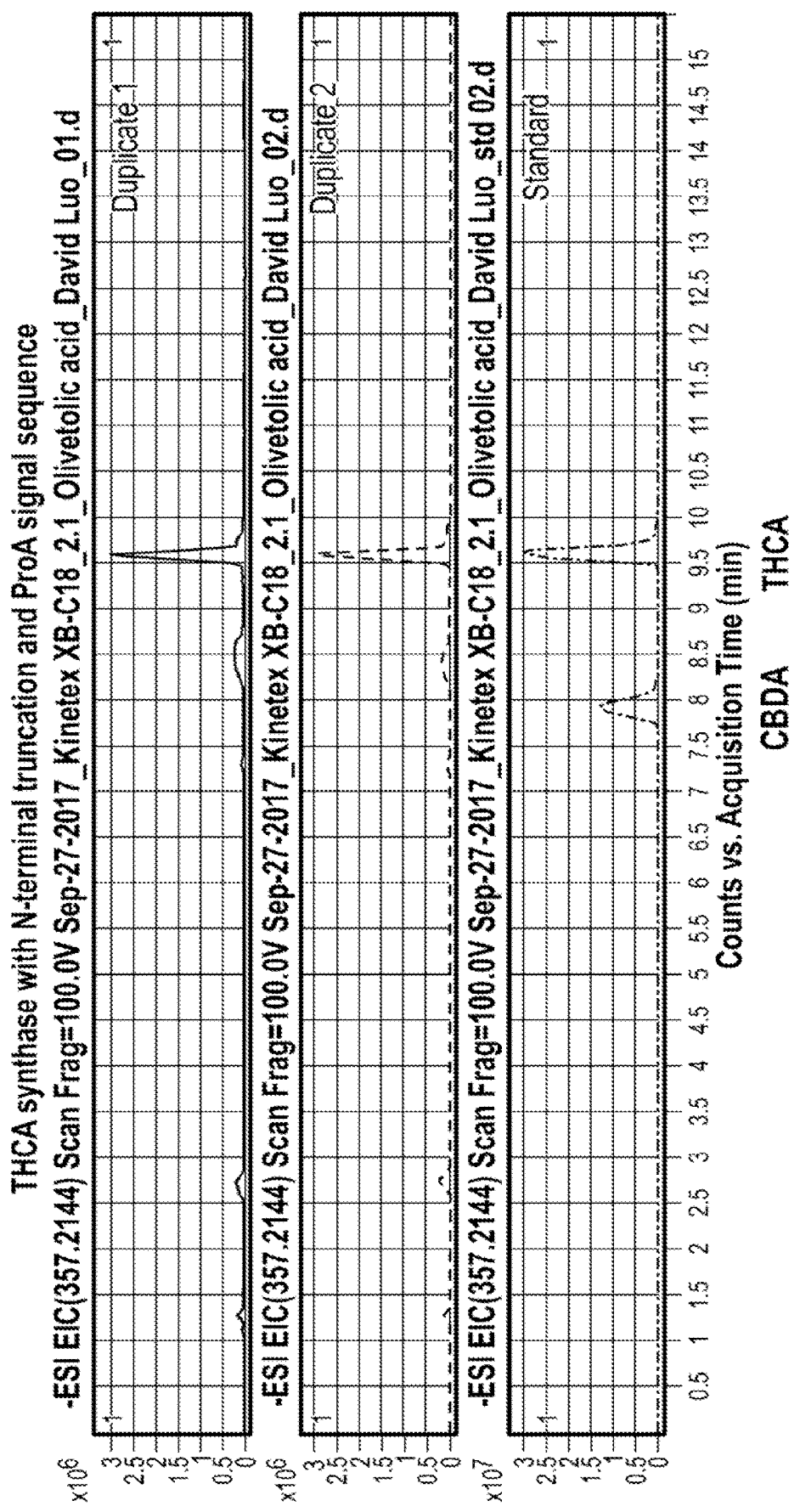
FIG. 27 depicts the production of THCA with a THCA synthase polypeptide with an N-terminal truncation and a ProA signal sequence. The figure illustrates an LC-MS trace (m/z=357.2144) for ethyl acetate extraction of yXL046 colony 1 (Duplicate 1, Top), yXL046 colony 2 (Duplicate 2, Middle), and a standard containing CBDA and THCA (Standard, Bottom). The peak at 7.9 mins indicated the presence of CBDA and the peak at 9.6 mins indicated the presence of THCA.
Figure 28:
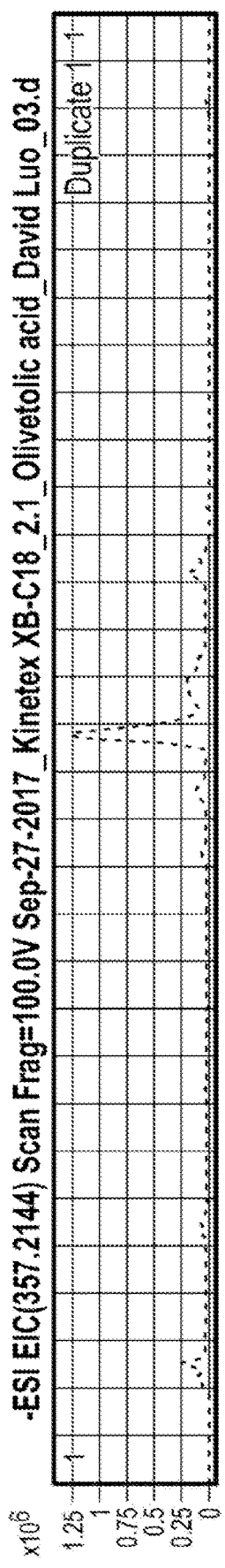
FIG. 28 depicts the production of CBDA with a CBDA synthase polypeptide with an N-terminal truncation and a ProA signal sequence. The figure illustrates an LC-MS trace (m/z=357.2144) for ethyl acetate extraction of yXL047 colony 1 (Duplicate 1), a yXL047 colony 2 (Duplicate 2), a negative control (Negative) and a standard containing CBDA and THCA (Standard). The peak at 7.9 mins indicated the presence of CBDA and the peak at 9.6 mins indicated the presence of THCA.
Figure 28:
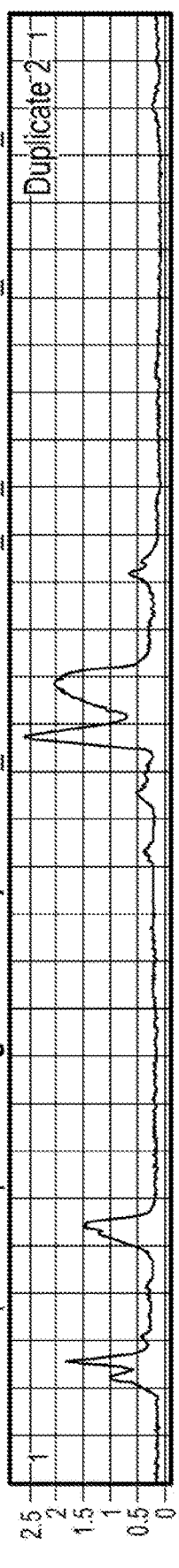
Figure 28:
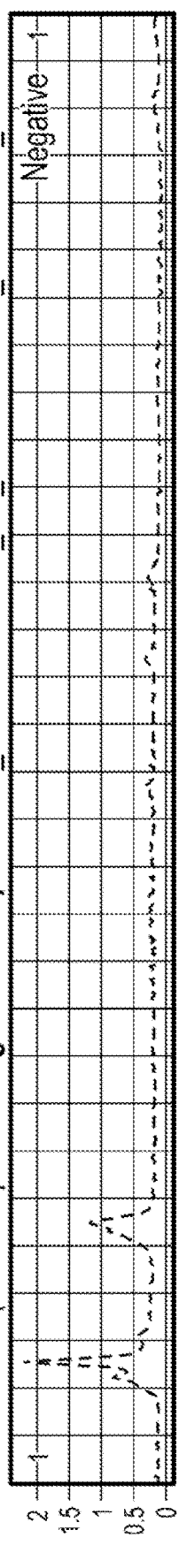
Figure 28:
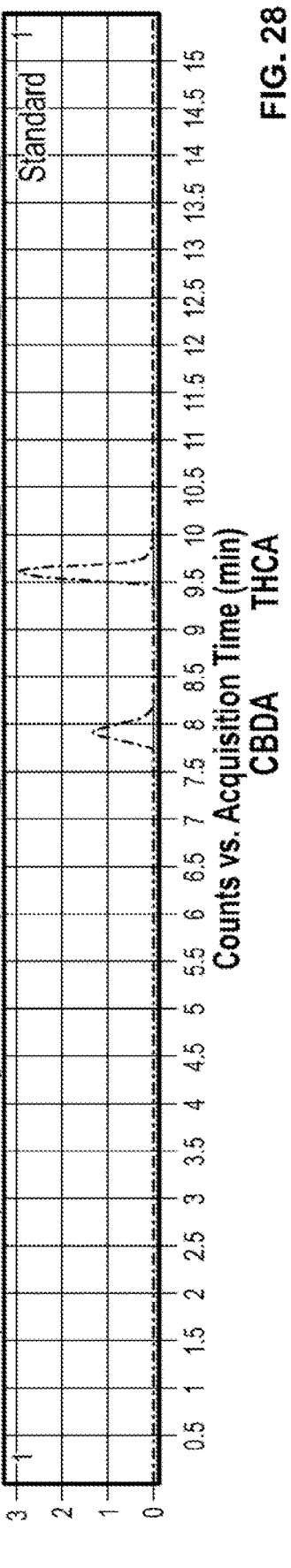

After confirming the transformation by PCR of THCAS or CBDAS, two colonies from each culture were inoculated into a defined medium (SC-Leu+2% Dextrose) and were incubated at 30° C. with shaking at 800 RPM. After two-day growth, the cultures were back-diluted 1:50 into inducing medium (SC-Leu+2% galactose+1 mM olivetolic acid+ $CuSO_4$) and incubated at 30° C. with shaking at 800 RPM for 4 days. After 4-day incubation, equal volume of ethyl acetate was added to the expression cultures and the mixtures were subjected to three rounds of bead beating. Then the mixtures were then spun down at 5000 RPM and the organic layers were sent for LC-MS analysis, which showed the production of THCA and CBGA from the corresponding cultures (FIGS. 27 and 28).

Example 4—Generation of a Base Yeast Strain Capable of High Flux to CBGA with Olivetolic Acid Feeding CBGA production strains were created from wild-type *Saccharomyces cerevisiae* strain (CEN.PK2) by expressing genes of the mevalonate pathway polypeptides and a GOT polypeptide under control of the GAL1 or GAL10 promoter. The S21 strain comprised the following chromosomally integrated mevalonate pathway genes from *S. cerevisiae*: ERG10, ERG13, truncated HMG1 (tHMGR), ERG12, ERG8, ERG19, and IDI1. The S21 strain additionally comprised the chromosomally integrated pyruvate decarboxylase (PDC) from *Zymomonas mobilis* to increase flux from pyruvate towards acetyl-CoA.

To generate additionally strains, a mutant form of ERG20, ERG20mut, which preferentially generates GPP was added to the S21 strain with the following chromosomally integrated GOTs from *C. sativa*: CsPT1 (S164), a truncated CsPT1 (CsPT1_t75, S165), or CsPT4 (S29). Constructs used in S29, S164, and S165 are shown in Table 11.

Yeast colonies verified to contain the expected DNA assembly comprising one or more heterologous nucleic acids disclosed herein were picked into 96-well microtiter plates containing 360 µL of YPD (10 g/L yeast extract, 20 g/L Bacto peptone, 20 g/L dextrose (glucose)) and sealed with a breathable film seal. Cells were cultured at 30° C. in a high capacity microtiter plate incubator shaking at 1000 rpm and 80% humidity for 3 days until the cultures reached carbon exhaustion. The growth-saturated cultures were sub-cultured into fresh plates containing YPGAL and olivetolic acid (10 g/L yeast extract, 20 g/L Bacto peptone, 20 g/L galactose, 1 g/L glucose and 1 mM olivetolic acid) by taking 14.4 µL from the saturated cultures and diluting into 360 µL of fresh media and sealed with a breathable film seal. Genetically modified host cells in the production media were cultured at 30° C. in a high capacity microtiter plate shaker at 1000 rpm and 80% humidity for an additional 3 days prior to extraction and analysis. Upon completion, 100 µL of whole cell broth was diluted into 900 µL of methanol, sealed with a foil seal, and shaken at 1500 rpm for 60 seconds to extract the cannabinoids. After shaking, the plate was centrifuged at 1000×g for 60 seconds to remove any solids. After centrifugation, 12 µL of supernatant was transferred to a fresh assay plate containing 228 µL of methanol, sealed with a foil seal, shaken for 60 seconds at 900 rpm, and analyzed by LC-MS.

Samples were analyzed by LC-MS mass spectrometer (Agilent 6470) using an Agilent Poroshell 120 Phenyl Hexyl 2.1×50 mm, 1.9 μm analytical column with the following gradient (Mobile Phase A: LC-MS grade water with 0.1% formic acid; Mobile Phase B: LC-MS grade acetonitrile with 0.1% formic acid):

| Time (minutes) | % B |
|---|---|
| 0 | 40 |
| 0.1 | 40 |
| 0.6 | 60 |
| 1 | 65 |
| 1.01 | 95 |
| 2.01 | 95 |
| 2.02 | 40 |
| 2.5 | 40 |

Figure 77:
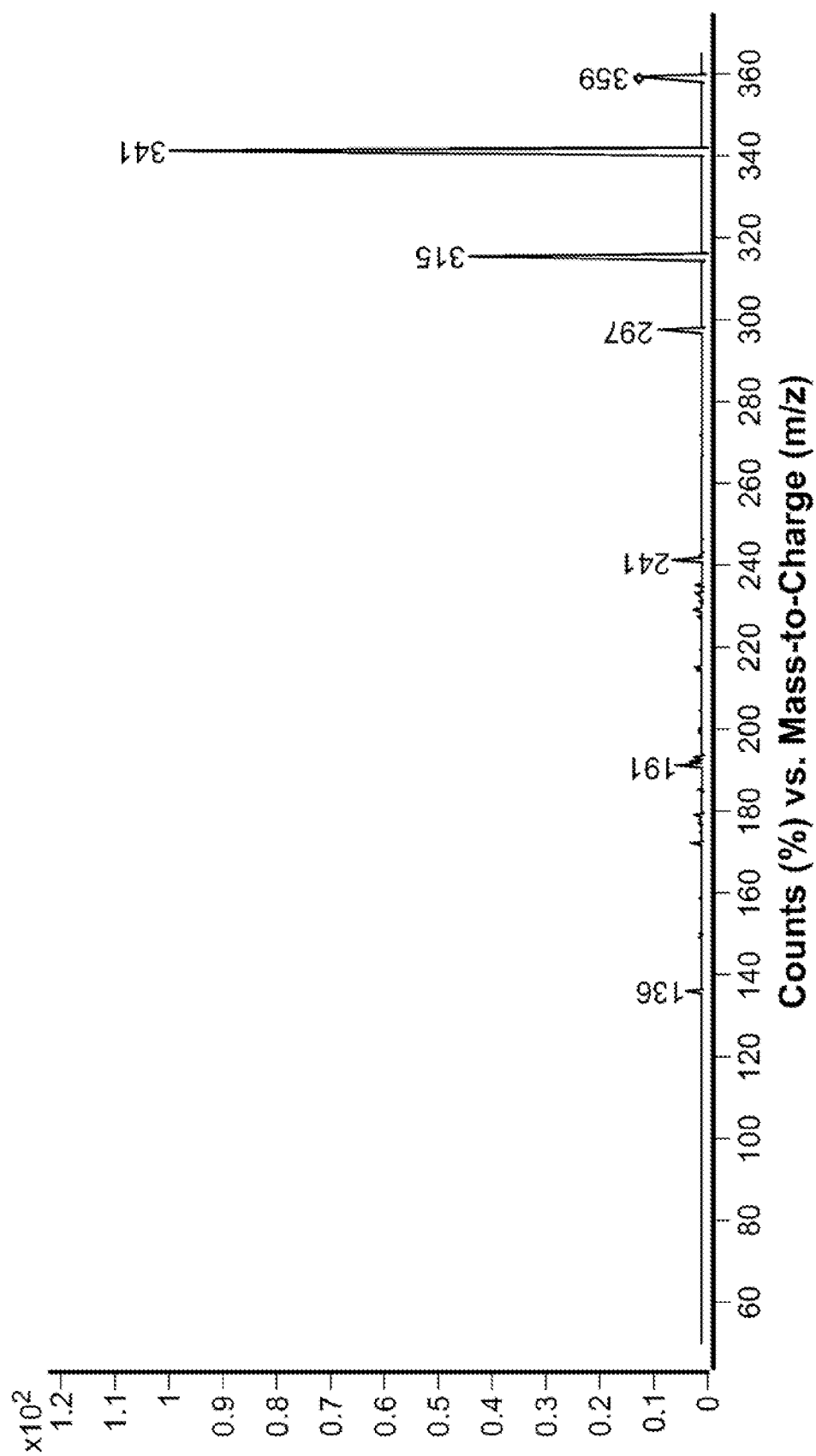
FIG. 77 depicts the MS/MS spectrum of the CBGA peak produced from a CsPT4 polypeptide expressing strain (S29).
Figure 78:
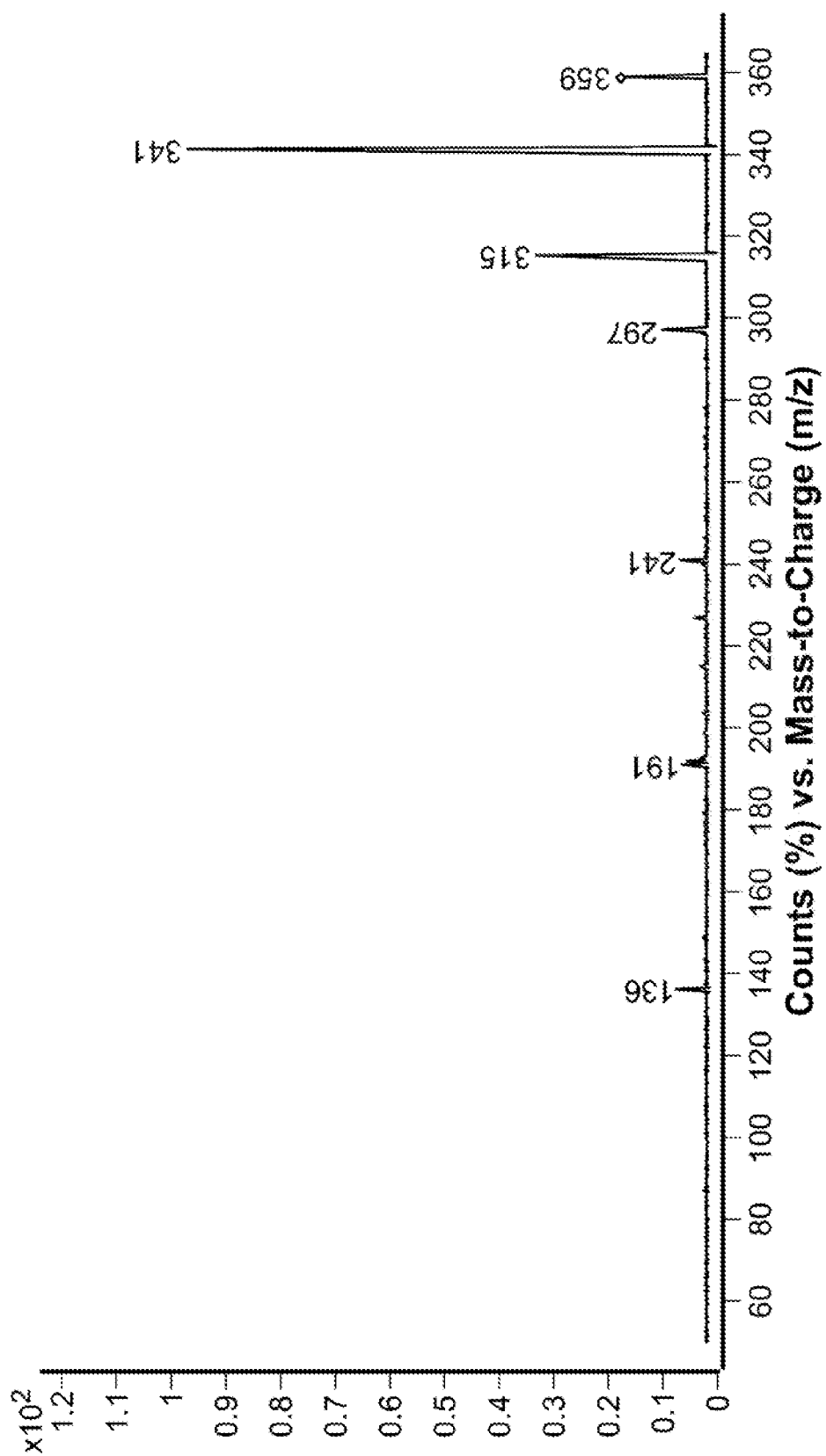
FIG. 78 depicts the MS/MS spectrum of an authentic CBGA standard.
Figure 79:
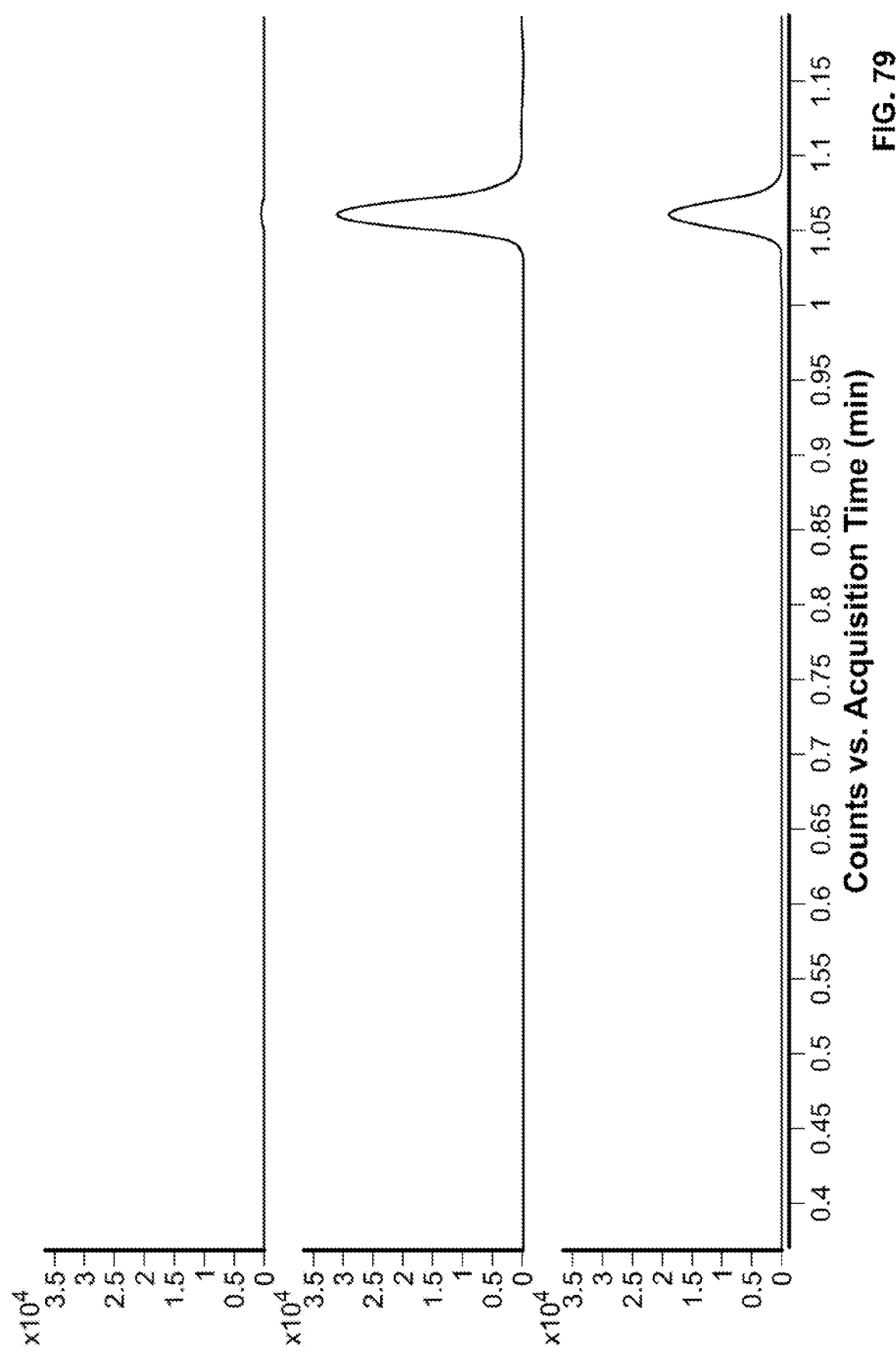
FIG. 79 depicts CBGA produced by a CsGOT polypeptide at 1.06 min (top), CBGA produced by a CsPT4 polypeptide at 1.06 min (middle), and authentic CBGA standard at 1.06 min (bottom).
Figure 80:
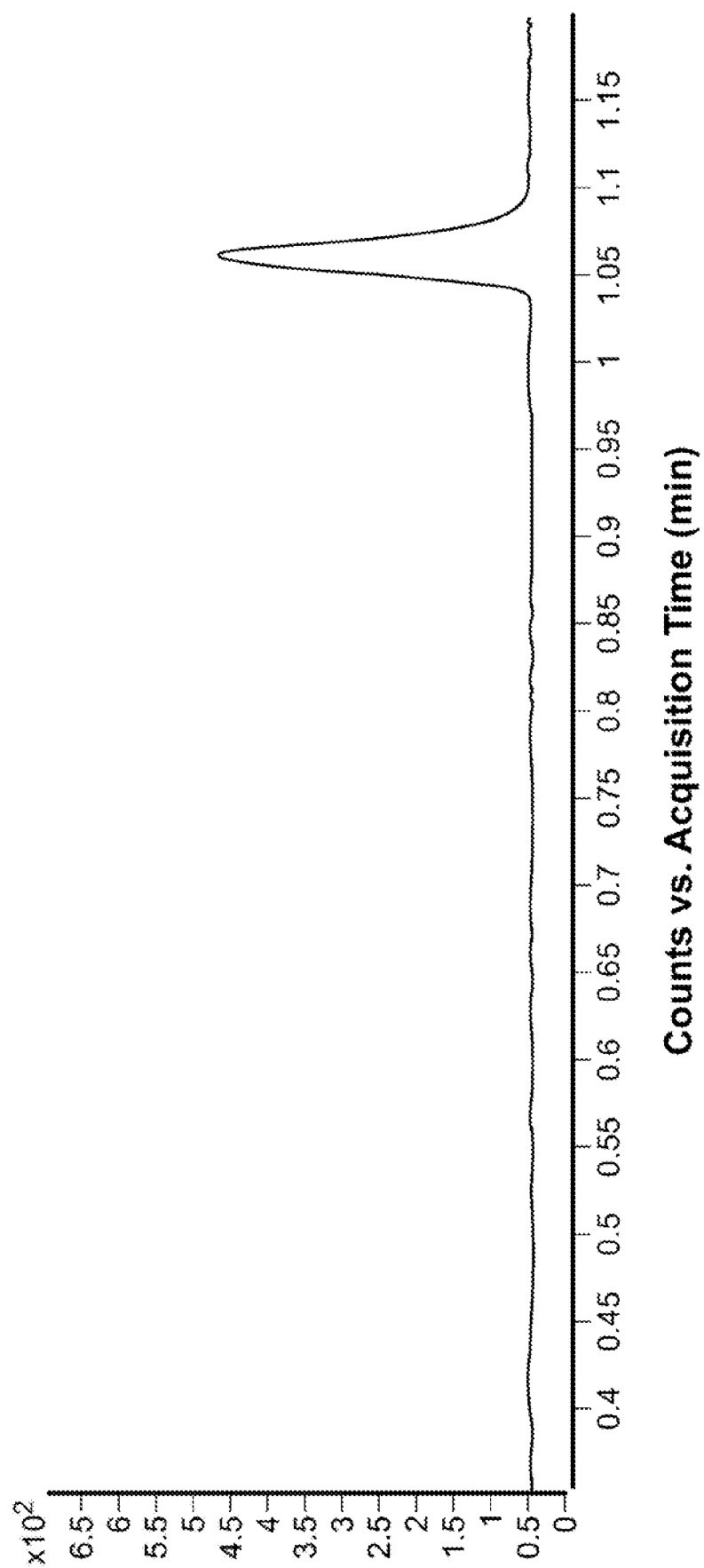
FIG. 80 depicts CBGA produced by a CsGOT polypeptide at 1.06 min (scale×102 units).
Figure 81:
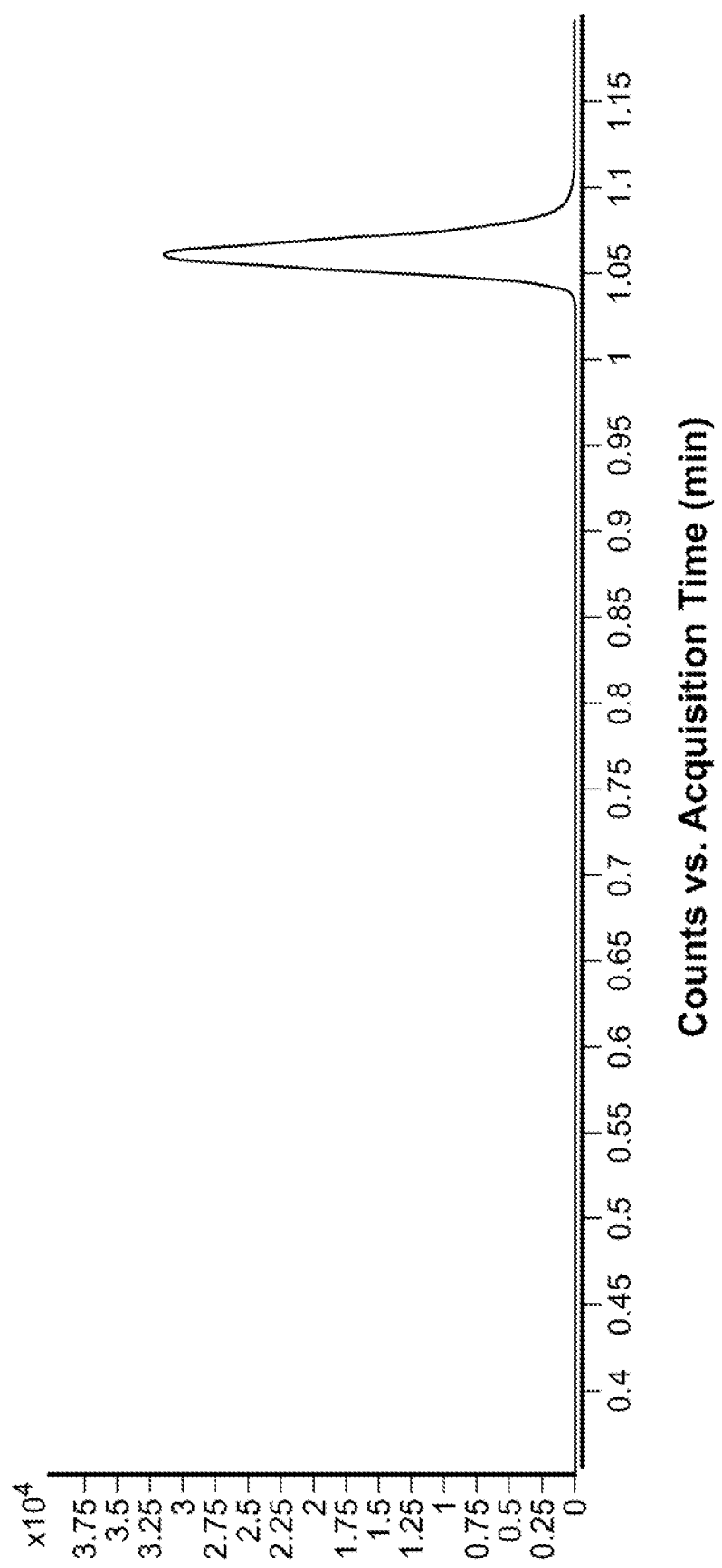
FIG. 81 depicts CBGA produced by a CsPT4 polypeptide at 1.06 min (scale×$10^4$ units)
Figure 82:
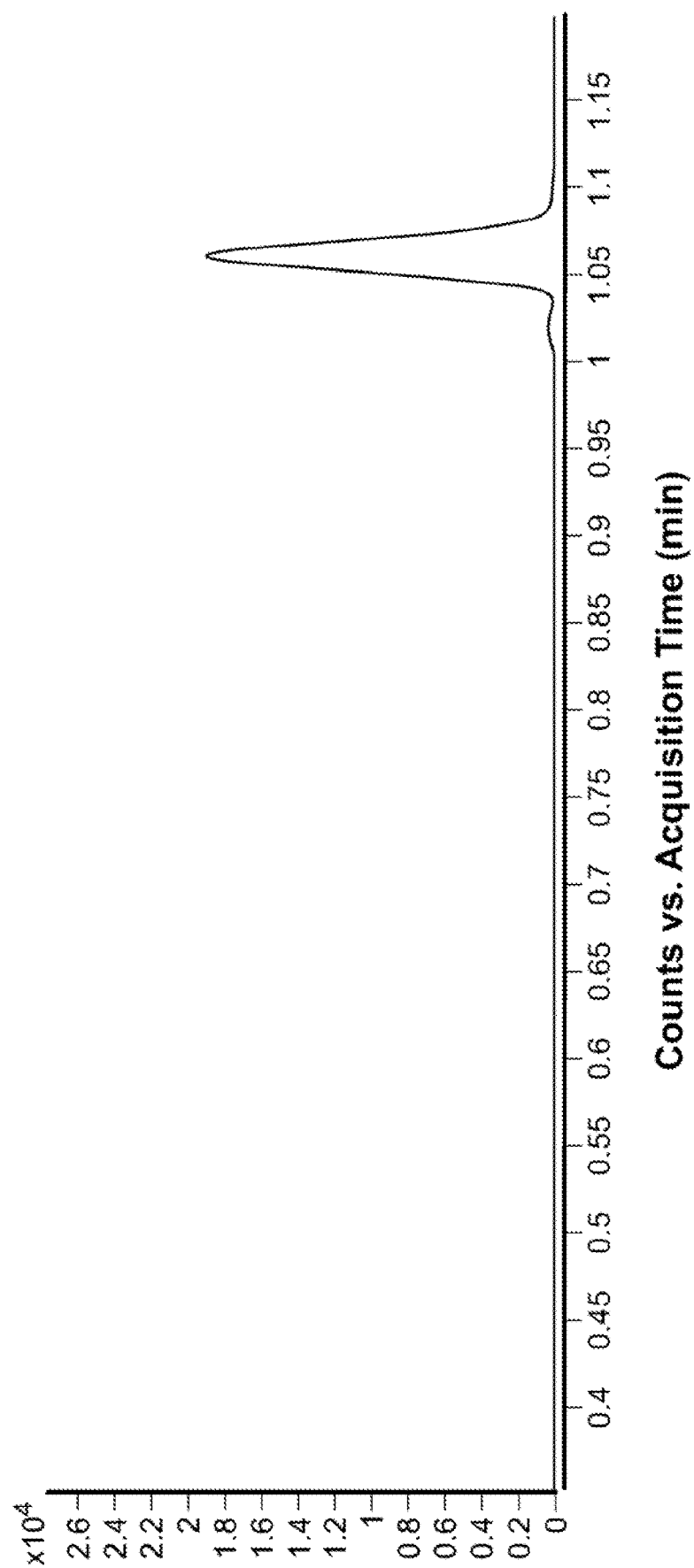
FIG. 82 depicts an authentic CBGA standard at 1.06 min (scale×$10^4$ units).

The mass spectrometer was operated in negative ion multiple reaction monitoring mode. Each cannabinoid was identified by retention time, determined from an authentic standard, and MRM transition (see FIGS. 77 and 78):

| Compound Name | Q1 Mass (Da) | Q3 Mass (Da) |
|---|---|---|
| CBGA | 359.2 | 341.1 |
| CBGA | 359.2 | 315.2 |

CsPT1 polypeptide and CsPT1_t75 polypeptide produced equivalent amounts of CBGA in vivo (1.3 mg/L CBGA). However, CsPT4 polypeptide produced 216 mg/L CBGA in vivo (see FIGS. 79-82).

Example 5—Determining the Minimal Catalytic Domain of CsPT4

To determine the minimal catalytic domain of CsPT4 polypeptide required for the conversion of GPP and olivetolic acid to CBGA, multiple N-terminal truncations of the CsPT4 polypeptide were generated (see Table 11) and expressed in vivo in the S21 strain with feeding of 1 mM olivetolic acid. Only full length CsPT4 polypeptide and CsPT4_t76 polypeptide (CsPT4t) displayed activity in vivo (Table 4).

TABLE 4

Screening of CsPT4 truncated polypeptides

| CsPT4 construct | Strain | Peak intensity |
|---|---|---|
| CsPT4 | S29 | 8901 |
| CsPT4_t76 | S147 | 6859 |
| CsPT4_t112 | S166 | 19 |
| CsPT4_t131 | S167 | 24 |
| CsPT4_t142 | S168 | 20 |
| CsPT4_t166 | S169 | 21 |
| CsPT4_t186 | S170 | 29 |

Example 6—Generation of a Base Yeast Strain Capable of High Flux to CBGA with Hexanoic Acid (Caproic Acid) Feeding To convert the high flux strain for the production of CBGA with olivetolic acid (S29) to a high flux stain for the production of CBGA with hexanoic acid, genes responsible for the production to olivetolic acid from fatty acids were expressed using the GAL1 or GAL10 promoter in S29. The strain comprised the following chromosomally integrated olivetolic acid pathway genes from *C. sativa*: three copies of TKS and three copies of OAC. Three different strains were generated with two copies of *C. sativa* AAE1 (S78), two copies of *C. sativa* AAE3 (S81), or two copies of *S. cerevisiae* FAA2 (S83) (see Table 11 for information on the strains). The strains were grown and tested as in Examples 4 and 5 but with 2 mM hexanoic acid added to the media instead of 1 mM olivetolic acid. Production of CBGA by the strains was observed (Table 5).

TABLE 5

Generation of CBGA

| | | Titer (mg/L) | | |
|---|---|---|---|---|
| Feed compound | Product | AAE1v1 (S78) | AAE3-Ctrunc (S81) | FAA2 (S83) |
| Hexanoic acid | CBGA | 38.5 | 32.1 | 35.1 |

Figure 83:
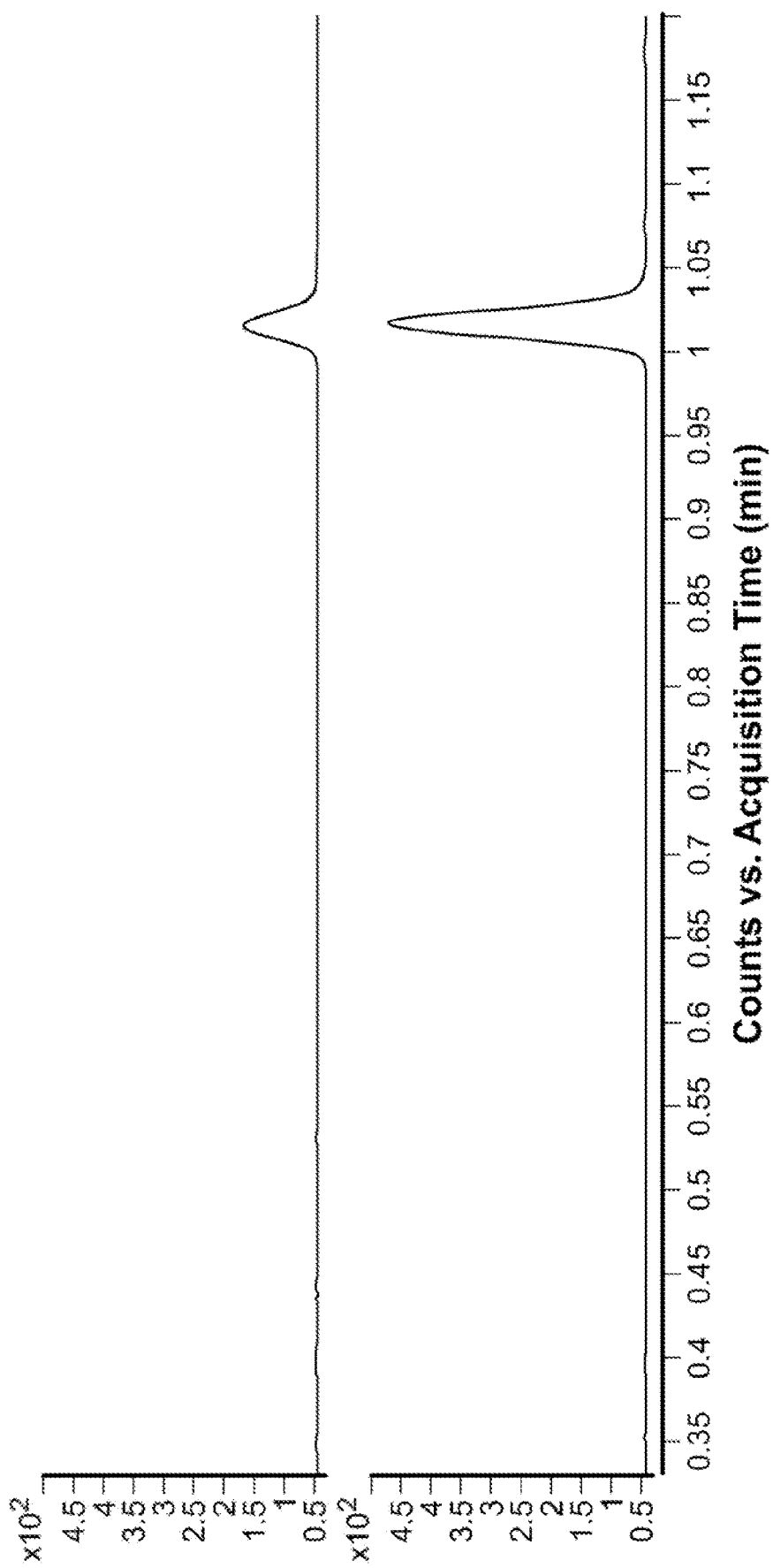
FIG. 83 depicts CBDA produced by S34 at 1.02 min (top) and an authentic CBDA standard at 1.02 min (bottom).
Figure 84:
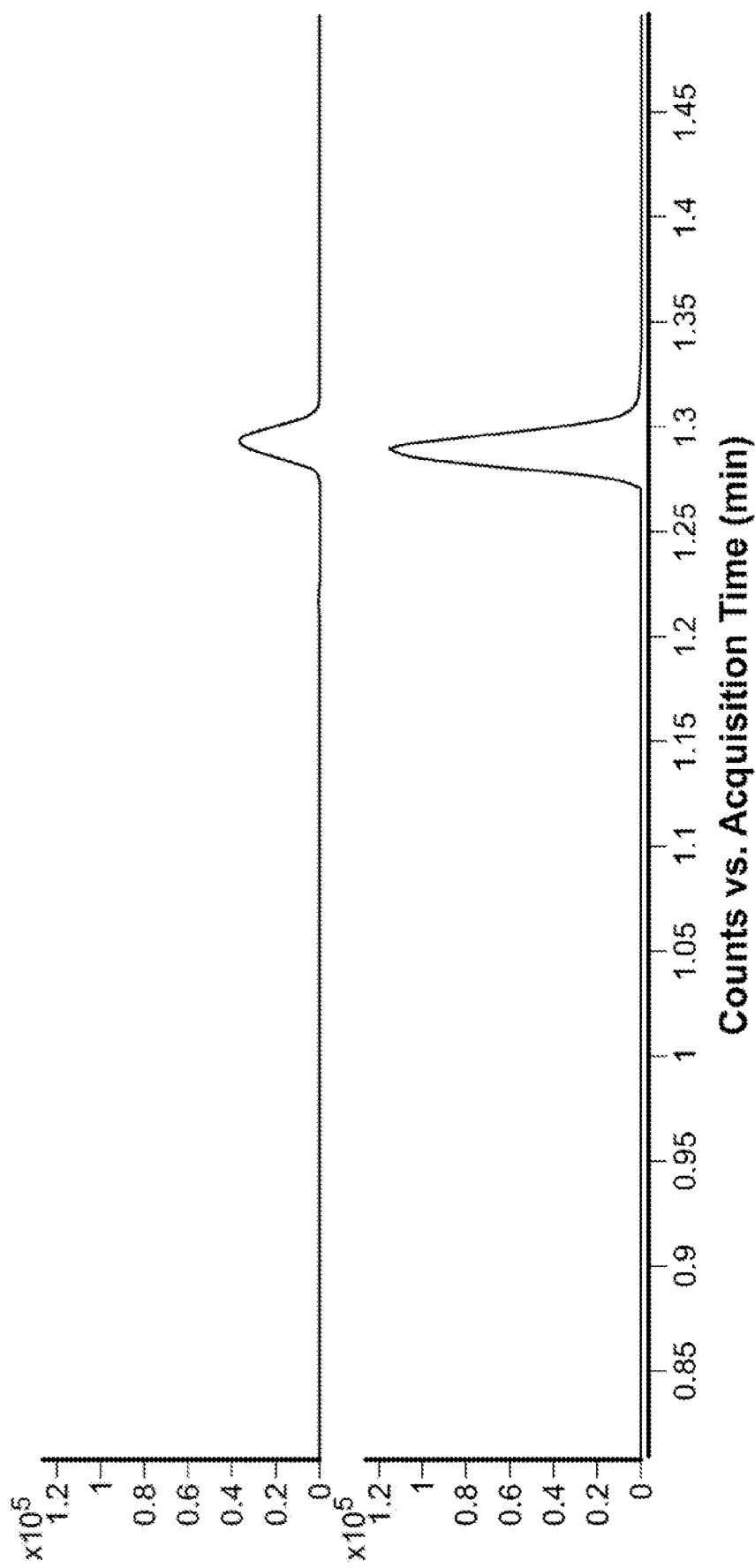
FIG. 84 depicts THCA produced from strain D123 at 1.29 min (top) and an authentic THCA standard at 1.29 min (bottom).

Example 7—Generation of a Base Yeast Strain Capable of High Flux to CBDA and THCA To convert the high flux strain for the production of CBGA to a high flux strain for the production of CBDA or THCA, a heterologous nucleic acid encoding CBDA synthase polypeptide (S34) or THCA synthase polypeptide (S123) was added to Strain S29 (see Table 11 for information on the strains). The strains were tested as in Examples 4 and 5 with 1 mM olivetolic acid in the media. CBDA and THCA were produced by the strains, as shown in FIGS. 83 and 84.

Example 8—Feeding of Cannabinoid Precursor Derivatives to Yeast to Produce Rare and Non-Naturally Occurring CBGA Derivatives Strains from Example 6 (S78, S81, and S83) were grown as in Examples 4 and 5 but with 2 mM of a carboxylic acid (detailed in Table 6) added to the media and analyzed as in Example 4. Table 6 details the products produced by the strains (product peak intensity).

TABLE 6

| | | | | | AAE3- | |
| | Product (IUPAC | Transition | Transition | AAE1v1 | Ctrunc | FAA2 |
| Feed compound | name) | 1 | 2 | (S78) | (S81) | (S83) |
|---|---|---|---|---|---|---|
| 2-methyl hexanoic acid | 3-[(2E)-3,7-dimethylocta-2,6-dien-1-yl]-6-(hexan-2-yl)-2,4-dihydroxybenzoic acid | 373 --> 355 | 373 --> 329 | 1136 | 1255 | 1301 |
| 4-methyl hexanoic acid | 3-[(2E)-3,7-dimethylocta-2,6-dien-1-yl]-2,4-dihydroxy-6-(3-methylpentyl)benzoic acid | 373 --> 355 | 373 --> 329 | 82453 | 91493 | 82517 |
| 5-methyl hexanoic acid | 3-[(2E)-3,7-dimethylocta-2,6-dien-1-yl]-2,4-dihydroxy-6-(4-methylpentyl)benzoic acid | 373 --> 355 | 373 --> 329 | 76145 | 77270 | 77145 |
| 2-hexenoic acid | 3-[(2E)-3,7-dimethylocta-2,6-dien-1-yl]-2,4-dihydroxy-6-[(1E)-pent-1-en-1-yl]benzoic acid | 357 --> 339 | 357 --> 313 | 311 | 536 | 588 |
| 3-hexenoic acid | 3-[(2E)-3,7-dimethylocta-2,6-dien-1-yl]-2,4-dihydroxy-6-[(2E)-pent-2-en-1-yl]benzoic acid | 357 --> 339 | 357 --> 313 | 90422 | 104366 | 112440 |
| 5-hexenoic acid | 3-[(2E)-3,7-dimethylocta-2,6-dien-1-yl]-2,4-dihydroxy-6-(pent-4-en-1-yl)benzoic acid | 357 --> 339 | 357 --> 313 | 302499 | 325854 | 365798 |
| butanoic acid | 3-[(2E)-3,7-dimethylocta-2,6-dien-1-yl]-2,4-dihydroxy-6-propylbenzoic acid | 331 --> 313 | 331 --> 287 | 92181 | 106229 | 103368 |
| pentanoic acid | 3-[(2E)-3,7-dimethylocta-2,6-dien-1-yl]-2,4-dihydroxy-6-butylbenzoic acid | 345 --> 327 | 345 --> 301 | 224003 | 232206 | 236366 |
| heptanoic acid | 3-[(2E)-3,7-dimethylocta-2,6-dien-1-yl]-2,4-dihydroxy-6-hexylbenzoic acid | 373 --> 355 | 373 --> 329 | 66544 | 67766 | 66570 |
| octanoic acid | 3-[(2E)-3,7-dimethylocta-2,6-dien-1-yl]-2,4-dihydroxy-6-heptylbenzoic acid | 387 --> 369 | 387 --> 343 | 4225 | 3212 | 3603 |
| 5-chloro pentanoic acid | 6-(4-chlorobutyl)-3-[(2E)-3,7-dimethylocta-2,6-dien-1-yl]-2,4-dihydroxybenzoic acid | 379 --> 361 | 379 --> 335 | 1023 | 947 | 902 |
| 5-(methyl sulfanyl) pentanoic acid | 3-[(2E)-3,7-dimethylocta-2,6-dien-1-yl]-2,4-dihydroxy-6-[4-(methylsulfanyl)butyl]benzoic acid | 391 --> 373 | 391 --> 347 | 18396 | 18704 | 19412 |

Example 9—Feeding of Cannabinoid Precursor Derivatives to Yeast to Produce Rare and Non-Naturally Occurring CBDA Derivatives Strains with (S34) or without a CBDA synthase polypeptide (S29) were tested as in Examples 4 and 5 with 1 mM of an olivetolic acid derivative (detailed in Table 7). Table 7 details the products produced by the strains.

TABLE 7

CBDA Derivatives Produced

| Feed compound | Product (IUPAC name) | Transition 1 | Transition 2 | CBGA derivative titer (mg/L) (S29) | CBDA derivative titer (mg/L) (S34) |
|---|---|---|---|---|---|
| Orsellinic Acid | 3-[(2E)-3,7-dimethylocta-2,6-dien-1-yl]-2,4-dihydroxy-6-methylbenzoic acid | 303 --> 285 | 303 --> 259 | 1.86 | 1.05 |
| Divarinic Acid | 3-[(2E)-3,7-dimethylocta-2,6-dien-1-yl]-2,4-dihydroxy-6-propylbenzoic acid | 331 --> 313 | 331 --> 287 | 29.54 | 3.06 |

Example 10—Feeding of Cannabinoid Precursors to Yeast to Produce CBDA or CBGA

As there are numerous ways to produce cannabinoid precursors (e.g., GPP), a number of different genes were tested in vivo to optimize cannabinoid production. Different GPP synthase polypeptides, CBDA synthase polypeptides, TKS polypeptides, OAC polypeptides, medium and long chain fatty acyl-CoA synthetase polypeptides were tested in various combinations as described below (see Table 11 for information on the strains).

Strains were constructed with different GPP synthase polypeptides to identify the best producer of GPP for production of CBGA when fed 1 mM olivetolic acid. Strain S21 was transformed with heterologous nucleic acids encoding a CsPT4 polypeptide and a GPP synthase polypeptide. CBGA titer was measured as described in Example 4. CBGA titers, titer standard deviations (SD) and number of replicates tested are indicated in Table 8.

TABLE 8

Production of CBGA

| Product | Strain | Titer (mg/L) | SD | n |
|---|---|---|---|---|
| CBGA | S29 | 215.6 | 12.2 | 8 |
| CBGA | S114 | 6.8 | 0.7 | 3 |
| CBGA | S116 | 15.5 | 2.0 | 4 |
| CBGA | S108 | 8.5 | 1.7 | 4 |
| CBGA | S112 | 9.9 | 1.6 | 4 |
| CBGA | S104 | 10.2 | 1.6 | 3 |
| CBGA | S115 | 9.2 | 1.9 | 4 |
| CBGA | S118 | 5.1 | NA | 1 |

To optimize production of CBDA, strain S29 was transformed with a series of constructs with two copies of a CBDA synthase polypeptide encoding heterologous nucleic acid and grown as in Examples 4 and 5 with 1 mM olivetolic acid. CBDA was measured as described in Example 4. CBDA peak intensity, peak intensity standard deviations (SD) and number of replicates tested are indicated in Table 9.

TABLE 9

Production of CBDA

| Product | Strain | Peak Area | SD | n |
|---|---|---|---|---|
| CBDA | S34 | 1651 | 329 | 4 |
| CBDA | S35 | 831 | 72 | 4 |
| CBDA | S37 | 505 | 26 | 4 |
| CBDA | S38 | 658 | 31 | 4 |
| CBDA | S39 | 1274 | 85 | 4 |
| CBDA | S41 | 2129 | 462 | 4 |
| CBDA | S42 | 72 | 4 | 4 |
| CBDA | S43 | 419 | 481 | 4 |
| CBDA | S44 | 758 | 68 | 4 |
| CBDA | S45 | 1253 | 177 | 4 |
| CBDA | S46 | 670 | 112 | 4 |
| CBDA | S47 | 300 | 15 | 4 |

To optimize production of CBGA from hexanoic acid, different combinations of TKS polypeptide, OAC polypeptide, and medium and long chain fatty acyl-CoA synthetase polypeptide were tested in vivo. All strains were daughters or granddaughters of strain S29. All strains were tested as described in Example 4 with 2 mM hexanoic acid added to the production media. CBGA titers, titer standard deviations (SD) and number of replicates tested are indicated in Table 10.

TABLE 10

Production of CBGA

| Product | Strain | Titer (mg/L) | SD | n |
|---|---|---|---|---|
| CBGA | S31 | 53.6 | 12.2 | 8 |
| CBGA | S49 | 55.7 | 9.3 | 8 |
| CBGA | S50 | 22.9 | 7.0 | 8 |
| CBGA | S90 | 67.5 | 2.8 | 4 |
| CBGA | S91 | 63.5 | 4.2 | 4 |
| CBGA | S78 | 38.5 | 2.5 | 4 |
| CBGA | S80 | 37.5 | 1.8 | 4 |
| CBGA | S81 | 32.1 | 5.8 | 4 |
| CBGA | S82 | 35.1 | 7.0 | 4 |
| CBGA | S83 | 35.1 | 2.6 | 4 |
| CBGA | S84 | 36.4 | 3.5 | 4 |
| CBGA | S85 | 34.4 | 4.3 | 4 |
| CBGA | S86 | 36.6 | 1.8 | 4 |
| CBGA | S87 | 32.2 | 4.9 | 4 |
| CBGA | S88 | 40.9 | 1.4 | 4 |
| CBGA | S89 | 39.3 | 2.7 | 4 |
| CBGA | S94 | 59.6 | 7.9 | 8 |
| CBGA | S95 | 58.5 | 9.2 | 8 |
| CBGA | S97 | 72.9 | 5.5 | 8 |

TABLE 11

Constructs and strains used in the Examples

Figure 29A:
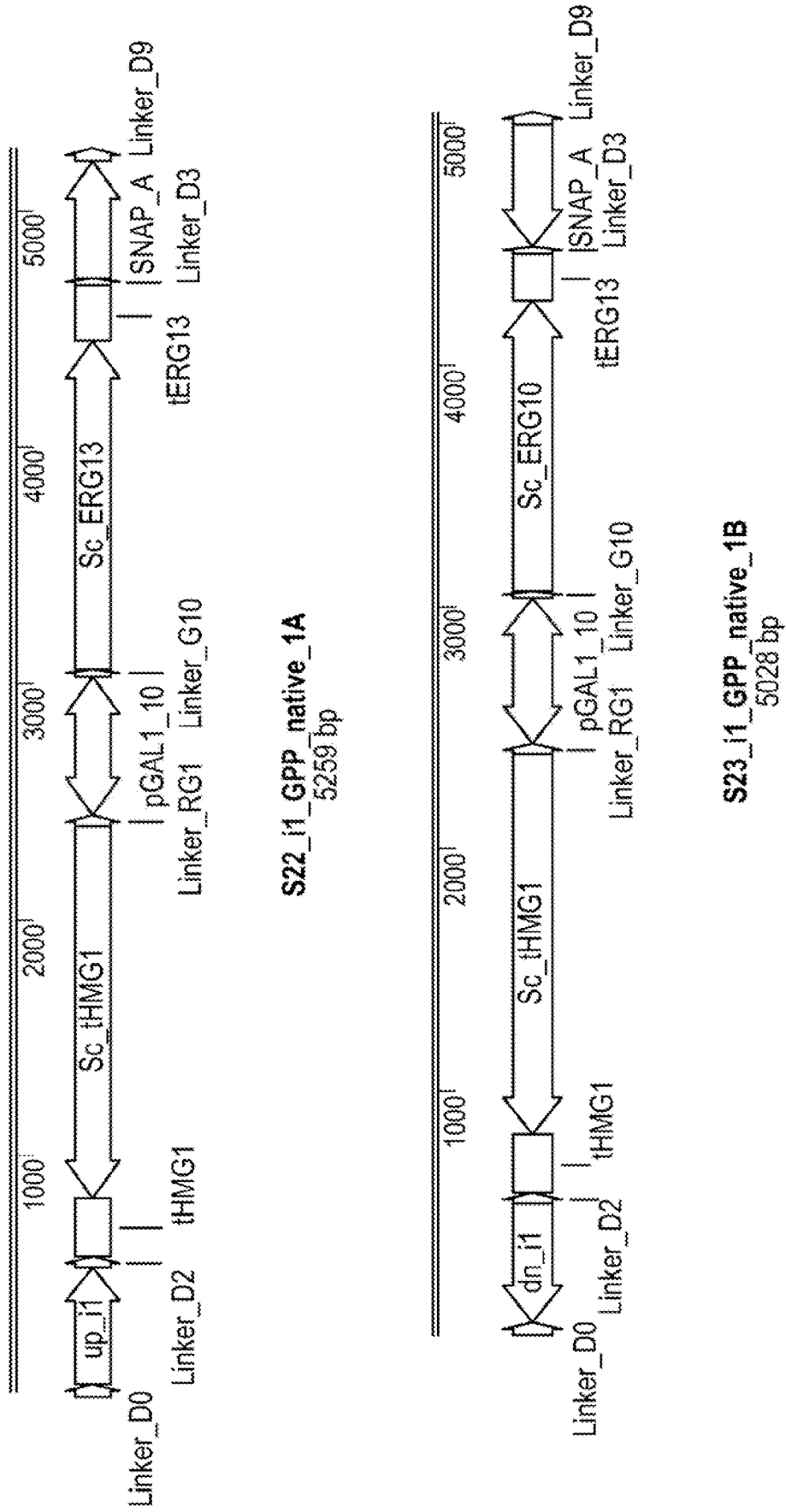
FIGS. 29A and 29B depict expression constructs used in the production of the S21 strain. The expression constructs depicted in FIGS. 29A and 29B are also used in the production of following strains: S29, S31, S34, S35, S37, S38, S39, S41, S42, S43, S44, S45, S46, S47, S49, S50, S51, S78, S80, S81, S82, S83, S84, S85, S86, S87, S88, S89, S90, S91, S94, S95, S97, S104, S108, S112, S114, S115, S116, S118, S123, S147, S164, S165, S166, S167, S168, S169, and S170.
Figure 29B:
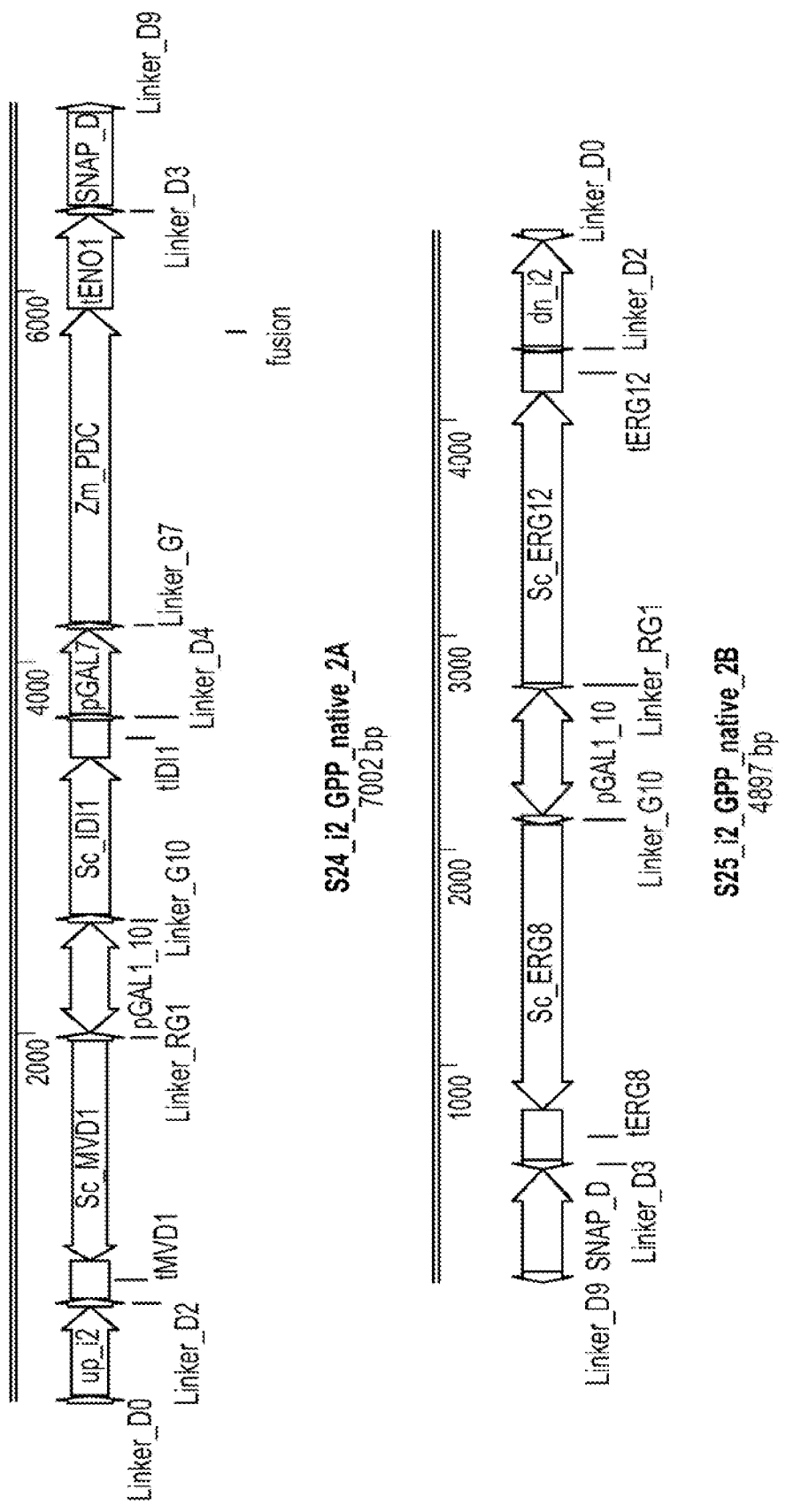
Figure 30A:
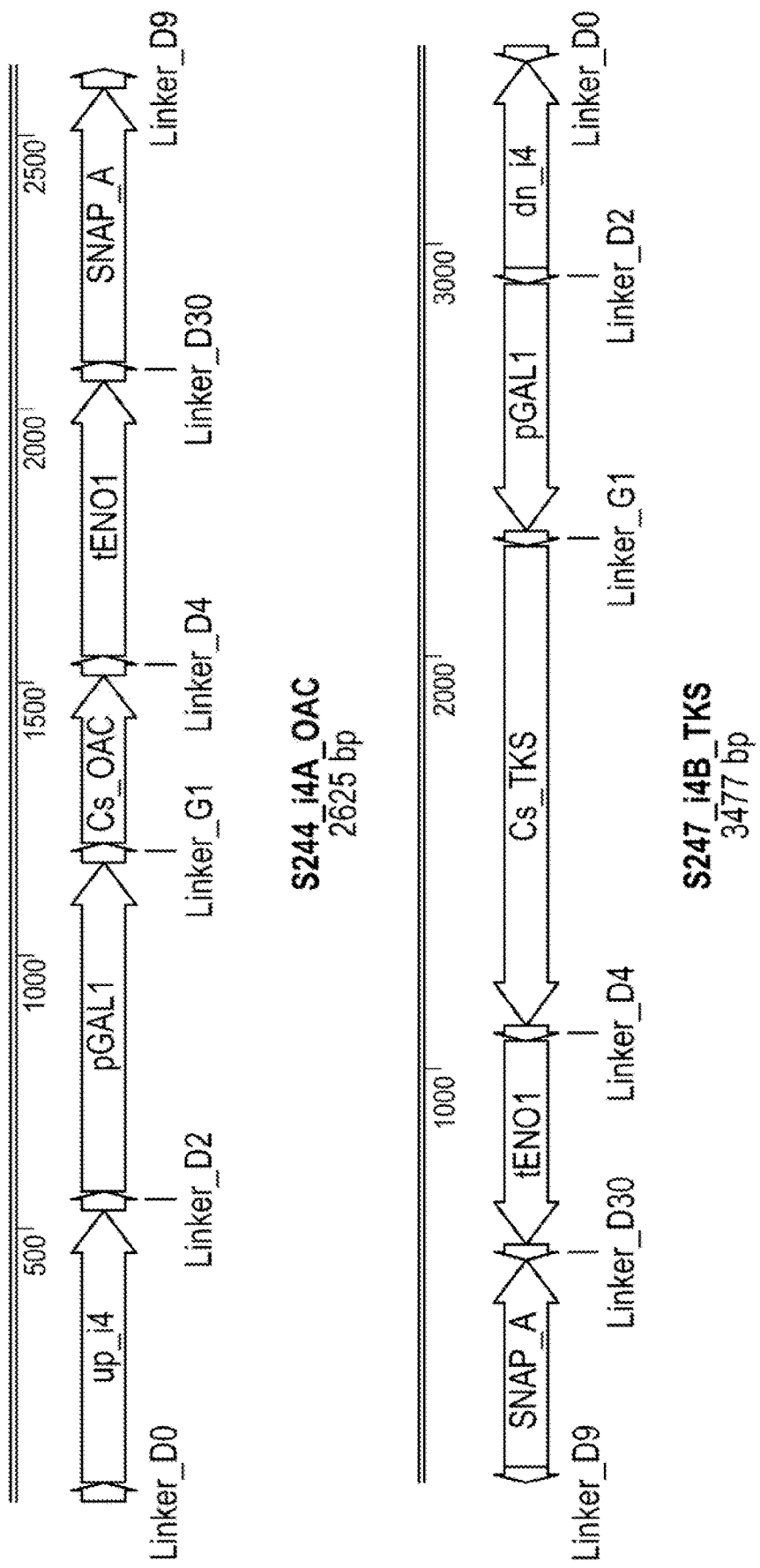
FIGS. 30A, 30B, and 30C depict expression constructs used in the production of the S31 strain. The expression constructs depicted in FIGS. 30A, 30B, and 30C are also used in the production of following strains: S94, S95, and S97.
Figure 30B:
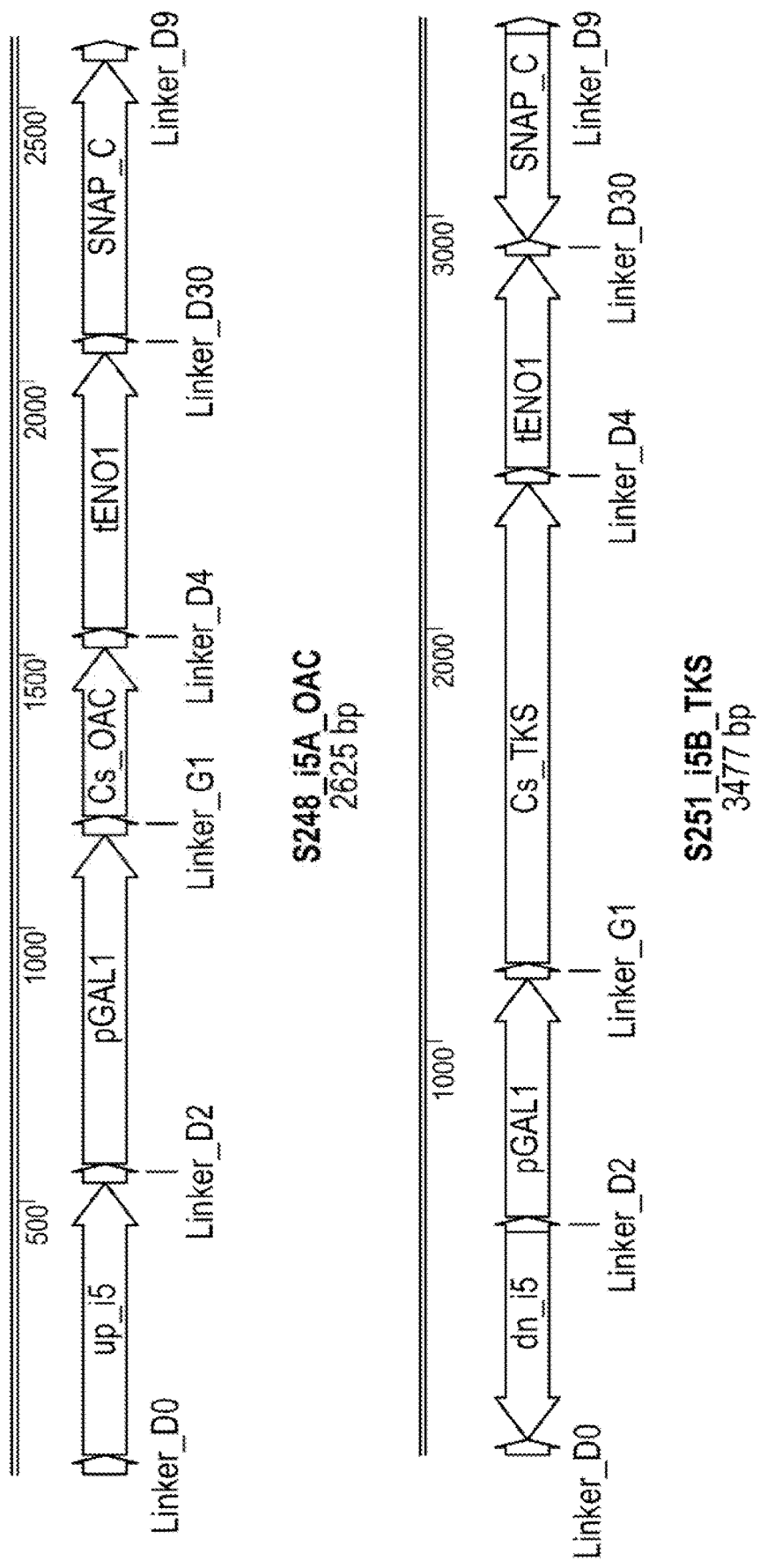
Figure 30C:
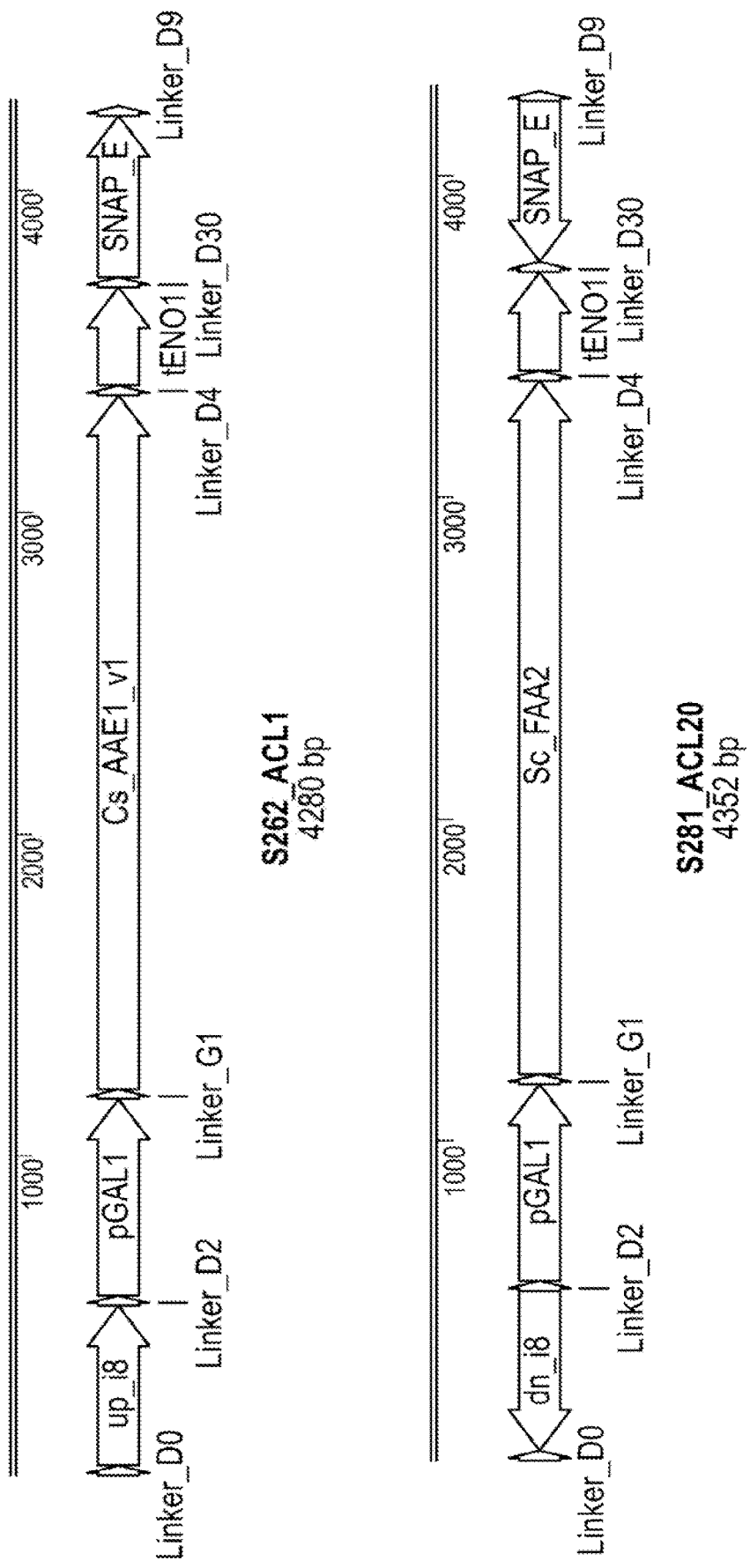
Figure 31:
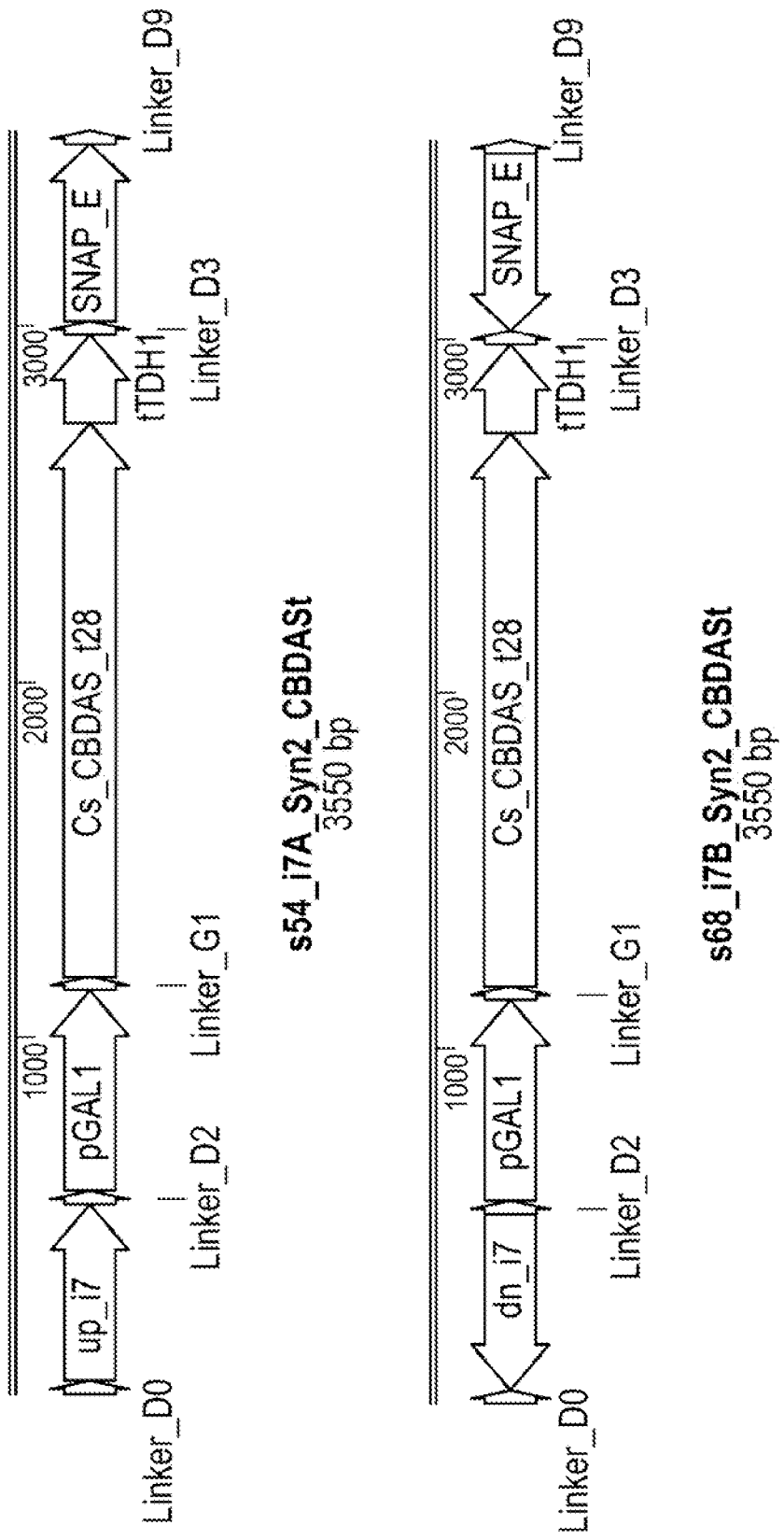
FIG. 31 depicts expression constructs used in the production of the S35 strain.
Figure 32:
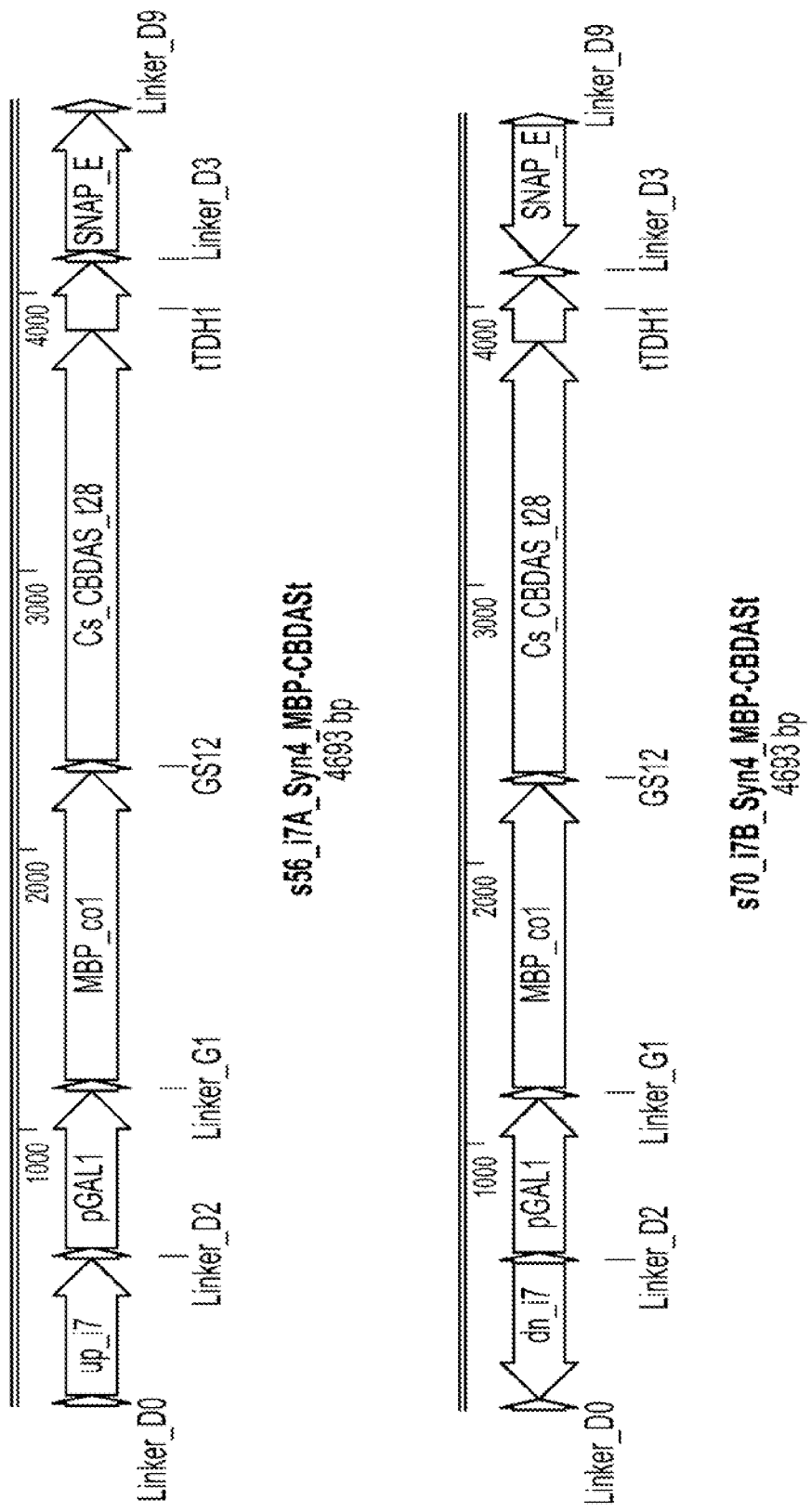
FIG. 32 depicts expression constructs used in the production of the S37 strain.
Figure 33:
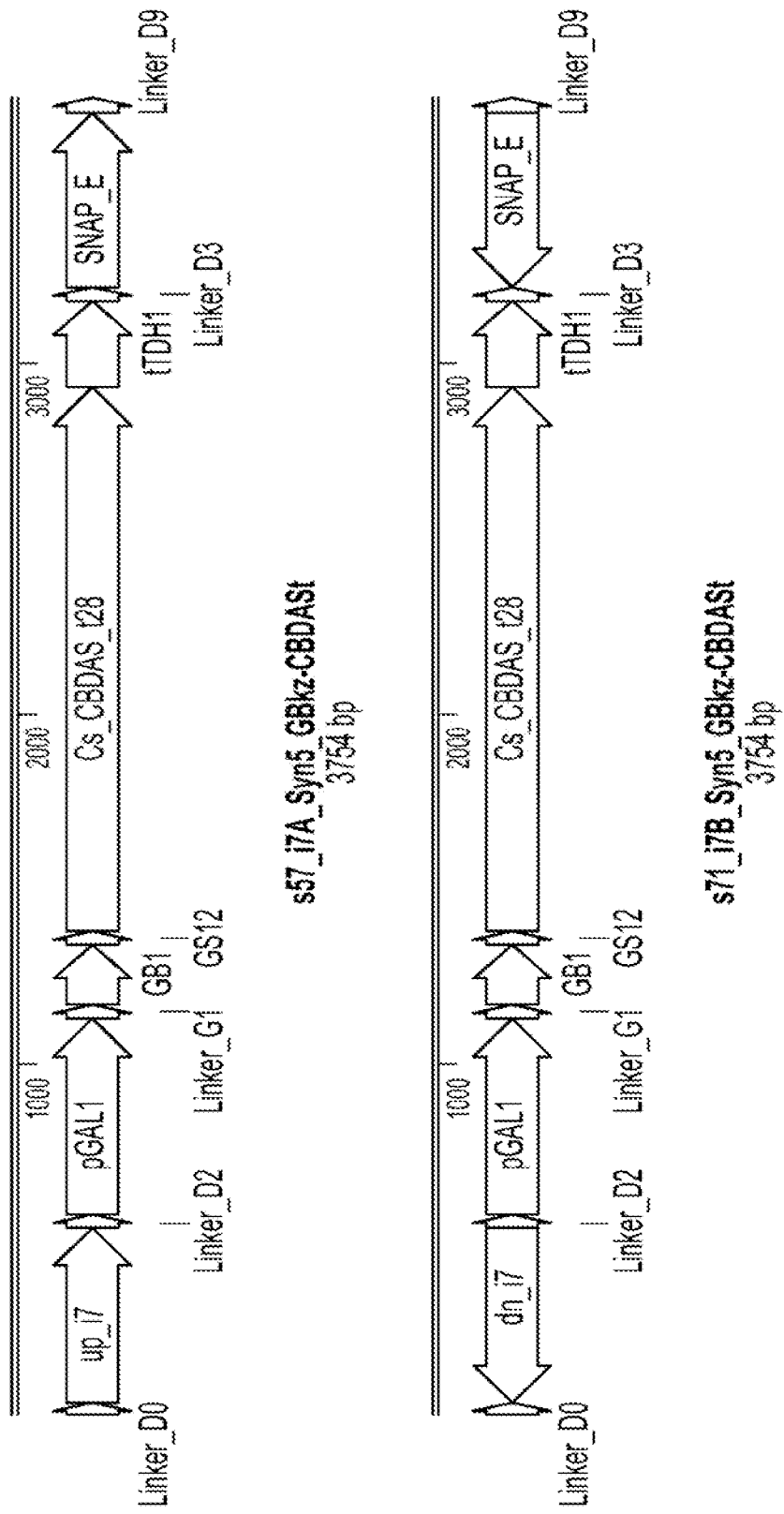
FIG. 33 depicts expression constructs used in the production of the S38 strain.
Figure 34:
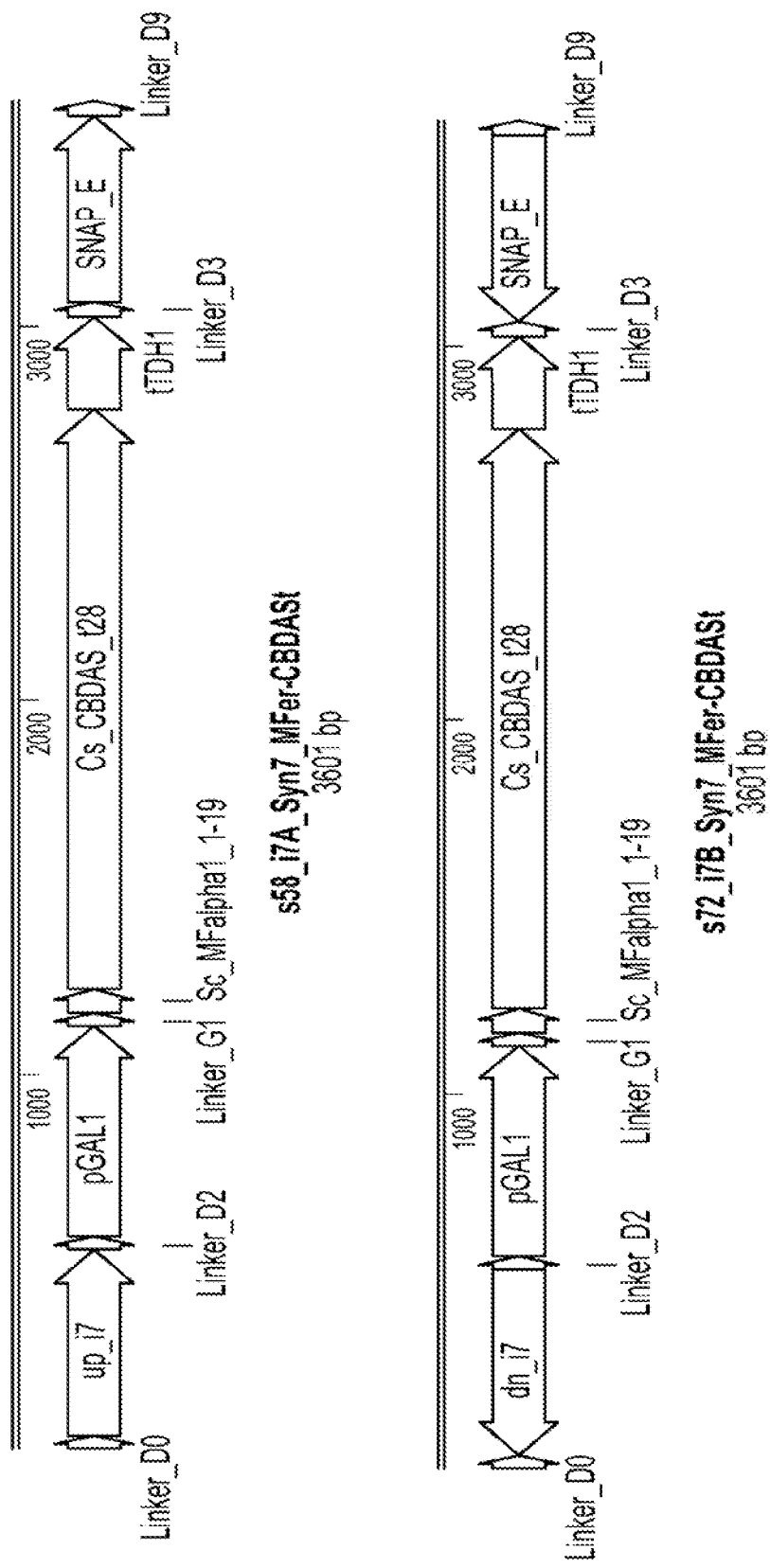
FIG. 34 depicts expression constructs used in the production of the S39 strain.
Figure 35:
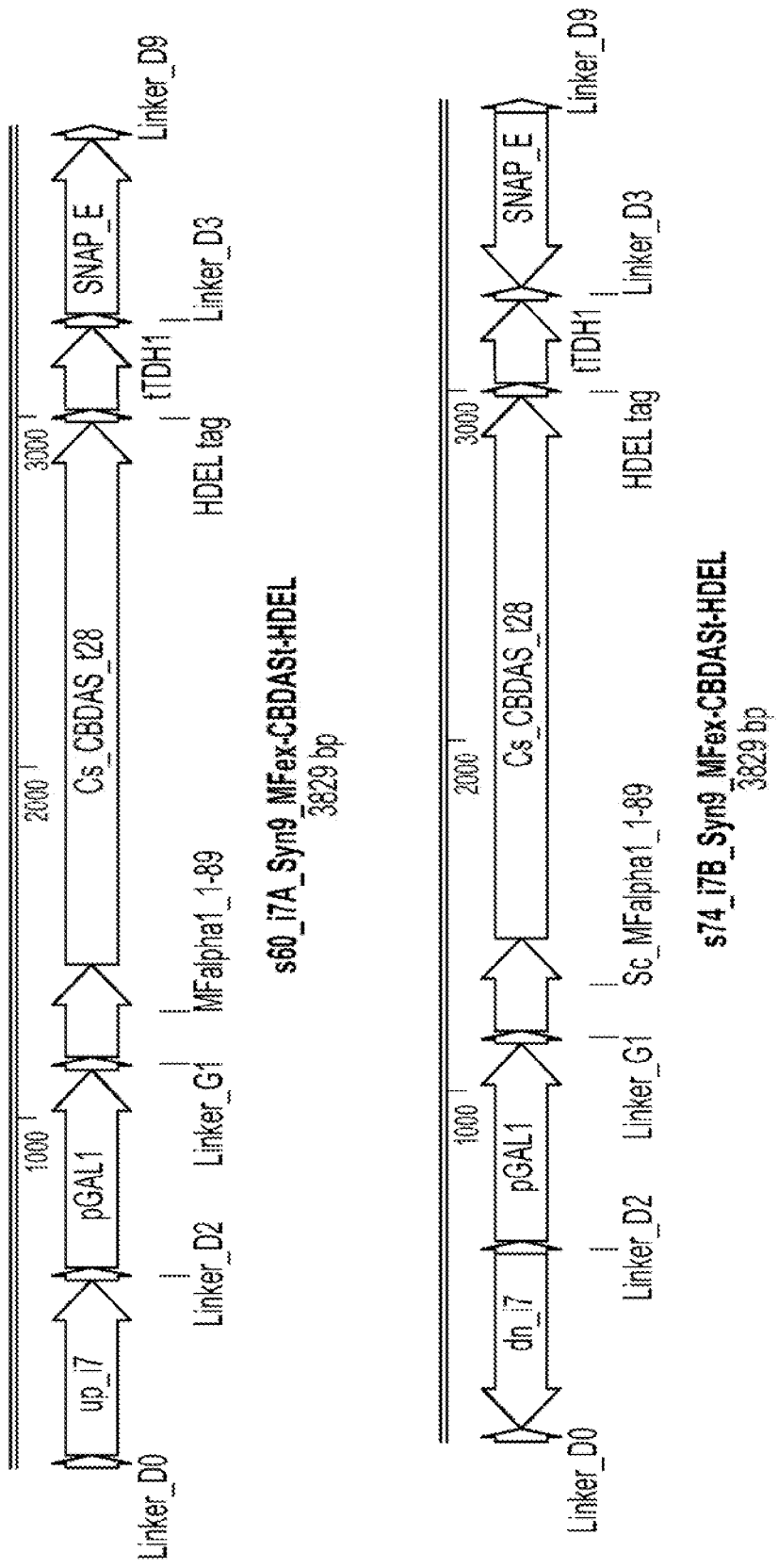
FIG. 35 depicts expression constructs used in the production of the S41 strain.
Figure 36:
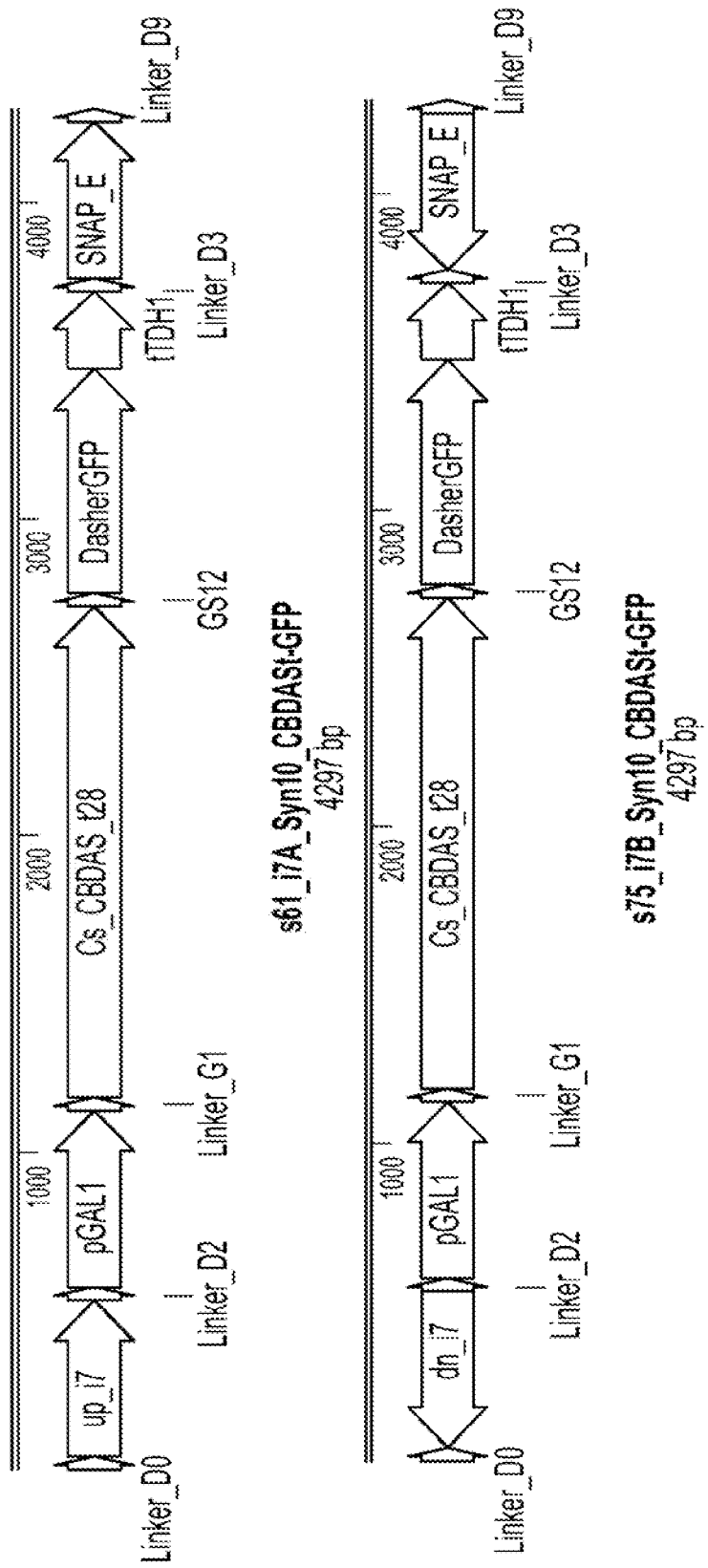
FIG. 36 depicts expression constructs used in the production of the S42 strain.
Figure 37:
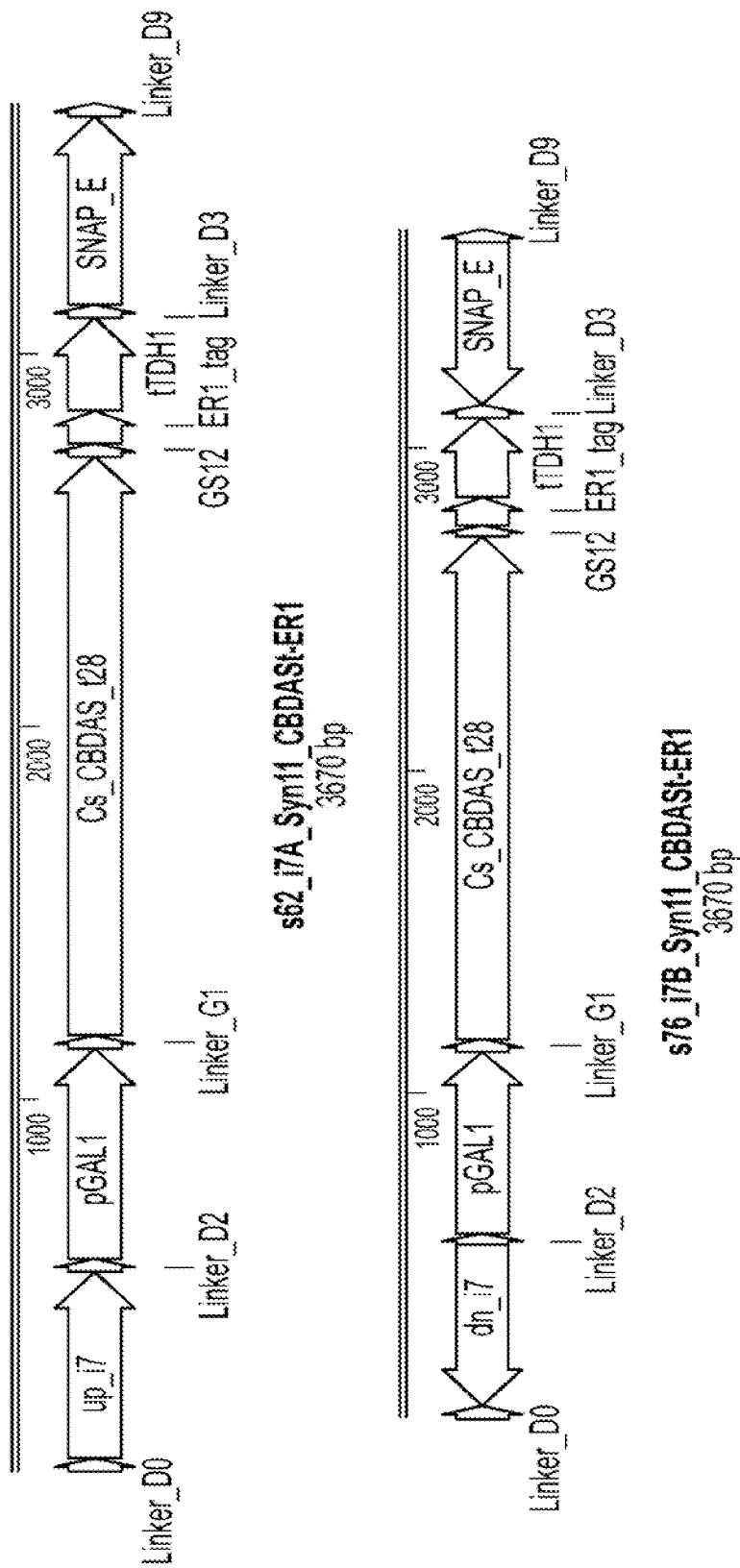
FIG. 37 depicts expression constructs used in the production of the S43 strain.
Figure 38:
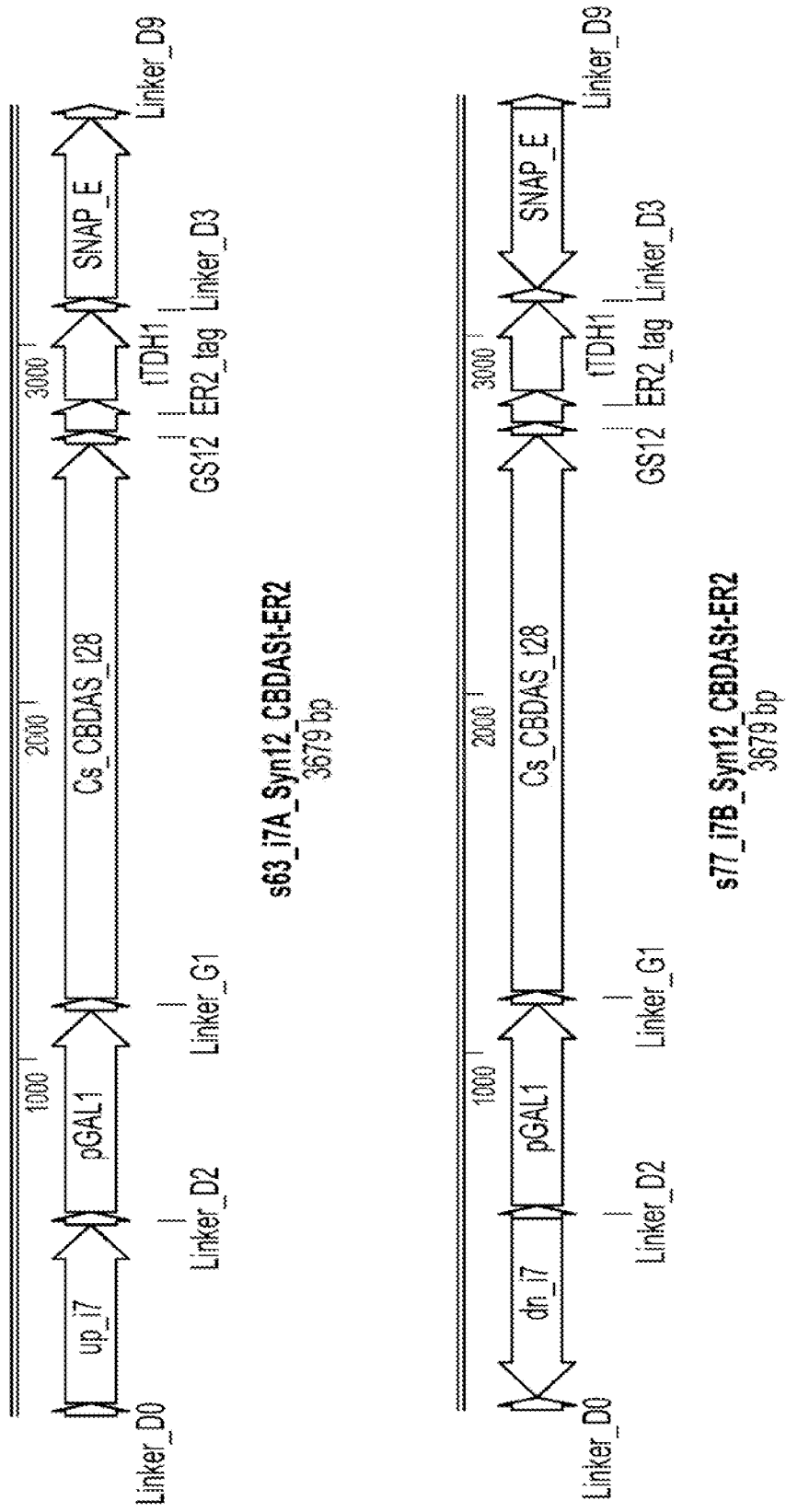
FIG. 38 depicts expression constructs used in the production of the S44 strain.
Figure 39:
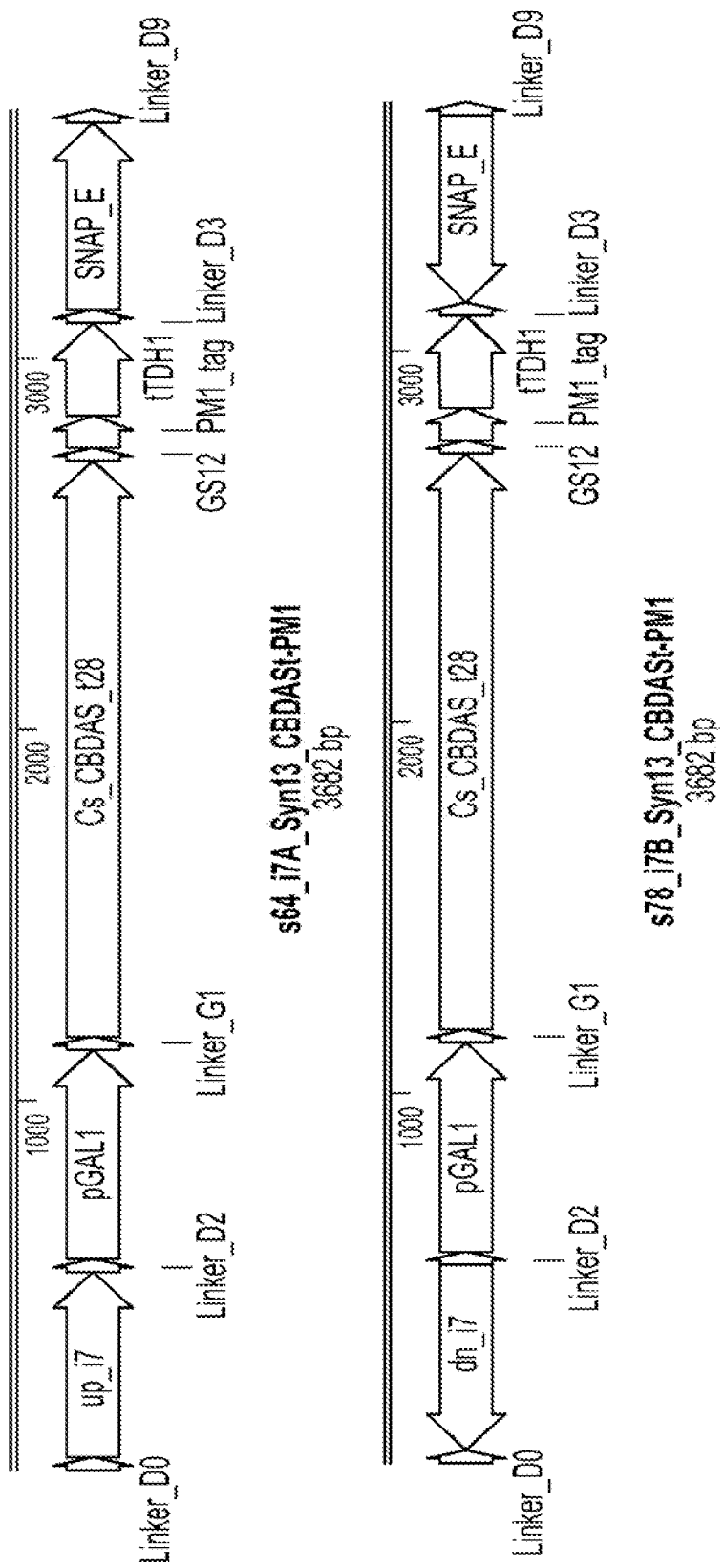
FIG. 39 depicts expression constructs used in the production of the S45 strain.
Figure 40:
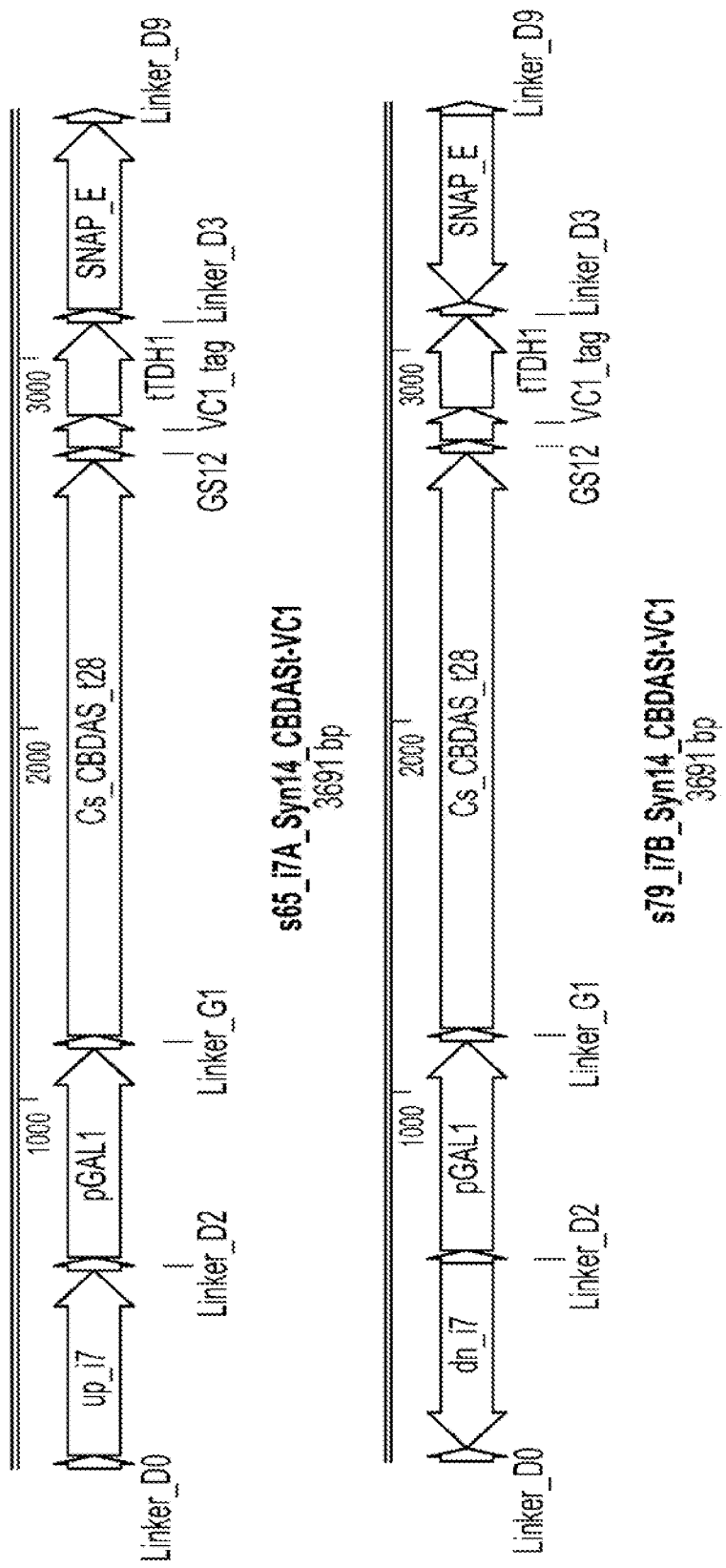
FIG. 40 depicts expression constructs used in the production of the S46 strain.
Figure 41:
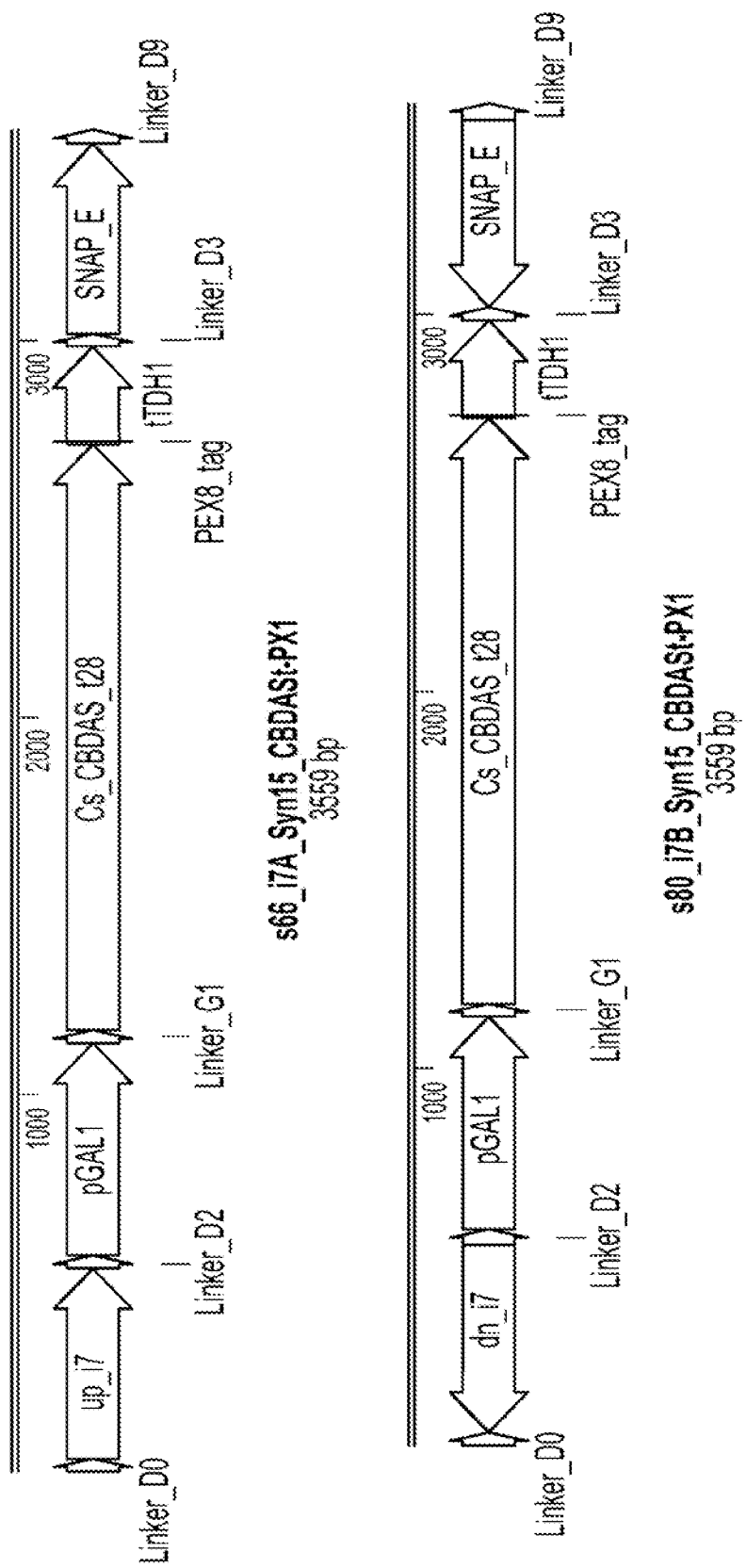
FIG. 41 depicts expression constructs used in the production of the S47 strain.
Figure 42A:
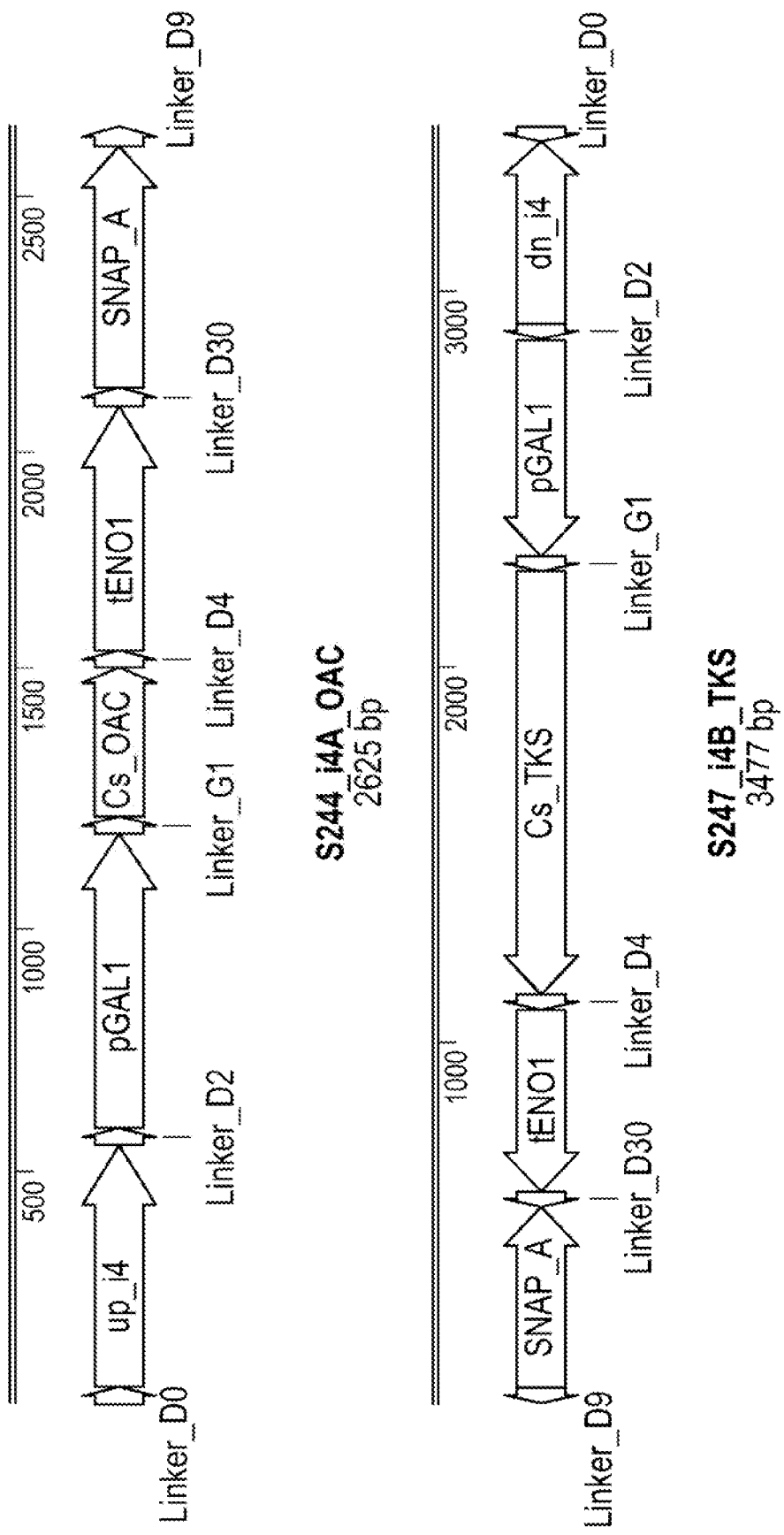
FIGS. 42A, 42B, and 42C depict expression constructs used in the production of the S49 strain.
Figure 42B:
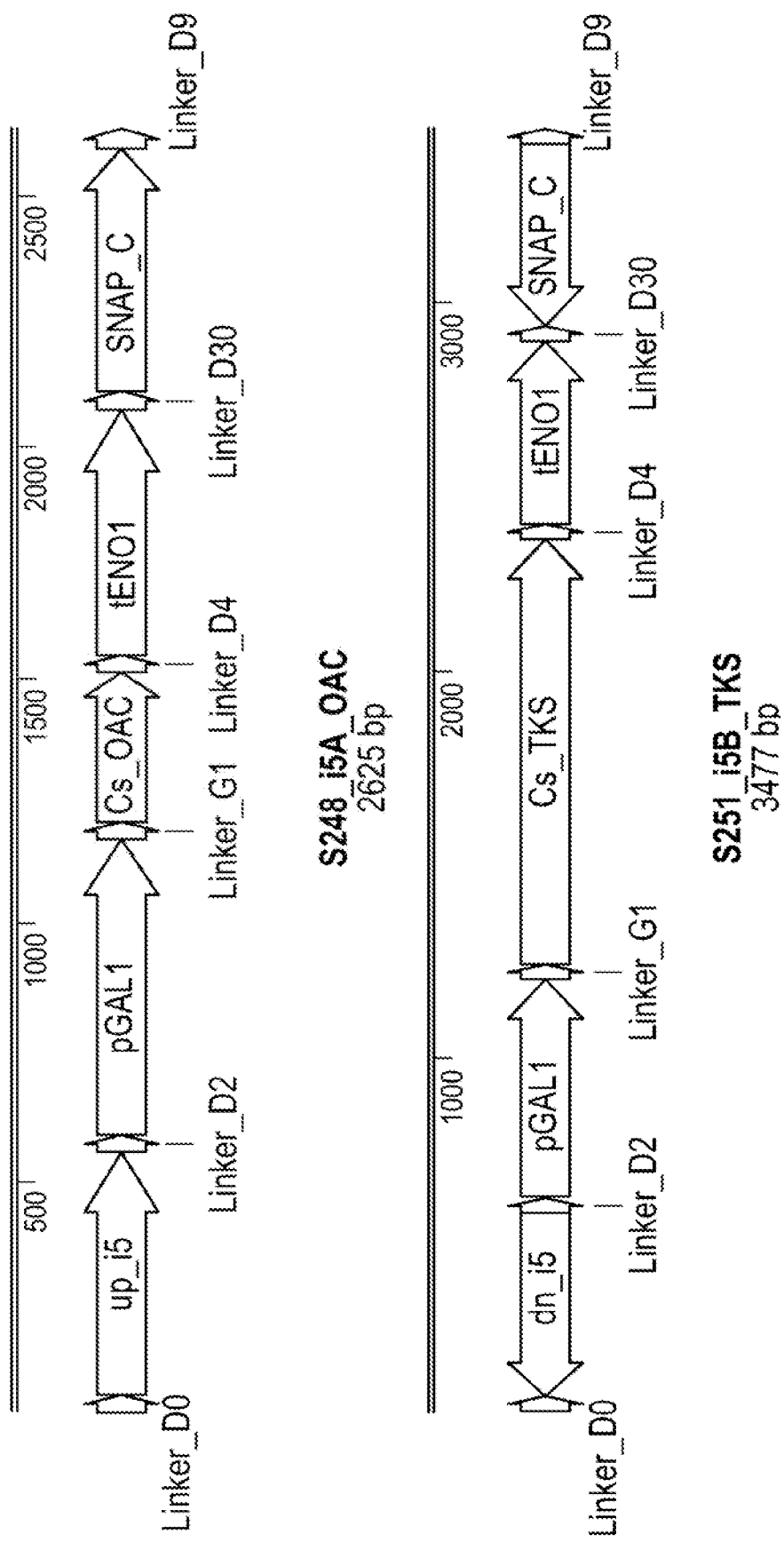
Figure 42C:
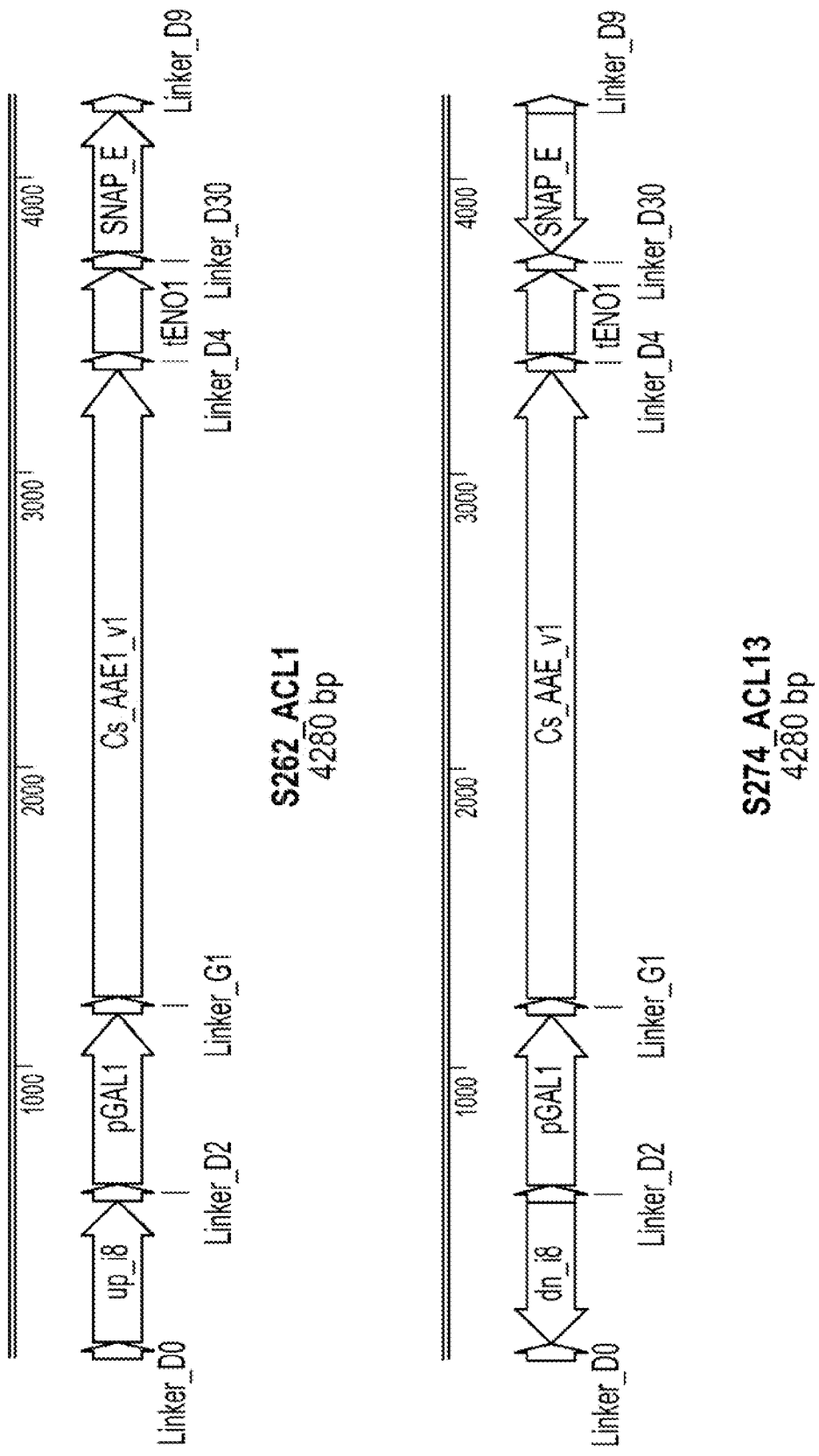
Figure 85:
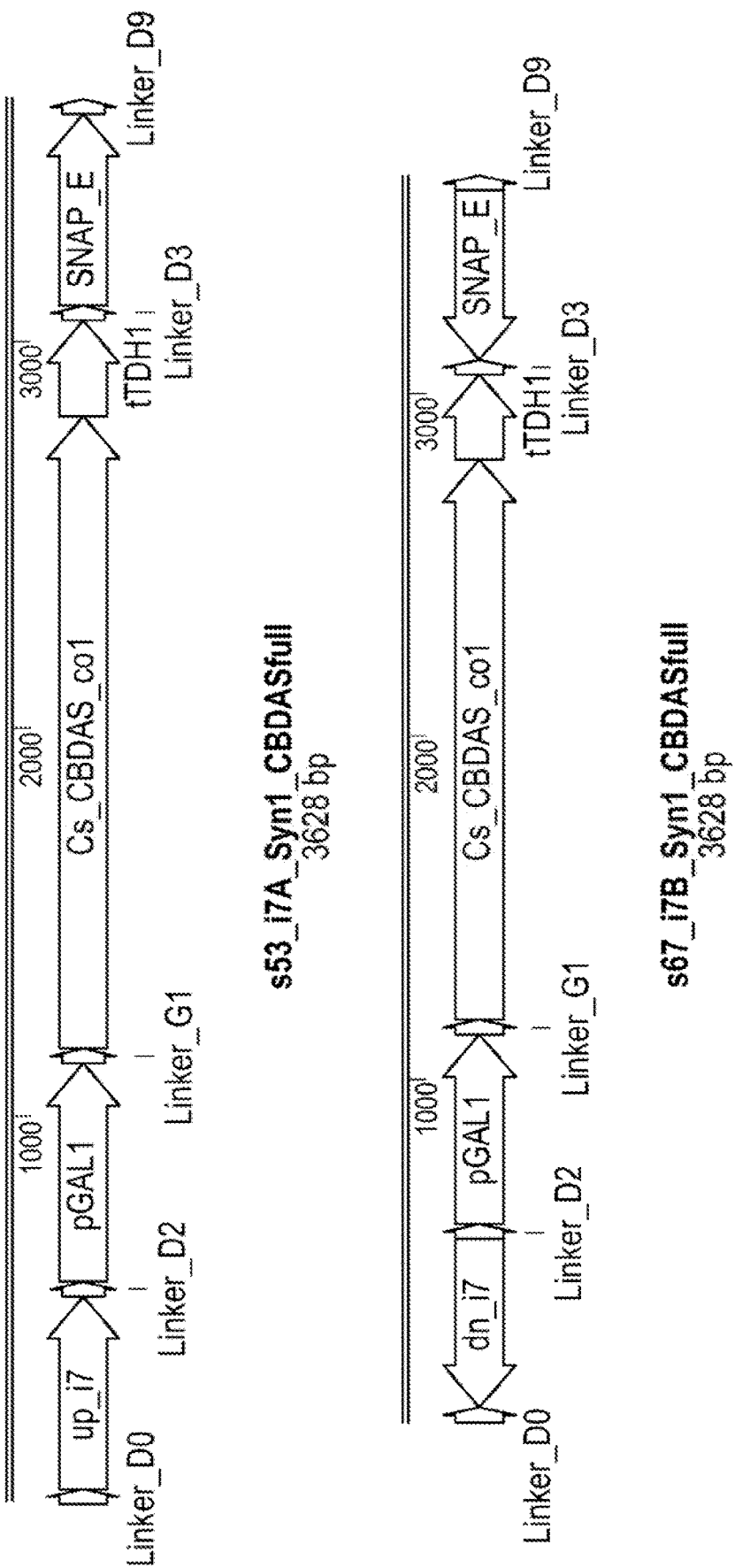
FIG. 85 depicts expression constructs used in the production of the S34 strain.
Figure 86:
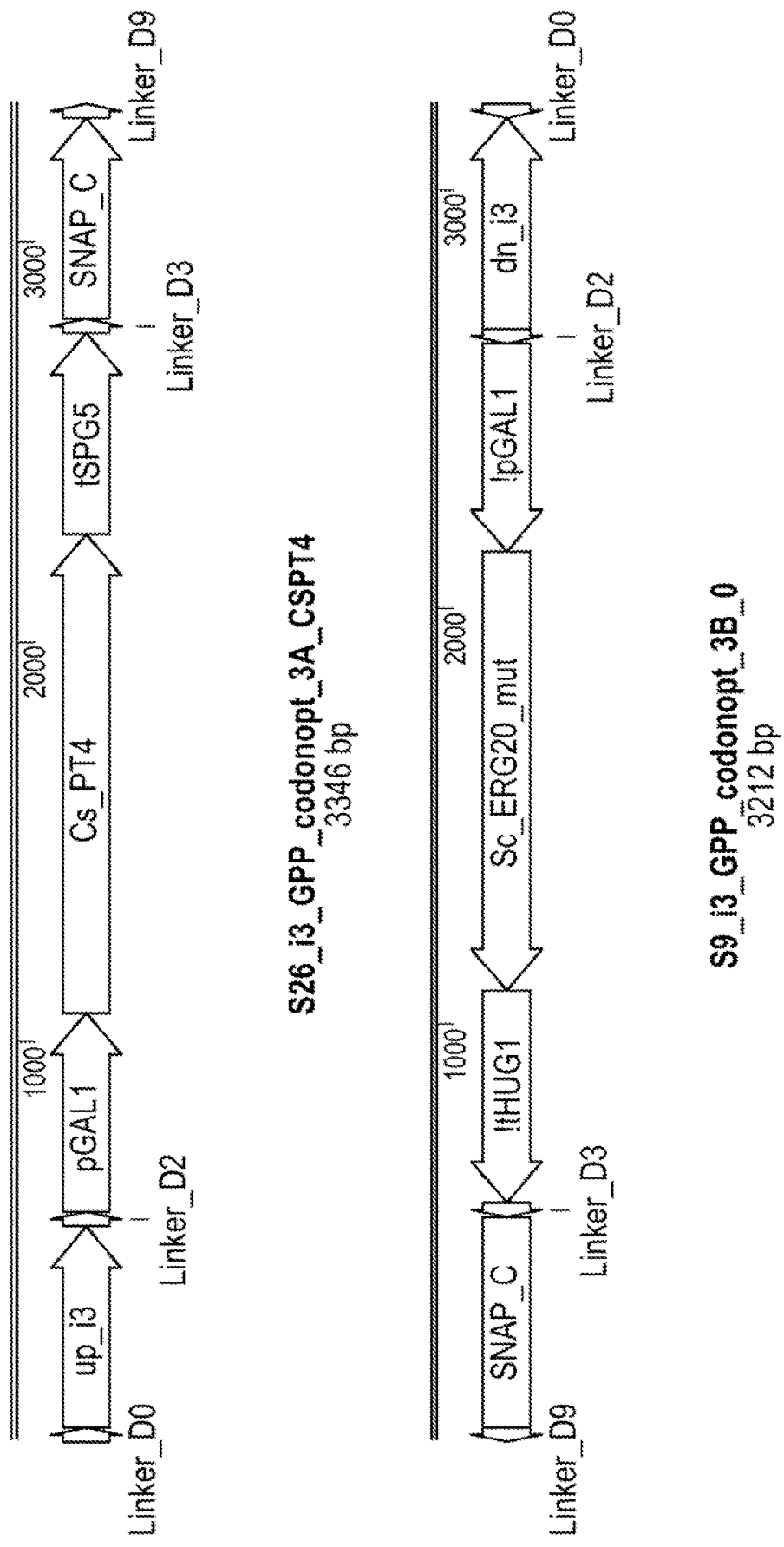
FIG. 86 depicts expression constructs used in the production of the S29 strain. The expression constructs depicted in FIG. 86 are also used in the production of following strains: S31, S34, S35, S37, S38, S39, S41, S42, S43, S44, S45, S46, S47, S49, S50, S51, S78, S80, S81, S82, S83, S84, S85, S86, S87, S88, S89, S90, S91, S94, S95, S97, and S123.

| Strain (Constructs) | Parent Strain* | Polypeptide SEQ ID NOs (Nucleotide SEQ ID NOs) |
|---|---|---|
| S21 (FIGS. 29A and 29B) | | Sc_tHMG1: SEQ ID NO: 208 (SEQ ID NO: 119)<br>Sc_ERG13: SEQ ID NO: 115 (SEQ ID NO: 120)<br>Sc_ERG10: SEQ ID NO: 25 (SEQ ID NO: 209)<br>Sc_MVD1 (Sc_ERG19): SEQ ID NO: 66 (SEQ ID NO: 65)<br>Sc_IDI1: SEQ ID NO: 58 (SEQ ID NO: 57)<br>Zm_PDC: SEQ ID NO: 117 (SEQ ID NO: 118)<br>Sc_ERG8: SEQ ID NO: 205 (SEQ ID NO: 204)<br>Sc_ERG12: SEQ ID NO: 64 (SEQ ID NO: 206) |
| S29 (FIG. 86) | S21 | Cs_PT4: SEQ ID NO: 110 (SEQ ID NO: 111)<br>Sc_ERG20_mut: SEQ ID NO: 60 (SEQ ID NO: 161) |
| S31 (FIGS. 30A, 30B, and 30C) | S29 | Cs_OAC: SEQ ID NO: 10 (SEQ ID NO: 163)<br>Cs_TKS: SEQ ID NO: 11 (SEQ ID NO: 162)<br>Cs_AAE1_v1: SEQ ID NO: 90 (SEQ ID NO: 164)<br>Sc_FAA2: SEQ ID NO: 169 (SEQ ID NO: 168) |
| S34 (FIG. 85) | S29 | Cs_CBDAS_col: SEQ ID NO: 88 (SEQ ID NO: 167) |
| S35 (FIG. 31) | S29 | Cs_CBDAS_t28: SEQ ID NO: 151 (SEQ ID NO: 152) |
| S37 (FIG. 32) | S29 | MBP_col: SEQ ID NO: 108 (SEQ ID NO: 170)<br>Cs_CBDAS_t28: SEQ ID NO: 151 (SEQ ID NO: 152)<br>GS12: SEQ ID NO: 172 (SEQ ID NO: 171) |
| S38 (FIG. 33) | S29 | Cs_CBDAS_t28: SEQ ID NO: 151 (SEQ ID NO: 152)<br>GB1: SEQ ID NO: 174 (SEQ ID NO: 173)<br>GS12: SEQ ID NO: 172 (SEQ ID NO: 171) |
| S39 (FIG. 34) | S29 | Cs_CBDAS_t28: SEQ ID NO: 151 (SEQ ID NO: 152)<br>Sc_MFalpha1_1-19: SEQ ID NO: 176 (SEQ ID NO: 175) |
| S41 (FIG. 35) | S29 | Cs_CBDAS_t28: SEQ ID NO: 151 (SEQ ID NO: 152)<br>Sc_MFalpha1_1-89: SEQ ID NO: 178 (SEQ ID NO: 177) |
| S42 (FIG. 36) | S29 | Cs_CBDAS_t28: SEQ ID NO: 151 (SEQ ID NO: 152)<br>DasherGFP: SEQ ID NO: 180 (SEQ ID NO: 179)<br>GS12: SEQ ID NO: 172 (SEQ ID NO: 171) |
| S43 (FIG. 37) | S29 | Cs_CBDAS_t28: SEQ ID NO: 151 (SEQ ID NO: 152)<br>GS12: SEQ ID NO: 172 (SEQ ID NO: 171)<br>ER1_tag: SEQ ID NO: 182 (SEQ ID NO: 181) |
| S44 (FIG. 38) | S29 | Cs_CBDAS_t28: SEQ ID NO: 151 (SEQ ID NO: 152)<br>GS12: SEQ ID NO: 172 (SEQ ID NO: 171)<br>ER2_tag: SEQ ID NO: 184 (SEQ ID NO: 183) |
| S45 (FIG. 39) | S29 | Cs_CBDAS_t28: SEQ ID NO: 151 (SEQ ID NO: 152)<br>GS12: SEQ ID NO: 172 (SEQ ID NO: 171)<br>PM1_tag: SEQ ID NO: 186 (SEQ ID NO: 185) |
| S46 (FIG. 40) | S29 | Cs_CBDAS_t28: SEQ ID NO: 151 (SEQ ID NO: 152)<br>GS12: SEQ ID NO: 172 (SEQ ID NO: 171)<br>VC1_tag: SEQ ID NO: 188 (SEQ ID NO: 187) |
| S47 (FIG. 41) | S29 | Cs_CBDAS_t28: SEQ ID NO: 151 (SEQ ID NO: 152)<br>PEX8_tag: SEQ ID NO: 190 (SEQ ID NO: 189) |
| S49 (FIGS. 42A, 42B, and 42C) | S29 | Cs_OAC: SEQ ID NO: 10 (SEQ ID NO: 163)<br>Cs_TKS: SEQ ID NO: 11 (SEQ ID NO: 162)<br>Cs_AAE1_v1: SEQ ID NO: 90 (SEQ ID NO: 164)<br>Cs_AAE_v1: SEQ ID NO: 90 (SEQ ID NO: 164) |

TABLE 11-continued

Constructs and strains used in the Examples

Figure 43A:
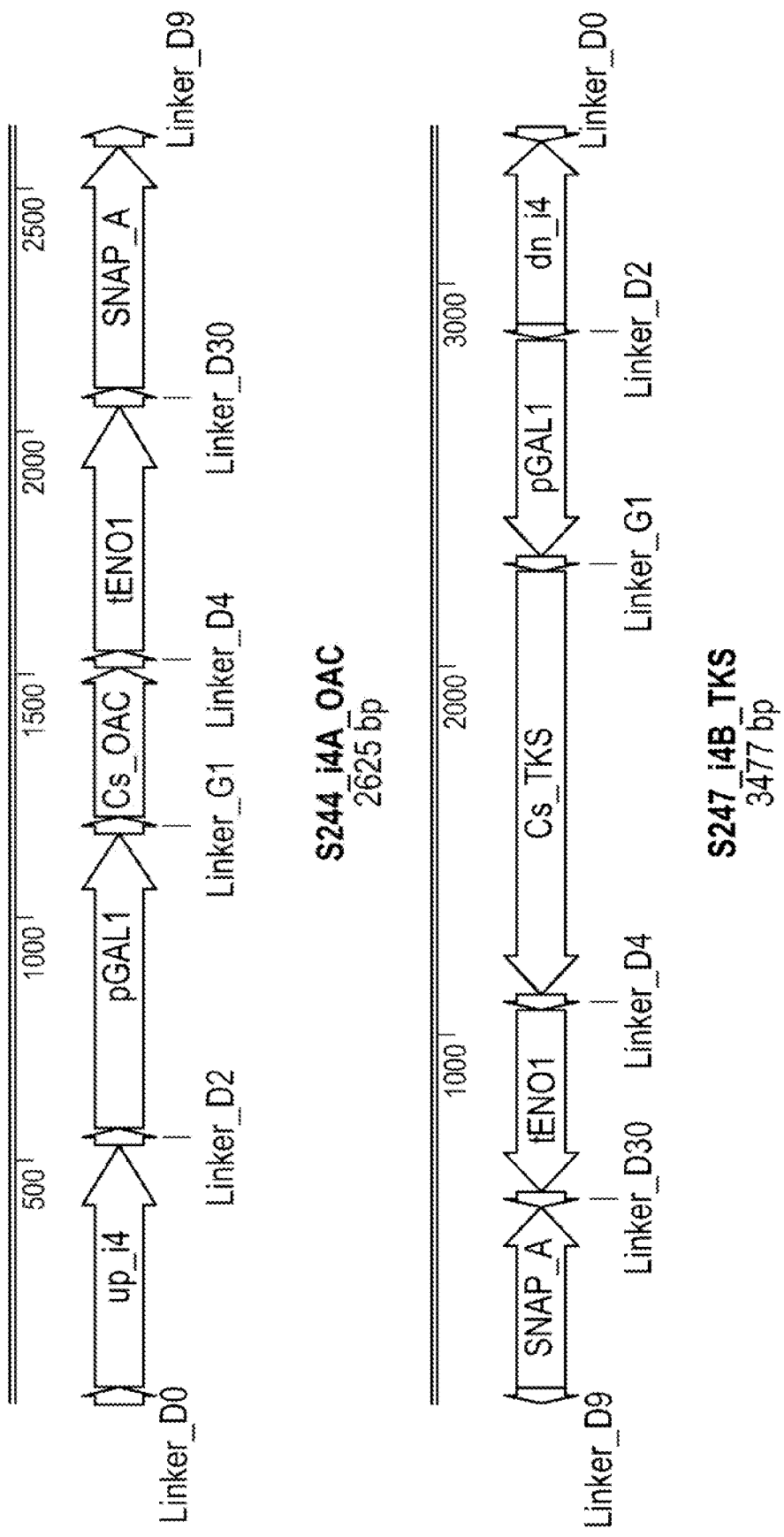
FIGS. 43A, 43B, and 43C depict expression constructs used in the production of the S50 strain.
Figure 43B:
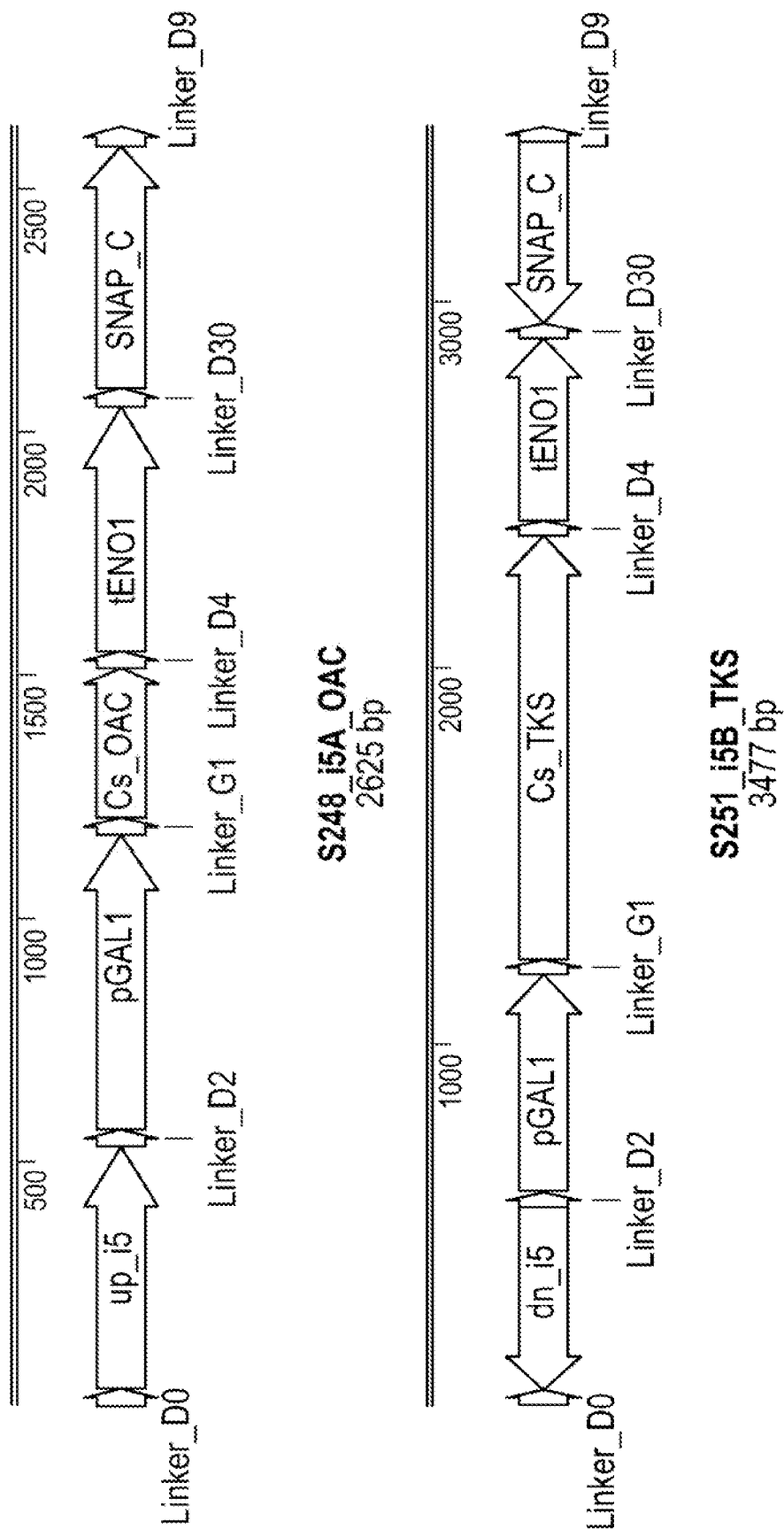
Figure 43C:
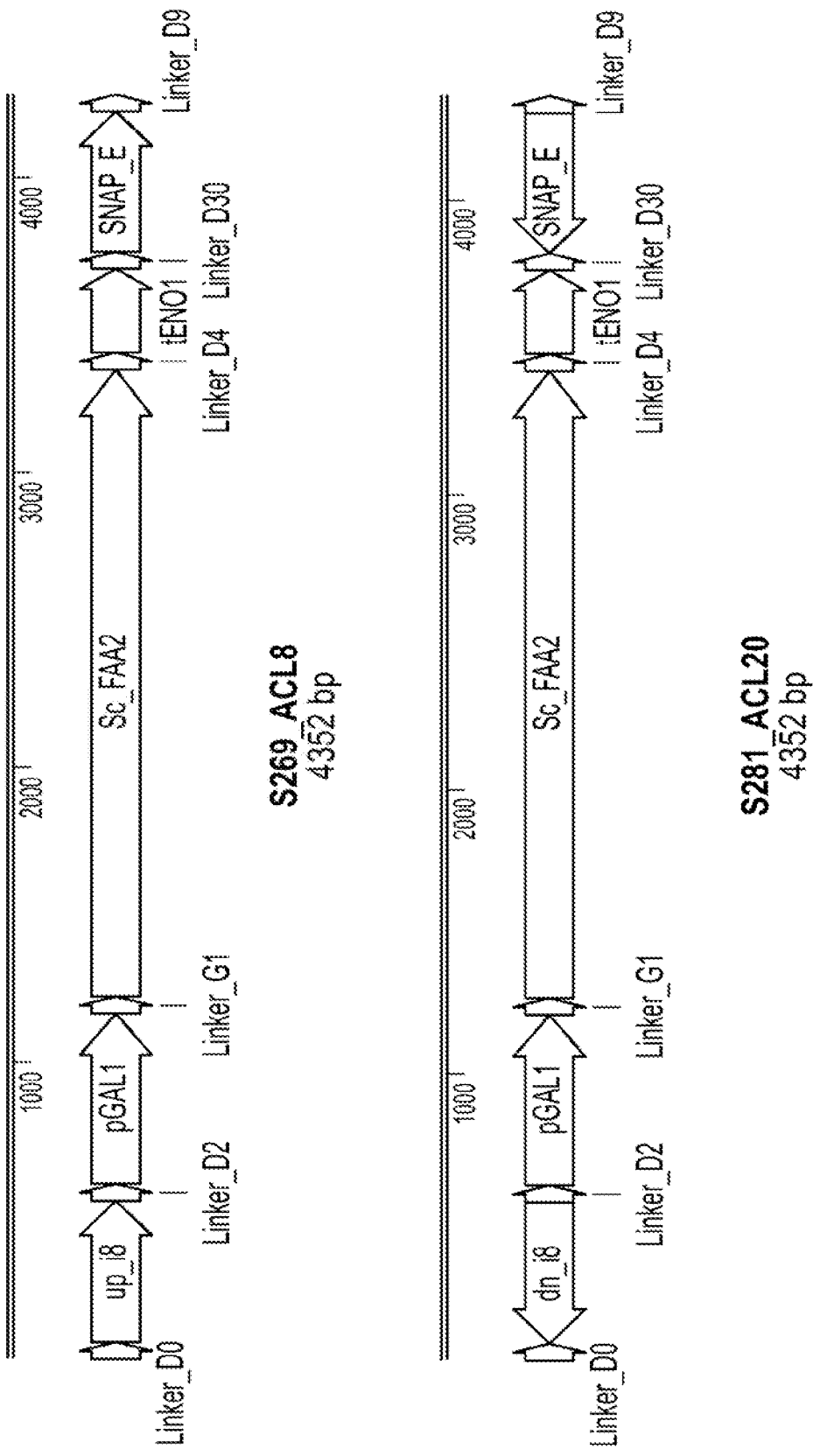
Figure 44A:
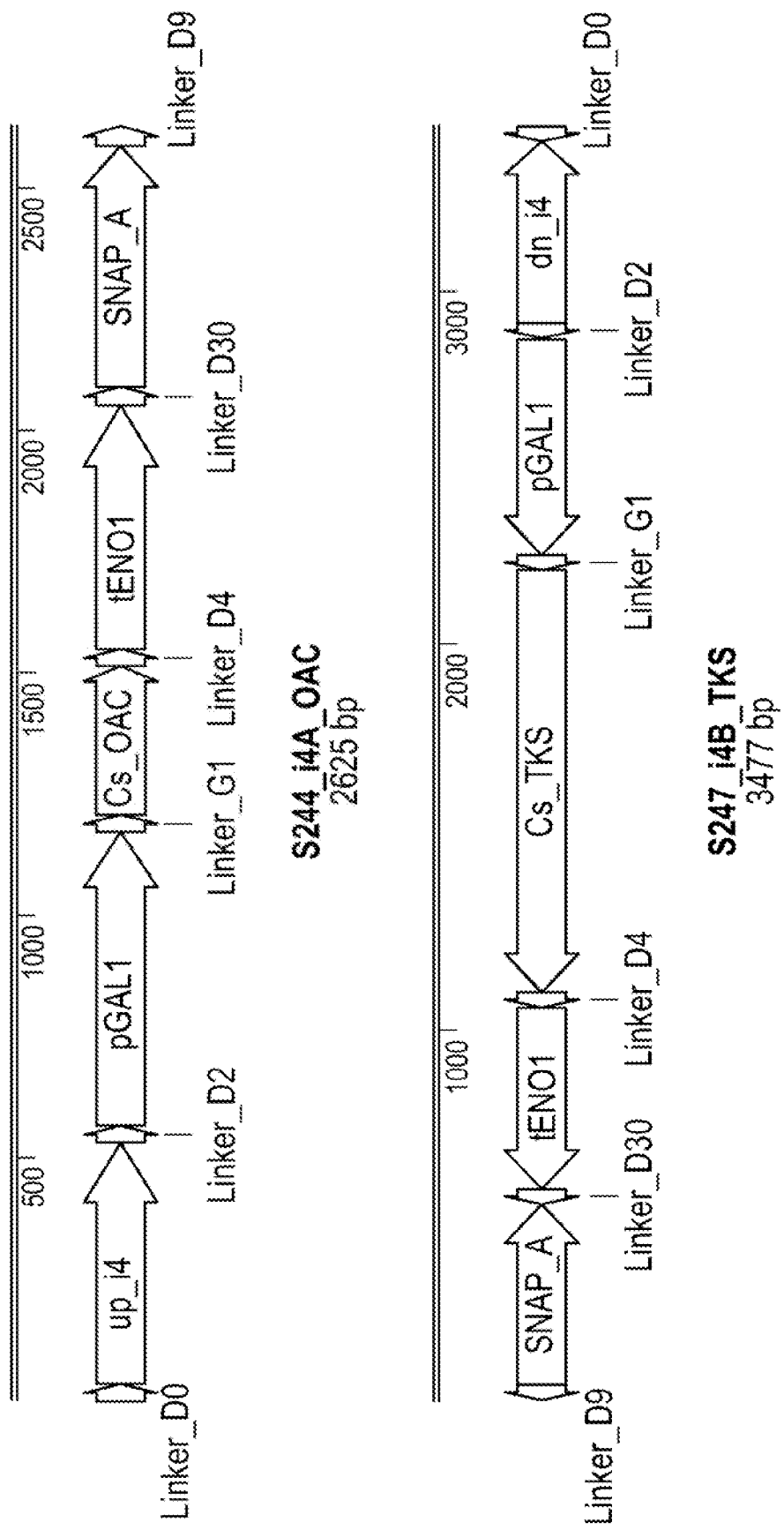
FIGS. 44A, 44B, and 44C depict expression constructs used in the production of the S51 strain. The expression constructs depicted in FIGS. 44A, 44B, and 44C are also used in the production of following strains: S78, S80, S81, S82, S83, S84, S85, S86, S87, S88, and S89.
Figure 44B:
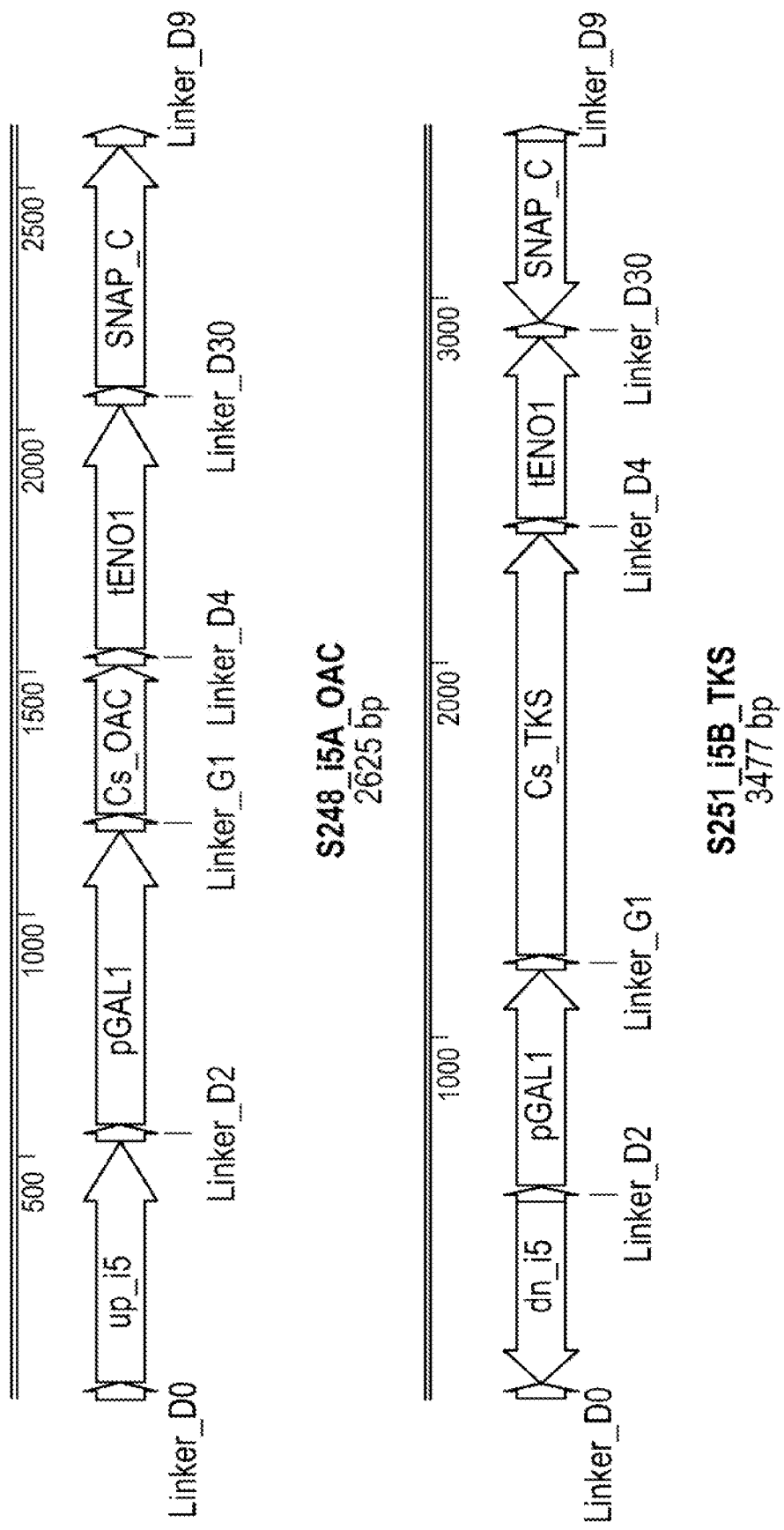
Figure 44C:
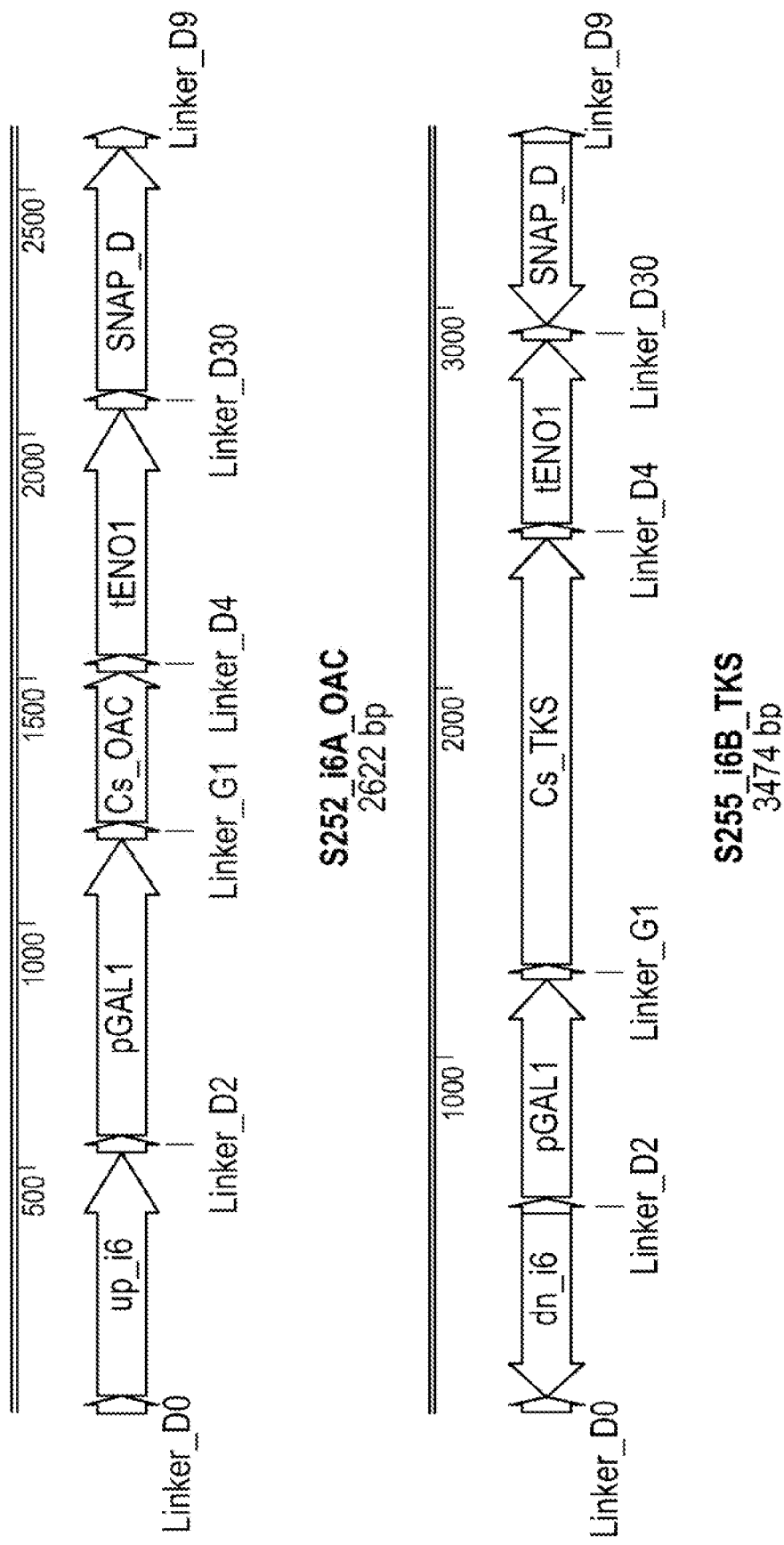
Figure 45:
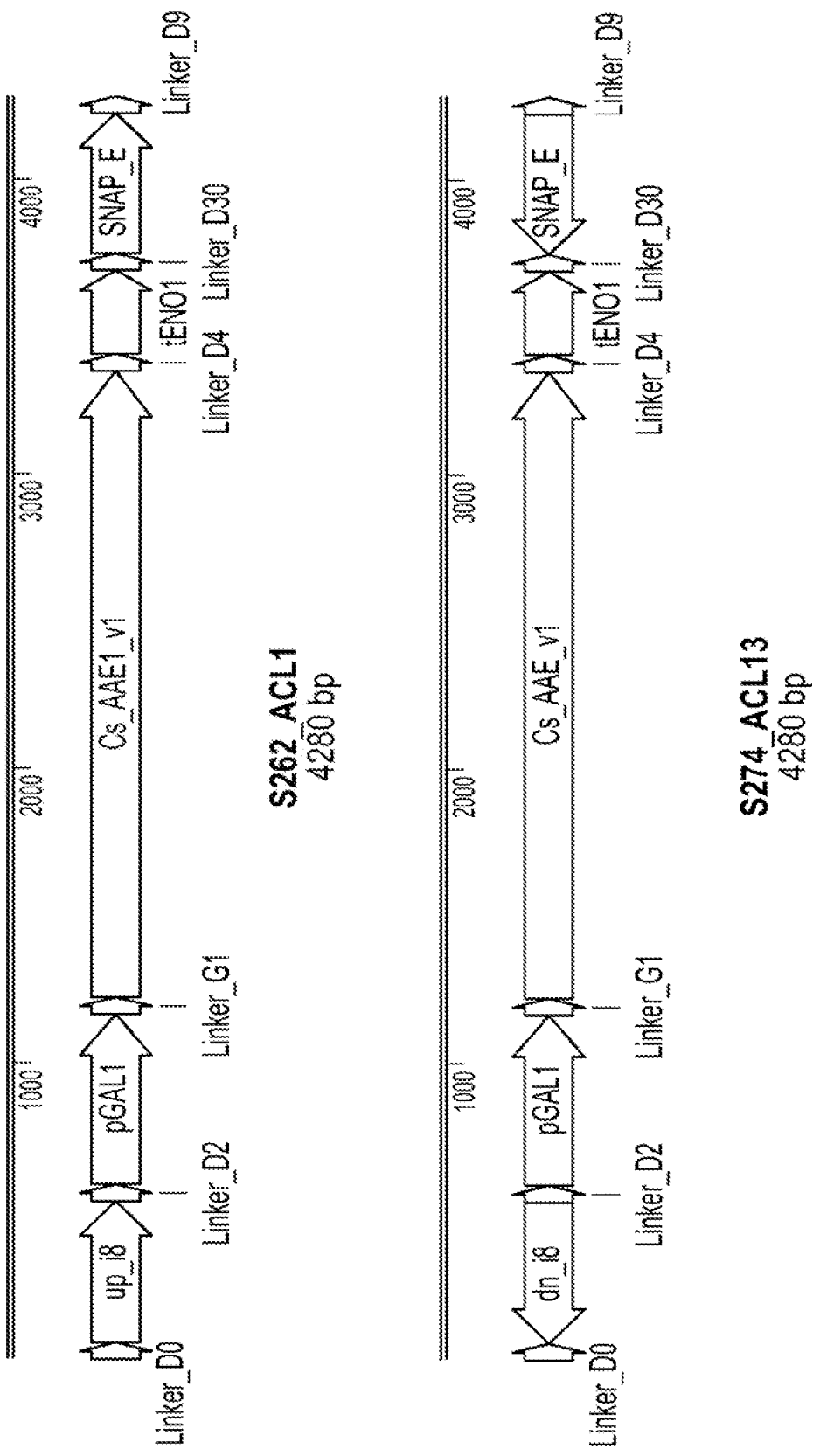
FIG. 45 depicts expression constructs used in the production of the S78 strain.
Figure 46:
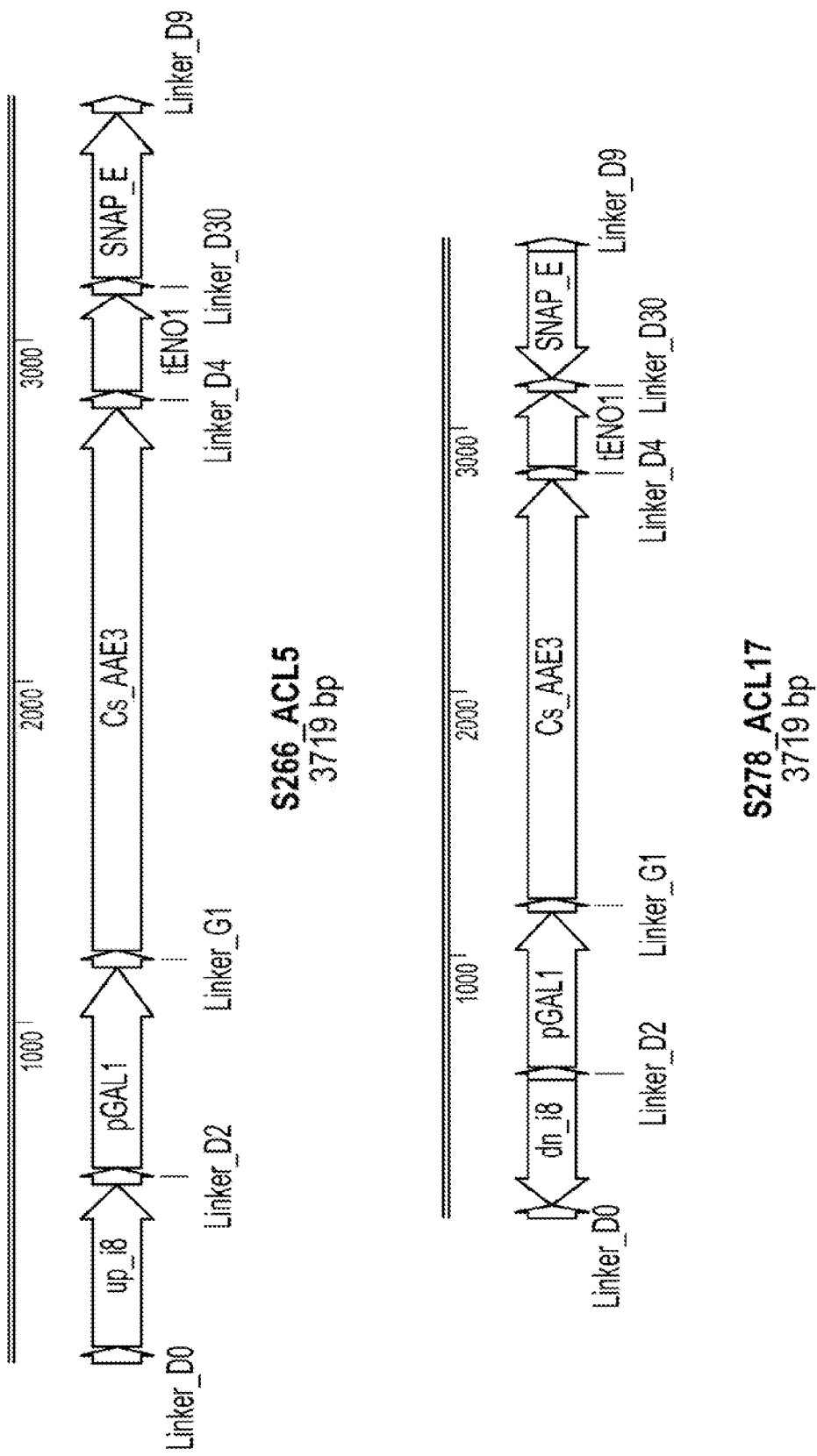
FIG. 46 depicts expression constructs used in the production of the S80 strain.
Figure 47:
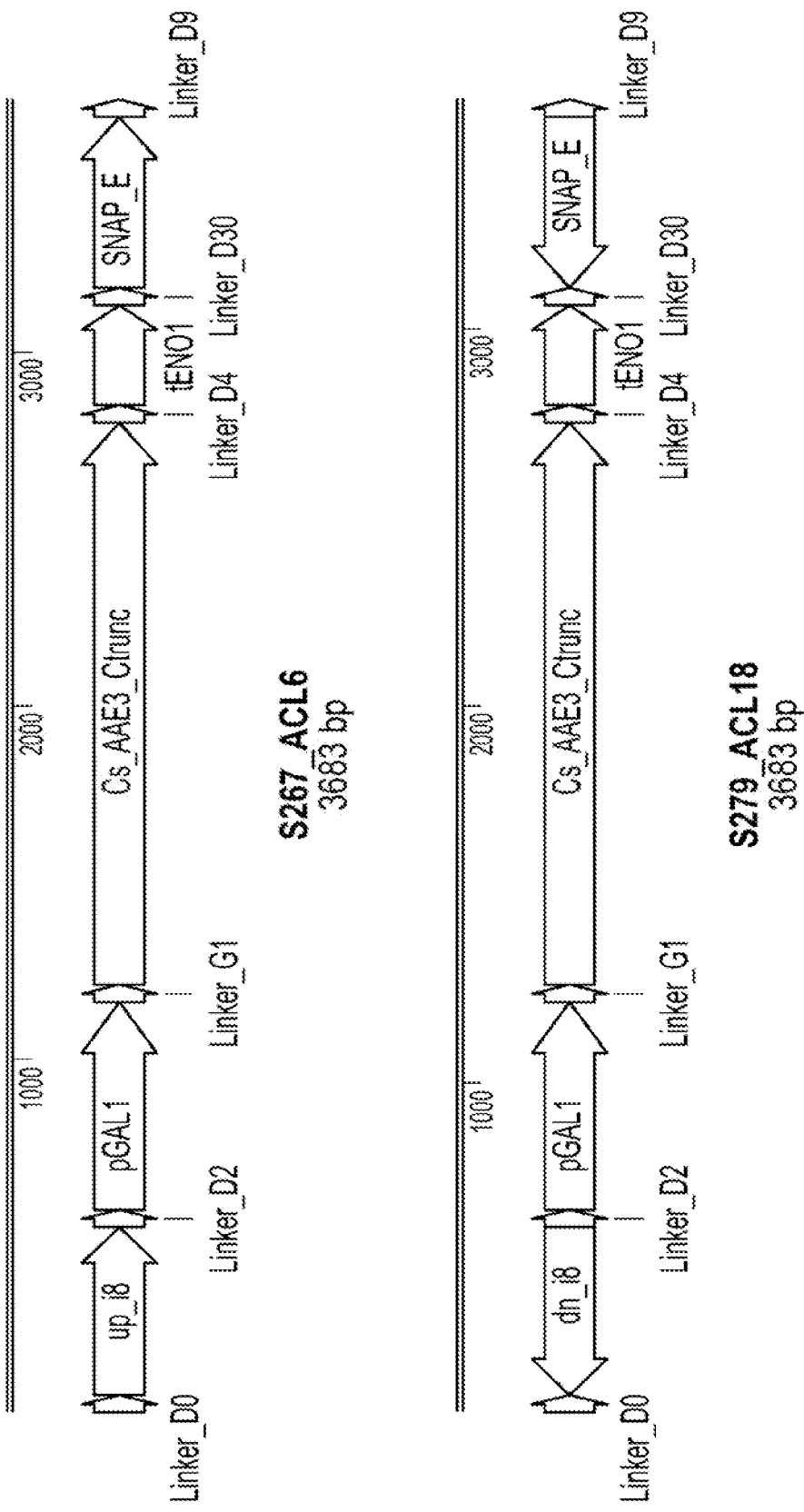
FIG. 47 depicts expression constructs used in the production of the S81 strain.
Figure 48:
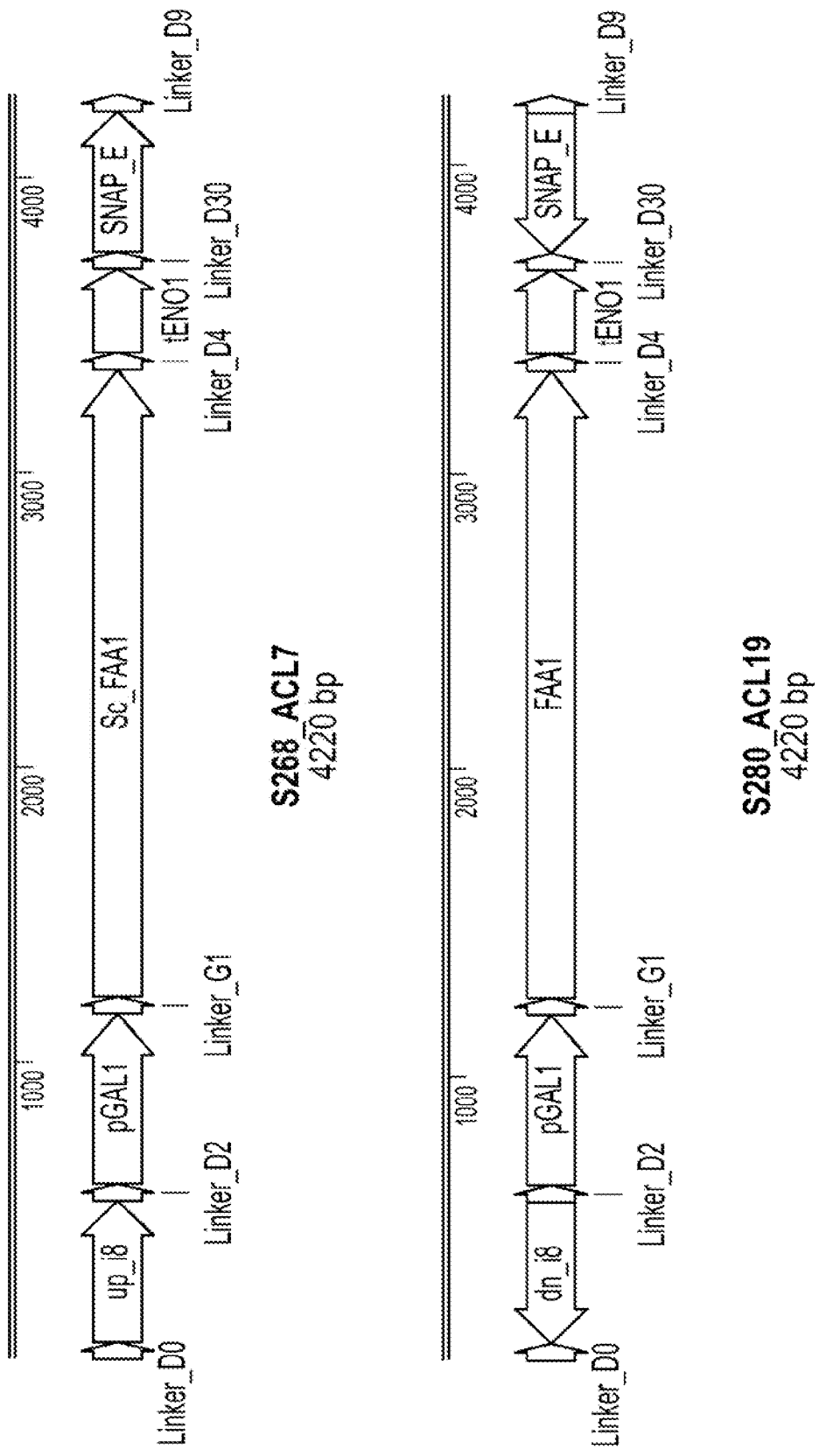
FIG. 48 depicts expression constructs used in the production of the S82 strain.
Figure 49:
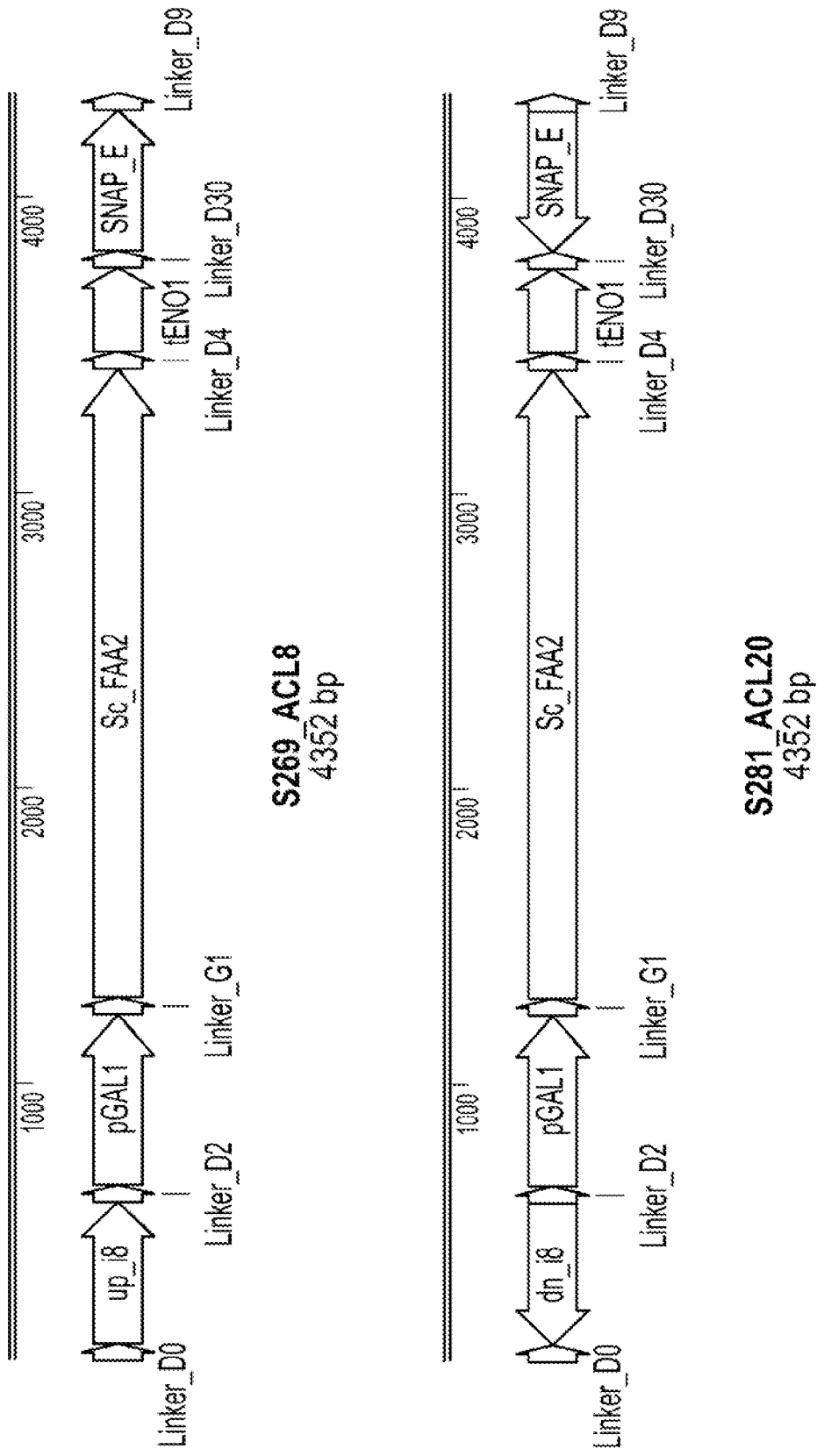
FIG. 49 depicts expression constructs used in the production of the S83 strain.
Figure 50:
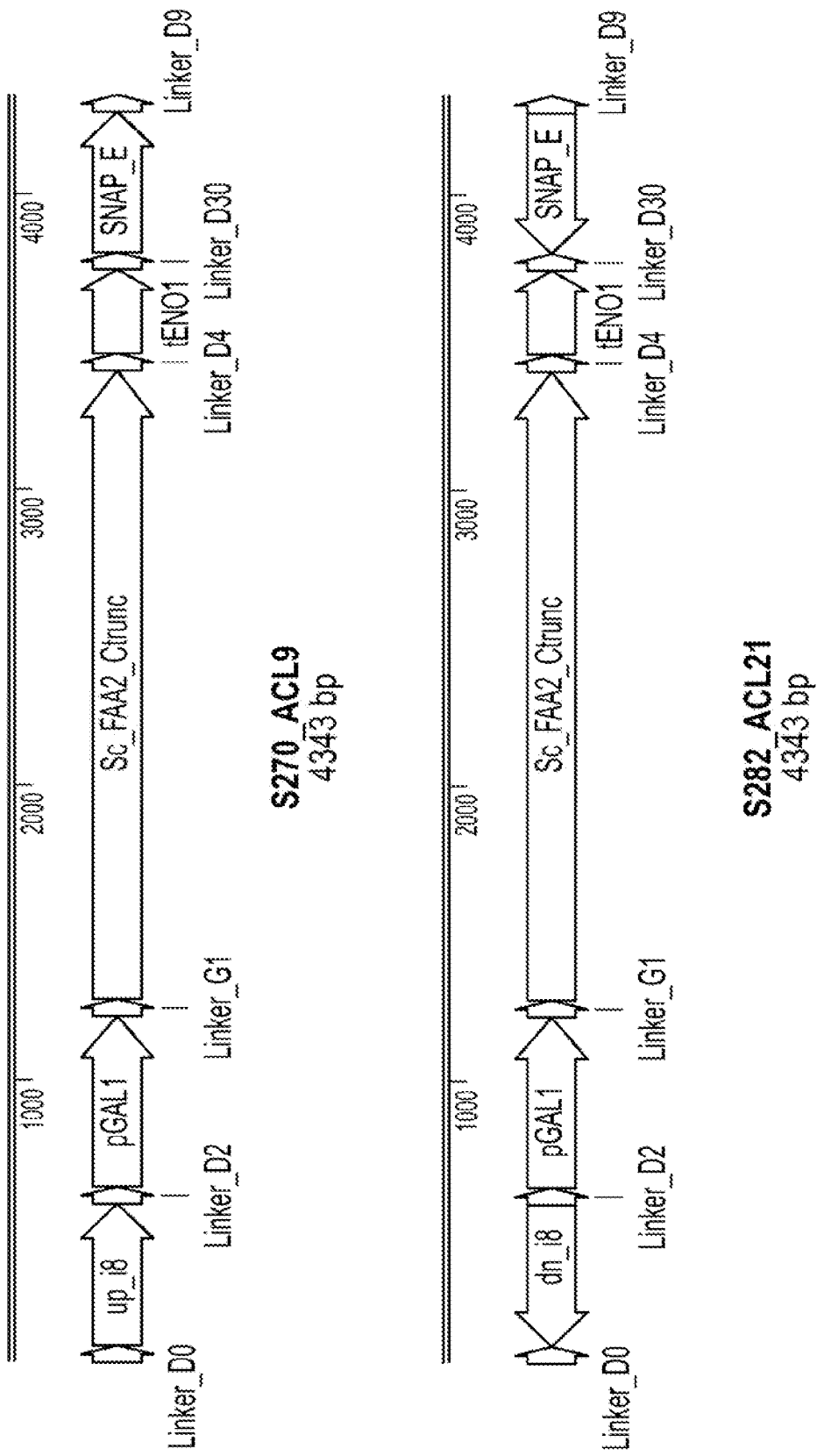
FIG. 50 depicts expression constructs used in the production of the S84 strain.
Figure 51:
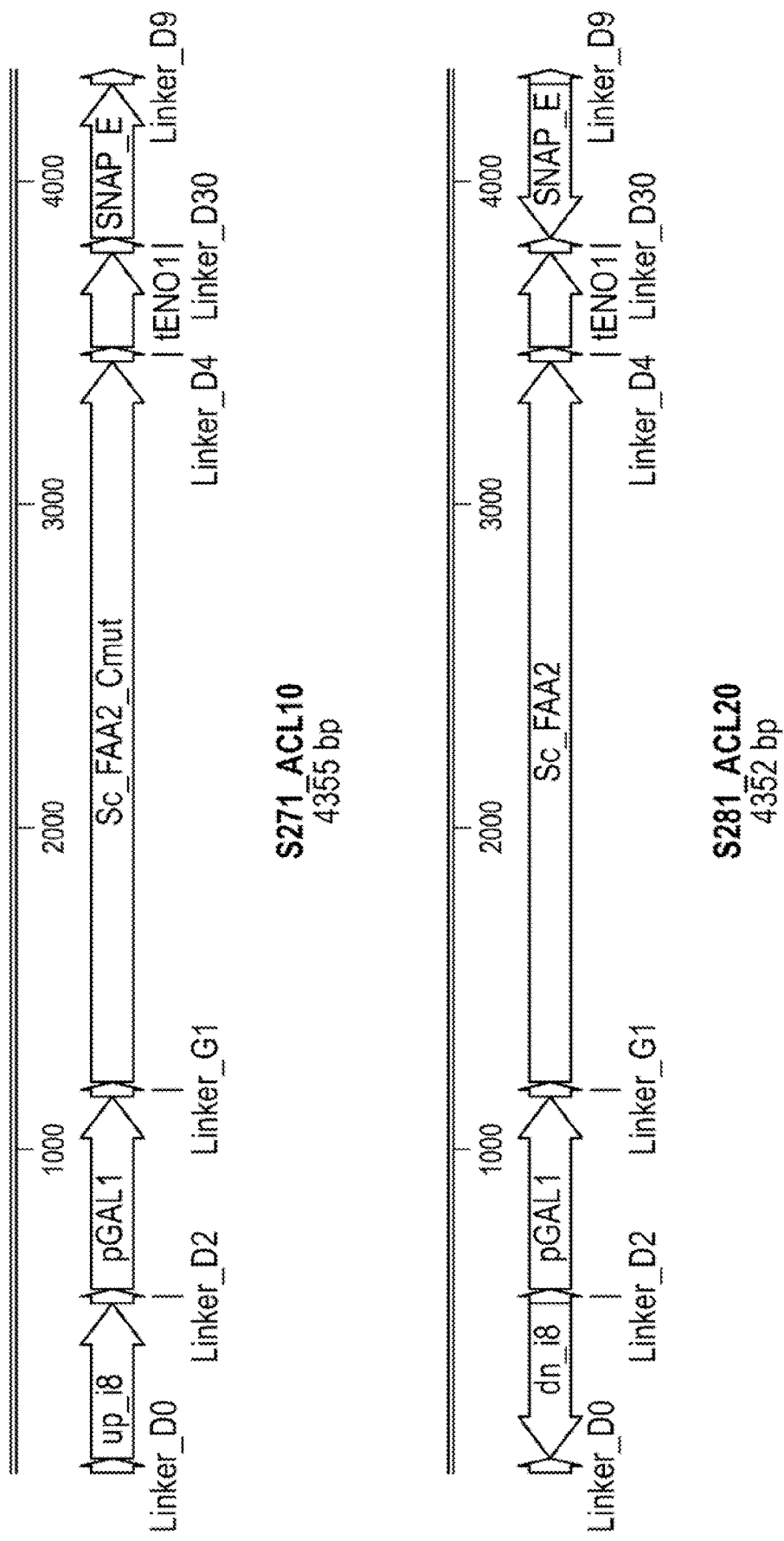
FIG. 51 depicts expression constructs used in the production of the S85 strain.
Figure 52:
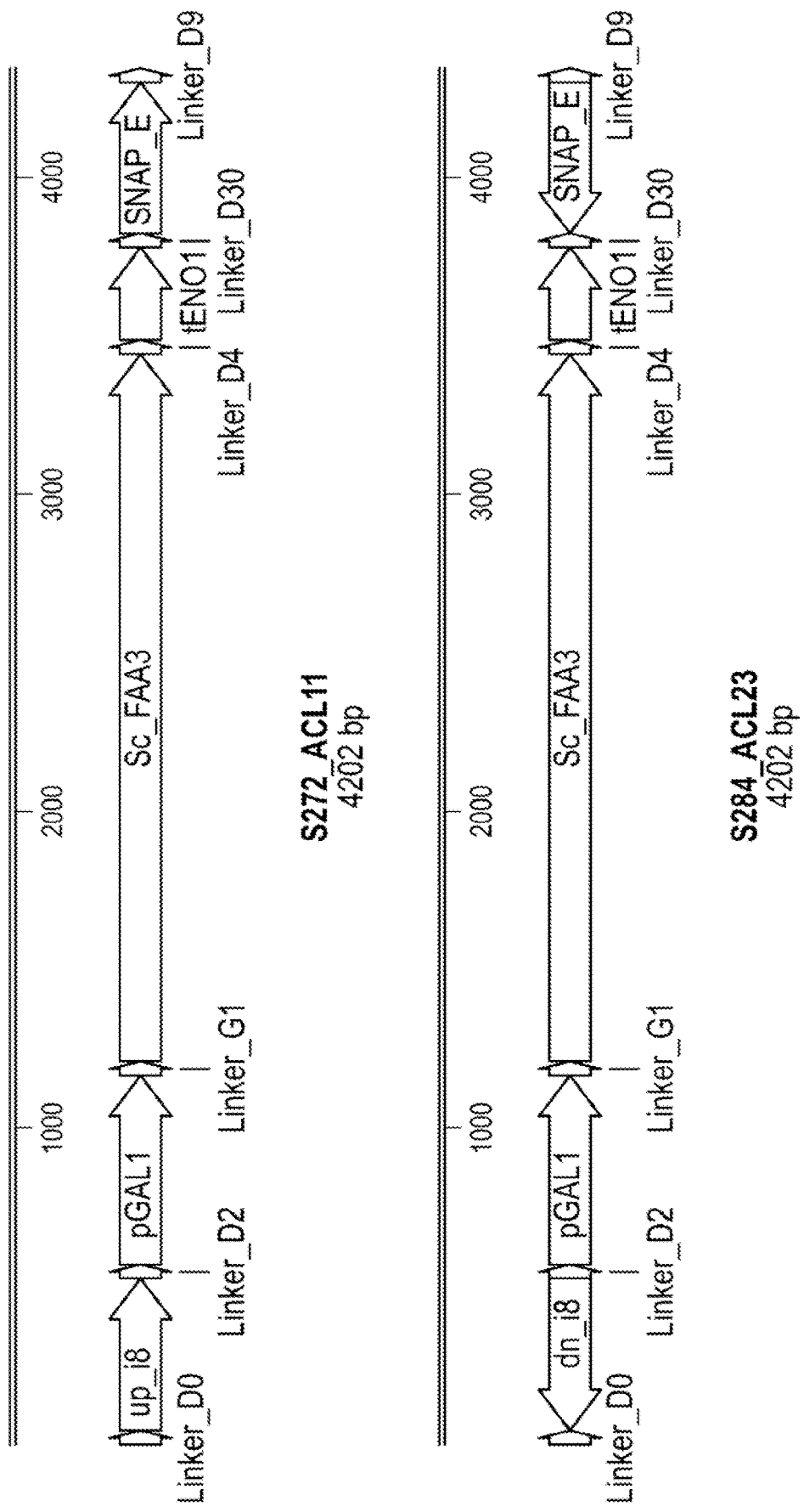
FIG. 52 depicts expression constructs used in the production of the S86 strain.
Figure 53:
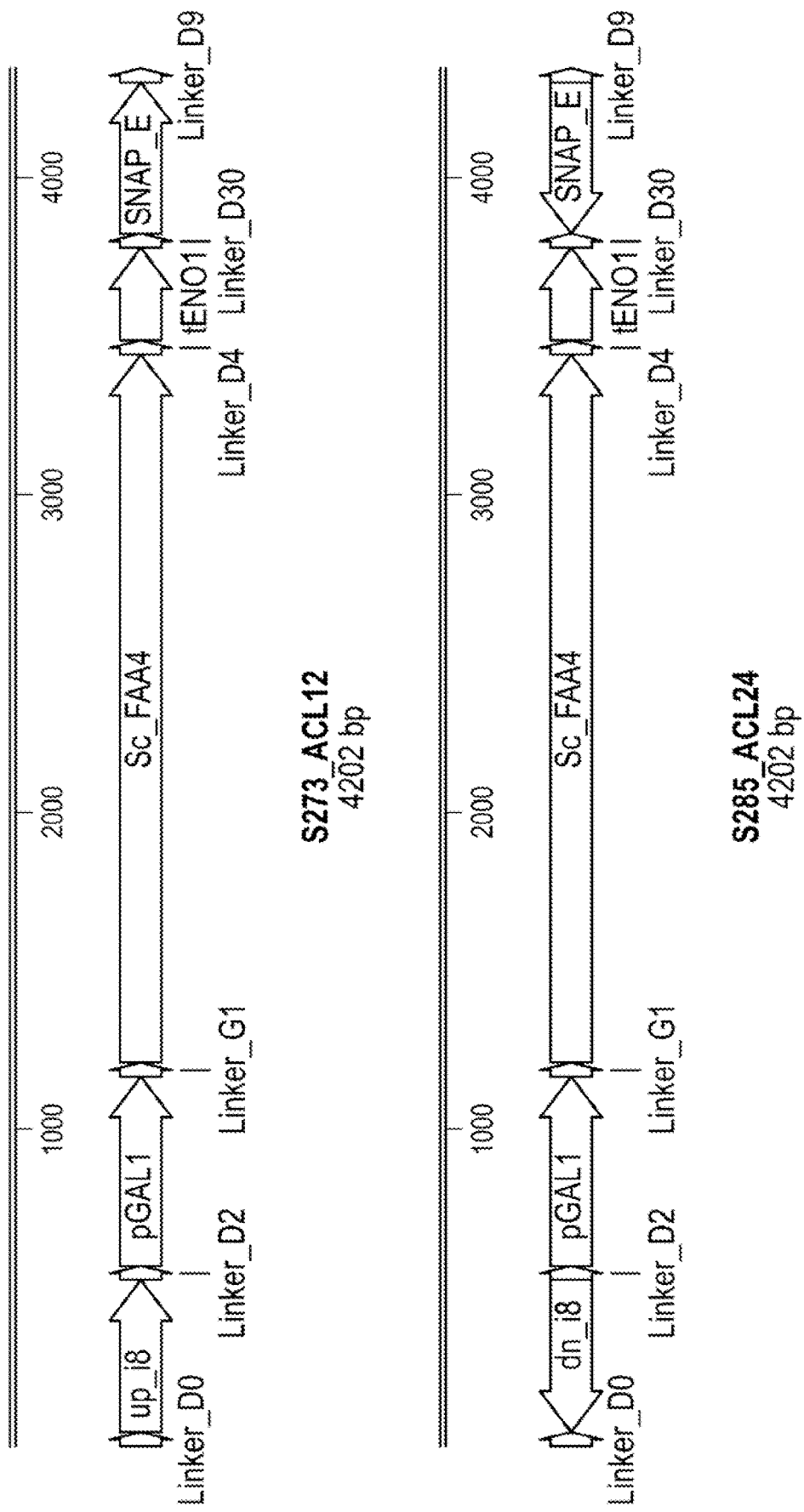
FIG. 53 depicts expression constructs used in the production of the S87 strain.
Figure 54:
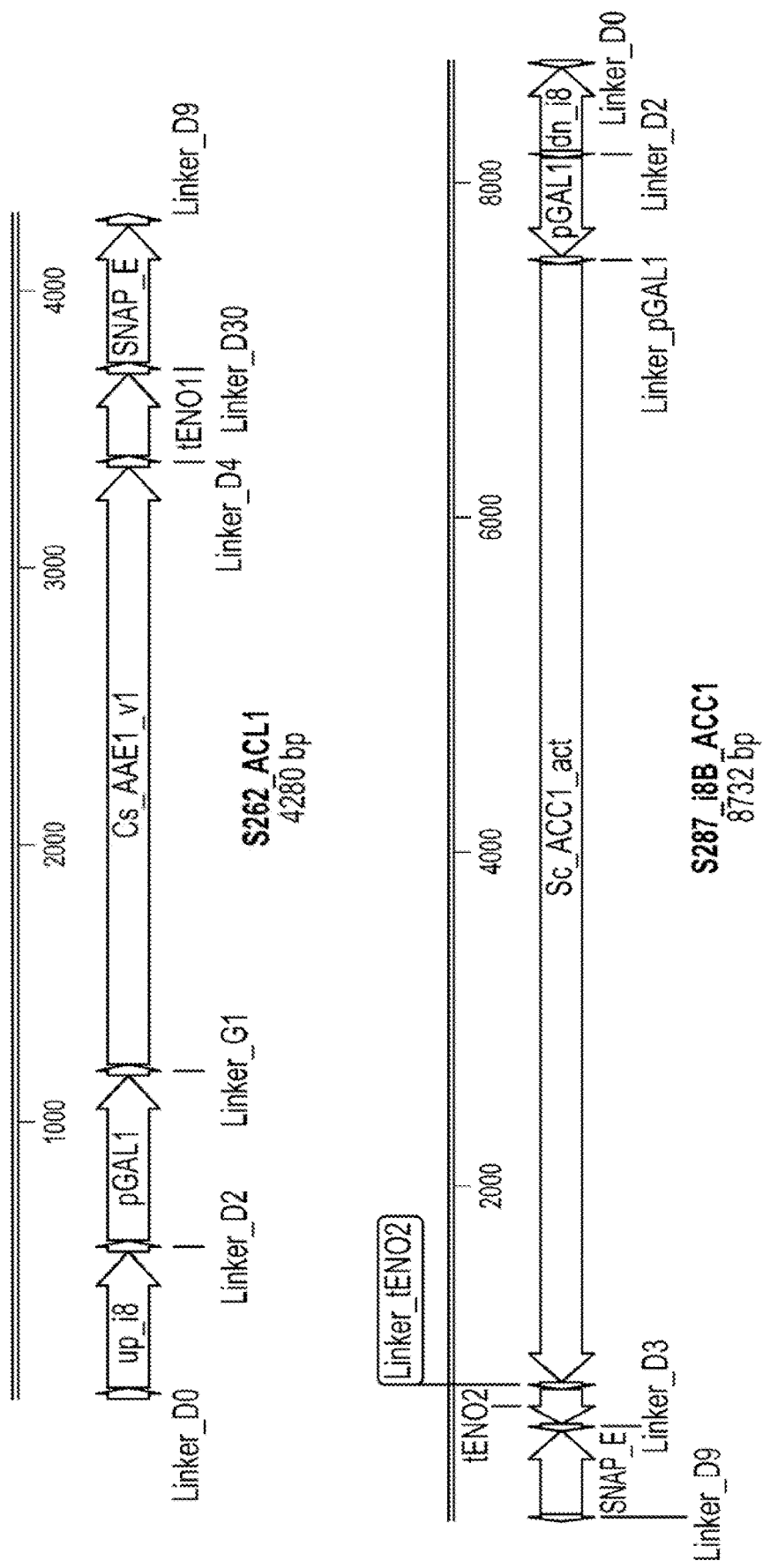
FIG. 54 depicts expression constructs used in the production of the S88 strain.
Figure 55:
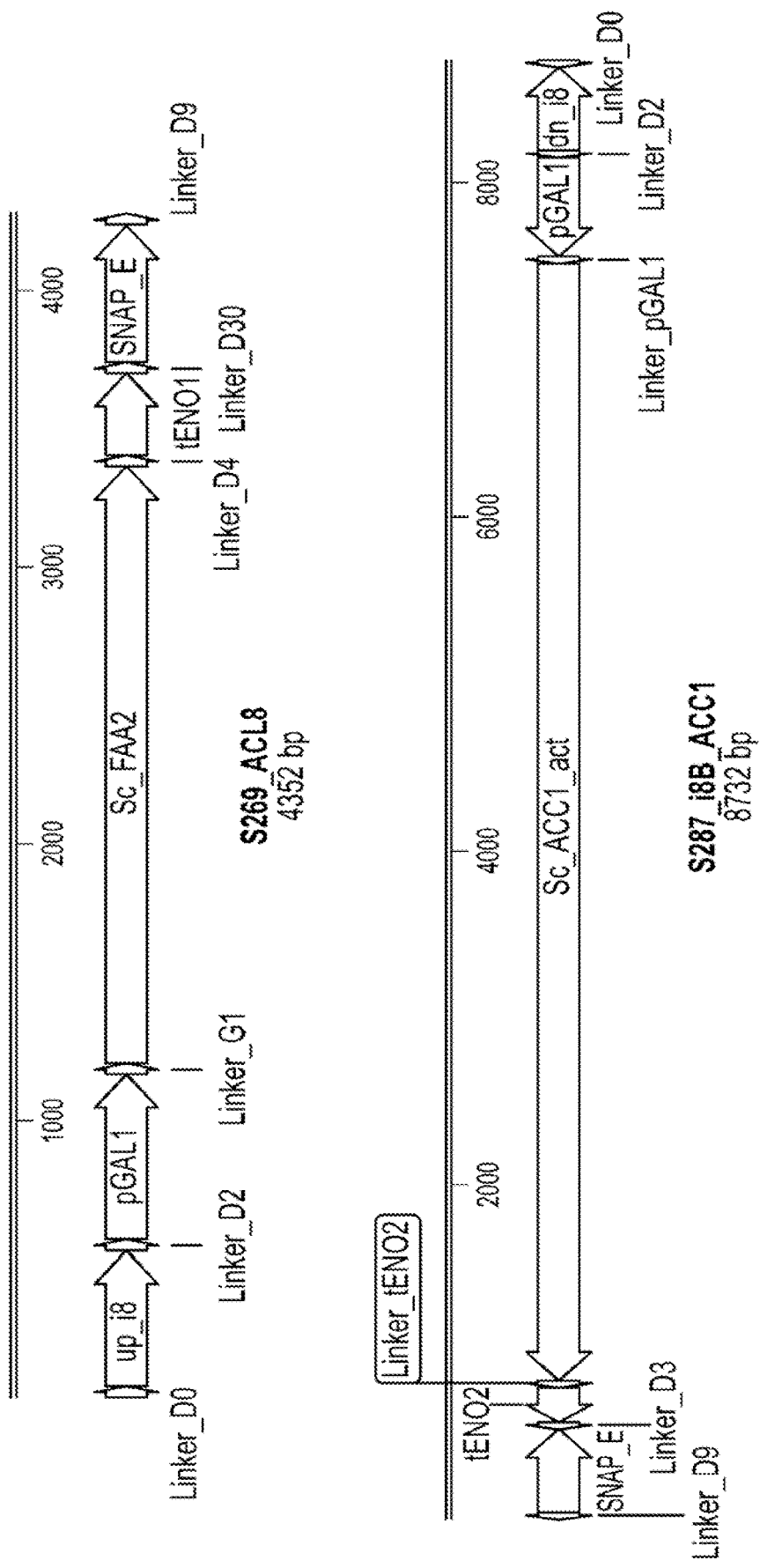
FIG. 55 depicts expression constructs used in the production of the S89 strain.
Figure 56A:
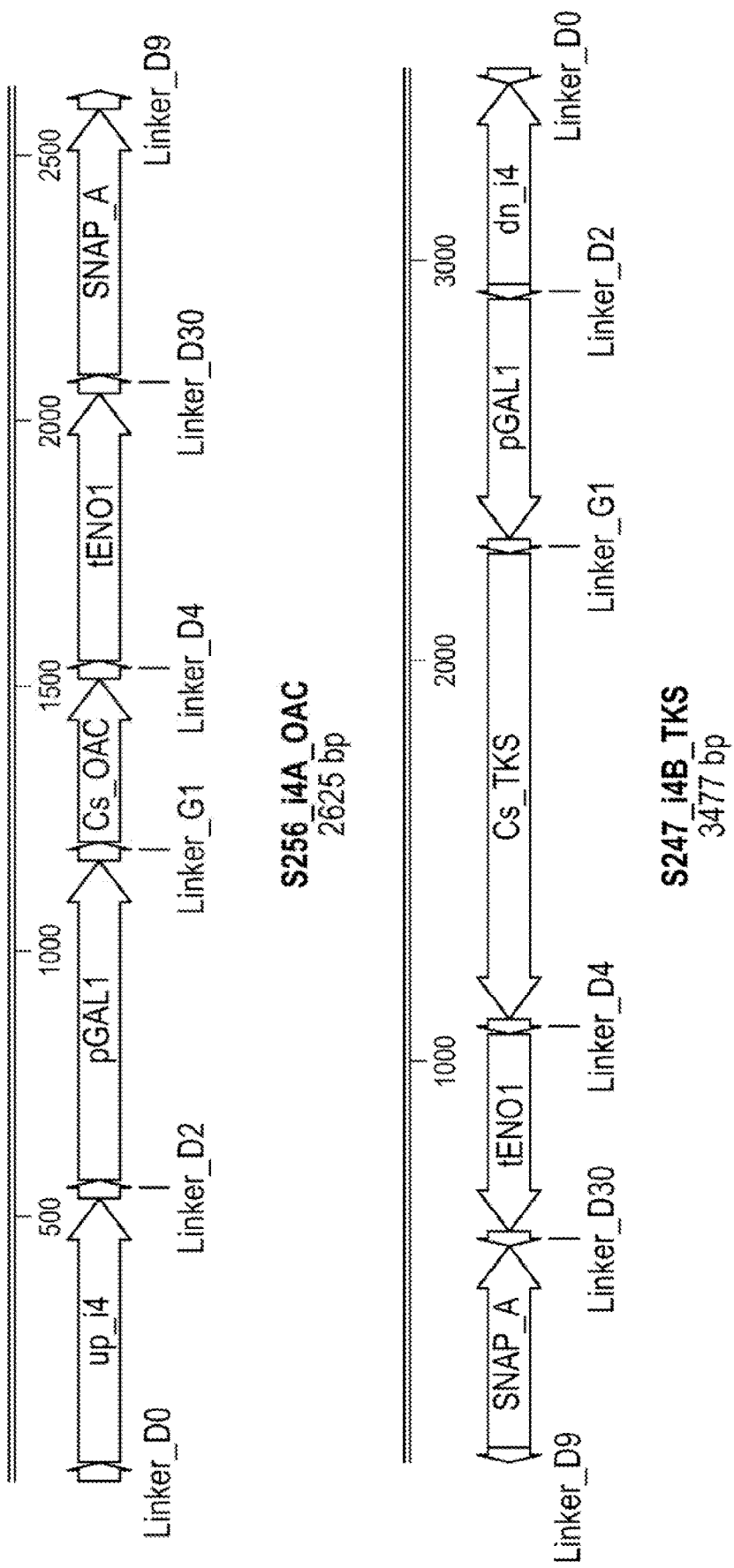
FIGS. 56A, 56B, and 56C depict expression constructs used in the production of the S90 strain.
Figure 56B:
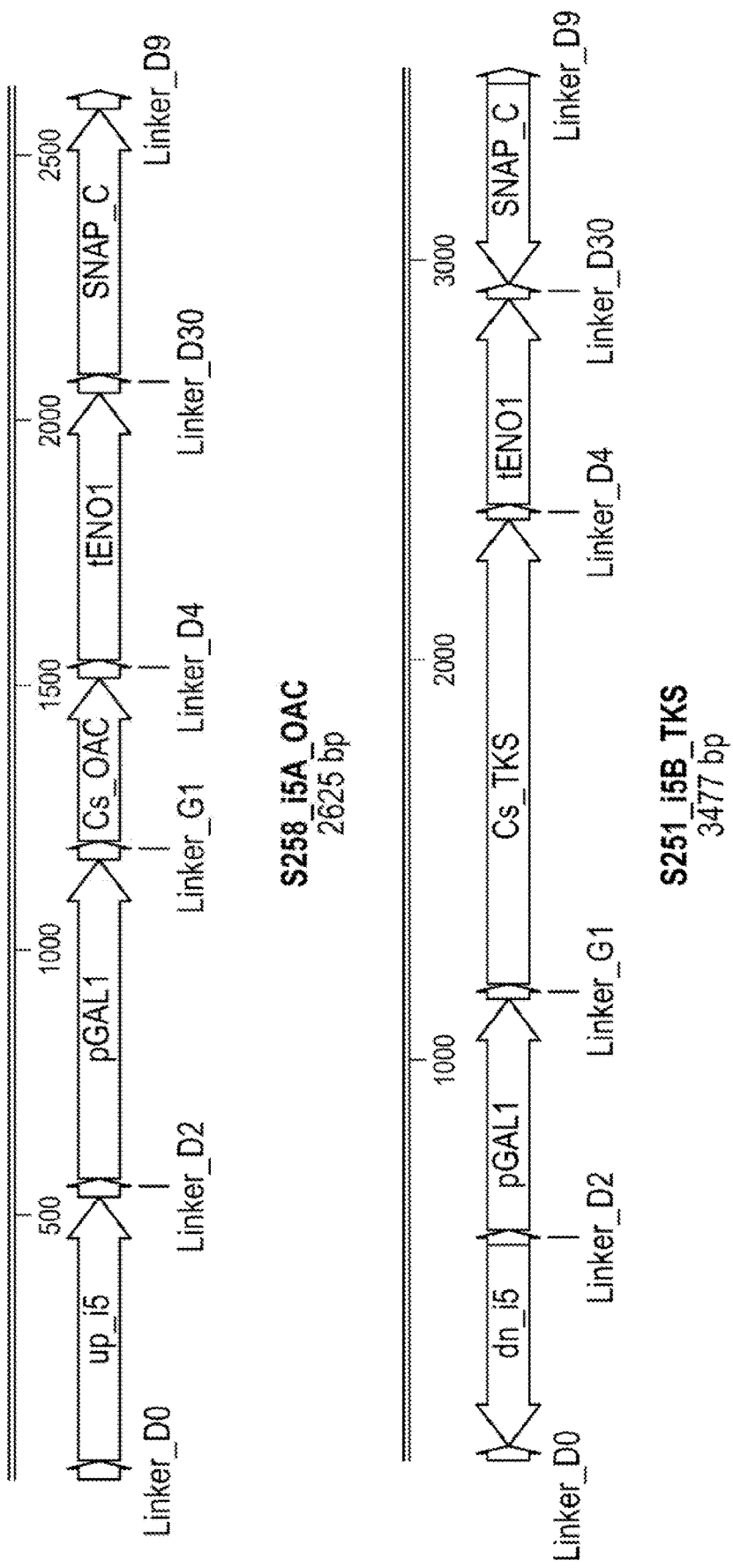
Figure 56C:
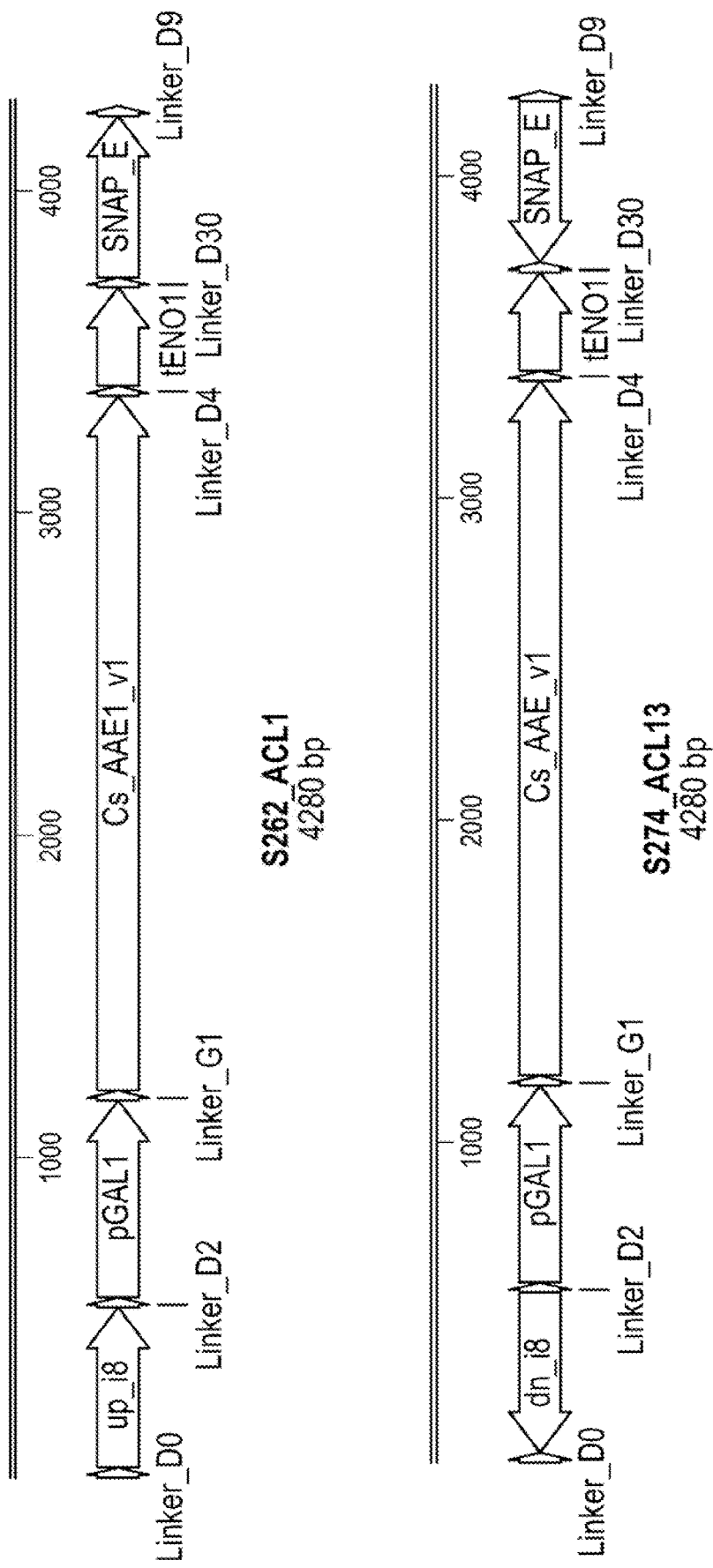
Figure 57A:
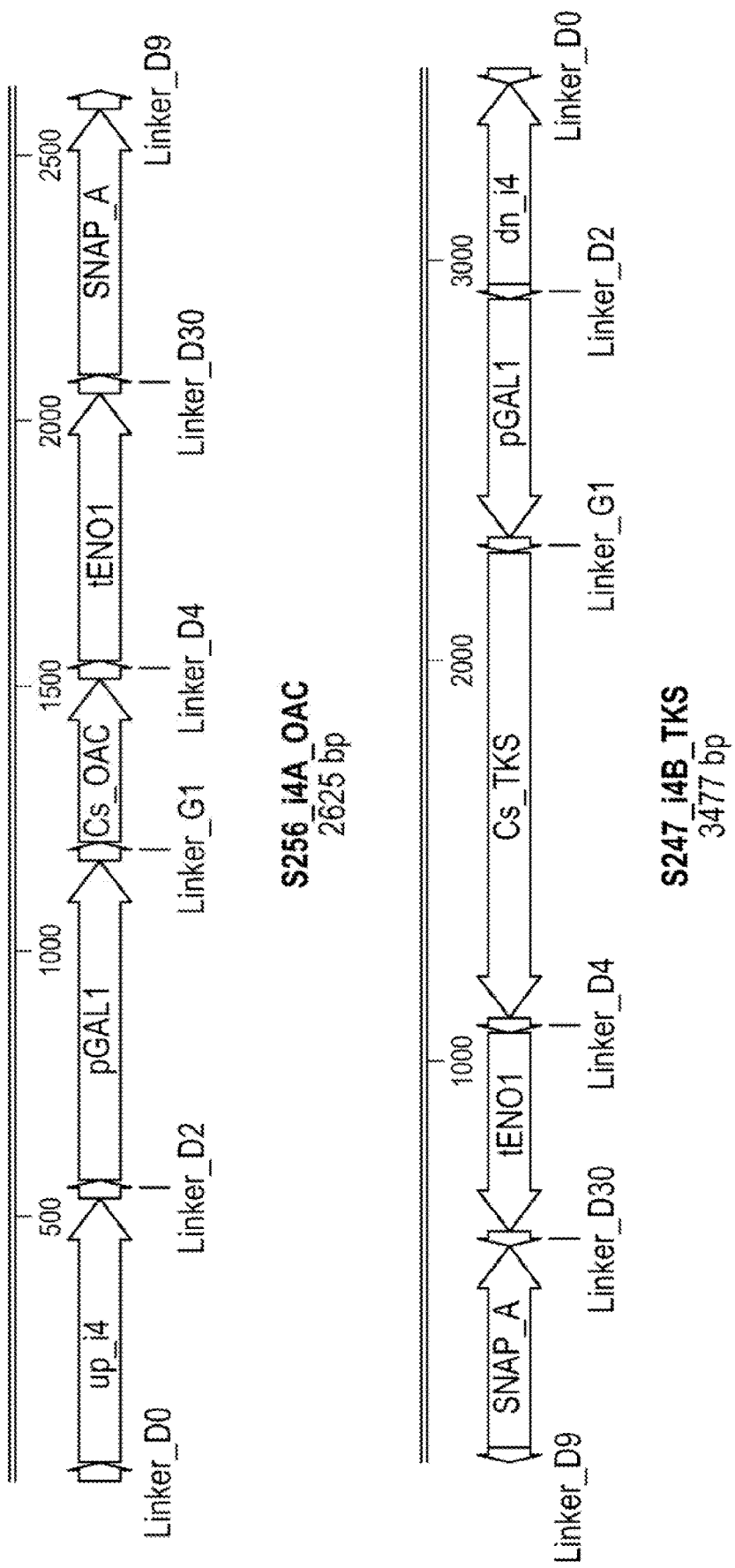
FIGS. 57A, 57B, and 57C depict expression constructs used in the production of the S91 strain.
Figure 57B:
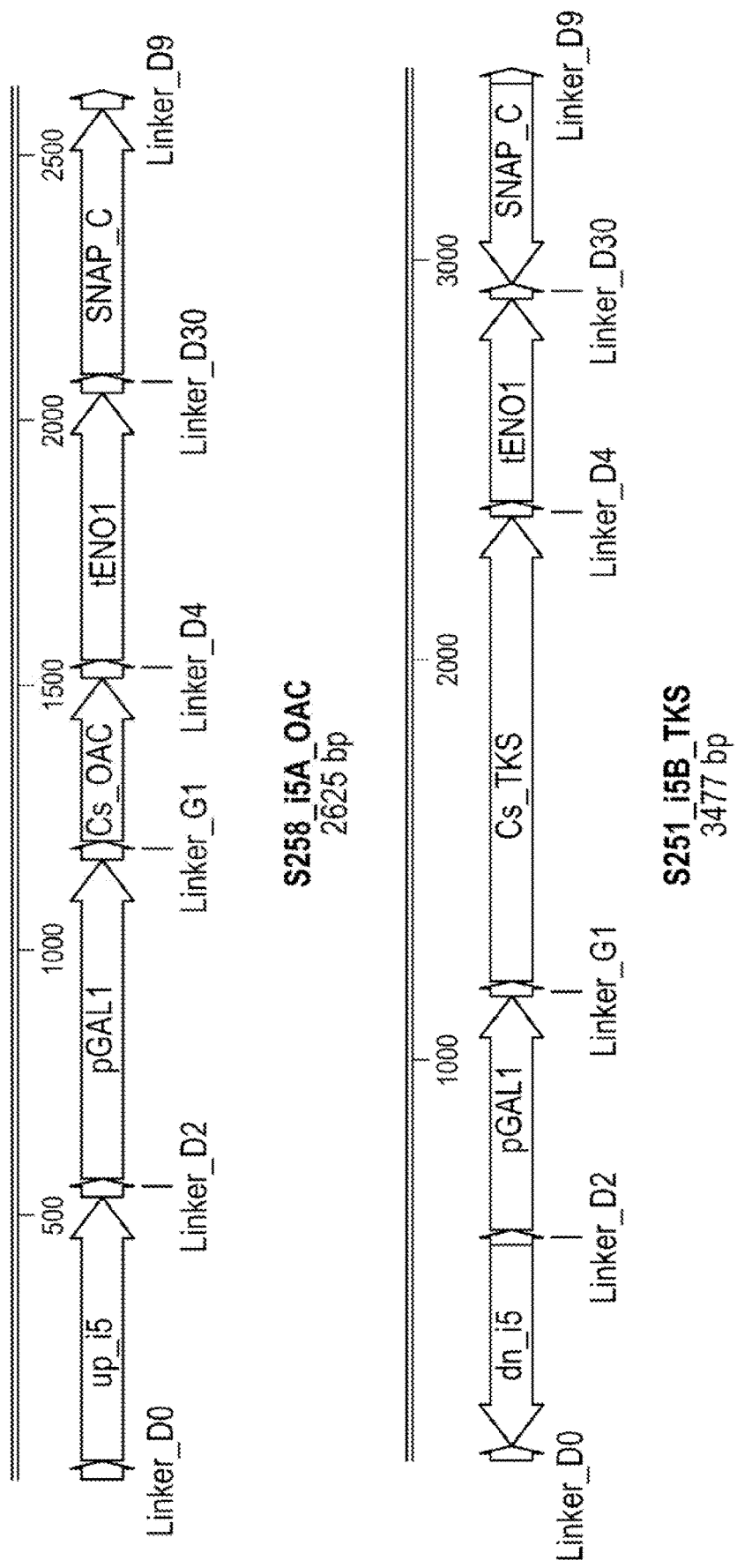
Figure 57C:
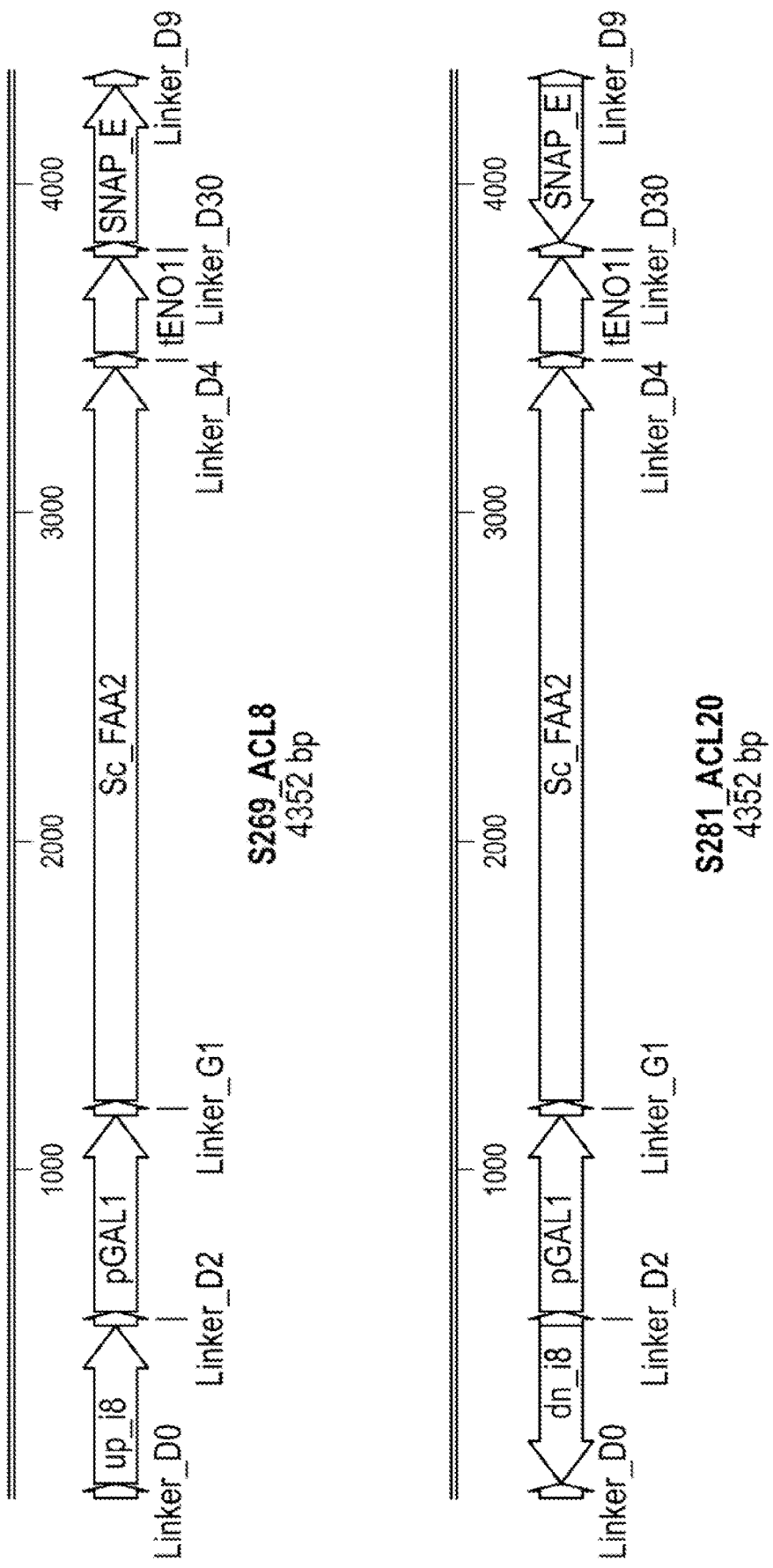
Figure 58:
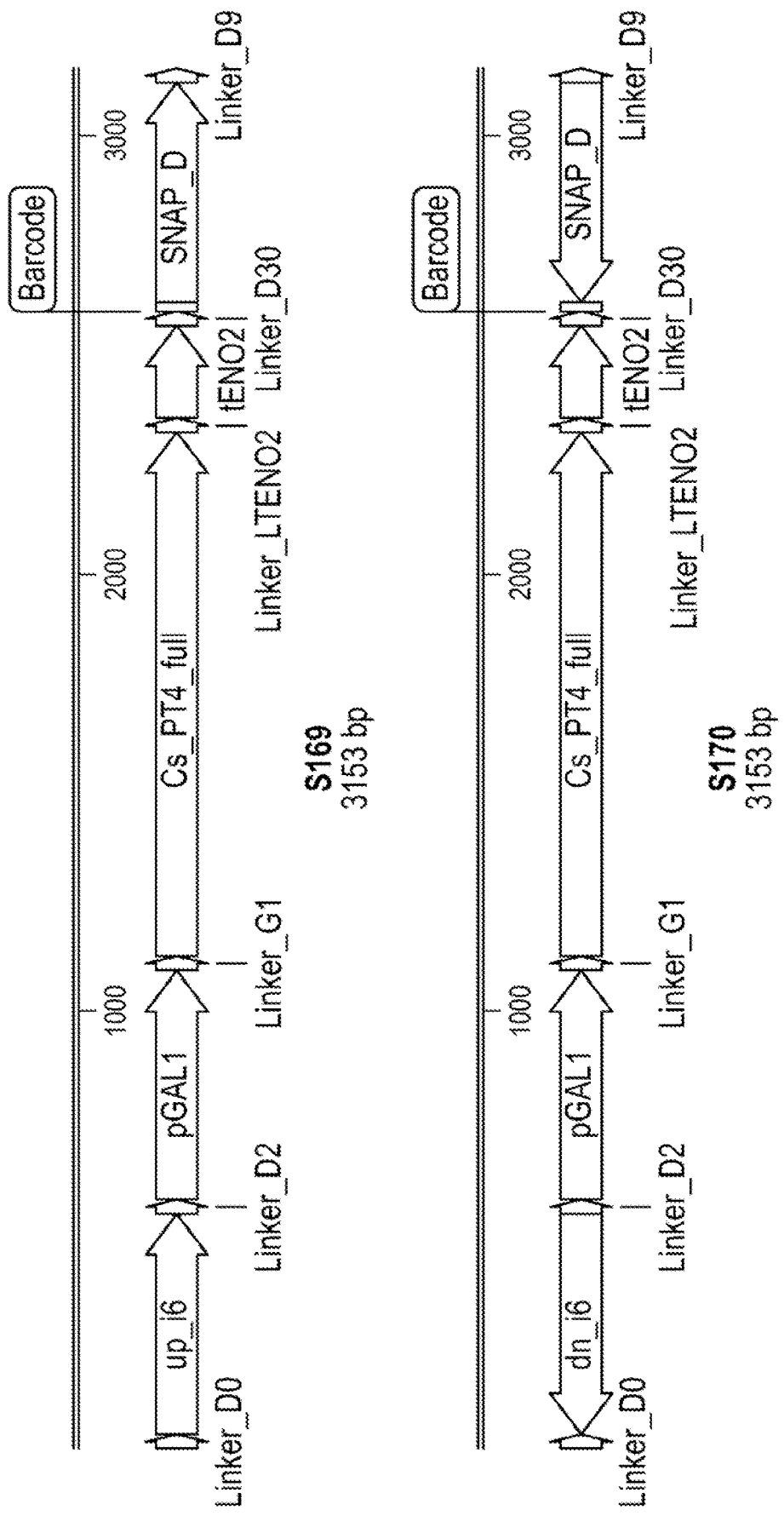
FIG. 58 depicts expression constructs used in the production of the S94 strain.
Figure 59:
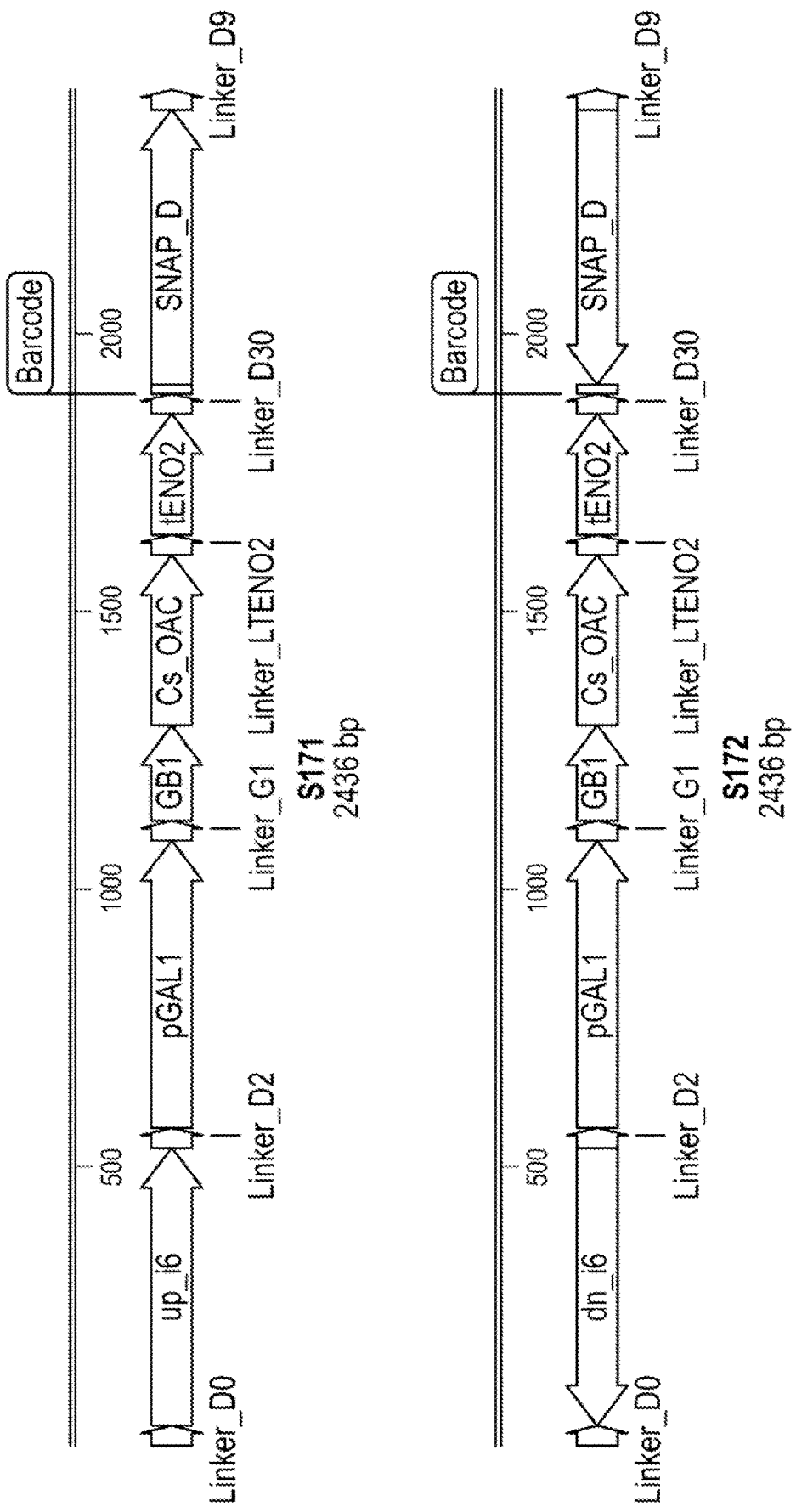
FIG. 59 depicts expression constructs used in the production of the S95 strain.
Figure 60:
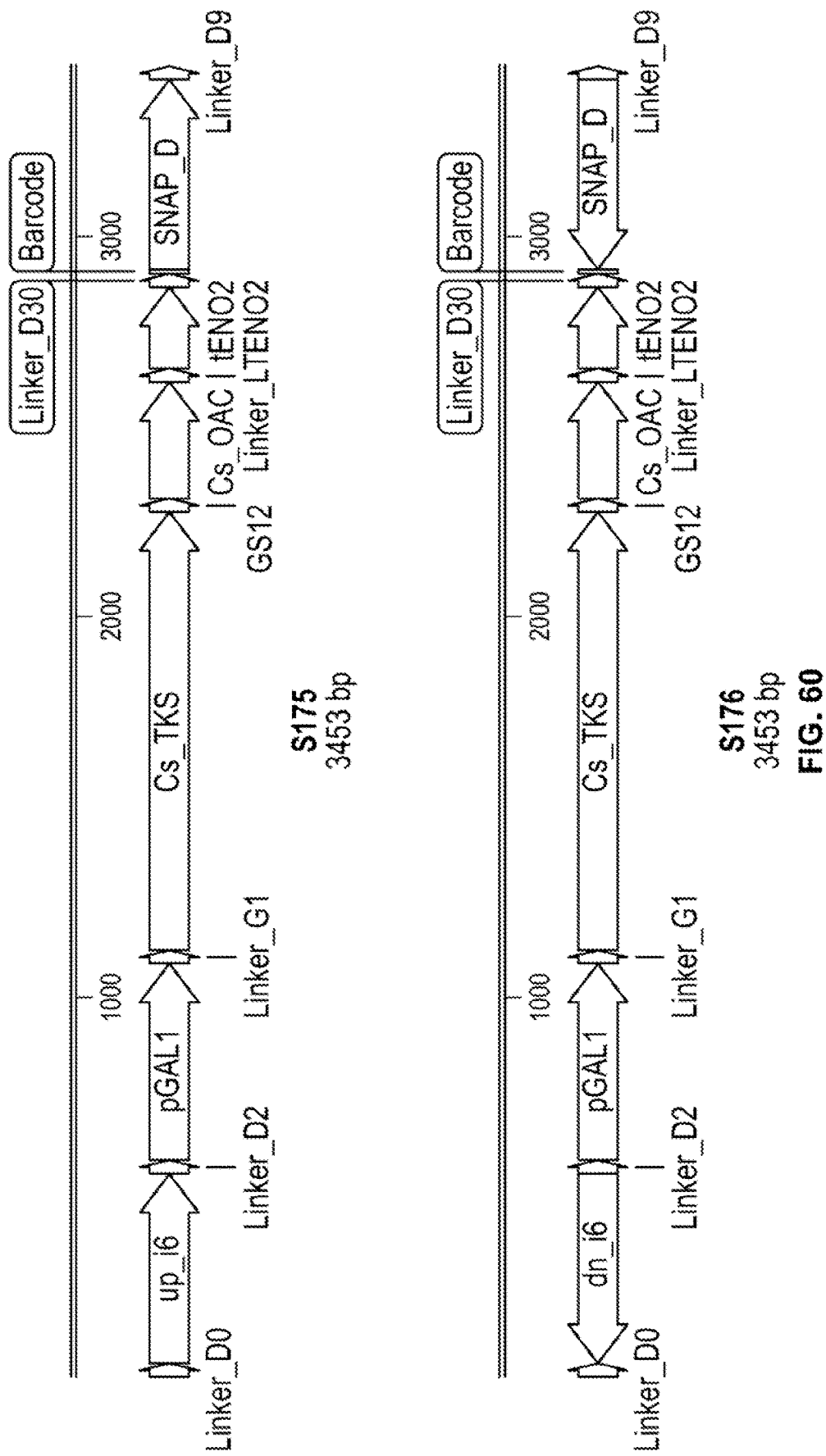
FIG. 60 depicts expression constructs used in the production of the S97 strain.
Figure 61:
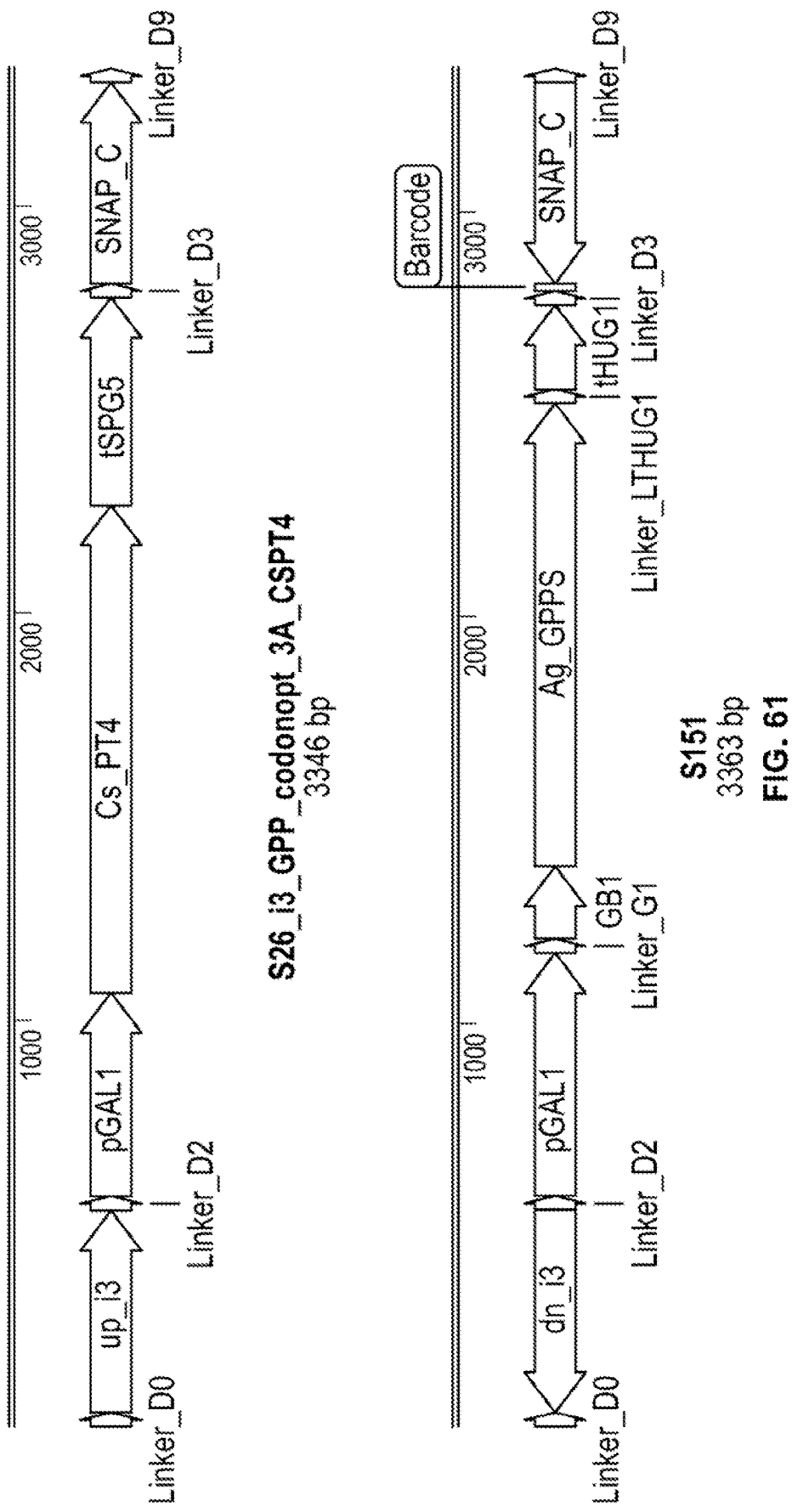
FIG. 61 depicts expression constructs used in the production of the S104 strain.
Figure 62:
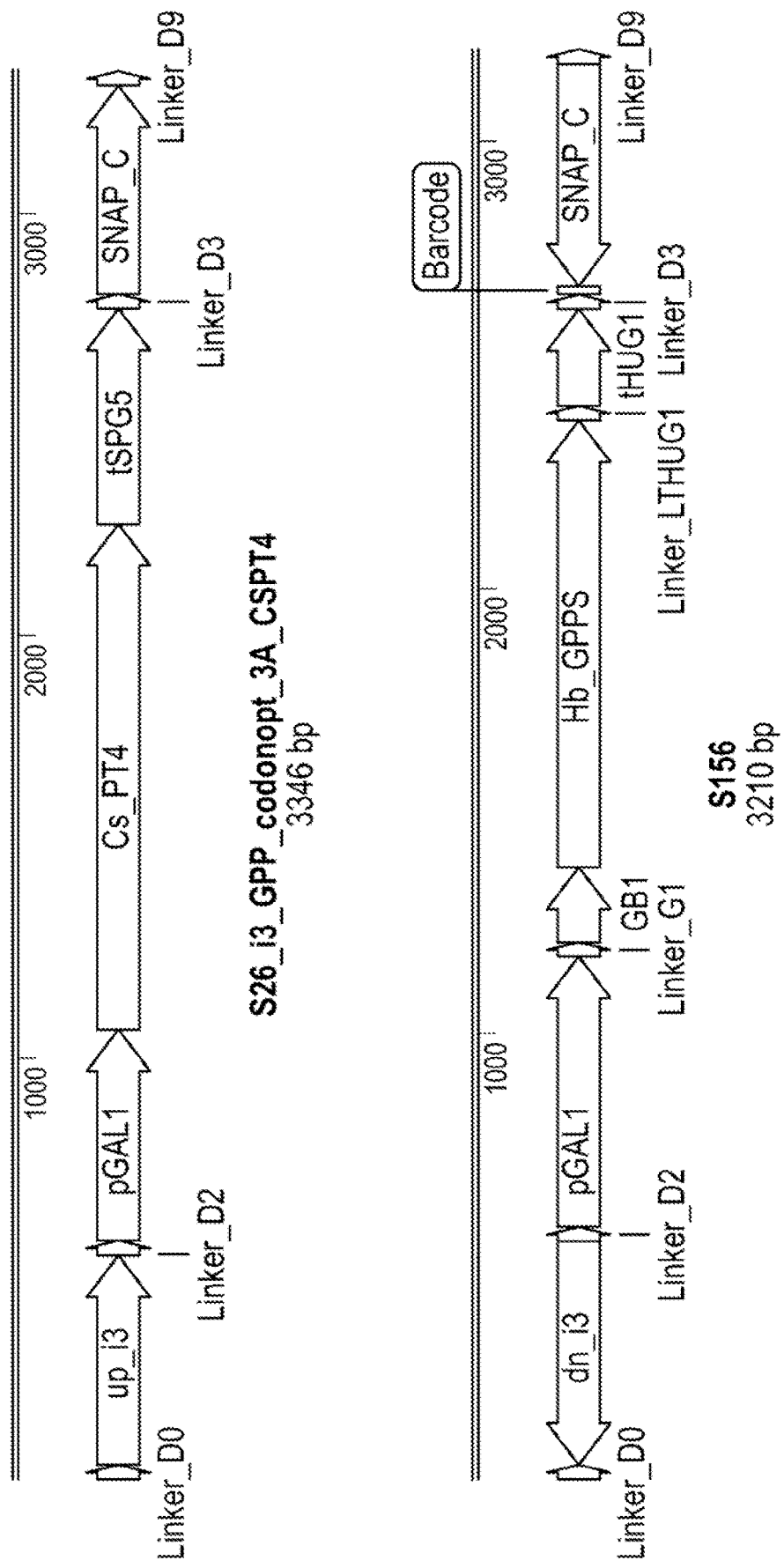
FIG. 62 depicts expression constructs used in the production of the S108 strain.
Figure 63:
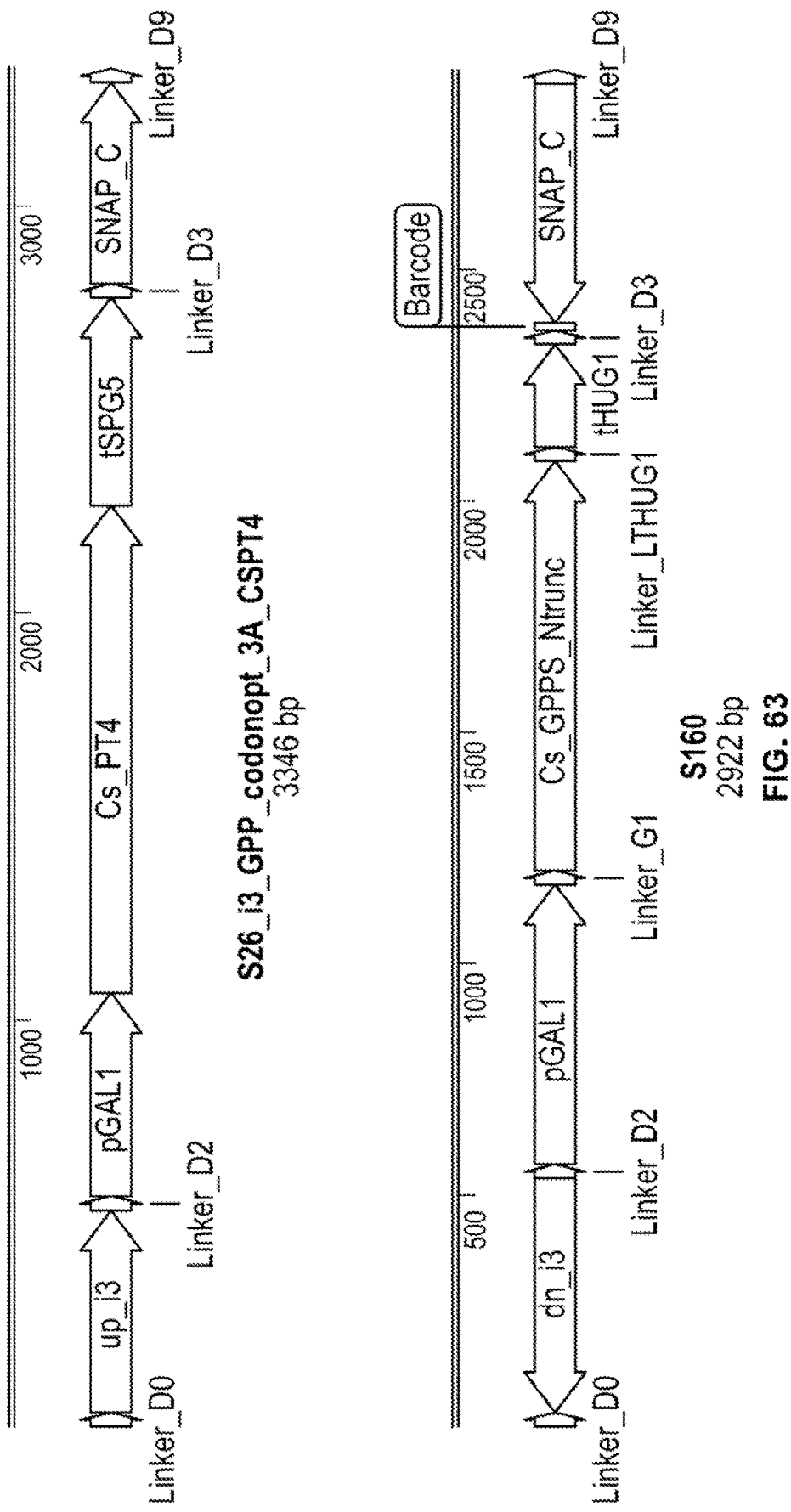
FIG. 63 depicts expression constructs used in the production of the S112 strain.
Figure 64:
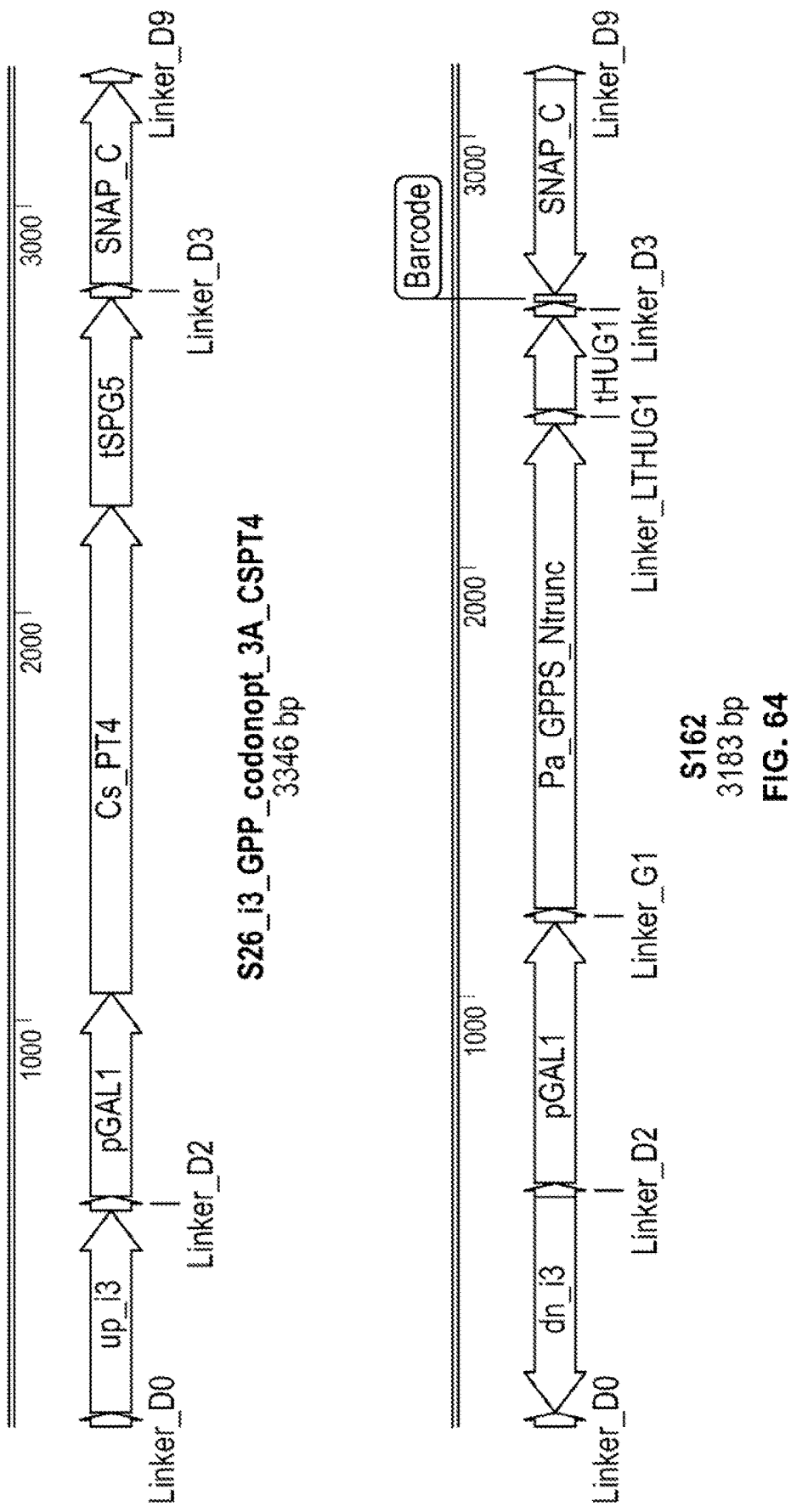
FIG. 64 depicts expression constructs used in the production of the S114 strain.
Figure 65:
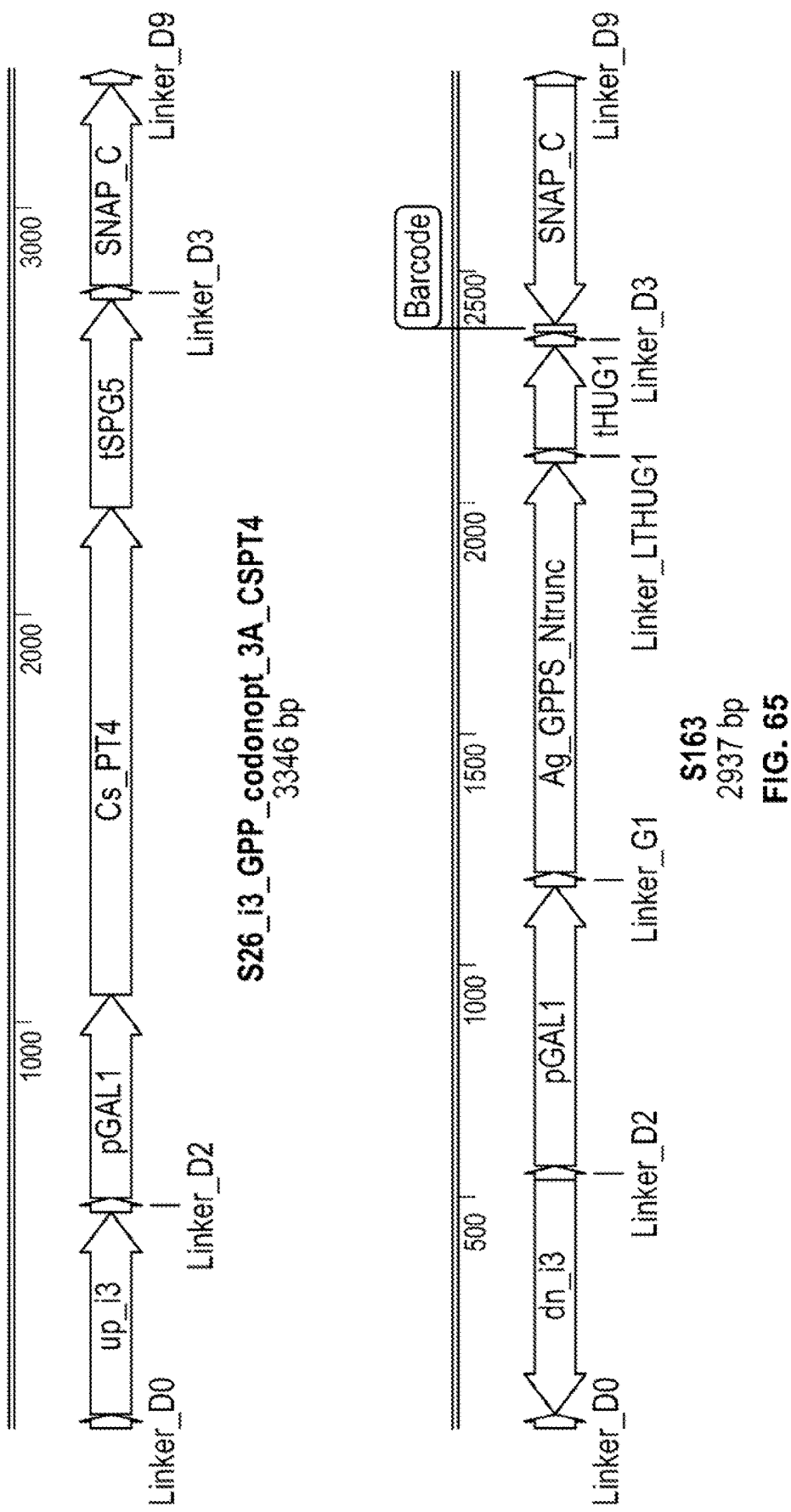
FIG. 65 depicts expression constructs used in the production of the S115 strain.

| Strain (Constructs) | Parent Strain* | Polypeptide SEQ ID NOs (Nucleotide SEQ ID NOs) |
|---|---|---|
| S50 (FIGS. 43A, 43B, and 43C) | S29 | Cs_OAC: SEQ ID NO: 10 (SEQ ID NO: 163)<br>Cs_TKS: SEQ ID NO: 11 (SEQ ID NO: 162)<br>Sc_FAA2: SEQ ID NO: 169 (SEQ ID NO: 168) |
| S51 (FIGS. 44A, 44B, and 44C) | S29 | Cs_OAC: SEQ ID NO: 10 (SEQ ID NO: 163)<br>Cs_TKS: SEQ ID NO: 11 (SEQ ID NO: 162) |
| S78 (FIG. 45) | S51 | Cs_AAE1_v1: SEQ ID NO: 90 (SEQ ID NO: 164)<br>Cs_AAE_v1: SEQ ID NO: 90 (SEQ ID NO: 164)<br>GB1: SEQ ID NO: 174 (SEQ ID NO: 173) |
| S80 (FIG. 46) | S51 | Cs_AAE3: SEQ ID NO: 92 (SEQ ID NO: 166) |
| S81 (FIG. 47) | S51 | Cs_AAE3_Ctrunc: SEQ ID NO: 149 (SEQ ID NO: 150) |
| S82 (FIG. 48) | S51 | Sc_FAA1: SEQ ID NO: 192 (SEQ ID NO: 191)<br>FAA1: SEQ ID NO: 192 (SEQ ID NO: 191) |
| S83 (FIG. 49) | S51 | Sc_FAA2: SEQ ID NO: 169 (SEQ ID NO: 168) |
| S84 (FIG. 50) | S51 | Sc_FAA2_Ctrunc: SEQ ID NO: 194 (SEQ ID NO: 193) |
| S85 (FIG. 51) | S51 | Sc_FAA2_Cmut: SEQ ID NO: 196 (SEQ ID NO: 195)<br>Sc_FAA2: SEQ ID NO: 169 (SEQ ID NO: 168) |
| S86 (FIG. 52) | S51 | Sc_FAA3: SEQ ID NO: 198 (SEQ ID NO: 197) |
| S87 (FIG. 53) | S51 | Sc_FAA4: SEQ ID NO: 200 (SEQ ID NO: 199) |
| S88 (FIG. 54) | S51 | Cs_AAE1_v1: SEQ ID NO: 90 (SEQ ID NO: 164)<br>Sc_ACC1_act: SEQ ID NO: 207 (SEQ ID NO: 201) |
| S89 (FIG. 55) | S51 | Sc_FAA2: SEQ ID NO: 169 (SEQ ID NO: 168)<br>Sc_ACC1_act: SEQ ID NO: 207 (SEQ ID NO: 201) |
| S90 (FIGS. 56A, 56B, and 56C) | S29 | Cs_OAC: SEQ ID NO: 10 (SEQ ID NO: 163)<br>Cs_TKS: SEQ ID NO: 11 (SEQ ID NO: 162)<br>Cs_AAE1_v1: SEQ ID NO: 90 (SEQ ID NO: 164)<br>Cs_AAE_v1: SEQ ID NO: 90 (SEQ ID NO: 164) |
| S91 (FIGS. 57A, 57B, and 57C) | S29 | Cs_OAC: SEQ ID NO: 10 (SEQ ID NO: 163)<br>Cs_TKS: SEQ ID NO: 11 (SEQ ID NO: 162)<br>Sc_FAA2: SEQ ID NO: 169 (SEQ ID NO: 168) |
| S94 (FIG. 58) | S31 | Cs_PT4_full: SEQ ID NO: 110 (SEQ ID NO: 111) |
| S95 (FIG. 59) | S31 | GB1: SEQ ID NO: 174 (SEQ ID NO: 173)<br>Cs_OAC: SEQ ID NO: 10 (SEQ ID NO: 163) |
| S97 (FIG. 60) | S31 | Cs_OAC: SEQ ID NO: 10 (SEQ ID NO: 163)<br>Cs_TKS: SEQ ID NO: 11 (SEQ ID NO: 162)<br>GS12: SEQ ID NO: 172 (SEQ ID NO: 171) |
| S104 (FIG. 61) | S21 | Cs_PT4: SEQ ID NO: 110 (SEQ ID NO: 111)<br>Ag_GPPS: SEQ ID NO: 133 (SEQ ID NO: 134)<br>GB1: SEQ ID NO: 174 (SEQ ID NO: 173) |
| S108 (FIG. 62) | S21 | Cs_PT4: SEQ ID NO: 110 (SEQ ID NO: 111)<br>Hb_GPPS: SEQ ID NO: 143 (SEQ ID NO: 144)<br>GB1: SEQ ID NO: 174 (SEQ ID NO: 173) |
| S112 (FIG. 63) | S21 | Cs_PT4: SEQ ID NO: 110 (SEQ ID NO: 111)<br>Cs_GPPS_NTrunc: SEQ ID NO: 127 (SEQ ID NO: 128) |
| S114 (FIG. 64) | S21 | Cs_PT4: SEQ ID NO: 110 (SEQ ID NO: 111)<br>Pa_GPPS_NTrunc: SEQ ID NO: 131 (SEQ ID NO: 132) |
| S115 (FIG. 65) | S21 | Cs_PT4: SEQ ID NO: 110 (SEQ ID NO: 111)<br>Ag_GPPS_NTrunc: SEQ ID NO: 203 (SEQ ID NO: 202) |

263
264

TABLE 11-continued

Constructs and strains used in the Examples

Figure 66:
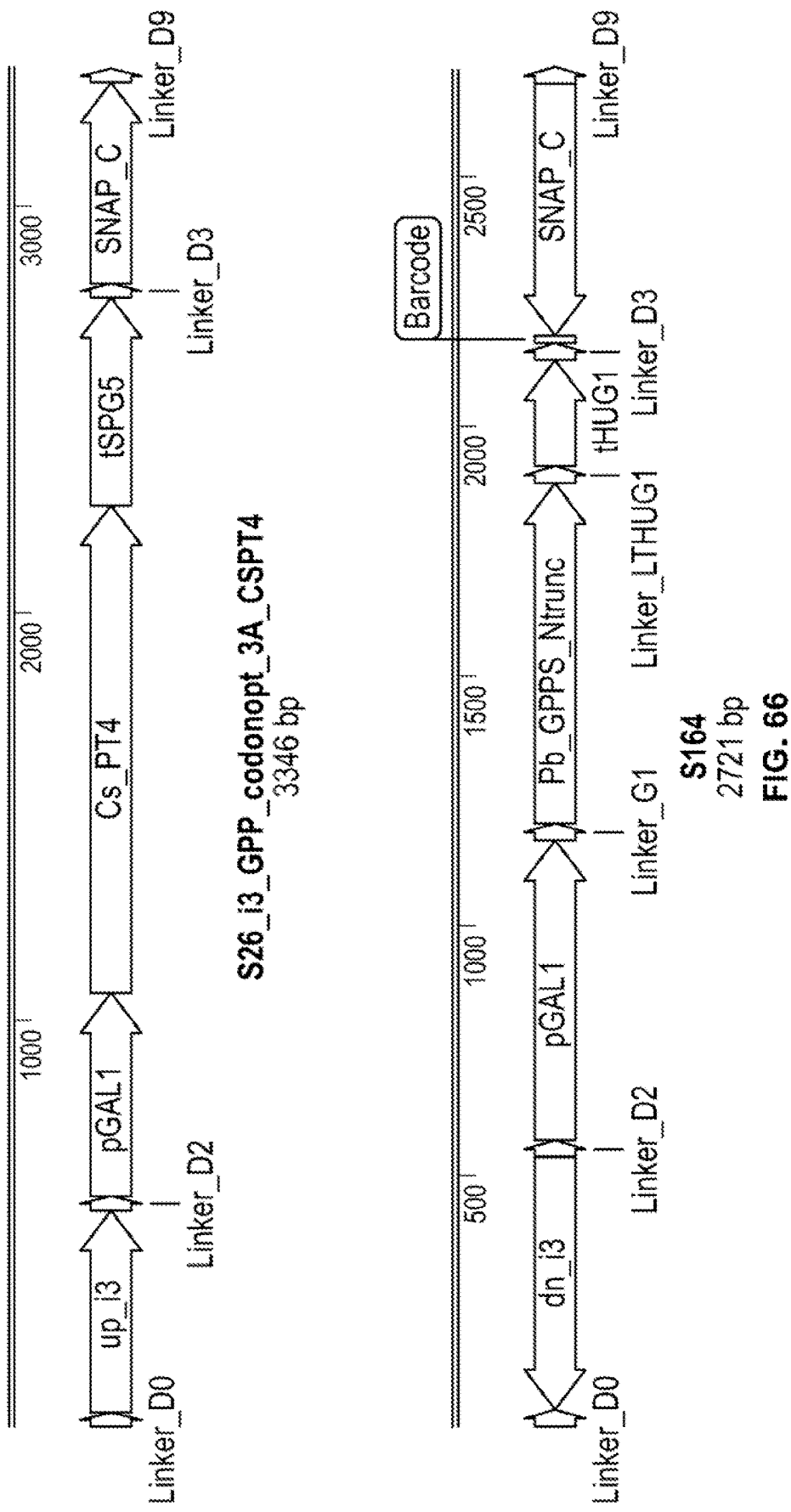
FIG. 66 depicts expression constructs used in the production of the S116 strain.
Figure 67:
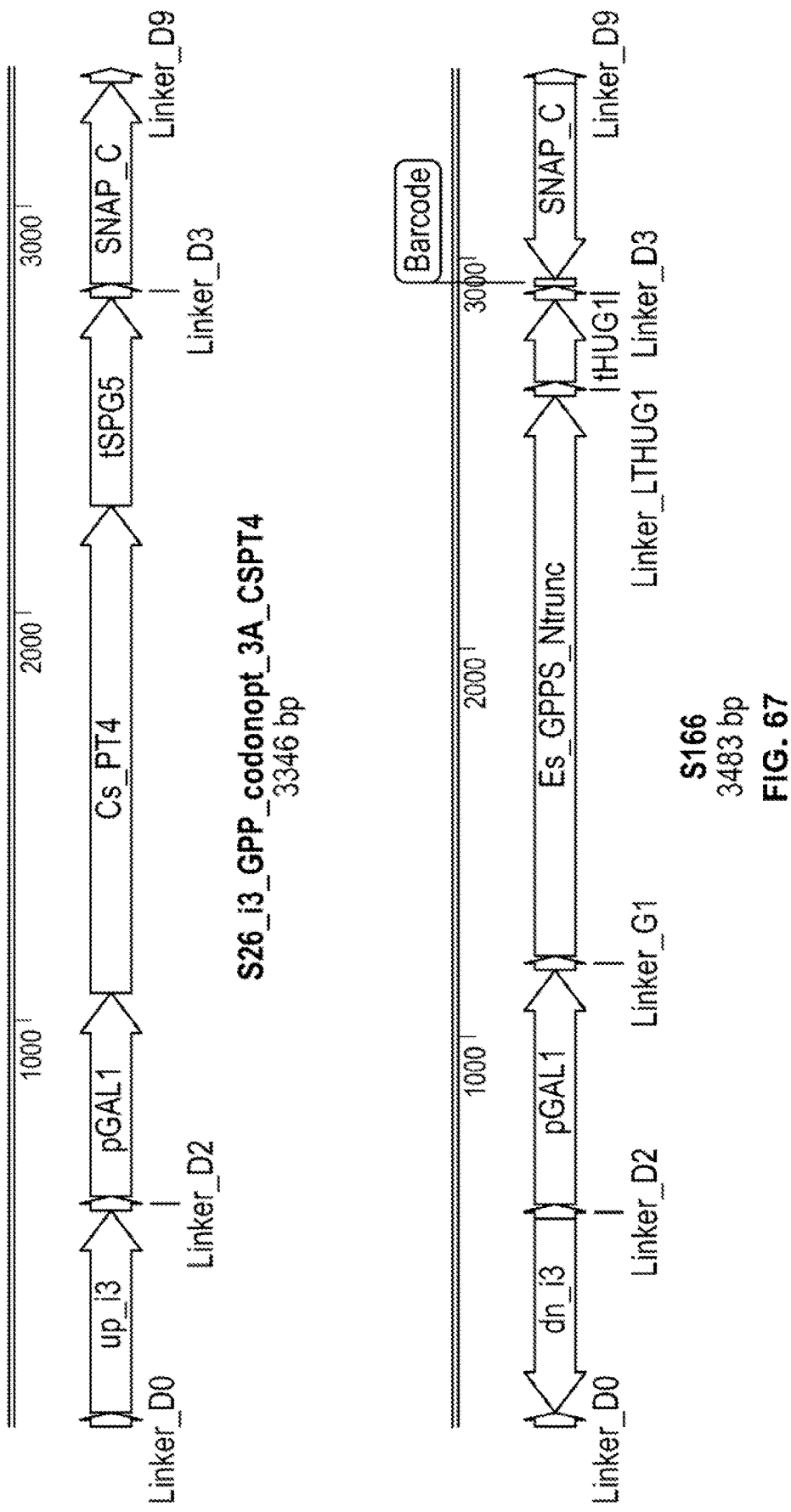
FIG. 67 depicts expression constructs used in the production of the S118 strain.
Figure 68:
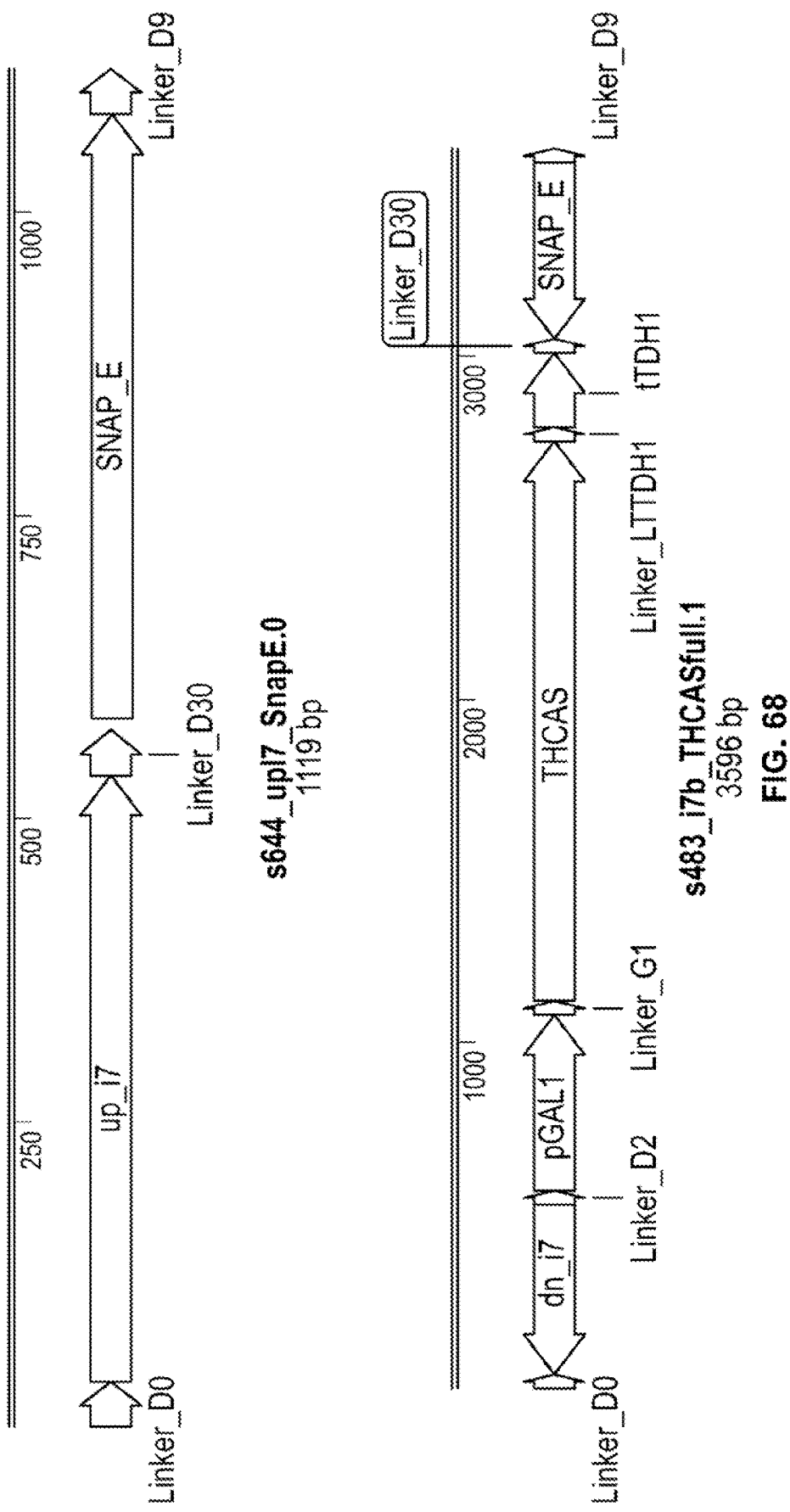
FIG. 68 depicts expression constructs used in the production of the S123 strain.
Figure 69:
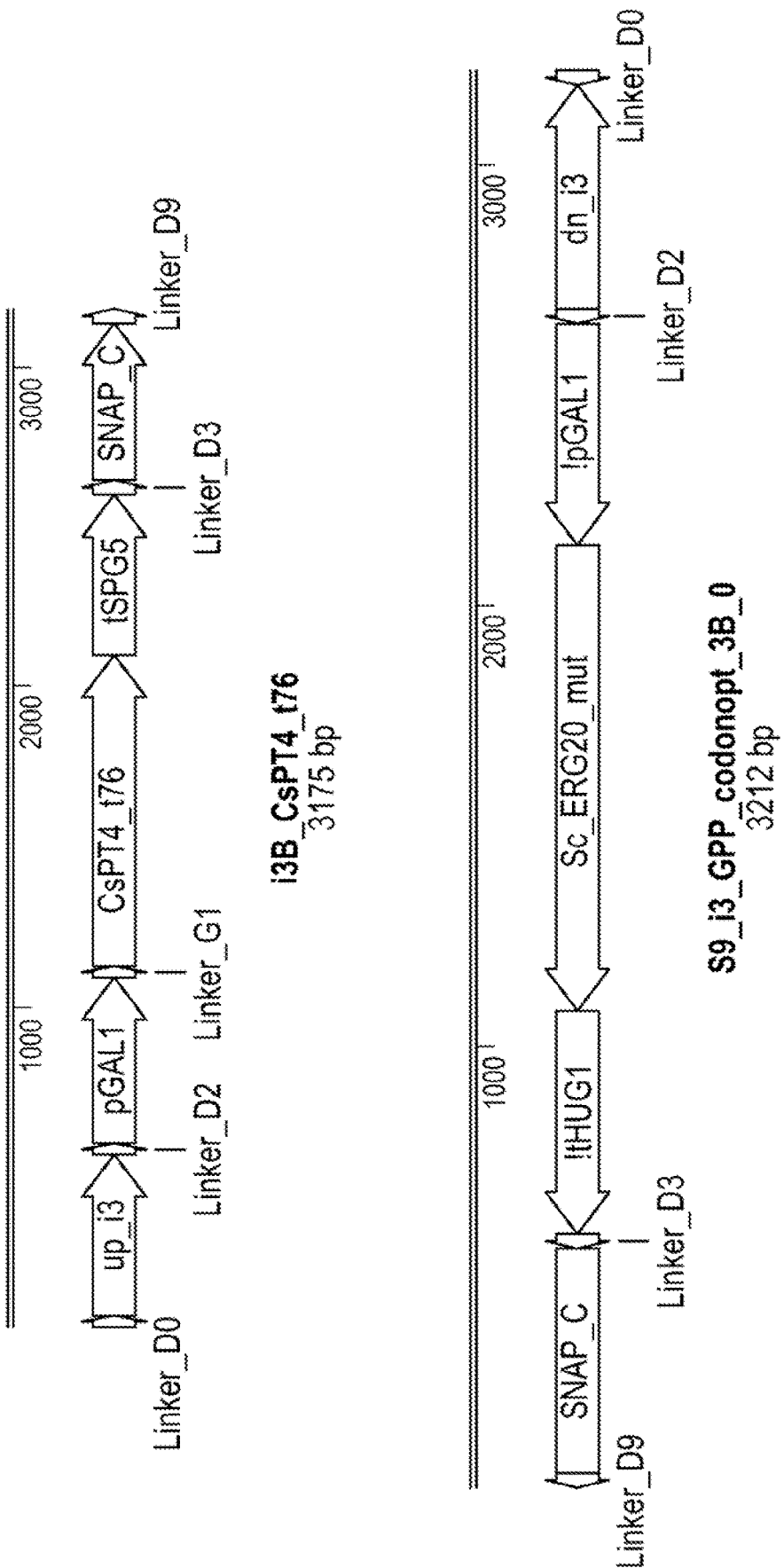
FIG. 69 depicts expression constructs used in the production of the S147 strain.
Figure 70:
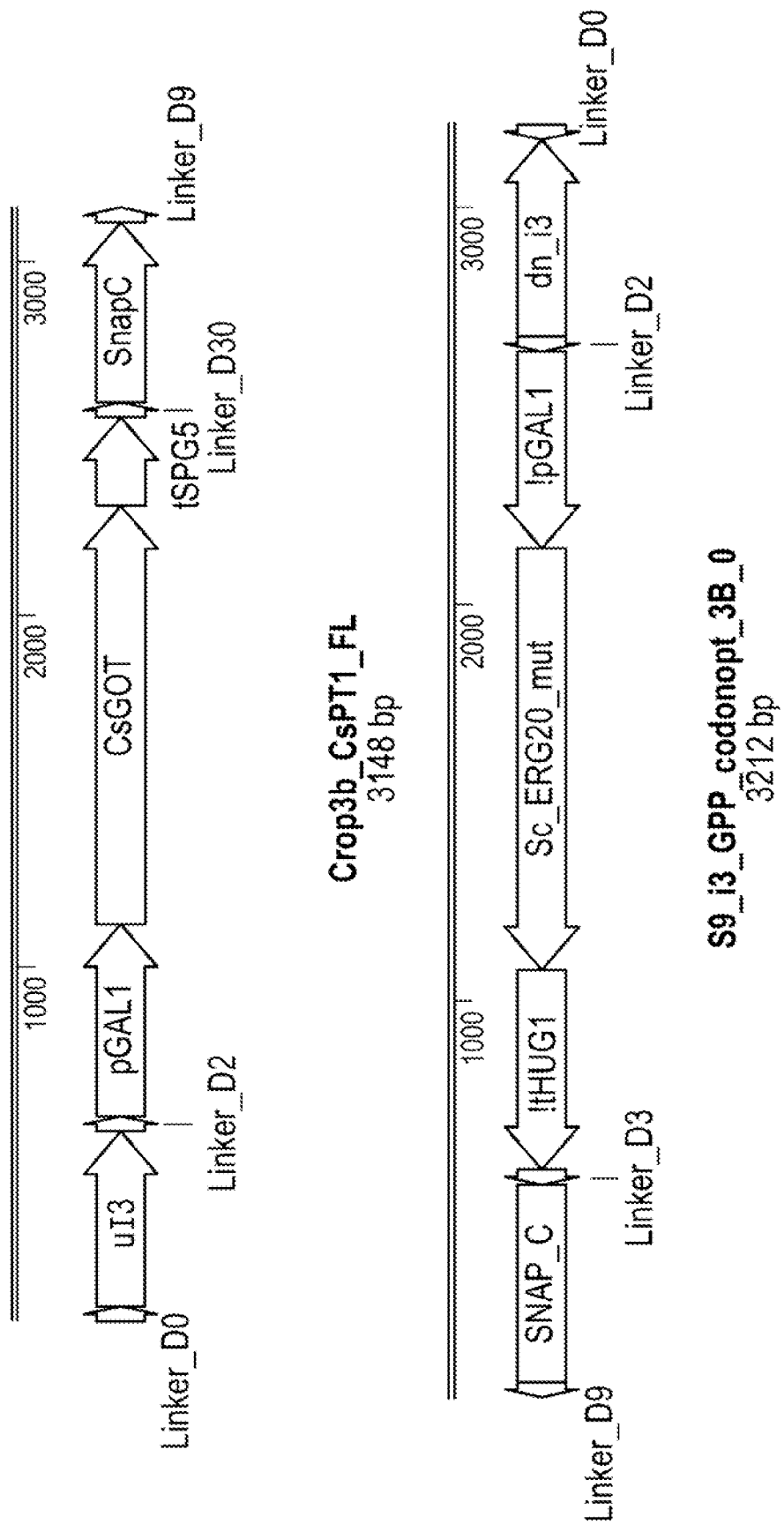
FIG. 70 depicts expression constructs used in the production of the S164 strain.
Figure 71:
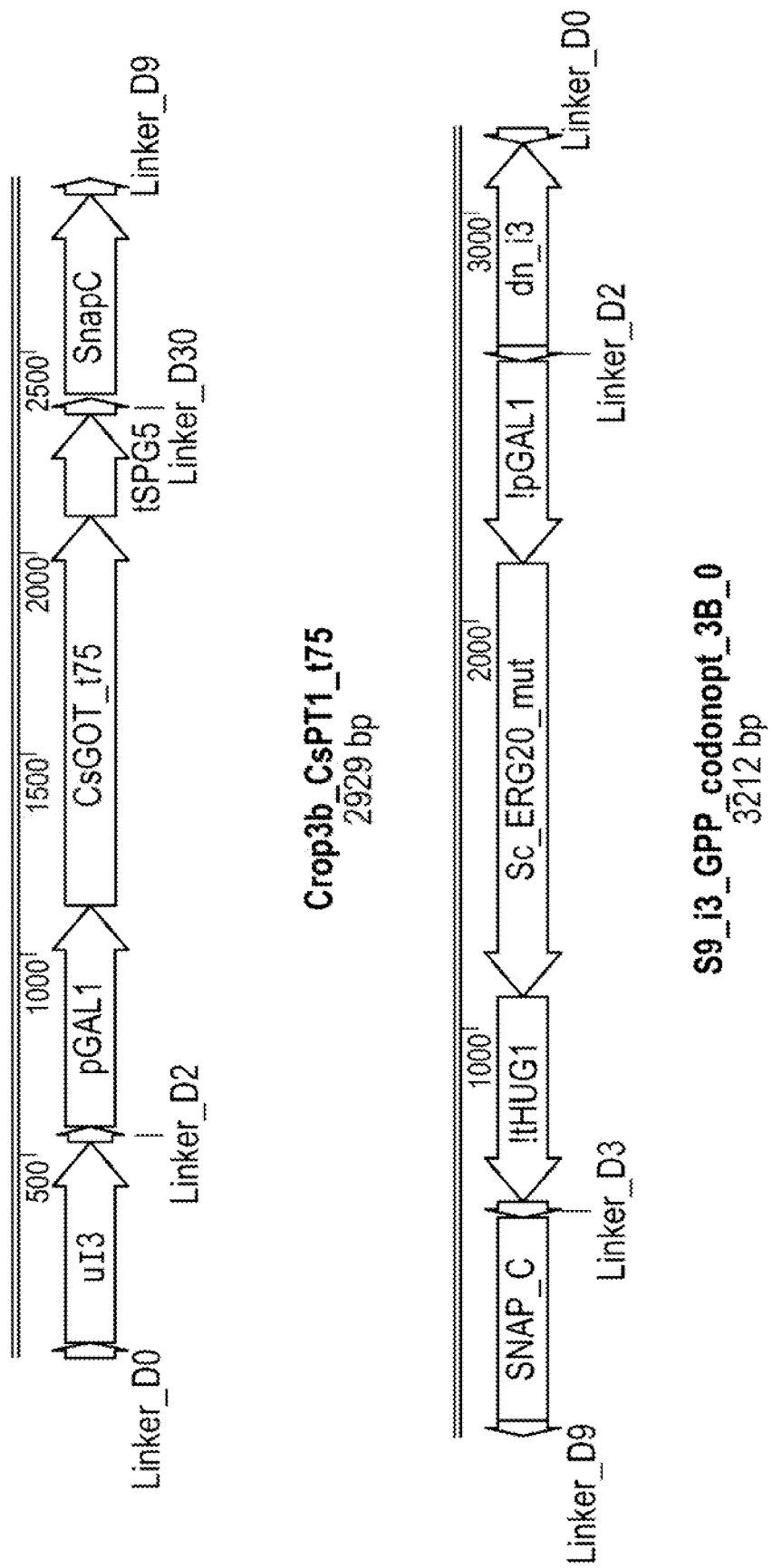
FIG. 71 depicts expression constructs used in the production of the S165 strain.
Figure 72:
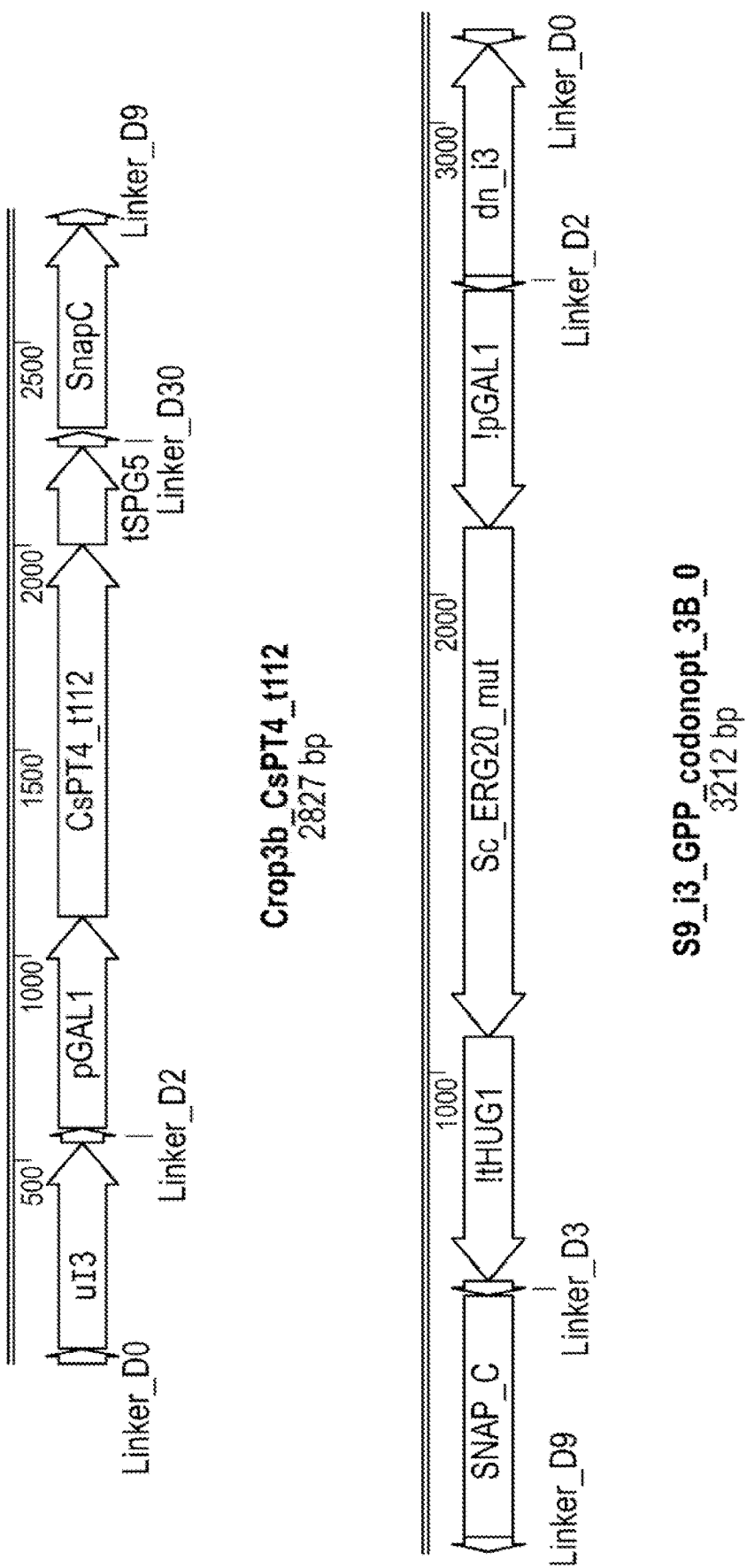
FIG. 72 depicts expression constructs used in the production of the S166 strain.
Figure 73:
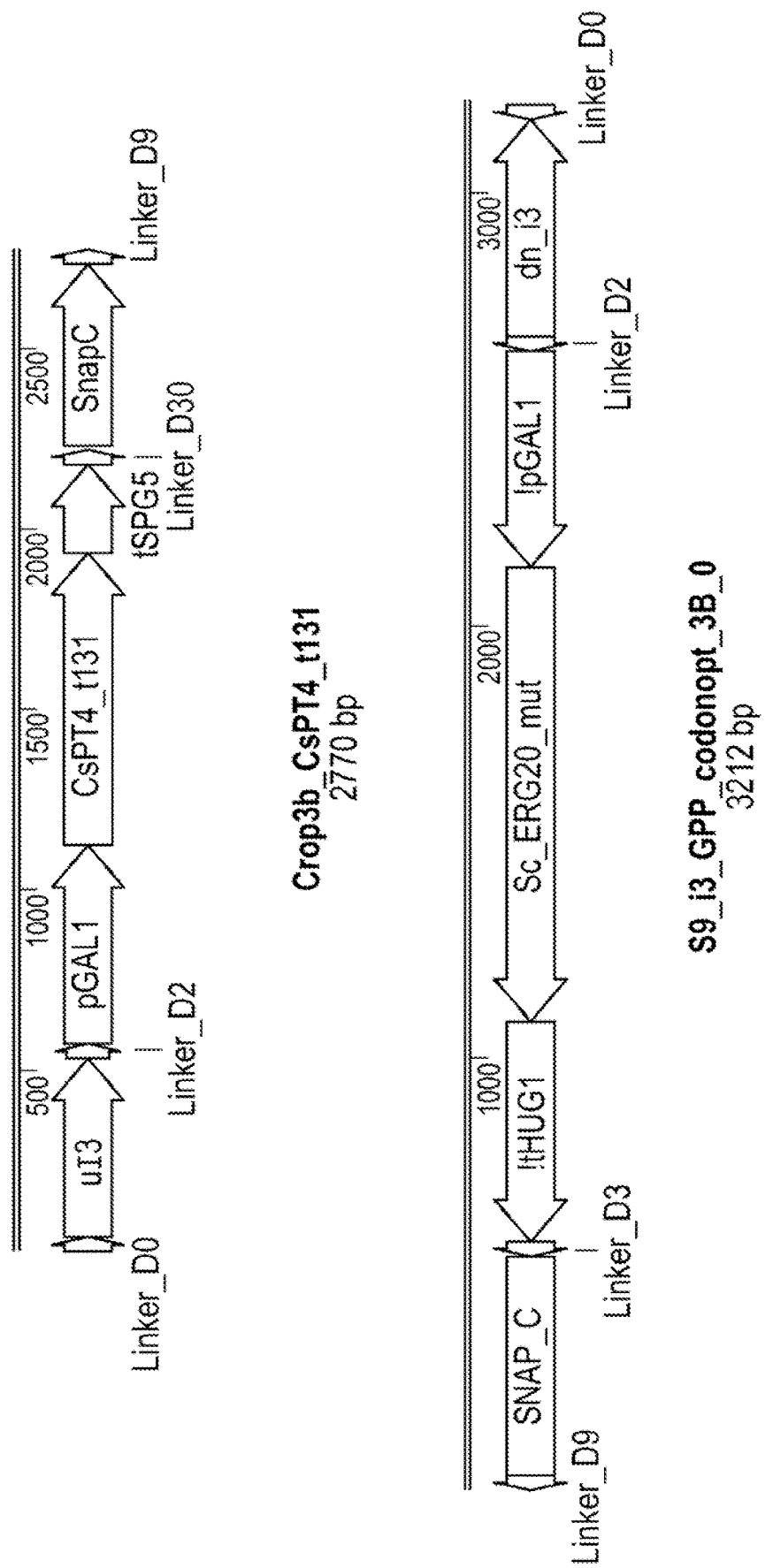
FIG. 73 depicts expression constructs used in the production of the S167 strain.
Figure 74:
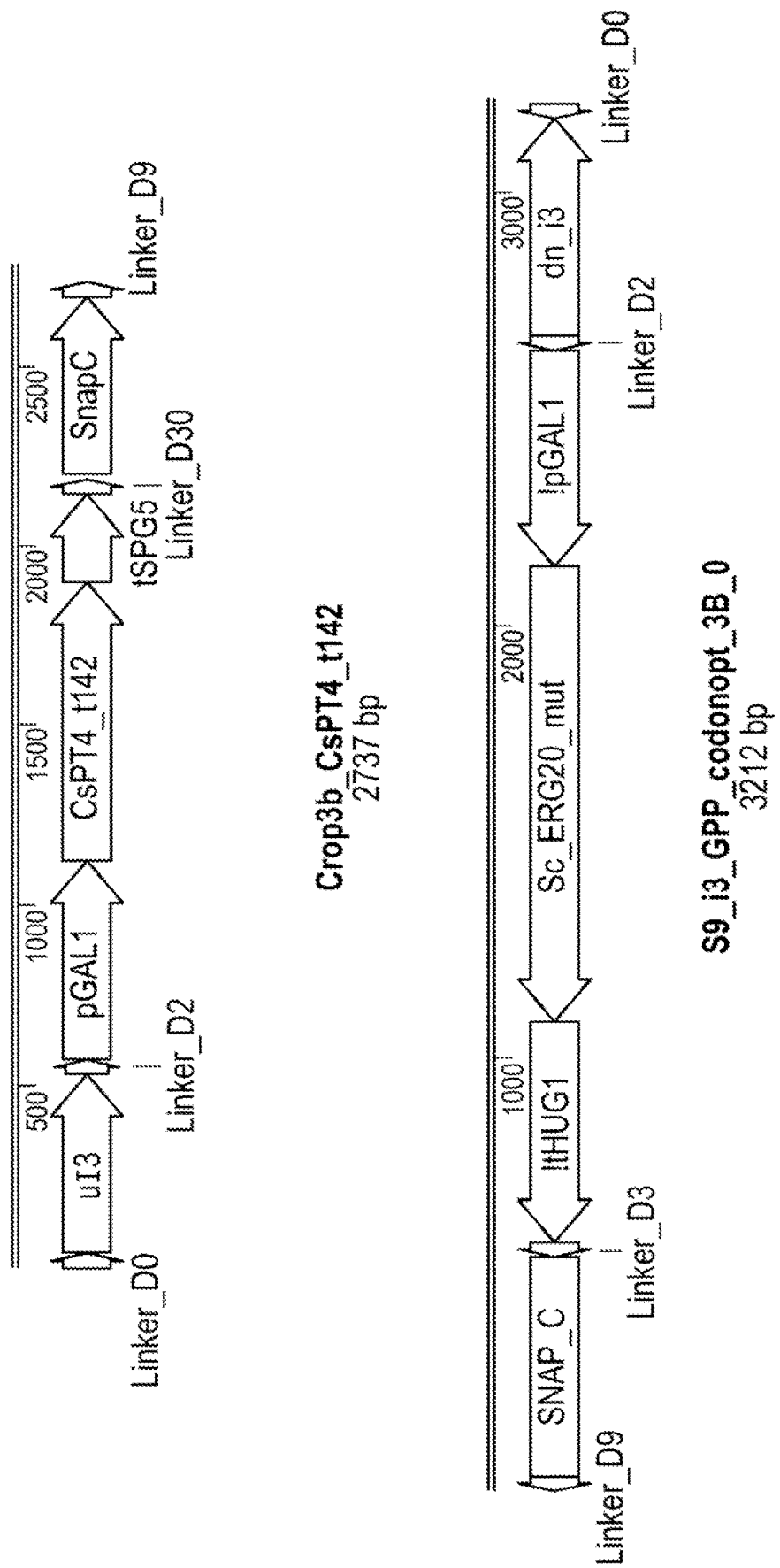
FIG. 74 depicts expression constructs used in the production of the S168 strain.
Figure 75:
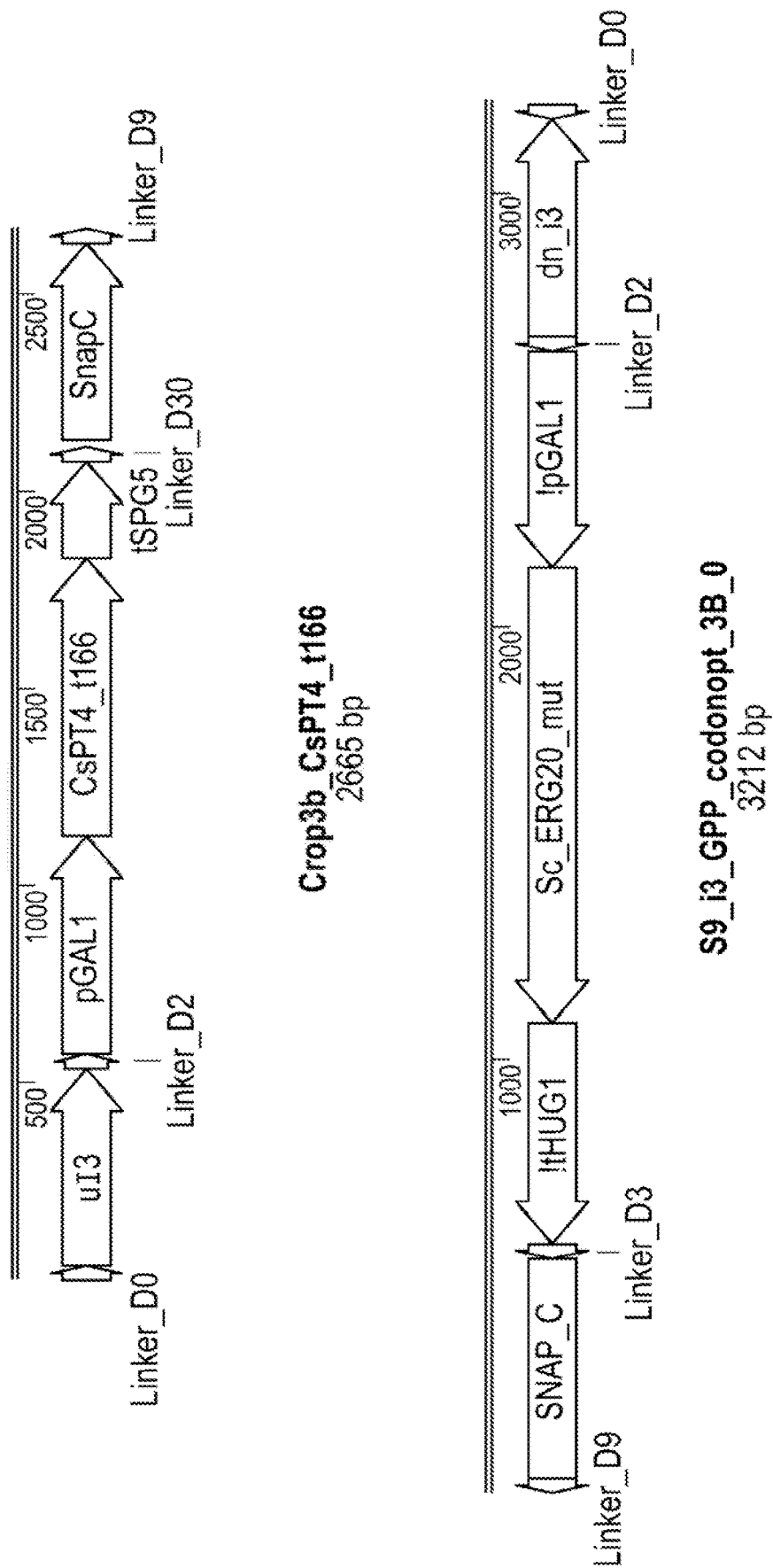
FIG. 75 depicts expression constructs used in the production of the S169 strain.
Figure 76:
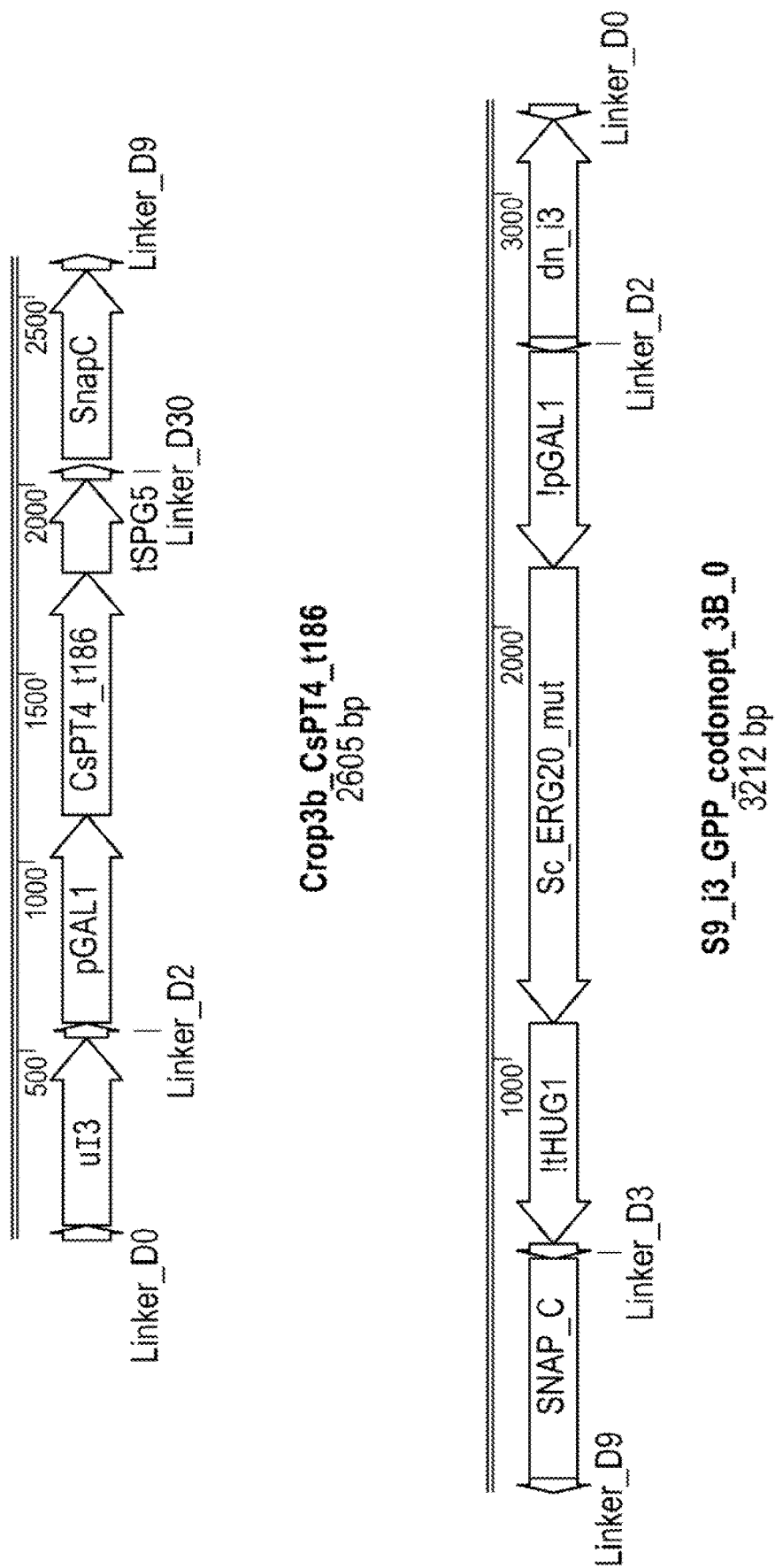
FIG. 76 depicts expression constructs used in the production of the S170 strain.

| Strain (Constructs) | Parent Strain* | Polypeptide SEQ ID NOs (Nucleotide SEQ ID NOs) |
|---|---|---|
| S116 (FIG. 66) | S21 | Cs_PT4: SEQ ID NO: 110 (SEQ ID NO: 111)<br>Pb_GPPS_NTrunc: SEQ ID NO: 135 (SEQ ID NO: 136) |
| S118 (FIG. 67) | S21 | Cs_PT4: SEQ ID NO: 110 (SEQ ID NO: 111)<br>Es_GPPS_NTrunc: SEQ ID NO: 139 (SEQ ID NO: 140) |
| S123 (FIG. 68) | S29 | Cs_THCAS_full: SEQ ID NO: 155 (SEQ ID NO: 156) |
| S147 (FIG. 69) | S21 | Cs_PT4t: SEQ ID NO: 100 (SEQ ID NO: 224)<br>Sc_ERG20_mut: SEQ ID NO: 60 (SEQ ID NO: 161) |
| S164 (FIG. 70) | S21 | Cs_PT1: SEQ ID NO: 82 (SEQ ID NO: 220)<br>Sc_ERG20_mut: SEQ ID NO: 60 (SEQ ID NO: 161) |
| S165 (FIG. 71) | S21 | CsPT1_t75: SEQ ID NO: 223 (SEQ ID NO: 222)<br>Sc_ERG20_mut: SEQ ID NO: 60 (SEQ ID NO: 161) |
| S166 (FIG. 72) | S21 | CsPT4_t112: SEQ ID NO: 211 (SEQ ID NO: 210)<br>Sc_ERG20_mut: SEQ ID NO: 60 (SEQ ID NO: 161) |
| S167 (FIG. 73) | S21 | CsPT4_t131: SEQ ID NO: 213 (SEQ ID NO: 212)<br>Sc_ERG20_mut: SEQ ID NO: 60 (SEQ ID NO: 161) |
| S168 (FIG. 74) | S21 | CsPT4_t142: SEQ ID NO: 215 (SEQ ID NO: 214)<br>Sc_ERG20_mut: SEQ ID NO: 60 (SEQ ID NO: 161) |
| S169 (FIG. 75) | S21 | CsPT4_t166: SEQ ID NO: 217 (SEQ ID NO: 216)<br>Sc_ERG20_mut: SEQ ID NO: 60 (SEQ ID NO: 161) |
| S170 (FIG. 76) | S21 | CsPT4_t186: SEQ ID NO: 219 (SEQ ID NO: 218)<br>Sc_ERG20_mut: SEQ ID NO: 60 (SEQ ID NO: 161) |

*If a strain has a parent strain, it is a child strain. All of the constructs present in the parent strain are also all present in the child strain.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

The invention claimed is:

1. A genetically modified host cell for producing a cannabinoid or a cannabinoid derivative, the cell comprising one or more heterologous nucleic acids encoding a geranyl pyrophosphate:olivetolic acid geranyltransferase, wherein the geranyltransferase catalyzes in the cell production of cannabigerolic acid from geranyl pyrophosphate and olivetolic acid in an amount at least ten times higher than CsPT1 comprising the amino acid sequence of SEQ ID NO:82, wherein the geranyltransferase is *Cannabis sativa* CsPT4 comprising the amino acid sequence of SEQ ID NO:110 or a truncated version thereof.

2. The genetically modified host cell of claim 1, wherein the geranyltransferase is CsPT4t comprising the amino acid sequence of SEQ ID NO:100.

3. The genetically modified host cell of claim 1, wherein the genetically modified host cell further comprises one or more heterologous nucleic acids encoding a tetraketide synthase (TKS) polypeptide and one or more heterologous nucleic acids encoding an olivetolic acid (OAC) polypeptide, or one or more heterologous nucleic acids encoding a fusion TKS and OAC polypeptide.

4. The genetically modified host cell of claim 1, wherein the genetically modified host cell further comprises one or more of the following:
   a) one or more heterologous nucleic acids encoding a polypeptide that generates an acyl-CoA compound or an acyl-CoA compound derivative;
   b) one or more heterologous nucleic acids encoding a polypeptide that generates geranyl pyrophosphate; or
   c) one or more heterologous nucleic acids encoding a polypeptide that generates malonyl-CoA.

5. The genetically modified host cell of claim 4, further comprising:

one or more heterologous nucleic acids encoding a polypeptide that generates an acyl-CoA compound or an acyl-CoA compound derivative, wherein the polypeptide that generates an acyl-CoA compound or an acyl-CoA compound derivative is an acyl-activating enzyme (AAE) polypeptide;

one or more heterologous nucleic acids encoding a polypeptide that generates an acyl-CoA compound or an acyl-CoA compound derivative, wherein the polypeptide that generates an acyl-CoA compound or an acyl-CoA compound derivative is a fatty acyl-CoA ligase polypeptide;

one or more heterologous nucleic acids encoding a polypeptide that generates an acyl-CoA compound or an acyl-CoA compound derivative, wherein the polypeptide that generates an acyl-CoA compound or an acyl-CoA compound derivative is a fatty acyl-CoA synthetase (FAA) polypeptide;

one or more heterologous nucleic acids encoding a polypeptide that generates geranyl pyrophosphate, wherein the polypeptide that generates geranyl pyrophosphate is a geranyl pyrophosphate synthetase (GPPS) polypeptide; or one or more heterologous nucleic acids encoding a polypeptide that generates malonyl-CoA, wherein the polypeptide that generates malonyl-CoA is an acetyl-CoA carboxylase-1 (ACC1) polypeptide.

6. The genetically modified host cell of claim 1, further comprising one or more of the following:
   a) one or more heterologous nucleic acids encoding a HMG-CoA synthase (HMGS) polypeptide;
   b) one or more heterologous nucleic acids encoding a 3-hydroxy-3-methyl-glutaryl-CoA reductase (HMGR) polypeptide;

c) one or more heterologous nucleic acids encoding a mevalonate kinase (MK) polypeptide;

d) one or more heterologous nucleic acids encoding a phosphomevalonate kinase (PMK) polypeptide;

e) one or more heterologous nucleic acids encoding a mevalonate pyrophosphate decarboxylase (MVD) polypeptide; or f) one or more heterologous nucleic acids encoding a isopentenyl diphosphate isomerase (IDI) polypeptide.

7. The genetically modified host cell of claim 1, further comprising one or more heterologous nucleic acids encoding a polypeptide that condenses two molecules of acetyl-CoA a to generate acetoacetyl-CoA.

8. The genetically modified host cell of claim 1, further comprising one or more heterologous nucleic acids encoding a pyruvate dehydrogenase complex (PDC) polypeptide.

9. The genetically modified host cell of claim 1, wherein the cell is a yeast cell.

10. The genetically modified host cell of claim 1, wherein:
at least one of the one or more heterologous nucleic acids is integrated into the chromosome of the genetically modified host cell;
at least one of the one or more heterologous nucleic acids is maintained extrachromosomally;
two or more of the one or more heterologous nucleic acids are present in a single expression vector;
at least one of the heterologous nucleic acids is operably linked to an inducible promoter; or
at least one of the heterologous nucleic acids is operably linked to a constitutive promoter.

11. The genetically modified host cell of claim 1, wherein the genetically modified host cell further comprises one or more heterologous nucleic acids encoding a cannabinoid a synthase polypeptide.

12. The genetically modified host cell of claim 1, wherein the cannabinoid is cannabigerolic acid, cannabigerol, $\Delta^9$-tetrahydrocannabinolic acid, $\Delta^9$-tetrahydrocannabinol, $\Delta^8$-tetrahydrocannabinolic acid, $\Delta^8$-tetrahydrocannabinol, cannabidiolic acid, cannabidiol, cannabichromenic acid, cannabichromene, cannabinolic acid, cannabinol, cannabidivarinic acid, cannabidivarin, tetrahydrocannabivarinic acid, tetrahydrocannabivarin, cannabichromevarinic acid, cannabichromevarin, cannabigerovarinic acid, cannabigerovarin, cannabicyclolic acid, a cannabicyclol, cannabielsoinic acid, cannabielsoin, cannabicitranic acid, or cannabicitran.

13. A method of producing a cannabinoid or a cannabinoid derivative in a genetically modified host cell, the method comprising:
a) culturing the genetically modified host cell of claim 1 in a medium to produce the cannabinoid or cannabinoid derivative; and
b) recovering the produced cannabinoid or cannabinoid derivative.

14. The method of claim 13, wherein the medium comprises:
a carboxylic acid; or
olivetolic acid or an olivetolic acid derivative.

15. The method of claim 13, wherein the medium comprises:
a fermentable sugar,
a pretreated cellulosic feedstock or a non-fermentable carbon source.

16. The method of claim 13, wherein the cannabinoid is cannabigerolic acid, cannabigerol, $\Delta^9$-tetrahydrocannabinolic acid, $\Delta^9$-tetrahydrocannabinol, $\Delta^8$-tetrahydrocannabinolic acid, $\Delta^8$-tetrahydrocannabinol, cannabidiolic acid, cannabidiol, cannabichromenic acid, cannabichromene, cannabinolic acid, cannabinol, cannabidivarinic acid, cannabidivarin, tetrahydrocannabivarinic acid, tetrahydrocannabivarin, cannabichromevarinic acid, cannabichromevarin, cannabigerovarinic acid, cannabigerovarin, cannabicyclolic acid, cannabicyclol, cannabielsoinic acid, cannabielsoin, cannabicitranic acid, or cannabicitran.

17. The genetically modified host cell of claim 1, wherein the cell is a *Saccharomyces cerevisiae*.

18. The genetically modified host cell of claim 1, wherein the cell is a protease-deficient strain of *Saccharomyces cerevisiae*.

19. The method of claim 13, wherein the medium comprises:
a carboxylic acid; and
olivetolic acid or an olivetolic acid derivative.

* * * * *

SEQUENCE LISTING

```
Sequence total quantity: 225
SEQ ID NO: 1             moltype = AA   length = 776
FEATURE                  Location/Qualifiers
source                   1..776
                         mol_type = protein
                         organism = Cannabis sativa
SEQUENCE: 1
MALELPHLLP YKLVKGQTLV AQAARAELAS SSSSSVILKS NFINNNYINY CNNNNNNERR   60
LVVRRDWETM ASSPSHSRNN NDIRTINHLR HVDSMATMPS GAGKIPRLNA VILGEALATE  120
ENDLVFPTDE FSQQAHVPSP QKYLEMYKRS IEDPAGFWSE IASQFYWKQK WDDSVYSENL  180
DVSKGRVNIE WFKGGITNIC YNCLDKNVEA GLGDKIALYW EGNDTGFDDS LTYSQLLHKV  240
CQLANYLKDM GVQKGDAVVI YLPMLLELPI TMLACARIGA VHSVVFAGFS AESLSQRIID  300
CKPKVVITCN AVKRGPKIIH LKDIVDAALV ESAKTGVPID TCLVYENQLA MKRDITKWQD  360
GRDIWWQDVI PKYPTECAVE WVDAEDPLFL LYTSGSTGKP KGVLHTTGGY MVYTATTFKY  420
AFDYKPSDVY WCTADCGWIT GHSYVTYGPL LNGASCIVFE GAPNYPDSGR CWDIVDKYKV  480
TIFYTAPTLV RSLMRDGDEY VTRYSRKSLR ILGSVGEPIN PSAWRWFYNV VGDSRCPISD  540
TWWQTETGGF MITPLPGAWP QKPGSATFPF FGVKPVIVDE KGVEIEGECS GYLCVKGSWP  600
GAFRTLYGDY ERYETTYFKP FTGYYFTDGD CSRDKDGYHW LTGRVDDVIN VSGHRIGTAE  660
VESALVSHPK CAEAAVVGIE HEVKGQAIYA FVTLVEGEPY SEELRKSLIL SVRKQIGAFA  720
APERIHWAPG LPKTRSGKIM RRILRKIASG QLDELGDTST LADPNVVEQL ISLSNC      776

SEQ ID NO: 2             moltype = AA   length = 579
FEATURE                  Location/Qualifiers
source                   1..579
```

```
                        mol_type = protein
                        organism = Streptomyces sp.
SEQUENCE: 2
MELALPAELA PTLPEALRLR SEQQPDTVAY VFLRDGETPE ETLTYGRLDR AARARAAALE   60
AAGLAGGTAV LLYPSGLEFV AALLGCMYAG TAGAPVQVPT RRRGMERARR IADDAGAKTI  120
LTTTAVKREV EEHFADLLTG LTVIDTESLP DVPDDAPAVR LPGPDDVALL QYTSGSTGDP  180
KGVEVTHANF RANVAETVEL WPVRSDGTVV NWLPLFHDMG LMFGVVMPLF TGVPAYLMAP  240
QSFIRRPARW LEAISRFRGT HAAAPSFAYE LCVRSVADTG LPAGLDLSSW RVAVNGAEPV  300
RWTAVADFTE AYAPAGFRPQ AMCPGYGLAE NTLKLSGSPE DRPPTLLRAD AAALQDGRVV  360
PLTGPGTDGV RLVGSGVTVP SSRVAVVDPG TGTEQPAGRV GEIWINGPCV ARGYHGRPAE  420
SAESFGARIA GQEARGTWLR TGDLGFLHDG EVFVAGRLKD VVIHQGRNFY PQDIELSAEV  480
SDRALHPNCA AAFALDDGRT ERLVLLVEAD GRALRNGGAD ALRARVHDAV WDRQRLRIDE  540
IVLLRRGALP KTSSGKVQRR LARSRYLDGE FGPAPAREA                        579

SEQ ID NO: 3            moltype = AA  length = 1671
FEATURE                 Location/Qualifiers
source                  1..1671
                        mol_type = protein
                        organism = Aspergillus sp.
SEQUENCE: 3
MVIQGKRLAA SSIQLLASSL DAKKLCYEYD ERQAPGVTQI TEEAPTEQPP LSTPPSLPQT   60
PNISPISASK IVIDDVALSR VQIVQALVAR KLKTAIAQLP TSKSIKELSG GRSSLQNELV  120
GDIHNEFSSI PDAPEQILLR DFGDANPTVQ LGKTSSAAVA KLISSKMPSD FNANAIRAHL  180
ANKWGLGPLR QTAVLLYAIA SEPPSRLASS SAAEEYWDNV SSMYAESCGI TLRPRQDTMN  240
EDAMASSAID PAVVAEFSKG HRRLGVQQFQ ALAEYLQIDL SGSQASQSDA LVAELQQKVD  300
LWTAEMTPEF LAGISPMLDV KKSRRYGSWW NMARQDVLAF YRRPSYSEFV DDALAPFKVFL  360
NRLCNRADEA LLNMVRSLSC DAYFKQGSLP GYHAASRLLE QAITSTVADC PKARLILPAV  420
GPHTTITKDG TIEYAEAPRQ GVSGPTAYIQ SLRQGASFIG LKSADVDTQS NLTDALLDAM  480
CLALHNGISF VGKTFLVTGA GQGSIGAGVV RLLLEGGARV LVTTSREPAT TSRYFQQMYD  540
NHGAKFSELR VVPCNLASAQ DCEGLIRHVY DPRGLNWDLD AILPFAAASD YSTEMHDIRG  600
QSELGHRLML VNVFRVLGHI VHCKRDAGVD CHPTQVLLPL SPNHGIFGGD GMYPESKLAL  660
ESLFHRIRSE SWSDQLSICG VRIGWTRSTG LMTAHDIIAE TVEEHGIRTF SVAEMALNIA  720
MLLTPDFVAH CEDGPLDADF TGSLGTLGSI PGFLAQLHQK VQLAAEVIRA VQAEDEHERF  780
LSPGTKPTLQ APVAPMHPRS SLRVGYPRLP DYEQEIRPLS PRLERLQDPA NAVVVVGYSE  840
LGPWGSARLR WEIESQGQWT SAGYVELAWL MNLIRHVNDE SYVGWVDTQT GKPVRDGEIQ  900
ALYGDHIDNH TGIRPIQSTS YNPERMEVLQ EVAVEEDLPE FEVSQLTADA MRLRHGANVS  960
IRPSGNPDAC HVKLKRGAVI LVPKTVPFVW GSCAGELPKG WTPAKYGIPE NLIHQVDPVT 1020
LYTICCVAEA FYSAGITHPL EVFRHIHLSE LGNFIGSSMG GPTKTRQLYR DVYFDHEIPS 1080
DVLQDTYLNT PAAWVNMLLL GCTGPIKTPV GACATGVESI DSGYESIMAG KTKMCLVGGY 1140
DDLQEEASYG FAQLKATVNV EEEIACGRQP SEMSRPMAES RAGFVEAHGC GVQLLCRGDI 1200
ALQMGLPIYA VIASSAMAAD KIGSSVPAPG QGILSFSRER ARSSMISVTS RPSSRSSTSS 1260
EVSDKSSLTS ITSISNPAPR AQRARSTTDM APLRAALATW GLTIDDLDVA SLHGTSTRGN 1320
DLNEPEVIET QMRHLGRTPG RPLWAICQKS VTGHPKAPAA AWMLNGCLQV LDSGLVPGNR 1380
NLDTLDEALR SASHLCFPTR TVQLREVKAF LLTSFGFGQK GGQVVGVAPK YFFATLPRPE 1440
VEGYYRKVRV RTEAGDRAYA AAVMSQAVVK IQTQNPYDEP DAPRIFLDPL ARISQDPSTG 1500
QYRFRSDATP ALDDDDALPPP GEPTELVKGI SSAWIEEKVR PHMSPGGTVG VDLVPLASFD 1560
AYKNAIFVER NYTVRERDWA EKSADVRAAY ASRWCAKEAV FKCLQTHSQG AGAAMKEIEI 1620
EHGGNGAPKV KLRGAAQTAA RQRGLEGVQL SISYGDDAVI AVALGLMSGA S          1671

SEQ ID NO: 4            moltype = AA  length = 1888
FEATURE                 Location/Qualifiers
source                  1..1888
                        mol_type = protein
                        organism = Aspergillus sp.
SEQUENCE: 4
MGSVSREHES IPIQAAQRGA ARICAAFGGQ GSNNLDVLKG LLELYKRYGP DLDELLDVAS   60
NTLSQLASSP AAIDVHEPWG FDLRQWLTTP EVAPSKEILA LPPRSFPLNT LLSLALYCAT  120
CRELELELDPGQ FRSLLHSSTG HSQGILAAVA ITQAESWPTF YDACRTVLQI SFWIGLEAYL  180
FTPSSAASDA MIQDCIEHGE GLLSSMLSVS GLSRSQVERV IEHVNKGLGE CNRWVHLALV  240
NSHEKFVLAG PPQSLWAVCL HVRRIRADND LDQSRILFRN RKPIVDILFL PISAPFHTPY  300
LDGVQDRVIE ALSSSASLALH SIKIPLYHTG TGSNLQELQP HQLIPTLIRA ITVDQLDWPL  360
VCRGLNATHV LDFGPGQTCS LIQELTQGTG VSVIQLTTQS GPKPVGGHLA AVNWEAEFGL  420
RLHANVHGAA KLHNRMTTLL GKPPVMVAGM TPTTVRWDFV AAVAQAGYHV ELAGGGYHAK  480
RQFEAEIRRL ATAIPADHGI TCNLLYAKPT TFSWQISVIK DLVRQGVPVE GITIGAGIPS  540
PEVVQECVQS IGLKHISFKP GSFEAIHQVI QIARTHPNFL IGLQWTAGRG GGHHSWEDFH  600
GPILATYAQI RSCPNILLVV GSGFGGGPDT FPYLTGQWAQ AFGYPCMPFD GVLLGSRMMV  660
AREAHTSAQA KRLIIDAQGV GDADWHKSFD EPTGGVVTVN SEFGQPIHVL ATRGVMLWKE  720
LDNRVFSIKD TSKRLEYLRN HRQEIVSRLN ADFARPWFAV DGHGQNVELE DMTYLEVLRR  780
LCDLTYVSHQ KRWVDPSYRI LLLDFVHLLR ERFQCAIDNP GEYPLDIIVR VEESLKDKAY  840
RTLYPEDVSL LMHLFSRRDI KPVPFIPRLD ERFETWFKKD SLWQSEDVEA VIGQDVQRIF  900
IIQGPMAVQY SISDDESVKD ILHNICNHYV EALQADSRET SIGDVHSITQ KPLSAFPGLK  960
VTTNRVQGLY KFEKVGAVPE MDVLFEHIVG LSKSWARTCL MSKSVFRDGS RLHNPIRAAL 1020
QLQRGDTIEV LLTADSEIRK IRLISPTGDG GSTSKVVLEI VSNDGQRVFA TLAPNIPLSP 1080
EPSVVFCFKV DQKPNEWTLE EDASGRAERI KALYMSLWNL GFPNKASVLG LNSQFTGEEL 1140
MITTDKIRDF ERVLRQTSPL QLQSWNPQGC VPIDYCVVIA WSALTKPLMV SSLKCDLLDL 1200
LHSAISPHYA PSVKPLRVGD IVKTSSRILA VSVRPRGTML TVSADIQRQG QHVVTVKSDF 1260
FLGGPVLACE TPFELTEEPE MVVHVDSEVR RAILHSRKWL MREDRALDLL GRQLLFRLKS 1320
EKLFRPDGQL ALLQVTGSVF SYSPDGSTTA FGRVYFSESES CTGNVMDFL HRYGAPRAQL 1380
LELQHPGWTG TSTVAVRGPR RSQSYARVSL DHNPIHVCPA FARYAGLSGP IVHGMETSAM 1440
```

```
MRRIAEWAIG DADRSRFRSW HITLQAPVHP NDPLRVELQH KAMEDGEMVL KVQAFNERTE  1500
ERVAEADAHV EQETTAYVFC GQGSQRQGMG MDLYVNCPEA KALWARADKH LWEKYGFSIL  1560
HIVQNNPPAL TVHFGSQRGR RIRANYLRMM GQPPIDGRHP PILKGLTRNS TSYTFSYSQG  1620
LLMSTQFAQP ALALMEMAQF EWLKAQGVVQ KGARFAGHSL GEYAALGACA SFLSFEDLIS  1680
LIFYRGLKMQ NALPRDANGH TDYGMLAADP SRIGKGFEEA SLKCLVHIIQ QETGWFVEVV  1740
NYNINSQQYV CAGHFRALWM LGKICDDLSC HPQPETVEGQ ELRAMVWKHV PTVEQVPRED  1800
RMERGRATIP LPGIDIPYHS TMLRGEIEPY REYLSERIKV GDVKPCELVG RWIPNVVGQP  1860
FSVDKSYVQL VHGITGSPRL HSLLQQMA                                    1888

SEQ ID NO: 5            moltype = AA   length = 377
FEATURE                 Location/Qualifiers
source                  1..377
                        mol_type = protein
                        organism = Mentha x piperita
SEQUENCE: 5
MSALVNPVAK WPQTIGVKDV HGGRRRRSRS TLFQSHPLRT EMPFSLYFSS PLKAPATFSV   60
SAVYTKEGSE IRDKDPAPST SPAFDFDGYM LRKAKSVNKA LEAAVQMKEP LKIHESMRYS  120
LLAGGKRVRP MLCIAACELV GGDESTAMPA ACAVEMIHTM SLMHDDLPCM DNDDLRRGKP  180
TNHMAFGESV AVLAGDALLS FAFEHVAAAT KGAPPERIVR VLGELAVSIG SEGLVAGQVV  240
DVCSEGMAEV GLDHLEFIHH HKTAALLQGS VVLGAILGGG KEEEVAKLRK FANCIGLLFQ  300
VVDDILDVTK SSKELGKTAG KDLVADKTTY PKLIGVEKSK EFADRLNREA QEQLLHFPH   360
RAAPLIALAN YIAYRDN                                                 377

SEQ ID NO: 6            moltype = AA   length = 313
FEATURE                 Location/Qualifiers
source                  1..313
                        mol_type = protein
                        organism = Mentha x piperita
SEQUENCE: 6
MAINLSHINS KTCFPLKTRS DLSRSSSARC MPTAAAAAFP TIATAAQSQP YWAAIEADIE   60
RYLKKSITIR PPETVFGPMH HLTFAAPATA ASTLCLAACE LVGGDRSQAM AAAAAIHLVH  120
AAAYVHEHLP LTDGSRPVSK PAIQHKYGPN VELLTDGGIV PFGFELLAGS VDPARTDDPD  180
RILRVIIEIS RAGGPEGMIS GLHREEEIVD GNTSLDFIEY VCKKKYGEMH ACGAACGAIL  240
GGAAEEEIQK LRNFGLYQGT LRGMMEMKNS HQLIDENIIG KLKELALEEL GGFHGKNAEL  300
MSSLVAEPSL YAA                                                    313

SEQ ID NO: 7            moltype = AA   length = 352
FEATURE                 Location/Qualifiers
source                  1..352
                        mol_type = protein
                        organism = Saccharomyces sp.
SEQUENCE: 7
MASEKEIRRE RFLNVFPKLV EELNASLLAY GMPKEACDWY AHSLNYNTPG GKLNRGLSVV   60
DTYAILSNKT VEQLGQEEYE KVAILGWCIE LLQAYFLVAD DMMDKSITRR GQPCWYKVPE  120
VGEIAINDAF MLEAAIYKLL KSHFRNEKYY IDITELFHEV TFQTELGQLM DLITAPEDKV  180
DLSKFSLKKH SFIVTFKTAY YSFYLPVALA MYVAGITDEK DLKQARDVLI PLGEYFQIQD  240
DYLDCFGTPE QIGKIGTDIQ DNKCSWVINK ALELASAEQR KTLDENYGKK DSVAEAKCKK  300
IFNDLKIEQL YHEYEESIAK DLKAKISQVD ESRGFKADVL TAFLNKVYKR SK          352

SEQ ID NO: 8            moltype = AA   length = 352
FEATURE                 Location/Qualifiers
REGION                  1..352
                        note = Mutated Erg20 farnesylpyrophosphate synthase (K197G)
source                  1..352
                        mol_type = protein
                        organism = synthetic construct
SEQUENCE: 8
MASEKEIRRE RFLNVFPKLV EELNASLLAY GMPKEACDWY AHSLNYNTPG GKLNRGLSVV   60
DTYAILSNKT VEQLGQEEYE KVAILGWCIE LLQAYFLVAD DMMDKSITRR GQPCWYKVPE  120
VGEIAINDAF MLEAAIYKLL KSHFRNEKYY IDITELFHEV TFQTELGQLM DLITAPEDKV  180
DLSKFSLKKH SFIVTFGTAY YSFYLPVALA MYVAGITDEK DLKQARDVLI PLGEYFQIQD  240
DYLDCFGTPE QIGKIGTDIQ DNKCSWVINK ALELASAEQR KTLDENYGKK DSVAEAKCKK  300
IFNDLKIEQL YHEYEESIAK DLKAKISQVD ESRGFKADVL TAFLNKVYKR SK          352

SEQ ID NO: 9            moltype = AA   length = 496
FEATURE                 Location/Qualifiers
source                  1..496
                        mol_type = protein
                        organism = Rhizophagus irregularis
SEQUENCE: 9
MRAQAHLGGG LKRIETQHQK GKLTARERAE LLLDPGSFNE YDTFVEHQCT DFGMDKNKII   60
GDGVVTGHGT INGRRVFTFS QDFTAFGGSL SKMHAQKICK IMDKAMLVGA PVIGLNDSGG  120
ARIQEGVDSL AGYADIFQRN VLSSGVVPQL SLIMGPCAGG AVYSPALTDF TPMVRDTSYL  180
FVTGPEVVKA VCNEDVTQEE LGGANTHTVI SGVAHAAFEN DIEAIQRIRD FMDFLPLSNR  240
EQAPTRYSDD PIDREDPSLN HIIPVDSTKA YDMREIITRL IDDGHFFEIM PDYAKNIVVG  300
FARMGGKTVS IVGNQPLVSS GVLDINSSVK AARFVRFCDA FNIPIITLVD VPGFLPGTAQ  360
EHNGIIRHGA KLLYAYAEAT VPKITIITRK AYGGAYDVMS SKHLRGDMNY SWPTGEIAVM  420
GAKGAVEIIF RHVEDRTQSE HEYIDKFANP IPAAQRGYID DIILPAATRK RIIEDLFVLS  480
HKQLPLIYKK HDNCPL                                                  496
```

```
SEQ ID NO: 10              moltype = AA  length = 101
FEATURE                    Location/Qualifiers
source                     1..101
                           mol_type = protein
                           organism = Cannabis sativa
SEQUENCE: 10
MAVKHLIVLK FKDEITEAQK EEFFKTYVNL VNIIPAMKDV YWGKDVTQKN KEEGYTHIVE   60
VTFESVETIQ DYIIHPAHVG FGDVYRSFWE KLLIFDYTPR K                     101

SEQ ID NO: 11              moltype = AA  length = 385
FEATURE                    Location/Qualifiers
source                     1..385
                           mol_type = protein
                           organism = Cannabis sativa
SEQUENCE: 11
MNHLRAEGPA SVLAIGTANP ENILLQDEFP DYYFRVTKSE HMTQLKEKFR KICDKSMIRK   60
RNCFLNEEHL KQNPRLVEHE MQTLDARQDM LVVEVPKLGK DACAKAIKEW GQPKSKITHL  120
IFTSASTTDM PGADYHCAKL LGLSPSVKRV MMYQLGCYGG GTVLRIAKDI AENNKGARVL  180
AVCCDIMACL FRGPSESDLE LLVGQAIFGD GAAAVIVGAE PDESVGERPI FELVSTGQTI  240
LPNSEGTIGG HIREAGLIFD LHKDVPMLIS NNIEKCLIEA FTPIGISDWN SIFWITHPGG  300
KAILDKVEEK LHLKSDKFVD SRHVLSEHGN MSSSTVLFVM DELRKRSLEE GKSTTGDGFE  360
WGVLFGFGPG LTVERVVVRS VPIKY                                       385

SEQ ID NO: 12              moltype = AA  length = 327
FEATURE                    Location/Qualifiers
REGION                     1..327
                           note = Truncated geranyl pyrophosphate olivetolic acid
                              geranyltransferase (GOT)
source                     1..327
                           mol_type = protein
                           organism = synthetic construct
SEQUENCE: 12
MNSIRAATTN QTEPPESDNH SVATKILNFG KACWKLQRPY TIIAFTSCAC GLFGKELLHN   60
TNLISWSLMF KAFFFLVAIL CIASFTTTIN QIYDLHIDRI NKPDLPLASG EISVNTAWIM  120
SIIVALFGLI ITIKMKGGPL YIFGYCFGIF GGIVYSVPPF RWKQNPSTAF LLNFLAHIIT  180
NFTFYYASRA ALGLPFELRP SFTFLLAFMK SMGSALALIK DASDVEGDTK FGISTLASKY  240
GSRNLTLFCS GIVLLSYVAA ILAGIIWPQA FNSNVMLLSH AILAFWLILQ TRDFALTNYD  300
PEAGRRFYEF MWKLYYAEYL VYVFIGS                                     327

SEQ ID NO: 13              moltype = AA  length = 332
FEATURE                    Location/Qualifiers
REGION                     1..332
                           note = Engineered geranyl pyrophosphate olivetolic acid
                              geranyltransferase (GOT)
source                     1..332
                           mol_type = protein
                           organism = synthetic construct
SEQUENCE: 13
MKDQRGNSIR ASAQIEDRPP ESGNLSALTN VKDFVSVCWE YVRPYTAKGV IICSSCLFGR   60
ELLENPNLFS WPLIFKAFFF LVAILCIASF TTTINQIYDL HIDRINKPDL PLASGEISVN  120
TAWIMSIIVA LFGLIITIKM KGGPLYIFGY CFGIFGGIVY SVPPFRWKQN PSTAFLLNFL  180
AHIITNFTFY YASRAALGLP FELRPSFTFL LAFMKSMGSA LALIKDASDV EGDTKFGIST  240
LASKYGSRNL TLFCSGIVLL SYVAAILAGI IWPQAFNSNV MLLSHAILAF WLILQTRDFA  300
LTNYDPEAGR RFYEFMWKLY YAEYLVYVFI GS                               332

SEQ ID NO: 14              moltype = AA  length = 547
FEATURE                    Location/Qualifiers
REGION                     1..547
                           note = Mutant tetrahydro cannabinolic acid synthase (THCAS)
source                     1..547
                           mol_type = protein
                           organism = synthetic construct
SEQUENCE: 14
MNCSAFSFWF VCKIIFFFLS FHIQISIANP RENFLKCFSK HIPNNVANPK LVYTQHDQLY   60
MSILNSTIQN LRFISDTTPK PLVIVTPSNN SHIQATILCS KKVGLQIRTR SGGHDAEGMS  120
YISQVPFVVV DLRNMHSIKI DVHSQTAWVE AGATLGEVYY WINEKNENLS FPGGYCPTVG  180
VGGHFSGGGY GALMRNYGLA ADNIIDAHLV NVDGKVLDRK SMGEDLFWAI RGGGGENFGI  240
IAAWKIKLVA VPSKSTIFSV KKNMEIHGLV KLFNKWQNIA YKYDKDLVLM THFITKNITD  300
NHGKNKTTVH GYFSSIFHGG VDSLVDLMNK SFPELGIKKT DCKEFSWIDT TIFYSGVVNF  360
NTANFKKEIL LDRSAGKKTA FSIKLDYVKK PIPETAMVKI LEKLYEEDVG AGMYVLYPYG  420
GIMEEISESA IPFPHRAGIM YELWYTASWE KQEDNEKHIN WVRSVYNFTT PYVSQNPRLA  480
YLNYRDLDLG KTNHASPNNY TQARIWGEKY FGKNFNRLVK VKTKVDPNNF FRNEQSIPPL  540
PPHHHGS                                                           547

SEQ ID NO: 15              moltype = AA  length = 520
FEATURE                    Location/Qualifiers
REGION                     1..520
                           note = Truncated tetrahydro cannabinolic acid synthase
```

```
                               (THCAS)
source                         1..520
                               mol_type = protein
                               organism = synthetic construct
SEQUENCE: 15
MNPRENFLKC FSKHIPNNVA NPKLVYTQHD QLYMSILNST IQNLRFISDT TPKPLVIVTP    60
SNNSHIQATI LCSKKVGLQI RTRSGGHDAE GMSYISQVPF VVVDLRNMHS IKIDVHSQTA   120
WVEAGATLGE VYYWINEKNE NLSFPGGYCP TVGVGGHFSG GGYGALMRNY GLAADNIIDA   180
HLVNVDGKVL DRKSMGEDLF WAIRGGGGEN FGIIAAWKIK LVAVPSKSTI FSVKKNMEIH   240
GLVKLFNKWQ NIAYKYDKDL VLMTHFITKN ITDNHGKNKT TVHGYFSSIF HGGVDSLVDL   300
MNKSFPELGI KKTDCKEFSW IDTTIFYSGV VNFNTANFKK EILLDRSAGK KTAFSIKLDY   360
VKKPIPETAM VKILEKLYEE DVGAGMYVLY PYGGIMEEIS ESAIPFPHRA GIMYELWYTA   420
SWEKQEDNEK HINWVRSVYN FTTPYVSQNP RLAYLNYRDL DLGKTNHASP NNYTQARIWG   480
EKYFGKNFNR LVKVKTKVDP NNFFRNEQSI PPLPPHHHGS                         520

SEQ ID NO: 16                  moltype = AA  length = 519
FEATURE                        Location/Qualifiers
REGION                         1..519
                               note = Truncated cannabidiolic acid synthase (CBDAS)
source                         1..519
                               mol_type = protein
                               organism = synthetic construct
SEQUENCE: 16
MNPRENFLKC FSQYIPNNAT NLKLVYTQNN PLYMSVLNST IHNLRFTSDT TPKPLVIVTP    60
SHVSHIQGTI LCSKKVGLQI RTRSGGHDSE GMSYISQVPF VIVDLRNMRS IKIDVHSQTA   120
WVEAGATLGE VYYWNEKNE NLSLAAGYCP TVCAGGHFGG GGYGEPLMRNY GLAADNIIDA   180
HLVNVHGKVL DRKSMGEDLF WALRGGGAES FGIIVAWKIR LVAVPKSTMF SVKKIMEIHE   240
LVKLVNKWQN IAYKYDKDLL LMTHFITRNI TDNQGKNKTA IHTYFSSVFL GGVDSLVDLM   300
NKSFPELGIK KTDCRQLSWI DTIIFYSGVV NYDTDNFNKE ILLDRSAGQN GAFKIKLDYV   360
KKPIPESVFV QILEKLYEED IGAGMYALYP YGGIMDEISE SAIPFPHRAG ILYELWYICS   420
WEKQEDNEKH LNWIRNIYNF MTPYVSKNPR LAYLNYRDLD IGINDPKNPN NYTQARIWGE   480
KYFGKNFDRL VKVKTLVDPN NFFRNEQSIP PLPRHRHGS                          519

SEQ ID NO: 17                  moltype = AA  length = 502
FEATURE                        Location/Qualifiers
REGION                         1..502
                               note = Truncated 3-hydroxy-3-methyl-glutaryl-CoA reductase
                               (HMGR)
source                         1..502
                               mol_type = protein
                               organism = synthetic construct
SEQUENCE: 17
MVLTNKTVIS GSKVKSLSSA QSSSSGPSSS SEEDDSRDIE SLDKKIRPLE ELEALLSSGN    60
TKQLKNKEVA ALVIHGKLPL YALEKKLGDT TRAVARRKA LSILAEAPVL ASDRLPYKNY   120
DYDRVFGACC ENVIGYMPLP VGVIGPLVID GTSYHIPMAT TEGCLVASAM RGCKAINAGG   180
GATTVLTKDG MTRGPVVRFP TLKRSGACKI WLDSEEGQNA IKKAFNSTSR FARLQHIQTC   240
LAGDLLFMRF RTTTGDAMGM NMISKGVEYS LKQMVEEYGW EDMEVVSVSG NYCTDKKPAA   300
INWIEGRGKS VVAEATIPGD VVRKVLKSDV SALVELNIAK NLVGSAMAGS VGGFNAHAAN   360
LVTAVFLALG QDPAQNVESS NCITLMKEVD GDLRISVSMP SIEVGTIGGG TVLEPQGAML   420
DLLGVRGPHA TAPGTNARQL ARIVACAVLA GELSLCAALA AGHLVQSHMT HNRKPAEPTK   480
PNNLDATDIN RLKDGSVTCI KS                                            502

SEQ ID NO: 18                  moltype = AA  length = 284
FEATURE                        Location/Qualifiers
source                         1..284
                               mol_type = protein
                               organism = Ralstonia sp.
SEQUENCE: 18
MSIRTVGIVG AGTMGNGIAQ ACAVVGLNVV MVDISDAAVQ KGVATVASSL DRLIKKEKLT    60
EADKASALAR IKGSTSYDDL KATDIVIEAA TENYDLKVKI LKQIDGIVGE NVIIASNTSS   120
ISITKLAAVT SRADRFIGMH FFNPVPVMAL VELIRGLQTS DTTHAAVEAL SKQLGKYPIT   180
VKNSPGFVVN RILCPMINEA FCVLGEGLAS PEEIDEGMKL GCNHPIGPLA LADMIGLDTM   240
LAVMEVLYTE FADPKYRPAM LMREMVAAGY LGRKTGRGVY VYSK                    284

SEQ ID NO: 19                  moltype = AA  length = 261
FEATURE                        Location/Qualifiers
source                         1..261
                               mol_type = protein
                               organism = Clostridium sp.
SEQUENCE: 19
MELNNVILEK EGKVAVVTIN RPKALNALNS DTLKEMDYVI GEIENDSEVL AVILTGAGEK    60
SFVAGADISE MKEMNTIEGR KFGILGNKVF RRLELLEKPV IAAVNGFALG GGCEIAMSCD   120
IRIASSNARF GQPEVGLGIT PGFGGTQRLS RLVGMGMAKQ LIFTAQNIKA DEALRIGLVN   180
KVVEPSELMN TAKEIANKIV SNAPVAVKLS KQAINRGMQC DIDTALAFES EAFGECFSTE   240
DQKKDAMTAFI EKRKIEGFKN R                                            261

SEQ ID NO: 20                  moltype = AA  length = 397
FEATURE                        Location/Qualifiers
source                         1..397
```

```
                           mol_type = protein
                           organism = Treponema sp.
SEQUENCE: 20
MIVKPMVRNN  ICLNAHPQGC  KKGVEDQIEY  TKKRITAEVK  AGAKAPKNVL  VLGCSNGYGL   60
ASRITAAFGY  GAATIGVSFE  KAGSETKYGT  PGWYNNLAFD  EAAKREGLYS  VTIDGDAFSD  120
EIKAQVIEEA  KKKGIKFDLI  VYSLASPVRT  DPDTGIMHKS  VLKPFGKTFT  GKTVDPFTGE  180
LKEISAEPAN  DEEAAATVKV  MGGEDWERWI  KQLSKEGLLE  EGCITLAYSY  IGPEATQALY  240
RKGTIGKAKE  HLEATAHRLN  KENPSIRAFV  SVNKGLVTRA  SAVIPVIPLY  LASLFKVMKE  300
KGNHEGCIEQ  ITRLYAERLY  RKDGTIPVDE  ENRIRIDDWE  LEEDVQKAVS  ALMEKVTGEN  360
AESLTDLAGY  RHDFLASNGF  DVEGINYEAE  VERFDRI                             397

SEQ ID NO: 21              moltype = AA  length = 394
FEATURE                    Location/Qualifiers
source                     1..394
                           mol_type = protein
                           organism = Ralstonia sp.
SEQUENCE: 21
MTREVVVVSG  VRTAIGTFGG  SLKDVAPAEL  GALVVREALA  RAQVSGDDVG  HVVFGNVIQT   60
EPRDMYLGRV  AAVNGGVTIN  APALTVNRLC  GSGLQAIVSA  AQTILLGDTD  VAIGGGAESM  120
SRAPYLAPAA  RWGARMGDAG  LVDMMLGALH  DPFHRIHMGV  TAENVAKEYD  ISRAQQDEAA  180
LESHRRASAA  IKAGYFKDQI  VPVVSKGRKG  DVTFDTDEHV  RHDATIDDMT  KLRPVFVKEN  240
GTVTAGNASG  LNDAAAAVVM  MERAEAERRG  LKPLARLVSY  GHAGVDPKAM  GIGPVPATKI  300
ALERAGLQVS  DLDVIEANEA  FAAQACAVTK  ALGLDPAKVN  PNGSGISLGH  PIGATGALIT  360
VKALHELNRV  QGRYALVTMC  IGGGQGIAAI  FERI                                394

SEQ ID NO: 22              moltype = AA  length = 813
FEATURE                    Location/Qualifiers
source                     1..813
                           mol_type = protein
                           organism = Enterococcus sp.
SEQUENCE: 22
MKEVVMIDAA  RTPIGKYRGS  LSPFTAVELG  TLVTKGLLDK  TKLKKDKIDQ  VIFGNVLQAG   60
NGQNVARQIA  LNSGLPVDVP  AMTINEVCGS  GMKAVILARQ  LIQLGEAAELV  IAGGTESMSQ  120
APMLKPYQSE  TNEYGEPISS  MVNDGLTDAF  SNAHMGLTVK  KVATQFSVSR  EEQDRYALSS  180
QLKAAHAVEA  GVFSEEIIPV  KISDEDVLSE  DEAVRGNSTL  EKLGTLRTVF  SEEGTVTAGN  240
ASPLNDGASV  VILASKEYAE  NNNLPYLATI  KEVAEVGIDP  SIMGIAPIKA  IQKLTDRSGM  300
NLSTIDLFEI  NEAFAASSIV  VSQELQLDEE  KVNIYGGAIA  LGHPIGASGA  RILTTLAYGL  360
LREQKRYGIA  SLCIGGGLGL  AVLLEANMEQ  THKDVQKKKF  YQLTPSERRS  QLIEKNVLTQ  420
ETALIFQEQT  LSEELSDHMI  ENQVSEVEIP  MGIAQNFQIN  GKKKWIPMAT  EEPSVIAAAS  480
NGAKICGNIC  AETPQRLMRG  QIVLSGKSEY  QAVINAVNHR  KEELILCANE  SYPSIVKRGG  540
GVQDISTREF  MGSFHAYLSI  DFLVDVKDAM  GANMINSILE  SVANKLREWF  PEEEILFSIL  600
SNFATESLAS  ACCEIPFERL  GRNKEIGEQI  AKKIQQAGEY  AKLDPYRAAT  HNKGIMNGIE  660
AVVAATGNDT  RAVSASIHAY  AARNGLYQGL  TDWQIKGDKL  VGKLTVPLAV  ATVGGASNIL  720
PKAKASLAML  DIDSAKELAQ  VIAAVGLAQN  LAALRALVTE  GIQKGHMGLQ  ARSLAISIGA  780
IGEEIEQVAK  KLREAEKMNQ  QTAIQILEKI  REK                                 813

SEQ ID NO: 23              moltype = AA  length = 389
FEATURE                    Location/Qualifiers
source                     1..389
                           mol_type = protein
                           organism = Lactobacillus plantarum
SEQUENCE: 23
MKIGIDKLHF  ATSHLYVDMA  ELATARQAEP  DKYLIGIGQS  KMAVIPPSQD  VVTLAANAAA   60
PMLTATDIAA  IDLVVGTES  GIDNSKASAI  YVAKLLGLSQ  RVRTIEMKEA  CYAATAGVQL  120
AQDHVRVHPD  KKALVIGSDV  ARYGLNTPGE  PTQGGGAVAM  LISADPKVLV  LGTESSLLSE  180
DVMDFWRPLY  HTEALVDGKY  SSNIYIDYFQ  DVFKNYLQTT  QTSPDTLTAL  VFHLPYTKMG  240
LKALRSVLPL  VDAEKQAQWL  AHFEHARQLN  RQVGNLYTGS  LYLSLLSQLL  TDPQLQPGNR  300
LGLFSYGSGA  EGEFYTGVIQ  PDYQTGLDHG  LPQRLARRRR  VSVAEYEALF  SHQLQWRADD  360
QSVSYADDPH  RFVLTGQKNE  QRQYLDQQV                                       389

SEQ ID NO: 24              moltype = AA  length = 491
FEATURE                    Location/Qualifiers
source                     1..491
                           mol_type = protein
                           organism = Saccharomyces cerevisiae
SEQUENCE: 24
MKLSTKLCWC  GIKGRLRPQK  QQQLHNTNLQ  MTELKKQKTA  EQKTRPQNVG  IKGIQIYIPT   60
QCVNQSELEK  FDGVSQGKYT  IGLGQTNMSF  VNDREDIYSM  SLTVLSKLIK  SYNIDTNKIG  120
RLEVGTETLI  DKSKSVKSVL  MQLFGENTDV  EGIDTLNACY  GGTNALFNSL  NWIESNAWDG  180
RDAIVVCGDI  AIYDKGAARP  TGGAGTVAMW  IGPDAPIVFD  SVRASMEHA   YDFYKPDFTS  240
EYPYVDGHFS  LTCYVKALDQ  VYKSYSKKAI  SKGLVSDPAG  SDALNVLKYF  DYNVFHPTC   300
KLVTKSYGRL  LYNDFRANPQ  LFPEVDAELA  TRDYDESLTD  KNIEKTFVNV  AKPFHKERVA  360
QSLIVPTNTG  NMYTASVYAA  FASLLNYVGS  DDLQGKRVGL  FSYGSGLAAS  LYSCKIVGDV  420
QHIIKELDIT  NKLAKRITET  PKDYEAAIEL  RENAHLKKNF  KPQGSIEHLQ  SGVYYLTNID  480
DKFRRSYDVK  K                                                           491

SEQ ID NO: 25              moltype = AA  length = 398
FEATURE                    Location/Qualifiers
source                     1..398
```

```
                        mol_type = protein
                        organism = Saccharomyces cerevisiae
SEQUENCE: 25
MSQNVYIVST ARTPIGSFQG SLSSKTAVEL GAVALKGALA KVPELDASKD FDEIIFGNVL    60
SANLGQAPAR QVALAAGLSN HIVASTVNKV CASAMKAIIL GAQSIKCGNA DVVVAGGCES   120
MTNAPYYMPA ARAGAKFGQT VLVDGVERDG LNDAYDGLAM GVHAEKCARD WDITREQQDN   180
FAIESYQKSQ KSQKEGKFDN EIVPVTIKGF RGKPDTQVTK DEEPARLHVE KLRSARTVFQ   240
KENGTVTAAN ASPINDGAAA VILVSEKVLK EKNLKPLAII KGWGEAAHQP ADFTWAPSLA   300
VPKALKHAGI EDINSVDYFE FNEAFSVVGL VNTKILKLDP SKVNVYGGAV ALGHPLGCSG   360
ARVVVTLLSI LQQEGGKIGV AAICNGGGGA SSIVIEKI                           398

SEQ ID NO: 26           moltype = AA   length = 247
FEATURE                 Location/Qualifiers
source                  1..247
                        mol_type = protein
                        organism = Bacteroides sp.
SEQUENCE: 26
MSDDKKIGSY KFIAEPFHVD FNGRLTMGVL GNHLLNCAGF HASERGFGIA TLNEDNYTWV    60
LSRLAIDLEE MPYQYEEFTV QTWVENVYRL FTDRNFAIID KDGKKIGYAR SVWAMINLNT   120
RKPADLLTLH GGSIVDYVCD EPCPIEKPSR IKVATDQPCA KLTAKYSDID INGHVNSIRY   180
IEHILDLFPI DLYKSKRIQR FEMAYVAESY YGDELSFFEE EVSENEYHVE IKKNGSEVVC   240
RAKVKFV                                                             247

SEQ ID NO: 27           moltype = AA   length = 247
FEATURE                 Location/Qualifiers
source                  1..247
                        mol_type = protein
                        organism = Bacteroides thetaiotaomicron
SEQUENCE: 27
MSEENKIGTY QFVAEPFHVD FNGRLTMGVL GNHLLNCAGF HASDRGFGIA TLNEDNYTWV    60
LSRLAIELDE MPYQYEKFSV QTWVENVYRL FTDRNFAVID KDGKKIGYAR SVWAMINLNT   120
RKPADLLALH GGSIVDYICD EPCPIEKPSR IKVTSNQPVA TLTAKYSDID INGHVNSIRY   180
IEHILDLFPI ELYQTKRIRR FEMAYVAESY FGDELSFFCD EVSENEFHVE VKKNGSEVVC   240
RSKVIFE                                                             247

SEQ ID NO: 28           moltype = AA   length = 238
FEATURE                 Location/Qualifiers
source                  1..238
                        mol_type = protein
                        organism = Bryantella formatexigen
SEQUENCE: 28
MIYMAYQYRS RIRYSEIGED KKLTLPGLVN YFQDCSTFQS EALGIGLDTL GARQRAWLLA    60
SWKIVIDRLP RLGEEVVTET WPYGFKGFQG NRNFRMLDQE GHTLAAAASV WIYLNVESGH   120
PCRIDGDVLE AYELEEELPL GPFSRKIPVP EESTERDSFL VMRSHLDTNH HVNNGQYILM   180
AEEYLPEGFK VKQIRVEYRK AAVLHDTIVP FVCTEPQRCT VSLCGSDEKP FAVVEFSE     238

SEQ ID NO: 29           moltype = AA   length = 246
FEATURE                 Location/Qualifiers
source                  1..246
                        mol_type = protein
                        organism = Lactobacillus brevis
SEQUENCE: 29
MAANEFSETH RVVYYEADDT GQLTLAMLIN LFVLVSEDQN DALGLSTAFV QSHGVGWVVT    60
QYHLHIDELP RTGAQVTIKT RATAYNRYFA YREYWLLDDA GQVLAYGEGI WVTMSYATRK   120
ITTIPAEVMA PYHSEEQTRL PRLPRPDHFD EAVNQTLKPY TVRYFDIDGN GHVNNAHYFD   180
WMLDVLPATF LRAHHPTDVK IRFENEVQYG HQVTSELSQA AALTTQHMIK VGDLTAVKAT   240
IQWDNR                                                              246

SEQ ID NO: 30           moltype = AA   length = 261
FEATURE                 Location/Qualifiers
source                  1..261
                        mol_type = protein
                        organism = Lactobacillus plantarum
SEQUENCE: 30
MATLGANASL YSEQHRITYY ECDRTGRATL TTLIDIAVLA SEDQSDALGL TTEMVQSHGV    60
GWVVTQYAID ITRMPRQDEV VTIAVRGSAY NPYFAYREFW IRDADGQQLA YITSIWVMMS   120
QTTRRIVKIL PELVAPYQSE VVKRIPRLPR PISFEATDTT ITKPYHVRFF DIDPNRHVNN   180
AHYFDWLVDT LPATFLLQHD LVHVDVRYEN EVKYGQTVTA HANILPSEVA DQVTTSHLIE   240
VDDEKCCEVT IQWRTLPEPI Q                                             261

SEQ ID NO: 31           moltype = AA   length = 250
FEATURE                 Location/Qualifiers
source                  1..250
                        mol_type = protein
                        organism = Streptococcus dysgalactiae
SEQUENCE: 31
MGLSYREDIK LPFELCDVKS DIKFPLLLDY CLTVSGRQSA QLGRSNDYLL EQYGLIWIVT    60
DYEATIHRLP HFQETITIET KALSYNKFFC YRQFYIYDQE GGLLVDILAY FALLNPDTRK   120
VATIPEDLVA PFETDFVKKL HRVPKMPLLE QSIDRDYYVR YFDIDMNGHV NNSKYLDWMY   180
```

```
DVLGCEFLKT HQPLKMTLKY VKEVSPGGQI TSSYHLDQLT SYHQITSDGQ LNAQAMIEWR   240
AIKQTESEID                                                         250

SEQ ID NO: 32          moltype = AA  length = 620
FEATURE                Location/Qualifiers
source                 1..620
                       mol_type = protein
                       organism = Escherichia coli
SEQUENCE: 32
MSFDIAKYPT LALVDSTQEL RLLPKESLPK LCDELRRYLL DSVSRSSGHF ASGLGTVELT    60
VALHYVYNTP FDQLIWDVGH QAYPHKILTG RRDKIGTIRQ KGGLHPFPWR GESEYDVLSV   120
GHSSTSISAG IGIAVAAEKE GKNRRTVCVI GDGAITAGMA FEAMNHAGDI RPDMLVILND   180
NEMSISENVG ALNNHLAQLL SGKLYSSLRE GGKKVFSGVP PIKELLKRTE EHIKGMVVPG   240
TLFEELGFNY IGPVDGHDVL GLITTLKNMR DLKGPQFLHI MTKKGRGYEP AEKDPITFHA   300
VPKFDPSSGC LPKSSGGLPS YSKIFGDWLC ETAAKDNKLM AITPAMREGS GMVEFSRKFP   360
DRYFDVAIAE QHAVTFAAGL AIGGYKPIVA IYSTFLQRAY DQVLHDVAIQ KLPVLFAIDR   420
AGIVGADGQT HQGAFDLSYL RCIPEMVIMT PSDENECRQM LYTGYHYNDG PSAVRYPRGN   480
AVGVELTPLE KLPIGKGIVK RRGEKLAILN FGTLMPEAAK VAESLNATLV DMRFVKPLDE   540
ALILEMAASH EALVTVEENA IMGGAGSGVN EVLMAHRKPV PVLNIGLPDF FIPQGTQEEM   600
RAELGLDAAG MEAKIKAWLA                                              620

SEQ ID NO: 33          moltype = AA  length = 398
FEATURE                Location/Qualifiers
source                 1..398
                       mol_type = protein
                       organism = Escherichia coli
SEQUENCE: 33
MKQLTILGST GSIGCSTLDV VRHNPEHFRV VALVAGKNVT RMVEQCLEFS PRYAVMDDEA    60
SAKLLKTMLQ QQGSRTEVLS GQQAACDMAA LEDVDQVMAA IVGAAGLLPT LAAIRAGKTI   120
LLANKESLVT CGRLFMDAVK QSKAQLLPVD SEHNAIFQSL PQPIQHNLGY ADLEQNGVVS   180
ILLTGSGGPF RETPLRDLAT MTPDQACRHP NWSMGRKISV DSATMMNKGL EYIEARWLFN   240
ASASASQMEVLI HPQSVIHSMV RYQDGSVLAQ LGEPDMRTPI AHTMAWPNRV NSGVKPLDFC   300
KLSALTFAAP DYDRYPCLKL AMEAFEQGQA ATTALNAANE ITVAAFLAQQ IRFTDIAALN   360
LSVLEKMDMR EPQCVDDVLS VDANAREVAR KEVMRLAS                          398

SEQ ID NO: 34          moltype = AA  length = 236
FEATURE                Location/Qualifiers
source                 1..236
                       mol_type = protein
                       organism = Escherichia coli
SEQUENCE: 34
MATTHLDVCA VVPAAGFGRR MQTECPKQYL SIGNQTILEH SVHALLAHPR VKRVVIAISP    60
GDSRFAQLPL ANHPRITVVD GGEERADSVL AGLKAAGDAQ WVLVHDAARP CLHQDDLARL   120
LALSETSRTG GILAAPVRDT MKRAEPGKNA IAHTVDRNGL WHALTPQFFP RELLHDCLTR   180
ALNEGATITD EASALEYCGF HPQLVEGRAD NIKVTRPEDL ALAEFYLTRT IHQENT       236

SEQ ID NO: 35          moltype = AA  length = 283
FEATURE                Location/Qualifiers
source                 1..283
                       mol_type = protein
                       organism = Escherichia coli
SEQUENCE: 35
MRTQWPSPAK LNLFLYITGQ RADGYHTLQT LFQFLDYGDT ISIELRDDGD IRLLTPVEGV    60
EHEDNLIVRA ARLLMKTAAD SGRLPTGSGA NISIDKRLPM GGGLGGGSSN AATVLVALNH   120
LWQCGLSMDE LAEMGLTLGA DVPVFVRGHA AFAEGVGEIL TPVDPPEKWY LVAHPGVSIP   180
TPVIFKDPEL PRNTPKRSIE TLLKCEFSND CEVIARKRFR EVDAVLSWLL EYAPSRLTGT   240
GACVFAEFDT ESEARQVLEQ APEWLNGFVA KGANLSPLHR AML                    283

SEQ ID NO: 36          moltype = AA  length = 159
FEATURE                Location/Qualifiers
source                 1..159
                       mol_type = protein
                       organism = Escherichia coli
SEQUENCE: 36
MRIGHGFDVH AFGGEGPIII GGVRIPYEKG LLAHSDGDVV LHALTDALLG AAALGDIGKL    60
FPDTDPAFKG ADSRELLREA WRRIQAKGYA LGNVDVTIIA QAPRMLPHIP QMRVFIAEDL   120
GCHMDDVNVK ATTTEKLGFT GRGEGIACEA VALLIKATK                         159

SEQ ID NO: 37          moltype = AA  length = 372
FEATURE                Location/Qualifiers
source                 1..372
                       mol_type = protein
                       organism = Escherichia coli
SEQUENCE: 37
MHNQAPIQRR KSTRIYVGNV PIGDGAPIAV QSMTNTRTTD VEATVNQIKA LERVGADIVR    60
VSVPTMDAAE AFKLIKQQVN VPLVADIHFD YRIALKVAEY GVDCLRINPG NIGNEERIRM   120
VVDCARDKNI PIRIGVNAGS LEKDLQEKYG EPTPQALLES AMRHVDHLDR LNFDQFKVSV   180
KASDVFLAVE SYRLLAKQID QPLHLGITEA GGARSGAVKS AIGLGLLLSE GIGDTLRVSL   240
AADPVEEIKV GFDILKSLRI RSRGINFIAC PTCSRQEFDV IGTVNALEQR LEDIITPMDV   300
```

-continued

```
SIIGCVVNGP GEALVSTLGV TGGNKKSGLY EDGVRKDRLD NNDMIDQLEA RIRAKASQLD  360
EARRIDVQQV EK                                                      372

SEQ ID NO: 38           moltype = AA  length = 316
FEATURE                 Location/Qualifiers
source                  1..316
                        mol_type = protein
                        organism = Escherichia coli
SEQUENCE: 38
MQILLANPRG FCAGVDRAIS IVENALAIYG APIYVRHEVV HNRYVVDSLR ERGAIFIEQI   60
SEVPDGAILI FSAHGVSQAV RNEAKSRDLT VFDATCPLVT KVHMEVARAS RRGEESILIG  120
HAGHPEVEGT MGQYSNPEGG MYLVESPDDV WKLTVKNEEK LSFMTQTTLS VDDTSDVIDA  180
LRKRFPKIVG PRKDDICYAT TNRQEAVRAL AEQAEVVLVV GSKNSSNSNR LAELAQRMGK  240
RAFLIDDATD IQEEWVKEAK CVGVTAGASA PDILVQNVVA RLQQLGGGEA IPLEGREENI  300
VFEVPKELRV DIREVD                                                  316

SEQ ID NO: 39           moltype = AA  length = 182
FEATURE                 Location/Qualifiers
source                  1..182
                        mol_type = protein
                        organism = Escherichia coli
SEQUENCE: 39
MQTEHVILLN AQGVPTGTLE KYAAHTADTR LHLAFSSWLF NAKGQLLVTR RALSKKAWPG   60
VWTNSVCGHP QLGESNEDAV IRRCRYELGV EITPPESIYP DFRYRATDPS GIVENEVCPV  120
FAARTTSALQ INDDEVMDYQ WCDLADVLHG IDATPWAFSP WMVMQATNRE ARKRLSAFTQ  180
LK                                                                 182

SEQ ID NO: 40           moltype = AA  length = 299
FEATURE                 Location/Qualifiers
source                  1..299
                        mol_type = protein
                        organism = Escherichia coli
SEQUENCE: 40
MDFPQQLEAC VKQANQALSR FIAPLPFQNT PVVETMQYGA LLGGKRLRPF LVYATGHMFG   60
VSTNTLDAPA AVECIHAYS LIHDDLPAMD DDDLRRGLPT CHVKFGEANA ILAGDALQTL   120
AFSILSDADM PEVSDRDRIS MISELASASG IAGMCGGQAL DLDAEGKHVP LDALERIHRH  180
KTGALIRAAV RLGALSAGDK GRRALPVLDK YAESIGLAFQ VQDDILDVVG DTATLGKRQG  240
ADQQLGKSTY PALLGLEQAR KKARDLIDDA RQSLKQLAEQ SLDTSALEAL ADYIIQRNK   299

SEQ ID NO: 41           moltype = DNA  length = 1083
FEATURE                 Location/Qualifiers
source                  1..1083
                        mol_type = genomic DNA
                        organism = Saccharomyces cerevisiae
SEQUENCE: 41
atgaagctac taaccttccc aggtcaaggg acctccatct ccatttcgat attaaaagcg   60
ataataagaa acaaatcaag agaattccaa acaatactga gtcagaacgg caaggaatca  120
aatgatctat tgcagtacat cttccagaac ccttccagcc ccggaagcat tgcagtctgc  180
tccaaccttt tctatcaatt gtaccagata ctctcgaatc cttctgatcc tcaagatcaa  240
gcaccaaaaa atatgactaa gatcgattcc cccgacaaga agacaatga acaatgttac  300
cttttgggtc actcgctagg cgagttaaca tgtctgagtg ttaattcact gtttttcgtta  360
aaggatcttt ttgatattgc taattttaga aataagttaa tggtaacatc tactgaaaag  420
tacttagtag cccacaatat caacagatcc aacaaatttg aaatgtgggc actctcttct  480
ccgagggcca cagatttacc gcaagaagtg caaaaactac taaattcccc taatttatta  540
tcatcttcac aaaaatacca ttctgtagca aatgcaaatt cagtaaagca atgtgtagtc  600
accggtctgg ttgatgattt agagtcctta gaacagaat tgaacttaag gttcccgcgt  660
ttaagaatta cagaattaac taacccatac aacatcccct tccataatag cactgtgttg  720
aggcccgttc aggaaccact ctatgactac atttgggata tattaaagaa aaacggaact  780
cacacgttga tggagttgaa ccatccaata atagctaact tagatggtaa tatatcttac  840
tatattcatc atgcccctaga tagattcgtt aagtgttcaa gcaggactgt gcaattcacc  900
atgtgttatg ataccataaa ctctggaacc ccagtggaaa ttgataagag tatttgctttt  960
ggcccgggca atgtgattta taaccttatt cggagaaatt gtccccaagt ggacactata 1020
gaatacacct ctttagcaac tatagacgct atcacaagg cggcagagga gaacaaagat 1080
tga                                                              1083

SEQ ID NO: 42           moltype = AA  length = 360
FEATURE                 Location/Qualifiers
source                  1..360
                        mol_type = protein
                        organism = Saccharomyces cerevisiae
SEQUENCE: 42
MKLLTFPGQG TSISISILKA IIRNKSREFQ TILSQNGKES NDLLQYIFQN PSSPGSIAVC   60
SNLFYQLYQI LSNPSDPQDQ APKNMTKIDS PDKKDNEQCY LLGHSLGELT CLSVNSLFSL  120
KDLFDIANFR NKLMVTSTEK YLVAHNINRS NKFEMWALSS PRATDLPQEV QKLLNSPNLL  180
SSSQNTISVA NANSVKQCVV TGLVDDLESL RTELNLRFPR LRITELTNPY NIPFHNSTVL  240
RPVQEPLYDY IWDILKKNGT HTLMELNHPI IANLDGNISY YIHHALDRFV KCSSRTVQFT  300
MCYDTINSGT PVEIDKSICF GPGNVIYNLI RRNCPQVDTI EYTSLATIDA YHKAAEENKD  360

SEQ ID NO: 43           moltype = DNA  length = 1191
```

| FEATURE | Location/Qualifiers |
|---|---|
| misc_feature | 1..1191 |
| | note = Artificial beta-ketothiolase (BktB) nucleotide sequence |
| source | 1..1191 |
| | mol_type = other DNA |
| | organism = synthetic construct |

SEQUENCE: 43

```
atgactagag aagttgtcgt cgtttccggt gtccgtaccg ctatcggtac tttcggtggt   60
tccttaaagg atgttgctcc tgctgaattg ggtgctttag ttgttagaga agcttttggc  120
agagcccaag tctccggtga cgacgttggt cacgtcgttt tcggtaacgt catccaaact  180
gaaccacgtg acatgtactt gggtagagtc gccgctgtta acggtggtgt caccatcaac  240
gctcctgcct taactgttaa cagattatgt ggttccggtt tacaagctat tgtctctgcc  300
gcccaaacta tcttgttggg tgatactgac gttgctattg gtggtgctga atcgatg     360
tctagagctc catacttggc tccagctgcc cgttggggtg ctagaatggg tgacgccggt  420
ttggtcgata tgatgttggg tgccttgcat gatccttcc acagaatcca catgggtgtt  480
accgctgaaa acgttgctaa ggaatacgat atctctagag ctcaacaaga tgaagccgct  540
ttagaatctc acagacgtgc ctccgccgct attaaggctg gttacttcaa ggaccaaatt  600
gttccagttg tctctaaggg tcgtaaaggt gatgttacct tgatactga cgaacacgtt   660
agacacgacg ccactattga cgatatgact aaattaagac cagtctttgt taaggagaat  720
ggtaccgtta ctgctggtaa cgcttctggt ttgaacgatg ccgccgctgc cgttgttatg  780
atggaaagag ctgaagccga aagacgtggt ttaaagccat tggccagatt agtctcctac  840
ggtcacgctg tgtcgaccc aaaggcatg ggtatcggtc cagttcctgc tactaagatt   900
gctttagaaa gagctggttt gcaagtttct gacttggacg tcatcgaagc caacgaagcc  960
ttcgctgctc aagcttgtgc tgtcaccaag gctttgggtt tggatccagc taaagttaac 1020
cctaatggtt ctggtatttc cttgggtcac ccaatcggtg ctaccggtgc tttaatcact 1080
gttaaagcct tacacgaatt gaacagagtt caaggtagat acgctttggt cactatgtgc 1140
atcggtggtg gtcaaggtat cgctgctatc ttcgaaagaa tcggatccta a          1191
```

| SEQ ID NO: 44 | moltype = AA  length = 396 |
|---|---|
| FEATURE | Location/Qualifiers |
| REGION | 1..396 |
| | note = Engineered beta-ketothiolase (BktB) |
| source | 1..396 |
| | mol_type = protein |
| | organism = synthetic construct |

SEQUENCE: 44

```
MTREVVVVSG VRTAIGTFGG SLKDVAPAEL GALVVREALA RAQVSGDDVG HVVFGNVIQT   60
EPRDMYLGRV AAVNGGVTIN APALTVNRLC GSGLQAIVSA AQTILLGDTD VAIGGGAESM  120
SRAPYLAPAA RWGARMGDAG LVDMMLGALH DPFHRIHMGV TAENVAKEYD ISRAQQDEAA  180
LESHRRASAS IKAGYFKDQI VPVVSKGRKG DVTFDTDEHV RHDATIDDMT KLRPVFVKEN  240
GTVTAGNASG LNDAAAAVVM MERAEAERRG LKPLARLVSY GHAGVDPKAM GIGPVPATKI  300
ALERAGLQVS DLDVIEANEA FAAQACAVTK ALGLDPAKVN PNGSGISLGH PIGATGALIT  360
VKALHELNRV QGRYALVTMC IGGGQGIAAI FERIGS                           396
```

| SEQ ID NO: 45 | moltype = DNA  length = 858 |
|---|---|
| FEATURE | Location/Qualifiers |
| misc_feature | 1..858 |
| | note = Artificial PaaH1: 3-hydroxyacyl-CoA dehydrogenase nucleotide sequence |
| source | 1..858 |
| | mol_type = other DNA |
| | organism = synthetic construct |

SEQUENCE: 45

```
atgtccatca gaactgtcgg tattgttggt gctggtacta tgggtaacgg tattgctcaa   60
gcctgtgctg tcgtcggttt gaacgtcgtc atggtcgaca tttctgacgc tgctgttcaa  120
aagggtgttg ctactgtcgc ttcctctttg acagattaa ttaagaagga aaagttgacc   180
gaagccgaca aggcctctgc cttggccaga attaagggtt ccacttctta tgacgacttg  240
aaagctaccg acattgttat cgaagctgct actgaaaact acgatttgaa agttaagatc  300
ttgaagcaaa ttgatggtat cgtcggtgag aacgtcatta ttgcttctaa cacttcctcc  360
atttctatca ctaaattagc cgccgtcacc tctagagccg acagatttat cggtatgcac  420
ttctttaatc cagttccagt catggctttg gtcgaattaa ttagaggttt gcaaacctcc  480
gacaccaccc acgccgccgt tgaagctttg tctaagcaat gggtaagta cccaatcacc  540
gttaaaaatt cccaggtttt cgttgtcaac cgtattttgt gccaatgat caatgaagct  600
ttctgtgtct ggggtgaggg tttggcctcc ccagaagaaa tcgatgaagg tatgaagtta  660
ggttgtaacc cccctattgg tccttttagcc ttggccgaca tgatcggttt agacactatg  720
ttggccgtta tggaagtctt gtacactgaa ttcgctgacc aaagtacag accagctatg  780
ttaatgagag aaatggttgc tgccggttat ttgggtagaa agactggtcg tggtgtttat  840
gtctactcta aagggatc                                                858
```

| SEQ ID NO: 46 | moltype = AA  length = 286 |
|---|---|
| FEATURE | Location/Qualifiers |
| REGION | 1..286 |
| | note = Engineered PaaH1: 3-hydroxyacyl-CoA dehydrogenase |
| source | 1..286 |
| | mol_type = protein |
| | organism = synthetic construct |

SEQUENCE: 46

```
MSIRTVGIVG AGTMGNGIAQ ACAVVGLNVV MVDISDAAVQ KGVATVASSL DRLIKKEKLT   60
```

```
EADKASALAR IKGSTSYDDL KATDIVIEAA TENYDLKVKI LKQIDGIVGE NVIIASNTSS   120
ISITKLAAVT SRADRFIGMH FFNPVPVMAL VELIRGLQTS DTTHAAVEAL SKQLGKYPIT   180
VKNSPGFVVN RILCPMINEA FCVLGEGLAS PEEIDEGMKL GCNHPIGPLA LADMIGLDTM   240
LAVMEVLYTE FADPKYRPAM LMREMVAAGY LGRKTGRGVY VYSKGI                 286

SEQ ID NO: 47             moltype = DNA  length = 792
FEATURE                   Location/Qualifiers
misc_feature              1..792
                          note = Artificial crotonase (Crt) nucleotide sequence
source                    1..792
                          mol_type = other DNA
                          organism = synthetic construct
SEQUENCE: 47
atggaattga acaacgttat tttggaaaag gaaggtaagg tcgctgtcgt tactatcaac   60
agaccaaagg ctttaaacgc tttgaactct gacaccttga agaaatggga ttatgttatc   120
ggtgaaatcg aaaatgactc tgaagttttg gccgttatct tgactggtgc tggtgaaaaa   180
tctttcgttg ctggtgctga catttctgaa atgaaggaga tgaataccat gaaggtagaa   240
aagttcggta tcttgggtaa caaggttttt agaagattgg aattgttgga aaaaccagtc   300
atcgctgctg ttaacggttt cgctttaggt ggtggttgtg aaatcgctat gtcctgtgac   360
attcgtatcg cctcctccaa tgctagattc ggtcaaccag aagttggttt aggtattact   420
ccaggtttcg gtggtaccca agattgtctt agattggtcg gtatgggtat ggctaagcaa   480
ttaattttca ctgctcaaaa cattaaggct gatgaagcct tacgtattgg tttggtcaac   540
aaggtcgttg aaccatctga attgatgaat accgctaagg aaattgctaa caaaattgtt   600
tctaatgccc cagttgctgt caagttgtcc aagcaagcta ttaacagagg tatgcaatgt   660
gatattgaca ctgctttggc tttcgaatcc gaagcttttg gtgaatgttt ttctaccgaa   720
gatcaaaagg atgctatgac cgctttcatc gagaagagaa agatcgaagg tttcaaaaac   780
agaggatcct aa                                                      792

SEQ ID NO: 48             moltype = AA  length = 263
FEATURE                   Location/Qualifiers
REGION                    1..263
                          note = Engineered crotonase (Crt)
source                    1..263
                          mol_type = protein
                          organism = synthetic construct
SEQUENCE: 48
MELNNVILEK EGKVAVVTIN RPKALNALNS DTLKEMDYVI GEIENDSEVL AVILTGAGEK   60
SFVAGADISE MKEMNTIEGR KFGILGNKVF RRLELLEKPV IAAVNGFALG GGCEIAMSCD   120
IRIASSNARF GQPEVGLGIT PGFGGTQRLS RLVGMGMAKQ LIFTAQNIKA DEALRIGLVN   180
KVVEPSELMN TAKEIANKIV SNAPVAVKLS KQAINRGMQC DIDTALAFES EAFGECFSTE   240
DQKDAMTAFI EKRKIEGFKN RGS                                          263

SEQ ID NO: 49             moltype = DNA  length = 1200
FEATURE                   Location/Qualifiers
misc_feature              1..1200
                          note = Artificial Ter: trans-2-enoyl-CoA reductase
                           nucleotide sequence
source                    1..1200
                          mol_type = other DNA
                          organism = synthetic construct
SEQUENCE: 49
atgattgtca aaccaatggt tcgtaacaac atttgtttaa atgcccaccc acaaggttgt   60
aagaagggtg ttgaagatca aatcgaatac actaaaaaga gaattaccgc tgaagttaaa   120
gctggtgcta aggccccaaa gaacgttttg gttttgggtt gttccaacgg ttacggtttg   180
gcctccagaa ttactgctgc ttttggttac ggtgccgcta ccatcggtgt ctcttttcgaa   240
aaggccggtt ccgaaactaa gtacggtact ccaggttggt acaataactt ggctttcgat   300
gaagctgcta agagagaagg tttgtattcc gttactattg acggtgatgc ctttttctgac   360
gaaatcaaag ctcaagtcat cgaagaagcc aaaaagaaag gtatcaagtt cgatttgatt   420
gtctactctt tagcctctcc tgttagaact gatccagata tgggtattat gcacaaatcc   480
gttttgaagc cattcggtaa gaccttcact ggtaaaactg tcgatccttt cactggtgaa   540
ttaaaggaaa tctctgctga acctgccaac gacgaagaag ctgctgccac tgttaaggtt   600
atgggtggta agactgggaa agatggatc agcaattat ctaaggaagg tttgttggaa   660
gaaggttgta tcaccttggc ttactcttac atcggtccag aagctaccca agctttgtac   720
agaaagggta ccattggtaa ggctaaagaa cacttggagg ctactgctca tagattgaac   780
aaggaaaatc catccatcag agcctttgtt tccgtcaata aaggttttggt cactagagcc   840
tctgccgtca ttccagttat cccctttatac ttggcttctt tgtttaaagt catgaaggaa   900
aagggtaacc atgaaggttg tatcgaacaa atcactcgtt gtacgctga acgtttatac   960
agaaaggacg gtaccacccc tgtccgtgaa gaaaacagaa tcagaatcac cgattgggaat   1020
tggaagaag atgttcaaaa agccgttttc gccttgatgg aaaaggtcac tggtgaaaat   1080
gccgaatcct tgactgactt agctggttac agacatgact tttagcttc taatggtttc   1140
gatgttgaag gtattaacta tgaggctgaa gtcgaaagat ttgacagaat cggatcctaa   1200

SEQ ID NO: 50             moltype = AA  length = 399
FEATURE                   Location/Qualifiers
REGION                    1..399
                          note = Engineered Ter: trans-2-enoyl-CoA reductase
source                    1..399
                          mol_type = protein
                          organism = synthetic construct
```

```
SEQUENCE: 50
MIVKPMVRNN ICLNAHPQGC KKGVEDQIEY TKKRITAEVK AGAKAPKNVL VLGCSNGYGL    60
ASRITAAFGY GAATIGVSFE KAGSETKYGT PGWYNNLAFD EAAKREGLYS VTIDGDAFSD   120
EIKAQVIEEA KKKGIKFDLI VYSLASPVRT DPDTGIMHKS VLKPFGKTFT GKTVDPFTGE   180
LKEISAEPAN DEEAAATVKV MGGEDWERWI KQLSKEGLLE EGCITLAYSY IGPEATQALY   240
RKGTIGKAKE HLEATAHRLN KENPSIRAFV SVNKGLVTRA SAVIPVIPLY LASLFKVMKE   300
KGNHEGCIEQ ITRLYAERLY RKDGTIPVDE ENRIRIDDWE LEEDVQKAVS ALMEKVTGEN   360
AESLTDLAGY RHDFLASNGF DVEGINYEAE VERFDRIGS                         399

SEQ ID NO: 51         moltype = DNA   length = 812
FEATURE               Location/Qualifiers
misc_feature          1..812
                      note = Truncated 3-hydroxy-3-methyl-glutaryl-CoA reductase
                         (tHMG1)
source                1..812
                      mol_type = other DNA
                      organism = synthetic construct
SEQUENCE: 51
atggcgcgtg accaattggt gaaaactgaa gtcaccaaga agtctttttac tgctcctgta    60
caaaaggctt ctacaccagt tttaaccaat aaaacagtca tttctggatc gaaagtcaaa   120
agtttatcat ctgcgcaatc gagctcatca ggaccttcat catctagtga ggaagatgat   180
tcccgcgata ttgaaagctt ggataagaaa atcgtcctt tagaagaatt agaagcatta    240
ttaagtagtg gaaatacaaa acaattgaag aacaaagagg tcgctgcctt ggttattcac   300
ggtaagttac ctttgtacgc tttggagaaa aaattaggtg atactacgag agcggttgcg   360
gtacgtagga aggctctttc aattttggca gaagctcctg tattagcatc tgatcgttta   420
ccatataaaa attatgacta cgaccgcgta tttggcgtt gttgtgaaaa tgttataggt    480
tacatgcctt tgcccgttgg tgttataggc cccttggtta tcgatggtac atcttatcat   540
ataccaatgg caactacaga gggttgtttg gtagcttctg ccatgcgtgg ctgtaaggca   600
atcaatgctg gcggtggtgc aacaactgtt ttaactaagg atggtatgac aagaggccca   660
gtagtccgtt tcccaacttt gaaaagatct ggtgcctgta agatatggtt agactcagaa   720
gagggacaaa acgcaattaa aaaagctttt aactctacat caagatttgc acgtctgcaa   780
catattcaaa cttgtctagc aggagatttg tt                                812

SEQ ID NO: 52         moltype = AA   length = 270
FEATURE               Location/Qualifiers
REGION                1..270
                      note = Truncated 3-hydroxy-3-methyl-glutaryl-CoA reductase
                         (tHMG1)
source                1..270
                      mol_type = protein
                      organism = synthetic construct
SEQUENCE: 52
MARDQLVKTE VTKKSFTAPV QKASTPVLTN KTVISGSKVK SLSSAQSSSS GPSSSSEEDD    60
SRDIESLDKK IRPLEELEAL LSSGNTKQLK NKEVAALVIH GKLPLYALEK KLGDTTRAVA   120
VRRKALSILA EAPVLASDRL PYKNYDYDRV FGACCENVIG YMPLPVGVIG PLVIDGTSYH   180
IPMATTEGCL VASAMRGCKA INAGGGATTV LTKDGMTRGP VVRFPTLKRS GACKIWLDSE   240
EGQNAIKKAF NSTSRFARLQ HIQTCLAGDL                                   270

SEQ ID NO: 53         moltype = DNA   length = 2412
FEATURE               Location/Qualifiers
source                1..2412
                      mol_type = genomic DNA
                      organism = Enterococcus sp.
SEQUENCE: 53
atgaagactg tcgttatcat agatgccttg agaacaccaa tcggtaaata caaaggttca    60
ttatcccaag tttccgccgt tgacttaggt actcatgtta ctacacaatt gttgaagaga   120
cactccacaa tcagtgaaga aatcgatcaa gtcatattcg gtaacgtatt gcaagctggt   180
aatggtcaaa acccagccag acaaatagct atcaattctg gtttatcaca tgaaattcct   240
gctatgacag taaacgaagt ttgtggttca ggcatgaaag cagtcattt ggccaagcaa    300
ttgatacaat taggtgaagc agaagtttta atcgccggtg gtatagaaaa catgagtcaa   360
gctccaaat tgcaaagatt caattacgaa actgaatctt acgatgcacc tttctcttcg    420
atgatgtatg atggtttgac tgacgctttt tctggtcaag caatgggttt aacagctgaa   480
aatgtcgcag aaaagtacca tgtaaccaga gaagaacaag atcaatttt cgttcacagt    540
caattaaaag ctgcacaagc acaagccgaa ggtatttcg ccgacgaaat agctcttcg    600
gaagtttctg gtacattagt cgaaaaggat gaaggtatta gacctaactc cagtgttgaa    660
aaattgggta ctttgaagac agtattcaag gaagacggta cagttaccgc tggtaatgcc   720
tctaccatta cgatggtgc tagtgcattg attatagctt tcaagaata tgccgaagct    780
catggttgc catacttagc tatcattaga gatagtgtag aagttggtat tgacccagca   840
tacatgggta tctctcctat aaaagcaatc caaaagttgt tagccagaaa ccaattgacc   900
actgaagaaa ttgatttgta cgaaattaac gaagcatttg ccgctacatc aatcgttgtc   960
caaagagaat tggcattgcc agaagaaaag gttaacatct atggtggtgg tatctccttg  1020
ggtcacgcta taggtgcaac cggtgccaga ttgttgactt ccttaagtta ccaattgaac  1080
caaaaggaaa agaaatacgg tgttgcttct ttatgcattg gtggtggttt gggttagca   1140
atgttgttag aaagaccaca acaaaagaaa aattccaaat gtccccaag                            1200
gaaagattgg cctcattgtt aaatgaaggt caaatttccg cagatactaa gaaagaattt  1260
gaaaacaccg ctttatcttc acaaatcgca accccatatg acgaaaacca aatctctgaa  1320
acagaagttc caatgggtgt cggtttgcac ttaactgtcg atgaaacaga ctatttggta  1380
ccaatggcta ccgaagaacc tagtgttatc gcagcctat ctaatggtgc taagatagca   1440
caaggtttta agactgttaa ccaacaagga ttgatgagag tcaaatcgt attctacgat  1500
```

-continued

```
gttgctgacc cagaatcatt aatcgataag ttgcaagtaa gagaagccga agttttcaa      1560
caagctgaat tgtcttaccc ttcaatagtt aagagaggtg gtggtttgag agatttgcaa      1620
tacagaactt ttgacgaatc cttcgtcagt gtagatttct tagttgatgt caaggacgcc      1680
atgggtgcta atattgttaa cgcaatgttg gaaggtgtcg ccgaattgtt tagagaatgg      1740
ttcgctgaac aaaagatttt gttttctatc ttgtcaaact acgctacaga atctgtagtt      1800
accatgaaaa ctgcaattcc agtttccaga ttgagtaagg ttctaacgg tagagaaatc      1860
gctgaaaaga ttgttttggc atcaagatat gcctccttag accttacag agctgttact      1920
cataataagg gtaatgaa cggtatcgaa gctgtcgtat tagcaaccgg taatgatact      1980
agagcagtat ctgcctcatg tcacgcattc gccgttaagg aaggtagata ccaaggtttg      2040
acatcatgga ccttggatgg tgaacaatta attggtgaaa tatccgttcc attggcttta      2100
gcaactgttg gtggtgctac aaaagtcttg cctaagagtc aagctgcagc cgatttgtta      2160
gccgtcactg acgctaagga attgtctaga gttgtcgctg cagtaggttt agctcaaaat      2220
ttggccgctt aagagcatt ggtttcgaaa ggtattcaaa aaggtcatat ggctttgcaa      2280
gcaagatcct tagccatgac agttggtgct accggtaaag aagtcgaagc cgtagctcaa      2340
caattaaaaa gacaaaagac aatgaaccaa gacagagcaa tggctatatt aaacgatttg      2400
agaaagcaat aa                                                          2412

SEQ ID NO: 54           moltype = AA  length = 803
FEATURE                 Location/Qualifiers
source                  1..803
                        mol_type = protein
                        organism = Enterococcus sp.
SEQUENCE: 54
MKTVVIIDAL RTPIGKYKGS LSQVSAVDLG THVTTQLLKR HSTISEEIDQ VIFGNVLQAG       60
NGQNPARQIA INSGLSHEIP AMTVNEVCGS GMKAVILAKQ LIQLGEAEVL IAGGIENMSQ       120
APKLQRFNYE TESYDAPFSS MMYDGLTDAF SGQAMGLTAE NVAEKYHVTR EEQDQFSVHS       180
QLKAAQAQAE GIFADEIAPL EVSGTLVEKD EGIRPNSSVE KLGTLKTVFK EDGTVTAGNA       240
STINDGASAL IIASQEYAEA HGLPYLAIIR DSVEVGIDPA YMGISPIKAI QKLLARNQLT       300
TEEIDLYEIN EAFAATSIVV QRELALPEEK VNIYGGGISL GHAIGATGAR LLTSLSYQLN       360
QKEKKYGVAS LCIGGGLGLA MLLERPQQKK NSRFYQMSPE ERLASLLNEG QISADTKKEF       420
ENTALSSQIA NHMIENQISE TEVPMGVGLH LTVDETDYLV PMATEEPSVI AALSNGAKIA       480
QGFKTVNQQR LMRGQIVFYD VADPESLIDK LQVREAEVPQ QAELSYPSIV KRGGGLRDLQ       540
YRTFDESFVS VDFLVDVKDA MGANIVNAML EGVAELFREW FAEQKILFSI LSNYATESVV       600
TMKTAIPVSR LSKGSNGREI AEKIVLASRY ASLDPYRAVT HNKGIMNGIE AVVLATGNDT       660
RAVSASCHAF AVKEGRYQGL TSWTLDGEQL IGEISVPLAL ATVGGATKVL PKSQAAADLL       720
AVTDAKELSR VVAAVGLAQN LAALRALVSE GIQKGHMALQ ARSLAMTVGA TGKEVEAVAQ       780
QLKRQKTMNQ DRAMAILNDL RKQ                                              803

SEQ ID NO: 55           moltype = DNA  length = 1152
FEATURE                 Location/Qualifiers
source                  1..1152
                        mol_type = genomic DNA
                        organism = Enterococcus sp.
SEQUENCE: 55
atgacaattg ggattgataa aattagtttt tttgtgcccc cttattatat tgatatgacg       60
gcactggctg aagccagaaa tgtagaccct ggaaaatttc atattggtat tgggcaagac      120
caaatggcgg tgaacccaat cagccaagat atttgtgcaa ttgcagcaaa tgccgcagaa      180
gcgatcttga ccaaagaaga taagagggcc attgatatgg tgattgtcgg gactgagtcc      240
agtatcgatg agtcaaaagc ggccgcagtt gtcttacatc gtttaatggg gattcaacct      300
ttcgctcgct ctttcgaaat caaggaagct tgttacggag caacagcagg cttacagtta      360
gctaagaatc acgtagcctt acatccagat aaaaaagtct tggtcgtagc gcagatatt      420
gcaaaatatg gcttaaattc tggcggtgag cctacacaag gagctggggc ggttgcaatg      480
ttagttgcta gtgaaccgcg cattttggct ttaaaagagg ataatgtgat gctgacgcaa      540
gatatctatg acttttggcg tccaacaggc cacccgtatc ctatggtcga tggtcctttg      600
tcaaacgaaa cctacatcca atcttttgcc caagtctggg atgaacataa aaaacgaacc      660
ggtcttgatt ttgcagatta tgatgcttta gcgttccata ttccttacac aaaaatgggc      720
aaaaaagcct tattagcaaa aatctccgac caaactgaag cagaacagga acgaatttta      780
gcccgttatg aagaaagtat cgtctatagt cgtcgcgtag gaaacttgta tacgggttca      840
ctttatctgg gactcatttc cctttaagaa aatgcaacga cttaaccgc aggcaatcaa      900
attggtttat tcagttatgg ttctggtgct gtcgctgaat ttttcactgg tgaattagta      960
gctggttatc aaaatcattt acaaaaagaa actcatttag cactgctgga taatcggaca     1020
gaactttcta tcgctgaata tgaagccatg tttgcagaaa ctttagacac agacattgat     1080
caaacgttag aagatgaatt aaaatatagt atttctgcta ttaataatac cgttcgttct     1140
tatcgaaact aa                                                          1152

SEQ ID NO: 56           moltype = AA  length = 383
FEATURE                 Location/Qualifiers
source                  1..383
                        mol_type = protein
                        organism = Enterococcus sp.
SEQUENCE: 56
MTIGIDKISF FVPPYYIDMT ALAEARNVDP GKFHIGIGQD QMAVNPISQD IVTFAANAAE        60
AILTKEDKEA IDMVIVGTES SIDESKAAAV VLHRLMGIQP FARSFEIKEA CYGATAGLQL       120
AKNHVALHPD KKVLVVAADI AKYGLNSGGE PTQGAGAVAM LVASEPRILA LKEDNVMLTQ       180
DIYDFWRPTG HPYPMVDGPL SNETYIQSFA QVWDEHKKRT GLDFADYDAL AFHIPYTKMG       240
KKALLAKISD QTEAEQERIL ARYEESIVYS RRVGNLYTGS LYLGLISLLE NATTLTAGNQ       300
IGLFSYGSGA VAEFFTGELV AGYQNHLQKE THLALLDNRT ELSIAEYEAM FAETLDTDID       360
QTLEDELKYS ISAINNTVRS YRN                                              383
```

```
SEQ ID NO: 57              moltype = DNA  length = 867
FEATURE                    Location/Qualifiers
source                     1..867
                           mol_type = genomic DNA
                           organism = Saccharomyces sp.
SEQUENCE: 57
atgactgccg acaacaatag tatgcccat ggtgcagtat ctagttacgc caaattagtg    60
caaaaccaaa cacctgaaga cattttggaa gagtttcctg aaattattcc attacaacaa  120
agacctaata cccgatctag tgagacgtca aatgacgaaa gcggagaaac atgttttct   180
ggtcatgatg aggagcaaat taagttaatg aatgaaaatt gtattgtttt ggattgggac  240
gataatgcta ttggtgccgg taccaagaaa gtttgtcatt aatgaaaaa tattgaaaag   300
ggtttactac atcgtgcatt ctccgtcttt attttcaatg aacaaggtga attacttta   360
caacaaagag ccactgaaaa aataactttc cctgatcttt ggacaacac atgctgctct   420
catccactat gtattgatga cgaattaggt ttgaaggta agctagacga taagattaag   480
ggcgctatta ctgcggcggt gagaaaacta gatcatgaat taggtattcc agaagatgaa  540
actaagacaa ggggtaagtt tcactttta aacagaatcc attacatggc accaagcaat   600
gaaccatggg gtgaacatga aattgattac atccattttt ataagatcaa cgctaaagaa  660
aacttgactg tcaacccaaa cgtcaatgaa gttagaact tcaaatggat ttcaccaaat   720
gatttgaaaa ctatgtttgc tgacccaagt tacaagttta cgccttggtt taagattatt  780
tgcgagaatt acttattcaa ctggtgggag caattagatg accttctga agtggaaat    840
gacaggcaaa ttcatagaat gctataa                                      867

SEQ ID NO: 58              moltype = AA  length = 288
FEATURE                    Location/Qualifiers
source                     1..288
                           mol_type = protein
                           organism = Saccharomyces sp.
SEQUENCE: 58
MTADNNSMPH GAVSSYAKLV QNQTPEDILE EFPEIIPLQQ RPNTRSSETS NDESGETCFS   60
GHDEEQIKLM NENCIVLDWD DNAIGAGTKK VCHLMENIEK GLLHRAFSVF IFNEQGELLL  120
QQRATEKITF PDLWTNTCCS HPLCIDDELG LKGKLDDKIK GAITAAVRKL DHELGIPEDE  180
TKTRGKFHFL NRIHYMAPSN EPWGEHEIDY ILFYKINAKE NLTVNPNVNE VRDFKWVSPN  240
DLKTMFADPS YKFTPWFKII CENYLFNWWE QLDDLSEVEN DRQIHRML               288

SEQ ID NO: 59              moltype = DNA  length = 1059
FEATURE                    Location/Qualifiers
misc_feature               1..1059
                           note = Mutant farnesyl pyrophosphate synthase (Erg20mut,
                           F96W, N127W)
source                     1..1059
                           mol_type = other DNA
                           organism = synthetic construct
SEQUENCE: 59
atggcttcag aaaaagaaat taggagagag agattcttga cgttttccc taaattagta    60
gaggaattga acgcatcgct tttggcttac ggtatgccta aggaagcatg tgactggtat   120
gcccactcat tgaactacaa cactccaggc ggtaagctaa atagaggttt gtccgttgtg  180
gacacgtatg ctattctctc caacaagacc gttgaacaat tggggcaaga agaatacgaa  240
aaggttgcca ttctaggttg gtgcattgag ttgttgcagg cttactggtt ggtcgccgat  300
gatatgatgg acaagtccat taccagaaga ggccaaccat gttggtacaa ggttcctgaa  360
gttgggaaa ttgccatctg ggacgcattc atgttagagg ctgctatcta caagcttttg   420
aaatctcact tcagaaacga aaatactac atagatatca ccgaattgtt ccatgaggtc   480
accttccaaa ccgaattggg ccaattgatg gacttaatca ctgcacctga agacaaagtc  540
gacttgagta agttctccct aaagaagcac tccttcatag ttactttcaa gactgcttac  600
tattcttct acttgcctgt cgcattggcc atgtacgttg ccggtatcac ggatgaaaag  660
gatttgaaac aagccagaga tgtcttgatt ccattgggta atacttcca aattcaagat   720
gactacttag actgcttcgg tacccccaga cagatcggta agatcggtac agatatccaa  780
gataacaat gttcttgggt aatcaacaag gcattggaac ttgcttccgc agaacaaga   840
aagactttag acgaaaatta cggtaagaag gactcagtcg cagaagccaa atgcaaaaag  900
attttcaatg acttgaaaat tgaacagcta taccacgaat atgaagagtc tattgccaag  960
gatttgaagg ccaaaatttc tcaggtcgat gagtctcgtg gcttcaaagc tgatgtctta 1020
actgcgttct tgaacaaagt ttacaagaga agcaaaatag                       1059

SEQ ID NO: 60              moltype = AA  length = 352
FEATURE                    Location/Qualifiers
REGION                     1..352
                           note = Mutant farnesyl pyrophosphate synthase (Erg20mut,
                           F96W, N127W)
source                     1..352
                           mol_type = protein
                           organism = synthetic construct
SEQUENCE: 60
MASEKEIRRE RFLNVFPKLV EELNASLLAY GMPKEACDWY AHSLNYNTPG GKLNRGLSVV   60
DTYAILSNKT VEQLGQEEYE KVAILGWCIE LLQAYWLVAD DMMDKSITRR GQPCWYKVPE  120
VGEIAIWDAF MLEAAIYKLL KSHFRNEKYY IDITELFHEV TFQTELGQLM DLITAPEDKV  180
DLSKFSLKKH SFIVTFKTAY YSFYLPVALA MYVAGITDEK DLKQARDVLI PLGEYFQIQD  240
DYLDCFGTPE QIGKIGTDIQ DNKCSWVINK ALELASAEQR KTLDENYGKK DSVAEAKCKK  300
IFNDLKIEQL YHEYEESIAK DLKAKISQVD ESRGFKADVL TAFLNKVYKR SK          352

SEQ ID NO: 61              moltype = DNA  length = 1356
```

| FEATURE | Location/Qualifiers |
|---|---|
| source | 1..1356 |
| | mol_type = genomic DNA |
| | organism = Saccharomyces sp. |

SEQUENCE: 61

```
atgtcagagt tgagagcctt cagtgcccca gggaaagcgt tactagctgg tggatattta   60
gttttagata caaaatatga agcatttgta gtcggattat cggcaagaat gcatgctgta  120
gcccatcctt acggttcatt gcaagggtct gataagtttg aagtgcgtgt gaaaagtaaa  180
caatttaaag atggggagtg gctgtaccat ataagtccta aaagtggctt cattcctgtt  240
tcgataggcg gatctaagaa ccctttcatt gaaaaagtta tcgctaacgt atttagctac  300
tttaaaccta acatggacga ctactgcaat agaaacttgt tcgttattga tattttctct  360
gatgatgcct accattctca ggaggatagc gttaccgaac atcgtggcaa cagaagattg  420
agttttcatt cgcacagaat tgaagaagtt cccaaaacag gctgggctc ctcggcaggt   480
ttagtcacag ttttaactac agctttggcc tccttttttg tatcggacct ggaaaataat  540
gtagacaaat atagagaagt tattcataat ttagcacaag ttgctcattg tcaagctcag  600
ggtaaaattg gaagcgggtt tgatgtagcg gcggcagcat atggatctat cagatataga  660
agattcccac ccgcattaat ctctaatttg ccagatattg aagtgctac ttacggcagt   720
aaactggcgc atttggttga tgaagaagac tggaatatta cgattaaaag taaccattta  780
ccttcgggat taactttatg gatgggcgat attaagaatg gttcagaaac agtaaaactg  840
gtccagaagg taaaaaattg gtatgattcg catatgccag aaagcttgaa atatataca   900
gaactcgatc atgcaaattc tagatttatg gatggactat ctaaactaga tcgcttacac  960
gagactcatg acgattacag cgatcagata tttgagtctc ttgagaggaa tgactgtacc 1020
tgtcaaaagt atcctgaaat cacagaagtt agagatgcag ttgccacaat tagacgttcc 1080
tttagaaaaa taactaaaga atccggtgcc gatatcgaac ctcccgtaca aactagctta 1140
ttggatgatt gccagacctt aaaaggagtt cttacttgct taatacctgg tgctggtggt 1200
tatgacgcca ttgcagtgat tactaagcaa gatgttgatc ttagggctca aaccgctaat 1260
gacaaaagat tttctaaggt tcaatggctc gatgtaactc aggctgactg gggtgttagg 1320
aaagaaaaag atccggaaac ttatcttgat aaataa                            1356
```

| SEQ ID NO: 62 | moltype = AA  length = 451 |
|---|---|
| FEATURE | Location/Qualifiers |
| source | 1..451 |
| | mol_type = protein |
| | organism = Saccharomyces sp. |

SEQUENCE: 62

```
MSELRAFSAP GKALLAGGYL VLDTKYEAFV VGLSARMHAV AHPYGSLQGS DKFEVRVKSK   60
QFKDGEWLYH ISPKSGFIPV SIGGSKNPFI EKVIANVFSY FKPNMDDYCN RNLFVIDIFS  120
DDAYHSQEDS VTEHRGNRRL SFHSHRIEEV PKTGLGSSAG LVTVLTTALA SFFVSDLENN  180
VDKYREVIHN LAQVAHCQAQ GKIGSGFDVA AAAYGSIRYR RFPPALISNL PDIGSATYGS  240
KLAHLVDEED WNITIKSNHL PSGLTLWMGD IKNGSETVKL VQKVKNWYDS HMPESLKIYT  300
ELDHANSRFM DGLSKLDRLH ETHDDYSDQI FESLERNDCT CQKYPEITEV RDAVATIRRS  360
FRKITKESGA DIEPPVQTSL LDDCQTLKGV LTCLIPGAGG YDAIAVITKQ DVDLRAQTAN  420
DKRFSKVQWL DVTQADWGVR KEKDPETYLD K                                 451
```

| SEQ ID NO: 63 | moltype = DNA  length = 1332 |
|---|---|
| FEATURE | Location/Qualifiers |
| source | 1..1332 |
| | mol_type = genomic DNA |
| | organism = Saccharomyces sp. |

SEQUENCE: 63

```
atgtcattac cgttcttaac ttctgcaccg ggaaaggtta ttatttttgg tgaacactct   60
gctgtgtaca acaagcctgc cgtcgctgct agtgtgtctg cgttgagaac ctacctgcta  120
ataagcgagt catctgcacc agatactatt gaattggact tcccggacat tagctttaat  180
cataagtggt ccatcaatga tttcaatgcc atcaccgagg atcaagtaaa ctcccaaaaa  240
ttggccaagg ctcaacaagc caccgatggc ttgtctcagg aactcgttag tcttttggat  300
ccgttgttag ctcaactatc cgaatccttc cactaccatg cagcgttttg tttcctgtat  360
atgtttgttt gcctatgccc ccatgccaag aatattaagt tttctttaaa gtctacttta  420
cccatccggtg ctgggttggg ctcaagcgcc tctatttctg tatcactggc cttagctatg  480
gcctacttgg gggggttaat aggatctaat gacttggaaa agctgtcaga aaacgataag  540
catatagtga atcaatgggc cttcataggt gaaaagtgta ttcacggtac cccttcagga  600
atagataacg ctgtgccac ttatggtaat gccctgctat tgaaaaaga ctcacataat    660
ggaacaataa acacaaacaa ttttaagttc ttagatgatt cccagcccat tccaatgatc  720
ctaacctata ctagaattcc aaggtctaca aaagatcttg ttgctcgcgt tcgtgtgttt  780
gtcaccgaga aattcctga agttatgaag ccaattctac atgccatggt tgaatgtacc   840
ctacaaggct tagagatcat gactaagtta agtaaatgta aaggcaccga tgacgaggct  900
gtagaaacta ataatgaact gtatgaacaa ctattggaat tgataagaat aaatcatgga  960
ctgcttgtct caatcggtgt ttctcatcct ggattagaac ttattaaaaa tctgagcgat 1020
gatttgagaa ttggctccac aaaacttacc ggtgctggtg gcggcggttg ctctttgact 1080
ttgttacgaa gagacattac tcaagagcaa attgacagct tcaaaaagaa attgcaagat 1140
gattttagtt acgagacatt tgaaacagac ttgggtggga ctggctgctg tttgttaagc 1200
gcaaaaaatt tgaataaaga tcttaaaatc aaatccctag tattccaatt atttgaaaat 1260
aaaactacca caaagcaaca aattgacgat ctattattgc caggaaacac gaatttacca 1320
tggacttcat aa                                                     1332
```

| SEQ ID NO: 64 | moltype = AA  length = 443 |
|---|---|
| FEATURE | Location/Qualifiers |
| source | 1..443 |
| | mol_type = protein |
| | organism = Saccharomyces sp. |

```
SEQUENCE: 64
MSLPFLTSAP GKVIIFGEHS AVYNKPAVAA SVSALRTYLL ISESSAPDTI ELDFPDISFN    60
HKWSINDFNA ITEDQVNSQK LAKAQQATDG LSQELVSLLD PLLAQLSESF HYHAAFCFLY   120
MFVCLCPHAK NIKFSLKSTL PIGAGLGSSA SISVSLALAM AYLGGLIGSN DLEKLSENDK   180
HIVNQWAFIG EKCIHGTPSG IDNAVATYGN ALLFEKDSHN GTINTNNFKF LDDFPAIPMI   240
LTYTRIPRST KDLVARVRVL VTEKFPEVMK PILDAMGECA LQGLEIMTKL SKCKGTDDEA   300
VETNNELYEQ LLELIRINHG LLVSIGVSHP GLELIKNLSD DLRIGSTKLT GAGGGGCSLT   360
LLRRDITQEQ IDSFKKKLQD DFSYETFETD LGGTGCCLLS AKNLNKDLKI KSLVFQLFEN   420
KTTTKQQIDD LLLPGNTNLP WTS                                          443

SEQ ID NO: 65           moltype = DNA   length = 1191
FEATURE                 Location/Qualifiers
source                  1..1191
                        mol_type = genomic DNA
                        organism = Saccharomyces sp.
SEQUENCE: 65
atgaccgttt acacagcatc cgttaccgca cccgtcaaca tcgcaaccct taagtattgg    60
gggaaaaggg acacgaagtt gaatctgccc accaattcgt ccatatcagt gactttatcg   120
caagatgacc tcagaacgtt gacctctgcg gctactgcac ctgagtttga acgcgacact   180
ttgtggttaa atggagaacc acacagcatc gacaatgaaa gaactcaaaa ttgtctgcgc   240
gacctacgcc aattaagaaa ggaaatggaa tcgaaggacg cctcattgcc cacattatct   300
caatgcgaaac tccacattgt ctccgaaaat aactttccta cagcagctgc tttagcttcc   360
tccgctgctg gctttgctgc attggtctct gcaattgcta agttatacca attaccacag   420
tcaacttcag aaatatctag aatagcaaga aaggggtctg gttcagcttg tagatcgttg   480
tttggcggat acgtggcctg ggaaatggga aaagctgaag atggtcatga ttccatggca   540
gtacaaatcg cagacagctc tgactggcct cagatgaaag cttgtgtcct agttgtcagc   600
gatattaaaa aggatgtgag ttccactcag ggtatgcaat tgaccgtggc aacctccgaa   660
ctatttaaag aaagaattga acatgtcgta ccaaagagat ttgaagtcat gcgtaaagcc   720
attgttgaaa aagatttcgc cacctttgca aggaaacaa tgatggattc caactctttc   780
catgccacat gtttggactc tttccctcca atattctaca tgaatgacac ttccaagcgt   840
atcatcagtt ggtgccacac cattaatcag ttttacggag aaacaatcgt tgcatacacg   900
tttgatgcag gtccaaatgc tgtgttgtac tacttagctg aaaatgagtc gaaactcttt   960
gcatttatct ataaattgtt tggctctgtt cctggatggg acaagaaatt tactactgag  1020
cagcttgagg ctttcaacca tcaatttgaa tcatctaact ttactgcacg tgaattggat  1080
cttgagttgc aaaaggatgt gccagagtg attttaactc aagtcggttc aggcccacaa  1140
gaaacaaacg aatctttgat tgacgcaaag actggtctac caaaggaata a           1191

SEQ ID NO: 66           moltype = AA   length = 396
FEATURE                 Location/Qualifiers
source                  1..396
                        mol_type = protein
                        organism = Saccharomyces sp.
SEQUENCE: 66
MTVYTASVTA PVNIATLKYW GKRDTKLNLP TNSSISVTLS QDDLRTLTSA ATAPEFERDT    60
LWLNGEPHSI DNERTQNCLR DLRQLRKEME SKDASLPTLS QWKLHIVSEN NFPTAAGLAS   120
SAAGFAALVS AIAKLYQLPQ STSEISRIAR KGSGSACRSL FGGYVAWEMG KAEDGHDSMA   180
VQIADSSDWP QMKACVLVVS DIKKDVSSTQ GMQLTVATSE LFKERIEHVV PKRFEVMRKA   240
IVEKDFATFA KETMMDSNSF HATCLDSFPP IFYMNDTSKR IISWCHTINQ FYGETIVAYT   300
FDAGPNAVLY YLAENESKLF AFIYKLFGSV PGWDKKFTTE QLEAFNHQFE SSNFTARELD   360
LELQKDVARV ILTQVGSGPQ ETNESLIDAK TGLPKE                             396

SEQ ID NO: 67           moltype = DNA   length = 2751
FEATURE                 Location/Qualifiers
misc_feature            1..2751
                        note = Engineered phosphomevalonate kinase/mevalonate
                        kinase (Erg8-T2A-Erg12)
source                  1..2751
                        mol_type = other DNA
                        organism = synthetic construct
SEQUENCE: 67
atgtcagagt tgagagcctt cagtgcccca gggaaagcgt tactagctgg tgatatttta    60
gttttagata caaaatatga agcatttgta gtcggattat cggcaagaat gcatgctgta   120
gcccatcctt acgttcatt gcaagggtct gataagtttg aagtgcgtgt gaaagtaaa   180
caatttaaag atggggagtg gctgtaccat ataagtccta aaagtggctt cattcctgtt   240
tcgataggcg gatctaagaa cccctttcatt gaaaaagtta tcgctaacgt atttagctac   300
tttaaaccta acatggacga ctactgcaat agaaacttgt tcgttattga tatttttctct   360
gatgatgcct accattctca ggaggatagc gttaccgaac atcgtggcaa cagaagattg   420
agttttcatt cgcacagaat tgaagaagtt cccaaaacag ggctgggctc ctcggcaggt   480
ttagtcacag ttttaactac agctttggcc tcctttttg tatcggacct tgaaaataat   540
gtagacaaat atagaaagt tattcataat ttagcaaag ttgctcattg tcaagctcag   600
ggtaaaattg gaagcgggtt tgatgtagcg cggcagcat atggatctat cagatataga   660
agattcccac ccgcattaat ctcaatttg ccagatattg aagtgctac ttacggcagt   720
aaactggcgc atttggttga tgaagaagac tggaatatta cgattaaaag taaccattta   780
ccttcgggat taactttatg gatgggcgat attaagaatg gttcagaac agtaaaactg   840
gtccagaagg taaaaattg gtatgattcg catatgccag aaagcttgaa atatatataca   900
gaactcgatc atgcaaattc tagatttatg gatggactat ctaaactaga tcgcttacac   960
gagactcatg acgattacag cgatcagata tttgagtctc ttgagaggaa tgactgtacc  1020
tgtcaaaagt atcctgaaat cacagaagtt agagatgcag ttgccacaat agacgttcc   1080
tttagaaaaa taactaaaga atctggtgcc gatatcgaac ctcccgtaca aactagctta  1140
```

```
ttggatgatt gccagacctt aaaaggagtt cttacttgct taatacctgg tgctggtggt  1200
tatgacgcca ttgcagtgat tactaagcaa gatgttgatc ttagggctca aaccgctaat  1260
gacaaaagat tttctaaggt tcaatggctg gatgtaactc aggctgactg gggtgttagg  1320
aaagaaaaag atccggaaac ttatcttgat aaaaagcttg agggcagagg aagtcttcta  1380
acatgcggtg acgtggagga gaatcccggc cctgctagca tgtcattacc gttcttaact  1440
tctgcaccgg gaaaggttat tatttttggt gaacactctg ctgtgtacaa caagcctgcc  1500
gtcgctgcta gtgtgtctgc gttgagaacc tacctgctaa taagcgagtc atctgcacca  1560
gatactattg aattggactt cccggacatt agctttaatc ataagtggtc catcaatgat  1620
ttcaatgcca tcaccgagga tcaagtaaac tcccaaaaat tggccaaggc tcaacaagcc  1680
accgatggct tgtctcagga actcgttagt cttttggatc cgttgttagc tcaactatcc  1740
gaatccttcc actaccatgc agcgttttgt ttcctgtata tgtttgtttg cctatgcccc  1800
catgccaaga atattaagtt ttctttaaag tctactttac ccatcggtgc tgggttgggc  1860
tcaagcgcct ctatttctgt atcactggcc ttagctatgg cctacttggg ggggttaata  1920
ggatctaatg acttggaaaa gctgtcagaa aacgataagc atatagtgaa tcaatgggca  1980
ttcataggtg aaaagtgtat tcacggtacc ccttcaggaa tagataacgc tgtggccact  2040
tatggtaatg ccctgctatt tgaaaaagac tcacataatg gaacaataaa cacaaacaat  2100
tttaagttct tagatgattt cccagccatt ccaatgatcc taacctatac tagaattcca  2160
aggtctacaa aagatcttgt tgctcgcgtt cgtgtgtttg tcaccgagaa atttcctgaa  2220
gttatgaagc caattctaga tgccatgggt gaatgtgccc tacaaggctt agatcatg  2280
actaagttaa gtaaatgtaa aggcaccgat gacgaggctg tagaaactaa taatgaactg  2340
tatgaacaac tattggaatt gataagaata aatcatggac tgcttgtctc aatcggtgtt  2400
tctcatcctg gattagaact tattaaaaat ctgagcgatg attggaat tggctccaca  2460
aaacttaccg gtgctggtgg cggcggttgc tcttttgactt tgttacgaag agacattact  2520
caagagcaaa ttgacagctt caaaagaaa ttgcaagatg atttagtta cgagacattt  2580
gaaacagact gggtgggac tggctgctgt tgttaagcg caaaaattt gaataaagat  2640
cttaaaatca aatccctagt attccaatta tttgaaaata aaactaccac aaagcaacaa  2700
attgacgatc tattattgcc aggaaacacg aatttaccat ggacttcata a            2751

SEQ ID NO: 68              moltype = AA  length = 916
FEATURE                    Location/Qualifiers
REGION                     1..916
                           note = Engineered phosphomevalonate kinase/mevalonate
                             kinase (Erg8-T2A-Erg12)
source                     1..916
                           mol_type = protein
                           organism = synthetic construct
SEQUENCE: 68
MSELRAFSAP GKALLAGGYL VLDTKYEAFV VGLSARMHAV AHPYGSLQGS DKFEVRVKSK   60
QFKDGEWLYH ISPKSGFIPV SIGGSKNPFI EKVIANVFSY FKPNMDDYCN RNLFVIDIFS  120
DDAYHSQEDS VTEHRGNRRL SFHSRIEEV PKTGLGSSAG LVTVLTTALA SFFVSDLENN  180
VDKYREVIHN LAQVAHCQAQ GKIGSGFDVA AAAYGSIRYR RFPPALISNL PDIGSATYGS  240
KLAHLVDEED WNITIKSNHL PSGLTLWMGD IKNGSETVKL VQKVKNWYDS HMPESLKIYT  300
ELDHANSRFM DGLSKLDRLH ETHDDYSDQI FESLERNDCT CQKYPEITEV RDAVATIRRS  360
FRKITKESGA DIEPPVQTSL LDDCQTLKGV LTCLIPGAGG YDAIAVITKQ DVDLRAQTAN  420
DKRFSKVQWL DVTQADWGVR KEKDPETYLD KKLEGRGSLL TCGDVEENPG PASMSLPFLT  480
SAPGKVIIFG EHSAVYNKPA VAASVSALRT YLLISESSAP DTIELDFPDI SFNHKWSIND  540
FNAITEDQVN SQKLAKAQQA TDGLSQELVS LLDPLLAQLS ESFHYHAAFC FLYMFVCLCP  600
HAKNIKFSLK STLPIGAGLG SSASISVSLA LAMAYLGGLI GSNDLEKLSE NDKHIVNQWA  660
FIGEKCIHGT PSGIDNAVAT YGNALLFEKD SHNGTINTNN FKFLDDFPAI PMILTYTRIP  720
RSTKDLVARV RVLVTEKFPE VMKPILDAMG ECALQGLEIM TKLSKCKGTD DEAVETNNEL  780
YEQLLELIRI NHGLLVSIGV SHPGLELIKN LSDDLRIGST KLTGAGGGGC SLTLLRRDIT  840
QEQIDSFKKK LQDDFSYETF ETDLGGTGCC LLSAKNLNKD LKIKSLVFQL FENKTTTKQQ  900
IDDLLLPGNT NLPWTS                                                  916

SEQ ID NO: 69              moltype = DNA  length = 756
FEATURE                    Location/Qualifiers
misc_feature               1..756
                           note = Artificial neryl pyrophosphate (NPP) synthase (NPPS)
                             nucleotide sequence
source                     1..756
                           mol_type = other DNA
                           organism = synthetic construct
SEQUENCE: 69
atgtgctcac ttaatttgca aacggaaaag ctatgctatg aagacaatga caatgacttg   60
gacgaggaac tgatgccgaa gcacatagcg ctaatcatgg atggtaatag acgtgggca  120
aaagacaagg gcttagaagt gtacgaaggg cacaaacata taatcccgaa actaaaagaa  180
atatgtgaca tatcctccaa gttggggatt cagatcatca cagcgttcgc gttctccaca  240
gagaactgga agagatccaa ggaggaagtc gatttcctat tgcagatgtt tgaagaaatc  300
tatgacgaat ttagccgttc tggggtgaga gtgagtatca tcggatgcaa aagcgatttg  360
ccgatgaccc ttcaaaaatg tatcgcattg acagaggaaa cgacgaaagg caataaggga  420
ttacacctgg tcatagcact taactacggt gggtattacg atatcctaca agcaacgaag  480
tccattgtaa acaaggctat gatggtttta ttggacgttg aagacatcaa taaaaatctg  540
ttcgaccaag aattagaaag caaatgccct aaccctgact gctgatcag aactggggaa  600
gaacagaggg tctctaattt tcttctatgg caattgcgtt atactgagtt ctatttttacc  660
aatactttat tccctgactt tggtgaagag gacctgaaag aagccatcat gaattttcaa  720
cagagacacc gtagattcgg aggacatact tattga                            756

SEQ ID NO: 70              moltype = AA  length = 251
FEATURE                    Location/Qualifiers
```

```
source                   1..251
                         mol_type = protein
                         organism = Solanum sp.
SEQUENCE: 70
MCSLNLQTEK LCYEDNDNDL DEELMPKHIA LIMDGNRRWA KDKGLEVYEG HKHIIPKLKE    60
ICDISSKLGI QIITAFAFST ENWKRSKEEV DFLLQMFEEI YDEFSRSGVR VSIIGCKSDL   120
PMTLQKCIAL TEETTKGNKG LHLVIALNYG GYYDILQATK SIVNKAMNGL LDVEDINKNL   180
FDQELESKCP NPDLLIRTGG EQRVSNFLLW QLAYTEFYFT NTLFPDFGEE DLKEAIMNFQ   240
QRHRRFGGHT Y                                                       251

SEQ ID NO: 71            moltype = DNA   length = 1113
FEATURE                  Location/Qualifiers
misc_feature             1..1113
                         note = Artificial geranylgeranyl pyrophosphate synthase
                          large subunit (GPPSlsu) nucleotide sequence
source                   1..1113
                         mol_type = other DNA
                         organism = synthetic construct
SEQUENCE: 71
atgagcaccg tgaatctgac ctgggtgcag acgtgctcta tgttcaacca gggcgggcgt    60
tcccgttcat tgtcaacctt caacttaaat ctgtaccatc cattgaagaa aacgcctttc   120
tctatccaga cacctaagca gaaaaggcca acttcccct  tctcatctat cagtgccgta   180
ttaacggagc aggaagcagt aaaggagggt gacgaggaaa aaagcatatt taacttcaaa   240
tcttatatgg ttcagaaagc taatagcgtg aatcaggcac tagattctgc ggtgttattg   300
agagaccca ttatgataca tgaatctatg cgttactctt tgcttgcggg cggcaagcgt    360
gtcagaccga tgttatgctt aagtgcgtgc gagttagtag gtggtaaaga gtctgtagca   420
atgcccgcag catgtgctgt agaaatgata cacacaatgt cactgattca cgatgatctt   480
ccttgcatgg ataacgacga tcttcgtaga ggtaagccaa ccaaccacaa ggtattcggg   540
gaagacgtgg cagttttagc aggagacgcg ctactagcgt tcgcgtttga acacatggca   600
gttagcacag taggagttcc agcagcaaaa atagttaggg ctataggaga gttagcaaag   660
tccatcggta gcgagggcct tgttgccgga caggtagttg atatcgatag tgaagggttg   720
gctaacgtgg gactagaaca actggagttc atccactac  acaagacagg ggcactgctt   780
gaagcgagtg ttgtacttgg ggctattctg ggggaggaa cagatgagga ggtagaaaaa   840
ctacgtagtt ttgccaggtg tataggacta ctatttgtag ttgtagatga tatccttgac   900
gtcacgaaga gtagtcaaga gttaggaaaa acagcaggga aagatctagt tgccgataaa   960
gtaacctacc ccaggctaat gggtatcgat aaatctcgtg agttcgccga caattaaat   1020
actgaggcta agcaacattt aagcgggttt gatcctatta aggctgcgcc gctgattgct  1080
ctagcaaact atattgcata tagacagaac tga                               1113

SEQ ID NO: 72            moltype = AA   length = 370
FEATURE                  Location/Qualifiers
source                   1..370
                         mol_type = protein
                         organism = Cannabis sativa
SEQUENCE: 72
MSTVNLTWVQ TCSMFNQGGR SRSLSTFNLN LYHPLKKTPF SIQTPKQKRP TSPFSSISAV    60
LTEQEAVKEG DEEKSIFNFK SYMVQKANSV NQALDSAVLL RDPIMIHESM RYSLLAGGKR   120
VRPMLCLSAC ELVGGKESVA MPAACAVEMI HTMSLIHDDL PCMDNDDLRR GKPTNHKVFG   180
EDVAVLGDA LLAFAFEHMA VSTVGVPAAK IVRAIGELAK SIGSEGLVAG QVVDIDSEGL   240
ANVGLEQLEF IHLHKTGALL EASVVLGAIL GGGTDEEVEK LRSFARCIGL LFQVVDDILD   300
VTKSSQELGK TAGKDLVADK VTYPRLMGID KSREFAEQLN TEAKQHLSGF DPIKAAPLIA   360
LANYIAYRQN                                                         370

SEQ ID NO: 73            moltype = DNA   length = 948
FEATURE                  Location/Qualifiers
misc_feature             1..948
                         note = Artificial geranylgeranyl pyrophosphate synthase
                          small subunit (GPPSssu) nucleotide sequence
source                   1..948
                         mol_type = other DNA
                         organism = synthetic construct
SEQUENCE: 73
atggctgttt acaacctttc aatcaactgt tctcccagat tcgtccatca tgtatacgtg    60
ccccatttta catgtaaatc aaataagagc ctgagccatg tccccatgag aatcacgatg   120
tcaaagcagc atcatcactc atactttgcc tctacaacgg cagatgtcga tgcccatcta   180
aaacaatcaa tcacaattaa accccgttg  tctgtccacg aagccatgta acttttatc    240
ttcagtacgc caccgaattt ggcgccatca ttatgtgtcg cagcatgtga attggttggg   300
ggtcaccagg gacaggcgat ggcagcggcc agcgcattaa gggtaataca tgctagcgta   360
gttacccacg atcaccttcc gttaacggga aggccaaacc ccacctcacc tgaggccgct   420
acgcacaatt cctataatcc aaacatacag ttgttattac ctgacgccat tacacccttc   480
gggtttgagc tattagcgtc cagtgatgat cttacacaca acaagagtga gagagttctt   540
agggtgatcg ttgaatttac gaggactttc ggttccagag cactataga cgcccaatac   600
cacgaaaagt tggctagtag gtttgatgtg gatagccatg aggcaaagac cgtaggatgg   660
gggcattacc catcattgaa aaaggaggga agccatgcag tcgcctgcga   720
gcaatattgg gtgaggctca tgaagaagaa gtgaaaaat  tgcgtacatt cgggctgtat   780
gtcggcatga tccaaggtta tgcgaacaga ttcatcatga gcagtacaga ggagaaaaaa   840
gaggctgaca ggataattga ggagcttacc aatttagcgc gtcaggagct gaaatacttc   900
gatggaagga acctagaacc gttttcaaca ttccttgttcc gtttgtag             948
```

| | | |
|---|---|---|
| SEQ ID NO: 74 | moltype = AA   length = 315 | |
| FEATURE | Location/Qualifiers | |
| source | 1..315<br>mol_type = protein<br>organism = Cannabis sativa | |
| SEQUENCE: 74 | | |

```
MAVYNLSINC SPRFVHHVYV PHFTCKSNKS LSHVPMRITM SKQHHHSYFA STTADVDAHL    60
KQSITIKPPL SVHEAMYNFI FSTPPNLAPS LCVAACELVG GHQGQAMAAA SALRVIHASI   120
VTHDHLPLTG RPNPTSPEAA THNSYNPNIQ LLLPDAITPF GPFELLASSDD LTHNKSERVL  180
RVIVEFTRTF GSRGTIDAQY HEKLASRFDV DSHEAKTVGW GHYPSLKKEG AMHACAAACG   240
AILGEAHEEE VEKLRTFGLY VGMIQGYANR FIMSSTEEKK EADRIIEELT NLARQELKYF   300
DGRNLEPFST FLFRL                                                   315
```

| | | |
|---|---|---|
| SEQ ID NO: 75 | moltype = DNA   length = 1161 | |
| FEATURE | Location/Qualifiers | |
| misc_feature | 1..1161<br>note = Artificial tetraketide synthase (TKS) nucleotide sequence | |
| source | 1..1161<br>mol_type = other DNA<br>organism = synthetic construct | |
| SEQUENCE: 75 | | |

```
atgaatcatt taagagctga aggtccagcc tccgttttgg ccatcggtac cgctaaccct    60
gaaaacattt tgttgcaaga cgaattccca gactactact tcagagtcac taagtccgaa   120
cacatgaccc aattgaagga agttcaga aagatttgtg acaagtccat gattagaaag    180
agaaactgtt tcttgaacga agaacacttg aagcaaaacc caagattggt tgaacatgaa   240
atgcaaactt tggacgctag acaagacatg ttggttgttg aagtccctaa gttgggtaag   300
gatgcctgtg ctaaggccat taagaatgg ggtcaaccta gtccaagat acccacttg     360
attttcacct ctgcctccac cactgacatg cctggtgctg attaccactg cgctaagtta   420
ttgggtttgt ctccatccgt taagagagtt atgatgtacc aattgggttg ctacggtggt   480
ggtactgttt taagaattgc taaggatatt gctgaaaaca caagggtgc cagagtctta   540
gctgtctgct gtgacattat ggcttgttta ttcagaggtc catctgaatc cgacttggaa   600
ttgttggttg gtcaagctat cttcggtgac ggtgctgctg ccgttattgt tggtgctgaa   660
ccagacgaat ccgttggtga aagaccaatt tttgaattgg tttccaccgg tcaaactatt   720
ttgccaaatt ccgaaggtac catcggtggt catatcagag aagccggttt gatcttcgac   780
ttacataagg atgtcccaat gttgatctct aacaacattg aaaagtgttt gatcgaagct   840
tttaccccaa ttggtatttc tgactggaac tctatcttct ggattaccca tcctggtggt   900
aaggctattt tggataaggt cgaggaaaaa ttgcacttga gtctgacaa gttcgttgac    960
tctagacacg tcttgtccga acatggtaat atgtcctctt ccaccgtttt attcgttatg   1020
gatgagttga aaagagatc cttagaagaa ggtaagtcca ccaccggtga tggttttgag   1080
tggggtgttt tgttcggttt cggtccaggt ttgaccgtcg aaagagttgt tgttagatct   1140
gtcccaatta agtacggatc c                                            1161
```

| | | |
|---|---|---|
| SEQ ID NO: 76 | moltype = AA   length = 387 | |
| FEATURE | Location/Qualifiers | |
| REGION | 1..387<br>note = Artificial tetraketide synthase (TKS) | |
| source | 1..387<br>mol_type = protein<br>organism = synthetic construct | |
| SEQUENCE: 76 | | |

```
MNHLRAEGPA SVLAIGTANP ENILLQDEFP DYYFRVTKSE HMTQLKEKFR KICDKSMIRK    60
RNCFLNEEHL KQNPRLVEHE MQTLDARQDM LVVEVPKLGK DACAKAIKEW GQPKSKITHL   120
IFTSASTTDM PGADYHCAKL LGLSPSVKRV MMYQLGCYGG GTVLRIAKDI AENNKGARVL   180
AVCCDIMACL FRGPSESDLE LLVGQAIFGD GAAAVIVGAE PDESVGERPI FELVSTGQTI   240
LPNSEGTIGG HIREAGLIFD LHKDVPMLIS NNIEKCLIEA FTPIGISDWN SIFWITHPGG   300
KAILDKVEEK LHLKSDKFVD SRHVLSEHGN MSSSTVLFVM DELRKRSLEE GKSTTGDGFE   360
WGVLFGFGPG LTVERVVVRS VPIKYGS                                      387
```

| | | |
|---|---|---|
| SEQ ID NO: 77 | moltype = DNA   length = 309 | |
| FEATURE | Location/Qualifiers | |
| misc_feature | 1..309<br>note = Artificial olivetolic acid cyclase (OAC) nucleotide sequence | |
| source | 1..309<br>mol_type = other DNA<br>organism = synthetic construct | |
| SEQUENCE: 77 | | |

```
atggccgtca agcacttgat cgttttgaag ttcaaggatg aaatcactga agctcaaaag    60
gaagaattct tcaaaaccta cgtcaactta gtcaatatta ttccagccat gaaggacgtc   120
tattggggta aggacgttac tcaaaagaat aaggaggaag ttatactca tcgttgag     180
gtcactttcg aatctgttga gactattcaa gactacatca tccacccagc ccacgttggt   240
ttcggtgatg tttatcgttc cttctgggaa aaattggtga tcttcgacta caccctaga    300
aagggatcc                                                          309
```

| | | |
|---|---|---|
| SEQ ID NO: 78 | moltype = AA   length = 103 | |
| FEATURE | Location/Qualifiers | |
| REGION | 1..103<br>note = Artificial olivetolic acid cyclase (OAC) | |

```
source                  1..103
                        mol_type = protein
                        organism = synthetic construct
SEQUENCE: 78
MAVKHLIVLK FKDEITEAQK EEFFKTYVNL VNIIPAMKDV YWGKDVTQKN KEEGYTHIVE    60
VTFESVETIQ DYIIHPAHVG FGDVYRSFWE KLLIFDYTPR KGS                    103

SEQ ID NO: 79           moltype = DNA    length = 1578
FEATURE                 Location/Qualifiers
misc_feature            1..1578
                        note = Fusion tetraketide synthase-olivetolic acid cyclase
                           (TKS-OAC)
source                  1..1578
                        mol_type = other DNA
                        organism = synthetic construct
SEQUENCE: 79
atgaatcatt taagagctga aggtccagcc tccgttttgg ccatcggtac cgctaaccct    60
gaaaacattt tgttgcaaga cgaattccca gactactact tcagagtcac taagtccgaa   120
cacatgaccc aattgaagga agagttcaga aagatttgtg acaagtccat gattagaaag   180
agaaactgtt tcttgaacga gaacactttg aagcaaaacc caagattggt tgaacatgaa   240
atgcaaactt ggacgctag acaagacatg ttggttgttg aagtccctaa gttgggtaag    300
gatgcctgtg ctaaggccat taaagaatgg ggtcaaccta gtccaagtaa tacccacttg   360
attttcacct ctgcctccac cactgacatg cctggtgctg attaccactg cgctaagtta   420
ttggggtttgt ctccatccgt taagagagtt atgatgtacc aattgggttg ctacggtggt   480
ggtactgttt taagaattgc taaggatatt gctgaaaaca caaggggtgc cagagtctta    540
gctgtctgct gtgacattat ggcttgttta ttcagagtc catctgaatc cgacttggaa    600
ttgttggttg gtcaagctat cttcggtgac ggtgctgctg ccgttattgt tggtgctgaa    660
ccagacgaat ccgttggtga agaccaattt tttgaattgg tttccaccgg tcaaactatt    720
ttgccaaatt ccgaaggtac catcggtggt catatcagag aagccggttt gatcttcgac    780
ttacataagg atgtcccaat gttgatctct aacaacattg aaaagtgttt gatcgaagct    840
tttaccccaa ttggtatttc tgactggaac tctatcttct ggattaccca tcctggtggt    900
aaggctattt tggataaggt cgaggaaaaa ttgcacttga gtctgacaa gttcgttgac     960
tctagacacg tcttgtccga acatggtaat atgtcctctt ccaccgtttt attcgttatg   1020
gatgagttga gaaagagatc cttagaagaa ggtaagtcca ccaccggtga tggttttgaa   1080
tgggggtgttt tgttcggttt cggtccaggt ttgaccgtcg aaagagttgt tgttagatct   1140
gtcccaatta agtacgcagc cacaagcggt tctacgggct ccacgggctc taccggcagt   1200
ggggaggagca ctgggtcaac gggatcaaca ggtagtggaa gatcacacat ggttgccgtc   1260
aagcacttga tcgttttgaa gttcaaggat gaaatcactg aagctcaaaa ggaagaattc   1320
ttcaaaacct acgtcaactt agtcaatatt attccagcca tgaaggacgt ctattggggt   1380
aaggacgtta tcaaaagaa taaggaggaa ggttatactc atatcgttga ggtcactttc   1440
gaatctgttg agactattca agactacatc atccacccag cccacgttgg tttcggtgat   1500
gtttatcgtt ccttctggga aaaattgttg atcttcgact acaccccag aaagggtaac   1560
tcgagagctt tgattaa                                                  1578

SEQ ID NO: 80           moltype = AA    length = 525
FEATURE                 Location/Qualifiers
REGION                  1..525
                        note = Fusion tetraketide synthase-olivetolic acid cyclase
                           (TKS-OAC)
source                  1..525
                        mol_type = protein
                        organism = synthetic construct
SEQUENCE: 80
MNHLRAEGPA SVLAIGTANP ENILLQDEFP DYYFRVTKSE HMTQLKEKFR KICDKSMIRK    60
RNCFLNEEHL KQNPRLVEHE MQTLDARQDM LVVEVPKLGK DACAKAIKEW GQPKSKITHL   120
IFTSASTTDM PGADYHCAKL LGLSPSVKRV MMYQLGCYGG GTVLRIAKDI AENNKGARVL   180
AVCCDIMACL FRGPSESDLE LLVGQAIFGD GAAAVIVGAE PDESVGERPI FELVSTGQTI   240
LPNSEGTIGG HIREAGLIFD LHKDVPMLIS NNIEKCLIEA FTPIGISDWN SIFWITHPGG   300
KAILDKVEEK LHLKSDKFVD SRHVLSEHGN MSSSTVLFVM DELRKRSLEE GKSTTGDGFE   360
WGVLFGFGPG LTVERVVVRS VPIKYAATSG STGSTGSTGS GRSTGSTGST GSGRSHMVAV   420
KHLIVLKFKD EITEAQKEEF FKTYVNLVNI IPAMKDVYWG KDVTQKNKEE GYTHIVEVTF   480
ESVETIQDYI IHPAHVGFGD VYRSFWEKLL IFDYTPRKGN SRAFD                    525

SEQ ID NO: 81           moltype = DNA    length = 1185
FEATURE                 Location/Qualifiers
source                  1..1185
                        mol_type = genomic DNA
                        organism = Cannabis sativa
SEQUENCE: 81
atgggattgt ccagcgtgtg caccttctca ttccaaacca actaccatac acttctcaat    60
ccgcacaata taacccgaa aaccagctta ttatgttata gacacccgaa gacgcctatt   120
aagtacagtt ataacaactt tcctagcaag cattgctcta ctaaaagttt tcatctgcaa   180
aacaagtgct ctgagtcctt gagtatagca agaatagca ttagagctgc aacgacaaat   240
caaaccgagc cgccggagtc tgataaccat agtgtggcga ccaagatact aaatttgaa   300
aaagcgtgtt ggaagctaca acgacctat actattatcg cgtttacgag ttgtgcatgt   360
gggctgttcg ggaaagagct cttgcacaat acaaacttaa tcagttggag tttgatgttc   420
aaagcatttt ttttttctcgt cgctatctta tgtatcgcgt catttaccac gaccataaat   480
caaatatacg atctgcatat cgatcgtatc aataagcccg acctcccact ggcctcaggt   540
gaaatttccg ttaacacggc gtggattatg agtataatcg tagcactatt tggacttatt   600
```

-continued

```
ataaccatca aaatgaaggg cggtcctcta tacattttg gatattgttt tgggattttt    660
ggaggtatag tctattccgt cccccccatt cagatggaaac aaaacccgtc caccgctttc  720
cttttaaatt tcttggcaca tatcatcaca aacttcacgt tttactatgc cagccgagcc  780
gcactgggac tcccgttcga gttgcgtccg tcattcacct tcctttagc ttttatgaaa   840
tctatgggaa gcgctttagc tttaattaag gacgcgagcg acgtggaagg ggacacgaaa  900
ttcggtataa gcacgctggc ttcaaaatat ggaagtcgta atctcactct attttgttct   960
gggattgtac tcctaagtta cgtagctgcg atactcgcag gcattatatg gccacaagct  1020
ttcaactcca acgtaatgtt gctatcacat gcaatcttgg ccttctggct catccttcaa  1080
actagagatt ttgcactaac gaactacgat ccagaagcgg tcgtcgatt ttacgaattt   1140
atgtggaaac tgtactatgc tgagtacctc gtctatgtgt tcata                  1185
```

```
SEQ ID NO: 82        moltype = AA   length = 395
FEATURE              Location/Qualifiers
source               1..395
                     mol_type = protein
                     organism = Cannabis sativa
SEQUENCE: 82
MGLSSVCTFS FQTNYHTLLN PHNNNPKTSL LCYRHPKTPI KYSYNNFPSK HCSTKSFHLQ    60
NKCSESLSIA KNSIRAATTN QTEPPESDNH SVATKILNFG KACWKLQRPY TIIAFTSCAC   120
GLFGKELLHN TNLISWSLMF KAFFFLVAIL CIASFTTTIN QIYDLHIDRI NKPDLPLASG   180
EISVNTAWIM SIIVALFGLI ITIKMKGGPL YIFGYCFGIF GGIVYSVPPF RWKQNPSTAF   240
LLNFLAHIIT NFTFYYASRA ALGLPFELRP SFTFLLAFMK SMGSALALIK DASDVEGDTK   300
FGISTLASKY GSRNLTLFCS GIVLLSYVAA ILAGIIWPGA FNSNVMLLSH AILAFWLILQ   360
TRDFALTNYD PEAGRRFYEF MWKLYYAEYL VYVFI                              395
```

```
SEQ ID NO: 83        moltype = DNA   length = 921
FEATURE              Location/Qualifiers
source               1..921
                     mol_type = genomic DNA
                     organism = Streptomyces sp.
SEQUENCE: 83
atgtctgagg cggcagacgt agagagagta tacgctgcta tggaggaagc ggctggatta    60
ttgggggtgg cttgtgccag agacaagata tatccgttac tgtctacttt ccaggacact  120
cttgtagaag gagggagtgt ggtggtgttt agtatggcat caggccgtca ttcaacagag  180
ctagatttca gtatatctgt gccaacaagt cacggtgatc catacgcaac cgtagtcgaa  240
aagggtcttt tcccggcaac agggcatcct gtagatgatt tgcttgccga cacacagaag  300
cacctgcccg tctccatgtt cgcaatcgat ggtgaggtga ccgaggatt taaaaagact  360
tacgctttct tcccgactga caatatgcca ggagttgccg agttgagtgc aataccatcc  420
atgccgccag cagtcgcgga gaacgccgaa ttgttccgca gttacggctt ggacaaagtc  480
caaatgacta gtatggacta taaaaagagg caggtgaatc tatatttcag cgaacttttct  540
gcccaaaccct tggaggcgga gagcgttta gcccttgtta gggagttagg gctacacgtc  600
ccgaatgagt tgggtttgaa attttgtaag cgtagctttt cagtatatcc gacgctgaac  660
tgggaagtag gaaagattga caggctatgc tttgcagtga tttctaatga ccctacgctt  720
gtaccttcct cagacgaggg cgacatcgag aaattccaca actatgccac aaaagctccg  780
tatgcctacg tcgcgaaaaa acgtactcta gtataccggtt tgactctgag tcccaaggaa  840
gagtattaca agctaggagc gtactatcat atcactgatg tgcaacgtgg cttgctgaaa  900
gccttcgact cctttagagga c                                           921
```

```
SEQ ID NO: 84        moltype = AA   length = 307
FEATURE              Location/Qualifiers
source               1..307
                     mol_type = protein
                     organism = Streptomyces sp.
SEQUENCE: 84
MSEAADVERV YAAMEEAAGL LGVACARDKI YPLLSTFQDT LVEGGSVVVF SMASGRHSTE    60
LDFSISVPTS HGDPYATVVE KGLFPATGHP VDDLLADTQK HLPVSMFAID GEVTGGFKKT   120
YAFFPTDNMP GVAELSAIPS MPPAVAENAE LFARYGLDKV QMTSMDYKKR QVNLYFSELS   180
AQTLEAESVL ALVRELGLHV PNELGLKFCK RSFSVYPTLN WETGKIDRLC FAVISNDPTL   240
VPSSDEGDIE KFHNYATKAP YAYVGEKRTL VYGLTLSPKE EYYKLGAYYH ITDVQRGLLK   300
AFDSLED                                                            307
```

```
SEQ ID NO: 85        moltype = DNA   length = 1635
FEATURE              Location/Qualifiers
source               1..1635
                     mol_type = genomic DNA
                     organism = Cannabis sativa
SEQUENCE: 85
atgaactgtt ccgcgtttag tttctggttc gtgtgcaaga tcatcttctt ttttctaagc    60
ttcaacattc aaatcagcat cgcgaatcct caggagaact tcctgaagtg tttctcagaa  120
tacataccaa ataatcccgc caatcctaaa tttatatata cccaacatga tcagctatac  180
atgagtgtat tgaactctac gattcagaat ctaagattca catctgatac aacgccgaaa  240
cctcagtaa tcgtgacacc gtctaatgtc tcccatattc aagcttctat cttgtgctca  300
aagaaagtcg gtcttcaaat aaggacacgt tctggcgggc atgacgccga ggcatgtca  360
tatatcagcc aagtaagaa tgtagtcgtg gatttaagaa acatgcattc tataaaaatc  420
gacgttcact cccaaacggc atgggtgaa gctggagcga cactggggga ggtgtactac  480
tggatcaatg aaaagaacga aaatttttcc ttccccggag gatattgtcc gacagttggg  540
gtgggggggcc acttctctgg cggcgggtac ggcgctctga tgcgtaatta tggactggcc  600
gcagataaca taatcgacgc gcatttggtg aacgttgacg gaaggttttt ggataggaag  660
tctatgggag aggacctatt ctgggcaatt agaggcggag gaggagagaa ttttggtatt  720
```

```
attgctgcat ggaagattaa attggttgcg gtgccgagta aaagtaccat cttttccgtc    780
aagaaaaaca tggagattca cggactagtt aagctgttta ataaatgcaa aaacatcgcc    840
tataagtacg acaaagattt ggttctgatg acgcatttca taactaagaa tataactgat    900
aatcacggca agaataagac cactgtgcac ggttatttta gttcaatatt ccatggcggc    960
gttgactccc ttgtcgattt gatgaataag agcttccctg aattgggtat caagaagaca   1020
gactgcaaag aattctcctg gattgatacg actatcttct attcaggggt cgtgaatttc   1080
aacactgcga atttcaaaaa ggagatattg ttagaccgtt ccgcgggaaa aaaaactgcg   1140
ttttctatta aactagatta tgtgaaaaaa ccgattcctg agacagccat ggttaagatt   1200
cttgaaaaat tgtatgaaga ggatgtcggg gtcggtatgt acgtccttta cccttacgga   1260
ggaatcatgg aagaaatatc cgaatctgca attcctttcc cgcatcgtgc cggtattatg   1320
tatgagctat ggtacaccgc tagctgggag aagcaggaag ataacgagaa gcatatcaat   1380
tgggtgaggt ctgtgtataa ttttacaaca ccatacgtca gtcaaaaccc tagattggcc   1440
tatcttaact atcgtgatct ggacttggga aaaacaaatc cagaatcccc aaataactac   1500
actcaagccc gtatatgggg cgagaagtac ttcggcaaaa atttcaatag actggtcaaa   1560
gttaagacga agcagaccc taataatttc ttccgtaacg aacaatcaat tccccgcttt   1620
ccgccacacc atcac                                                    1635

SEQ ID NO: 86          moltype = AA   length = 545
FEATURE                Location/Qualifiers
source                 1..545
                       mol_type = protein
                       organism = Cannabis sativa
SEQUENCE: 86
MNCSAFSFWF VCKIIFFFLS FNIQISIANP QENFLKCFSE YIPNNPANPK FIYTQHDQLY     60
MSVLNSTIQN LRFTSDTTPK PLVIVTPSNV SHIQASILCS KKVGLQIRTR SGGHDAEGMS    120
YISQVPFVVV DLRNMHSIKI DVHSQTAWVE AGATLGEVYY WINEKNENFS FPGGYCPTVG    180
VGGHFSGGGY GALMRNYGLA ADNIIDAHLV NVDGKVLDRK SMGEDLFWAI RGGGGENFGI    240
IAAWKIKLVA VPSKSTIFSV KKNMEIHGLV KLFNKWQNIA YKYDKDLVLM THFITKNITD    300
NHGKNKTTVH GYFSSIFHGG VDSLVDLMNK SFPELGIKKT DCKEFSWIDT TIFYSGVVNF    360
NTANFKKEIL LDRSAGKKTA FSIKLDYVKK PIPETAMVLI LEKLYEEDVG VGMYVLYPYG    420
GIMEEISESA IPFPHRAGIM YELWYTASWE KQEDNEKHIN WVRSVYNFTT PYVSQNPRLA    480
YLNYRDLDLG KTNPESPNNY TQARIWGEKY FGKNFNRLVK VKTKADPNNF FRNEQSIPPL    540
PPHHH                                                                545

SEQ ID NO: 87          moltype = DNA   length = 1632
FEATURE                Location/Qualifiers
source                 1..1632
                       mol_type = genomic DNA
                       organism = Cannabis sativa
SEQUENCE: 87
atgaaatgtt ctactttcag ttttttggttc gtgtgtaaga tcatcttttt cttttttcagc    60
ttcaatatac agacaagtat cgccaatcca agagaaaatt tcttaaaatg ttttttcacag    120
tacatcccta ataacgccac taacctgaaa ttagtgtaca cccaaaataa tcctctttat    180
atgtctgttt taaactccac gatccataat ttaaggttta catcagatac gacaccaaag    240
cccttggtaa tcgtgactcc cagccacgtg agccacatac aggggaccat cctgtgctct    300
aagaaagtag gcttgcagat caggacaaga tccggtggac acgacagtga gggaatgtcc    360
tatatttcac aagtcccctt cgttatagta gatctgagga acatgaggat cattaagatt    420
gatgtgcact cacaaacggc ttgggttgaa gctggagcca cattgggaga ggtttattac    480
tgggtgaatg agaagaacga gaaccttttca ttagcagcgg gatattgtcc cacggtgtgc    540
gcaggtgggc atttcggggg aggagggtac ggcccttttga tgagaaatta cgggctagcg    600
gcagcaaaca tcatcgatgc ccatctggtg aacgtgtgta gaaaagtact ggacagaaaa    660
tcaatgggcg aggacctgtt ttgggctttg agaggggcg gtgcagagtc atttggcatc    720
atagttgcat ggaaaatcag acttgttgcc gtcccaaagt ccacaatgtt ctctgttaag    780
aaaatcatgg agatacacga attggtgaaa ttagtgaata aatggcaaaa catagcgtac    840
aagtacgaca aagacttact gctgatgaca cacttttatca cccgtaatat tacagataat    900
cagggtaaga acaaaaccgc gatccataca tattttttcat ccgttttttct aggcggtgtc    960
gattcattag tagatctgat gaacaaatct ttccccgaac ttggtatcaa aaagactgat   1020
tgcagacagt tatcatggat tgatacaata attttctatt ctggtgtcgt aaattacgat   1080
accgataatt ttaataagga aatactatta gatcgttccg ctgggcagaa tggtgcattc   1140
aagataaaac ttgattatgt caaaaagccc attccagaga gtgtctttgt gcagatcctt   1200
gagaagttgt atgaagaaga cattggtgca gggatgtacg cgctatatcc gtacgggggt   1260
attatgacg agatttctga gagcgccata ccattccac acagagcagg aattttttatac   1320
gagttatggt atatctgctc atgggaaaaa caggaagaca acgagaagca cttaaactgg   1380
atacgtaata tctataattt tatgacccca tacgtatcaa aaatccgtac tcttcgctac   1440
cttaactaca gggacctgga cataggtata aacgacccaa aaaatccaa taattacacc   1500
caagctagaa tctgggggga gaagtatttc ggtaagaact tgaccgtttt ggtaaaagtc   1560
aaaactctgg tcgatccgaa caatttcttc cgtaacgagc aatccatacc tccgctaccg   1620
agacatagac at                                                      1632

SEQ ID NO: 88          moltype = AA   length = 544
FEATURE                Location/Qualifiers
source                 1..544
                       mol_type = protein
                       organism = Cannabis sativa
SEQUENCE: 88
MKCSTFSFWF VCKIIFFFFS FNIQTSIANP RENFLKCFSQ YIPNNATNLK LVYTQNNPLY     60
MSVLNSTIHN LRFTSDTTPK PLVIVTPSHV SHIQGTILCS KKVGLQIRTR SGGHDSEGMS    120
YISQVPFVIV DLRNMRSIKI DVHSQTAWVE AGATLGEVYY WVNEKNENLS LAAGYCPTVC    180
AGGHFGGGGY GPLMRNYGLA ADNIIDAHLV NVHGKVLDRK SMGEDLFWAL RGGGAESFGI    240
```

```
IVAWKIRLVA VPKSTMFSVK KIMEIHELVK LVNKWQNIAY KYDKDLLLMT HFITRNITDN    300
QGKNKTAIHT YFSSVFLGGV DSLVDLMNKS FPELGIKKTD CRQLSWIDTI IFYSGVVNYD    360
TDNFNKEILL DRSAGQNGAF KIKLDYVKKP IPESVFVQIL EKLYEEDIGA GMYALYPYGG    420
IMDEISESAI PFPHRAGILY ELWYICSWEK QEDNEKHLNW IRNIYNFMTP YVSKNPRLAY    480
LNYRDLDIGI NDPKNPNNYT QARIWGEKYF GKNFDRLVKV KTLVDPNNFF RNEQSIPPLP    540
RHRH                                                                544

SEQ ID NO: 89           moltype = DNA  length = 2160
FEATURE                 Location/Qualifiers
source                  1..2160
                        mol_type = genomic DNA
                        organism = Cannabis sativa
SEQUENCE: 89
atgggaaaaa actacaaaag tctggactcc gtcgtcgcgt cagacttcat tgccctaggc     60
ataacatcag aggtagcgga aaccttacac ggcagactag ccgagattgt ttgtaactac    120
ggggcggcta ctccccagac ttggatcaat atagccaatc acatattaag ccccgatttg    180
ccgttttccc ttcaccaaat gttgttctac ggctgctata aggactttgg accagcgccc    240
cccgcgtgga ttcctgatcc ggagaaagtt aaatccacga atcttgggcg attactagaa    300
aaacgtggca agaattcct aggagttaaa tataaggacc ccatatcttc cttttcacac     360
tttcaagaat tttcagttag aaacccagag gtttactgga ggacagtatt aatggatgag    420
atgaagataa gctttagtaa ggatccggag tgtattctgc gtagagatga cattaacaat    480
cctggcggaa gtgaatggct gcctggtggg tacctgaata gtgctaagaa ctgtttaaac    540
gtcaactcta ataaaaaatt gaatgataca atgattgtat ggagagacga agggaacgat    600
gacctaccat tgaacaagct gactctagat cagctacgta aacgtgtatg gttggtcggg    660
tacgcgctgg aggagatggg attagaaaaa ggatgcgcaa ttgctatcga catgcctatg    720
catgtggacg cggtagtcat ttacttggcc attgtcctag cgggttacgt gtcgtttca    780
attgcagaca gcttttctgc acccgaaatc agtacccgtc tgcgtttgtc taaagctaag    840
gcaatattta cccaagacca tataattaga ggcaagaagc gtataccgtt gtacagtagg    900
gttgtagagg caaagtcacc catggctatt gtgataccat gctctggctc taatatagga    960
gcggagctta gagatggtga catctcctgg gattactttc ttgaacgtgc taaggagttt    1020
aaaaaactgt aatttactgc aagagagcag cccgtggatg catacacaaa catattgttc    1080
tccagcggta ctacgggaga acctaaagca atacttgga cacaagctac accccttaaa    1140
gcggccgctg acgatggtc ccacctggat atcaggaagg gtgacgtcat agtttggccg    1200
actaacctgg gatggatgat gggccctctgg ctggttacg ctagccttct gaatggggcc    1260
agcattgcat tgtacaatgg ctcaccgctt gtatcaggct tcgcgaagtt cgtacaggac    1320
gccaaggtaa caatgctagg cgtagttccg tccatagtta ggtcttggaa gagcacgaac    1380
tgcgttagtg gctacgattg gagcactatt cgttgtttca gctcttctgg cgaggccagc    1440
aacgttgatg aatatttgtg gttgatgggg agagcgaact acaaacctgt tattgagatg    1500
tgcggcggaa ctgagattgg gggagcattc ccgccggtt cttttctaca agcccaaagt    1560
ttatcctctt ttagcagcca gtgcatgggc tgtacactat acattctgga caaaaatggt    1620
tatccgatgc cgaaaaacaa gccccggcatc ggagaactgg ccctaggacc cgtgatgttc    1680
ggcgctagta agacgttgtt gaatgggaat caccacgacg tttattttaa gggaatgcca    1740
actttgaatg gcgaagtact tcgtagacac ggagcatcct ttgagttgac ttcaaacggt    1800
tactaccacg ctcatggacg tgccgatgat acgatgaaca ttgggggaat taaaatttca    1860
tccatagaaa tagaacgtgt gtgtaacgaa gtcgatgatc gtgtattcga gactacagcg    1920
atcggtgtcc caccgttggg tgggggacca gaacaattgg taatcttttt tgttctgaaa    1980
gactccaacg atacgaccat cgacctaaat cagctgcgtc tatccttttaa tcctgggcttg    2040
cagaaaaagc taaatccttt attcaaagtc actagagttg ttcctttatc ttcattacca    2100
agaactgcaa caaataaaat aatgcgtaga gttctaaggc agcagtttag tcatttcgaa    2160

SEQ ID NO: 90           moltype = AA  length = 720
FEATURE                 Location/Qualifiers
source                  1..720
                        mol_type = protein
                        organism = Cannabis sativa
SEQUENCE: 90
MGKNYKSLDS VVASDFIALG ITSEVAETLH GRLAEIVCNY GAATPQTWIN IANHILSPDL     60
PFSLHQMLFY GCYKDFGPAP PAWIPDPEKV KSTNLGALLE KRGKEFLGVK YKDPISSFSH    120
FQEFSVRNPE VYWRTVLMDE MKISFSKDPE CILRRDDINN PGGSEWLPGG YLNSAKNCLN    180
VNSNKKLNDT MIVWRDEGND DLPLNKLTLD QLRKRVWLVG YALEEMGLEK GCAIAIDMPM    240
HVDAVVIYLA IVLAGYVVVS IADSFSAPEI STRLRLSKAK AIFTQDHIIR GKKRIPLYSR    300
VVEAKSPMAI VIPCSGSNIG AELRDGDISW DYFLERAKEF KNCEFTAREQ PVDAYTNILF    360
SSGTTGEPKA IPWTQATPLK AAADGWSHLD IRKGDVIVWP TNLGWMMGPW LVYASLLNGA    420
SIALYNGSPL VSGFAKFVQD AKVTMLGVVP SIVRSWKSTN CVSGYDWSTI RCFSSSGEAS    480
NVDEYLWLMG RANYKPVIEM CGGTEIGGAF SAGSFLQAQS LSSFSSQCMG CTLYILDKNG    540
YPMPKNKPGI GELALGPVMF GASKTLLNGN HHDVYFKGMP TLNGEVLRRH GDIFELTSNG    600
YYHAHGRADD TMNIGGIKIS SIEIERVCNE VDDRVFETTA IGVPPLGGGP EQLVIFFVLK    660
DSNDTTIDLN QLRLSFNLGL QKKLNPLFKV TRVVPLSSLP RTATNKIMRR VLRQQFSHFE    720

SEQ ID NO: 91           moltype = DNA  length = 1599
FEATURE                 Location/Qualifiers
source                  1..1599
                        mol_type = genomic DNA
                        organism = Cannabis sativa
SEQUENCE: 91
atggaaaagt ctggttatgg tagagatggt atctacaggt ctttaagacc accattgcat     60
ttgccaaaca caacaacttt gtccatggtc agtttcttgt tcagaaactc ttcttcctac    120
ccacaaaaac cagccttgat tgactctgaa actaatcaaa tcttgtccctt ctcccacttc    180
aaatccaccg ttattaaggt ttctcacggt ttcttgaact tgggtatcaa gagaatgac    240
```

```
tggttgatct acgctccaaa ctctattcat ttcccagttt gctttttggg tattattgct    300
tctggtgcta ttgctactac ttccaaccca ttatacaccg tcagtgaatt gtctaagcaa    360
gtcaaggatt ctaacccaaa gttgattatc accgttccac aattattgga aaaggtcaag    420
ggtttcaact tgccaaccat tttgattggt ccagactcag aacaagaatc tcttcagat     480
aaggttatga ccttcaacga tttggttaac ttgggtggtt cttctggttc tgaatttcca    540
atcgttgatg acttcaagca atctgatact gctgctttgt tgtactcttc tggtactact    600
ggtatgtcta aaggttggtt gactcacaag aactttatcg cctcttcttt gatggttacc    660
atggaacaag acttggttgg tgaaatggat aacgttttct tgtgcttctt gccaatgttc    720
catgttttcg gtttggccat tattacctac gctcaattgc aaagaggtaa cactgttatt    780
tccgccagat tcgatttgga aaagatgttg aaggacgtcg aaaagtatgt tactcatttg    840
tggtggcctc cagttatttt ggctttgtct aaaaactcca tggttaagtt caacttgtca    900
tccatcaagt acattggttc aggtgctgct ccattgggta aggatttgat ggaagaatgt    960
tctaaatggc catacggtat agttgctcaa ggttacggta tgactgaaac ttgtggtatc   1020
gtttctatgg aagatatcag aggtggtaag agaaattctg gttcagctgg tatgttggct   1080
tcaggtgttg aagctcaaat agtttctgtt gataccttga aaccattgcc accaaatcaa   1140
ttgggtgaaa tttgggttaa gggtccaaat atgatgcaag ttacttcaa caatccacaa    1200
gctaccaagt tgaccattga taagaaaggt tgggttcata ctggtgactt gggttacttt   1260
gatgaagatg gtcacttgta ctgggacaga atcaaagaat tgattaagta caagggtttt   1320
caagtcgctc cagctgaatt ggaaggtttg ttggttctc atccagaaat attggatgcc    1380
tggattccat ttccagatgc tgaagctggt gaagttccag ttgcttattg gagatcacca   1440
aactcttcat tgactgaaaa cgacgtcaag aagttcattg ctggtcaagt tgcttctttc   1500
aagagattga aaaggtcac cttcatcaac tctgttccaa aatctgcttc cggtaagatc    1560
ttgagaagag aattgatcca aaaggtcaga tccaatatg                           1599

SEQ ID NO: 92            moltype = AA  length = 533
FEATURE                  Location/Qualifiers
source                   1..533
                         mol_type = protein
                         organism = Cannabis sativa
SEQUENCE: 92
MEKSGYGRDG IYRSLRPPLH LPNNNNLSMV SFLFRNSSSY PQKPALIDSE TNQILSFSHF    60
KSTVIKVSHG FLNLGIKKND WLIYAPNSIH FPVCFLGIIA SGAIATTSNP LYTVSELSKQ   120
VKDSNPKLII TVPQLLEKVK GFNLPTILIG PDSEQESSSD KVMTFNDLVN LGGSSGSEFP   180
IVDDFKQSDT AALLYSSGTT GMSKGWLTHK NFIASSLMVT MEQDLVGEMD NVFLCFLPMF   240
HVFGLAIITY AQLQRGNTVI SARFDLEKML KDVEKYVTHL WWPPVILALS KNSMVKFNLS   300
SIKYIGSGAA PLGKDLMEEC SKWPYGIVAQ GYGMTETCGI VSMEDIRGGK RNSGSAGMLA   360
SGVEAQIVSV DTLKPLPPNQ LGEIWVKGPN MMQGYFNNPQ ATKLTIDKKG WVHTGDLGYF   420
DEDGHLYWDR IKELIKYKGF QVAPAELEGL LVSHPEILDA WIPFPDAEAG EVPVAYWRSP   480
NSSLTENDVK KFIAGQVASF KRLRKVTFIN SVPKSASGKI LRRELIQKVR SNM          533

SEQ ID NO: 93            moltype = DNA  length = 744
FEATURE                  Location/Qualifiers
misc_feature             1..744
                         note = Artificial acetoacetyl-CoA reductase (PhaB)
                         nucleotide sequence
source                   1..744
                         mol_type = other DNA
                         organism = synthetic construct
SEQUENCE: 93
atgacgcaga gaatcgccta tgtaacgggt gggatgggtg ggataggaac cgccatatgt     60
cagagactag caaaggacgg attcagggtt gtagccggtt gcggtcctaa tagtccaaga   120
agagagaaat ggttggaaca gcaaaaagct ctaggatttg attttatagc atcagaaggg   180
aatgttgctg actgggattc tacaaagacg gcatttgaca aagtgaaatc tgaagtcggc   240
gaggtcgatg tcctaattaa caacgccggc atcaccagag atgtggtttt caggaagatg   300
actagggctg actgggacgc cgttgatagac acaaatttga cgagcttgtt caacgtcaca   360
aagcaagtaa ttgacggcat ggcagatcgt gggtggggaa ggatagtcaa tatctccagc   420
gtcaacggtc agaaaggcca gttcggacag actaactact ccacagcgaa ggctggctta   480
cacgggattca cgatggcctt ggcccaagag gtggctacta aaggggtgac tgtgaacaca   540
gtgtcaccag gatacatcgc gacggatatg gtcaaagcta ttagacaaga tgtcctggac   600
aagattgttg ccactattcc cgtaaagagg cttgggttac cagaagagat agcttcaatt   660
tgcgcttggc tatctagtga ggaatcaggg ttcagcactg ggcggactt tcattaaac    720
ggtggattac acatgggagg atcc                                          744

SEQ ID NO: 94            moltype = AA  length = 248
FEATURE                  Location/Qualifiers
REGION                   1..248
                         note = Mutant acetoacetyl-CoA reductase (PhaB)
source                   1..248
                         mol_type = protein
                         organism = synthetic construct
SEQUENCE: 94
MTQRIAYVTG GMGGIGTAIC QRLAKDGFRV VAGCGPNSPR REKWLEQQKA LGFDFIASEG    60
NVADWDSTKT AFDKVKSEVG EVDVLINNAG ITRDVVFRKM TRADWDAVID TNLTSLFNVT   120
KQVIDGMADR GWGRIVNISS VNGQKGQFGQ TNYSTAKAGL HGFTMALAQE VATKGVTVNT   180
VSPGYIATDM VKAIRQDVLD KIVATIPVKR LGLPEEIASI CAWLSSEESG FSTGADFSLN   240
GGLHMGGS                                                            248

SEQ ID NO: 95            moltype = DNA  length = 408
FEATURE                  Location/Qualifiers
```

-continued

```
misc_feature            1..408
                        note = Artificial (R)-specific enoyl-CoA hydratase (PhaJ)
source                  1..408
                        mol_type = other DNA
                        organism = synthetic construct
SEQUENCE: 95
atgtctgccc agagtctgga agtcggtcaa aaagcaagac tgtcaaaaag atttggggcg   60
gcagaggtag cggcgttcgc ggcgctgtct gaggatttta atccactgca cttagatcct  120
gcgttcgccg cgacaacagc attcgagagg cccatcgtgc acggcatgct acttgcctgt  180
ttgttctcag gtctactggg tcaacagtta cctgggaaag gaagcatcta tctgggacag  240
tcattgtctt ttaagctgcc cgtcttcgtc ggcgatgagg tgacagcaga agtagaagtc  300
acagcattga gggaagacaa gcctattgcg acccttacta ctcgtatttt tactcagggc  360
ggagcct tag cagtgacagg agaagctgta gtaaaactac aggatcc             408

SEQ ID NO: 96           moltype = AA  length = 136
FEATURE                 Location/Qualifiers
REGION                  1..136
                        note = Mutant (R)-specific enoyl-CoA hydratase (PhaJ)
source                  1..136
                        mol_type = protein
                        organism = synthetic construct
SEQUENCE: 96
MSAQSLEVGQ KARLSKRFGA AEVAAFAALS EDFNPLHLDP AFAATTAFER PIVHGMLLAS   60
LFSGLLGQQL PGKGSIYLGQ SLSFKLPVFV GDEVTAEVEV TALREDKPIA TLTTRIFTQG  120
GALAVTGEAV VKLPGS                                                 136

SEQ ID NO: 97           moltype = AA  length = 2233
FEATURE                 Location/Qualifiers
REGION                  1..2233
                        note = Mutated acetyl-CoA carboxylase (ACC1) (S659A, S1157A)
source                  1..2233
                        mol_type = protein
                        organism = synthetic construct
SEQUENCE: 97
MSEESLFESS PQKMEYEITN YSERHTELPG HFIGLNTVDK LEESPLRDFV KSHGGHTVIS   60
KILIANNGIA AVKEIRSVRK WAYETFGDDR TVQFVAMATP EDLEANAEYI RMADQYIEVP  120
GGTNNNNYAN VDLIVDIAER ADVDAVWAGW GHASENPLLP EKLSQSKRKV IFIGPPGNAM  180
RSLGDKISST IVAQSAKVPC IPWSGTGVDT VHVDEKTGLV SVDDDIYQKG CCTSPEDGLQ  240
KAKRIGFPVM IKASEGGGGK GIRQVEREED FIALYHQAAN EIPGSPIFIM KLAGRARHLE  300
VQLLADQYGT NISLFGRDCS VQRRHQKIIE EAPVTIAKAE TFHEMEKAAV RLGKLVGYVS  360
AGTVEYLYSH DDGKFYFLEL NPRLQVEHPT TEMVSGVNLP AAQLQIAMGI PMHRISDIRT  420
LYGMNPHSAS EIDFEFKTQD ATKKQRRPIP KGHCTACRIT SEDPNDGFKP SGGTLHELNF  480
RSSSNVWGYF SVGNNGNIHS FSDSQFGHIF AFGENRQASR KHMVVALKEL SIRGDFRTTV  540
EYLIKLLETE DFEDNTITTG WLDDLITHKM TAEKPDPTLA VICGAATKAF LASEEARHKY  600
IESLQKGQVL SKDLLQTMFP VDFIHEGKRY KFTVAKSGND RYTLFINGSK CDIILRQLAD  660
GGLLIAIGGK SHTIYWKEEV AATRLSVDSM TTLEVENDP TQLRTPSPGK LVKFLVENGE  720
HIIKGQPYAE IEVMKMQMPL VSQENGIVQL LKQPGSTIVA GDIMAIMTLD DPSKVKHALP  780
FEGMLPDFGS PVIEGTKPAY KFKSLVSTLE NILKGYDNQV IMNASLQQLI EVLRNPKLPY  840
SEWKLHISAL HSRLPAKLDE QMEELVARSL RRGAVFPARQ LSKLIDMAVK NPEYNPDKLL  900
GAVVEPLADI AHKYSNGLEA HEHSIFVHFL EEYYEVEKLF NGPNVREENI ILKLRDENPK  960
DLDKVALTVL SHSKVSAKNN LILAILKHYQ PLCKLSSKVS AIFSTPLQHI VELESKATAK 1020
VALQAREILI QGALPSVKER TEQIEHILKS SVVKVAYGSS NPKRSEPDLN ILKDLIDSNY 1080
VVFDVLLQFL THQDPVVTAA AAQVIRRAY RAYTIGDIRV HEGVTVPIVE WKFQLPSAAF 1140
STFPTVKSKM GMNRAVSVAD LSYVANSQSS PLREGILMAV DHLDDVDEIL SQSLEVIPRH 1200
QSSSNGPAPD RSGSSASLSN VANVCVASTE GFESEEEILV RLREILDLNK QELINASIRR 1260
ITFMFGFKDG SYPKYYTFNG PNYNENETIR HIEPALAFQL ELGRLSNFNI KPIFTDNRNI 1320
HVYEAVSKTS PLDKRFFTRG IIRTGHIRDD ISIQEYLTSE ANRLMSDILD NLEVTDTSNS 1380
DLNHIFINFI AVFDISPEDV EAAFGGFLER FGKRLLRLRV SSAEIRIIIK DPQTGAPVPL 1440
RALINNVSGY VIKTEMYTEV KNAKGEWVFK SLGKPGSMHL RPIATPYPVK EWLQPKRYKA 1500
HLMGTTYVYD FPELFRQASS SQWKNFSADV KLTDDFFISN ELIEDENGEL TEVEREPGAN 1560
AIGMVAFKIT VKTPEYPRGR QFVVVANDIT FKIGSFGPQE DEFFNKVTEY ARKRGIPRIY 1620
LAANSGARIG MAEEIVPLFQ VAWNDAANPD KGFQYLYLTS EGMETLKKFD KENSVLTERT 1680
VINGEERFVI KTIIGSEDGL GVECLRGSGL IAGATSRAYH DIFTITLVTC RSVGIGAYLV 1740
RLGQRAIQVE GQPIILTGAP AINKMLGREV YTSNLQLGGT QIMYNNGVSH LTAVDDLAGV 1800
EKIVEWMSYV PAKRNMPVPI LETKDTWDRP VDFTPTNDET YDVRWMIEGR ETESGFEYGL 1860
FDKGSFFETL SGWAKGVVVG RARLGGIPLG VIGVETRTVE NLIPADPANP NSAETLIQEP 1920
GQVWHPNSAF KTAQAINDFN NGEQLPMMIL ANWRGFSGGQ RDMFNEVLKY GSFIVDALVD 1980
YKQPIIIYIP PTGELRGGSW VVVDPTINAD QMEMYADVNA RAGVLEPQGM VGIKFRREKL 2040
LDTMNRLDDK YRELRSQLSN KSLAPEVHQQ ISKQLADRER ELLPIYGQIS LQFADLHDRS 2100
SRMVAKGVIS KELEWTEARR FFFWRLRRRL NEEYLIKRLS HQVGEASRLE KIARIRSWYP 2160
ASVDHEDDRQ VATWIEENYK TLDDKLKGLK LESFAQDLAK KIRSDHDNAI DGLSEVIKML 2220
STDDKEKLLK TLK                                                   2233

SEQ ID NO: 98           moltype = AA  length = 321
FEATURE                 Location/Qualifiers
REGION                  1..321
                        note = Truncated geranyl pyrophosphate olivetolic acid
                               geranyltransferase CsGOTt75
source                  1..321
```

```
                         mol_type = protein
                         organism = synthetic construct
SEQUENCE: 98
MAATTNQTEP PESDNHSVAT KILNFGKACW KLQRPYTIIA FTSCACGLFG KELLHNTNLI    60
SWSLMPKAFF FLVAILCIAS FTTTINQIYD LHIDRINKPD LPLASGEISV NTAWIMSIIV   120
ALFGLIITIK MKGGPLYIFG YCFGIFGGIV YSVPPFRWKQ NPSTAFLLNF LAHIITNFTF   180
YYASRAALGL PFELRPSFTF LLAFMKSMGS ALALIKDASD VEGDTKFGIS TLASKYGSRN   240
LTLFCSGIVL LSYVAAILAG IIWPQAFNSN VMLLSHAILA FWLILQTRDF ALTNYDPEAG   300
RRFYEFMWKL YYAEYLVYVF I                                             321

SEQ ID NO: 99            moltype = AA   length = 363
FEATURE                  Location/Qualifiers
REGION                   1..363
                         note = Truncated geranyl pyrophosphate olivetolic acid
                          geranyltransferase CsGOTt33
source                   1..363
                         mol_type = protein
                         organism = synthetic construct
SEQUENCE: 99
MSHPKTPIKY SYNNFPSKHC STKSFHLQNK CSESLSIAKN SIRAATTNQT EPPESDNHSV    60
ATKILNFGKA CWKLQRPYTI IAFTSCACGL FGKELLHNTN LISWSLMFKA FFFLVAILCI   120
ASFTTTINQI YDLHIDRINK PDLPLASGEI SVNTAWIMSI IVALFGLIIT IKMKGGPLYI   180
FGYCFGIFGG IVYSVPPFRW KQNPSTAFLL NFLAHIITNF TFYYASRAAL GLPFELRPSF   240
TFLLAFMKSM GSALALIKDA SDVEGDTKFG ISTLASKYGS RNLTLFCSGI VLLSYVAAIL   300
AGIIWPQAFN SNVMLLSHAI LAFWLILQTR DFALTNYDPE AGRRFYEFMW KLYYAEYLVY   360
VFI                                                                 363

SEQ ID NO: 100           moltype = AA   length = 323
FEATURE                  Location/Qualifiers
REGION                   1..323
                         note = Truncated geranyl pyrophosphate olivetolic acid
                          geranyltransferase CsPT4t
source                   1..323
                         mol_type = protein
                         organism = synthetic construct
SEQUENCE: 100
MSAGSDQIEG SPHHESDNSI ATKILNFGHT CWKLQRPYVV KGMISIACGL FGRELFNNRH    60
LFSWGLMWKA FFALVPILSF NFFAAIMNQI YDVDIDRINK PDLPLVSGEM SIETAWILSI   120
IVALTGLIVT IKLKSAPLFV FIYIFGIFAG FAYSVPPIRW KQYPFTNFLI TISSHVGLAF   180
TSYSATTSAL GLPFVWRPAF SFIIAFMTVM GMTIAFAKDI SDIEGDAKYG VSTVATKLGA   240
RNMTFVVSGV LLLNYLVSIS IGIIWPQVFK SNIMILSHAI LAFCLIFQTR ELALANYASA   300
PSRQFFEFIW LLYYAEYFVY VFI                                           323

SEQ ID NO: 101           moltype = AA   length = 323
FEATURE                  Location/Qualifiers
REGION                   1..323
                         note = Truncated geranyl pyrophosphate olivetolic acid
                          geranyltransferase CsPT7t
source                   1..323
                         mol_type = protein
                         organism = synthetic construct
SEQUENCE: 101
MSTDTANQTE PPESNTKYSV VTKILSFGHT CWKLQRPYTF IGVISCACGL FGRELFHNTN    60
LLSWSLMLKA FSSLMVILSV NLCTNIINQI TDLDIDRINK PDLPLASGEM SIETAWIMSI   120
IVALTGLILT IKLNCGPLFI SLYCVSILVG ALYSVPPFRW KQNPNTAFSS YPMGLVIVM    180
TCYYASRAAF GLPFEMSPPF TFILAFVKSM GSALFLCKDV SDIEGDSKHG ISTLATRYGA   240
KNITFLCSGI VLLTYVSAIL AAIIWPQAFK SNVMLLSHAT LAFWLIFQTR EFALTNYNPE   300
AGRKFYEFMW KLHYAEYLVY VFI                                           323

SEQ ID NO: 102           moltype = AA   length = 315
FEATURE                  Location/Qualifiers
REGION                   1..315
                         note = Truncated geranyl pyrophosphate olivetolic acid
                          geranyltransferase HlPT1Lt
source                   1..315
                         mol_type = protein
                         organism = synthetic construct
SEQUENCE: 102
MDRPPESGNL SALTNVKDFV SVCWEYVRPY TAKGVIICSS CLFGRELLEN PNLFSWPLIF    60
RALLGMLAIL GSCFYTAGIN QIFDMDIDRI NKPDLPLVSG RISVESAWLL TLSPAIIGFI   120
LILKLNSGPL LTSLYCLAIL SGTIYSVPPF RWKKNPITAF LCILMIHAGL NFSVYYASRA   180
ALGLAFVWSP SFSFITAFIT FMTLTLASSK DLSDSINGDRK FGVETFATKL GAKNITLLGT   240
GLLLLNYVAA ISTAIIWPKA FKSNIMLLSH AILAFSLFFQ ARELDRTNYT PEACKSFYEF   300
IWILFSAEYV VYLFI                                                    315

SEQ ID NO: 103           moltype = AA   length = 329
FEATURE                  Location/Qualifiers
REGION                   1..329
                         note = Truncated geranyl pyrophosphate olivetolic acid
```

```
                            geranyltransferase H1PT2t
source                      1..329
                            mol_type = protein
                            organism = synthetic construct
SEQUENCE: 103
MGHLPRPNSL TAWSHQSEFP STIVTKGSNF GHASWKFVRP IPFVAVSIIC TSLFGAELLK    60
NPNLFSWQLM FDAFQGLVVI LLYHIYINGL NQIYDLESDR INKPDLPLAA EEMSVKSAWF   120
LTIFSAVASL LLMIKLKCGL FLTCMYCCYL VIGAMYSVPP FRWKMNTFTS TLWNFSEIGI   180
GINFLINYAS RATLGLPFQW RPPPFTFIIGF VSTLSIILSI LKDVPDVEGD KKVGMSTLPV   240
IFGARTIVLV GSGFFLLNYV AAIGVAIMWP QAFKGYIMIP AHAIFASALI FKTWLLDKAN   300
YAKEASDSYY HFLWFLMIAE YILYPFIST                                     329

SEQ ID NO: 104              moltype = AA  length = 514
FEATURE                     Location/Qualifiers
REGION                      1..514
                            note = Truncated tetrahydrocannabinolic acid synthase
                            THCASt28
source                      1..514
                            mol_type = protein
                            organism = synthetic construct
SEQUENCE: 104
MNFLKCFSEY IPNNPANPKF IYTQHDQLYM SVLNSTIQNL RFTSDTTPKP LVIVTPSNVS    60
HIQASILCSK KVGLQIRTRS GGHDAEGMSY ISQVPFVVVD LRNMHSIKID VHSQTAWVEA   120
GATLGEVYYW INEKNENFSF PGGYCPTVGV GGHFSGGGYG ALMRNYGLAA DNIIDAHLVN   180
VDGKVLDRKS MGEDLFWAIR GGGGENFGII AAWKIKLVAV PSKSTIFSVK KNMEIHGLVK   240
LFNKWQNIAY KYDKDLVLMT HFITKNITDN HGKNKTTVHG YFSSIFHGGV DSLVDLMNKS   300
FPELGIKKTD CKEFSWIDTT IFYSGVVNFN TANFKKEILL DRSAGKKTAF SIKLDYVKKP   360
IPETAMVKIL EKLYEEDVGV GMYVLYPYGG IMEEISESAI PFPHRAGIMY ELWYTASWEK   420
QEDNEKHINW VRSVYNFTTP YVSQNPRLAY LNYRDLDLGK TNPESPNNYT QARIWGEKYF   480
GKNFNRLVKV KTKADPNNFF RNEQSIPPLP PHHH                               514

SEQ ID NO: 105              moltype = AA  length = 517
FEATURE                     Location/Qualifiers
REGION                      1..517
                            note = Truncated cannabidiolic acid synthase CBDASt28*
source                      1..517
                            mol_type = protein
                            organism = synthetic construct
SEQUENCE: 105
MNPRENFLKC FSQYIPNNAT NLKLVYTQNN PLYMSVLNST IHNLRFTSDT TPKPLVIVTP    60
SHVSHIQGTI LCSKKVGLQI RTRSGGHDSE GMSYISQVPF VIVDLRNMRS IKIDVHSQTA   120
WVEAGATLGE VYYWVNEKNE NLSLAAGYCP TVCAGGHFGG GGYGPLMRNY GLAADNIIDA   180
HLVNVHGKVL DRKSMGEDLF WALRGGGAES FGIIVAWKIR LVAVPKSTMF SVKKIMEIHE   240
LVKLVNKWQN IAYKYDKDLL LMTHFITRNI TDNQGKNKTA IHTYFSSVFL GGVDSLVDLM   300
NKSFPELGIK KTDCRQLSWI DTIIFYSGVV NYDTDNFNKE ILLDRSAGQN GAFKIKLDYV   360
KKPIPESVFV QILEKLYEED IGAGMYALYP YGGIMDEISE SAIPFPHRAG ILYELWYICS   420
WEKQEDNEKH LNWIRNIYNF MTPYVSKNPR LAYLNYRDLD IGINDPKNPN NYTQARIWGE   480
KYFGKNFDRL VKVKTLVDPN NFFRNEQSIP PLPRHRH                            517

SEQ ID NO: 106              moltype = AA  length = 2051
FEATURE                     Location/Qualifiers
REGION                      1..2051
                            note = Mutated fatty acid synthase (FAS1, I306A, R1834K)
source                      1..2051
                            mol_type = protein
                            organism = synthetic construct
SEQUENCE: 106
MDAYSTRPLT LSHGSLEHVL LVPTASFFIA SQLQEQFNKI LPEPTEGFAA DDEPTTPAEL    60
VGKFLGYVSS LVEPSKVGQF DQVLNLCLTE FENCYLEGND IHALAAKLLQ ENDTTLVKTK   120
ELIKNYITAR IMAKRPFDKK SNSALFRAVG EGNAQLVAIF GGQGNTDDYF EELRDLYQTY   180
HVLVGDLIKF SAETLSELIR TTLDAEKVFT QGLNILEWLE NPSNTPDKDY LLSIPISCPL   240
IGVIQLAHYV VTAKLLGFTP GELRSYLKGA TGHSQGLVTA VAIAETDSWE SFFVSVRKAI   300
TVLFFGGVRC YEAYPNTSLP PSILEDSLEN NEGVPSPMLS ISNLTQEQVQ DYVNKTNSHL   360
PAGKQVEISL VNGAKNLVVS GPPQSLYGLN LTLRKAKAPS GLDQSRIPFS ERKLKFSNRF   420
LPVASPFHSH LLVPASDLIN KDLVKNNVSF NAKDIQIPVY DTFDGSDLRV LSGSISERIV   480
DCIIRLPVKW ETTTQFKATH ILDFGPGGAS GLGVLTHRNK DGTGVRVIVA GTLDINPDDD   540
YGFKQEIFDV TSNGLKKNPN WLEEYHPKLI KNKSGKIFVE TKFSKLIGRP PLLVPGMTPC   600
TVSPDFVAAT TNAGYTIELA GGGYFSAAGM TAAIDSVVSQ IEKGSTFGIN LIYVNPFMLQ   660
WGIPLIKELR SKGYPIQFLT IGAGVPSLEV ASEYIETLGL KYLGLKPGSI DAISQVINIA   720
KAHPNFPIAL QWTGGRGGGH HSFEDAHTPM LQMYSKIRRH PNIMLIFSGG FGSADDTYPY   780
LTGEWSTKFD YPPMPFDGFL FGSRVMIAKE VKTSPDAKKC IAACTGVPDD KWEQTYKKPT   840
GGIVTVRSEM GEPIHKIATR GVMLWKEFDE TIFNLPKNKL VPTLEAKRDY IISRLNADFQ   900
KPWFATVNGQ ARDLATMTYE EVAKRLVELM FIRSTNSWFD TWRTFTGDF LRRVEERFTK    960
SKTLSLIQSY SLLDKPDEAI EKVFNAYPAA REQFLNAQDI DHFLSMCQNP MQKPVPFVPV  1020
LDRRFEIFFK KDSLWQSEHL EAVVDQDVQR TCILHGPVAA QFTKVIDEPI KSIMDGIHDG  1080
HIKKLLHQYY GDDESKIPAV EYFGGESPVD VQSQVDSSSV SEDSAVFKAT SSTDEESWFK  1140
ALAGSEINWR HASFLCSFIT QDKMFVSNPI RKVFKPSQGM VVEISNGNTS SKTVVTLSEP  1200
VQGELKPTVI LKLLKENIIQ MEMIENRTMD GKPVSLPLLY NFNPDNGFAP ISEVMEDRNQ  1260
RIKEMYWKLW IDEPFNLDFD PRDVIKGKDF EITAKEVYDF THAVGNNCED FVSRPDRTML  1320
```

```
APMDFAIVVG WRAIIKAIFP NTVDGDLLKL VHLSNGYKMI PGAKPLQVGD VVSTTAVIES    1380
VVNQPTGKIV DVVGTLSRNG KPVMEVTSSF FYRGNYTDFE NTFQKTVEPV YQMHIKTSKD    1440
IAVLRSKEWF QLDDEDFDLL NKTLTFETET EVTFKNANIF SSVKCFGPIK VELPTKETVE    1500
IGIVDYEAGA SHGNPVVDFL KRNGSTLEQK VNLENPIPIA VLDSYTPSTN EPYARVSGDL    1560
NPIHVSRHFA SYANLPGTIT HGMFSSASVR ALIENWAADS VSSRVRGYTC QFVDMVLPNT    1620
ALKTSIQHVG MINGRKLIKF ETRNEDDVVV LTGEAEIEQP VTTFVFTGQG SQEQGMGMDL    1680
YKTSKAAQDV WNRADNHFKD TYGFSILDIV INNPVNLTIH FGGEKGKRIR ENYSAMIFET    1740
IVDGKLKTEK IFKEINEHST SYTFRSEKGL LSATQFTQPA LTLMEKAAFE DLKSKGLIPA    1800
DATFAGHSLG EYAALASLAD VMSIESLVEV VFYFGMTMQV AVPRDELGRS NYGMIAINPG    1860
RVAASFSQEA LQYVVERVGK RTGWLVEIVN YNVENQQYVA AGDLRALDTV TNVLNFIKLQ    1920
KIDIIELQKS LSLEEVEGHL FEIIDEASKK SAVKPRPLKL ERGFACIPLV GISVPPHSTY    1980
LMNGVKPFKS FLKKNIIKEN VKVARLAGKY IPNLTAKPFQ VTKEYFQDVY DLTGSEPIKE    2040
IIDNWEKYEQ S                                                        2051

SEQ ID NO: 107           moltype = AA   length = 1887
FEATURE                  Location/Qualifiers
REGION                   1..1887
                         note = Mutated fatty acid synthase (FAS2, G1250S)
source                   1..1887
                         mol_type = protein
                         organism = synthetic construct
SEQUENCE: 107
MKPEVEQELA HILLTELLAY QFASPVRWIE TQDVFLKDFN TERVVEIGPS PTLAGMAQRT    60
LKNKYESYDA ALSLHREILC YSKDAKEIYY TPDPSELAAK EEPAKEEAPA PTPAASAPAP    120
AAAAPAPVAA AAPAAAAAEI ADEPVKASLL LHVLVAHKLK KSLDSIPMSK TIKDLVGGKS    180
TVQNEILGDL GKEFGTTPEK PEETPLEELA ETFQDTFSGA LGKQSSSLLS RLISSKMPGG    240
FTITVARKYL QTRWGLPSGR QDGVLLVALS NEPAARLGSE ADAKAFLDSM AQKYASIVGV    300
DLSSAASASG AAGAGAAAGA AMIDAGALEE ITKDHKVLAR QQLQVLARYL KMDLDNGERK    360
FLKEKDTVAE LQAQLDYLNA ELGEFFVNGV ATSFSRKKAR TFDSSWNWAK QSLLSLYFEI    420
IHGVLKNVDR EVVSEAINIM NRSNDALIKF MEYHISNTGR TKGENYQLVK TLGEQLIENC    480
KQVLDVDPVY KDVAKPTGPK TAIDKNGNIT YSEEPREKVR KLSQYVQEMA LGGPITKESQ    540
PTIEEDLTRV YKAISAQADK QDISSSTRVE FEKLYSDLMK FLESSKEIDP SQTTQLAGMD    600
VEDALDKDST KEVASLPNKS TISKTVSSTI PRETIPFLHL RKKTPAGDWK YDRQLSSLFL    660
DGLEKAAFNG VTFKDKYVLI TGAGKGSIGA EVLQGLLQGS AKVVVTTSRF SKQVTDYYQS    720
IYAKYGAKGS TLIVVPFNQG SKQDVEALIE FIYDTEKNGG LGWDLDAIIP FAAIPEQGIE    780
LEHIDSKSEF AHRIMLTNIL RMMGCVKKQK SARGIETRPA QVILPMSPNH GTFGGDGMYS    840
ESKLSLETLF NRWHSESWAN QLTVCGAIIG WTRGTGLMSA NNIIAEGIEK MGVRTFSQKE    900
MAFNLLGLLT PEVVELCQKS PVMADLNGGL QFVPELKEFT AKLRKELVET SEVRKAVSIE    960
TALEHKVVNG NSADAAYAQV EIQPRANIQL DFPELKPYKQ VKQIAPAELE GLLDDLERVIV    1020
VTGFAEVGPW GSARTRWEME AFGEFSLEGC VEMAWIMGFI SYHNGNLKGR PYTGWVDSKT    1080
KEPVDDKDVK AKYETSILEH SGIRLIEPEL FNGYNPEKKE MIQEVIVEED LEPFEASKET    1140
AEQFKHQHGD KVDIFEIPET GEYSVKLLKG ATLYIPKALR FDRLVAGQIP TGWNAKTYGI    1200
SDDIISQVDP ITLFVLVSVV EAFIASGITD PYEMYKYVHV SEVGNCSGSS MGGVSALRGM    1260
FKDRFKDEPV QNDILQESFI NTMSAWVNML LISSSGPIKT PVGACATSVE SVDIGVETIL    1320
SGKARICIVG GYDDFQEEGS FEFGNMKATS NTLEEFEHGR TPAEMSRPAT TTRNGFMEAQ    1380
GAGIQIIMQA DLALKMGVPI YGIVAMAATA TDKIGRSVPA PGKGILTTAR EHHSSVKYAS    1440
PNLNMKYRKR QLVTREAQIK DWVENELEAL KLEAEEIPSE DQNEFLLERT REIHNEAESQ    1500
LRAAQQQWGN DFYKRDPRIA PLRGALATYG LTIDDLGVAS FHGTSTKAND KNESATINEM    1560
MKHLGRSEGN PVIGVFQKFL TGHPKGAAGA WMMNGALQIL NSGIIPGNRN ADNVDKILEQ    1620
FEYVLYPSKT LKTDGVRAVS ITSFGFGQKG GQAIVVHPDY LYGAITEDRY NEYVAKVSAR    1680
EKSAYKFFHN GMIYNKLFVS KEHAPYTDEL EEDVYLDPLA RVSKDKKSGS LTFNSKNIQS    1740
KDSYINANTI ETAKMIENMT KEKVSNGGVG VDVELITSIN VENDTFIERN FTPQEIEYCS    1800
AQPSVQSSFA GTWSAKEAVF KSLGVKSLGG GAALKDIEIV RVNKNAPAVE LHGNAKKAAE    1860
EAGVTDVKVS ISHDDLQAVA VAVSTKK                                       1887

SEQ ID NO: 108           moltype = AA   length = 371
FEATURE                  Location/Qualifiers
REGION                   1..371
                         note = MBPtag
source                   1..371
                         mol_type = protein
                         organism = synthetic construct
SEQUENCE: 108
MKIEEGKLVI WINGDKGYNG LAEVGKKFEK DTGIKVTVEH PDKLEEKFPQ VAATGDGPDI    60
IFWAHDRFGG YAQSGLLAEI TPDKAFQDKL YPFTWDAVRY NGKLIAYPIA VEALSLIYNK    120
DLLPNPPKTW EEIPALDKEL KAKGKSALMF NLQEPYFTWP LIAADGGYAF KYENGKYDIK    180
DVGVDNAGAK AGLTFLVDLI KNKHMNADTD YSIAEAAFNK GETAMTINGP WAWSNIDTSK    240
VNYGVTVLPT FKGQPSKPFV GVLSAGINAA SPNKELAKEF LENYLLTDEG LEAVNKDKPL    300
GAVALKSYEE ELAKDPRIAA TMENAQKGEI MPNIPQMSAF WYAVRTAVIN AASGRQTVDE    360
ALKDAQTRIT K                                                        371

SEQ ID NO: 109           moltype = AA   length = 24
FEATURE                  Location/Qualifiers
REGION                   1..24
                         note = ProA tag
source                   1..24
                         mol_type = protein
                         organism = synthetic construct
SEQUENCE: 109
```

```
                               MIFDGTTMSI AIGLLSTLGI GAEA                                   24

SEQ ID NO: 110           moltype = AA  length = 398
FEATURE                  Location/Qualifiers
source                   1..398
                         mol_type = protein
                         organism = Cannabis sativa
SEQUENCE: 110
MGLSLVCTFS FQTNYHTLLN PHNKNPKNSL LSYQHPKTPI IKSSYDNFPS KYCLTKNFHL    60
LGLNSHNRIS SQSRSIRAGS DQIEGSPHHE SDNSIATKIL NFGHTCWKLQ RPYVVKGMIS   120
IACGLFGREL FNNRHLFSWG LMWKAFFALV PILSFNFFAA IMNQIYDVDI DRINKPDLPL   180
VSGEMSIETA WILSIIVALT GLIVTIKLKS APLFVFIYIF GIFAGFAYSV PPIRWKQYPF   240
TNFLITISSH VGLAFTSYSA TTSALGLPFV WRPAFSFIIA FMTVMGMTIA FAKDISDIEG   300
DAKYGVSTVA TKLGARNMTF VVSGVLLLNY LVSISIGIIW PQVFKSNIMI LSHAILAFCL   360
IFQTRELALA NYASAPSRQF FEFIWLLYYA EYFVYVFI                          398

SEQ ID NO: 111           moltype = DNA  length = 1197
FEATURE                  Location/Qualifiers
source                   1..1197
                         mol_type = genomic DNA
                         organism = Cannabis sativa
SEQUENCE: 111
atgggtttat ctttggtctg caccttctcc tttcaaacta actaccacac tttattgaat    60
ccacataata agaatcctaa gaactcttta ttgtcctacc aacacccaaa gactcctatt   120
atcaagtcct cttacgataa cttcccatct aagtactgtt tgactaagaa tttccatttg   180
ttgggtttga attctcacaa cagaatttcc tcccaatccc gttctattag agccggttct   240
gatcaaatcg aaggttcccc tcatcatgag tccgataact ccattgctac taaaatttta   300
aatttcggtc atacttgttg gaagttgcaa cgtcctacg ttgtcaaggg tatgatctct   360
attgcttgtg gtttgttcgg tagagaattg tttaacaaca gacacttgtt ctcttggggt   420
ttgatgtgga aagcttttt cgctttggtc caaattttgt ctttcaattt cttcgccgcc   480
atcatgaacc aaatctacga tgttgatatc gaccgtatca caagccaga cttacccttta   540
gtttccggtg aaatgtccat tgaaactgct tggatcttgt ctatcattgt tgccttgact   600
ggtttaattg ttactattaa gttgaagtcc gctccattgt ttgtcttcat ctacatcttc   660
ggtatcttcg ctggtttcgc ttactccgtc ccacctatta gatggaaaca atatccttc   720
accaatttct tgatcactat ttcctctcat gttggtttgg ctttcacttc ttactctgcc   780
accacttctg ctttaggttt gccttttcgtt tggcgtcctg ccttctcttt cattattgct   840
ttcatgactg tcatgggtat gactattgcc tttgctaaag acatttctga tatcgaaggt   900
gatgctaagt acggtgtctc taccgttgct accaagttag gtgctagaaa tatgactttt   960
gttgtttctg gtgtcttatt gttgaactac ttggtttcta tctctattgg tatcatttgg  1020
ccacaagttt tcaagtctaa cattatgatc ttgtctcatg ctattttggc tttctgtttg  1080
atctttcaaa ctcgtgaatt agcctagca aattatgcct ctgccccatc ccgtcaattt  1140
ttcgaattca tctggttgtt atactatgcc gaatacttcg tttacgtctt catttaa     1197

SEQ ID NO: 112           moltype = AA  length = 522
FEATURE                  Location/Qualifiers
REGION                   1..522
                         note = Truncated acyl activating enzyme AAE (CsAAE3
                         truncation)
source                   1..522
                         mol_type = protein
                         organism = synthetic construct
SEQUENCE: 112
MEKSGYGRDG IYRSLRPPLH LPNNNNLSMV SFLFRNSSSY PQKPALIDSE TNQILSFSHF    60
KSTVIKVSHG FLNLGIKKND WLIYAPNSIH FPVCFLGIIA SGAIATTSNP LYTVSELSKQ   120
VKDSNPKLII TVPQLLEKVK GFNLPTILIG PDSEQESSSD KVMTFNDLVN LGGSSGEFP   180
IVDDFKQSDT AALLYSSGTT GMSKGWLTHK NFIASSLMVT MEQDLVGEMD NVFLCFLPMF   240
HVFGLAIITY AQLQRGNTVI SARFDLEKML KDVEKYVTHL WWPPVILALS KNSMVKFNLS   300
SIKYIGSGAA PLGKDLMEEC SKWPYGIVAQ GYGMTETCGI VSMEDIRGGK RNSGSAGMLA   360
SGVEAQIVSV DTLKPLPPNQ LGEIWVKGPN MMQGYFNNPQ ATKLTIDKKG WVHTGDLGYF   420
DEDGHLYWDR IKELIKYKGF QVAPAELEGL LVSHPEILDA WIPFPDAEAG EVPVAYWRSP   480
NSSLTENDVK KFIAGQVASF KRLRKVTFIN SVPKSASGKI LR                     522

SEQ ID NO: 113           moltype = AA  length = 526
FEATURE                  Location/Qualifiers
REGION                   1..526
                         note = Truncated 3-hydroxy-3-methyl-glutaryl-CoA reductase
                         (tHMG1)
source                   1..526
                         mol_type = protein
                         organism = synthetic construct
SEQUENCE: 113
MSDQLVKTEV TKKSFTAPVQ KASTPVLTNK TVISGSKVKS LSSAQSSSSG PSSSEEDDS    60
RDIESLDKKI RPLEELEALL SSGNTKQLKN KEVAALVIHG KLPLYALEKK LGDTTRAVAV   120
RRKALSILAE APVLASDRLP YKNYDYDRVF GACCENVIGY MPLPVGVIGP LVIDGTSYHI   180
PMATTEGCLV ASAMRGCKAI NAGGGATTVL TKDGMTRGPV VRFPTLKRSG ACKIWLDSEE   240
GQNAIKKAFN STSRFARLQH IQTCLAGDLL FMRFRTTTGD AMGMNMISKG VEYSLKQMVE   300
EYGWEDMEVV SVSGNYCTDK KPAAINWIEG RGKSVVAEAT IPGDVVRKVL KSDVSALVEL   360
NIAKNLVGSA MAGSVGGFNA HAANLVTAVF LALGQDPAQN VESSNCITLM KEVDGDLRIS   420
VSMPSIEVGT IGGGTVLEPQ GAMLDLLGVR GPHATAPGTN ARQLARIVAC AVLAGELSLC   480
```

```
AALAAGHLVQ SHMTHNRKPA EPTKPNNLDA TDINRLKDGS VTCIKS                      526

SEQ ID NO: 114          moltype = DNA  length = 1581
FEATURE                 Location/Qualifiers
misc_feature            1..1581
                        note = Truncated 3-hydroxy-3-methyl-glutaryl-CoA reductase
                        (tHMG1)
source                  1..1581
                        mol_type = other DNA
                        organism = synthetic construct
SEQUENCE: 114
atgtccgatc aattagtcaa gaccgaagtc accaagaagt ccttcaccgc cccagttcaa   60
aaagcctcca ctccagtctt aactaacaag accgttattt ctggttccaa ggttaagtct   120
ttatcctccg ctcaatcctc ctcttccggt ccatcttctt cctctgaaga agatgattcc   180
cgtgacattg agtccttgga taagaaaatc agacctttgg aagaattaga agctttgtta   240
tcctctggta atactaagca attgaaaaac aaggaagttg ctgctttggt tattcacggt   300
aaattacctt tgtacgcttt agagaagaag ttaggtgaca ctacccgtgc tgtcgccgtt   360
agaagaaaag ctttgtctat tttagctgag gcccctgttc tggcttctga cagattacca   420
tacaagaatt acgattacga tagagttttc ggtgcctgtt gtgagaacgt tatcggttat   480
atgccattac cagtcggtgt tatcggtcca ttggttattg acggtacctc ttaccacatc   540
ccaatggcta ctactgaagg ttgtttagtc gcctccgcca tgagaggttg taaggctatc   600
aatgctggtg tggtgctac taccgtcttg actaaggatg gtatgactag aggtccagtt   660
gtccgttttc caactttgaa agatctcggt gcttgtaaga tttggttgga ttctgaagaa   720
ggtcaaaatg ccattaagaa ggctttcaat tccacctcta gatttgccag attacaacat   780
attcaaacct gtttagccgg tgatttgttg ttcatgagat tcagaactac tactggtgat   840
gctatggtta tgaacatgat ctctaagggt gtcgaatatt ctttaaaaca aatggttgaa   900
gagtatggtt gggaagacat ggaggtcgtc tctgtctctg gtaactactg tactgataag   960
aaaccagctg ctatcaactg gatcgaaggt cgtggtaagt ctgttgttgc cgaagctact  1020
attccaggtg atgttgttag aaaggtttta aaatccgatg tctctgcctt ggttgagttg  1080
aacattgcta aaaacttggt tggttctgct atggctggtt ctgtcggtgg ttttaatgcc  1140
catgccgcca acttagtcac cgccgttttc ttagctttgg gtcaagatcc agctcaaaat  1200
gtcgaatcct ccaactgtat cactttgatg aaagaggtcg acggtgactt gcgtatctct  1260
gtttccatgc catctatcga agttggtact atcggtggtg gtactgtttt ggagccacaa  1320
ggtgctatgt tggacttatt gggtgttaga ggtccacacg ccactgctcc tggtaccaac  1380
gccagacaat tagctagaat cgttgcctgt gccgtcttag ctggtgagtt gtctttatgt  1440
gctgccttag ctgctggtca cttggtccaa tcccacatga ctcataacag aaagccagct  1500
gaacctacca agcctaacaa cttggatgcc accgatatta atcgtttaaa agatggttct  1560
gtcacttgca ttaagtccta a                                             1581

SEQ ID NO: 115          moltype = AA  length = 461
FEATURE                 Location/Qualifiers
source                  1..461
                        mol_type = protein
                        organism = Saccharomyces sp.
SEQUENCE: 115
MTELKKQKTA EQKTRPQNVG IKGIQIYIPT QCVNQSELEK FDGVSQGKYT IGLGQTNMSF    60
VNDREDIYSM SLTVLSKLIK SYNIDTNKIG RLEVGTETLI DKSKSVKSVL MQLFGENTDV   120
EGIDTLNACY GGTNALFNSL NWIESNAWDG RDAIVVCGDI AIYDKGAARP TGGAGTVAMW   180
IGPDAPIVFD SVRASYMEHA YDFYKPDFTS EYPYVDGHFS LTCYVKALDQ VYKSYSKKAI   240
SKGLVSDPAG SDALNVLKYF DYNVFHVPTC KLVTKSYGRL LYNDFRANPQ LFPEVDAELA   300
TRDYDESLTD KNIEKTFVNV AKPFHKERVA QSLIVPTNTG NMYTASVYAA FASLLNYVGS   360
DDLQGKRVGL FSYGSGLAAS LYSCKIVGDV QHIIKELDIT NKLAKRITET PKDYEAAIEL   420
RENAHLKKNF KPQGSIEHLQ SGVYYLTNID DKFRRSYDVK K                       461

SEQ ID NO: 116          moltype = DNA  length = 1386
FEATURE                 Location/Qualifiers
source                  1..1386
                        mol_type = genomic DNA
                        organism = Saccharomyces sp.
SEQUENCE: 116
atgaccgaat tgaagaagca aaagactgct gaacaaaaaa cccgtccaca aaatgttggt    60
atcaagggta ttcaaatcta cattccaact caatgcgtca accaatctga attggaaaaa   120
tttgatggtg tttctcaagg taaatacact attggtttgg gtcaaactaa tatgtccttc   180
gttaacgaca gagaagatat ttactccatg tccttgaccg tcttgtccaa attgattaag   240
tcttataata ttgacaccaa caagatcggt agattggaag ttggtactga aactttgatt   300
gataagtcta agtctgttaa gtctgtttta atgcaattgt tcggtgaaaa tactgacgtt   360
gaaggtattg acactttgaa cgcttgttac ggtggtacta tgctttatt taactctttg   420
aactggattg aatccaacgc ttgggacggt agagatgcca ttgtcgtttg tggtgacatt   480
gctatctatg acaagggtgc cgctcgtcca actggtggta ccgtcgctat gtggattggt   540
ccagatgctc cgatcgttt tgattctgtt cgtgcttctt acatggagca tgctacgact   600
ttttt ataagccaga cttttacctcc gaatatccat acgtcgatgg tcatttctct   660
ttgacctgct acgttaaagc cttagatcaa gtctacaagt cttactccaa gaaggccatt   720
tccaagggtt tagtctccga tccagctggt tccgatgctt taaacgtttt aaagtacttc   780
gattacaacg ttttccatgt ccctacttgt aaattggtta ccaaatctta cggtagatta   840
ttgtacaacg atttcagagc taatccacaa ttatttccag aagtcgatgc tgagttggct   900
actagagatt acgacgaatc cttgaccgac aaaaatattg aaaagacttt tgttaacgtt   960
gctaagccat tcacaaaaga gagagttgcc caatctttga ttgtcccaac taatactggt  1020
aatatgtata ctgcttctgt ttacgctgcc tttgcttctt tgttgaacta tgtcggttct  1080
gacgacttac aaggtaagcg tgtcggtttg ttctctccac gttccggttt ggctgcctct  1140
```

```
ttgtattctt gtaagattgt cggtgatgtt caacacatca tcaaggaatt ggatatcacc  1200
aataaattgg ccaagagaat cactgaaact cctaaagact atgaagctgc tatcgaattg  1260
agagaaaatg ctcatttaaa gaaaaacttt aaaccacaag gttctattga acacttgcaa  1320
tccggtgttt actacttaac taacatcgat gacaagttcc gtagatccta cgacgtcaag  1380
aagtaa                                                             1386

SEQ ID NO: 117           moltype = AA   length = 568
FEATURE                  Location/Qualifiers
source                   1..568
                         mol_type = protein
                         organism = Zymomonas mobilis
SEQUENCE: 117
MSYTVGTYLA ERLVQIGLKH HFAVAGDYNL VLLDNLLLNK NMEQVYCCNE LNCGFSAEGY   60
ARAKGAAAAV VTYSVGALSA FDAIGGAYAE NLPVILISGA PNNNDHAAGH VLHHALGKTD  120
YHYQLEMAKN ITAAAEAIYT PEEAPAKIDH VIKTALREKK PVYLEIACNI ASMPCAAPGP  180
ASALFNDEAS DEASLNAAVE ETLKFIANRD KVAVLVGSKL RAAGAEEAAV KFADALGGAV  240
ATMAAAKSFF PEENPHYIGT SWGEVSYPGV EKTMKEADAV IALAPVFNDY STTGWTDIPD  300
PKKLVLAEPR SVVVNGIRFP SVHLKDYLTR LAQKVSKKTG ALDFFKSLNA GELKKAAPAD  360
PSAPLVNAEI ARQVEALLTP NTTVIAETGD SWFNAQRMKL PNGARVEYEM QWGHIGWSVP  420
AAFGYAVGAP ERRNILMVGD GSFQLTAQEV AQMVRLKLPV IIFLINNYGY TIEVMIHDGP  480
YNNIKNWDYA GLMEVFNGNG GYDSGAGKGL KAKTGGELAE AIKVALANTD GPTLIECFIG  540
REDCTEELVK WGKRVAAANS RKPVNKLL                                     568

SEQ ID NO: 118           moltype = DNA   length = 1707
FEATURE                  Location/Qualifiers
source                   1..1707
                         mol_type = genomic DNA
                         organism = Zymomonas mobilis
SEQUENCE: 118
atgtcctaca ccgttggtac ctacttagct gagcgtttgg tccaaatcgg tttgaagcac    60
catttcgccg ttgctggtga ttacaacttg gtcttgttag ataatttatt attgaacaag   120
aacatggaac aagtctactg ctgtaatgaa ttgaactgtg gtttctctgc tgaaggttat   180
gctagagcta aaggtgccgc tgccgctgtt gtcacttact ctgttggtgc tttgtctgcc   240
ttcgacgcta ttggtggtgc ttacgccgag aatttacctg ttatttttaat ttctggtgcc   300
cctaacaata acgatcatgc tgctggtcat gttttacacc acgctttggg taaaactgac   360
taccattatc aattagagat ggccaaaaac atcaccgccg ctgccgaggc catttacact   420
ccagaagaag ccccagccaa aattgatcac gtcatcaaaa ccgccttgag agagaaaaaa   480
cctgtttact tggaaatcgc ctgtaatatc gcctctatgc cttgcgccgc tcctggtcct   540
gcttccgcct tattcaacga tgaggcttct gatgaagctt cctaaacgc tgctgttgag   600
gagacttttaa agttcatcgc taatagagat aaggtcgctg ttttagtcgg ttctaagttg   660
cgtgctgccg gtgccgagga agctgctgtt aaattcgccg atgctttagg tggtgctgtc   720
gccaccatgg ccgccgccaa atcctttttc cctgaagaaa acccacacta catcggtact   780
tctggggtg aagtctctta cccaggtgtc gaaaagacta tgaaggaagc cgatgccgtc   840
atcgccttgg ccccagtttt taatgattat tccaccactg gttggactga tatcccagat   900
cctaaaaagt tagttttag cgagcctaga tccgttgttg ttaacggtat tagattccct   960
tccgttcact tgaaggatta cttaactaga ttggctcaaa aggtttccaa gaagaccggt  1020
gctttggact ttttcaaatc tttgaacgcc ggtgagttaa agaaggccgc ccctgctgac  1080
ccatctgctc cattggttaa cgctgagatt gctagacaag tcgaagcttt attgaccca  1140
aacactaccg ttatcgccga aactggtgac tcttggttta atgctcaaag aatgaagtta  1200
ccaaatggtg ccagagttga gtacgaaatg caatggggtc atatcggttg gtctgtccca  1260
gctgcttttg gttatgctgt tggtgcccct gagagaagaa acatcttgat ggttggtgac  1320
ggttccttcc aattgactgc tcaagaagtc gctcaaatgg ttagattaaa attaccagtc  1380
atcatcttct tgatcaataa ctacggttac actatcgaag tcatgattca cgatggtcct  1440
tacaataata ttaagaactg ggactatgct ggtttgatgg aagtctttaa tggtaacggt  1500
ggttacgatt ccggtgctgg taaggggttta aaggctaaga ctggtggtga attagctgaa  1560
gccattaagg ttgccttggc taacaccgac ggtcctactt taatcgaatg tttcattggt  1620
agagaggatt gtaccgaaga gttagttaag tggggtaaga gagttgccgc tgctaattcc  1680
cgtaagcctg tcaataaatt gttataa                                      1707

SEQ ID NO: 119           moltype = DNA   length = 1575
FEATURE                  Location/Qualifiers
misc_feature             1..1575
                         note = Truncated 3-hydroxy-3-methyl-glutaryl-CoA reductase
                         (tHMG1)
source                   1..1575
                         mol_type = other DNA
                         organism = synthetic construct
SEQUENCE: 119
atgcaattgg tgaagactga agtcaccaag aagtcttta ctgctcctgt acaaaaggct     60
tctacaccag ttttaaccaa taaaacagtc atttctggat cgaaagtcaa aagtttatca   120
tctgcgcaat cgagctcatc aggaccttca tcatctagtg aggaagatga ttcccgcgat   180
attgaaagct ggataagaa aatacgtcct ttagaagaat tagaagcatt attaagtagt   240
ggaaatacaa acaattgaa gaacaaagag gtcgctgcct tggttattca cggtaagtta   300
cctttgtacg cttttggaaa aaaattaggt gatactacga gacggttgc agtacgtagg   360
aaggctcttt caattttggc agaagctcct gtattagcat ctgatcgttt accatataaa   420
aattatgact acgaccgcgt atttggcgct tgttgtgaaa atgttatagg ttacatgcct   480
ttgcccgttg gtgttatagg ccccttggtt atcgatggta catcttatca tataccaatg   540
gcaactacag agggttgttt ggtagcttct gccatgcgtg gctgtaaggc aatcaatgct   600
ggcggtggtg caacaactgt tttaactaag gatggtatga caagagggcc agtagtccgt   660
```

-continued

```
ttcccaactt tgaaaagatc tggtgcctgt aagatatggt tagactcaga agagggacaa    720
aacgcaatta aaaaagcttt taactctaca tcaagatttg cacgtctgca acatattcaa    780
acttgtctag caggagattt actcttcatg agatttagaa caactactgg tgacgcaatg    840
ggtatgaata tgatttctaa gggtgtcgaa tactcattaa agcaaatggt agaagagtat    900
ggctgggaag atatggaggt tgtctccgtt tctggtaact actgtaccga caaaaaacca    960
gctgccatca actggatcga aggtcgtggt aagagtgtcg tcgcagaagc tactattcct   1020
ggtgatgttg tcagaaaagt gttaaaaagt gatgtttccg cattggttga gttgaacatt   1080
gctaagaatt tggttggatc tgcaatggct gggtctgttg gtggatttaa cgcacatgca   1140
gctaatttag tgacagctgt tttcttggca ttaggacaag atcctgcaca aaatgtcgaa   1200
agttccaact gtataacatt gatgaaagaa gtggacggtg atttgagaat ttccgtatcc   1260
atgccatcca tcgaagtagg taccatcggt ggtggtactg ttctagaacc acaaggtgcc   1320
atgttggact tattaggtgt aagaggccca catgctaccg ctcctggtac caacgcacgt   1380
caattagcaa gaatagttgc ctgtgccgtc ttggcaggta aattatcctt atgtgctgcc   1440
ctagcagccg gccatttggt tcaaagtcat atgacccaca acaggaaacc tgctgaacca   1500
acaaaaccta acaatttgga cgccactgat ataaatcgtt gaaagatgg gtccgtcacc   1560
tgcattaaat cctaa                                                    1575

SEQ ID NO: 120          moltype = DNA  length = 1387
FEATURE                 Location/Qualifiers
source                  1..1387
                        mol_type = genomic DNA
                        organism = Saccharomyces sp.
SEQUENCE: 120
atgactgaac taaaaaaaca aaagaccgct gaacaaaaaa ccagacctca aaatgtcggt     60
attaaaggta tccaaattta catcccaact caatgtgtca accaatctga gctagagaaa    120
tttgatggcg tttctcaagg taaatacaca attggtcttg gccaaaccaa catgtctttt    180
gtcaatgaca gagaagatat ctactcgatg tccctaactg ttttgtctaa gttgatcaag    240
agttacaaca tcgacaccaa caaaattggt agattagaag tcggtactga aactctgatt    300
gacaagtcca gtctgtcaa gtctgtcttg atgcaattgt ttggtgaaaa cactgacgtc    360
gaaggtattg acacgcttaa tgcctgttac ggtggtacca ggcgttgtt caactctttg    420
aactggattg aatctaacgc atgggatggt agagacgcca ttgtagttg cggtgatatt    480
gccatctacg ataagggtgc cgcaagacca accggtggtg ccggtactgt tgctatgtgg    540
atcggtcctg atgctccaat tgtatttgac tctgtaagag cttcttacat ggaacacgcc    600
tacgattttt acaagccaga tttcaccagc gaatatcctt acgtcgatgg tcattttcta    660
ttaacttgtt acgtcaaggc tcttgatcaa gtttacaaga gttattccaa gaaggctatt    720
tctaaagggt tggttagcga tcccgctggt tcggatgctt tgaacgtttt gaaatatttc    780
gactacaacg ttttccatgt tccaacctgt aaattggtca caaatcata cggtagatta    840
ctatataacg atttcagagc caatcctcaa ttgttcccag aagttgacgc cgaattagct    900
actcgcgatt atgacgaatc tttaaccgat aagaacattg aaaaaacttt tgttaatgtt    960
gctaagccat tccacaaaga gagagttgcc caatctttga ttgttccaac aaacacaggt   1020
aacatgtaca ccgcatctgt ttatgccgcc tttgcatctc tattaaacta tgttggatct   1080
gacgacttac aaggcaagcg tgttggttta ttttcttacg gttccggttt agctgcatct   1140
ctatattctt gcaaaattgt tggtgacgtc caacatata tcaaggaatt agatattact   1200
aacaaaattag ccaagagaat caccgaaact ccaaaggatt acgaagctgc catcgaattg   1260
agagaaaatg cccatttgaa gaagaacttc aaacctcaag gttccattga gcatttgcaa   1320
agtggtgttt actacttgac caacatcgat gacaaattta aagatctta cgatgttaaa   1380
aaataat                                                             1387

SEQ ID NO: 121          moltype = AA  length = 420
FEATURE                 Location/Qualifiers
source                  1..420
                        mol_type = protein
                        organism = Catharanthus sp.
SEQUENCE: 121
MLFSRGLYRI ARTSLNRSRL LYPLQSQSPE LLQSFQFRSP IGSSQKVSGF RVIYSCVSSA     60
LANVGQQVQR QSNSVAEEPL DPFSLVADEL SILANRLRSM VVAEVPKLAS AAEYFFKLGV    120
EGKRFRPTVL LLMATAIDAP ISRTPPDTSL DTLSTELRLR QQSIAEITEM IHVASLLHDD    180
VLDDAETRRG IGSLNFVMGN KLAVLAGDFL LSRACVALAS LKNTEVVSLL ATVVEHLVTG    240
ETMQMTTTSD QRCSMEYYMQ KTYYKTASLI SNSCKAIALL AGQTSEVAML AYEYGKNLGL    300
AFQLIDDVLD FTGTSASLGK GSLSDIRHGI VTAPILFAIE EFPELRAVVD EGFENPYNVD    360
LALHYLGKSR GIQRTRELAI KHANLASDAI DSLPVTDDEH VLRSRRALVE LTQRVITRRK    420

SEQ ID NO: 122          moltype = DNA  length = 1263
FEATURE                 Location/Qualifiers
source                  1..1263
                        mol_type = genomic DNA
                        organism = Catharanthus sp.
SEQUENCE: 122
atgttattct ctcgtggttt atacagaatc gccagaactt ctttgaacag atcccgtttg     60
ttgtaccctt tacaatctca atctcctgaa ttgttacaat ccttccaatt cagatctcca    120
atcggttcct ctcaaaaggt ttccggtttc agagttatct actcctgcgt ttcctctgct    180
ttagctaact tggtcaaca agtccaaaga caatctaatt ccgttgctga gaacccttg     240
gacccattct ccttggttgc cgatgaatta tccattttag ctaacagatt gcgttctatg    300
gtcgtcgctg aagttccaaa gttagcctcc gccgccaat atttcttcaa gttgggtgtc    360
gagggtaaaa gattcagacc aactgttttg ttgttaatgg ccaccgccat tgatgcccca    420
atctctagaa ccccacctga cacctcctta gatactttat ccaccgaatt gcgtttgaga    480
caacaatcta tcgccgaaat tactgaaatg attcatgtcg cttccttgtt gcacgatgat    540
gttttgatg atgctgaaac tagaaggggt attggttctt taaattttgt catgggtaac    600
aaattggctg ttttggccgg tgacttctta ttatctagag cttgtgttgc cttagcttct    660
```

```
ttgaaaaaca ctgaagtcgt ctccttgtta gccactgtcg ttgaacactt agttactggt    720
gagactatgc aaatgactac cacctccgat caaagatgtt ctatggaata ctacatgcaa    780
aagacctatt acaagactgc ctctttgatt tctaactcct gtaaagccat tgccttgtta    840
gctggtcaaa cttctgaagt tgccatgttg gcttacgaat acggtaaaaa cttgggtttg    900
gcttttccaa tgattgatga tgttttgact ttcactggta cttctgcttc cttaggtaaa    960
ggttctttgt ctgatattcg tcacggtatc gttaccgccc caatcttgtt cgctattgaa   1020
gaattcccag agtaagagc tgttgttgac gaaggtttcg aaaacccta caatgttgac    1080
ttagccttgc actacttggg taaatctaga ggtattcaac gtaccagaga attagccatt   1140
aaacatgcta acttagcctc tgacgccatt gactctttac cagtcactga tgatgagcac   1200
gtcttacgtt ccagacgtgc cttagttgaa ttgactcaaa gagttattac tagaagaaag   1260
taa                                                                 1263

SEQ ID NO: 123          moltype = AA   length = 421
FEATURE                 Location/Qualifiers
source                  1..421
                        mol_type = protein
                        organism = Mangifera indica
SEQUENCE: 123
MLFSYGLSRI SINPRASLLT CRWLLSHLTG SLSPSTSSHT ISDSVHKVWG CREAYTWSVP    60
ALHGFRHQIH HQSSSLIEDQ LDPFSLVADE LSLVANRLRS MVVTEVPKLA SAAEYFFKMG   120
VEGKRFRPAV LLLMATALNV HVLEPLPEGA GDALMTELRT RQQCIAEITE MIHVASLLHD   180
DVLDDADTRR GIGSLNLVMG NKLAVLAGDF LLSRACVALA SLKNTEVVSL LATVVEHLVT   240
GETMQMTTSS DQRCSMEYYM QKTYYKTASL ISNSCKAIAL LAGQSAEVAM LAFEFGKNLG   300
LAYQLIDDVL DFTGTSASLG KGSLSDIRHG IVTAPILFAM EEFPQLRAVI DQGFENPSNV   360
DVALEYLGKS RGIQRTRELA TNHANLAAAA IDALPKTDNE EVRKSRRALL DLTQRVITRN   420
K                                                                  421

SEQ ID NO: 124          moltype = DNA   length = 1266
FEATURE                 Location/Qualifiers
source                  1..1266
                        mol_type = genomic DNA
                        organism = Mangifera indica
SEQUENCE: 124
atgttattct cttatggttt atctcgtatt tctattaacc ctcgtgcctc tttattgact     60
tgtagatggt tattatccca tttgactggt tctttatctc cttccacttc ttcccatact    120
atttctgact ccgtccataa agtctggggg tgcagagaag cctatacttg gtctgtccca    180
gctttacatg gttttagaca tcaaatccac catcaatcct cttccttgat tgaagatcaa    240
ttagacccat tctccttggt cgccgatgag ttgtccgtgg ttgctaaccg tttaagatct    300
atggttgtca ctgaagtccc taaattagcc tctgccgacg aatactttt caagatgggt    360
gtcgaaggta agcgtttcag accagctgtc ttgttgttaa tggccactgc cttaaacgtt    420
catgttttgg aacctttgcc tgaaggtgct ggtgacgctt taatgaccga gttgagaacc    480
cgtcaacaat gcattgctga aatcactgag atgatccacg tcgcctcttt attgcatgac    540
gatgttttag acgacgctga tactagaaga ggtattggtt ctttgaactt ggttatgggt    600
aacaaattgg ccgttttggc cggtgatttc ttgttatccc gtgcttgcgt tgctttagct    660
tctttgaaga cactgaagt tgtttctttg ttggccaccg tcgttgaaca cttagttact    720
ggtgagacta tgcaaatgac cacctcttct gaccaaagat gttccatgga atattacatg    780
caaaaaactt attacaaaac cgcctccttg atttctaact cctgtaaagc catcgcctta    840
ttagctggtc aatctgctga agttgccatg ttagccttcg agtttggtaa gaacttgggt    900
ttagcttacc aattgatcga tgatgtcttg gattttaccg gtacctctgc ttcttttgggt    960
aagggttcct tgtccgacat tagacacggt attgttaccg ccccaatctt attcgctatg   1020
gaagagtttc cacaattgag agctgttatc gaccaaggtt tcgagaaccc atctaacgtt   1080
gacgtcgcct tagagtattt aggtaaatct agaggtatcc aacgtacccg tgaattagct   1140
actaaccatg ctaacttagc cgccgccgcc atcgatgcct tgcctaaaac cgataatgaa   1200
gaagtccgta gtccagacg tgctttatta gatttgactc aaagagtcat caccagaaac   1260
aaatag                                                             1266

SEQ ID NO: 125          moltype = AA   length = 328
FEATURE                 Location/Qualifiers
source                  1..328
                        mol_type = protein
                        organism = Mangifera indica
SEQUENCE: 125
MPFVVPRRNR SLSVSAVLTK EETLREEEED PKPVFDFKSY MLQKGNSVNQ ALDAVVSIRE     60
PKKIHEAMRY SLLAGGKRVR PVLCIAACEL VGGNESMAMP AACAVEMIHT MSLIHDDLPC   120
MDNDDLRRGK PTNHKVFGED VAVLAGDALL AFSFENMAVS TVGVLPSRVV KAVGELAKSI   180
GIEGLVAGQV VDINSEGLKE VGLDHLEFIH QHKTAALLEG SVVLGAILGG GSDDEVEKLR   240
TFARCIGLLF QVVDDILDVT KSSRELGKTA GKDLVADKVT YPKLLGIEKS RELADKLNKD   300
AQQQLSGFDQ EKAAPLIALS NYIAYRQN                                     328

SEQ ID NO: 126          moltype = DNA   length = 987
FEATURE                 Location/Qualifiers
source                  1..987
                        mol_type = genomic DNA
                        organism = Mangifera indica
SEQUENCE: 126
atgccattcg ttgttcctag aagaaaccgt tctttgtccg tttccgccgt tttgaccaag     60
gaagaaactt taagagagga agaagaagat ccaaagccag ttttcgactt caaatcttac    120
atgttacaaa agggtaattc tgttaatcaa gcttggatg ctgtcgtttc cattagagaa    180
cctaagaaaa tccatgaggc tatgcgttac tctttgttgg ctggtggtaa agagagttcgt    240
```

```
cctgttttgt gtattgccgc ctgtgaattg gtcggtggta acgaatctat ggctatgcca    300
gccgcctgtg ctgtcgaaat gatccacact atgtccttga ttcacgatga tttgccatgt    360
atggataatg acgatttgcg tcgtggtaaa cctaccaacc ataaagtttt cggtgaagac    420
gtcgccgttt tggctggtga cgctttatta gcttttttcct tcgagaacat ggccgtttcc    480
actgttggtg tcttaccatc cagagttgtc aaggctgttg gtgaattgca caagtctatc    540
ggtattgaag gtttggttgc cggtcaagtc gtcgatatta attctgaggg tttaaaagag    600
gtcggtttag atcacttaga atttatccat caacacaaaa ccgctgcttt gttggagggt    660
tctgttgttt tgggtgctat tttaggtggt ggttctgatg atgaagtcga aaagttgcgt    720
accttttgcta gatgtatcgg tttgttgttt caagttgttg acgatattttt ggatgtcact    780
aagtcttcca gagaattggg taagaactgcc ggtaaagatt tggttgctga taaagttact    840
tatccaaagt tgttaggtat tgaaaagtct cgtgaattgg ccgataagtt aaacaaggat    900
gctcaacaac aattatccgg ttttgatcaa gagaaggctg ccccttttaat cgctttgtcc    960
aattacatcg cctacagaca aaactag                                         987

SEQ ID NO: 127             moltype = AA   length = 321
FEATURE                    Location/Qualifiers
REGION                     1..321
                           note = Truncated geranylgeranyl pyrophosphate synthase
                              Cs2_GPPS_NTrunc
source                     1..321
                           mol_type = protein
                           organism = synthetic construct
SEQUENCE: 127
MVIAEVPKLA SAAEYFFKMG VEGKRFRPTV LLLMATALNV RVPEPLHDGV EDASATELRT     60
RQQCIAEITE MIHVASLLHD DVLDDADTRR GIGSLNFVMG NKLAVLAGDF LLSRACVALA    120
SLKNTEVVTL LATVVEHLVT GETMQMTTSS DQRCSMDYYM QKTYYKTASL ISNSCKAIAL    180
LAGQTAEVAI LAFDYGKNLG LAYQLIDDVL DFTGTSASLG KGSLSDIRHG IITAPILFAM    240
EEFPQLRTVV EQGFEDSSNV DIALEYLGKS RGIQKTRELA VKHANLAAAA IDSLPENNDE    300
DVTKSRRALL DLTHRVITRN K                                              321

SEQ ID NO: 128             moltype = DNA   length = 966
FEATURE                    Location/Qualifiers
misc_feature               1..966
                           note = Truncated geranylgeranyl pyrophosphate synthase
                              Cs2_GPPS_NTrunc
source                     1..966
                           mol_type = other DNA
                           organism = synthetic construct
SEQUENCE: 128
atggtcattg ctgaagttcc taaattagcc tctgccgccg aatacttctt caagatgggt     60
gtcgagggta agagatttcg tcctaccgtt ttgttgttaa tggccaccgc cttaaacgtc    120
agagtccctg aaccattaca tgatggtgtt gaagatgcct ctgccaccga gttgagaact    180
agacaacaat gtattgctga aatcaccgag atgattcacg ttgcttcttt gttgcacgat    240
gatgttttgg atgatgctga tacccgtcgt ggtatcggtt ctttgaactt tgtcatgggt    300
aacaagttgg ctgtcttggc tggtgatttc ttattgtctc gtgcctgcgt tgccttagcc    360
tcttttaaaaa ataccgaagt tgttacttta ttggccactg ttgttgagca cttggttact    420
ggtgaaacta tgcaaatgac cacctcttcc gaccaacgtt gttccatgga ctattacatg    480
caaaagacct actacaagac cgcttctttg atttccaatt cttgtaaagc cattgcctta    540
ttagctggtc aaactgctga agttgccatc ttggccttcg actacggtaa aaacttgggt    600
ttagcttacc aattgattga tgacgtttta gattttactg gtacttctgc ttctttgggt    660
aaaggttctt tatccgatat tcgtcatggt atcattacgg ctccaatctt attcgctatg    720
gaagaatttc ctcaattgcg tactgtcgtt gaacaaggtt tcgaagactc tccaacgtt    780
gacattgcct tagaatactt gggtaagtct cgtggtattc aaaagacccg tgaattagcc    840
gttaaacatg ccaacttagc cgccgccgcc atcgattcct gcctgaaaaa aacgatgag    900
gatgtcacca gtcccgtcg tgcttgtta gatttaactc acagagttat tacccgtaac    960
aagtaa                                                                966

SEQ ID NO: 129             moltype = AA   length = 416
FEATURE                    Location/Qualifiers
source                     1..416
                           mol_type = protein
                           organism = Quercus sp.
SEQUENCE: 129
MLFSRISRIR RPGSNGFRWF LSHKTHLQFL NPPAYSYSST HKVLGCREIF SWGLPALHGF     60
RHNIHHQSSS IVEEQNDPFS LVADELSMVA NRLRSMVVTE VPKLASAAEY FFKMGVEGKR    120
FRPTVLLLMA TAMNISILEP SLRGPGDALT TELRARQQRI AEITEMIHVA SLLHDDVLDD    180
ADTRRGIGSL NFVMGNKLAV LAGDFLLSRA CVALASLKNT EVVSLLAKVV EHLVTGETMQ    240
MTTTCEQRCS MEYYMQKTYY KTASLISNSC KAIALLGGQT SEVAMLAYEY GKNLGLAYQL    300
IDDVLDFTGT SASLGKGSLS DIRHGIITAP ILFAMEEFPQ LREVVDRGFD DPANVVALD    360
YLGKSRGIQR ARELAKKHAN IAAEAIDSLP ESNDEDVRKS RRALLDLTER VITRTK        416

SEQ ID NO: 130             moltype = DNA   length = 1251
FEATURE                    Location/Qualifiers
source                     1..1251
                           mol_type = genomic DNA
                           organism = Quercus sp.
SEQUENCE: 130
atgttgttct ctcgtatttc tcgtatccgt agaccaggtt ctaatggttt cagatggttc     60
ttgtcccata gagactcattt acaattcttg aaccctccag cttattccta ctcttccact    120
```

```
cataaggtct tgggttgtag agaaatttttt tcctgggtt tacctgcctt acatggtttc   180
agacacaaca ttcaccacca atcttcctct attgttgaag aacaaaatga cccttttctct  240
ttggtcgctg atgagttgtc catggttgct aacagattgc gttctatggt tgttactgaa   300
gttcctaaat tagcctccgc cgctgaatac tttttttaaaa tgggtgttga aggtaagaga   360
ttcagaccaa ctgtttttatt gttgatggct accgccatga acatttccat cttagaacca   420
tctttgagag gtccaggtga cgctttgacc actgaattga gagccagaca caaagaatt    480
gctgaaatta ccgagatgat ccacgttgct ccttgttgc acgatgacgt tttggatgac    540
gctgatacta gaagaggtat tggttcctta aactttgtca tgggtaataa attagctgtt   600
ttggctggtg attttttgtt atctcgtgcc tgtgttgctt tagcttcttt gaagaaccact  660
gaagttgtct ccttgttagc caaggtcgtc gaacacttgg ttactggtga aactatgcaa   720
atgaccacta cttgtgaaca aagatgttcc atgaatact  acatgcaaaa gacttactat   780
aagaccgctt ctttaatttc caactcctgt aaagccattg ctttattagg tggtcaaact   840
tctgaggtcg ctatgttagc ctacgaatat ggtaaaaact tgggtttagc ttaccaattg   900
attgatgatg tcttggattt cactggtact tctgcttcct tgggtaaggg ttccttgtct   960
gatattagac atggtatcat tactgctcca attttgtttg ctatggaaga attcccacaa  1020
ttacgtgaag ttgtcgatag aggtttcgac gatcctgcca acgtcgatgt tgccttggac  1080
tacttgggta agtctagagg tatccaaaga gccagagagt tagctaaaaa acacgctaac  1140
attgctgccg aagccatcga ctctttgcca gaatccaacg acgaggacgt cagaaagtcc  1200
cgtcgtgctt tgttggactt gaccgaaaga gtcattactc gtactaagta a           1251

SEQ ID NO: 131          moltype = AA   length = 427
FEATURE                 Location/Qualifiers
REGION                  1..427
                        note = Truncated geranylgeranyl pyrophosphate synthase
                         Pa_GPPS_Ntrunc
source                  1..427
                        mol_type = protein
                        organism = synthetic construct
SEQUENCE: 131
MYTRCILRDK YSRFNLRRKF FTSAKSINAL NGLPDSGNPR GESNGISQFE IQQVFRCKEY    60
IWIDRHKFHD VGFQAHHKGS ITDEEQVDPF SLVADELSIL ANRLRSMILT EIPKLGTAAE   120
YFFKLGVEGK RFRPMVLLLM ASSLTIGIPE VAADCLRKGL DEEQRLRQQR IAEITEMIHV   180
ASLLHDDVLD DADTRRGVGS LNFVMGNKLA VLAGDFLLSR ASVALASLKN TEVVELLSKV   240
LEHLVTGEIM QMTNTNEQRC SMEYYMQKTF YKTASLMANS CKAIALIAGQ PAEVCMLAYD   300
YGRNLGLAYQ LLDDVLDFTG TTASLGKGSL SDIRQGIVTA PILFALEEFP QLHDVINRKF   360
KKPGDIDLAL EFLGKSDGIR KAKQLAAQHA GLAAFSVESF PPSESEYVKL CRKALIDLSE   420
KVITRTR                                                             427

SEQ ID NO: 132          moltype = DNA   length = 1284
FEATURE                 Location/Qualifiers
misc_feature            1..1284
                        note = Truncated geranylgeranyl pyrophosphate synthase
                         Pa_GPPS_N_trunc
source                  1..1284
                        mol_type = other DNA
                        organism = synthetic construct
SEQUENCE: 132
atgtataccc gttgcatttt aagagacaag tattctcgtt tcaacttgag acgtaaattc    60
ttcacttccg ctaaatccat caatgccttg aatggtttac ctgactctgg taaccctaga   120
ggtgaatcta acggtatctc ccaattcgaa attcaacaag ttttccgttg taagaatac    180
atttgaatcg atcgtcacaa gttccacgat gttggtttca aagctcatca caagggttcc   240
atcactgacg aggaacaagt tgacccttttt tctttagtcg ctgatgaatt gtccatctta   300
gctaatcgtt taagatccat gatcttaacc gagattccaa agttaggtac cgctgccgaa   360
tactttttca agttgggtgt cgaaggtaag agatttagac caatggtttt gttgttgatg   420
gcctctcttt taactattgg tatccctgaa gttgccgctg attgtttgcg taagggtttg   480
gacgaagaac aaagattacg tcaacaacgt atcgctgaaa ttactgaaat gattcatgtc   540
gcctctttgt tgcacgatga tgtttttggat gacgccgata ctagacgtgg tgttggttcc   600
ttgaactttg ttatgggtaa caagttggct gttttagccg tgatttcttt gttatctaga   660
gcttctgttg ccttagcttc tttaaagaac actgaggttg ttgagttatt gtctaaggtt   720
ttggagcact tagtcactgg tgagatcatg caaatgacta acactaatga acaaagatgt   780
tctatgaat attacatgca aaagactttc tacaagaccg cctctttgat ggctaattct   840
tgtaaagcca ttgccttgat cgctggtcaa cctgccgaag tctgcatgtt ggcctacgac   900
tacggtagaa acttgggttt agcttatcaa ttattggatg acgttttgga tttcactggt   960
accactgctt cttaggtaa gggttcctta tccgacataa gacaaggtat tgttactgca  1020
cctattttat tcgctttgga agaattccct caattacacg acgtcatcaa ccgtaagttc  1080
aaaaaaccag gtgacatcga tttggccttg gaatttttgg gtaagtctga tggtatccgt  1140
aaagccaaac aattggctgc tcaacatgct ggtttagctg ccttttctgt cgaatccttt  1200
ccaccatctg aatccgaata cgttaagtta tgtagaaagg ccttgatcga tttgtctgaa  1260
aaggtcatta ctcgtaccag ataa                                         1284

SEQ ID NO: 133          moltype = AA   length = 381
FEATURE                 Location/Qualifiers
source                  1..381
                        mol_type = protein
                        organism = Abies grandis
SEQUENCE: 133
MAYSAMATMG YNGMAASCHT LHPTSPLKPF HGASTSLEAF NGEHMGLLRG YSKRKLSSYK    60
NPASRSSNAT VAQLLNPPQK GKKAVEFDFN KYMDSKAMTV NEALNKAIPL RYPQKIYESM   120
RYSLLAGGKR VRPVLCIAAC ELVGGTEELA IPTACAIEMI HTMSLMHDDL PCIDNDDLRR   180
```

```
GKPTNHKIFG EDTAVTAGNA LHSYAFEHIA VSTSKTVGAD RILRMVSELG RATGSEGVMG    240
GQMVDIASEG DPSIDLQTLE WIHIHKTAML LECSVVCGAI IGGASEIVIE RARRYARCVG    300
LLFQVVDDIL DVTKSSDELG KTAGKDLISD KATYPKLMGL EKAKEFSDEL LNRAKGELSC    360
FDPVKAAPLL GLADYVAFRQ N                                              381

SEQ ID NO: 134          moltype = DNA   length = 1146
FEATURE                 Location/Qualifiers
source                  1..1146
                        mol_type = genomic DNA
                        organism = Abies grandis
SEQUENCE: 134
atggcttatt ctgctatggc tactatgggt tacaacggta tggctgcttc ttgtcacact      60
ttacacccaa cttctccatt gaaaccttt cacggtgctt ctacttcctt ggaagccttc     120
aatggtgaac acatgggttt gttaagaggt tattctaagc gtaagttgtc ctcttacaaa    180
aatccagctt ctcgttcctc caatgctacc gtcgctcaat tattgaaccc accacaaaag    240
ggtaagaagg ctgttgaatt tgacttcaat aagtatatgg attctaaggc tatgaccgtc    300
aacgaggctt tgaataaagc catcccattg cgttacccac aaaagatcta cgaatctatg    360
agatattctt tgttagctgg tggtaagaga gtccgtccag ttttgtgtat cgccgcttgt    420
gaattagtcg gtggtactga ggagttagct attccaaccg cctgtgccat cgaaatgatc    480
cacaccatgt ctttgatgca cgatgatttg ccatgtatcg acaacgatga cttgagacgt    540
ggtaaaccta ccaatcataa gattttcggt gaagatactg ctgttactgc cggtaacgct    600
ttacactctt acgccttcga acatattgct gtttctctct ccaagactgt tggtgctgat    660
agaatttga gaatggtttc tgaattaggt cgtgctactg gttccgaagg tgttatgggt    720
ggtcaaatgg tcgatattgc ttctgaaggt gaccttcca ttgatttgca aactttagaa    780
tggatccaca tccacaagac tgctatgtta ttagaatgtt ctgttgtctg tggtgccatc    840
atcggtggtg cttctgaaat tgttattgag agagccgaac gttatgctcg ttgtgtcggt    900
ttattgtttc aagttgttga cgacatttta gatgttacca atcttctga cgaattgggt    960
aaaactgctg gtaaagattt aatctccgat aaagccacct accctaagtt gatgggtttg   1020
gagaaggcca aagagtttc cgatgaatta ttaaacagag ctaaggtga attgtcttgc    1080
ttcgatccag ttaaggctgc cccattgtta ggtttggctg actacgttgc cttcagacaa   1140
aactaa                                                               1146

SEQ ID NO: 135          moltype = AA   length = 257
FEATURE                 Location/Qualifiers
REGION                  1..257
                        note = Truncated geranylgeranyl pyrophosphate synthase
                         Pb_GPPS_NTrunc
source                  1..257
                        mol_type = protein
                        organism = synthetic construct
SEQUENCE: 135
MAAIFPSIPS NFKPPQISQT LTRRRRPNRT LCTATSDQSY LSASSADIYS HLLRSLPATI     60
HPSVKAPIHS LLSSPIPPTI APPLCLAATE LVGGNPNSAI NAACAIHLIH AVTHTRTAPP    120
LAEFSPGVLL MTGDGLLVLA YEMLARSPAV DADTSVRVLK EVARTAAAVA AAYEGGREGE    180
LAAGAAACGV ILGGGNEEEV ERGRRVGMFA GKMELVEAEV ELRLGFEDAK AGAVRRLLEE    240
MRFTQSFVNV RNPFYGK                                                   257

SEQ ID NO: 136          moltype = DNA   length = 774
FEATURE                 Location/Qualifiers
misc_feature            1..774
                        note = Truncated geranylgeranyl pyrophosphate synthase
                         Pb_GPPS_NTrunc
source                  1..774
                        mol_type = other DNA
                        organism = synthetic construct
SEQUENCE: 136
atggctgcta tctttccatc cattccatcc aacttcaaac cacctcaaat ctctcaaact     60
tgaccagac gtagaagacc aaaccgtact ttatgtactg ccacctctga ccaatcttac    120
ttgtccgctt cttctgccga catttattct catttgttaa gatctttacc agctactatt    180
catccatctg ttaaagcccc aatccattct ttattgtcct ctccaattcc tccaaccatc    240
gctccacctt tgtgtttagc tgctaccgaa ttggttggtg gtaaccctaa ctctgccatt    300
aacgccgcct gtgccattca tttgattcat gctgttactc atactagaac cgctccacca    360
ttagctgaat tttctcctgg tgttttgttg atgactggta tggttttatt agttttggct    420
tacgagatgt tggccagatc cccagctgtt gatgccgata cttctgtccg tgttttgaag    480
gaagtcgcta gaaccgccgc cgccgtcgcc gctgcttatg aaggtggtag agaaggtgaa    540
ttagctgccg gtgccgctgc ttgtggtgtc attttgggtg gtggtaacga agaagaggtc    600
gaaagaggtc gtagagtcgg tatgttcgct ggtaaaatgg aattagttga agctgaagtc    660
gaattgagat tgggtttcga agatgctaaa gccggtgccg ttagaagatt gttggaagaa    720
atgcgtttca cccaatcttt tgtcaacgtt agaaacccct ttatggtaa gtaa           774

SEQ ID NO: 137          moltype = AA   length = 420
FEATURE                 Location/Qualifiers
source                  1..420
                        mol_type = protein
                        organism = Azadirachta indica
SEQUENCE: 137
MLFSRGLSRI SRIPRNSLIG CRWLVSYRPD TILSGSSHSV GDSTQKVLGC REAYLWSLPA     60
LHGIRHQIHQ QSSSLIEEEL DPFSLVADEL SLVANRLRSM VVAEVPKLAS AAEYFFKMGV    120
EGKRFRPTVL LLMASALNVQ VPQPLSDGVG DALTTELRTR QQCIAEITEM IHVASLLHDD    180
```

```
VLDDADTRRG IGSLNFVMGN KLAVLAGDFL LSRACVALAS LKNTEVVSLL ATVVEHLVTG    240
ETMQMTTTAE QRRSMDYYMQ KTYYKTASLI SNSCKAIALL AGQTTEVAML AFDGYKNLGL    300
APQLIDDVLD FTGTSASLGK GSLSDIRHGI VTAPILFAME EFPELRKVVD KGFDDPSNVD    360
IALEYLGKSR GIQRTRELAQ KHANLATVAL DSLPESNDDD VKKSRRALLD LAQRVITRNK    420

SEQ ID NO: 138          moltype = DNA  length = 1263
FEATURE                 Location/Qualifiers
source                  1..1263
                        mol_type = genomic DNA
                        organism = Azadirachta indica
SEQUENCE: 138
atgttgtttt ccagaggttt atctcgtatt tccagaatcc cacgtaactc tttgatcggt     60
tgtagatggt tagtttctta ccgtcctgat accattttat ctggttcctc tcactccgtt    120
ggtgactcta ctcaaaaggt tttaggttgt cgtgaagctt acttgtggtc tttaccagcc    180
ttgcacggta ttagacacca aattcatcaa caatcctctt ctttgattga agaagaattg    240
gatccattct ctttagttgc tgatgaattg tctttagtcg ctaaccgttt gagatccatg    300
gtcgtcgctg aagtcccaaa attagcctcc gccgccgagt acttcttcaa gatgggtgtt    360
gagggtaaga gattccgtcc aactgtctta ttgttgagtc cctccgcctt aaacgttcaa    420
gtcccacaac ctttgtctga cggtgttggt gatgctttga ctaccgagtt gagaactaga    480
caacaatgca ttgctgagat tactgaaatg atccatgttg cttctttgtt gcatgacgac    540
gttttggatg atgctgacac tagacgtggt atcggttctt tgaacttcgt tatgggtaac    600
aagttggctc tcttggctgg tgatttcttg ttgtccagag cctgtgttgc tttagcttct    660
ttgaagaata ctgaggttgt ctctttgttg gccaccgttg ttgaacactt ggtcaccggt    720
gaaactatgc aaatgactac tactgctgaa caaagacgtt ccatggatta ttacatgcaa    780
aagacttact ataagaccgc ctctttgatt tccaactctt gtaagccatt gccttgtta    840
gctggtcaaa ctaccgaagt tgctatgttg gctttcgatt acggtaagaa tttgggttta    900
gcttttcaat tgatcgatga cgtcttggat tttactggta cctctgcttc tttaggtaaa    960
ggttccttgt ctgatattag acacggtatc gttaccgctc caattttatt cgctatgaa    1020
gaattcccag aattaagaaa ggttgttgat aagggttttg acgacccttc aacgttgac    1080
attgctttgg agtatttggg taagtctaga ggtattcaaa gaaccagaga attggctcaa    1140
aaacatgcca atttggccac cgtcgccttg gattctttac cagaatccaa cgacgacgat    1200
gttaagaagt ctcgtagagc tttattggac ttggctcaaa gagttattac tagaaacaag    1260
taa                                                                 1263

SEQ ID NO: 139          moltype = AA  length = 513
FEATURE                 Location/Qualifiers
REGION                  1..513
                        note = Truncated geranylgeranyl pyrophosphate synthase
                         Es_GPPS_NTrunc
source                  1..513
                        mol_type = protein
                        organism = synthetic construct
SEQUENCE: 139
MRRSGSATAA AAATLARHAN ACCRARSPAL GLLPGAAASS STHRAALSSN SGHGGDGSGH     60
YDAAMRRRES CASRSRHRWS GQEAAAASAT TTTARRAPGG VAGASGQGSA AGSVRALSSS    120
FLADAVRETA TNHCIDRVVN GGLDGSVPVD KDTPTVEVQD FVYIDIDFAQR PSGASQSLAD    180
GPDPFELVSA ELAGLSDGIK SLIGTEHAVL NAAAKYFFEL DGGKKIRPTM VILMSQACNS    240
NSQQVRPDVQ PGTELVNPLQ LRLAEITEMI HAASLFHDDV IDEADTRRGV PSVNKVFGNK    300
LAILAGDFLL ARSSMSLARL RSLESVELMS AAIEHLVKGE VLQMRPTEDG GGAFEYYVRK    360
NYYKTGSLMA NSCKASAVLG QHDLEVQEVA FEYGKRVGLA FQLVDDILDF EGNTFTLGKP    420
ALNDLRQGLA TAPVLLAAEQ QPGLAKLISR KFRGPGDVDE ALELVHRSDG IARAKEVAVV    480
QAEKAMSAIL TLHDSPAQNA LVQLAHKIVN RNH                                513

SEQ ID NO: 140          moltype = DNA  length = 1542
FEATURE                 Location/Qualifiers
misc_feature            1..1542
                        note = Truncated geranylgeranyl pyrophosphate synthase
                         Es_GPPS_NTrunc
source                  1..1542
                        mol_type = other DNA
                        organism = synthetic construct
SEQUENCE: 140
atgcgtagat ccggttccgc taccgccgct gccgctgcca ccttagccag cacacgccaac    60
gctgttgta gagcccgttc ccagccttta ggtttgttgc ctggtgccgc cgcttcttcc    120
tctactcaca gagccgcctt gtcttctaat tctggtcatg gtggtgatgg ttccggtcat    180
tacgacgctg ctatgagaag aagagaatct tgcgcttcca gatctcgtca cagatggtcc    240
ggtcaagaag ctgccgccgc ctccgccact accaccaccg ctcgtcgtgc tccaggtggt    300
gtcgccggtc cttctggtca aggttctgct gccggttctc ttagagcctt atcctcttct    360
tttttagccg atgccgttcg tgaaaccgct actaaccact gtatcgaccg tgttgtcaac    420
ggtggtttgg acggttctgt cccagtcgat aaagatacc caactgtcga agttcaagac    480
tttgtttatg atattgactt tgctcaacgt ccatccggtg cctctcaatc tttagctgac    540
ggtccagatc cattcgagtt agtttccgct gagttggccg gtttgtctga tggtattaag    600
tcttttgattg gtaccgaaca tgctgtcttg aacgccgccg ccaaatattt cttcgaatta    660
gatggtggta aaaagatcag acctactatg gttcattaa tgtcccaagc ttgtaactct    720
aattcccaac aagttcgtcc tgacgttcaa ccaggtactg aattagtcaa tcctttgcaa    780
ttaagattgg ctgaaatcac cgagatgatt catgctgctt ctttattcca cgacgatgtt    840
attgatgagg ctgatactag acgtggtgtc cttctgtta taaagttttt cggtaacaaa    900
ttagccatct tggccggtga cttcttattg gctagatcct ctatgtccctt ggcccgttta    960
agatcctggg agtccgtcga attgatgtcc gccgctatcg aacacttggt caaaggtgaa   1020
```

```
gttttacaaa tgcgtccaac tgaggacggt ggtggtgctt tcgagtacta cgtcagaaaa 1080
aattactaca agactggttc tttgatggca aactcctgta aggcctccgc cgttttaggt 1140
caacacgact tagaagtcca agaggtcgct tttgaatacg gtaagagagt cggtttggct 1200
ttccaattgg ttgacgatat tttagatttt gaaggtaata ctttcacttt gggtaagcca 1260
gctttaaacg acttgagaca aggtttagcc actgcccctg tcttgttagt tgctgaacaa 1320
caacctggtt tagctaaatt gatctcccaga aagtttagag gtcctggtga tgtcgatgaa 1380
gctttggaat tggtccacag atccgacggt attgctagag ctaaggaggt tgctgttgtc 1440
caagccgaaa aagctatgtc tgccattttg accttgcatg actccccagc tcaaaatgct 1500
ttggttcaat tggctcacaa aatcgtcaat cgtaaccatt ag                    1542

SEQ ID NO: 141           moltype = AA   length = 415
FEATURE                  Location/Qualifiers
source                   1..415
                         mol_type = protein
                         organism = Solanum sp.
SEQUENCE: 141
MIFSKGLAQI SRNRFSRCRW LFSLRPIPQL HQSNHIHDPP KVLGCRVIHS WVSNALSGIG   60
QQIHQQSTAV AEEQVDPFSL VADELSLLTN RLRSMVVAEV PKLASAAEYF FKLGVEGKRF  120
RPTVLLLMAT ALNVQIPRSA PQVDVDSFSG DLRTRQQCIA EITEMIHVAS LLHDDVLDDA  180
DTRRGIGSLN FVMGNKLAVL AGDFLLSRAC VALASLKNTE VVCLLATVVE HLVTGETMQM  240
TTSSDERCSM EYYMQKTYYK TASLISNSCK AIALLAGHSA EVSVLAFDYG KNLGLAFQLI  300
DDVLDFTGTS ATLGKGSLSD IRHGIVTAPI LYAMEEFPQL RTLVDRGFDD PVNVEIALDY  360
LGKSRGIQRT RELARKHASL ASAAIDSLPE SDDEEVQRSR RALVELTHRV ITRTK       415

SEQ ID NO: 142           moltype = DNA   length = 1248
FEATURE                  Location/Qualifiers
source                   1..1248
                         mol_type = genomic DNA
                         organism = Solanum sp.
SEQUENCE: 142
atgatctttt ccaagggttt agctcaaatc tctcgtaata gattctctcg ttgcagatgg   60
ttattctctt tgcgtccaat tcctcaatta caccaatcca atcacatcca cgacccacca  120
aaagttttgg gttgtcgtgt cattcactct gggtttcta atgccttgtc tggtatcggt  180
caacaaatcc atcaacaatc tactgccgtt gccgaggaac aagtcgaccc ttttctcttg  240
gttgctgatg agttatcctt gttaaccaac agattgagat ccatggttgt cgctgaagtc  300
cctaagttag cctccgccgc tgagtatttc tttaagttag gtgtcgaagg taaacgtttc  360
cgtccaactg tcttgttgtt gatggccact gccttaaacg tccaaattcc tcgttctgct  420
ccacaagttg acgttgactc tttttctggt gacttgagaa ctagacaaca atgtatcgct  480
gaaattactg aaatgattca cgtcgcctca cttgttgcata atgacgtctt agatgatgct  540
gatactagaa gaggtattgg ttccttaaat tttgttatgg gtaataagtt ggctgttttg  600
gctggtgatt tcttgttatc cagagcctgc gtcgccttag cctccttgaa gaacaccgaa  660
gttgtctgtt tattggccac cgttgtcgaa catttggtta ccggtgaaac tatgcaaatg  720
actacctcct ccgatgaaag atgttccatg gaatactaca tgcaaaagac ctactataag  780
actgcctctg tgatttctaa ctcttgtaaa gccattgcct tgttagcgg tcactctgct  840
gaagtttctg tcttggcctt cgattacggt aagaacttag gtttggcttt tcaattgatc  900
gacgatgttt tggacttcac cggtacctct gctactttgg gtaaaggttc cttgtccgat  960
atcagacatg gtatcgttac tgctcctatt ttgtatgcta tggaagaatt ccctcaatta 1020
cgtactttgg ttgacagagg tttcgatgat ccagttaatg ttgagatcgc tttggattac 1080
ttgggtaaat cccgtggtat tcaaagaact agagaattag ccagaaagca tgcctcttta 1140
gcctctgccg ccatcgattc cttgcctgaa tccgacgatg aggaagttca agatctcgt  1200
agagctttgg tcgaattgac ccatagagtc attactcgta ctaagtaa              1248

SEQ ID NO: 143           moltype = AA   length = 330
FEATURE                  Location/Qualifiers
source                   1..330
                         mol_type = protein
                         organism = Hevea brasiliensis
SEQUENCE: 143
MQFLRGLSPI SRSGLRLFLS RQLYPFPVAN SSQLLGDSTQ KVFNRRETYS WSLVDSHGFK   60
QQIHHQSSFL SEEPLDPFSL VADELSLVAN RLRAMLVSEV PKLASAAEYF FKMGVEGKRL  120
RPTVLLLMAT ALNVHIHEPM PNGVDTLGA ELRTRQQCIA EITEMIHVAS LLHDDVLDDA   180
DTRRGIGSLN FVMGNKVAVL AGDFLLSRAC VALASLKNTE VVSLLATVVE HLVTGETMQM  240
TSTSEQRCSM DHYMQKTYYK TASLISDSCK AIALLAGQTT EVAMLAFEYG KSLGLAFQLI  300
DDVLDFTGTS ASLGKGSLSD IRHVIRLSLI                                  330

SEQ ID NO: 144           moltype = DNA   length = 993
FEATURE                  Location/Qualifiers
source                   1..993
                         mol_type = genomic DNA
                         organism = Hevea brasiliensis
SEQUENCE: 144
atgcaatttt tgagaggttt gtcccctatt tccagatccg gttgcgtttt attcttatct   60
cgtcaattat atccattccc agtcgccaac tcctcccaat tattaggtga ctctactcaa  120
aaggttttta acagacgtga gacttactca tggtcttttgg tcgactctca cggtttttaag 180
caacaaattc atcaccaatc ctcttttttg tctgaagaac cattggatcc attctctttg  240
gttgctgatg aattatcctt ggtcgctaac agattgcgtg ctatgttggt ttctgaagtc  300
ccaaaattag cctccgccgc tgaatatttt tcaagatgg gtgttgaagg taagagattg  360
cgtccaaccg tcttgttatt aatggccact gctttaaacg ttcatatcca tgaacctatg  420
cctaacggtg ttggtgacac ttttgggtgcc gaattgagaa ctagacaaca atgcatcgct  480
```

```
gaaatcaccg aaatgatcca tgttgcttct ttattacatg acgacgtttt agacgatgcc    540
gataccagaa gaggtattgg ttctttgaac ttcgttatgg gtaacaaggt tgctgttttg    600
gccggtgact ttttgttgtc cagagcttgt gttgccttag cttctttgaa gaataccgaa    660
gtcgtttctt tattggccac cgtcgtcgaa cacttggtta ctggtgagac tatgcaaatg    720
acctccactt ctgagcaacg ttgttccatg gatcattata tgcaaaagac ttactataag    780
accgcttcct taatctctga ttcctgtaaa gccatcgcct tgttagctgg tcaaactacc    840
gaggtcgcca tgttggcctt cgaatatggt aagtctttgg gttagctttt caattaatc     900
gacgatgttt tagacttcac cggtacttct gcttccttgg gtaagggttc tttgtccgac    960
attagacacg ttattagatt atccttaatt taa                                 993

SEQ ID NO: 145         moltype = AA   length = 566
FEATURE                Location/Qualifiers
REGION                 1..566
                       note = Mutant medium-chain fatty acid CoA ligase Ec_FADK_v1
source                 1..566
                       mol_type = protein
                       organism = synthetic construct
SEQUENCE: 145
MHPTGPHLGP DVLFRESNMK VTLTFNEQRR AAYRQQGLWG DASLADYWQQ TARAMPDKIA     60
VVDNHGASYT YSALDHAASC LANWMLAKGI ESGDRIAFQL PGWCEFTVIY LACLKIGAVS    120
VPLLPSWREA ELVWVLNKCQ AKMFFAPTLF KQTRPVDLIL PLQNQLPQLQ QIVGVDKLAP    180
ATSSLSLSQI IADNTSLTTA ITTHGDELAA VLFTSGTEIL PKGVMLTHNN ILASERAYCA    240
RLNLTWQDVF MMPAPLGHAT GFLHGVTAPF LIGARSVLLD IFTPDACLAL LEQQRCTCML    300
GATPFVYDLL NVLEKQPADL SALRFFLCGG TTIPKKVARE CQQRGIKLLS VYGSTESSPH    360
AVVNLDDPLS RFMHTDGYAA AGVEIKVVDD ARKTLPPGCE GEEASRGPNV FMGYFDEPEL    420
TARALDEEGW YYSGDLCRMD EAGYIKITGR KKDIIVRGGE NISSREVEDI LLQHPKIHDA    480
CVVAMSDERL GERSCAYVVL KAPHHSLSLE EVVAFFSRKR VAKYKYPEHI VVIEKLPRTT    540
SGKIQKFLLR KDIMRRLTQD VCEEIE                                         566

SEQ ID NO: 146         moltype = DNA   length = 1701
FEATURE                Location/Qualifiers
source                 1..1701
                       mol_type = genomic DNA
                       organism = Escherichia coli
SEQUENCE: 146
atgcatccaa ctggtccaca cttaggtcct gatgtcttat ttagagaatc taatatgaaa     60
gtcactttga cctttaatga acaaagacgt gccgcttaca gacaacaagg tttgtggggt    120
gacgcttctt tggctgacta ctggcaacaa actgctagag ctatgccaga caagatcgcc    180
gttgtcgata accacggtgc ttcttatacc tactctgctt tggatcatgc cgcttcttgt    240
ttggctaatt ggatgttggc taagggtatc gaatctggtg atcgtattgc tttttcaattg    300
ccaggttggt gtgaatttac cgttatctac ttggcttgtt tgaagattgg tgctgttttct    360
gtcccattgt tgccatcttg gagagaagcc gaattggttt gggttttgaa caaatgccaa    420
gctaagatgt tctttgctcc aaccttgttc aagcaaacta cagcagttga cttgattta    480
cctttacaaa atcaattacc acaattgcaa caaatcgttg gtgttgacaa gttagctcca    540
gccacctcct ctttgtcctt gtcccaaatt atcgctgata tacttctttt aaccaccgct    600
atcactactc acggtgatga gttggctgct gttttgttca cttccggtac tgagggtttg    660
ccaaaggtgt ttatgttgac ccacaataac attttgtctt ccgaaagagc ttattgtgct    720
cgtttgaact tgacctggca agatgttttc atgatgccag ctccattggg tcatgctact    780
ggtttcttgc acggtgttac tgcccccattc ttgattggtg ctagatcgt cttgttggat    840
atctttaccc cagacgcttg cttagcttta ttggaacaac aaagatgtac ctgtatgtta    900
ggtgctactc catttgttta cgatttattg aacgttttgg aaaaacaacc agctgattg    960
tctgccttga gatttttttt gtgtggtggt actactattc caaagaaagt tgctagaa     1020
tgccaacaaa gaggtatcaa gttgttgtcc gtctatggtt ccactgaatc ttctcctcat    1080
gctgttgtca atttagatga cccattgtct agattcatgc acaccgatgg ttacgccgct    1140
gctggtgttg agattaaggt tgtcgacgat gctagaaaga cctacctcc aggttgtgaa    1200
ggtgaagaag cctctagagg tccaaatgtc tttatgggtt acttcgacga gccagaattg    1260
actgctagag ctttagatga ggaaggttgg tattactctg gtgatttgtg tagaatggat    1320
gaagctggtt acattaaaat cactggtaga agaaggaca ttattgttag aggtggtgaa    1380
aatatctcct ccagagaagt tgaagatatt ttattgcaac acccaaagat tcatgatgct    1440
tgtgttgttg ctatgtccga tgagagatta ggtgaaagat cttgtgctta cgttgttttg    1500
aaggctccac atcactcttt gtctttagaa gaagtcgttg cttttcttc tagaaagaga    1560
gtcgccaagt acaagtaccc agaacacatt gttgttatcg aaaaattgcc tagaactact    1620
tctggtaaaa ttcaaaaatt cttgttgaga aaggatatca tgagacgttt gacccaagat    1680
gtctgtgaag aaattgaata a                                              1701

SEQ ID NO: 147         moltype = AA   length = 566
FEATURE                Location/Qualifiers
source                 1..566
                       mol_type = protein
                       organism = Escherichia coli
SEQUENCE: 147
MHPTGPHLGP DVLFRESNMK VTLTFNEQRR AAYRQQGLWG DASLADYWQQ TARAMPDKIA     60
VVDNHGASYT YSALDHAASC LANWMLAKGI ESGDRIAFQL PGWCEFTVIY LACLKIGAVS    120
VPLLPSWREA ELVWVLNKCQ AKMFFAPTLF KQTRPVDLIL PLQNQLPQLQ QIVGVDKLAP    180
ATSSLSLSQI IADNTSLTTA ITTHGDELAA VLFTSGTEGL PKGVMLTHNN ILASERAYCA    240
RLNLTWQDVF MMPAPLGHAT GFLHGVTAPF LIGARSVLLD IFTPDACLAL LEQQRCTCML    300
GATPFVYDLL NVLEKQPADL SALRFFLCGG TTIPKKVARE CQQRGIKLLS VYGSTESSPH    360
AVVNLDDPLS RFMHTDGYAA AGVEIKVVDD ARKTLPPGCE GEEASRGPNV FMGYFDEPEL    420
TARALDEEGW YYSGDLCRMD EAGYIKITGR KKDIIVRGGE NISSREVEDI LLQHPKIHDA    480
```

```
CVVAMSDERL GERSCAYVVL KAPHHSLSLE EVVAFFSRKR VAKYKYPEHI VVIEKLPRTT    540
SGKIQKFLLR KDIMRRLTQD VCEEIE                                        566

SEQ ID NO: 148          moltype = DNA  length = 1701
FEATURE                 Location/Qualifiers
misc_feature            1..1701
                        note = Artificial medium-chain fatty acid CoA ligase
                        Ec_FADK_v2 nucleotide sequence
source                  1..1701
                        mol_type = other DNA
                        organism = synthetic construct
SEQUENCE: 148
atgcatccaa ctggtcctca cttaggtcca gatgtcttat tcagagaatc taacatgaaa   60
gtcactttaa cttttaacga acaacgtaga gctgcttata gacaacaagg tttgtggggt  120
gatgcttcct tggctgacta ctggcaacaa actgctagag ccatgccaga taaaattgcc  180
gttgttgaca atcacggtgc ttcttacact tattctgcct tagatcacgc tgcttcctgt  240
ttagctaact ggatgttagc taagggtatt gaatccggtg atagaattgc tttccaattg  300
ccaggttggt gcgaatttac tgtcatttat ttagcttgtt taaagattgg tgccgtctcc  360
gtcccttttgt tgccatcctg gagagaggcc gagttggttt gggttttaaa caagtgtcaa  420
gctaaaatgt tctttgctcc taccttgttc aagcaaacca gaccagttga cttaattttg  480
ccattacaaa accaattacc acaattgcaa caaatcgtcg tgttgataa attagctcca   540
gccacttctt ctttgtcctt atcccaaatt attgctgata acacttcttt aactactgct  600
attactactc acggtgatga attggccgct gttttgttca cttccggtac tgaaggtttg  660
cctaaaggtg tcatgttgac tcacaacaac atttttggcct ctgaaagagc ttactgtgcc  720
cgtttaaatt tgacctggca agatgtcttc atgatgcctg ctccattggg tcacgctacc  780
ggtttcttac acggtgtcac tgccccattc ttgatcggtg tcgttctgtt tttattggat  840
atctttactc cagatgcttg cttggcttta ttggaacaac aaagatgtac ctgcatgtta  900
ggtgctactc ctttcgtcta tgatttattg aacgtcttag aaaaacaacc agctgattta  960
tccgctttaa gattctttt tgtggtggt actactatcc caaaaaggt cgccagaaa    1020
tgtcaacaaa gaggtattaa attattgtcc gtttatggtt ccactgaatc ttcccctcat 1080
gctgttgtca atttagacga ccctttgtcc agattcatgc acactgatgg ttacgccgct 1140
gctggtgtcg aaatcaaggt tgttgatgac gctagaaaaa cttaccacc tggttgcgaa  1200
ggtgaagagg cttccagagg tccaaacgtc tttatgggtt actttgatga accagaattg 1260
actgccagag cttttggatga ggaaggttgg tattattctg gtgatttgtg tagaatggat 1320
gaagccggtt acatcaagat caccggtaga agaaagaca tcatcgttag aggtggtgaa  1380
aacatttctt ctagaagagt tgaagacatt tgttgcaac acccaaagat ccacgacgct  1440
tgtgtcgtcg ccatgtctga cgaaagattg ggtgaacgtt cttgtgctta cgtcgtcttg 1500
aaagccccac accactcttt gtctttggaa gaagtcgttg ctttttttctc tcgtaagcgt 1560
gttgcaagt acaagtaccc agagcacatc gttgttattg aaaaattgcc tcgtactact  1620
tccggtaaga ttcaaaagtt cttattacgt aaggacatca tgagaagatt gactcaagac 1680
gtctgcgaag aaattgaata a                                           1701

SEQ ID NO: 149          moltype = AA  length = 521
FEATURE                 Location/Qualifiers
REGION                  1..521
                        note = Truncated acyl activating enzyme (Cs_AAE3_Ctrunc)
source                  1..521
                        mol_type = protein
                        organism = synthetic construct
SEQUENCE: 149
MEKSGYGRDG IYRSLRPPLH LPNNNNLSMV SFLFRNSSSY PQKPALIDSE TNQILSFSHF    60
KSTVIKVSHG FLNLGIKKND WLIYAPNSIH FPVCFLGIIA SGAIATTSNP LYTVSELSKQ   120
VKDSNPKLII TVPQLLEKVK GFNLPTILIG PDSEQESSSD KVMTFNDLVN LGGSSGSEFP   180
IVDDFKQSDT AALLYSSGTT GMSKGWLTHK NFIASSLMVT MEQDLVGEMD NVFLCFLPMF   240
HVFGLAIITY AQLQRGNTVI SARFDLEKML KDVEKYVTHL WWPVILALS KNSMVKFNLS    300
SIKYIGSGAA PLGKDLMEEC SKWPYGIVAQ GYGMTETCGI VSMEDIRGGK RNSGSAGMLA   360
SGVEAQIVSV DTLKPLPPNQ LGEIWVKGPN MMQGYFNNPQ ATKLTIDKKG WVHTGDLGYF   420
DEDGHLYWDR IKELIKYKGF QVAPAELEGL LVSHPEILDA WIPFPDAEAG EVPVAYWRSP   480
NSSLTENDVK KFIAGQVASF KRLRKVTFIN SVPKSASGKI L                      521

SEQ ID NO: 150          moltype = DNA  length = 1563
FEATURE                 Location/Qualifiers
misc_feature            1..1563
                        note = Truncated acyl activating enzyme (Cs_AAE3_Ctrunc)
source                  1..1563
                        mol_type = other DNA
                        organism = synthetic construct
SEQUENCE: 150
atggaaaaat ctggttatgg tagagacggt atctacagat ccttgcgtcc tccattacac   60
ttgccaaaca ataataactt atctatggtt tcctttttgt tccgtaactc ttcctcttac  120
ccacaaaaac ctgctttgat tgactccgaa accaatcaaa tcttgtcctt ttcccacttc  180
aaatctactg tcattaaagt ctctcacggt ttcttgaact taggtattaa gaagaacgac  240
tggttgatct acgctcctaa ttccatccac tttccagttg gtttcttggg tatcattgct  300
tctggtgcca ttgctaccac tttctaaccct ttatacactg tttctgagtt atcaagcaa  360
gttaaagatt ctaacccaaa attgattatc actgtcccac aattattaga aaaggtcaag  420
ggtttcaatt taccaaccat tttaatcggt ccagactccg aacaagagtc cttcctcgat  480
aaagttatga cttttaacga cttagttaac ttgggtggtt cttctggttc tgagttccca  540
atcgtcgatg atttcaagca atctgacacc gccgcttat tgtattcctc tggtactact  600
ggtatgtcta agggttggtt gactcacaaa aactttatcg cttcctcttt tgatggttacc  660
```

```
atggaacaag acttggttgg tgaaatggat aacgtcttct tgtgtttttt accaatgttc    720
catgttttcg gtttagctat cattacttac gctcaattac aaagaggtaa cactgtcatc    780
tctgctcgtt ttgacttaga aaagatgttg aaagacgttg aaaagtacgt tactcacttg    840
tggtggcctc ctgttatttt agctttgtct aagaattcta tggttaaatt caacttgtcc    900
tctatcaagt acattggttc tggtgccgct ccattaggta aggacttgat ggaagaatgt    960
tctaaatggc cttacggtat cgtcgctcaa ggttacggta tgactgaaac ttgtggtatc   1020
gtttctatgg aagacatcag aggtggtaag cgtaactccg ttctgctgg tatgttggct   1080
tccggtgttg aagcccaaat tgtttctgtc gatactttga aacctttgcc acctaaccaa   1140
ttaggtgaaa tttgggttaa aggtcctaac atgatgcaag gttacttcaa taaccctcaa   1200
gctactaagt taacattga taagaaggt tggttcata ctggtgattt gggttacttc   1260
gatgaagatg tcatttgta ctgggataga atcaaagaat taattaagta taaggtttc    1320
caagttgccc cagctgaatt ggaaggttg ttggtttctc atcctgaaat tttagatgct   1380
tggattcctt tcccagacgc tgaagccggt gaagttccag ttgcttactg agatcccct   1440
aactcttcct tgactgaaaa cgacgtcaag aagttcatcg ctggtcaagt tgcttccttt   1500
aagagattaa gaaaagtcac cttcatcaac tccgttccaa agtctgcttc cggtaagatt   1560
ttg                                                                 1563

SEQ ID NO: 151              moltype = AA   length = 518
FEATURE                     Location/Qualifiers
REGION                      1..518
                            note = Truncated cannabidiolic acid synthase Cs_CBDASt28
source                      1..518
                            mol_type = protein
                            organism = synthetic construct
SEQUENCE: 151
MSNPRENFLK CFSQYIPNNA TNLKLVYTQN NPLYMSVLNS TIHNLRFTSD TTPKPLVIVT     60
PSHVSHIQGT ILCSKKVGLQ IRTRSGGHDS EGMSYISQVP FVIVDLRNMR SIKIDVHSQT   120
AWVEAGATLG EVYYWVNEKN ENLSLAAGYC PTVCAGGHFG GGGYGPLMRN YGLAADNIID   180
AHLVNVHGKV LDRKSMGEDL FWALRGGGAE SFGIIVAWKI RLVAVPKSTM FSVKKIMEIH   240
ELVKLVNKWQ NIAYKYDKDL LLMTHFITRN ITDNQGKNKT AIHTYFSSVF LGGVDSLVDL   300
MNKSFPELGI KKTDCRQLSW IDTIIFYSGV VNYDTDNFNK EILLDRSAGQ NGAFKIKLDY   360
VKKPIPESVF VQILEKLYEE DIGAGMYALY PYGGIMDEIS ESAIPFPHRA GILYELWYIC   420
SWEKQEDNEK HLNWIRNIYN FMTPYVSKNP RLAYLNYRDL DIGINDPKNP NNYTQARIWG   480
EKYFGKNFDR LVKVKTLVDP NNFFRNEQSI PPLPRHRH                           518

SEQ ID NO: 152              moltype = DNA   length = 1557
FEATURE                     Location/Qualifiers
misc_feature                1..1557
                            note = Truncated cannabidiolic acid synthase Cs_CBDASt28
source                      1..1557
                            mol_type = other DNA
                            organism = synthetic construct
SEQUENCE: 152
atgtctaatc caagagagaa tttcttaaag tgttttctc aatacatccc aaacaatgct     60
actaacttaa agttggttta cactcaaaat aacccattgt acatgtctgt cttgaactct    120
accattcaca atttgcgttt tacttctgac accaccccta gccattagt tattgttacc    180
ccatcccacg tctctcacat ccaaggtact attttgtgt ctaaaaaggt tggtttgcaa    240
attagaacta gatctggtgg tcacgactcc gagggtatgt cttacatctc tcaagttcca    300
ttcgttattg tcgacttgcg taacatgcgt tccatcaaaa tcgatgttca ctcccaaact    360
gcttgggtcg aagccggtgc cactttaggt gaggtttatt actgggtcaa tgaagagaat    420
gagaatttgt ccttggctgc tggttattgt ccaacctgtc gtgctggtgg tcattttggt    480
ggtggtggtt acgtccatt aatgagaaac tatggttttgg ctgccgataa cattatcgac    540
gctcacttgg ttaatgtcca cggtaaggtc ttagatagaa atccatggg tgaggacttg    600
ttctggggctt tgagaggtgg tggtgctgag tcctttggta tcatcgttgc ttggaaaatt    660
cgtttagttg ctgtcccaaa atctactatg ttttctgtta agaagatcat ggaaattcac    720
gagttggtta agttggttaa taagtggcaa aatattgcct acaagtatga caaagacttg    780
ttattgatga ctcacttcat cactagaaac atcaccgata accaaggtaa aataaaaact    840
gctatccata cctacttctc ctccgttttc ttgggtggtg tcgactcctt agttgatttg    900
atgaacaaat cttttcctga attaggtatc aagaagactg attgtcgtca attgtcctgg    960
attgatacca ttatctttta ctctggtgtc gtcaattacg acaccgataa ttttcaataag   1020
gaaattttat tggacagatc tgccggtcaa acggtgcttt caagatcaa gttgactac   1080
gttaaaaaac caatcccaga atccgtcttt gtccaaattt tggagaagtt atacgaggaa   1140
gacatcggtg ctggtatgta tgcttatat ccatacggtg gtattatgga tgaaatttcc   1200
gaatctgcta tcccatttcc acatcgtgct ggtatttgt ataattatg gtacatttgc   1260
tcctgggaaa agcaagaaga taacgagaag cacttgaatt ggatcagaaa tatctacaat   1320
ttcatgactc cttacgtttc taagaatcct cgtttggctt acttgaacta cagagatttg   1380
gacatcggta ttaatgaccc aaagaaccca ataactata ctcaagctag aatttgggt   1440
gaaaagtact tcggtaaaaa ctttgacaga ttggttaagg ttaagacttt agttgatcca   1500
aataacttct tcagaaatga acaatccatc ccaccattgc tagacacag acactaa       1557

SEQ ID NO: 153              moltype = AA   length = 519
FEATURE                     Location/Qualifiers
REGION                      1..519
                            note = Truncated tetrahydrocannabinolic acid synthase
                                Cs_THCASt28
source                      1..519
                            mol_type = protein
                            organism = synthetic construct
SEQUENCE: 153
```

```
MSNPRENFLK CFSKHIPNNV ANPKLVYTQH DQLYMSILNS TIQNLRFISD TTPKPLVIVT    60
PSNNSHIQAT ILCSKKVGLQ IRTRSGGHDA EGMSYISQVP FVVVDLRNMH SIKIDVHSQT   120
AWVEAGATLG EVYYWINEKN ENLSFPGGYC PTVGVGGHFS GGGYGALMRN YGLAADNIID   180
AHLVNVDGKV LDRKSMGEDL FWAIRGGGGE NFGIIAAWKI KLVAVPSKST IFSVKKNMEI   240
HGLVKLFNKW QNIAYKYDKD LVLMTHFITK NITDNHGKNK TTVHGYFSSI FHGGVDSLVD   300
LMNKSFPELG IKKTDCKEFS WIDTTIFYSG VVNFNTANFK KEILLDRSAG KKTAFSIKLD   360
YVKKPIPETA MVKILEKLYE EDVGAGMYVL YPYGGIMEEI SESAIPFPHR AGIMYELWYT   420
ASWEKQEDNE KHINWVRSVY NFTTPYVSQN PRLAYLNYRD LDLGKTNHAS PNNYTQARIW   480
GEKYFGKNFN RLVKVKTKVD PNNFFRNEQS IPPLPPHHH                          519

SEQ ID NO: 154          moltype = DNA  length = 1560
FEATURE                 Location/Qualifiers
misc_feature            1..1560
                        note = Truncated tetrahydrocannabinolic acid synthase
                          Cs_THCASt28
source                  1..1560
                        mol_type = other DNA
                        organism = synthetic construct
SEQUENCE: 154
atgtctaacc ctcgtgagaa cttcttgaaa tgtttctcca aacatatccc aaacaatgtc    60
gctaacccta gttagttta cactcaacat gatcaattat atatgtctat cttgaactct   120
accatccaaa acttgagatt catctccgat accaccccaa aaccattggt tattgttacc   180
ccatccaaca attctcatat tcaagctacc attttgtgct ccaaaaaggt cggtttgcaa   240
atccgtacta gatctggtgg tcacgatgct gaaggtatgt cttacatttc caagtccca    300
ttcgttgttg tcgatttaag aaatatgcac tctatcaaaa tcgacgttca ctctcaaact   360
gcttgggttg aagccggtgc cactttaggt gaggtttact actggattaa cgaaaagaat   420
gaaaacttat cctttccagg tggttactgt ccaactgttg gtgttggtgg tcacttctct   480
ggtggtggtt atggtgcctt gatgagaaac tacggtttag ctgctgataa tattatcgac   540
gctcacttgg ttaatgtcga cggtaaggtt ttggacagaa aatccatggg tgaagattta   600
ttctgggcca ttagaggtgg tggtggtgaa aacttcggta tcattgctgc ttggaaaatt   660
aaattggtcg ctgtcccatc caagtctact attttctccg tcaagaaaaa catgaaatt   720
catggttttg ttaaattatt caacaagtgg caaaacattg cttacaaata cgacaaagac   780
ttagttttga tgacccactt cattactaaa acattaccg acaaccatgg taaaaataaa   840
actactgttc acggttactt ctcttccatt tttcatggtg gtgtcgactc cttggtcgat   900
ttaatgaaca aatctttccc tgagttgggg atcaagaaga ccgactgtaa agaattctct   960
tggatcgaca ctactatttt ctactctggt gtcgttaact tcaacaccgc taatttcaag  1020
aaggaaattt tattagatag atccgctggt aaaaagaccg cttctctat caattagac   1080
tacgttaaaa aaccaatccc agaaaccgct atggtcatga tcttggaaaa attatatgaa  1140
gaagacgttg gtgccggtat gtacgtctta tatccatatg gtggtattat ggaagagatc  1200
tctgaatccg ctatcccttt tccacacaga gccggtatta tgtacgaatt atggtacact  1260
gcttcctggg agaaacaaga agataatgaa aagcacatta actgggttag atctgtttac  1320
aacttcacta ctccatacgt ctctcaaaac caagattacc tacttaaaa ctaccgtgat  1380
ttggatttag gtaaaaactaa tcacgcttcc ccaaacaact acacccaagc tagaatttgg  1440
ggtgagaagt actttggtaa gaacttcaac cgtttagtca aggtcaagac taaagttgat  1500
ccaaacaatt ttttcagaaa cgaacaatct atcccacctt taccaccaca ccaccattag  1560

SEQ ID NO: 155          moltype = AA  length = 545
FEATURE                 Location/Qualifiers
source                  1..545
                        mol_type = protein
                        organism = Cannabis sativa
SEQUENCE: 155
MNCSAFSFWF VCKIIFFFLS FHIQISIANP RENFLKCFSK HIPNNVANPK LVYTQHDQLY    60
MSILNSTIQN LRFISDTTPK PLVIVTPSNN SHIQATILCS KKVGLQIRTR SGGHDAEGMS   120
YISQVPFVVV DLRNMHSIKI DVHSQTAWVE AGATLGEVYY WINEKNENLS FPGGYCPTVG   180
VGGHFSGGGY GALMRNYGLA ADNIIDAHLV NVDGKVLDRK SMGEDLFWAI RGGGGENFGI   240
IAAWKIKLVA VPSKSTIFSV KKNMEIHGLV KLFNKWQNIA YKYDKDLVLM THFITKNITD   300
NHGKNKTTVH GYFSSIFHGG VDSLVDLMNK SFPELGIKKT DCKEFSWIDT TIFYSGVVNF   360
NTANFKKEIL LDRSAGKKTA FSIKLDYVKK PIPETAMVKI LEKLYEEDVG AGMYVLYPYG   420
GIMEEISESA IPFPHRAGIM YELWYTASWE KQEDNEKHIN WVRSVYNFTT PYVSQNPRLA   480
YLNYRDLDLG KTNHASPNNY TQARIWGEKY FGKNFNRLVK VKTKVDPNNF FRNEQSIPPL   540
PPHHH                                                              545

SEQ ID NO: 156          moltype = DNA  length = 1638
FEATURE                 Location/Qualifiers
source                  1..1638
                        mol_type = genomic DNA
                        organism = Cannabis sativa
SEQUENCE: 156
atgaattgtt ctgctttctc tttctggttc gtttgtaaga tcatcttttt cttcttatct    60
ttccatattc aaatctctat cgctaaccct cgtgagaact tcttgaaatg tttctccaaa   120
catatcccaa acaatgtcgc taaccctaag ttagttaca ctcaacatga tcaattatat   180
atgtctatct tgaactctac catccaaaac ttgagattca tctccgatac caccccaaaa   240
ccattggttt gttaccccc atccaacaat tctcatattt aagctaccac tttgtgctcc   300
aaaaaggtcg gtttgcaaat ccgtactaga tctggtggtc acgatgctga aggtatgtct   360
tacatttccc aagtcccatt cgttgttgtc gatttaagaa atatgcactc tatcaaaatc   420
gacgttcact ctcaaactgc ttgggttgaa gccggtgcca ctttaggtga ggtttactac   480
tggattaacg aaaagaatga aaacttatcc tttccaggtg gttactgtcc aactgttggt   540
gttggtggtc acttctctgg tggtggttat ggtgccttga tgagaaacta cggtttagct   600
```

```
gctgataata ttatcgacgc tcacttggtt aatgtcgacg gtaaggtttt ggacagaaaa    660
tccatgggtg aagatttatt ctgggccatt agaggtggtg gtggtgaaaa cttcggtatc    720
attgctgctt ggaaaattaa attggtcgct gtcccatcca agtctactat tttctccgtc    780
aagaaaaaca tggaaattca tggtttggtt aaattattca acaagtggca aaacattgct    840
tacaaatacg acaaagactt agttttgatg acccacttca ttactaaaaa cattaccgac    900
aaccatggta aaaataaaac tactgttcac ggttacttct cttccatttt tcatggtggt    960
gtcgactcct tggtcgattt aatgaacaaa tcttttccctg agtgggtat caagaagacc   1020
gactgtaaag aattctcttg gatcgacact actattttct actctggtgt cgttaacttc   1080
aacaccgcta atttcaagaa ggaaattta ttagatagat ccgctggtaa aaagaccgct   1140
ttctctatca aattagacta cgttaaaaaa ccaatcccag aaaccgctat ggtcaaaatc   1200
ttggaaaaat tatatgaaga agacgttggt gccggtatgt acgtcttata tccatatggt   1260
ggtattatgg aagagatctc tgaatccgct atccctttc cacacagagc cggtattatg   1320
tacgaattat ggtacactgc ttcctgggag aaacaagaag ataatgaaaa gcacattaac   1380
tgggttagat ctgtttacaa cttcactact ccatacgtc ctcaaaaccc aagattagcc   1440
tacttaaact accgtgattt ggatttaggt aaaactaatc acgcttcccc aaacaactac   1500
acccaagcta gaatttgggg tgagaagtac tttggtaaga acttcaaccg tttagtcaag   1560
gtcaagacta agttgatcc aaacaatttt ttcagaaacg aacaatctat cccacccttta   1620
ccaccacacc accattag                                                1638

SEQ ID NO: 157          moltype = DNA    length = 1197
FEATURE                 Location/Qualifiers
misc_feature            1..1197
                        note = Artificial Erg10p: acetoacetyl CoA thiolase
                         nucleotide sequence
source                  1..1197
                        mol_type = other DNA
                        organism = synthetic construct
SEQUENCE: 157
atgtcccaaa atgtttacat tgtttctact gctagaactc ctatcggttc cttccaaggt     60
tccttatctt ccaaaactgc cgtcgaattg ggtgccgttg ccttgaaagg tgctttagct    120
aaagttccag agttagacgc ttccaaagat ttcgatgaaa ttatcttcgg taacgtttta    180
tccgctaact gggtcaagc tccagccaga caagttgcct tggctgccgg tttgtctaat    240
cacatcgttg cttctactgt caacaaagtt tgtgcctctg ctatgaaagc tatcattta    300
ggtgcccaat ctattaaatg tggtaatgct gacgttgttg tcgctggtgg ttgtgagtgc    360
atgaccaacg ccccttacta catgccagcc gccagagcg gtgccaaatt cggtcaaact    420
gttttggttg acggtgttga agagatggt ttgaacgatg cctatgacgg tttggctatg    480
ggtgttcacg ctgaaaagtg tgctagagac tgggacatta ccagaaaca caagataat    540
ttcgctattg aatcttacca aaagtcccaa aaatctcaaa aggaaggtaa gttgacaat    600
gaaatcgttc cagttactat caagggtttt cgtggtaagc ctgatactca agtcaccaag    660
gatgaagaac cagcccgttt cacgtcgaa aagttgagat ctgccagaac cgttttccaa    720
aaagaaaacg gtaccgttac tgctgccaat gcttctccaa tcaacgatgg tgccgctgct    780
gttatttag tctctgagaa ggttttgaag gagaaaaatt tgaagccttt agccatcatt    840
aagggtttgg gtgaagctgc tcaccaacca gctgatttca cttgggcccc ttctttagct    900
gtcccaaagg ctttaaaaca cgctggtatt gaagatatca actctgttga ctacttcgaa    960
ttcaatgaag cttctctgt cgtcggtttg gtcaatacca aaatcttgaa gttggatcct   1020
tctaaggtta acgtttacgg tggtgctgtc gcttagggc accctttagg ttgttctggt   1080
gctagagttg ttgtcacctt gttgtccatt ttacaacaag aagtggtaa gatcggtgtt   1140
gctgctatct gtaacggtgg tggtggtgct tcttccattg tcatcgaaaa gatctag      1197

SEQ ID NO: 158          moltype = DNA    length = 1191
FEATURE                 Location/Qualifiers
misc_feature            1..1191
                        note = Artificial mevalonate pyrophosphate decarboxylase
                         (Sc_ERG19) nucleotide sequence
source                  1..1191
                        mol_type = other DNA
                        organism = synthetic construct
SEQUENCE: 158
atgactgtct acactgcctc cgttactgcc cctgtcaaca ttgccacctt gaagtattgg     60
ggtaaaagag atactaaatt gaacttacca actaactcct ccatttctgt cactttgtct    120
caagatgatt tgagaacctt gacttccgct gccaccgccc ctgaatttga gagagatact    180
ttgtggttaa atggtgaacc tcattctatt gacaacgaaa gaacccaaaa ctgtttacgt    240
gacttgagac aattgcgtaa ggaaatggaa tctaaagacg cttctttacc taccttgtct    300
caatggaaat tgcatatcgt ttctgaaaat aacttccaa ctgtgccgg tttggcttcc    360
tccgctgctg gttttgctgc tttagtttct gccatcgcca attatatca attgccacaa    420
tccacttccg aaatctctag aatcgctaga aaggttccg gttctgcttg tagatccttg    480
ttcggtggtt acgttgcttg ggaaatgggt aaagctgaag acggtcatga ttctatggcc    540
gttcaaattg ccgactcctc cgattggcct caaatgaagg ttctgtctt ggttgtctcc    600
gatatcaaaa aggatgtctc ttctactcaa ggtatgcaat taactgttgc cacttccgaa    660
ttgttcaaag agcgtatcga acacgttgtt ccaaagagat tgaagttat gagaaaagct    720
atcgtcgaaa aggacttcgc taccctttgcc aaggagacta tgatggattc taactccttc    780
cacgctactt gtttggattc cttttccacct atttttctaca tgaatgacac ctccaaacgt    840
attatctctt ggtgtcacac cattaaccaa ttttatggtg aaactatcgt cgcttacact    900
tcgaaggccg gtccaaacgc tgtcttgtac tatttggtca aaacgaatc caagttattt    960
gcttttatct ataagttgtt cggttccgtc cctgtggg acaagaaatt caccactgaa   1020
caattggaag cttcaaccaa cccaattgaa tcttccaatt tcactgctag agaattagat   1080
ttggaattac aaaaggatgt cgctagagtc atccttaactc aagttggttc cggtccacaa   1140
gaaactaacg aatctttgat tgatgctaaa actggtttgc ctaaagaata a            1191
```

| SEQ ID NO: 159 | moltype = DNA length = 867 |
| --- | --- |
| FEATURE | Location/Qualifiers |
| misc_feature | 1..867 |
| | note = Artificial isopentenyl pyrophosphate isomerase Sc_IDI1 nucleotide sequence |
| source | 1..867 |
| | mol_type = other DNA |
| | organism = synthetic construct |

SEQUENCE: 159

```
atgaccgctg acaacaactc catgccacat ggtgctgtct cctcctacgc taaattagtc   60
caaaaccaaa cccctgaaga catttttagaa gagttccctg aaatcattcc attgcaacaa  120
agaccaaaca ctagatcctc cgagacttct aacgatgaat ctggtgaaac ttgttttttct  180
ggtcatgatg aagaacaaat caagttgatg aacgagaatt gtattgtttt ggactgggat  240
gacaacgcta tcggtgctgg taccaaaaag gtctgtcact tgatgaaaaa catcgaaaag  300
ggtttgttgc atagagcctt ttccgtcttc atcttcaacg aacaaggtga gttattattg  360
caacaaagag ccactgaaaa aatcaccttt ccagatttat ggaccaacac ctgttgctcc  420
catccattgt gtattgatga tgaattgggt ttgaaaggta gttggacga caagattaaa  480
ggtgccatca ccgccgctgt tcgtaagtta gaccatgaat tgggtatccc tgaagacgaa  540
actaagacta gaggtaaatt ccatttcttg aatcgtattc actacatggc tccttccaat  600
gaaccatggg gtgaacacga aatcgactac attttgtttt acaaaattaa tgctaaagaa  660
aatttaaccg ttaacccaaa cgtcaacgag ttagagatt tcaagtgggt ctctccaaac  720
gatttgaaga ctatgttcgc tgacccatcc tacaagttca ctccatggtt taagatcatc  780
tgtgaaaact atttgtttaa ctggtgggag caattggacg acttatctga agttgaaaat  840
gatcgtcaaa ttcaccgtat gttgtaa                                      867
```

| SEQ ID NO: 160 | moltype = DNA length = 1356 |
| --- | --- |
| FEATURE | Location/Qualifiers |
| misc_feature | 1..1356 |
| | note = Artificial phosphomevalonate kinase Sc_ERG8 nucleotide sequence |
| source | 1..1356 |
| | mol_type = other DNA |
| | organism = synthetic construct |

SEQUENCE: 160

```
atgtccgagt taagagcctt ctccgctcct ggtaaagcct tattagctgg tggttactta    60
gtcttggata ctaaatatga agccttcgtc gtcggtttat ctgccagaat gcatgccgtc   120
gcccatccat acgttccttt gcaaggttct gacaagtttg aggtcgtgt caagtctaaa   180
caattcaaag atggtgaatg gttgtatcat atttctccaa aatccggttt cattccagtt   240
tctatcggtg gttctaagaa cccattcatc gaaaaagtca tcgctaacgt tttctcttac   300
ttcaagccta atatgatga ttattgcaat agaaatttat tcgttattga tatcttctcc   360
gatgacgcct atcattccca agaagactct gttaccgagc atagaggtaa cagaagatta   420
tctttccact ctcacagaat tgaagaagtt ccaaaaactg gtttaggttc ttctgctggt   480
ttagtcaccg ttttaaccac tgccttggct tcttttcttg tttccgactt agaaaataac   540
gtcgacaagt atcgtgaagt catccacaac ttggcccaag ttgctcattg tcaagctcaa   600
ggtaagattg gttccggttt cgatgttgct gccgccgcct acggttccat cagatataga   660
agattccctc cagctttgat ttctaactta ccagatattg gttctgctac ttatggttcc   720
aagttgaccc acttggttga cgaagaagat tggaacatta ccatcaagtc caatcacttg   780
ccatctggtt taactttgtg gatgggtgat atcaagaacg ttctgaaac tgtcaaattg   840
gtccaaaagg tcaaaaattg gtacgattcc catatgccag agtctttgaa gatctatact   900
gaattggacc acgctaactc tcgtttcatg gatggttttgt ctaagttgga cagattgcat   960
gaaactgaca cgactactc tgaccaaatt ttcgagtcct tggaaagaaa cgactgcact  1020
tgtcaaaagt atccgagaat caccgaggtt agagatgccg ttgctactat tagaagatcc  1080
ttcagaaaga ttaccaagga atccggtgct gatattgagc tcccagttca aacttctttg  1140
ttggatgatt gccaaacttt aaaaggtgtt taaacttgtt taattcctgg tgctggtggt  1200
tacgacgcca tcgccgttat caccaaacaa gacgtcgact aagagccca aactgccaac  1260
gacaaaagat tctccaaggt tcaatggttg gacgtcactc aagctgattg gggtgttaga  1320
aagaaaaagg acccagagac ttacttggat aaatag                            1356
```

| SEQ ID NO: 161 | moltype = DNA length = 1059 |
| --- | --- |
| FEATURE | Location/Qualifiers |
| misc_feature | 1..1059 |
| | note = Mutant farnesyl pyrophosphate synthase (Erg20mut, F96W, N127W) |
| source | 1..1059 |
| | mol_type = other DNA |
| | organism = synthetic construct |

SEQUENCE: 161

```
atggcttctg agaaggagat tcgtcgtgag agattcttga atgttttttcc taaattagtc   60
gaggaattga acgcttcttt gttggcttat ggtatgccta aggaagcttg tgattggtat  120
gctcactcct tgaattataa tactccaggt ggtaaattga ccgtggtttt gtctgttgtt  180
gacacttacg ctatttttatc taacaagacc gtcgagcaat gggtcaagaa agagtatgaa  240
aaggtcgcta tttttaggttg gtgtattgaa ttgttgcaag cttactggtt ggttgccgat  300
gacatgatgg acaagtctat tactcgtcgt ggtcaacctg ctggtataaa ggtcccagag  360
gttggtgaaa ttgctatctg ggacgctttc gtgttggaga ctgctatcta taattgttg  420
aaatccccact tcagaaacga gaaatactac attgacatca ccgagttgtt ccacgaagtc  480
actttccaaa ctgagttagg tcaattaatg gacttgatca ccgctccaga agacaaagtt  540
gacttgtcca gttttccttt gaaaaagcac tctttcatcg ttactttcaa gactgcttat  600
tactctttct acttaccagt tgcctggct atgtacgtcc ccggtatcac tgacgaaaag  660
gacttgaagc aagctcgtga cgtttttgatt ccattaggtg aatatttcca aatccaagat  720
```

```
gactacttag actgttttgg tacccctgaa caaatcggta agatcggtac tgatattcaa   780
gataacaagt gctcttgggt tatcaacaag gctttagagt tagcctccgc cgaacaacgt   840
aaaactttag atgaaaacta cggtaaaaaa gactctgttg ctgaggccaa gtgtaagaag   900
attttaacg atttaaaat cgaacaattg tatcacgaat atgaagagtc cattgctaag   960
gatttgaagg ctaaaatttc tcaagttgac gaatcccgtg gtttcaaagc tgacgttttg  1020
actgctttt taaacaaggt ttacaagcgt tccaaataa                          1059

SEQ ID NO: 162        moltype = DNA   length = 1158
FEATURE               Location/Qualifiers
misc_feature          1..1158
                      note = Artificial tetraketide synthase (TKS) nucleotide
                        sequence
source                1..1158
                      mol_type = other DNA
                      organism = synthetic construct
SEQUENCE: 162
atgaaccatt taagagctga gggtccagct tccgtcttgg ctatcggtac tgctaatcca    60
gagaacattt tattacaaga tgagtttcca gattactgta tccgtgttac ttcaagtccg   120
catatgaccc aattgaaaga aaagttccgt aaaatctgtg ataaatctat gattagaaaa   180
agaaactgct ttttaaacga agaacacttg aagcaaaacc caagattagt tgaacacgag   240
atgcaaacct ggacgctag acaagatatg ttggttgtcg aggttcctaa attgggtaaa   300
gacgcctgtg ctaaagctat caaagagtgg ggtcaaccta agtccaagat cactcactta   360
atcttcactt ccgcttccac cactgacatg cctggtgctg attaccactg tgccaagtta   420
ttggggtttgt ctccttctgt caagagagtt atgatgtacc aattaggttg ttacggtggt   480
ggtactgtct taagaattgc taaggacatc gctgaaaaca caaaggtgc tagagtttta   540
gccgtttgtt gtgacatcat ggcttgttta tttcgtgtc catctgaatc tgacttggag   600
ttgttggttg tcaagctat ttttggtgat ggtgccgctg ccgtcatcgt tggtgctgag   660
ccagatgaat ccgttggtga agaccaattt tcgaattag tctctactgg tcaaactatt   720
ttgccaaact ccgaggtac tatccggtggt catattcgtg aagccggttt aatctttgat   780
ttgcacaaag acgttccaat gttgatctct aacaacatcg aaaagtgttt aattgaggct   840
tttactccaa ttggtatctc tgactgaac tctatcttct ggatcactca tccaggtggt   900
aaggctatct tggacaaggt tgaagaaaaa ttacattta agtccgataa attcgtcgat   960
tctcgtcatg ttttgtctga acacggtaac atgtcttcct ccactgtctt gtttgttatg  1020
gatgaattac gtaagagatc ttttggaggag ggtaagtcta ctactggtga tggttttcgaa  1080
tggggtgttt tgttcggttt cggtcctggt ttgactgttg aacgtgttgt tgttagatct  1140
gttccaatta agtactag                                                 1158

SEQ ID NO: 163        moltype = DNA   length = 306
FEATURE               Location/Qualifiers
misc_feature          1..306
                      note = Artificial olivetolic acid cyclase (OAC) nucleotide
                        sequence
source                1..306
                      mol_type = other DNA
                      organism = synthetic construct
SEQUENCE: 163
atggccgtca aacacttgat cgtcttaaaa ttcaaggatg aaattactga agctcaaaaa    60
gaagagttct tcaaaaccta tgtcaattta gtcaacatta ttcctgctat gaaggacgtt   120
tactggggta aggatgtcac ccaaaagaac aaggaagaag gttacactca cattgttgaa   180
gtcactttcg aatctgttga aactatccaa gattatatta tccacccagc tcatgtccgt   240
tttggtgatg tttacagatc tttttgggaa aaattgttga tctttgacta tactccaaga   300
aaataa                                                              306

SEQ ID NO: 164        moltype = DNA   length = 2163
FEATURE               Location/Qualifiers
misc_feature          1..2163
                      note = Artificial acyl-activating enzyme Cs_AAE1_v1
                        nucleotide sequence
source                1..2163
                      mol_type = other DNA
                      organism = synthetic construct
SEQUENCE: 164
atgggtaaga attacaagtc cttagactct gttgttgctt ctgactttat tgctttaggt    60
attacttccg aagttgctga aaccttacac ggtagattgg ctgaaattgt ttgcaactac   120
ggtgctgcta cccctcaaac ttggattaac attgctaatc atattttgtc tccagatttg   180
ccattttctt tacaccaaat gttgttctac ggttgttaca aggatttcgg tcctgctcct   240
ccagcttgga ttcctgatcc agaaaaagtc aaatctacta cttgggtgc tttgttgaa   300
aagagaggta aggagttttt gggtgttaag tacaaggacc caatttcttc tttctctcac   360
ttccaagaat tctctgttag aaaccctgaa gtttactgga gaactgtttt gatgcattgga   420
atgaagattt cttttttctaa ggacccagtg tgtatcttaa gaagagacga cattaacaat   480
ccaggtggtt ctgagtggtt accaggtgt tacttgaact ctgccaaaaa ttgcttgaac   540
gttaactcta caagaaatt gaatgacact atgattgtct ggagagatga gggtaacgat   600
gatttgcctt tgaataaatt gactttggat caattgaaga aagagtctg ttggttggt   660
tacgctttgg aagaaatggg ttttagaaaa agttcctcatga tatgcctatg    720
cacgttgatg ctgttgttat ttatttggct attgttttag ctggttatgt tgttgtttcc   780
atcgccgact ccttctctgc tccagaaatc tccaccagat gagattgtc taagccaaa   840
gccattttca cccaagacca catcattaga ggtaagaagc gtattccatt gtattctcgt   900
gttgttgaag ctaaatctcc tatggctatc gtcatcccat gctctggttc taacatcggt   960
gctgaattaa gagacggtga tatttcttgg gactactttt tagaaagagc taagaattc  1020
```

```
aaaaactgcg agtttactgc tagagaacaa cctgtcgacg cttatactaa tattttattc    1080
tcttctggta ctactggtga acctaaggct attccatgga cccaagctac tcctttgaaa    1140
gccgctgctg atggttggtc ccatttagac atcagaaaag gtgatgtcat cgtctggcca    1200
actaacttag gttggatgat gggtccatgg ttagtctacg cttctttgtt gaatggtgcc    1260
tctatcgcct tatataatgg ttccccttta gtctctggtt ttgctaaatt cgttcaagat    1320
gctaaggtta ccatgttagg tgttgtccct tctatcgtta gatcttggaa atctactaac    1380
tgtgtttctg gttacgactg gtccactatt cgttgtttct cttcttctgg tgaagcttcc    1440
aatgtcgatg agtacttatg gttaatgggt cgtgctaact acaagccagt catcgaaatg    1500
tgcggtggta ctgaaattgg tggtgctttt tccgctggtt ctttttttaca agcccaatcc    1560
ttgtcttcct tctcctctca atgtatgggt tgtactttat atatcttaga taagaatggt    1620
taccctatgc ctaaaaacaa gccaggtatt ggtgaattag ctttgggtcc tgttatgttt    1680
ggtgcttcta aaaccttgtt aaatggtaat catcacgacg tttacttcaa aggtatgcct    1740
actttgaacg gtgaggtttt gagacgtcat ggtgatattt cgaattaac ttccaacggt     1800
tattatcacg ctcacggtag agctgatgat actatgaaca ttggtggtat taagatctct    1860
tccatcgaaa ttgagagagt ttgtaacgag gttgacgatc gtgtttttcga aactactgct    1920
attggtgtcc ctcctttagg tggtggtcca gaacaattgg ttatctttt cgtcttgaag     1980
gactccaacg acaccactat cgacttaaac caattgaagt tgtctttcaa cttgggtttg    2040
caaaagaagt tgaatccatt atttaaggtt actcgtgtcg ttccattgtc ctccttgcca    2100
agaactgcta ccaacaagat tatgcgtaga gtcttgagac aacaattctc tcactttgag    2160
taa                                                                 2163

SEQ ID NO: 165         moltype = DNA  length = 2163
FEATURE                Location/Qualifiers
misc_feature           1..2163
                       note = Artificial acyl-activating enzyme Cs_AAE1_v2
                        nucleotide sequence
source                 1..2163
                       mol_type = other DNA
                       organism = synthetic construct
SEQUENCE: 165
atgggtaaga actacaaatc cttagattcc gtcgtcgctt ctgatttcat cgctttgggt     60
attacttctg aagttgctga aaccttgcat ggtagattgg ctgaaattgt ctgtaactac    120
ggtgctgcta ccccacaaac ttggatcaac attgctaacc acatcttatc ccctgacttg    180
ccattctcct tacaccaaat gttgttctac ggttgttata aagtttcgg tccagctcct    240
cctgcttgga ttcctgaccc agagaaggtt aagtctacta atttaggtgc tttgttagag    300
aagagaggta aggaatttt aggtgttaag tataaagatc caatttcttc cttctctcac    360
ttccaagaat tttctgttag aaacccagaa gtttactgga gaactgtttt gatggatgaa    420
atgaagatct cttttttccaa ggaccggag tgtattttga gacgtgatga catcaacaat    480
ccaggtggtt ctgagtggtt accaggtggt tacttgaact ctgccaagaa ttgtttgaac    540
gttaactcta acaaaagtt gaacgatacc atgattgttt ggagagacga aggtaacgat    600
gatttgccat tgaataagtt aaccttggat caattgagaa aaagagtctg ttagtcggt    660
tacgctttgg aagagatggg tttggaaaag ggttgtgcta tcgccatcga tatgccaatg    720
catgttgatg ctgttgttat ctatttggcc attgttttcg ctggttacgt tgttgtttcc    780
atcgctgact cctttctgc tccagaaatt tctactagat taagattgtc taaagccaaa    840
gccatttca ctcaagacca tattattaga ggtaagaaaa gaattccatt gtattccaga     900
gttgttgaag ctaaatcccc aatggccatc gtcatcccat gctctggttc taatattggt    960
gccgaattga gagacggtga tatctcttgg gactacttt tggagcgtgc taaagaattt    1020
aaaaactgcg aattcaccgc cagagaacaa ccagttgacg cctacactaa cattttgttt    1080
tcttctggta ctactggtga acctaaggct attccatgga ctcaagctac tccattgaaa    1140
gccgccgccg atggttggtc ccactagat attagaaagg gtgatgtcat cgtctggcct    1200
actaacttgg gttggatgat gggtccttgg ttggttacg cttccttatt gaacggtgcc    1260
tctatcgctt tatataatgg ttccccttta gtttctggtt ttgctaaatt cgttcaagat    1320
gctaaggtta ctatgttggg tgtcgtccca tccattgtcc gttcctggaa gtctaccaat    1380
tgtgtttctg gttatgattg gtctactatt cgttgttttt cttcctctgg tgaagcttcc    1440
aatgtcgata aatatttgtg gttaatgggt agagctaact acaagccagt tattgaaatg    1500
tgtggtggta ctgaaattgg tggtgctttc tctgctggtt ccttttgca agctcaatcc    1560
ttgtcttctt tctcctccca atgtatgggt tgcactttat acatcttgga caagaatggt    1620
taccctatgc caaagaataa accaggtatt ggtgaattgg ctttgggtcc agtcatgttc    1680
ggtgcttcta agactttgtt gaacggtaac catcatgacg tctacttcaa gggtatgcct    1740
accttgaacg gtgaagtttt aagacgtcac ggtgacattt cgaattgac ttccaacggt     1800
tattatcatg ctcacggtag agctgacgac actatgaaca tcggtggtat taagatctct    1860
tctatcgaaa ttgaaagagt ttgcaacgag gttgatgatc gtgtcttcga aaccactgct    1920
attggtgtcc ctcctttagg tggtggtcct gagcaattgg ttattttctt tgtcttaaag    1980
gattcaacg acaccactat tgacttaaat caattgaagt tgtccttcaa tttgggtttg     2040
caaaagaagt tgaacccatt attcaaggtt actcgtgtcg ttcctttgtc ctcttgcca    2100
agaaccgcta ccaataaaat tatgagacgt gttttgcgtc aacaattctc tcactttgaa    2160
taa                                                                 2163

SEQ ID NO: 166         moltype = DNA  length = 1602
FEATURE                Location/Qualifiers
misc_feature           1..1602
                       note = Artificial acyl-activating enzyme Cs_AAE3 nucleotide
                        sequence
source                 1..1602
                       mol_type = other DNA
                       organism = synthetic construct
SEQUENCE: 166
atggaaaaat ctggttatgg tagagacggt atctacagat ccttgcgtcc tccattacac     60
ttgccaaaca ataataactt atctatggtt tcctttttgt tccgtaactc ttcctcttac    120
```

```
ccacaaaaac ctgctttgat tgactccgaa accaatcaaa tcttgtcctt ttcccacttc   180
aaatctactg tcattaaagt ctctcacggt ttcttgaact taggtattaa gaagaacgac   240
tggttgatct acgctcctaa ttccatccac tttccagttt gtttcttggg tatcattgct   300
tctggtgcca ttgctaccac ttctaaccct ttatacactg tttctgagtt atctaagcaa   360
gttaaagatt ctaacccaaa attgattatc actgtcccac aattattaga aaaggtcaag   420
ggtttcaatt taccaaccat tttaatcggt ccagactccg aacaagagtc ttcttccgat   480
aaagttatga cttttaacga cttagttaac ttgggtggtt cttctggttc tgagttccca   540
atcgtcgatg atttcaagca atctgacacc gccgctttat tgtattcctc tggtactact   600
ggtatgtcta agggttggtt gactcacaaa aactttatcg cttcctcttt gatggttacc   660
atggaacaag acttggttgg tgaaatggat aacgtcttct tgtgtttttt accaatgttc   720
catgttttcg gtttagctat cattacttac gctcaattac aaagaggtaa cactgtcatc   780
tctgctcgtt ttgacttaga aaagatgttg aaagacgttg aaaagtacgt tactcacttg   840
tggtggcctc ctgttatttt agctttgtct aagaattcta tggttaaatt caacttgtcc   900
tctatcaagt acattggttc tggtgccgct ccattaggta aggacttgat ggaagaatgt   960
tctaaatggc cttacggtat cgtcgctcaa ggttacggta tgactgaaac ttgtggtatc  1020
gtttctatgg aagacatcag aggtggtaag cgtaactccg ttctgctgg tatgttggct  1080
tccggtgttg aagcccaaat tgtttctgtc gatactttga aacctttgcc acctaaccaa  1140
ttaggtgaaa tttgggttaa aggtcctaac atgatgcaag gttacttcaa taaccctcaa  1200
gctactaagt taactattga taagaagggt tgggttcata ctggtgattt gggttacttc  1260
gatgaagatg gtcatttgta ctgggataga atcaaagaat taattaagta taaaggtttc  1320
caagttgccc cagctgaatt ggaaggtttg ttggtttctc atcctgaaat tttagatgct  1380
tggattcctt tcccagacgc tgaagccggt gaagttccag ttcttactg gagatcccct  1440
aactcttcct tgactgaaaa cgacgtcaag aagttcatcg ctggtcaagt tgcttccttt  1500
aagagattaa gaaagtcac cttcatcaac tccgttccaa agtctgcttc cggtaagatt  1560
ttgagaagag aattaatcca aaaggttcgt tccaacatgt ag                     1602

SEQ ID NO: 167          moltype = DNA  length = 1635
FEATURE                 Location/Qualifiers
misc_feature            1..1635
                        note = Artificial cannabidiolic acid synthase (CBDAS)
                         nucleotide sequence
source                  1..1635
                        mol_type = other DNA
                        organism = synthetic construct
SEQUENCE: 167
atgaaatgtt ccacctttc tttctggttt gtttgtaaga tcatcttctt cttcttctcc     60
ttcaacatcc aaacttccat cgctaatcca agagagaatt tcttaaagtg ttttttctcaa  120
tacatcccaa acaatgctac taacttaaag ttggtttaca ctcaaaataa cccattgtac   180
atgtctgtct tgaactctac cattcacaat ttgcgttttta cttctgacac caccccttaag  240
ccattagtta ttgttacccc atcccacgtc tctcacatcc aaggtactat tttgtgttct    300
aaaaaggttg gtttgcaaat tagaactaga tctggtggtc acgactccga gggtatgtct    360
tacatctctc aagttccatt cgttattgtc gacttgcgta acatgcgttc catcaaaatc    420
gatgttcact cccaaactgc ttgggtcgaa gccggtgcca cttaggtga ggtttattac     480
tgggtcaatg agaagaatga gaatttgtcc ttggctgctg gttattgtcc aaccgtctgt    540
gctggtggtc attttggtgg tggtggttac ggtccattaa tgagaaacta tggtttggct    600
gccgataaca ttatcgacgc tcacttggtt aatgtccacg taaggtcttt agatagaaaa    660
tccatgggtg aggacttgtt ctgggctttg agaggtggtg gtgctgaatc cttggtatc    720
atcgttgctt ggaaaattcg tttagttgct gtcccaaat ctactatgtt ttctgttaag    780
aagatcatgg aaattcacga gttggttaag ttggttaata agtggcaaaa tattgcctac    840
aagtatgaca aagacttgtt attgatgact cacttcatca ctagaaacat caccgataac    900
caaggtaaaa ataaaactgc tatccatacc tacttctcct ccgtttttctt gggtggtttc   960
gactccttag ttgatttgat gaacaaatct tttcctgaat taggtatcaa gaagactgat  1020
tgtcgtcaat tgtcctggat tgataccatt atctttact ctggtgtcgt caattacgac   1080
accgataatt tcaataagga aatttttatttg gacagatctg ccggtcaaaa cggtgctttc  1140
aagatcaagt tggactacgt taaaaaaacca atcccagaat ccgtctttgt ccaaatttttg  1200
gagaagttat acgaggaaga catcggtgct ggtatgtatg ccttatatcc atacggtggt   1260
attatggatg aaatttccga atctgctatc ccattttccac atcgtgctgg tattttgtat   1320
gaattatggt acatttgttc ctgggaaaag caagaagata acgagaagca cttgaattgg   1380
atcagaaata tctacaattt catgactcct tacgtttcta agaatcctcg tttggcttac  1440
ttgaactaca gagatttgga catcggtatt aatgacccaa agaacccaaa taactatact  1500
caagctagaa tttgggggtga aagtacttc ggtaaaaact tgacagatt ggttaaggtt     1560
aagacttag ttgatccaaa taacttcttc agaaatgaac aatccatccc accattgcct   1620
agacacagac actaa                                                   1635

SEQ ID NO: 168          moltype = DNA  length = 2235
FEATURE                 Location/Qualifiers
source                  1..2235
                        mol_type = genomic DNA
                        organism = Saccharomyces sp.
SEQUENCE: 168
atggccgctc cagattatgc acttaccgat ttaattgaat cggatcctcg tttcgaaagt     60
ttgaagacaa gattagccgg ttacaccaaa ggctctgatg aatatattga agagctatac    120
tctcaattac cactgaccag ctaccccagg tacaaaacat tttaaagaa acaggcggtt    180
gccatttcga atccggtaaa tgaagctggt tttagctcga ttataggag ttctctttct   240
tctgaaaatc tagtgagctg tgtggataaa aacttaagaa ctgcatacga tcacttcatg   300
ttttctgcaa ggagatggcc tcaacgtgac tgtttaggtt caaggccaat tgataaagcc   360
acaggcacct gggaggaaac attccgtttc gagtcgtact ccacggtatc taaaagatgt   420
cataatatcg gaagtggtat attgtctttg gtaaacacga aaggaaacg tcctttggaa     480
gccaatgatt ttgttgttgc tatcttatca cacaacaacc ctgaatggat cctaacagat   540
```

```
ttggcctgtc aggcctattc tctaactaac acggctttgt acgaaacatt aggtccaaac   600
acctccgagt acatattgaa tttaaccgag gcccccattc tgattttgc aaaatcaaat    660
atgtatcatg tattgaagat ggtgcctgat atgaaatttg ttaatacttt ggtttgtatg   720
gatgaattaa ctcatgacga gctccgtatg ctaaatgaat cgttgctacc cgttaagtgc   780
aactctctca atgaaaaaat cacattttt tcattggagc aggtagaaca agttggttgc    840
tttaacaaaa ttcctgcaat tccacctacc ccagattcct tgtatactat ttcgtttact   900
tctggtacta caggtttacc taaaggtgtg gaaatgtctc acagaaacat tgcgtctggg   960
atagcatttg cttttctac cttcagaata ccgccagata aagaaacca acagttatat    1020
gatatgtgtt ttttgccatt ggctcatatt tttgaaagaa tggttattgc gtatgatcta  1080
gccatcgggt ttggaatagg cttcttacat aaaccagacc caactgtatt ggtagaggat  1140
ttgaagattt tgaaaccta cgcggttgcc ctggttccta gaatattaac acggtttgaa   1200
gccggtataa aaatgctttt ggataaatcg actgtccaga ggaacgtagc aaatactata  1260
ttggattcta aatcggccag atttaccgca agaggtggtc cagataaatc gattatgaat  1320
tttctagttt atcatcgcgt attgattgat aaaatcagag actctttagg tttgtccaat  1380
aactcgttta taattaccgg atcagctccc atatctaaag ataccttact attttaaga   1440
agcgccttgg atattggtat aagacagggc tacggcttaa ctgaaacttt tgctggtgtc  1500
tgtttaagcg aaccgtttga aaaagatgtc ggatcttgtg gtgccatagg tatttctgca  1560
gaatgtagat tgaagtctgt tccagaaatg gttaccatga ccgacaagga tttaaaaggt  1620
gaactgcaaa ttcgtggccc acaggttttt gaaagatatt ttaaaaatcc gaatgaaact  1680
tcaaaagccg ttgaccaaga tggttggttt tccacgggag atgttgcatt tatcgatgca  1740
aaaggtcgca tcagcgtcat tgatcgagtc aagaacttt tcaagctagc acatggtgaa  1800
tatattgctc cagagaaaat cgaaaatatt tatttatcat catgcccca tatcacgcaa  1860
atatttgtct ttggagatcc tttgaagaca tttttagttg gcatcgttgg tgttgatgtt  1920
gatgcagcgc aaccgatttt agctgcaaag cacccagagg tgaaacgtg gactaaggaa   1980
gtgctagtag aaaacttaaa tcgtaataaa agctaagga aggattttt aaacaaaatt    2040
aataaatgca tcgatgggct acaagggattt gaaaaattgc acaacatcaa agtcggactt  2100
gagcctttga ctctcgagga tgatgttgtg acgccaactt ttaaaataaa gcgtgccaaa   2160
gcatcaaaat tcttcaaaga tacattagac caactatacg ccgaaggttc actagtcaag   2220
acagaaaagc tttag                                                    2235

SEQ ID NO: 169          moltype = AA    length = 744
FEATURE                 Location/Qualifiers
source                  1..744
                        mol_type = protein
                        organism = Saccharomyces sp.
SEQUENCE: 169
MAAPDYALTD LIESDPRFES LKTRLAGYTK GSDEYIEELY SQLPLTSYPR YKTFLKKQAV    60
AISNPDNEAG FSSIYRSSLS SENLVSCVDK NLRTAYDHFM FSARRWPQRD CLGSRPIDKA   120
TGTVEEFTRF ESYSTVSKRC HNIGSGILSL VNTKRKRPLE ANDFVVAILS HNNPEWILTD   180
LACQAYSLTN TALYETLGPN TSEYILNLTE APILIFAKSN MYHVLKMVPD MKFVNTLVCM   240
DELTHDELRM LNESLLPVKC NSLNEKITFF SLEQVEQVGC FNKIPAIPPT PDSLYTISFT   300
SGTTGLPKGV EMSHRNIASG IAFAFSTFRI PPDKRNQQLY DMCFLPLAHI FERMVIAYDL   360
AIGFGIGFLH KPDPTVLVED LKILKPYAVA LVPRILTRFE AGIKNALDKS TVQRNVANTI   420
LDSKSARFTA RGGPDKSIMN FLVYHRVLID KIRDSLGLSN NSFIITGSAP ISKDTLLFLR   480
SALDIGIRQG YGLTETFAGV CLSEPFEKDV GSCGAIGISA ECRLKSVPEM GYHADKDLKG   540
ELQIRGPQVF ERYFKNPNET SKAVDQDGWF STGDVAFIDA KGRISVIDRV KNFFKLAHGE   600
YIAPEKIENI YLSSCPYITQ IFVFGDPLKT FLVGIVGVDV DAAQPILAAK HPEVKTWTKE   660
VLVENLNRNK KLRKEFLNKI NKCIDGLQGF EKLHNIKVGL EPLTLEDDVV TPTFKIKRAK   720
ASKFFKDTLD QLYAEGSLVK TEKL                                         744

SEQ ID NO: 170          moltype = DNA    length = 1113
FEATURE                 Location/Qualifiers
misc_feature            1..1113
                        note = MBPtag
source                  1..1113
                        mol_type = other DNA
                        organism = synthetic construct
SEQUENCE: 170
atgaaaatcg aagagggtaa attggtcatc tggatcaatg gtgacaaagg ttacaacggt    60
ttggctgaag tcggtaaaaa attgagaaa gacactggta ttaaggttac cgtcgaacac    120
ccagataagt ggaagaaaa attccacaa gttgccgcta ctggtgatgg tccagacatc    180
attttctggg cccacgacag atttggtggt tatgctcaat ctggtttgtt agccgagatc    240
accccagaca agcctttca agataaatta tacccattta cctgggatgc tgtccgttac    300
aacggtaagt tgatcgctta cccaatcgcc gttgaacgtt tgtctttaat ctacaataaa    360
gacttattgc caaaccctcc aaagacctgg gaagaaattc tgccttgga taaggaatta    420
aaggctaaag gtaaatctgc cttaatgttc aacttacaag agccttactt tacttggcca    480
ttgattgctg ctgatggtgg ttatgctttt aagtacgaaa atggtaaata cgacattaaa    540
gatgttggtg ttgacaatgc cggtgcactaa gccggttaa cttcttagt cgacttgatc    600
aagaacaagc acatgaatgc tgacactgat tattctatcg ctgaagccgc cttcaacaag    660
ggtgaaactg ctatgactat caatggtcct tgggcctggt ctaatattga cacctccaaa    720
gtcaactacg gtgttactgt cttaccaact ttcaaaggtc aaccttccaa gccatttgtc    780
ggtgttttgt ctgctggtat aacgctgcc tctccaaaca aagaattggc caaggaattt    840
ttggaaaact acttgttgac tgacgaaggt ttagaggctg ttaacaaaga caaaccattg    900
ggtgctgtcg ccttgaaatc tacgaagaa gaattagcca agatccaaga aatcgccgct    960
accatggaaa atgctcaaaa aggtgaaatt atgccaaaca ttccacaaat gtccgctttt  1020
tggtacgctg ttagaactgc tgttattaat gctgcttctg gtagacaaac tgtcgatgaa  1080
gctttgaagg acgctcaaac cagaatcact aag                                1113

SEQ ID NO: 171          moltype = DNA    length = 36
```

```
FEATURE                 Location/Qualifiers
misc_feature            1..36
                        note = GS12 Linker
source                  1..36
                        mol_type = other DNA
                        organism = synthetic construct
SEQUENCE: 171
ggaggtggag gaggtggttc cggaggaggt ggttct                              36

SEQ ID NO: 172          moltype = AA  length = 12
FEATURE                 Location/Qualifiers
REGION                  1..12
                        note = GS12 Linker
source                  1..12
                        mol_type = protein
                        organism = synthetic construct
SEQUENCE: 172
GGGGGGSGGG GS                                                        12

SEQ ID NO: 173          moltype = DNA  length = 174
FEATURE                 Location/Qualifiers
misc_feature            1..174
                        note = GB1 tag
source                  1..174
                        mol_type = other DNA
                        organism = synthetic construct
SEQUENCE: 173
atgtctgaca cttacaagtt gatcttgaac ggtaagactt tgaaaggtga aactactacc    60
gaagctgttg atgctgccac tgctgaaaag gtttttaagc aatacgccaa tgataacggt   120
gtcgacggta atggactta cgatgatgcc actaagactt ttaccgttac tgaa           174

SEQ ID NO: 174          moltype = AA  length = 58
FEATURE                 Location/Qualifiers
REGION                  1..58
                        note = GB1 tag
source                  1..58
                        mol_type = protein
                        organism = synthetic construct
SEQUENCE: 174
MSDTYKLILN GKTLKGETTT EAVDAATAEK VFKQYANDNG VDGEWTYDDA TKTFTVTE      58

SEQ ID NO: 175          moltype = DNA  length = 57
FEATURE                 Location/Qualifiers
misc_feature            1..57
                        note = MFalpha1_1-19
source                  1..57
                        mol_type = other DNA
                        organism = synthetic construct
SEQUENCE: 175
atgagatttc cttcaatttt tactgcagtt ttattcgcag catcctccgc attagct        57

SEQ ID NO: 176          moltype = AA  length = 19
FEATURE                 Location/Qualifiers
REGION                  1..19
                        note = MFalpha1_1-19
source                  1..19
                        mol_type = protein
                        organism = synthetic construct
SEQUENCE: 176
MRFPSIFTAV LFAASSALA                                                 19

SEQ ID NO: 177          moltype = DNA  length = 267
FEATURE                 Location/Qualifiers
misc_feature            1..267
                        note = MFalpha1_1-89
source                  1..267
                        mol_type = other DNA
                        organism = synthetic construct
SEQUENCE: 177
atgagatttc cttcaatttt tactgcagtt ttattcgcag catcctccgc attagctgct    60
ccagtcaaca ctacaacaga agatgaaacg gcacaaattc cggctgaagc tgtcatcggt   120
tacttagatt tagaagggga tttcgatgtt gctgttttgc cattttccaa cagcacaaat   180
aacgggttat tgtttataaa tactactatt gccagcattg ctgctaaaga agaagggta    240
tctttggata aagagaggc tgaagct                                        267

SEQ ID NO: 178          moltype = AA  length = 89
FEATURE                 Location/Qualifiers
REGION                  1..89
                        note = MFalpha1_1-89
```

```
source                     1..89
                           mol_type = protein
                           organism = synthetic construct
SEQUENCE: 178
MRFPSIFTAV LFAASSALAA PVNTTTEDET AQIPAEAVIG YLDLEGDFDV AVLPFSNSTN    60
NGLLFINTTI ASIAAKEEGV SLDKREAEA                                     89

SEQ ID NO: 179             moltype = DNA   length = 714
FEATURE                    Location/Qualifiers
misc_feature               1..714
                           note = DasherGFP
source                     1..714
                           mol_type = other DNA
                           organism = synthetic construct
SEQUENCE: 179
atgaccgcac taacagaagg agctaaaacta ttcgaaaagg agattcctta cattacagaa   60
ttagagggtg atgtcgaagg aatgaaattc attatcaagg gcgagggtac tggtgacgct  120
actaccggta cgattaaagc aaagtacatc tgtacaacag gtgaccttcc tgttccgtgg  180
gctactctgg tgagcacttt gtcttatgga gttcaatgtt ttgctaaata ccccttcgcac 240
attaaagact ttttcaaaag tgcaatgcct gagggctata ctcaggagag aacaatatct  300
ttcgaaggag atggtgtgta taagactagg gctatggtca cgtatgaaag aggatccatc  360
tacaatagag taacttttaac tggtgaaaac ttcaaaaagg acggtcacat ccttagaaag  420
aatgttgcct ttcaatgccc accatccatc ttgtacattt tgccagacac agttaacaat  480
ggtatcagag ttgagtttaa ccaagcttat gacatagagg gtgtcaccga aaagttggtt  540
acaaaatgtt cacagatgaa tcgtcccctg gcaggatcag ctgccgtcca tatcccacgt  600
taccatcata tcacttatca taccaagctg tccaaagatc gtgatgagag aagggatcac  660
atgtgtttgg ttgaagtggt aaaggccgtg gatttggata cttaccaagg ttga        714

SEQ ID NO: 180             moltype = AA   length = 237
FEATURE                    Location/Qualifiers
REGION                     1..237
                           note = DasherGFP
source                     1..237
                           mol_type = protein
                           organism = synthetic construct
SEQUENCE: 180
MTALTEGAKL FEKEIPYITE LEGDVEGMKF IIKGEGTGDA TTGTIKAKYI CTTGDLPVPW    60
ATLVSTLSYG VQCFAKYPSH IKDFFKSAMP EGYTQERTIS FEGDGVYKTR AMVTYERGSI   120
YNRVTLTGEN FKKDGHILRK NVAFQCPPSI LYILPDTVNN GIRVEFNQAY DIEGVTEKLV   180
TKCSQMNRPL AGSAAVHIPR YHHITYHTKL SKDRDERRDH MCLVEVVKAV DLDTYQG      237

SEQ ID NO: 181             moltype = DNA   length = 87
FEATURE                    Location/Qualifiers
misc_feature               1..87
                           note = ER1 tag
source                     1..87
                           mol_type = other DNA
                           organism = synthetic construct
SEQUENCE: 181
atattagagc aacctctgaa atttgtgctt actgcggccg tcgtgctctt gacgacgtcg    60
gttctttgtt gtgtagtatt tacataa                                       87

SEQ ID NO: 182             moltype = AA   length = 28
FEATURE                    Location/Qualifiers
REGION                     1..28
                           note = ER1 tag
source                     1..28
                           mol_type = protein
                           organism = synthetic construct
SEQUENCE: 182
ILEQPLKFVL TAAVVLLTTS VLCCVVFT                                       28

SEQ ID NO: 183             moltype = DNA   length = 96
FEATURE                    Location/Qualifiers
misc_feature               1..96
                           note = ER2 tag
source                     1..96
                           mol_type = other DNA
                           organism = synthetic construct
SEQUENCE: 183
tctacctctg aaaaccaaag taaaggtagt ggtacattgg ttgtcatatt ggccatttta    60
atgctaggtg ttgcttatta tttgttgaac gaataa                              96

SEQ ID NO: 184             moltype = AA   length = 31
FEATURE                    Location/Qualifiers
REGION                     1..31
                           note = ER2 tag
source                     1..31
                           mol_type = protein
```

```
                        organism = synthetic construct
SEQUENCE: 184
STSENQSKGS GTLVVILAIL MLGVAYYLLN E                                         31

SEQ ID NO: 185          moltype = DNA  length = 99
FEATURE                 Location/Qualifiers
misc_feature            1..99
                        note = PM1 tag
source                  1..99
                        mol_type = other DNA
                        organism = synthetic construct
SEQUENCE: 185
tggtacaagg atctaaaaat gaagatgtgt ctggctttag taatcatcat attgcttgtt          60
gtaatcatcg tccccattgc tgttcacttt agtcgataa                                99

SEQ ID NO: 186          moltype = AA  length = 32
FEATURE                 Location/Qualifiers
REGION                  1..32
                        note = PM1 tag
source                  1..32
                        mol_type = protein
                        organism = synthetic construct
SEQUENCE: 186
WYKDLKMKMC LALVIIILLV VIIVPIAVHF SR                                        32

SEQ ID NO: 187          moltype = DNA  length = 108
FEATURE                 Location/Qualifiers
misc_feature            1..108
                        note = VC1 tag
source                  1..108
                        mol_type = other DNA
                        organism = synthetic construct
SEQUENCE: 187
aatataaaag aaataatgtg gtggcagaag gtcaaaaata ttacgttatt aactttcact          60
attatactat ttgtaagtgc tgctttcatg tttttctatc tgtggtaa                      108

SEQ ID NO: 188          moltype = AA  length = 35
FEATURE                 Location/Qualifiers
REGION                  1..35
                        note = VC1 tag
source                  1..35
                        mol_type = protein
                        organism = synthetic construct
SEQUENCE: 188
NIKEIMWWQK VKNITLLTFT IILFVSAAFM FFYLW                                     35

SEQ ID NO: 189          moltype = DNA  length = 12
FEATURE                 Location/Qualifiers
misc_feature            1..12
                        note = PEX8 tag
source                  1..12
                        mol_type = other DNA
                        organism = synthetic construct
SEQUENCE: 189
tctaaattat aa                                                             12

SEQ ID NO: 190          moltype =  length =
SEQUENCE: 190
000

SEQ ID NO: 191          moltype = DNA  length = 2103
FEATURE                 Location/Qualifiers
source                  1..2103
                        mol_type = genomic DNA
                        organism = Saccharomyces cerevisiae
SEQUENCE: 191
atggttgctc aatataccgt tccagttggg aaagccgcca atgagcatga aactgctcca          60
agaagaaatt atcaatgccg cgagaagccg ctcgtcagac cgcctaacac aaagtgttcc         120
actgtttatg agtttgttct agagtgcttt cagaagaaca aaaattcaaa tgctatgcgt         180
tggagggatg ttaaggaaat tcatgaagaa tccaaatcgg ttatgaaaaa agttgatggc         240
aaggagactt cagtggaaaa gaaatggatg tattatgaac tatcgcatta tcattataat         300
tcatttgacc aattgaccga tatcatgcat gaaattggtc gtgggttggt gaaaatagga         360
ttaaagccta atgatgatga caaattacat ctttacgcag ccacttctca caagtggatg         420
aagatgttct taggagcgca gtctcaaggt attcctgtcg tcactgccta cgatactttg         480
ggagagaaag ggctaattca ttctttggtg caaacggggt ctaaggccat ttttaccgat         540
aactctttat taccatcctt gatcaaacca gtgcaagccg ctcaagacgt aaaatacata         600
attcatttcg attccatcag ttctgaggac aggaggcaaa gtggtaagat ctatcaatct         660
gctcatgatg ccatcaacag aattaaagaa gttagacctg atatcaagac ctttagcttt         720
gacgacatct tgaagctagg taaagaatcc tgtaacgaaa tcgatgttca tccacctggc         780
```

```
aaggatgatc tttgttgcat catgtatacg tctggttcta caggtgagcc aaagggtgtt    840
gtcttgaaac attcaaatgt tgtcgcaggt gttggtggtg caagtttgaa tgttttgaag    900
tttgtgggca ataccgaccg tgttatctgt tttttgccac tagctcatat ttttgaattg    960
gttttcgaac tattgtcctt ttattggggg gcctgcattg gttatgccac cgtaaaaact   1020
ttaactagca gctctgtgag aaaattgtca aggtgatttg aagaattcaa gcccacaatc   1080
atggttggtg tcgccgctgt ttgggaaaca gtgagaaaag ggatcttaaa ccaaattgat   1140
aatttgccct tcctcaccaa gaaaatcttc tggaccgcgt ataataccaa gttgaacatg   1200
caacgtctcc acatccctgg tggcggcgcc ttaggaaact tggttttcaa aaaaatcaga   1260
actgccacag gtggccaatt aagatatttg ttaaacggtg gttctccaat cagtcgggat   1320
gctcaggaat tcatcacaaa tttaatctgc cctatgctta ttggttacgg tttaaccgag   1380
acatgcgcta gtaccaccat cttggatcct gctaattttg aactcggcgt cgctggtgac   1440
ctaacaggtt gtgttaccgt caaactagtt gatgttgaag aattaggtta ttttgctaaa   1500
aacaaccaag gtgaagtttg gatcacaggt gccaatgtca cgcctgaata ttataagaat   1560
gaggaagaaa cttctcaagc tttaacaagc gatggttggt tcaagaccgg tgacatcggt   1620
gaatgggaag caaatggcca tttgaaaata attgacagga agaaaaactt ggtcaaaaca   1680
atgaacggtg aatatatcgc actcgagaaa ttagagtccg tttacagatc taacgaatat   1740
gttgctaaca tttgtgttta tgccgaccaa tctaagacta agccagttgg tattattgta   1800
ccaaatcatg ctccattaac gaagcttgct aaaaagttgg aattatgga acaaaaagac   1860
agttcaatta atatcgaaaa ttatttggag gatgcaaaat tgattaaagc tgtttattct   1920
gatcttttga agacaggtaa agaccaaggt ttggttggca ttgaattact agcaggcata   1980
gtgttctttg acggcgaatg gactccacaa aacggttttg ttacgtccgc tcagaaattg   2040
aaaagaaaag acattttgaa tgctgtcaaa gataaagttg acgccgttta tagttcgtct   2100
taa                                                                 2103

SEQ ID NO: 192        moltype = AA  length = 700
FEATURE               Location/Qualifiers
source                1..700
                      mol_type = protein
                      organism = Saccharomyces cerevisiae
SEQUENCE: 192
MVAQYTVPVG KAANEHETAP RRNYQCREKP LVRPPNTKCS TVYEFVLECF QKNKNSNAMG     60
WRDVKEIHEE SKSVMKKVDG KETSVEKKWM YYELSHYHYN SFDQLTDIMH EIGRGLVKIG    120
LKPNDDDKLH LYAATSHKWM KMFLGAQSQG IPVVTAYDTL GEKGLIHSLV QTGSKAIFTD    180
NSLLPSLIKP VQAAQDVKYI IHFDSISSED RRQSGKIYQS AHDAINRIKE VRPDIKTFSF    240
DDILKLGKES CNEIDVHPPG KDDLCCIMYT SGSTGEPKGV VLKHSNVVAG VGGASLNVLK    300
FVGNTDRVIC FLPLAHIFEL VFELLSFYWG ACIGYATVKT LTSSSVRNCQ GDLQEFKPTI    360
MVGVAAVWET VRKGILNQID NLPFLTKKIF WTAYNTKLNM QRLHIPGGGA LGNLVFKKIR    420
TATGGQLRYL LNGGSPISRD AQEFITNLIC PMLIGYGLTE TCASTTILDP ANFELGVAGD    480
LTGCVTVKLV DVEELGYFAK NNQGEVWITG ANVTPEYYKN EEETSQALTS DGWFKTGDIG    540
EWEANGHLKI IDRKKNLVKT MNGEYIALEK LESVYRSNEY VANICVYADQ SKTKPVGIIV    600
PNHAPLTKLA KKLGIMEQKD SSINIENYLE DAKLIKAVYS DLLKTGKDQG LVGIELLAGI    660
VFFDGEWTPQ NGFVTSAQKL KRKDILNAVK DKVDAVYSSS                          700

SEQ ID NO: 193        moltype = DNA  length = 2226
FEATURE               Location/Qualifiers
misc_feature          1..2226
                      note = Truncated medium chain fatty acyl-CoA synthetase
                      Sc_FAA2_Ctrunc
source                1..2226
                      mol_type = other DNA
                      organism = synthetic construct
SEQUENCE: 193
atggccgctc cagattatgc acttaccgat ttaattgaat cggatcctcg tttcgaaagt     60
ttgaagacaa gattagccgg ttacaccaaa ggctctgatg aatatattga agagctatac    120
tctcaattac cactgaccag ctaccccagg tacaaaacat ttttaaagaa acaggcggtt    180
gccatttcga atccggataa tgaagctggt tttagctcga tttataggag ttctctttct    240
tctgaaaatc tagtgagctg tgtggataaa aacttaagaa ctgcatacga tcacttcatg    300
tttctgcaa ggagatggcc tcaacgtgac tgtttaggtt caaggccaat tgataaagcc    360
acaggcacct gggaggaaac attccgtttc gagtcgtact ccacggtatc taaaagatgt    420
cataatatcg gaagtggtat attgtctttg gtaaacacga aaaggaaacg tcctttggaa    480
gccaatgatt ttgttgttgc tatcttatca cacaacaacc ctgaatggat cctaacagat    540
ttggcctgtc aggccattc tctaactaac acggctttgt acgaaacatt aggtccaaac    600
acctccgagt acatattgaa tttaaccgag ccccattc tgattttgc aaaatcaat    660
atgtatcatg tattgaagat ggtgcctgat atgaaattg ttaatacttt ggtttgtatt    720
gatgaattaa ctcatgacga gctccgtatg ctaaatgaat cgttgctacc cgttaagtgc    780
aactctctca tgaaaaat cacatttttt tcattggagc aggtagaaca agttggttgc    840
tttaacaaaa ttcctgcaat tccacctacc ccagattcct gtatactat ttcgtttact    900
tctggtacta caggttttacc taaaggtgtg gaaatgtctc acagaaacat tgcgtctggg    960
atagcatttg cttttttctac cttcagaata ccgccagata aagaaaccc acagttatat   1020
gatatgtgtt ttttgccatt ggctcatatt tttgaaagaa tggttattgc gtatgatcta   1080
gccatcgggt tggaataag cttcttacat aaaccagacc caactgtatt ggtagaggat   1140
ttgaagattt tgaaacctta cgcggttgcc ctggttccta gaatattaac acggtttgaa   1200
gccggtataa aaaatgcttt ggataaatcg actgtccaga ggaacgtagc aaatactata   1260
ttggctcta aatcggccag atttaccgca agaggtggtc cagataaatc gattatgaat   1320
tttctagtgt atcatcgcgt attgattgat aaaatcagaa actctttagg tttgtccaat   1380
aactcgttta taattaccgg atcagctccc atatctaaag atccttact atttttaaga   1440
agcgccttgg atattggtat aagacagggc tacggcttaa ctgaaacttt tgctggtgtc   1500
tgtttaagcg aaccgtttga aaaagatgtc ggatcttgtg gtgccatagg tatttctgca   1560
gaatgtgat tgaagtctgt tccagaaatg ggttaccatg ccgacaagga tttaaaaggt   1620
```

```
gaactgcaaa ttcgtggccc acaggttttt gaaagatatt ttaaaaatcc gaatgaaact  1680
tcaaaagccg ttgaccaaga tggttggttt tccacgggag atgttgcatt tatcgatgca  1740
aaaggtcgca tcagcgtcat tgatcgagtc aagaactttt tcaagctagc acatggtgaa  1800
tatattgctc cagagaaaat cgaaaatatt tatttatcat catgcccta  tatcacgcaa  1860
atatttgtct ttggagatcc tttgaagaca ttttagttg  gcatcgttgg tgttgatgtt  1920
gatgcagcgc aaccgatttt agctgcaaag cacccagagg tgaaaacgtg gactaaggaa  1980
gtgctagtag aaaacttaaa tcgtaataaa aagctaagga aggaatttt  aaacaaaatt  2040
aataaatgca tcgatgggct acaaggattt gaaaaattgc acaacatcaa agtcggactt  2100
gagccttga  ctctcgagga tgatgttgtg acgccaactt ttaaaataaa gcgtgccaaa  2160
gcatcaaaat tcttcaaaga tacattagac caactatacg ccgaaggttc actagtcaag  2220
acatag                                                              2226

SEQ ID NO: 194         moltype = AA  length = 741
FEATURE                Location/Qualifiers
REGION                 1..741
                       note = Truncated medium chain fatty acyl-CoA synthetase
                       Sc_FAA2_Ctrunc
source                 1..741
                       mol_type = protein
                       organism = synthetic construct
SEQUENCE: 194
MAAPDYALTD LIESDPRFES LKTRLAGYTK GSDEYIEELY SQLPLTSYPR YKTFLKKQAV   60
AISNPDNEAG FSSIYRSSLS SENLVSCVDK NLRTAYDHFM FSARRWPQRD CLGSRPIDKA  120
TGTWEETFRF ESYSTVSKRC HNIGSGILSL VNTKRKRPLE ANDFVVAILS HNNPEWILTD  180
LACQAYSLTN TALYETLGPN TSEYILNLTE APILIFAKSN MYHVLKMVPD MKFVNTLVCM  240
DELTHDELRM LNESLLPVKC NSLNEKITFF SLEQVEQVGC FNKIPAIPPT PDSLYTISFT  300
SGTTGLPKGV EMSHRNIASG IAFAFSTFRI PPDKRNQQLY DMCFLPLAHI FERMVIAYDL  360
AIGFGIGFLH KPDPTVLVED LKILKPYAVA LVPRILTRFE AGIKNALDKS TVQRNVANTI  420
LDSKSARFTA RGGPDKSIMN FLVYHRVLID KIRDSLGLSN NSFIITGSAP ISKDTLLFLR  480
SALDIGIRQG YGLTETFAGV CLSEPFEKDV GSCGAIGISA ECRLKSVPEM GYHADKDLKG  540
ELQIRGPQVF ERYFKNPNET SKAVDQDGWF STGDVAFIDA KGRISVIDRV KNFFKLAHGE  600
YIAPEKIENI YLSSCPYITQ IFVFGDPLKT FLVGIVGVDV DAAQPILAAK HPEVKTWTKE  660
VLVENLNRNK KLRKEFLNKI NKCIDGLQGF EKLHNIKVGL EPLTLEDDVV TPTFKIKRAK  720
ASKFFKDTLD QLYAEGSLVK T                                            741

SEQ ID NO: 195         moltype = DNA  length = 2238
FEATURE                Location/Qualifiers
misc_feature           1..2238
                       note = Mutated medium chain fatty acyl-CoA synthetase
                       Sc_FAA2_Cmut
source                 1..2238
                       mol_type = other DNA
                       organism = synthetic construct
SEQUENCE: 195
atggccgctc cagattatgc acttaccgat ttaattgaat cggatcctcg tttcgaaagt   60
ttgaagacaa gattagccgg ttacaccaaa ggctctgatg aatatattga agagctatac  120
tctcaattac cactgaccag ctaccccagg tacaaaacat ttaaagaa  acaggcggtt  180
gccatttcga atccggataa tgaagctggt tttagctcga tttataggag ttctcttct   240
tctgaaaatc tagtgagctg tgtggataaa aacttaagaa ctgcatacga tcacttcatg  300
ttttctgcaa ggagatggcc tcaacgtgac tgtttaggtt caaggccaat tgataaagcc  360
acaggcacct gggaggaaac attccgtttc gagtcgtact ccacggtatc taaaagatgt  420
cataatatcg gaagtggtat attgtctttg gtaaacacga aaaggaaacg tcctttggaa  480
gccaatgatt ttgttgttgc tatcttatca cacaacaacc ctgaatggat cctaacagat  540
ttggcctgtc aggcctattc tctaactaac acggctttgt acgaaacatt aggtccaaac  600
acctccgagt acatattgaa tttaaccgag gccccccattc tgattttgc  aaaatcaaat  660
atgtatcatg tattgaagat ggtgcctgat atgaaatttg ttaatactt  ggttgtatg   720
gatgaattaa ctcatgacga gctccgtatg ctaaatgaat cgttgctacc cgttaagtgc  780
aactctctca tgaaaaaat  cacatttttt tcattggagc aggtagaaca agttggttgc  840
tttaacaaaa ttcctgcaat tccacctacc ccagattcct tgtatactat ttcgtttact  900
tctggtacta caggtttacc taaaggtgtg gaaatgtctc acagaaacat tgcgtctggg  960
atagcatttg cttttctac  cttcagaata ccgccagata aagaaacca  acagttatat 1020
gatatgtgtt ttttgccatt ggctcatatt tttgaaagaa tggttattgc gtatgatcta 1080
gccatcgggt ttggaatagg cttcttacat aaaccagacc caactgtatt ggtagaggat 1140
ttgaagattt tgaaaccta  cgcggttgcc ctggttcata agattattac acggtttgaa 1200
gccggtataa aaaatgcttt ggataaatcg actgtccaga gaacgtagc  aaatactata 1260
ttggattcta atcggccag  atttaccgca gagggtggtc cagataaatc gattatgaat 1320
tttctagttt atcatcgcgt attgattgat aaaatcagag actctttagg tttgtccaat 1380
aactcgttta taattaccgg atcagctccc atatctaaga taccttact  attttaaga  1440
agcgccttgg atattggtat aagacagggc tacggcttaa ctgaaacttt tgctggtgtc 1500
tgtttaagcg aaccgtttga aaaagatgtc ggatcttgtg gtgccatagg tatttctgca 1560
gaatgtagat tgaagtctgt tccagaaatg ggttaccatg ccgacaagga tttaaaaggt 1620
gaactgcaaa ttcgtggccc acaggttttt gaaagatatt ttaaaaatcc gaatgaaact 1680
tcaaaagccg ttgaccaaga tggttggttt tccacgggag atgttgcatt tatcgatgca 1740
aaaggtcgca tcagcgtcat tgatcgagtc aagaactttt tcaagctagc acatggtgaa 1800
tatattgctc cagagaaaat cgaaaatatt tatttatcat catgcccta  tatcacgcaa 1860
atatttgtct ttggagatcc tttgaagaca ttttagttg  gcatcgttgg tgttgatgtt 1920
gatgcagcgc aaccgatttt agctgcaaag cacccagagg tgaaaacgtg gactaaggaa 1980
gtgctagtag aaaacttaaa tcgtaataaa aagctaagga aggaatttt  aaacaaaatt 2040
aataaatgca tcgatgggct acaaggattt gaaaaattgc acaacatcaa agtcggactt 2100
```

```
gagcctttga ctctcgagga tgatgttgtg acgccaactt ttaaaataaa gcgtgccaaa    2160
gcatcaaaat tcttcaaaga tacattagac caactatacg ccgaaggttc actagtcaag    2220
acagaaaagc ttaaatag                                                  2238

SEQ ID NO: 196          moltype = AA  length = 745
FEATURE                 Location/Qualifiers
REGION                  1..745
                        note = Mutated medium chain fatty acyl-CoA synthetase
                        Sc_FAA2_Cmut
source                  1..745
                        mol_type = protein
                        organism = synthetic construct
SEQUENCE: 196
MAAPDYALTD LIESDPRFES LKTRLAGYTK GSDEYIEELY SQLPLTSYPR YKTFLKKQAV    60
AISNPDNEAG FSSIYRSSLS SENLVSCVDK NLRTAYDHFM FSARRWPQRD CLGSRPIDKA    120
TGTWEETFRF ESYSTVSKRC HNIGSGILSL VNTKRKRPLE ANDFVVAILS HNNPEWILTD    180
LACQAYSLTN TALYETLGPN TSEYILNLTE APILIFAKSN MYHVLKMVPD MKFVNTLVCM    240
DELTHDELRM LNESLLPVKC NSLNEKITFF SLEQVEQVGC FNKIPAIPPT PDSLYTISFT    300
SGTTGLPKGV EMSHRNIASG IAFAFSTFRI PPDKRNQQLY DMCFLPLAHI FERMVIAYDL    360
AIGFGIGFLH KPDPTVLVED LKILKPYAVA LVPRILTRFE AGIKNALDKS TVQRNVANTI    420
LDSKSARFTA RGGPDKSIMN FLVYHRVLID KIRDSLGLSN NSFIITGSAP ISKDTLLFLR    480
SALDIGIRQG YGLTETFAGV CLSEPFEKDV GSCGAIGISA ECRLKSVPEM GYHADKDLKG    540
ELQIRGPQVF ERYFKNPNET SKAVDQDGWF STGDVAFIDA KGRISVIDRV KNFFKLAHGE    600
YIAPEKIENI YLSSCPYITQ IFVFGDPLKT FLVGIVGVDV DAAQPILAAK HPEVKTWTKE    660
VLVENLNRNK KLRKEFLNKI NKCIDGLQGF EKLHNIKVGL EPLTLEDDVV TPTFKIKRAK    720
ASKFFKDTLD QLYAEGSLVK TEKLK                                          745

SEQ ID NO: 197          moltype = DNA  length = 2085
FEATURE                 Location/Qualifiers
source                  1..2085
                        mol_type = genomic DNA
                        organism = Saccharomyces cerevisiae
SEQUENCE: 197
atgtccgaac aacactctgt cgcagtcggt aaagctgcta atgagcacga gactgcccct    60
aggagaaatg ttagagtcaa gaagcggccc ttaattagac cattgaactc gtcagcatct    120
acgctgtatg aatttgccct agagtgtttc aacaagggtg aaaacgaga tggtatggct    180
tggagagatg tcatcgagat tcatgagaca aagaaaacca ttgtgagaaa ggtagacggc    240
aaggataaat ctatagaaaa gacatggctg tattatgaaa tgtcaccata taaaatgatg    300
acctaccagg aactgatctg ggtgatgcac gatatgggct ggcaaaaatag gc           360
atcaagccca atggagaaca caaattccaa atcttcgcat ctacttccca taaatgatg    420
aagattttcc ttggttgcat atcccagggt atccccgtag taaccgcgta tgatactttg    480
ggtgagagcg gtttgattca ctccatggtt gaaaccgagt ctgctgctat tttcactgat    540
aatcaattat tggctaaaat gatagtgcct ttgcaatctg ctaaagatat caaatttcct    600
atccataacg aacctatcga ccccaatgac agaagacaaa acggcaaact ttacaaggct    660
gctaaggatg ccattaataa gatcagagaa gttaggccag acataaaaat ttatagtttt    720
gaagaagttg tcaagatagg taaaaaaagt aaagatgagg tcaaacttca tccacctgag    780
ccaaaagatt tggcttgtat catgtacacc tcgggctgca tcagtgcacc aaaaggtgta    840
gtattgactc attataatat tgtttcgggt atcgctggtg taggtcacaa cgtctttgga    900
tggatcggct ctacagaccg tgttttgtcg ttcttgccat tggctcatat ttttgaactg    960
gtctttgaat tcgaagcctt ttactggaac ggtattcttg ggtacggtag tgttaagact    1020
ttgactaata cttcgactcg taattgtaag ggtgacctgg ttgagtttaa gcctactatt    1080
atgatcggtg tggctgccgt ttgggaaact gtgagaaaag ctattttgga aaagatcagc    1140
gatttaactc ccgtactcca aaagattttt ggtctgcct atagtatgaa agaaaagagt    1200
gtaccatgca ccgggttttt aagtcgtatg gtcttcaaga aagtcagaca agccaccggt    1260
ggtcatctta agtatattat gaacgtgggt tctgcgatca gtgatgc tcagaaattc       1320
ttttctatcg tcctgtgtcc tatgattatc ggttacggcc ttactgaaac agttgcgaat    1380
gcttgtgttt tggagcctga tcatttcgaa tatggtatag ttggtgatct tgttggatcg    1440
gtcactgcca aattggtgga tgttaaggac ctaggttatt atgcaaaaaa caatcaaggt    1500
gaattgcttc taaagggtgc gccggtctgt tctgaatatt ataagaatcc aatagaaacg    1560
gcggtctctt tcacttacga tggatggttt cgtactggtg atattgttga atggactccc    1620
aagggacaac ttaaaattat tgatagaaga aagaatttgg ttaaaccct aaatggtgaa    1680
tatattgcat tagaaaagtt agaatctgtt tacaggtcaa actccatgtg aaaaatatc    1740
tgtgtttatg ccgatgaaag tagggttaaa ccggtgggta ttgtggtacc caacccagga    1800
cccctatcta aatttgctgt caaattgcgt attatgaaaa agggtgaaga catcgaaaac    1860
tatatccatg acaaagcatt acgaaatgct gttttcaaag agatgatcgc aacagccaaa    1920
tctcaaggtt tggttggtat tgaactatta tgtggtattg ttttcttga tgaagaatgg    1980
acacctgaaa atggctttgt cacatctgct caaaaattaa agagaagaga aatcttagcc    2040
gctgttaaat cagaagtcga aagggtttac aaagaaaatt cttag                    2085

SEQ ID NO: 198          moltype = AA  length = 694
FEATURE                 Location/Qualifiers
source                  1..694
                        mol_type = protein
                        organism = Saccharomyces cerevisiae
SEQUENCE: 198
MSEQHSVAVG KAANEHETAP RRNVRVKKRP LIRPLNSSAS TLYEFALECF NKGGKRDGMA    60
WRDVIEIHET KKTIVRKVDG KDKSIEKTWL YYEMSPYKMM TYQELIWVMH DMGRGLAKIG    120
IKPNGEHKFH IFASTSHKWM KIFLGCISQG IPVVTAYDTL GESGLIHSMV ETESAAIFTD    180
NQLLAKMIVP LQSAKDIKFL IHNEPIDPND RRQNGKLYKA AKDAINKIRE VRPDIKIYSF    240
```

```
EEVVKIGKKS KDEVKLHPPE PKDLACIMYT SGSISAPKGV VLTHYNIVSG IAGVGHNVFG    300
WIGSTDRVLS FLPLAHIFEL VFEFEAFYWN GILGYGSVKT LTNTSTRNCK GDLVEFKPTI    360
MIGVAAVWET VRKAILEKIS DLTPVLQKIF WSAYSMKEKS VPCTGFLSRM VFKKVRQATG    420
GHLKYIMNGG SAISIDAQKF FSIVLCPMII GYGLTETVAN ACVLEPDHFE YGIVGDLVGS    480
VTAKLVDVKD LGYYAKNNQG ELLLKGAPVC SEYYKNPIET AVSFTYDGWF RTGDIVEWTP    540
KGQLKIIDRR KNLVKTLNGE YIALEKLESV YRSNSYVKNI CVYADESRVK PVGIVVPNPG    600
PLSKFAVKLR IMKKGEDIEN YIHDKALRNA VFKEMIATAK SQGLVGIELL CGIVFFDEEW    660
TPENGFVTSA QKLKRREILA AVKSEVERVY KENS                                694

SEQ ID NO: 199          moltype = DNA   length = 2085
FEATURE                 Location/Qualifiers
source                  1..2085
                        mol_type = genomic DNA
                        organism = Saccharomyces cerevisiae
SEQUENCE: 199
atgaccgaac aatattccgt tgcagttggc gaagccgaca atgagcatga aaccgctcca      60
agaagaaata tcagggttaa agacaagcct ttgattagac ccataaactc ctcagcatct     120
acactgtacg aattcgccct ggaatgtttt accaaaggtg gtaagagaga cggtatggca     180
tggagagata tttatagatat acatgagacg aaaaaaacca tagtcaagag ggtggatggt     240
aaggataagc ccatcgaaaa aacatggttg tactacgaaa tgactcccta cataaccatg     300
acatacgagg agatgatctg cgtaatgcac gacattggac gtgggctgat aaagattggt     360
gttaaaccta acggtgagaa caagttccac atctttgcct ctacatctca caagtggata     420
aaaactttc ttggttgcat gtcacaaggt attcctgtgg tcaccgcgta cgacactttg      480
ggtgagagcg gtttgattca ctccatgtgt gaaacggatt ccgtcgccat tttcacggac     540
aaccagctgt tgtccaaatt agcagttcct ttgaaaaccg ccaagaacgt aaaattcgtc     600
attcacaacg aacccatcga tccaagtgac aaaagacaaa atggtaagct ttacaaggct     660
gccaaggatg ctgttgacaa aatcaaggaa gttagaccgg acataaaaat ctacagtttc     720
gatgaaatta ttgagatagg taaaaaggcc aaggacgagg ttgaattgca tttccccaag     780
cctgaagatc cagcttgtat catgtacact tctggttcca ctggtacacc aaagggtgtg     840
gtattgacac attacaatat tgtagctggt attggtggca cggttatcgga     900
tggattggcc caacgaccg tattatcgca ttccttgccat tggctcatat ttttgaatta     960
atctttgaat tcgaagcgtt ctactggaat ggtatcctag ggtacgccac tgtcaagact    1020
ttaacccaa cttctacacg taattgccaa ggtgacctga tggagtttaa acctaccgta    1080
atggtaggtg ttgccgcagt ttgggaaaca gtgagaaaag gtatcctggc caagatcaaa    1140
gaattgcccg gttggtctca aacgcttttc tggactgtct atgctttgaa agagagaaat    1200
ataccatgca gcggcttgct gagtgggttg atcttcaaga gaatcagaga agcaaccggt    1260
ggaaacttaa ggtttattct gaacggtggg tctgcaatca gcatagacgc ccaaaaattc    1320
ctctccaacc ttctatgtcc tatgctcatt ggatatgggc taactgaggg tgtggctaat    1380
gcctgtgtcc tggagcctga acattttgat tacgtagtgg ctgacctt tgtcggaact    1440
attacagcta aattggtgga tgtcgaagat ttgggctatt ttgccaagaa taaccaaggt    1500
gaattgctgt taagggtgc acccatctgt tctgaatact ataagaatcc tgaagaaact    1560
gctgcggcct ttaccgatga tggctggttc cgtaccggtg atatcgctga atggaccccc    1620
aagggacaaa ttaagatcat tgatagaaag aaaaatttgg tcaagaccttt aacggtgga    1680
tacattgcat tggaaaaatt agaatccatt tacagatcaa atcctacgt ccaaaacatc    1740
tgtgtctacg ctgatgaaaa caagttaag cctgtcggta ttgtggtccc taacttagga    1800
cacttgtcta agctggctat cgaattaggt ataatggtac aggtgaaga tgtcgaaagc    1860
tatatccatg aaaagaagct acaggatgcc gtttgcaaga atatgctgtc aactgccaaa    1920
tctcaaggct tgaatggtat tgaattatta tgtggcattg tttctcttga gaagaatgat    1980
actccagaaa acggtcttgt tacatccgcc caaaaattaa agagaagaga tattctagcg    2040
gctgtcaagc cagatgtgga aagagtttat aaagaaaaca cttaa                   2085

SEQ ID NO: 200          moltype = AA   length = 694
FEATURE                 Location/Qualifiers
source                  1..694
                        mol_type = protein
                        organism = Saccharomyces cerevisiae
SEQUENCE: 200
MTEQYSVAVG EADNEHETAP RRNIRVKDKP LIRPINSSAS TLYEFALECF TKGGKRDGMA     60
WRDIIDIHET KKTIVKRVDG KDKPIEKTWL YYELTPYITM TYEEMICVMH DIGRGLIKIG    120
VKPNGENKFH IFASTSHKWM KTFLGCMSQG IPVVTAYDTL GESGLIHSMV ETDSVAIFTD    180
NQLLSKLAVP LKTAKNVKFV IHNEPIDPSD KRQNGKLYKA AKDAVDKIKE VRPDIKIYSF    240
DEIIEIGKKA KDEVELHFPK PEDPACIMYT SGSTGTPKGV VLTHYNIVAG IGGVGHNVIG    300
WIGPTDRIIA FLPLAHIFEL IFEFEAFYWN GILGYATVKT LTPTSTRNCQ GDLMEFKPTI    360
MVGVAAVWET VRKGILAKIN ELPGWSQTLF WTVYALKERN IPCSGLLSGL IFKRIREATG    420
GNLRFILNGG SAISIDAQKF LSNLLCPMLI GYGLTEGVAN ACVLEPEHFD YGIAGDLVGT    480
ITAKLVDVED LGYFAKNNQG ELLLKGAPIC SEYYKNPEET AAAFTDDGWF RTGDIAEWTP    540
KGQIKIIDRK KNLVKTLNGE YIALEKLESI YRSNPYVQNI CVYADENKVK PVGIVVPNLG    600
HLSKLAIELG IMVPGEDVES YIHEKKLQDA VCKDMLSTAK SQGLNGIELL CGIVFFEEEW    660
TPENGLVTSA QKLKRRDILA AVKPDVERVY KENT                                694

SEQ ID NO: 201          moltype = DNA   length = 6702
FEATURE                 Location/Qualifiers
misc_feature            1..6702
                        note = Mutated acetyl-CoA carboxylase (ACC1) (S659A, S1157A)
source                  1..6702
                        mol_type = other DNA
                        organism = synthetic construct
SEQUENCE: 201
atgagcgaag aaagctttat cgagtcttct ccacagaaga tggagtacga aattacaaac     60
```

```
tactcagaaa gacatacaga acttccaggt catttcattg gcctcaatac agtagataaa    120
ctagaggagt ccccgttaag ggactttgtt aagagtcacg gtggtcacac ggtcatatcc    180
aagatcctga tagcaaataa tggtattgcc gccgtgaaag aaattagatc cgtcagaaaa    240
tgggcatacg agacgttcgg cgatgacaga accgtccaat tcgtcgccat ggccacccca    300
gaagatctgg aggccaacgc agaatatatc cgtatggccg atcaatacat tgaagtgcca    360
ggtggtacta ataataacaa ctacgctaac gtagacttga tcgtagacat cgccgaaaga    420
gcagacgtag acgccgtatg ggctggctgg ggtcacgcct ccgagaatcc actattgcct    480
gaaaaattgt cccagtctaa gaggaaagtc atctttattg ggcctccagg taacgccatg    540
aggtctttag gtgataaaat ctcctctacc attgtcgctc aaagtgctaa agtcccatgt    600
attccatggt ctggtaccgg tgttgacacc gttcacgtgg acgagaaaac cggtctggtc    660
tctgtcgacg atgacatcta tcaaaagggt tgttgtacct ctcctgaaga tggtttacaa    720
aaggccaagc gtattggttt tcctgtcatg attaaggcat ccgaaggtgg tggtggtaaa    780
ggtatcagac aagttgaacg tgaagaagat ttcatcgctt tataccacca ggcagccaac    840
gaaattccag gctcccccat tttcatcatg aagttggccg gtagagcgcg tcacttggaa    900
gttcaactgc tagcagatca gtacggtaca aatatttcct tgttcggtag agactgttcc    960
gttcagagac gtcatcaaaa aattatcgaa gaagcaccag ttacaattgc caaggctgaa   1020
acatttcacg agatggaaaa ggctgccgtc agactgggga aactagtcgg ttatgtctct   1080
gccggtaccg tggagtatct atattctcat gatgatgaaa aattctactt tttagaattg   1140
aacccaagat tacaagtcga gcatccaaca acggaaatgg tctccggtgt taacttacct   1200
gcagctcaat tacaaatcgc tatgggtatc cctatgcata gaataagtga cattagaact   1260
ttatatggta tgaatcctca ttctgcctca gaaatcgatt tcgaattcaa aactcaagat   1320
gccaccaaga aacaaagaag acctattcca aagggtcatt gtaccgcttg tcgtatcaca   1380
tcagaagatc caaacgatgg attcaagcca tcgggtggta ctttgcatga actaaacttc   1440
cgttcttcct ctaatgtttg gggttacttc tccgtgggta caatggtaa tattcactcc    1500
ttttcggact ctcagttcgg ccatatttt gcttttggtg aaaatagaca agcttccagg   1560
aaacacatgg ttgttgccct gaaggaattg tccattaggg gtgatttcag aactactgtg   1620
gaatacttga tcaaacttttt ggaaactgaa gatttcgagg ataacactat taccaccggt   1680
tggttggacg atttgattac tcataaaatg accgctgaaa agcctgatcc aactcttgcc   1740
gtcatttgcg gtgccgctac aaaggctttc ttagcatctg aagaagcccg ccacaagtat   1800
atcgaatcct tacaaaaggg acaagttcta tctaaagacc tactgcaaac tatgttccct   1860
gtagatttta tccatgaggg taaaagatac aagttcaccg tagctaaatc cggtaatgac   1920
cgttacacat tatttatcaa tggttctaaa tgtgatatca tactgcgtca actatctgat   1980
ggtggtcttt tgattgccat aggcggtaaa tcgcatacca tctattggaa agaagaagtt   2040
gctgctacaa gattatccgt tgactctatg actactttgt tggaagttga aaacgatcca   2100
acccagttgc gtactccatc ccctggtaaa ttggttaaat tcttggtgga aaatggtgaa   2160
cacattatca agggccaacc atatgcagaa attgaagtta tgaaaatgca aatgcctttg   2220
gtttctcaag aaaatggtat cgtccagtta ttaaagcaac ctggttctac cattgttgca   2280
ggtgatatca tggctattat gactcttgac gatccatcca aggtcaagca cgctctacca   2340
tttgaaggta tgctgccaga ttttggttct ccagttactg aaggaaccaa acctgcctat   2400
aaattcaagt cattagtgtc tactttggaa aacattttga aggggttatga caaccaagtt   2460
attatgaacg cttccttgca acaattgata gaggttttga gaaatccaaa actgccttac   2520
tcagaatgga aactacacat tctgctttta cattcaagat tgcctgctaa gctagatgaa   2580
caaatggaag agttagttgc acgttcttttg agacgtgggc ctgtttttccc agctagacaa   2640
ttaagtaaat tgattgatat ggccgtgaag aatcctgaat acaacccccga caaattgctg   2700
ggcgccgtcg tggaaccatt ggcggatatt gctcataagt actctaacgg gttagaagcc   2760
catgaacatt ctatatttgt ccatttcttg gaagaatatt acgaagttga aaagttattc   2820
aatggtccaa atgttcgtga ggaaaaatat atttctgaat tgcgtgatga aaaccctaaa   2880
gatctagata aagttgcgct aactgttttg tctcattcga aagtttcagc gaagaataac   2940
ctgatcctag ctatcttgaa acattatcaa ccattgtgca agtatccttc taaagttctct   3000
gccatttttct ctactcctct acaacatatt gttgaactag aatctaaggc taccgctaag   3060
gtcgctctac aagcaagaga aattttgatt caaggcgctt taccttccgg caaggaaaga   3120
actgaacaaa ttgaacatat cttaaaatcc tctgttgtga aggttgccta tggctcatcc   3180
aatccaaagc gctctgaacc agatttgaat atcttgaagg acttgatcga ttctaattac   3240
gttgtgttcg atgtttttact tcaattccta acccatcaag acccagttgt gactgctgca   3300
gctgctcaga tctatattcg tcgtgcttat cgtgcttaca ccataggaga tattagagtt   3360
cacgaaggtg tcacagttcc aattgttgaa tggaaattcc aactaccttc agctgcgttc   3420
tccacctttc caactgttaa atctaaaatg ggtatgaaca gggctgtttc tgtttcagat   3480
ttgtcatatg ttgcaaacag tcagtcatct ccgttaagag aaggtatttt gatggctgtg   3540
gatcatttag atgatgttga tgaaattttg tcacaaagtt tggaagttat tcctcgtcaa   3600
caatcttctt ctaacggacc tgctcctgat cgttctggta gctccgcatc gttgagtaat   3660
gttgctaatg tttgtgttgc ttctacagaa ggtttcgaat ctgaagagga aatttttggta   3720
aggttgagag aaattttgga tttgaataag caggaattaa tcaatgcttc tatccgtcgt   3780
atcacattta tgttcggttt taaagatggg tcttatccaa agtattatac ttttaacggt   3840
ccaaattata acgaaaatga aacaattcgt cacattggac ccgctttggc cttccaactg   3900
gaattaggaa gattgtccaa cttcaacatt aaaccaattt tcactgataa tagaaacatc   3960
catgtctacg aagctgttag taagacttct ccattggata agagattctt tacaagaggt   4020
attattagaa cgggtcatat ccgtgatgac atttctattc aagaatatct gacttctgaa   4080
gctaacagat tgatgagtga tatattggat aattagaag tcaccgacac ttcaaattct   4140
gatttgaatc atatcttcat caacttcatt gcggtgttg atatctctcc agaagatgtc   4200
gaagccgcct tcgtggggttt cttagaaaga tttggtaaga gattgttgag attgcgtgtt   4260
tcttctgccg aaattagaat catcatcaaa gatcctcaaa caggtgcccc agtaccattg   4320
cgtgccttga tcaataacgt ttctggttat gttatcaaaa cagaaatgta caccgaagtc   4380
aagaacgcaa aaggtgaatg ggtatttaag tcttgggta aacctggatc catgcattta   4440
agacctattg ctactcctta ccctgttaag gaatggttgc aaccaaaaacg ttataaggca   4500
cacttgatgg gtaccacata tgtctatgac ttcccagaat tattccgcca agcatcgtca   4560
tcccaatgga aaaatttctc tgcagatgtt aagttaacag atgattcttt tatttccaac   4620
gagttgattg aagatgaaaa cggcgaatta actgaggtgg aaagagaacc tggtgccaac   4680
gctattggta tggttgcctt taagattact gtaaagactc ctgaatatcc aagaggccgt   4740
caatttgttt ttgttgctaa cgatatcaca ttcaagatcg gttcctttgg tccacaagaa   4800
```

```
gacgaattct tcaataaggt tactgaatat gctagaaagc gtggtatccc aagaatttac    4860
ttggctgcaa actcaggtgc cagaattggt atggctgaag agattgttcc actatttcaa    4920
gttgcatgga atgatgctgc caatccggac aagggcttcc aatacttata cttaacaagt    4980
gaaggtatgg aaactttaaa gaaatttgac aaagaaaatt ctgttctcac tgaacgtact    5040
gttataaacg gtgaagaaag attttgtcatc aagacaatta ttggttctga agatgggtta    5100
ggtgtcgaat gtctacgtgg atctggttta attgctggtg caacgtcaag ggcttaccac    5160
gatatcttca ctatcacctt agtcacttgt agatccgtcg gtatcggtgc ttatttggtt    5220
cgtttgggtc aaagagctat tcaggtcgaa ggccagccaa ttattttaac tggtgctcct    5280
gcaatcaaca aaatgctggg tagagaagtt tatacttcta acttacaatt gggtggtact    5340
caaatcatgt ataacaacgg tgtttcacat ttgactgctg ttgacgattt agctggtgta    5400
gagaagattg ttgaatggat gtcttatgtt ccagccaagc gtaatatgcc agttcctatc    5460
ttggaaacta agacacatg ggatagacca gttgatttca ctccaactaa tgatgaaact    5520
tacgatgtaa gatggatgat tgaaggtcgt gagactgaaa gtggatttga atatggtttg    5580
tttgataaag ggtctttctt tgaaactttg tcaggatggg ccaaaggtgt tgtcgttggt    5640
agagcccgtc ttggtggtat tccactgggg gttattggtg ttgaaacaag aactgtcgag    5700
aacttgattc ctgctgatcc agctaatcca aatagtgctg aaacattaat tcaagaacct    5760
ggtcaagttt ggcatccaaa ctccgccttc aagactgctc aagctatcaa tgactttaac    5820
aacggtgaac aattgccaat gatgattttg gccaactgga gaggtttctc tggtggtcaa    5880
cgtgatatgt tcaacgaagt cttgaagtat ggttcgttta ttgttgacgc attggtggat    5940
tacaaacaac caattattat ctatatccca cctaccggtg aactaagagg tggttcatgg    6000
gttgttgtcg atccaactat caacgctgac caaatgaaaa tgtatgccga cgtcaacgct    6060
agagctggtg ttttggaacc acaaggtatg gttggtatca agttccgtag agaaaaattg    6120
ctggacacca tgaacagatt ggatgacaag tacagagaat tgagatctca attatccaac    6180
aagagtttgg ctcagaagt acatcagcaa atatccaagc aattagctga tcgtgagaga    6240
gaactattgc caatttacgg acaaatcagt cttcaatttg ctgatttgca cgataggtct    6300
tcacgtatgg tggccaaggg tgttatttct aaggaactgg aatggaccga ggcacgtcgt    6360
ttcttcttct ggagattgag aagaagattg aacgaagaat atttgattaa aaggttgagc    6420
catcaggtag gcgaagcatc aagattagaa aagatcgcaa gaattagatc gtggtaccct    6480
gcttcagtgg accatgaaga tgataggcaa gtcgcaacat ggattgaaga aaactacaaa    6540
actttggacg ataaactaaa gggtttgaaa ttagagtcat tcgctcaaga cttagctaaa    6600
aagatcagaa gcgaccatga caatgctatt gatgattat caagatgtta    6660
tctaccgatg ataaagaaaa attgttgaag actttgaaat aa    6702

SEQ ID NO: 202        moltype = DNA   length = 894
FEATURE               Location/Qualifiers
misc_feature          1..894
                      note = Truncated geranylgeranyl pyrophosphate synthase
                      Ag_GPPS_Ntrunc
source                1..894
                      mol_type = other DNA
                      organism = synthetic construct
SEQUENCE: 202
atgtcttttg acttcaataa gtatatggat tctaaggcta tgaccgtcaa cgaggctttg     60
aataaagcca tcccattgcg ttacccacaa aagatctacg aatctatgag atattctttg    120
ttagctggtg gtaagagagt ccgtccagtt ttgtgtatcg ccgcttgtga attagtcggt    180
ggtactgagg agttagctat tccaaccgcc tgtgccatcg aaatgatcca caccatgtct    240
ttgatgcacg atgatttgcc atgtatcgac aacgatgact tgagacgttg taaacctacc    300
aatcataaga ttttcggtga agatactgct gttactgccg gtaacgcttt acactcttac    360
gccttcgaac atattgctgt ttctacttcc aagactgttg gtgctgatag aattttgaga    420
atggtttctg aattaggtcg tgctactggt tccgaaggtg ttatgggtgg tcaaatggtc    480
gatattgctt ctgaaggtga cccttccatt gatttgcaaa ctttagaatg gatccacatc    540
cacaagactg ctatgttatt agaatgttct gttgtctgtg gtgccatcat cggtggtgct    600
tctgaaattg ttattgagag agccagacgt tatgctcgtt gtgtcggttt attgtttcaa    660
gttgttgacg acatttttaga tgttaccaaa tcttctgacg aattgggtaa aactgctggt    720
aaagatttaa tctccgataa agccacctac cctaagttga tgggtttgga gaaggccaaa    780
gagttttccg atgaattatt aaacagagct aaaggtgaat tgtcttgctt cgatccagtt    840
aaggctgccc cattgttagg tttggctgac tacgttgcct tcagacaaaa ctaa          894

SEQ ID NO: 203        moltype = AA    length = 297
FEATURE               Location/Qualifiers
REGION                1..297
                      note = Truncated geranylgeranyl pyrophosphate synthase
                      Ag_GPPS_Ntrunc
source                1..297
                      mol_type = protein
                      organism = synthetic construct
SEQUENCE: 203
MSFDFNKYMD SKAMTVNEAL NKAIPLRYPQ KIYESMRYSL LAGGKRVRPV LCIAACELVG     60
GTEELAIPTA CAIEMIHTMS LMHDDLPCID NDDLRRGKPT NHKIFGEDTA VTAGNALHSY    120
AFEHIAVSTS KTVGADRILR MVSELGRATG SEGVMGGQMV DIASEGDPSI DLQTLEWIHI    180
HKTAMLLECS VVCGAIIGGA SEIVIERARR YARCVGLLFQ VVDDILDVTK SSDELGKTAG    240
KDLISDKATY PKLMGLEKAK EFSDELLNRA KGELSCFDPV KAAPLLGLAD YVAFRQN       297

SEQ ID NO: 204        moltype = DNA   length = 1356
FEATURE               Location/Qualifiers
source                1..1356
                      mol_type = genomic DNA
                      organism = Saccharomyces cerevisiae
SEQUENCE: 204
```

```
ttatttatca agataagttt ccggatcttt tctttccta acaccccagt cagcctgagt   60
tacatccagc cattgaacct tagaaaatct tttgtcatca gcggtttgag ccctaagatc  120
aacatcttgc ttagcaatca ctgcaatggc gtcataacca ccagcaccag gtattaagca  180
agtaagaact cctttaagg tctggcaatc atccaataag ctagtttgta cgggaggttc   240
gatatcggca ccagattctt tagttatttt tctaaaggaa cgtctaattg tggcaactga  300
atctctaact tctgtgatct caggatactt ttgacaggta cagtcattcc tctcaagaga  360
ctcaaatatc tgatcgctgt aatcgtcatg agtctcgtgt aagcgatcta gtttagatag  420
tccatccata aatctagaat ttgcatgatc gagttctgta tatattttca agcttttccgg 480
catatgcgaa tcataccaat tttttacctt ctggaccagt tttactgttt ctgaaccatt  540
cttaatatcg cccatccata aagttaatcc cgaaggtaaa tggttacttt taatcgttat  600
attccagtct tcttcattaa ccaaatgcgc cagtttactg ccgtaagtag cacttccaat  660
atctggcaaa ttagagatta atgcgggtgg aatcttcta tatctgatag atccatatgc   720
tgccgccgct acatcaaacc cgcttccaat tttaccctga gcttgacaat gagcaacttg  780
tgataaatta tgaataactt ctctatattt gtctacatta ttttccaggt ccgataccaa  840
aaaggaggcc aaagctgtag ttaaaactgt gactaaacct gccgaggagc ccagccctgt  900
tttgggaact tcttcaattc tgtgcgaatg aaaactcaat cttctgttgc cacgatgttc  960
ggtaacgctg tcctcctgag aatggtaggc atcatcagag aaaatatcaa taacgaacaa 1020
gttttctattg cagtagtcgt ccatgttagg cttaaagtag ctaaatagt tagcgataac 1080
ttttcaatg aaagggttct tagatccgcc tatcgaaaca ggaatgaagc cagttttagg 1140
acttatatgg tacagccact ccccatcttt aaattgttta cttttcacac gcacttcaaa 1200
cttatcagac tcttgcaatg aaccgtaagg atgggctaca gcatgcattc ttgccgaaaa 1260
tccgactaca aatgcttcat atttcggatc taaaactaaa tatccaccag ctagtaacgc 1320
tttccctggg gcactgaagg ctctcaactc tgacat                              1356

SEQ ID NO: 205          moltype = AA  length = 451
FEATURE                 Location/Qualifiers
source                  1..451
                        mol_type = protein
                        organism = Saccharomyces cerevisiae
SEQUENCE: 205
MSELRAFSAP GKALLAGGYL VLDPKYEAFV VGLSARMHAV AHPYGSLQES DKFEVRVKSK   60
QFKDGEWLYH ISPKTGFIPV SIGGSKNPFI EKVIANVFSY FKPNMDDYCN RNLFVIDIFS  120
DDAYHSQEDS VTEHRGNRRL SFHSRIEEV PKTGLGSSAG LVTVLTTALA SFFVSDLENN   180
VDKYREVIHN LSQVAHCQAQ GKIGSGFDVA AAAYGSIRYR RFPPALISNL PDIGSATYGS  240
KLAHLVNEED WNITIKSNHL PSGLTLWMGD IKNGSETVKL VQKVKNWYDS HMPESLKIYT   300
ELDHANSRFM DGLSKLDRLH ETHDDYSDQI FESLERNDCT CQKYPEITEV RDAVATIRRS  360
FRKITKESGA DIEPPVQTSL LDDCQTLKGV LTCLIPGAGG YDAIAVIAKQ DVDLRAQTAD  420
DKRFSKVQWL DVTQADWGVR KEKDPETYLD K                                  451

SEQ ID NO: 206          moltype = DNA  length = 1332
FEATURE                 Location/Qualifiers
source                  1..1332
                        mol_type = genomic DNA
                        organism = Saccharomyces cerevisiae
SEQUENCE: 206
atgtcattac cgttcttaac ttctgcaccg ggaaaggtta ttattttttgg tgaacactct  60
gctgtgtaca acaagcctgc cgtcgctgct agtgtgtctg cgttgagaac ctacctgcta 120
ataagcgagt catctgcacc agatactatt gaattggact tcccggacat tagctttaat 180
cataagtggt ccatcaatga tttcaatgcc atcaccgagg atcaagtaaa ctcccaaaaa 240
ttggccaagg ctcaacaagc caccgatggc ttgtctcagg aactcgttag tcttttggat 300
ccgttgttag ctcaactatc cgaatccttc cactaccagt cagcgttttg tttcctgtat 360
atgtttgttt gcctatgccc ccatgccaag aatattaagt tttctttaaa gtctacttta 420
cccatcggtg ctgggttggg ctcaagcgcc tctatttctg tatcactggc cttagctatg 480
gcctacttgg ggggttaat aggatctaat gacttggaaa agctgtcaga aaacgataag 540
catatagtga atcaatggc cttcataggt gaaagtgta ttcacggtac ccttccagga 600
atagataacg ctgtggccac ttatggtaat gccctgctat ttgaaaaaga ctcacataat 660
ggaacaataa acacaaacaa ttttaagttc ttagatgatt tcccagccat tccaatgatc 720
ctaacctata ctagaattcc aaggtctaca aaagatcttg ttgctcgcgt tcgtgtgttt 780
gtcaccgaga aatttcctga agttatgaag ccaattctag atgccatggg tgaatgtgcc 840
ctacaaggct tagagatcat gactaagtta agtaaatgaa aaggcaccga tgacgaggct 900
gtagaaacta ataatgaact gtatgaacaa ctattggaat tgataagaat aaatcatgga 960
ctgcttgtct caatcggtgt ttctcatcct ggattagaac ttattaaaaa tctgagcgat 1020
gatttgagaa ttggctccac aaaacttacc ggtgctggtg gcggcggttg ctcttttgact 1080
ttgttacgaa gagacattac tcaagagcaa attgcaatt tcaaaaagaa attgcaagat 1140
gattttagtt acgagacatt tgaaacagac ttgggtggga ctgctctg tttgttaagc 1200
gcaaaaaatt tgaataaaga tcttaaaatc aaatccctag tattccaatt atttgaaaat 1260
aaaactacca caaagcaaca aattgacgat ctattattgc caggaaacac gaatttacca 1320
tggacttcat aa                                                       1332

SEQ ID NO: 207          moltype = AA  length = 2233
FEATURE                 Location/Qualifiers
REGION                  1..2233
                        note = Mutated acetyl-CoA carboxylase (ACC1) (S659A, S1157A)
source                  1..2233
                        mol_type = protein
                        organism = synthetic construct
SEQUENCE: 207
MSEESLFESS PQKMEYEITN YSERHTELPG HFIGLNTVDK LEESPLRDFV KSHGGHTVIS   60
KILIANNGIA AVKEIRSVRK WAYETFGDDR TVQFVAMATP EDLEANAEYI RMADQYIEVP  120
```

-continued

```
GGTNNNNYAN VDLIVDIAER ADVDAVWAGW GHASENPLLP EKLSQSKRKV IFIGPPGNAM    180
RSLGDKISST IVAQSAKVPC IPWSGTGVDT VHVDEKTGLV SVDDDIYQKG CCTSPEDGLQ    240
KAKRIGFPVM IKASEGGGGK GIRQVEREED FIALYHQAAN EIPGSPIFIM KLAGRARHLE    300
VQLLADQYGT NISLFGRDCS VQRRHQKIIE EAPVTIAKAE TFHEMEKAAV RLGKLVGYVS    360
AGTVEYLYSH DDGKFYFLEL NPRLQVEHPT TEMVSGVNLP AAQLQIAMGI PMHRISDIRT    420
LYGMNPHSAS EIDFEFKTQD ATKKQRRPIP KGHCTACRIT SEDPNDGFKP SGGTLHELNF    480
RSSSNVWGYF SVGNNGNIHS FSDSQFGHIF AFGENRQASR KHMVVALKEL SIRGDFRTTV    540
EYLIKLLETE DFEDNTITTG WLDDLITHKM TAEKPDPTLA VICGAATKAF LASEEARHKY    600
IESLQKGQVL SKDLLQTMFP VDFIHEGKRY KFTVAKSGND RYTLFINGSK CDIILRQLSD    660
GGLLIAIGGK SHTIYWKEEV AATRLSVDSM TTLLEVENDP TQLRTPSPGK LVKFLVENGE    720
HIIKGQPYAE IEVMKMQMPL VSQENGIVQL LKQPGSTIVA GDIMAIMTLD DPSKVKHALP    780
FEGMLPDFGS PVIEGTKPAY KFKSLVSTLE NILKGYDNQV IMNASLQQLI EVLRNPKLPY    840
SEWKLHISAL HSRLPAKLDE QMEELVARSL RRGAVFPARQ LSKLIDMAVK NPEYNPDKLL    900
GAVVEPLADI AHKYSNGLEA HEHSIFVHFL EEYYEVEKLF NGPNVREENI ILKLRDENPK    960
DLDKVALTVL SHSKVSAKNN LILAILKHYQ PLCKLSSKVS AIFSTPLQHI VELESKATAK   1020
VALQAREILI QGALPSVKER TEQIEHILKS SVVKVAYGSS NPKRSEPDLN ILKDLIDSNY   1080
VVFDVLLQFL THQDPVVTAA AAQVYIRRAY RAYTIGDIRV HEGVTVPIVE WKFQLPSAAF   1140
STFPTVKSKM GMNRAVSVSD LSYVANSQSS PLREGILMAV DHLDDVDEIL SQSLEVIPRH   1200
QSSSNGPAPD RSGSSASLSN VANVCVASTE GFESEEEILV RLREILDLNK QELINASIRR   1260
ITFMFGFKDG SYPKYYTFNG PNYNENETIR HIEPALAFQL ELGRLSNFNI KPIFTDNRNI   1320
HVYEAVSKTS PLDKRFFTRG IIRTGHIRDD ISIQEYLTSE ANRLMSDILD NLEVTDTSNS   1380
DLNHIFINFI AVFDISPEDV EAAFGGFLER FGKRLLRLVN SSAEIRIIIK DPQTGAPVPL   1440
RALINNVSGY VIKTEMYTEV KNAKGEWVFK SLGKPGSMHL RPIATPYPVK EWLQPKRYKA   1500
HLMGTTYVYD FPELFRQASS SQWKNFSADV KLTDDFFISN ELIEDENGEL TEVEREPGAN   1560
AIGMVAFKIT VKTPEYPRGR QFVVVANDIT FKIGSFGPQE DEFFNKVTEY ARKRGIPRIY   1620
LAANSGARIG MAEEIVPLFQ VAWNDAANPD KGFQYLYLTS EGMETLKKFD KENSVLTERT   1680
VINGEERFVI KTIIGSEDGL GVECLRGSGL IAGATSRAYH DIFTITLVTC RSVGIGAYLV   1740
RLGQRAIQVE GQPIILTGAP AINKMLGREV YTSNLQLGGT QIMYNNGVSH LTAVDDLAGV   1800
EKIVEWMSYV PAKRNMPVPI LETKDTWDRP VDFTPTNDET YDVRWMIEGR ETESGFEYGL   1860
FDKGSFFETL SGWAKGVVVG RARLGGIPLG VIGVETRTVE NLIPADPANP NSAETLIQEP   1920
GQVWHPNSAF KTAQAINDFN NGEQLPMMIL ANWRGFSGGQ RDMFNEVLKY GSFIVDALVD   1980
YKQPIIIYIP PTGELRGGSW VVVDPTINAD QMEMYADVNA RAGVLEPQGM VGIKFRREKL   2040
LDTMNRLDDK YRELRSQLSN KSLAPEVHQQ ISKQLADRER ELLPIYGQIS LQFADLHDRS   2100
SRMVAKGVIS KELEWTEARR FFFWRLRRRL NEEYLIKRLS HQVGEASRLE KIARIRSWYP   2160
ASVDHEDDRQ VATWIEENYK TLDDKLKGLK LESFAQDLAK KIRSDHDNAI DGLSEVIKML   2220
STDDKEKLLK TLK                                                      2233

SEQ ID NO: 208        moltype = AA  length = 524
FEATURE               Location/Qualifiers
REGION                1..524
                      note = Truncated 3-hydroxy-3-methyl-glutaryl-CoA reductase
                       (Sc_tHMG1)
source                1..524
                      mol_type = protein
                      organism = synthetic construct
SEQUENCE: 208
MQLVKTEVTK KSFTAPVQKA STPVLTNKTV ISGSKVKSLS SAQSSSSGPS SSSEEDDSRD     60
IESLDKKIRP LEELEALLSS GNTKQLKNKE VAALVIHGKL PLYALEKKLG DTTRAVAVRR   120
KALSILAEAP VLASDRLPYK NYDYDRVFGA CCENVIGYMP LPVGVIGPLV IDGTSYHIPM   180
ATTEGCLVAS AMRGCKAINA GGGATTVLTK DGMTRGPVVR FPTLKRSGAC KIWLDSEEGQ   240
NAIKKAFNST SRFARLQHIQ TCLAGDLLFM RFRTTTGDAM GMNMISKGVE YSLKQMVEEY   300
GWEDMEVVSV SGNYCTDKKP AAINWIEGRG KSVVAEATIP GDVVRKVLKS DVSALVELNI   360
AKNLVGSAMA GSVGGFNAHA ANLVTAVFLA LGQDPAQNVE SSNCITLMKE VDGDLRISVS   420
MPSIEVGTIG GGTVLEPQGA MLDLLGVRGP HATAPGTNAR QLARIVACAV LAGELSLCAA   480
LAAGHLVQSH MTHNRKPAEP TKPNNLDATD INRLKDGSVT CIKS                    524

SEQ ID NO: 209        moltype = DNA  length = 1197
FEATURE               Location/Qualifiers
source                1..1197
                      mol_type = genomic DNA
                      organism = Saccharomyces cerevisiae
SEQUENCE: 209
atgtctcaga acgtttacat tgtatcgact gccagaaccc caattggttc attccagggt     60
tctctatcct ccaagacagc agtggaattg ggtgctgttg cttttaaagg cgccttgcct    120
aaggttccag aattggatgc atccaaggat tttgacgaaa ttatttttgg taacgttctt    180
tctgccaatt gggccaagc tccggccaga caagttgctt ggctgccgg tttgagtaat     240
catatcgttg caagcacagt taacaaggtc tgtgcatccg ctatgaaggc aatcattttg    300
ggtgctcaat ccatcaaatg tggtaatgct gatgttgtcg tagctggtgg ttgtgaatct    360
atgactaacg taccatacta catgccagca gcccgtgcgg gtgccaaatt tggccaaact    420
gttcttgttg atggtgtcga aagagatggg ttgaacgatg cgtacgatgg tctagccatg    480
ggtgtacacg cagaaaagtg tgcccgtgat gggatatta ctagagaaca caagacaat     540
tttgccatcg aatcctacca aaatctcaa aatctcaa aggaaggtaa attcgacaat     600
gaaattgtac tctgttacca taagggattt agaggtaagc ctgatactca agtcacgaag    660
gacgaggaac ctgtcgatgt acacgttgaa aaattgatt gtcaaggac tgttttcaa     720
aaagaaaacg gtactgttac tgccgctaac gcttctccaa tcaacgatgg tgctgcagcc    780
gtcatcttgg tttccgaaaa agttttgaag gaaagaatt tgaagccttt ggctattatc    840
aaaggttggg gtgaggccgc tcatcaacca gctgatttta catgggctcc atctcttgca    900
gttccaaagg ctttgaaaca tgctggcatc gaagacatca ttctgttga ttactttgaa    960
ttcaatgaag ccttttcggt tgtcggtttg gtgaacacta gattttgaa gctagaccca   1020
```

```
tctaaggtta atgtatatgg tggtgctgtt gctctaggtc acccattggg ttgttctggt   1080
gctagagtgg ttgttacact gctatccatc ttacagcaag aaggaggtaa gatcggtgtt   1140
gccgccattt gtaatggtgg tggtggtgct tcctctattg tcattgaaaa gatatga      1197

SEQ ID NO: 210          moltype = DNA   length = 867
FEATURE                 Location/Qualifiers
misc_feature            1..867
                        note = Artificial truncated geranyl pyrophosphate
                        olivetolic acid geranyltransferase CsPT4_t112
source                  1..867
                        mol_type = other DNA
                        organism = synthetic construct
SEQUENCE: 210
atgtcttacg ttgtcaaggg tatgatctct attgcttgtg gtttgttcgg tagagaattg    60
tttaacaaca gacacttgtt ctcttggggt ttgatgtgga aagctttctt cgcttttggtc  120
ccaatttttgt ctttcaattt cttcgccgcc atcatgaacc aaatctacga tgttgatatc  180
gaccgtatca acaagccaga cttaccttta gtttccggtg aaatgtccat tgaaactgct   240
tggatcttgt ctatcattgt tgccttgact ggtttaattg ttactattaa gttgaagtcc   300
gctccattgt ttgtcttcat ctacatcttc ggtatcttcg ctggtttcgc ttactccgtc   360
ccacctatta gatggaaaca atatcctttt accaatttct tgatcactat ttcctctcat   420
gttggtttga ctttcacttc ttactctgcc accacttctg ctttaggttt gcctttcgtt   480
tggcgtcctg ccttctcttt cattattgct tcatgaagtc tcatgggtat gactattgcc   540
tttgctaaag acatttctga tatcgaaggt gatgctaagt acggtgtctc taccgttgct   600
accaagttag gtgctagaaa tatgactttt gttgtttctg gtgtcttatt gttgaactac   660
ttggtttcta tctctattgg tatcatttgg ccacaagttt tcaagtctaa cattatgatc   720
ttgtctctca tgctattttgg cttctgtttg atctttcaaa ctcgtgaatt agccttagcc   780
aattatgcct ctgccccatc ccgtcaattt tcgaattca tctggttgtt atactatgcc   840
gaatactcg tttacgtctt catttaa                                         867

SEQ ID NO: 211          moltype = AA   length = 288
FEATURE                 Location/Qualifiers
REGION                  1..288
                        note = Truncated geranyl pyrophosphate olivetolic acid
                        geranyltransferase CsPT4_t112
source                  1..288
                        mol_type = protein
                        organism = synthetic construct
SEQUENCE: 211
MSYVVKGMIS IACGLFGREL FNNRHLFSWG LMWKAFFALV PILSFNFFAA IMNQIYDVDI   60
DRINKPDLPL VSGEMSIETA WILSIIVALT GLIVTIKLKS APLFVFIYIF GIFAGFAYSV  120
PPIRWKQYPF TNFLITISSH VGLAFTSYSA TTSALGLPFV WRPAFSFIIA FMTVMGMTIA  180
FAKDISDIEG DAKYGVSTVA TKLGARNMTF VVSGVLLLNY LVSISIGIIW PQVFKSNIMI  240
LSHAILAFCL IFQTRELALA NYASAPSRQF FEFIWLLYYA EYFVYVFI               288

SEQ ID NO: 212          moltype = DNA   length = 810
FEATURE                 Location/Qualifiers
misc_feature            1..810
                        note = Artificial truncated geranyl pyrophosphate
                        olivetolic acid geranyltransferase CsPT4_t131 nucleotide
                        sequence
source                  1..810
                        mol_type = other DNA
                        organism = synthetic construct
SEQUENCE: 212
atgtctaaca acagacactt gttctccttgg ggtttgatgt ggaaagcttt cttcgctttg    60
gtcccaattt tgtctttcaa tttcttcgcc gccatcatga accaaatcta cgatgttgat   120
atcgaccgta tcaacaagcc agacttacct ttagtttccg gtgaaatgtc cattgaaact   180
gcttggatct tgtctatcat tgttgccttg actggtttaa ttgttactat taagttgaag   240
tccgctccat gtttgtcttc atctacatc ttcggtatct tcgctggttt cgcttactcc   300
gtcccaccta ttagatggaa acaatatcct tttaccaatt tcttgatcac tatttcctct   360
catgttggtt tggctttcac ttcttactct gccaccactt ctgctttagg tttgcctttc   420
gtttggcgtc ctgccttctc tttcattatt gctttcatga ctgtcatggg tatgactatt   480
gccttttgcta aagacatttc tgatatcgaa ggtgatgcta agtacggtgt ctctaccgtt   540
gctaccaagt taggtgctag aaatatgact tttgttgttt ctggtgtctt attgttgaac   600
tacttggttt ctatctctat tggtatcatt tggccacaag ttttcaagtc taacattatg   660
atcttgtctc atgctatttt ggctttcgtg ttgatctttc aaactcgtga attagcctta   720
gccaattatg cctctgcccc atcccgtcaa ttttcgaat tcatctggtt gttatactat   780
gccgaatact cgtttacgt cttcatttaa                                    810

SEQ ID NO: 213          moltype = AA   length = 269
FEATURE                 Location/Qualifiers
REGION                  1..269
                        note = Truncated geranyl pyrophosphate olivetolic acid
                        geranyltransferase CsPT4_t131
source                  1..269
                        mol_type = protein
                        organism = synthetic construct
SEQUENCE: 213
MSNNRHLFSW GLMWKAFFAL VPILSFNFFA AIMNQIYDVD IDRINKPDLP LVSGEMSIET   60
```

-continued

```
AWILSIIVAL  TGLIVTIKLK  SAPLFVFIYI  FGIFAGFAYS  VPPIRWKQYP  FTNFLITISS   120
HVGLAFTSYS  ATTSALGLPF  VWRPAFSFII  AFMTVMGMTI  AFAKDISDIE  GDAKYGVSTV   180
ATKLGARNMT  FVVSGVLLLN  YLVSISIGII  WPQVFKSNIM  ILSHAILAFC  LIFQTRELAL   240
ANYASAPSRQ  FFEFIWLLYY  AEYFVYVFI                                       269

SEQ ID NO: 214              moltype = DNA  length = 777
FEATURE                     Location/Qualifiers
misc_feature                1..777
                            note = Artificial truncated geranyl pyrophosphate
                              olivetolic acid geranyltransferase CsPT4_t142 nucleotide
                              sequence
source                      1..777
                            mol_type = other DNA
                            organism = synthetic construct
SEQUENCE: 214
atgtcttgga aagctttctt cgctttggtc ccaattttgt ctttcaattt cttcgccgcc   60
atcatgaacc aaatctacga tgttgatatc gaccgtatca caagccaga cttacccttta  120
gtttccggtg aaatgtccat tgaaactgct tggatcttgt ctatcattgt tgccttgact  180
ggtttaattg ttactattaa gttgaagtcc gctccattgt ttgtcttcat ctacatcttc  240
ggtatcttcg ctggtttcgc ttactccgtc ccacctatta gatggaaaca atatccttt   300
accaattttct tgatcactat ttcctctcat gttggtttgg ctttcacttc ttactctgcc  360
accacttctg ctttaggttt gccttttcgtt tggcgtcctg cttcttcttt cattattgct  420
ttcatgactg tcatgggtat gactattgcc tttgctaaag acatttctga tatcgaaggt  480
gatgctaagt acggtgtctc taccgttgct accaagttag gtgctagaaa tatgactttt  540
gttgtttctg gtgtcttatt gttgaactac ttggtttcta tctctattgg tatcatttgg  600
ccacaagttt tcaagtctaa cattatgatc ttgtctcatg ctattttgg cttctgtttg  660
atctttcaaa ctcgtgaatt agccttagcc aattatgcct ctgccccatc cgtcaattt   720
ttcgaattca tctggttgtt atactatgcc gaatacttcg tttacgtctt catttaa     777

SEQ ID NO: 215              moltype = AA  length = 258
FEATURE                     Location/Qualifiers
REGION                      1..258
                            note = Truncated geranyl pyrophosphate olivetolic acid
                              geranyltransferase CsPT4_t142
source                      1..258
                            mol_type = protein
                            organism = synthetic construct
SEQUENCE: 215
MSWKAFFALV  PILSFNFFAA  IMNQIYDVDI  DRINKPDLPL  VSGEMSIETA  WILSIIVALT   60
GLIVTIKLKS  APLFVFIYIF  GIFAGFAYSV  PPIRWKQYPF  TNFLITISSH  VGLAFTSYSA  120
TTSALGLPFV  WRPAFSFIIA  FMTVMGMTIA  FAKDISDIEG  DAKYGVSTVA  TKLGARNMTF  180
VVSGVLLLNY  LVSISIGIIW  PQVFKSNIMI  LSHAILAFCL  IFQTRELALA  NYASAPSRQF  240
FEFIWLLYYA  EYFVYVFI                                                   258

SEQ ID NO: 216              moltype = DNA  length = 705
FEATURE                     Location/Qualifiers
misc_feature                1..705
                            note = Artificial truncated geranyl pyrophosphate
                              olivetolic acid geranyltransferase CsPT4_t166 nucleotide
                              sequence
source                      1..705
                            mol_type = other DNA
                            organism = synthetic construct
SEQUENCE: 216
atgtctgatg ttgatatcga ccgtatcaac aagccagact acctttagt ttccggtgaa   60
atgtccattg aaactgcttg gatcttgtct atcattgttg ccttgactgg tttaattgtt  120
actattaagt tgaagtccgc tccattgttt gtcttcatct acatcttcgg tatcttcgct  180
ggtttcgctt actccgtccc acctattaga tggaaacaat atccttttac caatttcttg  240
atcactattt cctctcatgt tggtttggct ttcacttctt actctgccac cacttctgct  300
ttaggtttgc cttttcgttt ggcgtcctgc ttctctttca ttattgcttt catgactgtc  360
atgggtatga ctattgcctt tgctaaagac atttctgata tcgaaggtga tgctaagtac  420
ggtgtctcta ccgttgctac caagttaggt gctagaaata tgacttttgt tgtttctggt  480
gtcttattgt tgaactactt ggtttctatc tctattggta tcatttggcc acaagttttc  540
aagtctaaca ttatgatctt gtctcatgct attttggct tctgtttgat ctttcaaact  600
cgtgaattag ccttagccaa ttatgcctct gccccatccc gtcaattttt cgaattcatc  660
tggttgttat actatgccga atacttcgtt tacgtcttca tttaa                   705

SEQ ID NO: 217              moltype = AA  length = 234
FEATURE                     Location/Qualifiers
REGION                      1..234
                            note = Truncated geranyl pyrophosphate olivetolic acid
                              geranyltransferase CsPT4_t166
source                      1..234
                            mol_type = protein
                            organism = synthetic construct
SEQUENCE: 217
MSDVDIDRIN  KPDLPLVSGE  MSIETAWILS  IIVALTGLIV  TIKLKSAPLF  VFIYIFGIFA   60
GFAYSVPPIR  WKQYPFTNFL  ITISSHVGLA  FTSYSATTSA  LGLPFVWRPA  FSFIIAFMTV  120
MGMTIAFAKD  ISDIEGDAKY  GVSTVATKLG  ARNMTFVVSG  VLLLNYLVSI  SIGIIWPQVF  180
```

KSNIMILSHA ILAFCLIFQT RELALANYAS APSRQFFEFI WLLYYAEYFV YVFI        234

```
SEQ ID NO: 218              moltype = DNA   length = 645
FEATURE                     Location/Qualifiers
misc_feature                1..645
                            note = Artificial truncated geranyl pyrophosphate
                               olivetolic acid geranyltransferase CsPT4_t186 nucleotide
                               sequence
source                      1..645
                            mol_type = other DNA
                            organism = synthetic construct
SEQUENCE: 218
atgtctattg aaactgcttg gatcttgtct atcattgttg ccttgactgg tttaattgtt    60
actattaagt tgaagtccgc tccattgttt gtcttcatct acatcttcgg tatcttcgct   120
ggtttcgctt actccgtccc acctattaga tggaaacaat atcctttac caatttcttg    180
atcactattt cctctcatgt tggtttggct ttcacttctt actctgccac cacttctgct   240
ttaggtttgc ctttcgtttg gcgtcctgcc ttctctttca ttattgcttt catgactgtc   300
atgggtatga ctattgcctt tgctaaagac atttctgata tcgaaggtga tgctaagtac   360
ggtgtctcta ccgttgctac caagttaggt gctagaaata tgactttgt tgtttctggt   420
gtcttattgt tgaactactt ggtttctatc tctattggta tcatttggcc acaagttttc   480
aagtctaaca ttatgatctt gtctcatgct atttttggctt tctgtttgat ctttcaaact   540
cgtgaattag cctagccaa ttatgcctct gccccatccc gtcaattttt cgaattcatc    600
tggttgttat actatgccga atacttcgtt tacgtcttca tttaa                  645

SEQ ID NO: 219              moltype = AA   length = 214
FEATURE                     Location/Qualifiers
REGION                      1..214
                            note = Truncated geranyl pyrophosphate olivetolic acid
                               geranyltransferase CsPT4_t186
source                      1..214
                            mol_type = protein
                            organism = synthetic construct
SEQUENCE: 219
MSIETAWILS IIVALTGLIV TIKLKSAPLF VFIYIFGIFA GFAYSVPPIR WKQYPFTNFL    60
ITISSHVGLA FTSYSATTSA LGLPFVWRPA FSFIIAFMTV MGMTIAFAKD ISDIEGDAKY   120
GVSTVATKLG ARNMTFVVSG VLLLNYLVSI SIGIIWPQVF KSNIMILSHA ILAFCLIFQT   180
RELALANYAS APSRQFFEFI WLLYYAEYFV YVFI                              214

SEQ ID NO: 220              moltype = DNA   length = 1188
FEATURE                     Location/Qualifiers
misc_feature                1..1188
                            note = Artificial geranyl pyrophosphate olivetolic acid
                               geranyltransferase CsGOT (CsPT1) nucleotide sequence
source                      1..1188
                            mol_type = other DNA
                            organism = synthetic construct
SEQUENCE: 220
atgggtttat cttccgtttg tactttttct ttccaaacta actaccacac tttgttaaat    60
ccacacaaca acaaccctaa aacctccttg ttatgttaca gacacccaaa gaccccctatt   120
aaatactcct caacaacctt cccatccaaa cactgctcca ctaagtcctt tcacttgcaa   180
aacaagtgtt ctgaatcctt gtccattgcc aagaactcta ttcgtgccgc tactactaac   240
caaactgagc cacctgaatc cgataaccac tccgtcgcca ccaagatctt gaattttggt   300
aaagcttgct ggaaattgca agaccatac actattattg ctttcacttc ctgtgcttgt    360
ggtttattcg gtaaggaatt attgcataac ccaacttga tttcttggtc ttaatgttc     420
aaagccttct tctttttagt tgccattta tgtattgctt ctttcactac tactattaat    480
caaatttacg atttgcacat tgacagaatc aataagcctg acttgccatt agcttccggt   540
gaaatttctg ttaacactgc ttggatcatg tccatcattg tcgctttgtt cggtttaatt   600
atcaccatca aatgaaggg tggtccttg tacatcttcg ttattgctt cggtattttc     660
ggtggtattg tctactctgt cccaccattc agatggaagc aaaacccatc cactgccttt   720
ttgttgaatt tcttggctca catcattacc aatttactt tctactatgc ctcccgtgct    780
gcttaggtt tgcctttga gttacgtcca tccttcactt ttttattggc tttttatgaag    840
tccatgggtt ctgctttagc cttaattaag gacgcctctg acgttgaagg tgatactaag   900
ttcggtatct ctacttagc tctcaagtac ggttctcgta acttgacctt gttctgttct    960
ggtattgtct tgttgctta cgtcgccgct attttggcg gtatcatctg gccacaagct    1020
ttcaactcta acgttatgtt gttgtctcat gctatctag cttttctggtt gatcttacaa   1080
accagagact tcgctttgac taactacgac ccagaagccg tcgtagatt ctacgaattc   1140
atgtggaat tgtactacgc cgagtacttg gtctacgttt tcatttag                1188

SEQ ID NO: 221              moltype = DNA   length = 972
FEATURE                     Location/Qualifiers
misc_feature                1..972
                            note = Artificial truncated geranyl pyrophosphate
                               olivetolic acid geranyltransferase CsPT4t nucleotide
                               sequence
source                      1..972
                            mol_type = other DNA
                            organism = synthetic construct
SEQUENCE: 221
atgtctgctg gctctgacca aattgaaggt tccccgcatc acgaatcaga taatagtatt    60
```

```
gccacaaaga tcttaaactt tgggcataca tgttggaaat tacaaaggcc ctacgtcgtc    120
aaaggaatga taagcatcgc ttgcggtctg ttcggaaggg aattatttaa caataggcat    180
ctattcagct gggggttaat gtggaaagct ttcttcgcgt tagtgccaat cctaagcttt    240
aacttttcg ccgccatcat gaaccagatt tatgatgttg atatcgacag gataaataag    300
ccagatcttc cattggtatc cggtgaaatg tcaatagaca ctgcatggat attatctatt    360
atcgttgcgc tgaccggact gatagtaaca atcaaattga aatctgcacc cctgtttgtt    420
tttatatata tatttggtat tttcgctgga ttcgcttact cagtgccacc tatcaggtgg    480
aagcagtacc cattcacgaa ttttctgatc acgatctcta gccacgtcgg ttagcgttc    540
acatcttact ctgcaaccac gagtgccttg gggcttcctt tcgtctggcg tccagctttt    600
agttttatca ttgcctttat gaccgtaatg ggaatgacga tcgcattcgc aaaggacatt    660
tctgacatag aggggatgc aaaatacggt gtctccactg tggcgacaaa attaggagct    720
aggaatatga ctttcgtggt gtccggtgta ttattactaa attatctggt atctataagt    780
atcggcatca tatggccgca agtgtttaaa tccaacatta tgatactgag tcatgctatt    840
ttggctttt gtctgatttt tcagacgcgt gagttggcgc ttgcaaacta tgcctctgcg    900
cccagcaggc agtttttga attcatatgg ttattgtact atgccgagta tttcgtctac    960
gtatttattt aa                                                        972

SEQ ID NO: 222          moltype = DNA  length = 969
FEATURE                 Location/Qualifiers
misc_feature            1..969
                        note = Artificial truncated geranyl pyrophosphate
                         olivetolic acid geranyltransferase CsGOT_t75 (CsPT1_t75)
                         nucleotide sequence
source                  1..969
                        mol_type = other DNA
                        organism = synthetic construct
SEQUENCE: 222
atgtctgccg ctactactaa ccaaactgag ccacctgaat ccgataacca ctccgtcgcc     60
accaagatct tgaattttgg taaagcttgc tggaaattgc aaagaccata cactattatt    120
gctttcactt cctgtgcttg tggtttattc ggtaaggaat tattgcataa caccaacttg    180
atttcttggt ccttaatgtt caaagccttc ttctttttag ttgccatttt atgtattgct    240
tctttcacta ctactattaa tcaaatttac gatttgcaca ttgacagaat caataagcct    300
gacttgccat tagcttccgg tgaaattct gttaacactg cttggatcat gtccatcatt    360
gtcgctttgt tcggtttaat tatcaccatc aaaatgaagg gtggtccttt gtacatcttt    420
ggttattgct tcggtatttt cggtggtatt gtctactctg tcccaccatt cagatggaag    480
caaaacccat ccactgcctt tttgttgaat ttcttggctc acatcattac caattttact    540
ttctactatg cctcccgtgc tgctttaggt ttgccttttg agttacgtcc atccttcact    600
tttttattgg cttttatgaa gtccatgggt tctgctttag ccttaattaa ggacgcctct    660
gacgttgaag gtgatactaa gttcggtatc tctacttag cctctaagta cggttctgt    720
aacttgacct tgttctgttc tggtattgtc ttgttgtctt acgtcgccgc tattttggcc    780
ggtatcatct ggccacaagc tttcaactct aacgttatgt tgttgtctca tgctatctta    840
gctttctggt tgatcttaca aaccagagac ttcgctttga ctaactacga cccagaagcc    900
ggtcgtagat tctacgaatt catgtggaaa ttgtactacg ccgagtactt ggtctacgtt    960
ttcatttag                                                            969

SEQ ID NO: 223          moltype = AA  length = 322
FEATURE                 Location/Qualifiers
REGION                  1..322
                        note = Truncated geranyl pyrophosphate olivetolic acid
                         geranyltransferase CsGOT_t75 (CsPT1_t75)
source                  1..322
                        mol_type = protein
                        organism = synthetic construct
SEQUENCE: 223
MSAATTNQTE PPESDNHSVA TKILNFGKAC WKLQRPYTII AFTSCACGLF GKELLHNTNL     60
ISWSLMFKAF FFLVAILCIA SFTTTINQIY DLHIDRINKP DLPLASGEIS VNTAWIMSII    120
VALFGLIITI KMKGGPLYIF GYCFGIFGGI VYSVPPFRWK QNPSTAFLLN FLAHIITNFT    180
FYYASRAALG LPFELRPSFT FLLAFMKSMG SALALIKDAS DVEGDTKFGI STLASKYGSR    240
NLTLFCSGIV LLSYVAAILA GIIWPQAFNS NVMLLSHAIL AFWLILQTRD FALTNYDPEA    300
GRRFYEFMWK LYYAEYLVYV FI                                             322

SEQ ID NO: 224          moltype = DNA  length = 972
FEATURE                 Location/Qualifiers
misc_feature            1..972
                        note = Artificial truncated geranyl pyrophosphate
                         olivetolic acid geranyltransferase CsPT4_t76 (CsPT4t)
                         nucleotide sequence
source                  1..972
                        mol_type = other DNA
                        organism = synthetic construct
SEQUENCE: 224
atgtccgccg gttctgatca aatcgaaggt tcccctcatc atgagtccga taactccatt     60
gctactaaaa ttttaaattt cggtcatact tgttggaagt tgcaacgtcc ttacgttgtc    120
aagggtatga tctctattgc ttgtgghttg ttcggtaagg aattgtttaa caacagacac    180
ttgttctctt ggggtttgat gtggaaagct ttcttcgctt tggtcccaat tttgtctttc    240
aatttcttcg ccgccatcat gaaccaaatc tacgatgttg atatcgaccg tatcaacaag    300
ccagacttac ctttagttc cggtgaaatg tccattgaaa ctgcttggat cttgtctatc    360
attgttgcct tgactggtt aattgttact attaagttga agtccgctcc attgtttgtc    420
ttcatctaca tcttccggtat cttcgctggt ttcgcttact ccgtcccacc tattagatgg    480
```

```
aaacaatatc cttttaccaa tttcttgatc actatttcct ctcatgttgg tttggctttc  540
acttcttact ctgccaccac ttctgcttta ggtttgcctt tcgtttggcg tcctgccttc  600
tctttcatta ttgctttcat gactgtcatg ggtatgacta ttgcctttgc taaagacatt  660
tctgatatcg aaggtgatgc taagtacggt gtctctaccg ttgctaccaa gttaggtgct  720
agaaatatga cttttgttgt ttctggtgtc ttattgttga actacttggt ttctatctct  780
attggtatca tttggccaca agttttcaag tctaacatta tgatcttgtc tcatgctatt  840
ttggctttct gtttgatctt tcaaactcgt gaattagcct tagccaatta tgcctctgcc  900
ccatcccgtc aatttttcga attcatctgg ttgttatact atgccgaata cttcgtttac  960
gtcttcattt aa                                                     972

SEQ ID NO: 225       moltype = DNA  length = 1197
FEATURE              Location/Qualifiers
source               1..1197
                     mol_type = genomic DNA
                     organism = Cannabis sativa
SEQUENCE: 225
atgggactct cattagtttg taccttttca tttcaaacta attatcatac tttattaaac   60
cctcataata agaatcccaa aaactcatta ttatcttatc aacacccaa aacaccaata   120
attaaatcct cttatgataa ttttcccctct aaatattgct taaccaagaa ctttcattta  180
cttggactca attcacacaa cagaataagc tcacaatcaa ggtccattag ggcaggtagc  240
gatcaaattg aaggttctcc tcatcatgaa tctgataatt caatagcaac taaaatttta  300
aattttggac atacttgttg gaaacttcaa agaccatatg tagtaaaagg gatgatttca  360
atcgcttgtg gtttgtttgg gagagagttg ttcaataaca gacatttatt cagttggggt  420
ttgatgtgga aggcattctt tgctttggtg cctatattgt ccttcaattt ctttgcagca  480
atcatgaatc aaatttacga tgtggacatc gacaggataa acaagcctga tctaccacta  540
gtttcagggg aaatgtcaat tgaaacagct tggattttga gcataattgt ggcactaact  600
gggttgatag taactataaa attgaaatct gcaccacttt ttgtttttcat ttacattttt  660
ggtatatttg ctgggtttgc ctattctgtt ccaccaatta gatggaagca atatcctttt  720
accaattttc taattaccat atcgagtcat gtgggcttag cttcacatc atattctgca  780
accacatcag ctcttggttt accatttgtg tggaggcctg cttttagttt catcatagca  840
ttcatgacag ttatgggtat gactattgct tttgccaaag atatttcaga tattgaaggc  900
gacgccaaat atgggtatc aactgttgca accaaattag gtgctaggaa catgacattt  960
gttgtttctg gagttcttct tctaaactac ttggtttcta tatctattgg gataatttgg 1020
cctcaggttt tcaagagtaa cataatgata ctttctcatg caatcttagc attttgctta 1080
atcttccaga ctcgtgagct tgctctagca aattacgcct cggcgccaag cagacaattc 1140
ttcgagttta tctggttgct atattatgct gaatactttg tatatgtatt tatataa    1197
```